US008076108B2

(12) United States Patent
Brazeau et al.

(10) Patent No.: US 8,076,108 B2
(45) Date of Patent: *Dec. 13, 2011

(54) POLYPEPTIDES AND BIOSYNTHETIC PATHWAYS FOR THE PRODUCTION OF STEREOISOMERS OF MONATIN AND THEIR PRECURSORS

(75) Inventors: Brian J. Brazeau, Oskaloosa, IA (US); Mervyn L. De Souza, Plymouth, MN (US); Steven J. Gort, Brooklyn Center, MN (US); Paula M. Hicks, Eden Prairie, MN (US); Sherry R. Kollmann, Maple Grove, MN (US); Jose M. Laplaza, Plymouth, MN (US); Sara C. McFarlan, St. Paul, MN (US); Fernando A. Sanchez-Riera, Eden Prairie, MN (US); Christopher Solheid, Minneapolis, MN (US)

(73) Assignee: Cargill, Incorporated, Wayzata, MN (US)

( * ) Notice: Subject to any disclaimer, the term of this patent is extended or adjusted under 35 U.S.C. 154(b) by 738 days.

This patent is subject to a terminal disclaimer.

(21) Appl. No.: 11/714,279

(22) Filed: Mar. 6, 2007

(65) Prior Publication Data

US 2008/0020434 A1   Jan. 24, 2008

Related U.S. Application Data

(63) Continuation-in-part of application No. 11/584,016, filed on Oct. 20, 2006, now abandoned, which is a continuation-in-part of application No. 11/411,229, filed on Apr. 26, 2006, now Pat. No. 7,582,455.

(60) Provisional application No. 60/674,932, filed on Apr. 26, 2005.

(51) Int. Cl.
    *C12P 17/10* (2006.01)
(52) U.S. Cl. ................ 435/121; 435/108; 435/193
(58) Field of Classification Search ............ 435/108, 435/121, 193, 232, 252.3
    See application file for complete search history.

(56) References Cited

U.S. PATENT DOCUMENTS

| | | | |
|---|---|---|---|
| 3,002,889 A | 10/1961 | Kinoshita et al. | |
| 3,128,237 A | 4/1964 | Motozaki et al. | |
| 3,399,114 A | 8/1968 | Ohsawa et al. | |
| 4,371,614 A | 2/1983 | Anderson et al. | |
| 4,975,298 A | 12/1990 | Van Wyk et al. | |
| 5,128,164 A | 7/1992 | Van Wyk et al. | |
| 5,128,482 A | 7/1992 | Olivier et al. | |
| 5,300,437 A | 4/1994 | Stirling et al. | |
| 5,360,724 A | 11/1994 | Matcham et al. | |
| 5,985,617 A | 11/1999 | Liao | |
| 5,994,559 A | 11/1999 | Abushanab et al. | |
| 6,207,427 B1 | 3/2001 | Hashimoto et al. | |
| 6,264,999 B1 | 7/2001 | Yatka et al. | |
| 6,489,100 B1 | 12/2002 | Liao | |
| 7,064,219 B2 | 6/2006 | Kawahara et al. | |
| 7,354,746 B1 | 4/2008 | Suzuki et al. | |
| 7,396,941 B2 | 7/2008 | Mori et al. | |
| 7,534,898 B2 | 5/2009 | Amino et al. | |
| 7,670,822 B2 | 3/2010 | Smirnov et al. | |
| 7,781,005 B2 | 8/2010 | Mori | |
| 7,816,541 B2 | 10/2010 | Kawahara et al. | |
| 2002/0136737 A1 | 9/2002 | Frankel | |
| 2003/0228403 A1 | 12/2003 | Amino et al. | |
| 2005/0004394 A1 | 1/2005 | Kawahara et al. | |
| 2005/0009153 A1* | 1/2005 | Sugiyama et al. | ............ 435/121 |
| 2005/0020508 A1 | 1/2005 | Amino et al. | |
| 2005/0095670 A1 | 5/2005 | Ikeda et al. | |
| 2005/0106305 A1 | 5/2005 | Abraham et al. | |
| 2005/0112260 A1 | 5/2005 | Abraham et al. | |
| 2005/0118317 A1 | 6/2005 | Amino et al. | |
| 2005/0137246 A1 | 6/2005 | Amino et al. | |
| 2005/0153405 A1 | 7/2005 | Sugiyama et al. | |
| 2005/0170041 A1 | 8/2005 | Abraham et al. | |
| 2005/0221453 A1 | 10/2005 | Takagi et al. | |
| 2005/0221455 A1 | 10/2005 | McFarlan et al. | |
| 2005/0244937 A1 | 11/2005 | Abraham et al. | |
| 2005/0244939 A1 | 11/2005 | Sugiyama et al. | |
| 2005/0272939 A1 | 12/2005 | Amino et al. | |
| 2005/0282260 A1 | 12/2005 | Hicks et al. | |
| 2006/0003411 A1 | 1/2006 | Sugiyama et al. | |
| 2006/0003426 A1 | 1/2006 | Sugiyama et al. | |
| 2006/0009394 A1 | 1/2006 | Amino | |
| 2006/0014819 A1 | 1/2006 | Mori et al. | |
| 2006/0074249 A1 | 4/2006 | Kawahara et al. | |
| 2006/0083695 A1 | 4/2006 | Mori | |
| 2006/0154343 A1 | 7/2006 | Mori et al. | |
| 2006/0172396 A1 | 8/2006 | Sugiyama et al. | |

(Continued)

FOREIGN PATENT DOCUMENTS

EP        0 438 314        4/1994

(Continued)

OTHER PUBLICATIONS

Ackerman, "Structure elucidation of and synthetic approaches to monatin, a metabolite from *schlerochiton ilicifolius*," PhD dissertation, University of Stellenbosch, Jul. 1990. Ager et al., "Commercial, Synthetic Nonnutritive Sweeteners," *Agnew. Chem. Int. Ed.*, 1998, 37:1802-1817.
Ager et al., "Novel biosynthetic routes to non-proteinogenic amino acids as chiral pharmaceutical intermediates," *Journal of Molecular Catalysis B: Enzymatic*, 2001, 11:199-205.
Azuma et al., "Hyper-production of L-tryptophan via fermentation with crystallization," *Appl. Microbiol. Biotechnol.*, 1993;39:471-476.
Bae et al., "Production of aromatic D-amino acids from α-keto acids and ammonia by coupling of four enzyme reactions," *Journal of Molecular Catalysis B: Enzymatic*, 1999, 6:241-247.
Bassoli, "'Chemistry-Nature,' still an open match for the discovery of new intensive sweeteners," *Agro FOOD industry hi-tech*, 2004, 15(4):27-29.

(Continued)

Primary Examiner — Tekchand Saidha

(57) ABSTRACT

Monatin and certain stereoisomers of monatin, such as R,R monatin and S,R monatin, as well as salts thereof, are produced using polypeptides and biosynthetic pathways. These polypeptides and biosynthetic pathways are also useful in the production of R-2-hydroxy-2-(indoly-3-ylmethyl)-4-keto glutaric acid, an intermediate that is formed in certain monatin synthesis pathways, including some biosynthetic pathways.

8 Claims, 13 Drawing Sheets

U.S. PATENT DOCUMENTS

| | | |
|---|---|---|
| 2007/0099277 A1 | 5/2007 | Anderson et al. |
| 2007/0105938 A1 | 5/2007 | Anderson et al. |
| 2008/0015361 A1 | 1/2008 | Khare et al. |
| 2008/0020434 A1 | 1/2008 | Brazeau et al. |
| 2008/0020435 A1 | 1/2008 | Burke et al. |
| 2008/0193984 A1 | 8/2008 | Sugiyama et al. |
| 2008/0274518 A1 | 11/2008 | Hicks et al. |
| 2009/0087829 A1 | 4/2009 | Brady et al. |
| 2009/0087888 A1 | 4/2009 | Buddoo et al. |
| 2009/0088577 A1 | 4/2009 | Buddoo et al. |
| 2009/0117625 A1 | 5/2009 | Abraham et al. |
| 2009/0130285 A1 | 5/2009 | Abraham et al. |
| 2009/0198072 A1 | 8/2009 | Khare et al. |
| 2010/0095390 A1 | 4/2010 | Weiner et al. |
| 2011/0020882 A1 | 1/2011 | De Souza et al. |
| 2011/0045547 A1 | 2/2011 | De Souza et al. |

FOREIGN PATENT DOCUMENTS

| | | |
|---|---|---|
| EP | 1 045 029 | 10/2000 |
| EP | 1 445 323 | 8/2004 |
| EP | 1 449 832 | 8/2004 |
| EP | 1 533 376 | 5/2005 |
| EP | 1 580 268 | 9/2005 |
| EP | 1 605 041 | 12/2005 |
| EP | 1 350 791 | 9/2006 |
| EP | 1 719 758 | 11/2006 |
| JP | 2002-060382 | 8/2001 |
| JP | 2003-171365 | 11/2001 |
| JP | 2004-222657 | 1/2003 |
| JP | 2004-331644 | 11/2003 |
| JP | 2004-331650 | 3/2004 |
| WO | WO 87/01130 | 2/1987 |
| WO | WO 89/11212 | 11/1989 |
| WO | WO 99/55877 | 11/1999 |
| WO | WO 03/000913 | 1/2003 |
| WO | WO 03/045914 | 6/2003 |
| WO | WO 03/056026 | 7/2003 |
| WO | WO 03/059865 | 7/2003 |
| WO | WO 03/091396 | 11/2003 |
| WO | WO 2004/018672 | 3/2004 |
| WO | WO 2004/053125 | 6/2004 |
| WO | WO2004/085624 | 10/2004 |
| WO | WO 2005/001105 | 1/2005 |
| WO | WO 2005/014839 | 2/2005 |
| WO | WO 2005/016022 | 2/2005 |
| WO | WO 2005/020721 | 3/2005 |
| WO | WO 2005/042756 | 5/2005 |
| WO | WO 2005/082850 | 9/2005 |
| WO | WO 2006/011613 | 2/2006 |
| WO | WO2006/093322 | 9/2006 |
| WO | WO 2006/113897 | 10/2006 |
| WO | WO 2006/116487 | 11/2006 |
| WO | WO 2007/103389 | 9/2007 |
| WO | WO2010/105014 | 9/2010 |
| WO | WO2010/138513 | 12/2010 |

OTHER PUBLICATIONS

Bassoli et al., "Design and synthesis of new monatin derivatives," *13th International Symposium on Olfaction and Taste (ISOT XIII) 14th. European Chemoreception Research Organization Congress (ECRO XIV)*, Jul. 20-24, 2000, p. 162, Abstract.

Bassoli et al., "General Pseudoreceptor Model for Sweet Compounds: A Semiquantitative Prediction of Binding Affinity for Sweet-Tasting Molecules," *J. Med. Chem.*, 2002, 45:4402-4409.

Bassoli et al., "Monatin and Its Stereoisomers: Chemoenzymatic Synthesis and Taste Properties," *Eur. J. Org. Chem.*, 2005, 8:1652-1658.

Bhatnagar et al., "The Broad-specificity, Membrane-bound Lactate Dehydrogenase of *Neisseria gonorrhoeae*: Ties to Aromatic Metabolism," *Journal of General Microbiology*, 1989, 135:353-360.

Bommarius et al., "Some new developments in reductive amination with cofactor regeneration," *Biocatalysis*, 1994, 10:37-47.

Bongaerts et al., "Metabolic Engineering for Microbial Production of Aromatic Amino Acids and Derived Compounds," *Metabolic Engineering*, 2001, 3:289-300.

Brandl and Lindow, "Cloning and characterization of a locus encoding an indolepyruvate decarboxylase involved in indole-3-acetic acid synthesis in *Erwinia herbicola*," *Appl. Environ. Microbiol.*, 1996, 62:4121-4128.

Camargo (Ediclea Cristina Fregonese Camargo), "Preparation of amino acids not proteinogênicos, structurally related to adoçante natural Monatina" [translated by Google], Jan. 2003, Universidade Estadual de Campinas Instituto de Quimica, Dissertation of Masters.

DeLuna et al., "NADP-Glutamate Dehydrogenase Isoenzymes of *Saccharomyces cerevisiae*: Purification, Kinetic Properties, and Physiological Roles," *J. Biol. Chem.*, 2001, 276(47):43775-43783.

Eggeling and Sahm, "Amino-acid production: principles of metabolic engineering," *Metabolic Engineering*, 1999, Lee & Papoutsakis eds., Marcel Dekker, Inc., New York.

Eikmanns et al., "Cloning, sequence analysis, expression, and inactivation of the *Corynebacterium glutamicum* icd gene encoding isocitrate dehydrogenase and biochemical characterization of the enzyme," *J. Bacteriol.*, 1995, 177:774-782.

El-Abyad and Farid, "Optimization of culture conditions for indole-3-pyruvic acid production by *Streptomyces griseoflavus*," *Can. J. Microbiol.*, 1994, 40:754-760.

Flores et al., "Pathway engineering for the production of aromatic compounds in *Escherichia coli*," *Nature Biotechnology*, 1996, 14:620-623.

Floyd et al., "A Simple Strategy for obtaining both Enantiomers from an Aldolase Reaction: Preparation of L- and D-4-Hydroxy-2-ketoglutarate," *J. Chem. Soc. Perkin Trans. 1*, 1992, 1085-1086.

Fotheringham et al., "The cloning and sequence analysis of the aspC and tyrB genes from *Escherichia coli* K12," *Biochem. J.*, 1986, 234:593-604.

Furuya et al., "A Novel Enzyme, L-Tryptophan Oxidase, from a Basidiomycete, *Coprinus* sp. SF-1: Purification and Characterization," *Biosci. Biotechnol. Biochem.*, 2000, 64(7):1486-1493.

Galkin et al., "Synthesis of optically active amino acids from alpha-keto acids with *Escherichia coli* cells expressing heterologous genes," *Appl. Environ. Microbiol.*, 1997, 63(12):4651-4656.

Gosset et al., "A direct comparison of approaches for increasing carbon flow to aromatic biosynthesis in *Escherichia coli*," *J. Industrial Microbiol.*, 1996, 17:47-52.

Hayashi et al., "*Escherichia coli* Aromatic Amino Acid Aminotransferase: Characterization and Comparison with Aspartate Aminotransferase," *Biochemistry*, 1993, 32:12229-12239.

Holzapfel et al., "A simple cycloaddition approach to a racemase of the natural sweetener monatin," *Synthetic Communications*, 1994, 24(22):3197-3211.

Holzapfel et al., "The synthesis of a gamma-keto-alpha-amino acid, a key intermediate in the synthesis of monatin, a new natural sweetener," *Synthetic Communications*, 1993, 23(18):2511-2526.

Izumi, "Introduction," *Synthetic Production and Utilization of Amino Acids*, 1974, Kankeko et al. (eds.), Halstad Press, Chapter 1, pp. 3-16.

Jetten et al., "Metabolic Engineering of *Corynebacterium glutamicum*," *Ann. N. Y. Acad. Sci.*, 1994, 721:12-29.

Jetten et al., "Recent advances in the physiology and genetics of amino acid-producing bacteria," *Critical Reviews in Biotechnology*, 1995, 15:73-103.

Juhl et al., "Catalytic asymmetric homo-aldol reaction of pyruvate—a chiral Lewis acid catalyst that mimics aldolase enzymes," *Chem. Commun.*, 2000, 2211-2212.

Katsumata et al., "Hyperproduction of Tryptophan in *Corynebacterium glutamicum* by Pathway Engineering," *Bio/Technology*, 1993, 11:921-925.

Kawasaki et al., "L-Tryptophan Production by Pyruvic Acid-Producing *Escherichia coli* Strain Carrying the *Enterobacter aerogenes* Tryptophanase Gene," *Journal of Fermentation and Bioengineering*, 1996, 82(6):604-606.

Kino et al., "Synthesis of DL-tryptophan by modified broad specificity amino acid racemase from *Pseudomonas putida* IFO 12996," *Applied Microbiology and Biotechnology*, 2007, 73(6):1299-1305.

Koeller et al., "Enzymes for chemical synthesis," *Nature*, 2001, 409:232-240.

Koffas et al., "Engineering metabolism and product formation in *Corynebacterium glutamicum* by coordinated gene overexpression," *Metabolic Engineering*, 2003, 5:32-41.

Koga et al., "Involvement of L-tryptophan aminotransferase in indole-3-acetic acid biosynthesis in *Enterobacter cloacae*," *Biochim. Biophys. Acta*, 1994, 1209:241-247.

Kogiso et al., "Control of Lactamization during the Synthesis of the Monatin Analogue," *Peptide Science*, 2003, pp. 195-198.

Labrou et al., "Oxaloacetate Decarboxylase from *Pseudomonas stutzeri*: Purification and Characterization," *Archives of Biochemistry and Biophysics*, 1999, 365(1):17-24.

Li et al., "Nonproteinogenic alpha-Amino Acid Preparation Using Equilibrium Shifted Transamination," *Organic Process Research & Development*, 2002, 6:533-538.

Liao et al., "Pathway Analysis, Engineering, and Physiological Considerations for Redirecting Central Metabolism," *Biotechnology and Bioengineering*, 1996, 52:129-140.

Nakamura et al., "Total Synthesis of Monatin," *Organic Letters*, 2000, 2(19):2967-2970.

Nakamura et al., "Total Synthesis of Monatin and the Taste Experience," *Peptide Science*, 2003, pp. 61-64.

Nishihara and Dekker, "A stereospecific 2-keto-4-hydroxyglutarate aldolase from *Escherichia coli*," *Biochim Biophys. Acta*, 1969, 185(1):255-257.

Oliveira et al., "Highly diastereoselective alkylation of a pyroglutamate derivative with an electrophile obtained from indole. Synthesis of a potential intermediate for the preparation of the natural sweetener (-)-monatin," *Synthetic Communications*, 2000, 30(12):2143-2159.

Oliveira et al., "Diastereoselective formation of a quaternary center in a pyroglutamate derivative. Formal synthesis of Monatin," *Tetrahedron Letters*, 2001,42:6793-6796.

Passerat et al., "Large-scale enzymatic synthesis of diastereoisomeric γ-hydroxy 1-glutamic acids," *Tetrahedron Letters*, 1987, 28(12):1277-1280.

Patil et al., "Cloning, nucleotide sequence, overexpression, and inactivation of the *Escherichia coli* 2-keto-4-hydroxyglutarate aldolase gene," *J. Bacteriol.*, 1992, 174(1):102-107.

Patnaik et al., "Engineering of *Escherichia coli* Central Metabolism for Aromatic Metabolite Production with Near Theoretical Yield," *Applied and Environmental Microbiology*, 1994, 60(11):3903-3908.

Rijnen et al., "Genetic Characterization of the Major Lactococcal Aromatic Aminotransferase and Its Involvement in Conversion of Amino Acids to Aroma Compounds," *Applied Environmental Biology*, 1999, 65(11):4873-4880.

Ro et al., "Site-directed mutagenesis of the amino acid residues in beta-strand III [Val30-Val36] of D-amino acid aminotransferase of *Bacillus* sp. Ym-1," *FEBS Lett.*, 1996, 398:141-145.

Roise et al., "Inactivation of the *Pseudomonas striata* broad specificity amino acid racemase by D and L isomers of beta-substituted alanines: kinetics, stoichiometry, active site peptide, and mechanistic studies," *Biochemistry*, 1984, 23:5195-5201.

Shelton et al., "2-Keto-3-deoxy-6-phosphogluconate Aldolases as Catalysts for Stereocontrolled Carbon-Carbon Bond Formation," *J. Am. Chem. Soc.*, 1996, 118(9):2117-2125.

Sugio et al, "Crystal structure of a D-amino acid aminotransferase: how the protein controls stereoselectivity," *Biochemistry*, 1995, 34:9661-9669.

Tamura et al., "Highly stereoselective synthesis of (-)-monatin, a high-intensity sweetener, using chelation-controlled nitrone cycloaddition," *Chemical Communications*, 2003, 21:2678-2679.

Tamura et al., "Stereoselective Synthesis of 4-Hydroxy 4-Substituted Glutamic Acids," *J. Org. Chem.*, 2005, 70(12):4569-77.

Tanizawa et al., "Thermostable D-amino acid aminotransferase from a thermophilic *Bacillus* species. Purification, characterization, and active site sequence determination," *J. Biol. Chem.*, 1989, 264:2445-2449.

Vleggaar et al., "Structure elucidation of monatin, a high-intensity sweetener isolated from the plant *Schlerochiton ilicifolius*," *J. Chem. Soc. Perkin Transactions 1: Organic and Bio-Organic Chemistry (1972-1999)*, 1992,22:3095-3098.

Wolf et al., "A Biocatalytic Route to Enantiomerically Pure Unsaturated -H—Amino Acids," *Adv. Snyth. & Catalysis*, 2001, 343:662-674.

Yonaha et al., "D-Amino Acid Aminotransferase of *Bacillus sphaericus*," *J. Biol. Chem.*, 250(17):6983-6989.

Yoshimura et al., "Unique stereospecificity of D-amino acid aminotransferase and branched-chain L-amino acid aminotransferase for C-4' hydrogen transfer of the coenzyme," *J. Am. Chem. Soc.*, 1993, 15:3897:3900.

Yoshimura and Esaki, "Amino Acid Racemases: Functions and Mechanisms," *J. Biosci. Bioeng.*, 2003, 96:103-109.

Zeman et al., "Enzyme Synthesis of L-Tryptophan," *Folia Microbiol.*, 1990, 35:200-204.

GenBank Accession No. AAP44215 dated Aug. 16, 2004.

GenBank Accession No. P10724 dated Jun. 16, 2009.

Kishimoto et al., "Mutation of arginine 98, which serves as a substrate-recognition site of D-amino acid aminotransferase, can be partly compensated for by mutation of tyrosine 88 to an arginyl residue," *J. Biochem.*, 1997, 122(6):1182-1189.

Authorized Officer Agnes Wittmann-Regis, International Preliminary Report on Patentability, PCT/US2007/81932 mailed Apr. 30, 2009, 10 pages.

Authorized Officer Nashaat T. Nashed, International Preliminary Examination Report, PCT/US06/15930 mailed Jul. 13, 2009, 8 pages.

Buldain et al., "Carbon-13 Nuclear Magnetic Resnoance Spectra of the Hydrate, Keto, and Enol Forms of Oxalacetic Acid," *Magnetic Resonance Chemistry*, 1985, 23(6):478-481.

Guo et al., "Protein tolerance to random amino acid charge," *Proc. Natl. Acad. Sci. USA*, 2004, 101(25):9205-9210.

Seffernick et al., "Melamine deaminase and atrazine chlorohydrolase: 98 percent identical but functionally different," *J. Bacteriology*, 2001, 183(8):2405-2410.

Seo Jeong-Sun et al., "The genome sequence of the ethanologenic bacterium *Zymomonas mobilis* ZM4," *Nature Biotechnology*, 2005, 23(1):63-68.

Whisstock et al., "Prediction of protein function from protein sequence," *Q. Rev. Biophysics*, 2003, 36(3):307-340.

Witkowski et al., "Conversion of b-ketoacyl synthase to a malonyl decarboxylase by replacement of the active-site cysteine with glutamine," *Biochemistry*, 1999, 38:11643-11650.

Broun et al., "Catalytic plasticity of fatty acid modification enzymes underlying chemical diversity of plant lipids", *Science* 1998, 282:1315-1317.

Chica et al., "Semi-rational approaches to engineering enzyme activity: combining the benefits of directed evolution and rational design", *Current Opinion in Biotechnology*, 2005, 16:378-384.

Devos et al., "Practical limits of function prediction", *PROTEINS: Structure, Function and Genetics*, 2000, 41:98-107.

Koshiba et al., "L- and D-Tryptophan Aminotransferases from Maize Coleoptiles", *J. Plant Res*, 1993, 106:25-29.

Moriya et al., "A facile synthesis of 6-chloro-D-tryptophan", *Bulletin of the Chemical Society of Japan*, 1975, vol. 48,: 2217-2218 (abstract).

"EC 2.6.1.27—tryptophan transaminase" Brenda the Comprehensive Enzyme Information System, [Online] Retrieved from the Internet: http://www.brenda-enzymes.org/php/result_ flat.php4?ecno=2.6.1.27 [retrieved on Jul. 16, 2011].

Berger et al; "Methionine Regeneration and Aminotransferases in *Bacillus subtilis*, *Bacillus cereus*, and *Bacillus anthracis*." Journal of Bacteriology; Apr. 2003; vol. 185, No. 8.

\* cited by examiner

BsphDATgene     1  mays---lwndqive--egsitispedrgyqfgdgiyevikvynghmfta
B. halodurans   1  mdyc---lyqdqlvp--reqlkidpedrgyhfgdgiyevvhvyhgkafal
GsteDATgene     1  mgyt---lwndqivk--deevkidkedrgyqfgdgvyevvkvyngemftv
B.cereus 145    1  layekfvlwndevidttkqqtyieleergsqfgdgvyevirlykgnfhll
BsubDAT         1  -mkv---lvngrlig--rseasidledrgyqfgdgiyevirvykgvlfgl
B.lichenifomis  1  -mkv---lfngrlme--rsecavdiedrgyqfgdgvyeviriyngilftl BsphDATgene    136 qehidrfyasaekirlvipytkdvlhkllhdlieknnlnt-ghvyfqitr
B. halodurans  136 sdhltrfkesaekldlpmlystdklgelvqqlieknkleh-gmvyfqmtr
GsteDATgene    136 nehidrlyasaekiritipytkdkfhqllhelveknelnt-ghiyfqvtr
B.cereus 145   151 dphitrlyrsmeevelslpfskaelitllykliernhfhedgtiylqvsr
BsubDAT         45 rehaerffrsaaeigislpfsiedlewdlqklvqenavse-gavyiqttr
B.lichenifomis 133 dehiarlyksaaeigidlsfseaelksqlkelvdinqrrd-gglylqvtr
                                                                    ←
BsphDATgene    283 gttsrnhifpdasvpavl--tgnvktgersienfekgvkatlvedvrwlr
B. halodurans  283 gisprnhlytrnetp-vl--tgfskp---lpdekresvrlyltddirwlr
GsteDATgene    283 gtsprahqfpentvkpvi--igytkenprplenlekgvkatfvedirwlr
B.cereus 145   301 gvqarthvf-sydtppti--yayitkkerpalwieygiraisepdtrwlr
BsubDAT         94 gvaprkhqy-eaglepqt--taytftvkkpeqeqaygvaaitdedlrwlr
B.lichenifomis 280 gkaprkhqygagltpqvtaytfpiqkpekeqqn---gvsaitaddmrwlr R1
                        -----    R2
                                ←------                            ←
BsphDATgene    427 cdikslnllgavlakqeasekgcyeailhrgdiitecssanvygikdgkl
B. halodurans  415 cdiktinllgnvlakreatdhqcdeallhrdgtvtegsssnvfliknetl
GsteDATgene    427 cdikslnllgavlakqeahekgcyeailhrnntvtegsssnvfgikdgil
B.cereus 145   442 cdikslnllpnvlaatkaerkgckeallvrngivtegshsnffliknqtl
BsubDAT        141 cdikslnllynvmtkqrayeagafeaillrdgvvtegtssnvyavingtv
B.lichenifomis 421 cdikslnllynvmikqkaqeasafeailirdglvtegtssnvyvakqnvi
```

FIG. 9B

```
                    R3
                    ------
BsphDATgene     577 ythpannyilngitrqvilkcaaeinlpvieepmtkgdlltmdeiivssv
B. halodurans   565 ythpatnlilngitrqitirlakakgytvveepfpkevikdadeafitst
GsteDATgene     577 ythpannmilkgitrdvviacaneinmpvkeipftthealkmdelfvtst
B.cereus 145    592 ythpanhlilngiirqyvlslantlhipvqeelfsvrdvyqadecfftgt
BsubDAT         191 rthpanrlilngitrmnilgliekngikldetpvseeelkqaeeifisst
B.lichenifomis  571 ythpvttlilngitrmkvlqlceenglnyeekavtkdellnadevfitst BsphDATgene     727 ssevtpvidvdgqqigagvpgewtrklqkafeaklp--isina*----
B. halodurans   715 iheitpvtevigdetahfpvgpvtkmlqqafaeeia--khsqtamkq*
GsteDATgene     727 tseitpvieidgklirdgkvgewtrklqkqfetkip--kplhi*----
B.cereus 145    742 tieilpmthldgtaiqdgqvgaitkklqksfn-kil--lqsnmsss*-
BsubDAT         241 taeiipvvtldgqsigsgkpgpvtkqlqaafqesiqqaasis------
B.lichenifomis  721 taevipvtsidgqtigsgapgpltknvqtalqnsi---lsetaktv*-
```

FIG. 10A

**Alignment of *B. sphaericus* with ATCC 4978 (*B. rotans*) sequence (72% homology)**

```
BsphDATgene    1   mayslwndqiveegsitispedrgyqfgdgiyevikvynghmftagehid
ATCC4978DAAT   1   msyslwndqivndeevvvdkedrgyqfgdgvyevvkvyngelftaeehvd BsphDATgene    151 rfyasaekirlvipytkdvlhkllhdlieknnlntghvyfqitrgttsrn
ATCC4978DAAT   151 rfyasaekirvtipytkdklhgllhglvemnkvgtghiyfqitrgagprn BsphDATgene    301 hifpdasvpavltgnvktgersienfekgvkatlvedvrwlrcdikslnl
ATCC4978DAAT   301 hifpgdevkpvltgntkenprpvanfekgvkatfvedirwlrcdikslnl BsphDATgene    451 lgavlakqeasekgcyeailhrgdiitecssanvygikdgklythpanny
ATCC4978DAAT   451 lgavlakqeahekgcyeavlhrdeivtegsssniygikdgvlythpannf BsphDATgene    601 ilngitrqvilkcaaeinlpvieepmtkgdlltmdeiivssvssevtpvi
ATCC4978DAAT   601 ilngitrqviikcaaeiglpvkeeamtktgllamdevivssttsevtpii BsphDATgene    751 dvdgqqigagvpgewtrklqkafeaklpisina*
ATCC4978DAAT   751 didgtvigagkpgdwtrklqaqfdtkipkgira*
```

FIG. 10B

**Alignment of *B. sphaericus* with ATCC 7063 (*B. serositidis*) sequence (67% homology)**

```
BsphDAATpep      1  mayslwmdqiveegsitispedrgyqfgdgiyevikvynghmftaqehid
ATCC7063DAAT     1  msytlwndkivddngvfinkedrgyqfgdgvyevikvydgemftatehid BsphDAATpep     51  rfyasaekirlvipytkdvlhkllhdlieknnlntghvyfqitrgttsrn
ATCC7063DAAT   151  rfyasaekikltvpytkhklhgllhelveanelktgnlyfqitrgasprn BsphDAATpep    101  hifpdasvpavltgnvktgersienfekgvkatlvedvrwlrcdikslnl
ATCC7063DAAT   301  hlfpgddvlpvltgnvkeaprsienagkgvkatfaedirwlrcdikslnl BsphDAATpep    151  lgavlakqeasekgcyeailhrgdiitecssanvygikdgklythpanny
ATCC7063DAAT   451  lgavlakqeahekgcyeailhrgetitegsstnvfgikngvlythpadnf BsphDAATpep    201  ilngitrqvilkcaaeinlpvieepmtkgdlltmdeiivssvssevtpvi
ATCC7063DAAT   601  ilggitrgvvlacaneiglpvkgeaftkdkalgmdemfvssttseitpvi BsphDAATpep    251  dvdgqqigagvpgewtrklqkafeaklpis--ina-----
ATCC7063DAAT   751  dldgvainggeigewtrklqkqfatklpgspaynlteyk*
```

POLYPEPTIDES AND BIOSYNTHETIC PATHWAYS FOR THE PRODUCTION OF STEREOISOMERS OF MONATIN AND THEIR PRECURSORS

CROSS-REFERENCE TO RELATED APPLICATION

This application is a continuation-in-part of U.S. application Ser. No. 11/584,016, filed Oct. 20, 2006, now abandoned which is a continuation-in-part of U.S. application Ser. No. 11/411,229, filed Apr. 26, 2006, now U.S. Pat. No. 7,582,455 which claims the benefit of U.S. Provisional Application No. 60/674,932, filed Apr. 26, 2005.

BACKGROUND OF THE INVENTION

1. Field of the Invention

This disclosure provides polypeptides and biosynthetic pathways that are useful in the production of D-tryptophan, indole-3-pyruvate, R-2-hydroxy-2-(indol-3ylmethyl)-4-keto glutaric acid (R-MP) and certain stereoisomers of monatin, such as R,R and S,R monatin, and salts thereof.

2. Background Art

Monatin is a high-intensity sweetener having the chemical formula:

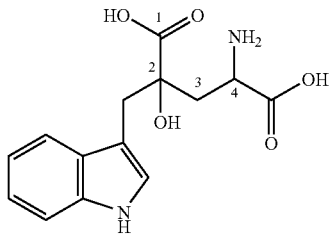

Monatin includes two chiral centers leading to four potential stereoisomeric configurations. The R,R configuration (the "R,R stereoisomer" or "R,R monatin"); the S,S configuration (the "S,S stereoisomer" or "S,S monatin"); the R,S configuration (the "R,S stereoisomer" or "R,S monatin"); and the S,R configuration (the "S,R stereoisomer" or "S,R monatin"). As used herein, unless stated otherwise, the term "monatin" is used to refer to compositions including all four stereoisomers of monatin, compositions including any combination of monatin stereoisomers, (e.g., a composition including only the R,R and S,S, stereoisomers of monatin), as well as a single isomeric form.

For purposes of this disclosure, the monatin carbon backbone will be numbered as illustrated above, with the carbon directly covalently attached to the alcohol group being identified as the 2-position carbon and the carbon directly covalently attached to the amino group being identified as the 4-position carbon. Consequently, references herein to R,R monatin, S,S monatin, R,S monatin, and S,R monatin mean: 2R,4R monatin, 2S,4S monatin, 2R,4S monatin, and 2S,4R monatin, respectively, unless otherwise indicated.

It should be noted that in the literature, the monatin carbon backbone has also been numbered using an alternative convention, with the carbon attached to the alcohol group being the 4-position carbon, and the carbon attached to the amino group being the 2-position carbon. Accordingly, for example, references to 2S,4R monatin in this disclosure would be the same as references to 2R,4S monatin in literature using the alternative numbering convention.

Furthermore, because of various naming conventions, monatin is known by a number of alternative chemical names, including: 2-hydroxy-2-(indol-3-ylmethyl)-4-aminoglutaric acid; 4-amino-2-hydroxy-2-(1H-indol-3-ylmethyl)-pentanedioic acid; 4-hydroxy-4-(3-indolylmethyl)glutamic acid; and, 3-(1-amino-1,3-dicarboxy-3-hydroxy-but-4-yl)indole.

Certain isomeric forms of monatin can be found in the bark of roots of the *Schlerochiton ilicifolius* plant located in the Transvaal Region of South Africa. U.S. patent application Ser. No. 10/422,366 ("the '366 application"), Ser. No. 10/979,821 ("the '821 Application"), and Ser. No. 11/114,922 ("the '922 application), which are hereby incorporated by reference, discloses, inter alia, polypeptides, pathways, and microorganisms for in vitro and in vivo production of monatin.

BRIEF SUMMARY OF THE INVENTION

This disclosure provides, among other things, polypeptides and biosynthetic pathways that are useful in the production of D-tryptophan, indole-3-pyruvate, R-2-hydroxy 2-(indol-3ylmethyl)-4-keto glutaric acid (also referred to as R-alpha keto acid monatin, R-monatin precursor, R-MP, and the alpha keto form of monatin) and certain stereoisomers of monatin, such as R,R and S,R monatin, and salts thereof. The methods include the use of one or more polypeptides, and in particular, enzymes, such as racemases (e.g., glutamate racemases, aspartate racemases and alanine racemases), broad specificity D-aminotransferases (also called D-alanine aminotransferases, D-amino acid aminotransferases and D-aspartate aminotransferases), L-aminotransferases (including L-tryptophan-aminotransferases, L-aromatic aminotransferases, L-aspartate aminotransferases, and L-alanine-aminotransferases), aldolases (e.g., R-specific aldolases), D-phenylglycine aminotransferases (also called D-4-hydroxyphenylglycine aminotransferase), D-methionine aminotransferases, glutamate decarboxylases, aspartate decarboxylases and aspartate-4-decarboxylases to produce monatin compositions enriched with the 4-R isomer forms and/or to produce R,R monatin without having to use stoichiometric amounts of D-amino acid substrate as the amino acid donor for MP amination.

In an effort to be concise, wherever intermediates/products are identified in the specification and claims (e.g. monatin or monatin precursor) as being formed, the term "and/or salts thereof" should be understood to be included where applicable. In other words, for example, the phrase "indole-3-pyruvate is converted to MP" should be understood to read "indole-3-pyruvic acid is converted to MP and/or salts thereof." A person of ordinary skill, in fact, would appreciate that under reaction conditions shown the salts of the intermediates/products are in fact present or also present.

According to some embodiments, the method produces a monatin composition wherein the monatin component of the composition includes only the R,R and S,R form of monatin. The term "only," when used to indicate that only certain isomers are formed, unless otherwise stated means that the pathway would produce only the identified isomers if racemization did not occur. Consequently, the term "only" should not be taken to mean absence of other isomers, but rather a person of ordinary skill would understand that other isomeric forms may be present in a relatively small amount due to racemization which may occur. According to some embodiments, the method produces a monatin composition wherein the monatin component of the composition includes only the R,R form of monatin (thus meaning except to the extent racemization occurs resulting in other isomeric forms).

As used herein, the phrase "monatin composition" means a composition including one or more isomers of monatin; the term can also mean a composition including only a single isomeric form of monatin and nothing else, depending on the context.

In some embodiments, in accordance with the present invention, a process for producing a monatin composition is provided, which includes producing indole-3-pyruvate from L-tryptophan, producing 2-hydroxy 2-(indol-3ylmethyl)-4-ketoglutaric acid ("monatin precursor" or "MP") from indole-3-pyruvate, and producing monatin from MP. The reaction of L-tryptophan to produce indole-3-pyruvate is facilitated by an enzyme having greater specificity, greater activity, or both for L-tryptophan as a substrate than for R-MP, R,R monatin, or both. According to certain embodiments, the reaction of indole-3-pyruvate is facilitated by an enzyme having R-specific aldolase activity and consequently produces R-MP. According to certain embodiments, a racemase enzyme is provided that can facilitate epimerization of the amino acid that is formed as a byproduct of the L-tryptophan transamination reaction (or that is formed from another amino acid that is a byproduct of the tryptophan reaction) from one isomeric form to another isomeric form.

In some embodiments according to the invention, a process for producing a monatin composition is provided, which includes producing indole-3-pyruvate from L-tryptophan, producing 2-hydroxy 2-(indol-3ylmethyl)-4-keto glutaric acid ("monatin precursor" or "MP") from indole-3-pyruvate, and producing monatin from MP. The reaction of L-tryptophan to produce indole-3-pyruvate is facilitated by an enzyme having greater specificity, greater activity, or both for L-tryptophan as a substrate than for R-MP, R,R monatin, or both, and the reaction of MP to form monatin is facilitated by an enzyme, which is stereoselective for R-MP.

It should be noted that, where references are made to a series of reactions such as in the preceding paragraphs, the invention does not require each step to be explicitly performed; it is sufficient that the steps may be implicitly performed. In other words, for example, the process for producing a monatin composition, which includes producing indole-3-pyruvate from L-tryptophan, producing 2-hydroxy 2-(indol-3ylmethyl)-4-keto glutaric acid ("monatin precursor" or "MP") from indole-3-pyruvate, and producing monatin from MP, wherein each reaction is facilitated by an appropriate enzyme, can be performed by combining L-tryptophan with the enzymes and setting conditions so that the enumerated reactions could occur. In such an instance L-tryptophan could react to produce indole-3-pyruvate, the indole-3-pyruvate produced from the L-tryptophan reaction could react to form MP, and the MP produced from the indole-3-pyruvate reaction could react to form monatin. The process could also be performed, by way of example, by providing a compound that can produce L-tryptophan, under conditions suitable for L-tryptophan production to occur and combining that compound with enzymes capable of facilitating the series of reactions set forth under conditions which would be suitable for those reactions to occur. As yet another example, the process could be performed by providing a microorganism genetically engineered to produce monatin according to the described pathway, and providing appropriate conditions for the fermentation process to occur. For example, a microorganism, which naturally produces large amounts of L-tryptophan (or D-tryptophan) could be genetically engineered to produce or over-produce one or more of the enzymes used to facilitate reactions in the pathway to monatin, and appropriate conditions could be provided so that the microorganism would thereby produce monatin.

In other embodiments according to the invention, a process for producing monatin is provided, in which an α-keto acid substrate forms an L-amino acid when L-tryptophan is converted to indole-3-pyruvate, indole-3-pyruvate reacts to form MP (which can include both R-MP and S-MP though preferably includes only or predominately R-MP), and the L-amino acid reacts to regenerate (also referred to as "recycle") the α-keto acid substrate when R-MP is converted to R,R monatin. The reaction of R-MP to form R,R monatin is facilitated by a stereoinverting aminotransferase such as D-methionine aminotransferase (EC 2.6.1.41) or an enzyme derived from a D-phenylglycine aminotransferase.

In other embodiments according to the invention, a process for producing a monatin composition is provided, which includes producing D-tryptophan from L-tryptophan, producing indole-3-pyruvate from D-tryptophan, producing R-MP from indole-3-pyruvate, and producing R,R monatin from R-MP. The production of the D-tryptophan from the L-tryptophan is facilitated by a tryptophan racemase and functional equivalents thereof. In certain further embodiments, the reactions of D-tryptophan to form indole-3-pyruvate and of MP to form monatin are facilitated by the same enzyme. In yet other further embodiments, the reaction of indole-3-pyruvate is facilitated by an enzyme having R-specific aldolase activity and consequently R-MP is formed, and the reactions of D-tryptophan to form indole-3-pyruvate and of R-MP to form R,R monatin are facilitated by the same enzyme.

In other embodiments according to the invention, a method for producing R,R-monatin, or a salt thereof, comprising, or consisting essentially of, (a) producing D-tryptophan from L-tryptophan utilizing a tryptophan racemase (the racemase should have limited or no activity on monatin), (b) producing indole-3-pyruvate from D-tryptophan, (c) producing R-monatin precursor from indole-3-pyruvate, and (d) producing R,R-monatin from R-monatin precursor is disclosed herein.

While multiple embodiments are disclosed, still other embodiments of the present invention may become apparent to those skilled in the art from the specification. As should be realized from the description herein, the invention is capable of modifications in various aspects, all without departing from the spirit and scope of the present invention. Accordingly, the drawings and detailed description are to be regarded as illustrative in nature and not restrictive.

R-MP is reacted in a reversible manner with a D-aminotransferase and D-alanine to form R,R monatin and pyruvate. An L-alanine aminotransferase and pyruvate are used to reversibly convert the L-glutamate that was a product of the L-aminotransferase reaction back to α-KG, with L-alanine as a co-product. An alanine racemase reversibly converts the L-alanine to the D-alanine that is useful in the third reaction, (the D-aminotransferase reaction. For the purposes of the invention, it is not required that the reactions shown as being reversible proceed in the reverse direction.

FIG. 9(A and B) show the amino acid sequence alignment of various published *Bacillus* D-amino acid aminotransferases ("DAATs"). Underlined amino acids indicate the regions of homology. Five PCR primers were designed based on the conserved regions. The PCR primers are as follows: 5'-GAAGACCGTGGTTATCAATTT-3' (SEQ ID NO:65) (forward primer, F1 as indicated in FIG. 9A), 5'-GATGG-TATTTACGAAGTAATC-3' (SEQ ID NO:66) (forward primer, F2 as indicated in FIG. 9A), 5'-AGATTTAATATCA-CAACGTAAC-3' (SEQ ID NO:67) (reverse primer, R1 as indicated in FIG. 9A), 5'-GCCAAGTAAAATTTAA-GATTTA-3' (SEQ ID NO:68) (reverse primer, R2 as indicated in FIG. 9A), 5'-ATTTGCTGGGTGCGTATAAAG-3' (SEQ ID NO:69) (reverse primer, R3 as indicated in FIG. 9B). The D-amino acid aminotransferase encoded by the Bsph-DATgene is SEQ ID NO:205, the D-amino acid aminotransferase of *B. halodurans* is SEQ ID NO:206, the D-amino acid aminotransferase encoded by the GsteDATgene is SEQ ID NO:207, the D-amino acid aminotransferase of *B. cereus* 145 is SEQ ID NO:208; the BsubDAT is SEQ ID NO:209, and the D-amino acid aminotransferase of *B. lichenifomis* is SEQ ID NO:210.

FIG. 10(A and B) show the amino acid sequence alignment of the two novel DAATs: one from ATCC 4978 (*B. rotans*, FIG. 10A; SEQ ID NO:211) and one from ATCC 7063 (*B. serositidis*, FIG. 10B (SEQ ID NO:212) with the *B. sphaericus* DAAT (SEQ ID NO:205 and SEQ ID NO:213) cloned in Example 18. Non-homologous amino acids are underlined.

Figure 11:
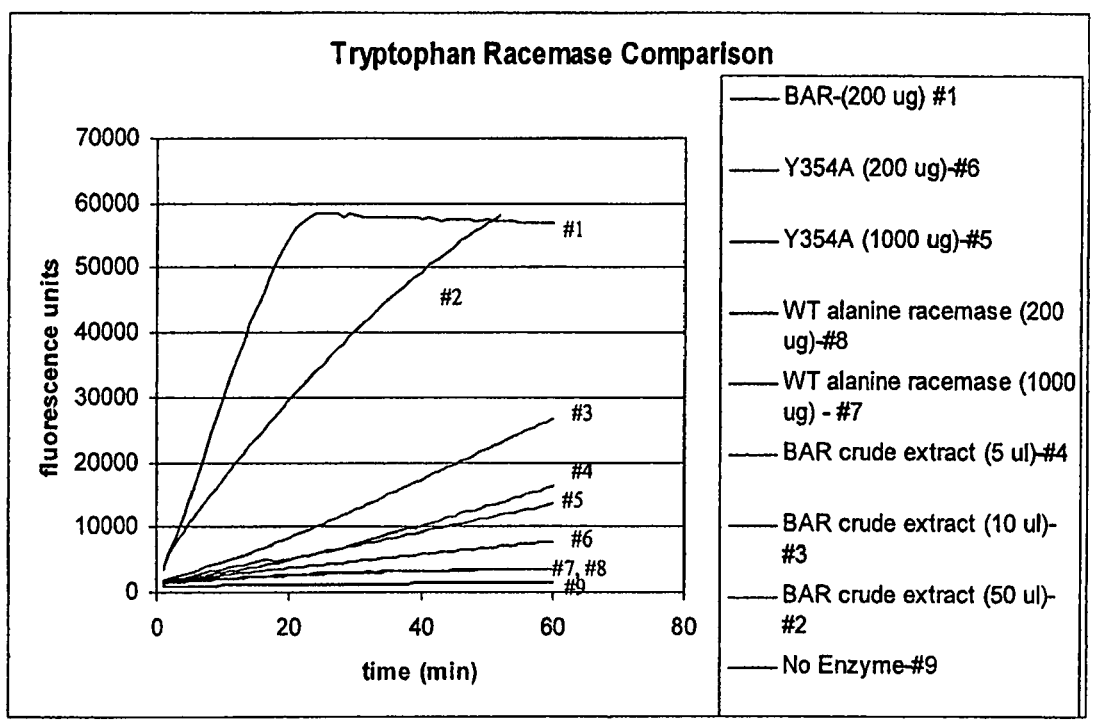

FIG. 11 shows the tryptophan racemization assay results of the broad specificity amino acid racemase ("BAR") compared with an alanine racemase from *G. stearothermophilus* and a mutant thereof (Y354A). The racemase preparations compared were (#1) BAR-200 µg (#2) BAR crude extract-50 µL; (#3) BAR crude extract-10 µL; (#4) BAR crude extract-5 µL; (#5) Y354A-1000 µg; (6) Y354A-200 µg; (#7) wild-type (WT) alanine racemase-1000 µg; (#8) wild-type (WT) alanine racemase-200 µg; (9) no enzyme.

DETAILED DESCRIPTION OF THE INVENTION

Abbreviations and Terms

The following explanations of terms and methods are provided to better describe the present disclosure and to guide those of ordinary skill in the art in the practice of the present disclosure. As used herein, "including" means "comprising." Wherever the term "includes" is used, it should be understood that "includes but is not limited to" is meant, whether or not "is limited to" is explicitly stated. In addition, the singular forms "a" or "an" or "the" include plural references unless the context clearly dictates otherwise. For example, reference to "comprising a protein" includes one or a plurality of such proteins, and reference to "comprising the cell" includes reference to one or more cells and equivalents thereof known to those skilled in the art, and so forth. The term "about" encompasses the range of experimental error that occurs in any measurement. Unless otherwise stated, all measurement numbers are presumed to have the word "about" in front of them even if the word "about" is not expressly used.

Conservative substitution: a substitution of one amino acid for another amino acid in a polypeptide, which substitution has little to no impact on the activity of the polypeptide. The substitution is considered conservative independent of whether the exchanged amino acids appear structurally or functionally similar. For example, ideally, a tryptophan aminotransferase polypeptide including one or more conservative substitutions retains tryptophan aminotransferase activity. A polypeptide can be produced to contain one or more conservative substitutions by manipulating the nucleotide sequence that encodes that polypeptide using, for example, standard procedures such as site-directed mutagenesis or PCR or other methods known to those in the art.

Non-limiting examples of amino acids that may be substituted for an original amino acid in a protein and that may be regarded as conservative substitutions if there is little to no impact on the activity of the polypeptide include: ala substituted with ser or thr; arg substituted with gln, his or lys; asn substituted with glu, gln, lys, his or asp; asp substituted with asn, glu or gln; cys substituted with ser or ala; gln substituted with asn, glu, lys, his, asp or arg; glu substituted with asn, gln lys or asp; gly substituted with pro; his substituted with asn, lys, gln, arg or tyr; ile substituted with leu, met, val or phe; leu substituted with ile, met, val or phe; lys substituted with asn, glu, gln, his or arg; met substituted with ile, leu, val or phe; phe substituted with trp, tyr, met, ile or leu; ser substituted with thr or ala; thr substituted with ser or ala; trp substituted with phe or tyr; tyr substituted with his, phe or trp; and val substituted with met, ile or leu.

Further information about conservative substitutions can be found in, among other locations, Ben-Bassat et al., *J. Bacteriol.* 169:751-757, (1987); O'Regan et al., *Gene* 77:237-251, (1989); Sahin-Toth et al., *Protein Sci.* 3:240-247, (1994); Hochuli et al., *Bio/Technology* 6:1321-1325, (1988); WO 00/67796 (Curd et al.) and in standard textbooks of genetics and molecular biology.

Derived: For purposes of the specification and claims, a substance is "derived" from an organism or source if any one or more of the following are true: 1) the substance is present in the organism/source; 2) the substance is removed from the native host; or, 3) the substance is removed from the native host and is evolved, for example, by mutagenesis.

Isolated: The term "isolated" as used herein refers to any substance removed from its native host; the substance need not exhibit any specific degree of purity. For example "isolated nucleic acid" refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid because non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

A nucleic acid existing among hundreds to millions of other nucleic acid molecules within, for example, cDNA or genomic libraries, or gel slices containing a genomic DNA restriction digest is not to be considered an isolated nucleic acid.

Fragment: A "fragment" as used herein with regard to a protein or polypeptide or nucleic acid is a portion of the protein, polypeptide or nucleic acid, respectively. Fragments can have the same or substantially the same amino acid or nucleic acid sequence as the longer protein, polypeptide or nucleic acid sequence from which the fragment is derived. Fragments which have different three dimensional structures as compared to that of the longer protein, polypeptide or nucleic acid are also included. An example of this, is a "pro-form" molecule, such as a low activity proprotein that can be modified by cleavage to produce a mature enzyme with significantly higher activity. A fragment of a protein or polypeptide can be an enzymatically active portion of a protein or polypeptide.

Purified: The term "purified" as used herein indicates that contaminants have been removed from the sample of interest. The term "purified" does not require absolute purity, but rather is intended as a relative term, unless otherwise indicated by the context. Thus, for example, a purified polypeptide or nucleic acid preparation can be one in which the subject polypeptide or nucleic acid is at a higher concentration than the polypeptide or nucleic acid would be in its natural environment within an organism or at a higher concentration than in the environment from which it was removed.

Stereoinverting aminotransferase: A "stereoinverting aminotransferase" is a polypeptide capable of preferentially or selectively producing a chiral amino acid product (such as monatin) while using an opposite chirality substrate as the amino donor. For example, a stereoinverting aminotransferase may be a D-phenylglycine aminotransferase (also called D-4-hydroxyphenylglycine aminotransferase) that preferentially or selectively uses L-glutamate as a substrate to produce R,R monatin. Non-limiting examples of stereoinverting aminotransferases include D-methionine aminotransferase (EC 2.6.1.41) and enzymes having D-phenylglycine aminotransferase activity or D-4-hydroxyphenylglycine aminotransferase activity.

Complementing Gene: A "complementing gene" is a gene that, when expressed, nullifies a mutation in an organism. For example, if an organism has a null mutation in one of the genes required for synthesis of tryptophan by the cell, a complementing gene could be one that, when expressed, allows the strain to grow on minimal medium (i.e., without tryptophan).

Stereoselective Enzyme: A "stereoselective enzyme" is an enzyme that has greater specificity and/or greater activity for one stereoisomer, as compared to the specificity and/or activity for another stereoisomer. For example, a stereoselective enzyme is one that has greater specificity and/or activity for R-MP than for S-MP. In preferred embodiments, a stereoselective enzyme has limited activity for one stereoisomer as compared to another. "Limited" activity means activity that is minimally or not perceptible, for example as determined according to experiments provided herein. Example 6, for example, identifies HEXAspCP9T/R122G as an enzyme with limited activity on S,S monatin. Example 8 identifies the *S. meliloti* TatA as another enzyme with limited activity for S-MP. In Example 18, the *B. halodurans* D-aminotransferase had higher selectivity for R-MP as compared with S-MP, resulting in higher stereopurity of R,R monatin. Also, Example 19 indicates that the hybrid DAT has limited activity on S-MP compared to R-MP.

Homolog: The term "homolog" as used herein indicates that a protein or a nucleic acid exhibits a relatively high degree of sequence identity to a sequence of another protein or nucleic acid when the two sequences are aligned using standard methods. For example, an R-specific aldolase is a homolog of the aldolase of SEQ ID NO:22 if the R-specific aldolase contains at least about 50% sequence identity to the aldolase of SEQ ID NO:22 when the two sequences are aligned using standard methods.

EC number: The enzyme classification number as assigned by the International Union of Biochemistry and Molecular Biology.

Monatin derivative: As used herein, the phrase "monatin derivative" has the following structure:

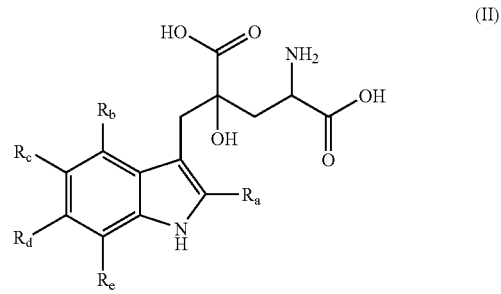

(II)

wherein, $R_a$, $R_b$, $R_c$, $R_d$, and $R_e$ each independently represent any substituent selected from a hydrogen atom, a hydroxyl group, a $C_1$-$C_3$ alkyl group, a $C_1$-$C_3$ alkoxy group, an amino group, or a halogen atom, such as an iodine atom, bromine atom, chlorine atom, or fluorine atom. However, $R_a$, $R_b$, $R_c$, $R_d$, and $R_e$ cannot simultaneously all be hydrogen. Alternatively, $R_b$ and $R_c$, and/or $R_d$ and $R_e$ may together form a $C_1$-$C_4$ alkylene group, respectively.

Substituted Tryptophan: As used herein, "substituted tryptophan" means one or more carbon atoms of the indole ring of the tryptophan is independently substituted with one or more of the $R_a$, $R_b$, $R_c$, $R_d$, and $R_e$ substituent groups defined above. However, $R_a$, $R_b$, $R_c$, $R_d$, and $R_e$ cannot simultaneously all be hydrogen. In one embodiment, the substituted tryptophan contains the same substituent group(s) on the indole ring as the final monatin derivative.

Biosynthetic Pathways to Produce R,R and Other Stereoisomers of Monatin

As described, inter alia, in WO 03/091396 A2 (see, e.g., FIGS. 1-3 and 11-13), monatin can be produced from tryptophan through a multi-step pathway involving biological conversions (i.e. facilitating the reaction of a substrate to a product with a polypeptide). A pathway described involves biologically converting tryptophan to indole-3-pyruvate, biologically converting indole-3-pyruvate to 2-hydroxy 2-(indol-3-ylmethyl)-4-keto glutaric acid ("MP"), and biologically converting MP to monatin. The biosynthesis pathway of the present invention that is used to produce monatin may comprise, or consist essentially of, one or more of the steps, mechanisms and/or pathways described below. The steps, mechanisms, and/or pathways described below are simply intended to be exemplary.

One method of producing monatin, or a salt thereof, comprises (a) producing indole-3-pyruvate from L-tryptophan, (b) producing monatin precursor from the indole-3-pyruvate, and (c) producing monatin from the monatin precursor.

Enzymes useful for converting tryptophan to indole-3-pyruvate include members of the enzyme classifications ("EC") 2.6.1.27, 1.4.1.19, 1.4.99.1, 2.6.1.28, 1.4.3.2, 1.4.3.3, 2.6.1.5, 2.6.1.-, 2.6.1.1, 2.6.1.21 and 3.5.1.-. These classes include polypeptides such as: tryptophan aminotransferase, which converts L-tryptophan and α-KG (i.e., α-ketoglutarate, also called 2-oxoglutarate) to indole-3-pyruvate and L-glutamate; D-tryptophan aminotransferase, which converts D-tryptophan and a 2-oxo acid to indole-3-pyruvate and an amino acid; tryptophan dehydrogenase, which converts L-tryptophan and NAD(P) to indole-3-pyruvate and $NH_3$ and NAD(P)H; D-amino acid dehydrogenase, which converts D-amino acids and FAD to indole-3-pyruvate and $NH_3$ and $FADH_2$; tryptophan-phenylpyruvate transaminase, which converts L-tryptophan and phenylpyruvate to indole-3-pyruvate and L-phenylalanine; L-amino acid oxidase, which converts an L-amino acid and $H_2O$ and $O_2$ to a 2-oxo acid and $NH_3$ and $H_2O_2$; D-amino acid oxidase, which converts a D-amino acid and $H_2O$ and $O_2$ to a 2-oxo acid and $NH_3$ and $H_2O_2$; and tryptophan oxidase, which converts L-tryptophan and $H_2O$ and $O_2$ to indole-3-pyruvate and $NH_3$ and $H_2O_2$. These classes also contain tyrosine (aromatic) aminotransferase, aspartate aminotransferase, D-amino acid (or D-alanine) aminotransferase, and broad (multiple substrate) aminotransferase which have multiple aminotransferase activities, some of which can convert tryptophan and a 2-oxo acid to indole-3-pyruvate and an amino acid. In addition, these classes include phenylalanine deaminases, which can convert tryptophan to indole-3-pyruvate and ammonium in the presence of water.

Enzymes useful for converting indole-3-pyruvate to MP include members of enzyme classes EC 4.1.3.-, 4.1.3.16, 4.1.3.17, and 4.1.2.-. These classes include carbon-carbon synthases/lyases, such as aldolases that catalyze the condensation of two carboxylic acid substrates. Enzyme class EC 4.1.3.- are those synthases/lyases that form carbon-carbon bonds utilizing oxo-acid substrates (such as indole-3-pyruvate) as the electrophile, while EC 4.1.2.- are synthases/lyases that form carbon-carbon bonds utilizing aldehyde substrates (such as benzaldehyde) as the electrophile. For example, KHG aldolase (EC 4.1.3.16) and ProA aldolase (EC 4.1.3.17), are known to convert indole-3-pyruvate and pyruvate to MP. Although ProA aldolase can be thought to identify only the 4-hydroxy-4-methyl-2-oxoglutarate aldolase derived from Comamonas testosteroni, herein the term ProA aldolase is used to mean any polypeptide with 4-hydroxy-4-methyl-2-oxoglutarate aldolase activity unless otherwise stated. Suitable examples of Pro aldolases include Comamonas testosteroni ProA (SEQ ID NO:1 (nucleic acid sequence), SEQ ID NO:2 (amino acid sequence)) and Sinorhizobium meliloti ProA (NCBI Accession No.: CAC46344), or enzymes that display homology to Comamonas testosteroni ProA (SEQ ID NO:1 (nucleic acid sequence), SEQ ID NO:2 (amino acid sequence)) and/or Sinorhizobium meliloti ProA (NCBI Accession No.: CAC46344). For example, suitable enzymes may have at least about 40%, 50%, 60%, 70%, 80%, 90%, 95%, and/or 99% amino acid sequence identity with Comamonas testosteroni ProA (SEQ ID NO: 2) and/or Sinorhizobium meliloti ProA (NCBI Accession No.: CAC46344). MP can also be generated using chemical reactions, such as the aldol condensations.

Figure 2:
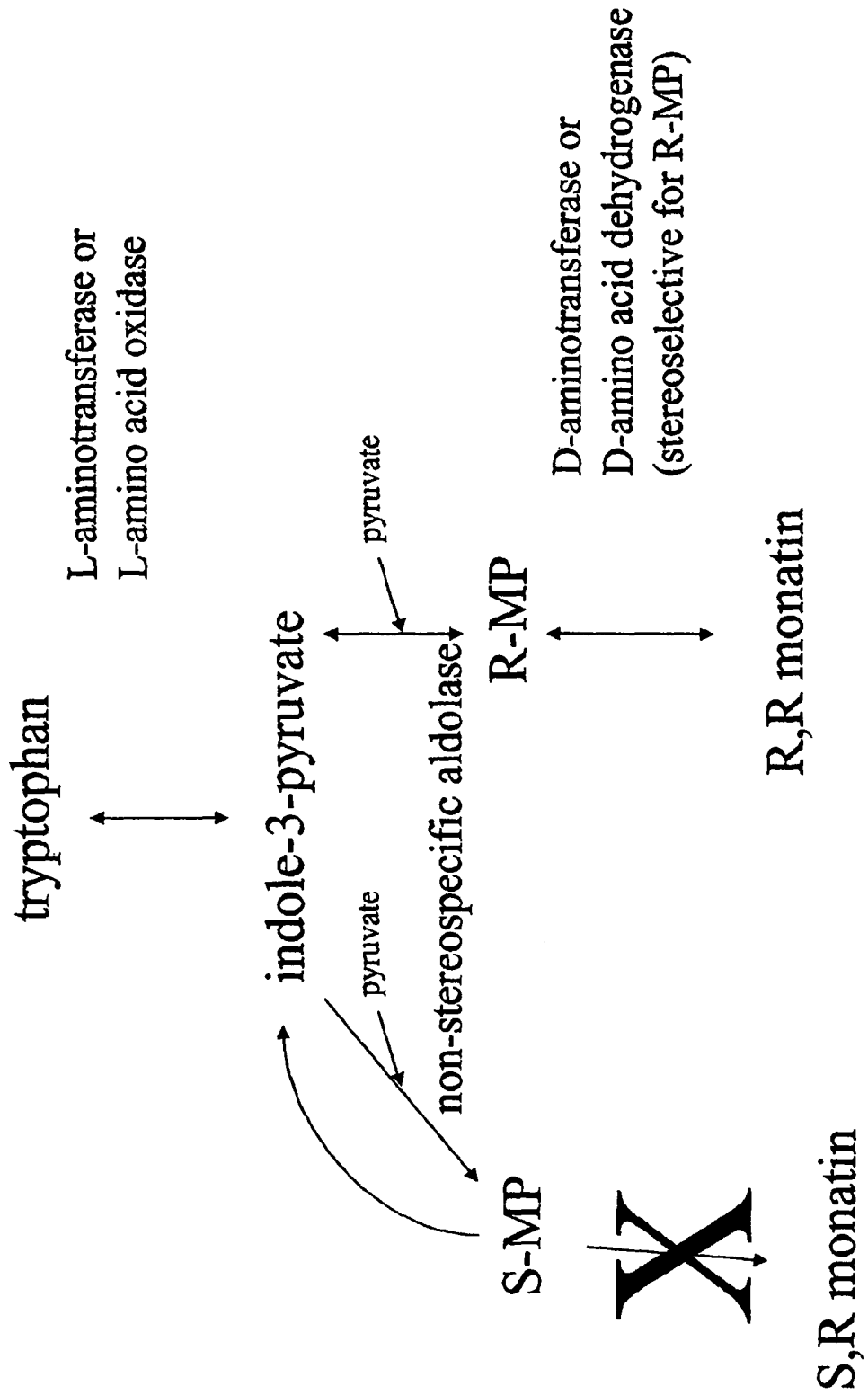
FIG. 2 is a flow chart that shows an example of another process for producing R,R monatin in accordance with the invention. In this example, the process includes using an enzyme to convert R-MP to monatin which is stereoselective for R-MP. In the specific example diagrammed in FIG. 2, tryptophan is shown to be converted to indole-3-pyruvate in a reversible reaction. The indole-3-pyruvate can be reacted with a non-stereospecific aldolase to reversibly form alpha-keto acid monatin (both R- and S-MP). The R-MP is reversibly converted to R,R monatin by a stereoselective D-aminotransferase or a stereoselective D-amino acid dehydrogenase. Any S-MP that is formed by the non-stereospecific aldolase can be converted back into indole-3-pyruvate if a stereoselective D-aminotransferase or D-amino acid dehydrogenase is utilized. For the purposes of the invention, it is not required that the reactions shown as being reversible proceed in the reverse direction.

Enzymes useful for the conversion of MP to monatin include members of the enzyme classes (EC): tryptophan aminotransferases (2.6.1.27), tryptophan dehydrogenases (1.4.1.19), D-amino acid dehydrogenases (1.4.99.1), glutamate dehydrogenases (1.4.1.2-4), phenylalanine dehydrogenase (1.4.1.20), tryptophan-phenylpyruvate transaminases (2.6.1.28), or more generally members of the aminotransferase family (2.6.1.-) such as aspartate aminotransferase (EC 2.6.1.1), tyrosine (aromatic) aminotransferase (2.6.1.5), D-tryptophan aminotransferase, or D-alanine (2.6.1.21) aminotransferase (see FIG. 2 of WO 03/091396 A2). This reaction can also be performed using chemical reactions. Amination of the keto acid (MP) is performed by reductive amination using ammonia and sodium cyanoborohydride. FIGS. 11-13 of WO 03/091396 A2 show additional polypeptides that can be used to convert MP to monatin, as well as providing increased yields of monatin from indole-3-pyruvate or tryptophan.

The taste profile of a monatin composition can be altered by controlling the relative amount of the various stereoisomers of monatin in the composition. The present disclosure provides pathways and substances for producing monatin compositions with a desired percentage of R,R monatin and/or S,R monatin.

The chirality of the monatin compounds that is produced by pathways such as those exemplified herein can be altered both by pH and by the polypeptides used for the biological conversions. When monatin is formed using a biosynthetic pathway, the following can be considered. In a biocatalytic reaction, the chirality of the monatin carbon-2 (see chemical structure above) is determined by the enzyme that converts indole-3-pyruvate to MP. Multiple enzymes (e.g., from EC 4.1.2.-, 4.1.3.-) can convert indole-3-pyruvate to MP. Thus, one can choose the enzyme that forms the desired isomer. Alternatively, the enantiospecificity of the enzyme that converts indole-3-pyruvate to MP can be modified through the use of directed evolution or catalytic antibodies can be engineered to catalyze the desired reaction. Once MP is produced (either enzymatically or by chemical condensation), the amino group can be added stereospecifically. Either the R or S configuration of carbon-4 (see previous chemical structure) can be generated depending on whether a D- or L-aromatic acid aminotransferase is used. Many aminotransferases are specific for the L-isomer, however, D-tryptophan aminotransferases exist in certain plants (Kohiba and Mito, Proceedings of the 8th International Symposium on Vitamin $B_6$ and Carbonyl Catalysis, Osaka, Japan 1990). Moreover, D-alanine aminotransferases (EC 2.6.1.21), D-methionine-pyruvate aminotransferases (EC 2.6.1.41) and both (R)-3-amino-2-methylpropanoate aminotransferase (EC 2.6.1.61), (S)-3-amino-2-methylpropanoate aminotransferase (EC 2.6.1.22), and D-phenylglycine aminotransferase have been identified. Certain aminotransferases may only accept the substrate for this reaction with a particular configuration at the C2 carbon. Therefore, even if the conversion to MP is not stereospecific, the stereochemistry of the final product can be controlled through the appropriate selection of an aminotransferase.

Because the reaction is reversible, the unreacted MP (undesired isomer) can be recycled back to its constituents and a racemic mixture of MP can be reformed.

Referring now to the figures, the following should be noted. The flow charts identify examples of pathways for producing monatin, but the pathways shown on the figures, and the methods of the invention, are not limited to any particular method for practicing the pathways, unless otherwise stated. For example, the pathways may be practiced in vivo, in vitro, or a combination thereof.

Furthermore, practice of a method of the invention utilizing one or more of the pathways disclosed herein does not require that each of the identified components (e.g. reactants and enzymes) is explicitly provided by the practitioner; rather, it is sufficient that the components, (or sources of components), and reaction conditions are present in the composition (or host cell) or otherwise available so that the pathway can potentially proceed. In other words, for example, if a figure depicts a process for producing a monatin composition, which includes producing indole-3-pyruvate from L-tryptophan, producing 2-hydroxy 2-(indol-3ylmethyl)-4-keto glutaric acid ("monatin precursor" or "MP") from indole-3-pyruvate, and producing monatin from MP, wherein each reaction is facilitated by an appropriate enzyme, it is contemplated that practice of that pathway includes combining L-tryptophan with α-ketoglutarate and enzymes contemplated for facilitating the identified reactions, and under conditions suitable for each of the reactions to occur without also explicitly providing indole-3-pyruvate or MP. In such an instance L-tryptophan could react with α-ketoglutarate to produce indole-3-pyruvate. Depending upon the conditions and the provided enzyme, the indole-3-pyruvate produced from the L-tryptophan reaction can react to form MP, and then depending upon the conditions and the provided enzyme, the MP produced from the indole-3-pyruvate reaction can react to form monatin.

It should also be noted that practice of a method of the invention utilizing one or more of the pathways disclosed herein does not require the practitioner to explicitly provide the identified starting materials or enzymes, if such materials or enzymes are otherwise already present or available, or capable of being synthesized from a substance that is already present or available in the reaction milieu. In other words, it is contemplated that practice of any pathways that identify L-tryptophan as a starting material would include providing a compound that can produce L-tryptophan, under conditions suitable for L-tryptophan production to occur and combining that compound with enzymes capable of facilitating the series of reactions set forth under conditions that would be suitable for those reactions to occur. As another example, it is also contemplated that practicing the identified pathway includes providing a microorganism genetically engineered to produce monatin according to the described pathway, and providing appropriate conditions for the fermentation process to occur. For example, a microorganism, which naturally produces large amounts of L-tryptophan or D-tryptophan (see U.S. Pat. No. 5,728,555) be can be genetically engineered to produce or over-produce one or more of the enzymes used to facilitate (catalyze) reactions in the pathway to monatin, and appropriate conditions can be provided so that the microorganism would thereby produce monatin.

Figure 1:
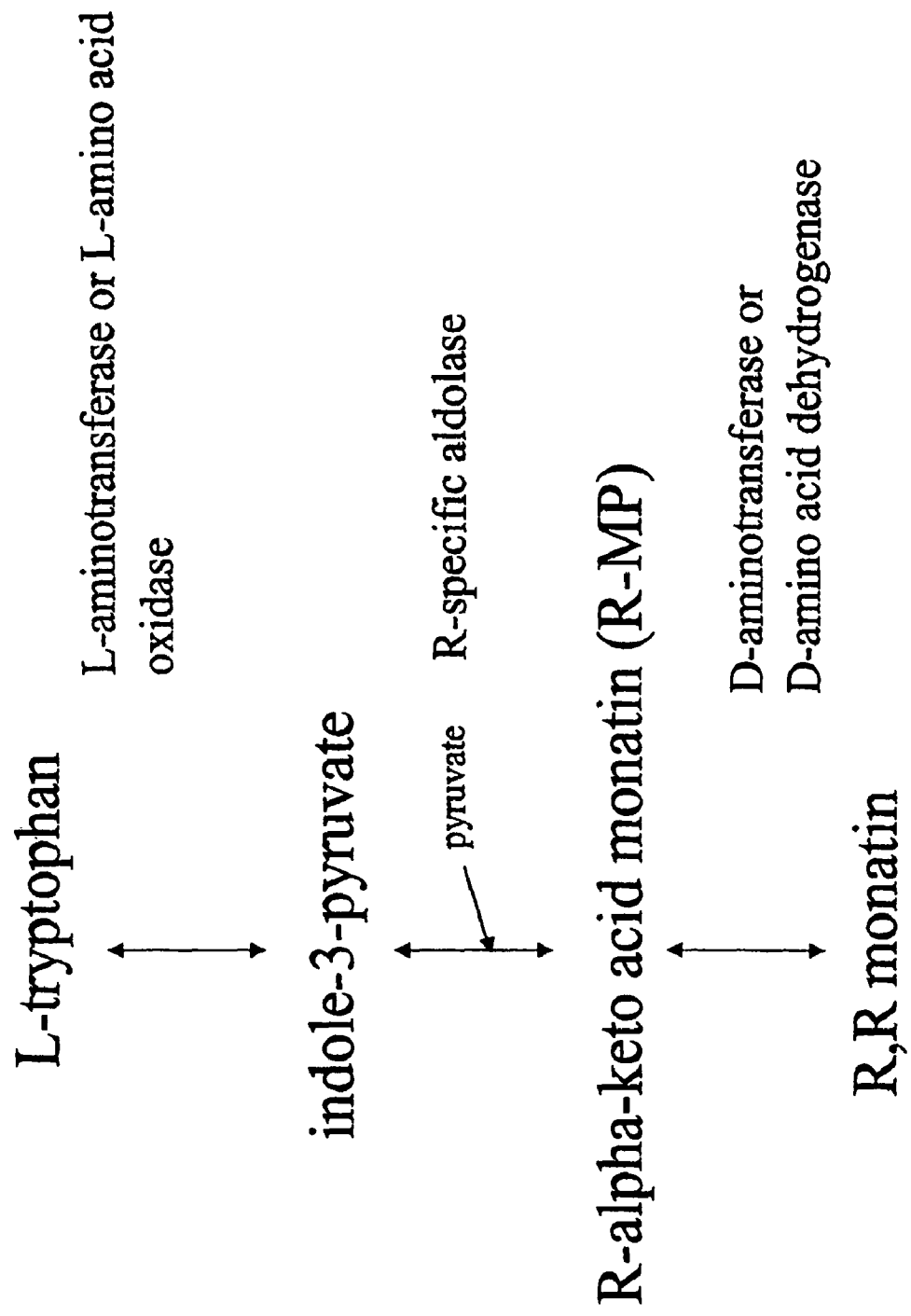
FIG. 1 is a flow chart that shows an example of an enzymatic process for producing R,R monatin from L-tryptophan in accordance with the invention. In this example, the process includes using an L-aminotransferase (examples of which include an L-tryptophan aminotransferase, an L-aromatic aminotransferase, an L-aspartate aminotransferase, and an L-alanine aminotransferase) in the reaction of L-tryptophan that has greater specificity and/or selectivity for L-tryptophan as a substrate than for R-MP and/or the process includes using an L-amino acid oxidase with limited activity and/or specificity for R,R monatin as a substrate. In the specific example diagrammed in FIG. 1, an L-aminotransferase or L-amino acid oxidase converts L-tryptophan to indole-3-pyruvate, indole-3-pyruvate is reacted with an R-specific aldolase and pyruvate to produce R-alpha-keto acid monatin (R-MP), and R-MP is converted to R,R monatin by a D-aminotransferase or a D-amino acid dehydrogenase. As shown on FIG. 1, the reactions are reversible, but for the purposes of the invention, it is not required that the reactions proceed in the reverse direction.

Turning now to FIG. 1, the flow chart shown schematically depicts a process in accordance with the invention for making a monatin composition including R,R monatin. As shown in FIG. 1, the overall pathway involves a reaction of tryptophan to form indole-3-pyruvate, a reaction of indole-3-pyruvate to produce MP, and a reaction of MP to produce monatin, including R,R monatin.

FIG. 1 further illustrates specific permutations of this overall pathway, designed to increase the production of the R,R form of monatin at the expense of the S,S, R,S and S,R forms of monatin. In particular, FIG. 1 illustrates the embodiment wherein: the aminotransferase enzyme utilized in the L-tryptophan reaction has greater activity and/or specificity for that reaction versus the reactions of MP and 4S monatin or the oxidase has greater activity and/or specificity for L-tryptophan than for 4R monatin; the enzyme which facilitates the reaction of indole-3-pyruvate is an R-specific aldolase; and, the enzyme which facilitates the reaction of MP is a broad specificity D-enzyme, preferably evolved to work more efficiently with the R isomer of MP.

FIG. 1 also illustrates particular permutations designed to make the production of R,R monatin more economical. For example, in FIG. 1 L-tryptophan—as opposed to D-tryptophan or combinations of L- and D-tryptophan—is identified as the starting material. While the choice of the specific form of tryptophan does not impact the chirality of the ultimate monatin compounds in the monatin composition (because the tryptophan reaction forms indole-3-pyruvate, which has no chirality), some may prefer utilizing L-tryptophan as a starting material at least because L-tryptophan is currently less expensive and more easily obtainable than D-tryptophan.

Focusing now on the first reaction shown in FIG. 1, when tryptophan is converted to indole-3-pyruvate any one or more of alpha-ketoglutarate, oxaloacetate, and/or pyruvate reacts with the tryptophan to form an amino acid (glutamate, aspartate, and alanine respectively) and indole-3-pyruvate. FIG. 1 depicts the embodiment wherein the tryptophan starting material is L-tryptophan, and the alpha-ketoglutarate, oxaloacetate, and/or pyruvate produce the L-isomer form of the amino acid (e.g. L-glutamate, L-aspartate, and/or L-alanine, respectively).

As shown in FIG. 1, an approach to enhancing the production of R,R monatin involves facilitating the reaction of L-tryptophan with an enzyme having greater specificity, greater activity, or both for tryptophan as opposed to MP or monatin, and facilitating the reaction of MP with a D-specific enzyme. As is disclosed in WO 03/091396 A2, certain enzymes can facilitate the reaction of tryptophan to produce indole-3-pyruvate, as well as the amination reaction of MP to produce monatin. Use of an L-aminotransferase in the amination step creates an S chiral center at the monatin C-4 position, whereas use of a D-enzyme creates a D chiral center at the monatin C-4 position. Thus, in the instance where an L-aminotransferase, which facilitates the tryptophan reaction, is also active in the MP reaction, R,S and S,S monatin can be formed, depending on the form of MP present. In addition, certain other enzymes—the L-amino acid oxidases—can not only facilitate the reaction of tryptophan to indole-3-pyruvate, but may have a side activity for the degradation of R,R monatin. According to some embodiments, this 4R side activity is minimized or eliminated. An oxidase side activity on 4S forms of monatin would decrease or minimize them from the final product and could be desirable depending on the final composition desired. Consequently, the greater the specificity and/or activity of the L-enzyme chosen for tryptophan versus the MP or monatin, the greater the amount of R,R and S,R produced versus S,S and R,S monatin.

Suitable enzymes for the tryptophan reaction, in accordance with the embodiment illustrated in FIG. 1, include:

L-aminotransferases capable of facilitating a reaction of L-tryptophan to form indole-3-pyruvate, and which have greater specificity for that reaction over the reaction of R-MP to form 4S isomers of monatin; and, L-amino acid oxidases capable of facilitating a reaction of L-tryptophan to form indole-3-pyruvate, and which have greater specificity and/or activity for that reaction versus the reaction of 4R isomers of monatin to form MP, and functional equivalents of any of the foregoing. More specifically, non-limiting examples of suitable enzymes can be chosen from L-tryptophan aminotransferases (EC 2.6.1.27) and tyrosine (aromatic) aminotransferases (EC 2.6.1.5) and L-amino acid oxidases (EC 1.4.3.2), and mutants derived from enzymes having aspartate aminotransferase activity.

Example 6 identifies a specific enzyme, a mutant HEX-aspC polypeptide which includes a Pro 9 to Tyr substitution and an Arg 122 to Gly substitution useful for facilitating the reactions of L-tryptophan and α-KG, oxaloacetate, pyruvate, or combinations thereof to form indole-3-pyruvate and L-glutamate, L-aspartate, and L-alanine, respectively. Another specific enzyme having "limited" activity is TatA, the L-tryptophan aminotransferase from *S. meliloti*. Other enzymes suitable for the tryptophan reaction in accordance with preferred embodiments of the pathway shown in FIG. 1 include those with the following characteristics: an enzyme that transaminates MP at $\frac{1}{10}$ the rate or less than the rate of L-tryptophan as in Example 6 or an enzyme when used with a racemase, as in Example 9, that produces greater than 90% of the 4R isomers of monatin.

Examples of enzymes not having a high degree of specificity for the L-tryptophan to indole-3-pyruvate conversion compared to the MP to monatin conversion include: HEX-AspC (Example 6), *Leishmania major* broad specificity aminotransferase (WO 03/091396 A2), the Porcine aminotransferase (WO 03/091396 A2) and *Rhodobacter sphaeroides* TatA (Example 9). These enzymes may, however, be evolved, for example through mutagenesis to have limited activity for R-MP and/or R,R monatin versus tryptophan.

Focusing now on the second reaction identified in FIG. 1, the choice of enzyme for facilitating (or catalyzing) the reaction of indole-3-pyruvate to MP influences the relative amount of R,R monatin versus S,R monatin produced. In general, the greater the relative amount of R-MP versus S-MP produced, the greater the relative amount of R,R monatin versus S,R monatin produced (when a D-enzyme facilitates the reaction of MP to monatin). Enzymes useful in this regard include any enzymes that produce a higher R-MP:S-MP ratio than that produced by the reaction of indole-3-pyruvate and pyruvate when facilitated by any one of the *E. coli* KHG aldolase (Genbank Accession No. AAC74920.1), the *Bacillus* KHG aldolase (Genbank Accession No. CAB 14127.1) or the *Comamonas testosteroni* ProA aldolase (SEQ ID NO:1 (nucleic acid sequence), SEQ ID NO:2 (amino acid sequence)). Thus, if it is desired to preferentially produce R-MP, one or more enzymes capable of producing greater amounts of R-MP relative to S-MP can be used. When a monatin composition having the R,R form of monatin as its only monatin component is desired, an enzyme that selectively produces R-MP as opposed to S-MP (an "R-specific enzyme") should be used. Examples of R-specific enzymes that may be used to selectively produce R-MP as opposed to S-MP are the aldolase of SEQ ID NO:22, the aldolase of SEQ ID NO:104 and *Sinorhizobium meliloti* HMG aldolase, as shown in Example 3.

FIG. 1 identifies the particular embodiment wherein an R-specific aldolase facilitates the reaction of indole-3-pyruvate and pyruvate to form R-MP. Also contemplated, however, is the use of aldolases for the indole-3-pyruvate and pyruvate reaction which preferentially produce R-MP, as well as aldolases that produce a higher R-MP:S-MP ratio than is produced by any one of the *E. coli* KHG aldolase (Genbank Accession No. AAC74920.1), the *Bacillus* KHG aldolase (Genbank Accession No. CAB14127.1) or the *Comamonas testosteroni* ProA aldolase (SEQ ID NO:1 (nucleic acid sequence), SEQ ID NO:2 (amino acid sequence)). In addition, it is also contemplated that indole-3-pyruvate may react with a different C3 source (for example serine or cysteine) to form R-MP and consequently other enzymes (for example other lyases or synthases) may facilitate such a reaction. Other substrates that are readily converted to pyruvate (such as oxaloacetate) may also be used. Example 3 provides sources of aldolase enzymes that may preferentially or selectively produce R-MP or produce a higher R-MP:S-MP ratio than is produced by the reaction of indole-3-pyruvate and pyruvate when facilitated by any one of the *E. coli* KHG aldolase (Genbank Accession No. AAC74920. 1), the *Bacillus* KHG aldolase (Genbank Accession No. CAB14127.1), the *Comamonas testosteroni* ProA aldolase (SEQ ID NO:1 (nucleic acid sequence), SEQ ID NO:2 (amino acid sequence)), the aldolase of SEQ ID NO:22 or the aldolase of SEQ ID NO:104. Example 5 also provides screening methods for identifying such enzymes. It is also contemplated that enzymes, which preferentially or selectively produce R-MP or produce more R-MP than any one of the *E. coli* KHG aldolase (Genbank Accession No. AAC74920. 1), the *Bacillus* KHG aldolase (Genbank Accession No. CAB14127.1) or the *Comamonas testosteroni* ProA aldolase (SEQ ID NO:1 (nucleic acid sequence), SEQ ID NO:2 (amino acid sequence)) may be evolved from aldolases known or found in nature. Any techniques known in the art for evolving enzymes, for example to improve a desired characteristic—such as to increase the activity of an enzyme for a substrate—as compared to the wild-type enzyme can be used. Examples 4, 5, 6, 7, 9, 10, and 11 provide some techniques for evolving enzymes.

Focusing now on the last step of the pathway identified in FIG. 1, the reaction of R-MP to form R,R monatin is shown to be facilitated by a broad specificity D-aminotransferase, for example D-alanine aminotransferase (EC 2.6.1.21, also known as D-amino acid aminotransferase or D-aspartate aminotransferase) or a D-amino acid dehydrogenase. As discussed above, the conversion of MP to monatin is an amination reaction, which creates a chiral center at the monatin C-4 carbon. Where the R-chiral form is desired at the C-4 position, enzymes should be used which produce "R" chiral centers in amino acids. Non-limiting exemplary enzymes include: a D-alanine-aminotransferase derived from *Bacillus* (Examples 15-18), including the D-alanine-aminotransferase derived from *Bacillus halodurans* (Example 18), a mutated branched chain aminotransferase that has modified stereospecificity (Example 7), and mutated D-aminotransferases derived from *Bacillus* (Example 6B).

Another exemplary enzyme includes a hybrid D-aminotransferase. The hybrid D-aminotransferase can contain structural elements from two differing amino acid aminotransferases. The hybrid D-aminotransferase can then be further evolved (e.g. via mutagenesis or recombinant engineering) for improved performance in converting MP to monatin. An example of such a hybrid D-aminotransferase is shown in Example 19. The hybrid D-aminotransferase illustrated in Example 19 included elements from a D-aminotransferase from *B. sphaericus* and a D-aminotransferase from *G. stearothermophilus*. R,R-monatin was produced utilizing this D-aminotransferase (Example 19).

Example 2 also illustrates the production of R,R monatin utilizing various D-aminotransferases.

According to some embodiments, the D-aminotransferase has greater specificity, greater activity, or both for the R-MP as a substrate than for indole-3-pyruvate. In certain other embodiments, the D-aminotransferase has limited activity for the indole-3-pyruvate as a substrate. Enzymes with such characteristics may be evolved or mutated from existing enzymes, for example as shown in Example 6.

Also, in some embodiments, the reaction of R-MP to form R,R monatin can be facilitated by a D-amino acid dehydrogenase. Example 20 illustrates the production of R,R monatin from R-MP utilizing a D-amino acid dehydrogenase (D-AADH-101 through 108, BioCatalytics). These D-amino acid dehydrogenases may be further evolved (e.g. via mutagenesis or recombinant engineering) for improved performance.

FIG. 2 depicts another strategy for targeting production of R,R monatin. Whereas in the embodiment of FIG. 1, the aldolase used in the reaction of indole-3-pyruvate to form R-MP influences the ratio of R,R:S,R formed, in the embodiment of FIG. 2, the D-enzyme that facilitates the conversion of MP to monatin influences the ratio of R,R:S,R formed. According to the embodiment of FIG. 2, a non-stereospecific enzyme may be used to facilitate the conversion of indole-3-pyruvate to MP, and consequently both S-MP and R-MP can be formed. To obtain a desired ratio of R,R monatin to S,R monatin, a D-enzyme is chosen (or evolved) with appropriate stereoselectivity for R-MP versus S-MP. Where a monatin composition having the R,R form of monatin as its only monatin component is desired, an enzyme that selectively facilitates the reaction of R-MP to monatin as opposed to S-MP to monatin would be preferred. For example, the *Bacillus halodurans* D-aminotransferase (Example 18) and the hybrid D-aminotransferase containing structural elements from both *Bacillus sphaericus* and *Geobacillus stearothermophilus* (Example 19) may be utilized as the enzyme that selectively facilitates the reaction of R-MP to monatin.

Figure 3:
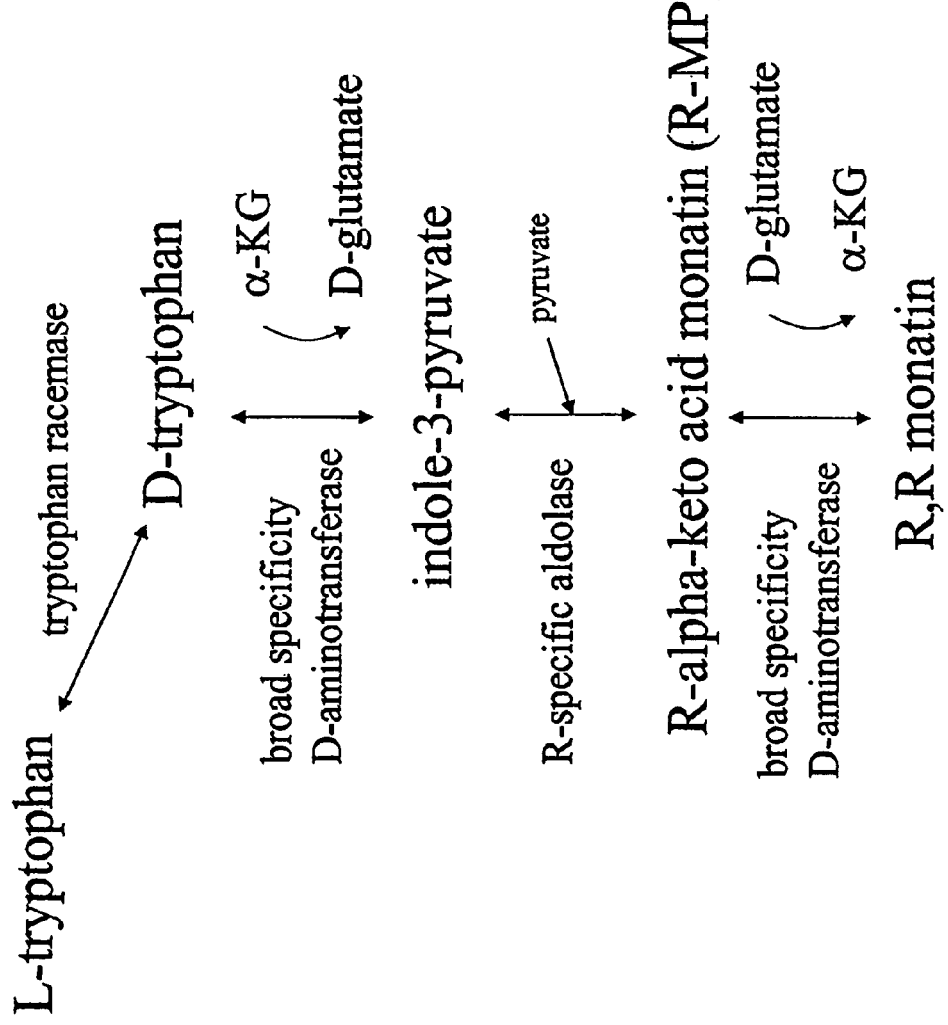
FIG. 3 is a flow chart that shows an example of yet another process for producing R,R monatin from L-tryptophan in accordance with the invention In this example, the process includes converting L-tryptophan to D-tryptophan using a tryptophan racemase and using a D-amino acid product in the reaction coupled to the reaction forming indole-3-pyruvate as a substrate in the reaction coupled to the reaction forming R,R monatin. In the specific example diagrammed in FIG. 3, L-tryptophan is converted to D-tryptophan by a tryptophan racemase in a reversible reaction. The D-tryptophan is reacted with alpha-ketoglutarate ($\alpha$-KG) and a broad specificity D-aminotransferase to produce indole-3-pyruvate and D-glutamate. Indole-3-pyruvate is reacted with pyruvate and an R-specific aldolase and converted to R-alpha-keto acid monatin (R-MP), and R-MP is reacted with a broad specificity D-aminotransferase and D-glutamate to form R,R monatin and alpha-ketoglutarate ($\alpha$-KG). As shown on FIG. 3, each of the reactions are reversible, but for the purposes of the invention, it is not required that the reactions proceed in the reverse direction.

FIG. 3 illustrates another alternative pathway for production of compositions enriched in R,R monatin. The pathway of FIG. 3 is a modification of the pathway of FIG. 1. In the pathway shown in FIG. 3, indole-3-pyruvate is produced indirectly, rather than directly, from L-tryptophan. More specifically, L-tryptophan is converted to D-tryptophan, and D-tryptophan is then converted to indole-3-pyruvate. Example 4 illustrates the production of R,R monatin from L-tryptophan using a tryptophan racemase or a broad specificity amino acid racemase.

The conversion of L-tryptophan to D-tryptophan can be facilitated by a tryptophan racemase or functional equivalent thereof. Example 4 provides potential sources of tryptophan racemases and broad specificity amino acid racemases and screening methods for identifying such enzymes. Example 4 describes examples of tryptophan racemases and broad specificity amino acid racemases that are capable of converting L-tryptophan into D-tryptophan. These tryptophan racemases can be further evolved (e.g. via mutagenesis or recombinant engineering) for improved performance. An example of a racemase having the activity of a tryptophan racemase is an alanine racemase isolated from *Geobacillus stearothermophilus*. More specifically, examples of racemases having the activity of a tryptophan racemase are alanine racemases derived from SEQ ID NO:41, such as an alanine racemase corresponding to SEQ ID NO:41 with a Y354A mutation.

Non-limiting examples of tryptophan racemases include homologs or mutants of amino acid racemases (EC 5.1.1.-), for example serine racemase, in which the homologs or mutants are capable of converting L-tryptophan to D-tryptophan. Non-limiting examples of sources from which the amino acid racemase may be derived include microorganisms such as *Salmonella typhimurium*, *Escherichia coli*, *Bacillus subtilis*, *Bacillus sphaericus*, *Bacillus halodurans*, *Geobacillus stearothermophilus*, *Bacillus licheniformis*, *Pseudomonas aeruginosa*, *Vibrio cholerae*, *Schizosaccharomyces pombe*, *Bacillus cereus*, *Enterococcus gallinarum*, *Pediococcus pentosaceus*, *Bacillus pumilus*, *Lactobacillus fermenti*, *Lactobacillus brevis*, *Aquifex pyrophilus*, *Lactobacilli*, *Streptococcus*, *Anabaena* sp., *Pseudomonas striata*, *Lentinus edodes*, *Scapharca brouhtonii Desulfurococcus* sp., *Thermococcus* sp., and *Pseudomonas striata*. Additional non-limiting examples of sources from which the amino acid racemase may be derived include silkworm, rat brain, or mouse brain. These amino acid racemases may be evolved (e.g. via mutagenesis or recombinant engineering) for improved performance in converting L-tryptophan to D-tryptophan.

Non-limiting examples of potential sources from which suitable tryptophan racemases may be derived include: microorganisms such as *Pseudomonas*, for example *Pseudomonas chlororaphis* (*Pseudomonas aurereofaciens*) (ATCC15926), and *Burkholderia pyrrocina* (ATCC15958). Additional non-limiting examples of potential sources from which suitable tryptophan racemases may be derived include plants, for example tobacco plants, such as *Nicotiana tabacum*, wheat plants, such as *Triticum aestivum*, beets, tomatoes, and *Sclerochiton ilicifolius*.

Non-limiting examples of suitable broad specificity amino acid racemases include broad specificity amino acid racemase is chosen from a broad specificity amino acid racemase of SEQ ID NO:120, a broad specificity amino acid racemase corresponding to SEQ ID NO:120 with a Y396C mutation, a broad specificity amino acid racemase of SEQ ID NO:128, a broad specificity amino acid racemase corresponding to SEQ ID NO:128 with a I384M mutation, an alanine racemase from *Vibrio fischeri*, an alanine racemase of Genbank Accession No. AAW85230.1, an alanine racemase of Genbank Accession No. YP_204118, a broad specificity amino acid racemase isolated from *Pseudomonas taetrolens*, a broad specificity amino acid racemase corresponding to the broad specificity amino acid racemase isolated from *Pseudomonas taetrolens* with a I384M mutation, a broad specificity amino acid racemase isolated from *Pseudomonas putida* (also known as *Pseudomonas striata*), a broad specificity amino acid racemase containing a partial sequence of SEQ ID NO:116, a broad specificity amino acid racemase of Genbank Accession No. ZP_00898332.1 GI:82735470, a broad specificity amino acid racemase of ATCC 4683, a broad specificity amino acid racemase of SEQ ID NO:204, a broad specificity amino acid racemase corresponding to SEQ ID NO:204 with a I384M mutation, a broad specificity amino acid racemase isolated from *P. putida* KT2440, a broad specificity amino acid racemase isolated from *P. putida* NBRC 12996, a broad specificity amino acid racemase of ATCC 7966, a broad specificity amino acid racemase isolated from *Pseudomonas* strain 2150, a broad specificity amino acid racemase isolated from *P. oleovorans*, a broad specificity amino acid racemase isolated from *P. aureofaciens*, a broad specificity amino acid racemase isolated from *P. putida* 12633, a broad specificity amino acid racemase isolated from *P. fluorescens*, a broad specificity amino acid racemase isolated from *P. putida* SCRC-744, a broad specificity amino acid racemase isolated from *P. graveolens*, a broad specificity amino acid racemase isolated from *P. striata* AKU 083, an enzyme having the activity of a broad specificity amino acid racemase isolated from *Pseudomonas taetrolens* containing amino acids 24-409, an enzyme having the activity of a broad specificity amino acid racemase containing amino acids 24-409 of SEQ ID NO:204, an enzyme having the activity of a broad specificity amino acid racemase isolated from *Aeromonas jandei*, an enzyme having the activity of a broad specificity amino acid racemase of ATCC 49572, an enzyme having the activity of a broad specificity amino acid racemase of SEQ ID NO:194, an enzyme having the activity of a broad specificity amino acid racemase isolated from *Aeromonas sobria*, an enzyme having the activity of a broad specificity racemase of ATCC 35994, an enzyme having the activity of a broad specificity amino acid racemase of SEQ ID NO:192, an enzyme corresponding to the broad specificity amino acid racemase isolated from *Aeromonas caviae* with a L383M mutation, an enzyme having the activity of a broad specificity amino acid racemase of ATCC 14486 with a L383M mutation, an enzyme having the activity of a broad specificity amino acid racemase encoded by a gene containing a partial sequence of SEQ ID NO:195, an enzyme having the activity of a broad specificity amino acid racemase encoded by a gene containing a partial sequence of SEQ ID NO:196, an enzyme having the activity of a broad specificity amino acid racemase containing a partial sequence of SEQ ID NO:201, an enzyme having the activity of a broad specificity amino acid racemase containing a partial sequence of SEQ ID NO:202, an enzyme corresponding to the amino acid racemase from *Aeromonas caviae* with a D76N mutation, an enzyme having the activity of a broad specificity amino acid racemase corresponding to SEQ ID NO:179 with a D76N mutation, a broad specificity amino acid racemase isolated from *Aeromonas hydrophila*, a broad specificity amino acid racemase of SEQ ID NO:177, a broad specificity amino acid racemase containing amino acids 22-408 of SEQ ID NO:177, a broad specificity amino acid racemase containing a partial sequence of SEQ ID NO:146, a broad specificity amino acid racemase isolated from *Aeromonas caviae*, a broad specificity amino acid racemase of SEQ ID NO:179, a broad specificity amino acid racemase containing amino acids 22-408 of SEQ ID NO:179, a broad specificity amino acid racemase containing a partial sequence of SEQ ID NO:155, a broad specificity amino acid racemase of SEQ ID NO:151, and active fragments and homologs thereof.

Other non-limiting examples of suitable broad specificity amino acid racemases include one or more enzymes comprising a sequence having a percent sequence identity of at least 90% to one or more broad specificity amino acid racemases chosen from a broad specificity amino acid racemase of SEQ ID NO:120, a broad specificity amino acid racemase corresponding to SEQ ID NO:120 with a Y396C mutation, a broad specificity amino acid racemase of SEQ ID NO:128, a broad specificity amino acid racemase corresponding to SEQ ID NO:128 with a I384M mutation, an alanine racemase from *Vibrio fischeri*, an alanine racemase of Genbank Accession No. AAW85230.1, an alanine racemase of Genbank Accession No. YP_204118, a broad specificity amino acid racemase isolated from *Pseudomonas taetrolens*, a broad specificity amino acid racemase corresponding to the broad specificity amino acid racemase isolated from *Pseudomonas taetrolens* with a I384M mutation, a broad specificity amino acid racemase isolated from *Pseudomonas putida* (also known as *Pseudomonas striata*), a broad specificity amino acid racemase containing a partial sequence of SEQ ID NO:116, a broad specificity amino acid racemase of Genbank Accession No. ZP_00898332.1 GI:82735470, a broad specificity amino acid racemase of ATCC 4683, a broad specificity amino acid racemase of SEQ ID NO:204, a broad specificity amino acid racemase corresponding to SEQ ID NO:204 with a I384M mutation, a broad specificity amino acid racemase isolated from *P. putida* KT2440, a broad specificity amino acid racemase isolated from *P. putida* NBRC 12996, a broad specificity amino acid racemase of ATCC 7966, a broad specificity amino acid racemase isolated from *Pseudomonas* strain 2150, a broad specificity amino acid racemase isolated from *P. oleovorans*, a broad specificity amino acid racemase isolated from *P. aureofaciens*, a broad specificity amino acid racemase isolated from *P. putida* 12633, a broad specificity amino acid racemase isolated from *P. fluorescens*, a broad specificity amino acid racemase isolated from *P. putida* SCRC-744, a broad specificity amino acid racemase isolated from *P. graveolens*, a broad specificity amino acid racemase isolated from *P. striata* AKU 083, an enzyme having the activity of a broad specificity amino acid racemase isolated from *Pseudomonas taetrolens* containing amino acids 24-409, an enzyme having the activity of a broad specificity amino acid racemase containing amino acids 24-409 of SEQ ID NO:204, an enzyme having the activity of a broad specificity amino acid racemase isolated from *Aeromonas jandei*, an enzyme having the activity of a broad specificity amino acid racemase of ATCC 49572, an enzyme having the activity of a broad specificity amino acid racemase of SEQ ID NO:194, an enzyme having the activity of a broad specificity amino acid racemase isolated from *Aeromonas sobria*, an enzyme having the activity of a broad specificity racemase of ATCC 35994, an enzyme having the activity of a broad specificity amino acid racemase of SEQ ID NO:192, an enzyme corresponding to the broad specificity amino acid racemase isolated from *Aeromonas caviae* with a L383M mutation, an enzyme having the activity of a broad specificity amino acid racemase of ATCC 14486 with a L383M mutation, an enzyme having the activity of a broad specificity amino acid racemase encoded by a gene containing a partial sequence of SEQ ID NO:195, an enzyme having the activity of a broad specificity amino acid racemase encoded by a gene containing a partial sequence of SEQ ID NO:196, an enzyme having the activity of a broad specificity amino acid racemase containing a partial sequence of SEQ ID NO:201, an enzyme having the activity of a broad specificity amino acid racemase containing a partial sequence of SEQ ID NO:202, an enzyme corresponding to the amino acid racemase from *Aeromonas caviae* with a D76N mutation, an enzyme having the activity of a broad specificity amino acid racemase corresponding to SEQ ID NO:179 with a D76N mutation, a broad specificity amino acid racemase isolated from *Aeromonas hydrophila*, a broad specificity amino acid racemase of SEQ ID NO:177, a broad specificity amino acid racemase containing amino acids 22-408 of SEQ ID NO:177, a broad specificity amino acid racemase containing a partial sequence of SEQ ID NO:146, a broad specificity amino acid racemase isolated from *Aeromonas caviae*, a broad specificity amino acid racemase of SEQ ID NO:179, a broad specificity amino acid racemase containing amino acids 22-408 of SEQ ID NO:179, a broad specificity amino acid racemase containing a partial sequence of SEQ ID NO:155, a broad specificity amino acid racemase of SEQ ID NO:151, and active fragments thereof. In some embodiments, the percent sequence identity is at least 95%.

Still other non-limiting examples of suitable broad specificity amino acid racemases include a broad specificity amino acid racemase encoded by Genbank Accession No. AB096176, a broad specificity amino acid racemase encoded by a nucleic acid sequence corresponding to Genbank Accession No. AB096176 with a substitution such that the racemase includes a I384M mutation, a broad specificity amino acid racemase encoded by SEQ ID NO:119, a broad specificity amino acid racemase encoded by SEQ ID NO:127, a broad specificity amino acid racemase encoded by CP 000020.1

GI:59478708 region 800842 . . . 802053, a broad specificity amino acid racemase encoded by NC_006840, a broad specificity amino acid racemase encoded by KT2440 Bar DNA, a broad specificity amino acid racemase encoded by a nucleic acid sequence corresponding to SEQ ID NO:119 with a substitution such that the racemase includes a Y396C mutation, a broad specificity amino acid racemase encoded by a nucleic acid sequence corresponding to SEQ ID NO:127 with a substitution such that the racemase includes a I384M mutation, a broad specificity amino acid racemase encoded by the partial gene sequence of SEQ ID NO:151, a broad specificity amino acid racemase encoded by the partial gene sequence of SEQ ID NO:154, a broad specificity amino acid racemase encoded by NZ_AALM01000002 nucleotides 53173 . . . 54402, a broad specificity racemase encoded by a nucleic acid sequence corresponding to SEQ ID NO:140, a broad specificity racemase encoded by a nucleic acid sequence corresponding to SEQ ID NO:140 with a substitution such that the racemase includes a I384M mutation, a broad specificity racemase enclded by a nucleic acid sequence corresponding to SEQ ID NO:178, a broad specificity racemase enclded by a nucleic acid sequence corresponding to SEQ ID NO:178 with a substitution such that the racemase includes a L383M mutation, a broad specificity racemase enclded by a nucleic acid sequence corresponding to SEQ ID NO:193, a broad specificity racemase enclded by a nucleic acid sequence corresponding to SEQ ID NO:176, and homologs thereof.

Other non-limiting examples of suitable broad specificity amino acid racemases include a broad specificity amino acid racemase having a percent sequence identity of at least 90% to one or more broad specificity amino acid racemases chosen from a broad specificity amino acid racemase encoded by Genbank Accession No. AB096176, a broad specificity amino acid racemase encoded by a nucleic acid sequence corresponding to Genbank Accession No. AB096176 with a substitution such that the racemase includes a I384M mutation, a broad specificity amino acid racemase encoded by SEQ ID NO:119, a broad specificity amino acid racemase encoded by SEQ ID NO:127, a broad specificity amino acid racemase encoded by CP 000020.1 GI:59478708 region 800842 . . . 802053, a broad specificity amino acid racemase encoded by NC_006840, a broad specificity amino acid racemase encoded by KT2440 Bar DNA, a broad specificity amino acid racemase encoded by a nucleic acid sequence corresponding to SEQ ID NO:119 with a substitution such that the racemase includes a Y396C mutation, a broad specificity amino acid racemase encoded by a nucleic acid sequence corresponding to SEQ ID NO:127 with a substitution such that the racemase includes a I384M mutation, a broad specificity amino acid racemase encoded by the partial gene sequence of SEQ ID NO:151, a broad specificity amino acid racemase encoded by the partial gene sequence of SEQ ID NO:154, a broad specificity amino acid racemase encoded by NZ AALM01000002 nucleotides 53173 . . . 54402, a broad specificity racemase encoded by a nucleic acid sequence corresponding to SEQ ID NO:140, a broad specificity racemase enclded by a nucleic acid sequence corresponding to SEQ ID NO:140 with a substitution such that the racemase includes a I384M mutation, a broad specificity racemase enclded by a nucleic acid sequence corresponding to SEQ ID NO:178, a broad specificity racemase enclded by a nucleic acid sequence corresponding to SEQ ID NO:178 with a substitution such that the racemase includes a L383M mutation, a broad specificity racemase enclded by a nucleic acid sequence corresponding to SEQ ID NO:193, and a broad specificity racemase enclded by a nucleic acid sequence corresponding to SEQ ID NO:176. In some embodiments, said percent sequence identity is at least 95%.

In some embodiments, D-tryptophan is produced from L-tryptophan or L-tryptophan is produced from D-tryptophan utilizing one or more enzymes chosen from an enzyme having the activity of an alanine racemase from *Vibrio fischeri*, an enzyme having the activity of an alanine racemase of Genbank Accession No. AAW85230.1, an enzyme having the activity of an alanine racemase of Genbank Accession No. YP_204118, an enzyme having the activity of a broad specificity amino acid racemase isolated from *Pseudomonas taetrolens*, an enzyme having the activity of a broad specificity amino acid racemase corresponding to the broad specificity amino acid racemase isolated from *Pseudomonas taetrolens* with a I384M mutation, an enzyme having the activity of a broad specificity amino acid racemase of SEQ ID NO:204, an enzyme having the activity of a broad specificity amino acid racemase corresponding to SEQ ID NO:204 with a I384M mutation, an enzyme having the activity of a broad specificity amino acid racemase isolated from *Pseudomonas taetrolens* containing amino acids 24-409 an enzyme having the activity of a broad specificity amino acid racemase containing amino acids 24-409 of SEQ ID NO:204, an enzyme having the activity of a broad specificity amino acid racemase isolated from *Aeromonas jandei*, an enzyme having the activity of a broad specificity amino acid racemase of ATCC 49572, an enzyme having the activity of a broad specificity amino acid racemase of SEQ ID NO:194, an enzyme having the activity of a broad specificity amino acid racemase isolated from *Aeromonas sobria*, an enzyme having the activity of a broad specificity racemase of ATCC 35994, an enzyme having the activity of a broad specificity amino acid racemase of SEQ ID NO:192, an enzyme corresponding to the broad specificity amino acid racemase isolated from *Pseudomonas putida* with a L383M mutation, an enzyme corresponding to the amino acid racemase *Pseudomonas putida* KT2440 BAR with a L383M mutation, an enzyme having the activity of a broad specificity amino acid racemase of ATCC 35994 with a L383M mutation, an enzyme having the activity of a broad specificity amino acid racemase corresponding to SEQ ID NO:120 with a L383M mutation, an enzyme having the activity of a broad specificity amino acid racemase encoded by a gene containing a partial sequence of SEQ ID NO:195, an enzyme having the activity of a broad specificity amino acid racemase encoded by a gene containing a partial sequence of SEQ ID NO:196, an enzyme having the activity of a broad specificity amino acid racemase containing a partial sequence of SEQ ID NO:201, an enzyme having the activity of a broad specificity amino acid racemase containing a partial sequence of SEQ ID NO:202, an enzyme corresponding to the amino acid racemase from *Aeromonas caviae* with a D76N mutation, an enzyme having the activity of a broad specificity amino acid racemase corresponding to SEQ ID NO:179 with a D76N mutation, an enzyme having the activity of a broad specificity amino acid racemase isolated from *Aeromonas hydrophila*, an enzyme having the activity of a broad specificity amino acid racemase of SEQ ID NO:177, an enzyme having the activity of a broad specificity amino acid racemase containing amino acids 22-408 of SEQ ID NO:177, an enzyme having the activity of a broad specificity amino acid racemase containing a partial sequence of SEQ ID NO:146, an enzyme having the activity of a broad specificity amino acid racemase isolated from *Aeromonas caviae*, an enzyme having the activity of a broad specificity amino acid racemase of SEQ ID NO:179, an enzyme having the activity of a broad specificity amino acid racemase containing amino acids 22-408 of SEQ ID NO:179, an enzyme having the activity of a broad specificity amino acid racemase containing a partial sequence of SEQ ID NO:155, and an enzyme having the activity of a broad specificity amino acid racemase of SEQ ID NO:151 and active fragments thereof.

The pathway shown in FIG. 3 has certain benefits, including that even when R,R monatin is the desired product, the same enzyme can be used for the reaction that produces indole-3-pyruvate as for the reaction that produces monatin as a product. That is, in the pathway illustrated in FIG. 1, an L-aminotransferase (or suitable L-enzyme) facilitates the reaction producing indole-3-pyruvate, but a D-aminotransferase facilitates the reaction producing monatin. By contrast in the pathway of FIG. 3, a certain D-aminotransferase that facilitates the reaction producing indole-3-pyruvate, can also facilitate the reaction producing monatin. Consequently, in pathways according to FIG. 3, broad specificity D-aminotransferases may be preferred when there is a desire to use the same enzyme for the reaction forming indole-3-pyruvate as for the reaction forming monatin. By contrast, in pathways according to FIGS. 1, 2, 4, 6, 7, and 8 production of monatin may be more efficient when a D-aminotransferase is chosen that has limited activity and/or specificity for indole-3-pyruvate as compared to R-MP.

Another benefit of the pathway schematically represented in FIG. 3 is that the amino acid product of the reaction coupled to the reaction producing indole-3-pyruvate can now be used as a substrate in the reaction coupled to the reaction producing monatin. That is, in the pathway illustrated in FIG. 1, L-tryptophan reacts to produce indole-3-pyruvate and at the same time oxaloacetate, alpha-ketoglutarate and/or pyruvate react to produce an L-amino acid. Because the reaction of R-MP to form monatin is coupled with a reaction utilizing a D-amino acid as a substrate, the L-amino acid of the reaction forming indole-3-pyruvate is not, under the conditions shown, recycled for use in the reaction coupled to the R-MP reaction. By contrast, in the pathway illustrated in FIG. 3, the reaction of D-tryptophan to form indole-3-pyruvate is coupled to a reaction forming a D-amino acid product, which D-amino acid can be recycled for use in the reaction coupled to the R-MP reaction. This allows one to use non-stoichiometric amounts of amino acceptor in step one and the amino donor for step 3 is produced in step 1. In some embodiments of the invention, the D-amino acid is D-alanine.

Figure 4:
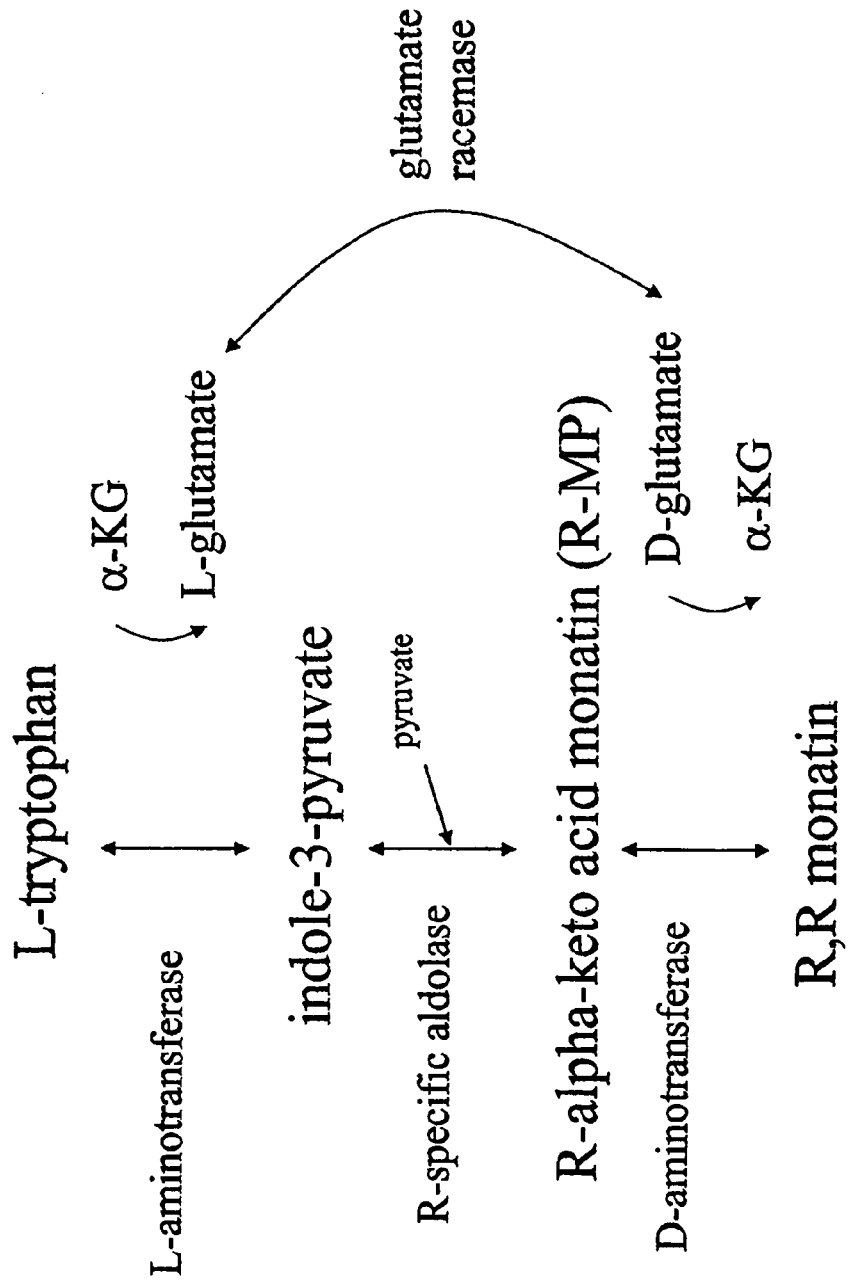
FIG. 4 is a flow chart that shows an example of yet another process for producing R,R monatin from L-tryptophan in accordance with the invention. In this example, the process includes converting the L-amino acid formed in the reaction coupled with the L-tryptophan reaction to a D-amino acid; this D-amino acid acts as an amino donor for the reaction in which R-MP is converted to R,R monatin. In the specific example diagrammed in FIG. 4, L-tryptophan is reacted with an L-aminotransferase and alpha-ketoglutarate to produce indole-3-pyruvate and L-glutamate. Indole-3-pyruvate is reacted with pyruvate and an R-specific aldolase and converted to R-alpha-keto acid monatin (R-MP), and R-MP is reacted with a broad specificity D-aminotransferase and D-glutamate to form R,R monatin and alpha-ketoglutarate. As shown on FIG. 4, the reactions are reversible, but for the purposes of the invention, it is not required that the reactions proceed in the reverse direction.
Figure 5:
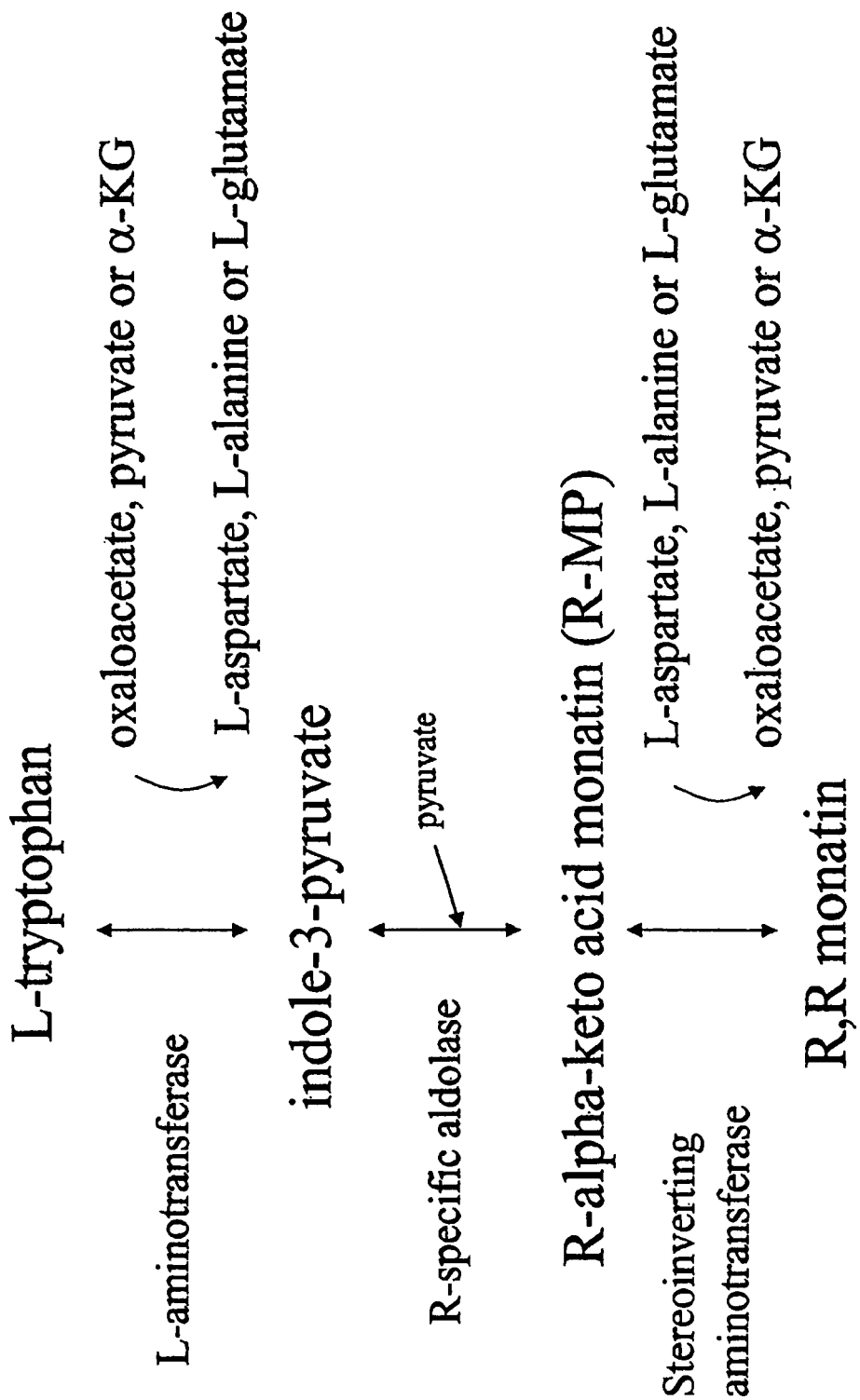
FIG. 5 is a flow chart that shows an example of yet another process for producing R,R monatin from L-tryptophan in accordance with the invention. In this example, the process includes enzymatically facilitating the conversion of R-MP to R,R monatin using a stereoinverting enzyme so that the L-amino acid formed by the reaction coupled to the L-tryptophan reaction can be used as a substrate for the reaction coupled to the R-MP to R,R monatin reaction. In the specific example diagrammed in FIG. 5, L-tryptophan is reacted with an L-aminotransferase and oxaloacetate, pyruvate or alpha-ketoglutarate ($\alpha$-KG) to produce indole-3-pyruvate, and L-aspartate (if oxaloacetate is used), L-alanine (if pyruvate is used) or L-glutamate (if $\alpha$-KG is used). Indole-3-pyruvate is reacted with pyruvate and an R-specific aldolase and converted to R-alpha-keto acid monatin (R-MP), and R-MP is reacted with a stereoinverting aminotransferase and L-aspartate, L-alanine or L-glutamate to form R,R monatin and oxaloacetate (if L-aspartate is used), pyruvate (if L-alanine is used) or alpha-ketoglutarate ($\alpha$-KG, if L-glutamate is used). As shown on FIG. 5, the reactions are reversible, but for the purposes of the invention, it is not required that the reactions proceed in the reverse direction.

FIGS. 4 and 5 illustrate additional modifications of the pathway shown in FIG. 1. These modifications are directed to recycling the amino acid product formed by the reaction coupled with the L-tryptophan transamination reaction with the amino acid reactant of the reaction coupled to the MP to monatin reaction.

Turning to FIG. 4, the recycling is accomplished by providing an enzyme that can facilitate the conversion of an L-amino acid to a D-amino acid and vice versa. More specifically, where, as is shown in FIG. 4, α-KG reacts to form L-glutamate when L-tryptophan reacts to form indole-3-pyruvate, a glutamate racemase (EC 5.1.1.3) or functional equivalent can be provided that can facilitate the conversion of L-glutamate to D-glutamate and vice versa. In such an instance, the L-glutamate formed as a product along with the production of indole-3-pyruvate is partially removed by virtue of its conversion to D-glutamate, and the D-glutamate formed from the conversion of L-glutamate is then available as a substrate for the reaction coupled with the MP to monatin reaction. Similarly, the α-KG formed in the reaction of D-glutamate is available as a substrate for the reaction coupled to the L-tryptophan to indole-3-pyruvate reaction.

Non-limited examples of potential sources from which a glutamate racemase may be derived include *Pediococcus pentosaceus, Bacillus pumilus, Lactobacillus fermenti, Lactobacillus brevis, E. coli, Aquifex pyrophilus,* and *Bacillus subtilis*. More specifically (also non-limiting), the glutamate racemase may be expressed from a nucleic acid such as *Pediococcus pentaosaceus* murI gene (Genbank Accession No. L22789), or *Lactobacillus brevis* glutamate racemase.

Where oxaloacetate reacts to form L-aspartate when L-tryptophan reacts to form indole-3-pyruvate, an aspartate racemase (EC 5.1.1.13) or functional equivalent can be provided to convert L-aspartate to D-aspartate. In such an instance, the L-aspartate that is formed in the same reaction that produces indole-3-pyruvate is partially removed by virtue of its conversion to D-aspartate, and the D-aspartate is then available to as a substrate for the reaction coupled to the MP to monatin reaction. Similarly, the oxaloacetate formed in the reaction of D-aspartate is available to act as a substrate for the reaction coupled to the L-tryptophan to indole-3-pyruvate reaction.

Non-limiting examples of suitable enzymes having aspartate racemase activity include ASPR-101 (BioCatalytics, Inc., 129 N. Hill Ave, Suite 103, Pasadena, Calif. 91106-1955) and homologs or mutants of an amino acid racemase (EC 5.1.1.-) which are capable of facilitating the conversion of L-aspartate to D-aspartate.

Non-limiting examples of potential sources from which aspartate racemases may be derived include: *Desulfurococcus, Thermococcus,* bivalve mollusk *Scapharca brouhtonii, Acinetobacter, Agrobacterium, Archaeoglobus, Bacillus, Bordetella, Bradyrhizobium, Brevibacterium, Burkholderia, Campylobacter, Candida, Caulobacter, Clostridium, Desulfitobacterium, Desulfotalea, Enterococcus, Erwinia, Escherichia, Ferroplasma, Helicobacter, Klebsiella, Lactobacillus, Mannheimia, Medicago, Mesorhizobium, Methanococcus, Methanosarcina, Oceanobacillus, Oenococcus, Pediococcus, Polaribacter, Pseudomonas, Pyrococcus, Ralsonia, Shigella, Sinorhizobium, Salmonella, Sphingomonas, Streptococcus, Thermoanaerobacter, Vibrio, Wolinella, Xanthomonas, Xanthobacter, Yersinia* and *Zymomonas*.

Where pyruvate reacts to form L-alanine when L-tryptophan reacts to form indole-3-pyruvate, an alanine racemase or functional equivalent can be provided to convert L-alanine to D-alanine. In such an instance, the L-alanine that is formed in the same reaction that produces indole-3-pyruvate is removed by virtue of its conversion to D-alanine, and the D-alanine formed from the conversion of L-alanine is then available to act as a substrate for the reaction coupled to the MP to monatin reaction. Similarly, the pyruvate formed in the reaction of D-alanine is available to act as a substrate for the reaction couple with the L-tryptophan to indole-3-pyruvate reaction.

Non-limiting examples of suitable alanine racemases include A8936 (Sigma, PO Box 14508, St. Louis, Mo., 63178) and the *Geobacillus stearothermophilus* alanine racemase as described in Example 4.

Non-limiting examples of potential sources from which the alanine racemase may be derived include: *Brucella abortus, Streptococcus faecalis Salmonella typhimurium, Escherichia coli, Bacillus subtilis, Pseudomonas aeruginosa, Vibrio cholerae, Schizosaccharomyces pombe, Bacillus cereus,* and *Lentinus edodes*.

Examples 9 and 12 illustrate the use of the above racemases, their impact on increasing the ratio of the desired monatin product, and provide potential sources for the racemase enzymes.

Turning to FIG. 5, a stereoinverting aminotransferase is used to facilitate the reaction of R-MP to monatin. Although typically the R-MP (or S-MP) reaction to form R,R monatin (or S,R monatin) is coupled with the reaction of a D-amino acid, a stereoinverting aminotransferase may facilitate the coupled reactions of R-MP (or S-MP) to form R,R monatin (or S,R monatin) using an L-amino acid. In this way, the L-amino acid product of the L-tryptophan aminotransferase reaction may be used as a substrate for the transamination of MP to monatin, and the product (i.e. oxaloacetate, pyruvate, and/or α-KG) of the reaction coupled to the MP to monatin reaction can be used as a starting material for the reaction coupled to the L-tryptophan to indole-3-pyruvate reaction. Non-limiting examples of stereoinverting aminotransferases that may be used include mutants derived from D-phenylglycine aminotransferase (EC 2.6.1.72, also known as D-4-hydroxyphenylglycine aminotransferase), D-methionine aminotransferase (EC 2.6.1.41, also known as D-met-aminotransferase and D-methionine-pyruvate aminotransferase), and homologs thereof. Non-limiting examples of potential sources from which the mutants of D-phenylglycine aminotransferase may be derived include *Pseudomonas*, such as *Pseudomonas putida* LW-4 and *Pseudomonas stutzeri* ST-201. Non-limiting examples of potential sources from which the D-methionine aminotransferase may be derived include cauliflower and peanut.

Examples 10 and 11 together provide potential sources of stereoinverting enzymes, and methods of making such enzymes. The examples also provide screening methods for identifying such enzymes. It is also contemplated that such enzymes may be evolved from stereoinverting enzymes known or found in nature. As a non-limiting example, the stereoinverting aminotransferase can be a homolog or mutant of a D-amino acid aminotransferase or a homolog or mutant of an amino acid racemase (EC 5.1.1.-).

Figure 6:
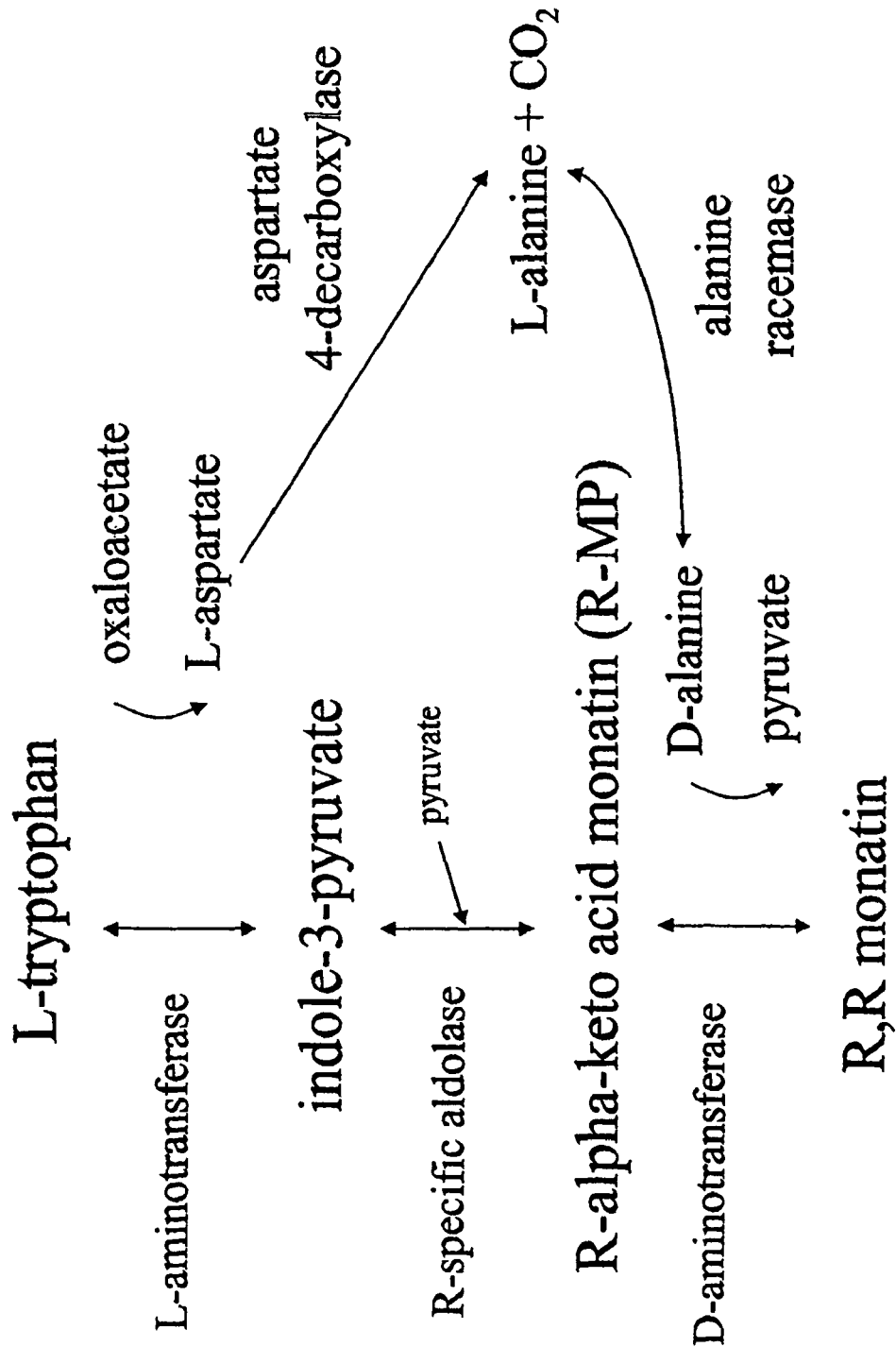
FIG. 6 is a flow chart that shows an example of yet another process for producing R,R monatin in accordance with the present invention. In this example, the process includes recycling the L-amino acid produced in the reaction forming indole-3-pyruvate with the D-amino acid used as a reactant with R-MP in the reaction forming R,R monatin through a series of conversion reactions. In the specific example diagrammed in FIG. 6, L-tryptophan is reversibly reacted with an L-aminotransferase and oxaloacetate to produce indole-3-pyruvate and L-aspartate. Indole-3-pyruvate is reacted in a reversible manner with pyruvate and an R-specific aldolase and converted to R-alpha-keto acid monatin (R-MP), and R-MP is reversibly reacted with a D-aminotransferase and D-alanine to form R,R monatin and pyruvate. The L-aspartate is converted to L-alanine and $CO_2$ using an aspartate 4-decarboxylase. The L-alanine is converted to D-alanine with an alanine racemase. For the purposes of the invention, it is not required that the reactions shown as being reversible proceed in the reverse direction.
Figure 7:
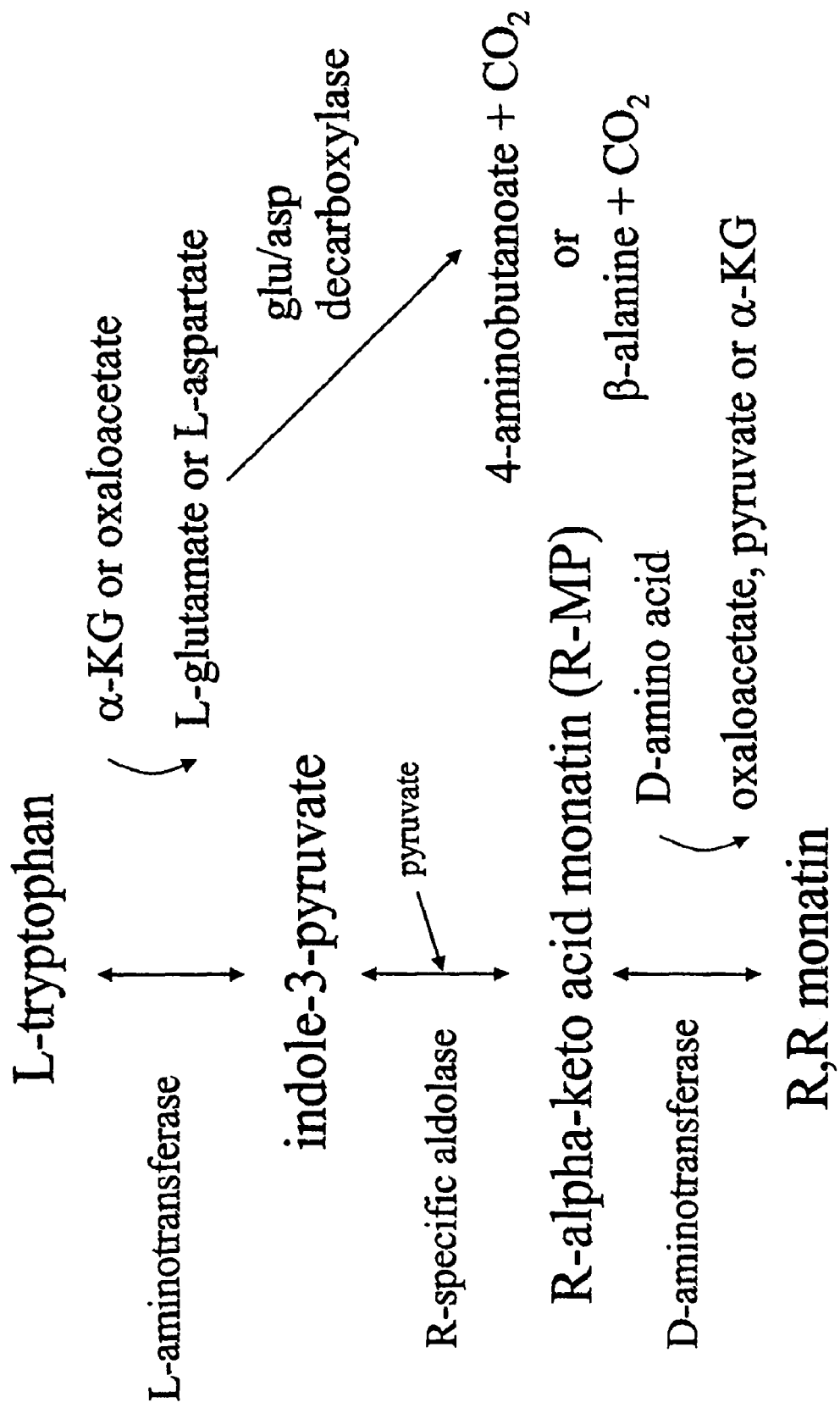
FIG. 7 is a flow chart that shows an example of yet another process for producing R,R monatin in accordance with the present invention. In this example, the process includes pushing the L-tryptophan reaction forward (i.e., driving the reaction toward the production of indole-3-pyruvate) by converting the L-amino acid byproduct of that reaction into another product. In this example, the L-amino acid L-aspartate byproduct is converted into L-alanine in an irreversible reaction using a decarboxylase. In the specific example diagrammed in FIG. 7, L-tryptophan is reversibly reacted with an L-aminotransferase and with alpha-ketoglutarate ($\alpha$-KG) or oxaloacetate to produce indole-3-pyruvate and L-glutamate (if $\alpha$-KG is used) or L-aspartate (if oxaloacetate is used). Indole-3-pyruvate is reversibly reacted with pyruvate and an R-specific aldolase and converted to R-alpha-keto acid monatin (R-MP). R-MP is reacted in a reversible manner with a D-aminotransferase and a D-amino acid to form R,R monatin and any of oxaloacetate, pyruvate or $\alpha$-KG. The L-glutamate or L-aspartate that was a product of the L-aminotransferase reaction is converted to either 4-aminobutanoate and $CO_2$ (if L-glutamate is the substrate) or to P-alanine and $CO_2$ (if L-aspartate is the substrate) using a glutamic acid or an aspartate decarboxylase. For the purposes of the invention, it is not required that the reactions shown as being reversible proceed in the reverse direction.

FIGS. 6 and 7 also illustrate modifications to the pathway of FIG. 1. The pathways illustrated in FIGS. 6 and 7 provide methods to push equilibrium reactions forward (i.e., toward the direction of monatin production) by removing the byproduct of the tryptophan reaction with an irreversible reaction and in some cases providing substrate for the MP reaction.

Turning to FIG. 6, the pathway shown removes the L-amino acid product of the reaction coupled to the tryptophan reaction by converting it to a different L-amino acid and $CO_2$, and then provides a substrate for the reaction coupled to the MP reaction by converting the newly formed L-amino acid to a D-amino acid. Specifically, L-tryptophan is shown to react alongside oxaloacetate to form indole-3-pyruvate and L-aspartate. An aspartate 4-decarboxylase (EC 4.1.1.12) or functional equivalent is used to facilitate the conversion of L-aspartate to L-alanine and carbon dioxide, and an enzyme with alanine racemase activity is used to facilitate the conversion of L-alanine to D-alanine, which D-alanine can serve as an amino donor for the conversion of R-MP to monatin.

Turning to FIG. 7, the pathway shown illustrates additional methods for removing the L-amino acid product of the reaction coupled to the tryptophan reaction. Embodiments as presented in the figure produce a byproduct(s) that is unavailable to react in the reverse direction, for example due to volatility (e.g., carbon dioxide) or by spontaneous conversion to an unreactive endproduct. An example of such an approach includes embodiments in which α-KG reacts alongside L-tryptophan to produce L-glutamate, and, if desired, a glutamate decarboxylase (EC 4.1.1.15) or functional equivalent can be provided to facilitate the conversion of L-glutamate to 4-aminobutanoate (with carbon dioxide as a byproduct). Non-limiting examples of potential sources from which the L-glutamate decarboxylase can be derived include: *Clostridium perfringens, C. welchii*, or *E. coli*.

Another example of such an approach for driving the tryptophan reaction forward (in the direction of monatin production) includes reactions in which oxaloacetate is utilized as a co-substrate in the reaction that utilizes L-tryptophan and in which the oxaloacetate is converted to L-aspartate; if desired, an aspartate decarboxylase (EC 4.1.1.11) or functional equivalent can be provided to facilitate the conversion of L-aspartate to β-alanine (with carbon dioxide as a byproduct).

Figure 8:
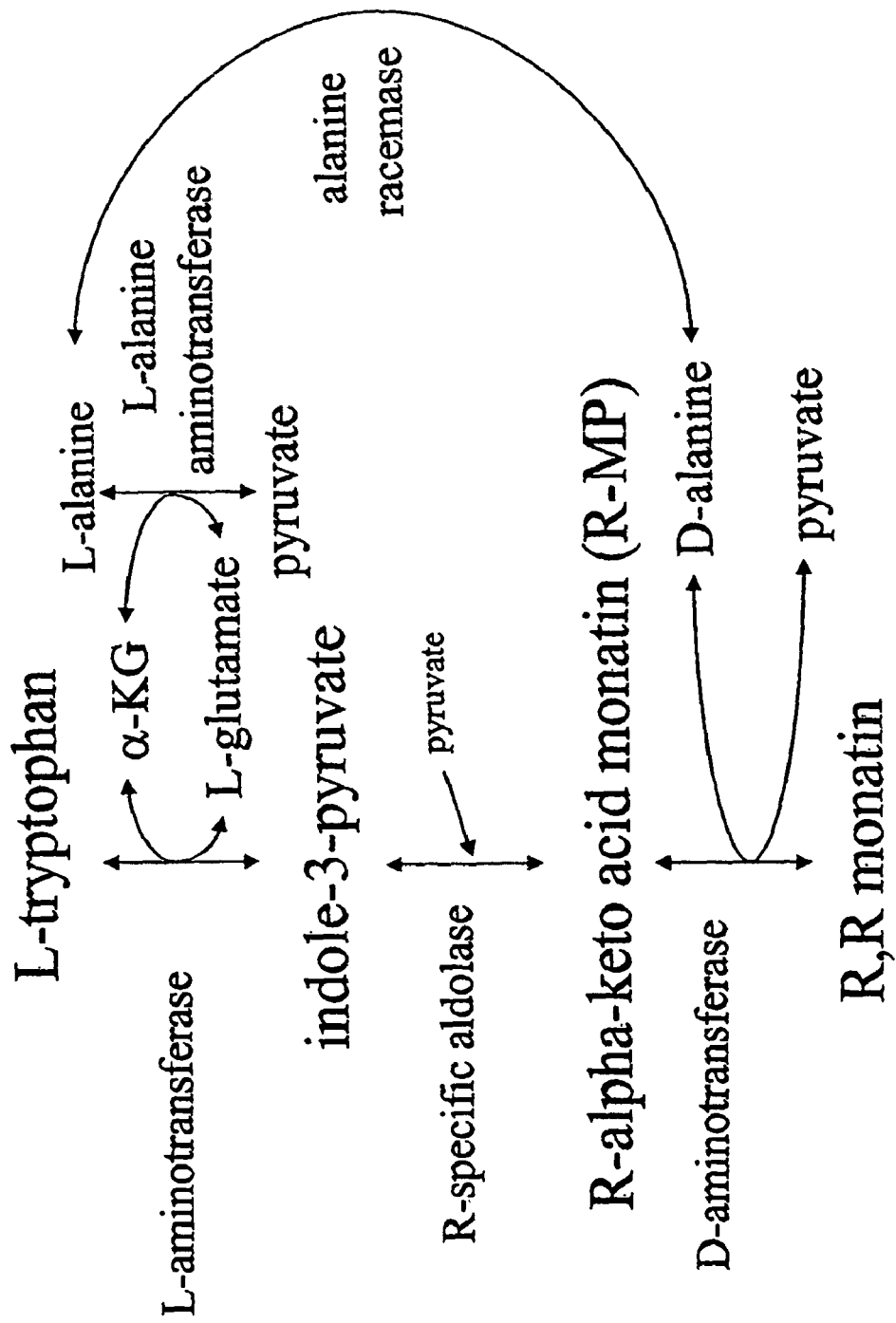
FIG. 8 is a flow chart that shows an example of yet another process for producing R,R monatin in accordance with the present invention. In this example, the process includes recycling the amino acid byproduct of the L-tryptophan reaction with the amino acid reactant of the R-MP reaction through a series of conversion reactions. In the specific example diagrammed in FIG. 8, L-tryptophan is reacted reversibly with an L-aminotransferase and with alpha-ketoglutarate ($\alpha$-KG) to produce indole-3-pyruvate and L-glutamate. Indole-3-pyruvate is reversibly reacted with pyruvate and an R-specific aldolase and converted to R-alpha-keto acid monatin (R-MP).

Turning to FIG. 8, the pathway shown illustrates yet additional methods for converting the L-amino acid product of the reaction coupled to the tryptophan reaction to a substrate for the reaction coupled to the MP reaction. Specifically, where α-KG is utilized in the same reaction as L-tryptophan, and in which the α-KG forms L-glutamate, an enzyme with L-alanine aminotransferase activity and pyruvate can be provided, wherein the L-alanine aminotransferase enzyme facilitates the reaction of pyruvate and L-glutamate to form L-alanine. An alanine racemase or functional equivalent can also be provided in order to facilitate the conversion of the L-alanine to D-alanine, which D-alanine can be used as a substrate along with MP to form monatin and pyruvate. See Example 12.

Implicitly described in the biosynthesis pathways above, and in the reactions described in the Examples below, are mixtures containing one or more compounds and/or enzymes required in the biosynthesis pathways for producing monatin, including R,R monatin, or monatin precursor, including R monatin precursor.

For production in vitro, any or all of the biosynthetic pathways described herein or individual steps in the pathways described herein can be conducted in in vitro solution or in vivo, in a host cell, in series or in parallel. When the method of the invention utilizes one or more reactions that are performed in vitro, the biosynthetic reaction that is performed in vitro can be performed by combining the desired ingredients for the reaction(s) by admixture in an aqueous reaction medium or solution. The reaction mixture so formed is maintained for a period of time sufficient for the desired product(s) to be synthesized.

Additionally, the activity of one or more enzymes can be enhanced through the continuous use of cofactors during purification of the one or more enzymes. For example, including pyridoxal-5'-phosphate when purifying *B. sphaericus* D-alanine aminotransferase results in increased activity (Example 14).

When one or more of the reactions in the pathways of the invention are to be performed in vitro, any or all of the enzymes utilized in the biosynthesis pathways described herein can optionally be immobilized onto a solid support. Examples of such solid supports include those that contain epoxy, aldehyde, chelators, or primary amine groups. Specific examples of suitable solid supports include, but are not limited to, Eupergit® C (Rohm and Haas Company, Philadelphia, Pa.) resin beads and SEPABEADS® EC-EP (Resindion). Example 21 illustrates the immobilization of the *B. sphaericus* D-alanine aminotransferase onto Eupergit® C resin beads. Example 22 illustrates the immobilization of the *Sinorhizobium meliloti* ProA aldolase onto Eupergit® C resin beads. Production of R,R monatin utilizing these immobilized enzymes is shown in Example 23.

When one or more of the reactions in the pathways of the invention are to be performed in vivo, a person of ordinary skill in the art may routinely optimize production of monatin in a microorganism, including R,R monatin, by various methods. Such a microorganism can be one that naturally is better than another in one or more of the following, non-limiting example embodiments, or that (relative to the microorganism before such modification) has been modified to:

Increase the uptake of tryptophan by the microorganism, such as genetically-engineering a microorganism to express or overexpress a tnaT gene;

Increase the uptake of D-tryptophan by the microorganism, such as by (i) growing a microorganism in a medium that contains only minimal amounts of L-amino acids, (ii) modifying the phenylalanine permease protein, and/or (iii) creating a chimeric protein that has at least that part of the sequence that confers the activity of a general aromatic amino acid permease protein and at least that part of the sequence that confers the activity of a phenylalanine permease protein (Cosgriff A J, Brasier G, Pi J, Dogovski C, Sarsero J P, Pittard A J. "A study of AroP-PheP chimeric proteins and identification of a residue involved in tryptophan transport," *J Bacteriol.*, 182(8): 2207-17 (2000));

Prevent or decrease secretion of indole-3-pyruvate by the microorganism;

Increase the uptake of indole-3-pyruvate by the microorganism;

Prevent or decrease the available indole-3-pyruvate from being degraded within the microorganism; and Alleviate the toxicity of D-tryptophan, such as by (i) overproducing tRNA$^{trp}$ in a microorganism that is not deficient in deacylase, (ii) genetically-engineering a microorganism to express or overexpress an appropriate D-amino acid deacylase, (iii) genetically-engineering a microorganism to express or overexpress tRNA$^{trp}$ and to express or overexpress an appropriate D-amino acid deacylase, (iv) generating a biomass of a genetically engineered microorganism and then induce the monatin operon, (v) using peptides or proteins rich in phenylalanine, tyrosine, and isoleucine to complement auxotrophs, (vi) genetically-engineering a microorganism to express or overexpress the general aromatic amino acid permease, (vii) not using or minimizing the use of D-amino acids other than D-tryptophan, (viii) providing L-tryptophan as the external substrate and genetically-engineering a microorganism to express or overexpress a racemase that converts the L-tryptophan to D-tryptophan, and/or (ix) providing D-tryptophan at a level below the threshold at which inhibition of D-tryptophan uptake occurs.

The above embodiments are described in more detail below.

The relative effect of each optimization method may be determined by comparing the amount of monatin produced by a genetically-engineered microorganism, with an appropriate control, e.g., a microorganism that has not been genetically engineered and/or exposed to the optimization method. The appropriate control to be utilized will be obvious to a person of ordinary skill in the art from the optimization method being tested.

As indicated above, one method for increasing the amount of monatin produced by a microorganism is to increase the uptake of tryptophan, one of the substrates utilized in the monatin biosynthesis pathways described above, by the microorganism. One way in which the amount of tryptophan that a microorganism uptakes may be increased is to genetically-engineer the microorganism to express or overexpress in monatin production strains a tnaT gene that encodes a protein that is homologous to, or in the family of, a sodium-dependent neurotransmitter transporter. In one embodiment, such a tnaT gene is that from *Symbiobacterium thermophilum*. Without being bound by theory, it is believed that expression of the *S. thermophilum* tnaT gene in *E. coli* confers on the bacterial host the ability to accumulate tryptophan from the medium and the ability to grow on tryptophan as a sole carbon source. Therefore, genetically-engineering the microorganism to express or overexpress the tnaT gene, for example tnaT from *S. thermophilum*, may be used to provide increased tryptophan uptake from the medium in which the microorganism is grown. Homologs of the tnaT gene from *S. thermophilum* found in bacteria and Archaea may also be used. Thus, genetically engineering the microorganism to express or overexpress a tnaT gene, for example a tnaT gene from *S. thermophilum*, or a homolog thereof, may be used to increase the amount of monatin, including R,R monatin, produced by a microorganism.

In some embodiments, in vivo monatin production, including R,R monatin production, may be increased by increasing the uptake of D-tryptophan, a substrate that may be utilized in a monatin biosynthesis pathway. One way in which the amount of D-tryptophan that a microorganism uptakes may be increased is to only include low amounts of L-amino acids in the growth medium of the microorganism. Without being bound by theory, it is believed that upon depletion of L-amino acids in the growth medium, the general aromatic amino acid permease system mediates the uptake of D-tryptophan from the growth medium. Thus, growing the microorganism in a growth medium with low amounts of L-amino acids may be used to increase the amount of monatin, including R,R monatin, produced by the genetically engineered microorganism.

In some embodiments, in vivo monatin production, including R,R monatin production, may be increased by modifying the phenylalanine permease protein to increase D-tryptophan uptake. The microorganism may be genetically engineered to express or overexpress such a modified phenylalanine permease protein, as well as to express or overexpress a TnaT transporter, to increase the amount of D-tryptophan available inside the microorganism which may then be converted into monatin. Thus, genetically-engineering the microorganism to express or overexpress a modified phenylalanine permease protein may be used to increase the amount of monatin, including R,R monatin, produced by the genetically engineered microorganism.

In some embodiments, in vivo monatin production, including R,R monatin production, may be increased by creating a chimeric protein that has at least that part of the sequence that confers the activity of a general aromatic amino acid permease protein and at least that part of the sequence that confers the activity of a phenylalanine permease protein. A chimeric protein of the general aromatic amino acid permease protein and the phenylalanine permease protein may be more effective in transporting tryptophan. Thus, genetically-engineering the microorganism to express or overexpress a chimeric protein of the general aromatic amino acid permease protein and the phenylalanine permease protein may be used to help maximize the amount of monatin, including R,R monatin, produced by the genetically engineered microorganism.

In some embodiments, in vivo monatin production, including R,R monatin production, may be increased by preventing or decreasing secretion of indole-3-pyruvate from a microorganism. Indole-3-pyruvate is an intermediate in the monatin synthetic pathways described above. One way in which secretion of indole-3-pyruvate from the microorganism may be prevented or decreased is to eliminate the activity of transporters that have the ability to transport indole-3-pyruvate or related compounds, such as auxins, from the microorganisms. For example, these transporters may be "knocked out" in the microorganisms used to produce monatin. Thus, monatin, including R,R monatin, may be produced in a microorganism in which the transporters that have the ability to transport indole-3-pyruvate from the microorganism are "knocked out."

In some embodiments, in vivo monatin production, including R,R monatin production, may be increased by increasing the uptake of indole-3-pyruvate by the microorganism. One way in which the uptake of indole-3-pyruvate by a microorganism may be increased is to increase expression of transporters that transport indole-3-pyruvate into the microorganism. Examples of transporters that may be activated or the activity of which may be increased include, but are not limited to, the amino acid/auxin family of transporters and proton symport permeases that exhibit homology to AUX1. All of these transporters have been reported to exist in fungi, such as *Saccharomyces cerevisiae*. Prusty, R., and Grisafi, P., *Proc. Natl Acad. Sci. USA* 101:4153-4157 (2004). Additionally, homologous transporters from other microorganisms may also be utilized. Thus, genetically-engineering the microorganism to express or overexpress a transporter that increases the uptake of indole-3-pyruvate into the microorganism may be used to increase the amount of monatin, including R,R monatin, produced by the genetically engineered microorganism.

In some embodiments, in vivo monatin production, including R,R monatin production, may be increased by preventing or decreasing the available indole-3-pyruvate from being degraded within the microorganism. A high concentration of the monatin precursor, a product of a reaction between indole-3-pyruvate and pyruvate will shift the equilibrium toward production of monatin. One way in which the indole-3-pyruvate may be prevented or decreased from being degraded within the microorganism is to "knock out" the ipdC gene, or homologs thereof The ipdC gene, or homologs thereof, encode indole-3-pyruvate decarboxylase. Indole-3-pyruvate decarboxylase decarboxylates indole-3-pyruvate to yield indole-3-acetaldehyde. The presence of indole-3-acetaldehyde initiates a cascade of additional degradation reactions. By "knocking out" production of indole-3-pyruvate decarboxylase, the available indole-3-pyruvate should not be degraded. The higher concentration of indole-3-pyruvate should shift the equilibrium toward production of monatin. Thus, genetically-engineering the microorganism so that expression or overexpression of the ipdC gene, or homologs thereof, is decreased may be used to increase the amount of monatin, including R,R monatin, produced by the genetically engineered microorganism.

In some embodiments, in vivo monatin production, including R,R monatin production, may be increased by inactivating the indole-3-acetaldehyde dehydrogenase. Indole-3-acetaldehyde dehydrogenase is involved in the degradation pathway of indole-3-acetaldehyde. By inactivating the indole-3-acetaldehyde dehydrogenase, the concentration of indole-3-acetaldehyde should be increased, shifting the equilibrium back toward production of indole-3-pyruvate. As a result, the higher concentration of indole-3-pyruvate should shift the equilibrium of the reaction toward production of monatin. Thus, genetically-engineering the microorganism so that expression of indole-3-acetaldehyde is decreased may be effective in increasing the amount of monatin, including R,R monatin, produced by the genetically engineered microorganism.

In some embodiments, in vivo monatin production, including R,R monatin production, may be increased by alleviating the toxicity of D-tryptophan and/or increasing the tolerance and uptake of D-tryptophan by the microorganism. Although some of the biosynthetic pathways for production of monatin described above utilize D-tryptophan as a starting material, D-tryptophan may be toxic to the microorganism. Therefore, alleviating the toxicity and/or increasing the tolerance and uptake of D-tryptophan by the microorganism may be used to increase the amount of monatin, including R,R monatin, produced by a microorganism.

One way in which the toxicity of D-tryptophan may be alleviated or the tolerance and uptake of D-tryptophan may be increased is to genetically-engineer a microorganism that is not deficient in deacylase to overproduce tRNA$^{trp}$, (i.e., the tRNA for tryptophan).

Another way in which the toxicity of D-tryptophan may be alleviated or the tolerance and uptake of D-tryptophan may be increased is to genetically-engineer the microorganism to express or overexpress the appropriate D-amino acid deacylases, including the tyrosine or tryptophan D-amino acid deacylases. By expressing or overexpressing the appropriate D-amino acid deacylase, it is expected that recycling of the tRNA species would occur and that a build up of a pool of tRNAs charged with D-amino acids, such as tRNA$^{trp}$, would be avoided. Thus, genetically-engineering the microorganism to express or overexpress the appropriate D-amino deacylase may be effective in increasing the amount of monatin, including R,R monatin, produced by the microorganism.

Yet another way in which the toxicity of D-tryptophan may be alleviated or the tolerance and uptake of D-tryptophan may be increased is to genetically-engineer a microorganism to express or overexpress tRNA$^{trp}$ and to express or overexpress the appropriate D-amino acid deacylases, including tyrosine or tryptophan D-amino acid deacylases. Thus, genetically-engineering the microorganism to express or overexpress the appropriate D-amino deacylase, in combination with expression or overexpression of tRNA$^{trp}$, may be used to increase the amount of monatin, including R,R monatin, produced by the microorganism.

Still yet another way in which the toxicity of D-tryptophan may be alleviated or the tolerance and uptake of D-tryptophan may be increased is to generate a biomass of a genetically engineered microorganism, and then, induce the monatin operon. The biomass induced for monatin production may then be transferred to fresh media that is depleted of L-amino acids. The transfer of the biomass to the fresh media depleted of L-amino acids should alleviate the inhibitory effects of L-tyrosine and also promote D-tryptophan uptake. Thus, generating a biomass and transferring it to a medium with low concentrations of L-amino acids may be used to increase the amount of monatin, including R,R monatin, produced by the genetically engineered microorganism.

Another way in which the toxicity of D-tryptophan may be alleviated or the tolerance and uptake of D-tryptophan may be increased in auxotrophic strains, especially tyrosine and phenylalanine auxotrophic strains, is to use peptides or proteins rich in phenylalanine, tyrosine, and isoleucine to complement auxotrophs and alleviate competition for the transport of the D-amino acids, such as D-tryptophan. Thus, growing the microorganism in a medium containing peptides or protein rich in phenylalanine, tyrosine, and isoleucine may be used to increase the amount of monatin, including R,R monatin, produced by the microorganism.

Yet another way in which the toxicity of D-tryptophan may be alleviated or the tolerance and uptake of D-tryptophan may be increased is to genetically-engineer the microorganism to express or overexpress the general aromatic amino acid permease ("aroP"), which will increase D-tryptophan uptake. The expression or overexpression of the aroP gene may be increased by cloning the aroP gene on a high copy number plasmid. The aroP gene and the monatin operon may be induced concurrently to generate cells that are capable of both uptaking D-tryptophan and then converting the D-tryptophan to monatin. Thus, genetically-engineering the microorganism to express or overexpress the aroP gene and concurrently inducing the monatin operon may be used to increase the amount of monatin, including R,R monatin, produced by the genetically engineered microorganism.

Still yet another way in which the toxicity of D-tryptophan may be alleviated or the tolerance and uptake of D-tryptophan may be increased is to avoid the use of D-amino acids, other than D-tryptophan. Thus, growing the microorganism in a medium that does not contain D-amino acids other than D-tryptophan may be used to increase the amount of monatin, including R,R monatin, produced by the microorganism.

Another mechanism in which the toxicity of D-tryptophan may be alleviated or the tolerance and uptake of D-tryptophan may be increased is to provide L-tryptophan as the external substrate, rather than D-tryptophan. A racemase may then be used to convert the L-tryptophan to D-tryptophan. Genetically-engineering the microorganism to express or overexpress a racemase, such as those described above, that converts L-tryptophan to D-tryptophan may be used to increase the amount of monatin, including R,R monatin, produced by the microorganism.

Yet another mechanism in which the toxicity of D-tryptophan may be alleviated or the tolerance and uptake of D-tryptophan may be increased is to provide D-tryptophan at a level below the threshold at which inhibition of D-tryptophan uptake occurs. Thus, growing the microorganism in a medium that contains D-tryptophan in an amount that is lower than the inhibition amount may be used to increase the amount of monatin, including R,R monatin, produced by the genetically engineered microorganism.

Furthermore, the biosynthetic pathways described herein can utilize a substituted tryptophan to yield monatin derivatives that are likely to be sweet. In some embodiments, the substituted tryptophan to be used in the biosynthetic pathways described herein includes chlorinated tryptophan and 5-hydroxytryptophan.

For example, chlorinated D-tryptophans, which have structural similarities to R,R monatin, have been identified as non-nutritive sweeteners (particularly 6-chloro-D-tryptophan). Similarly, halogenated and hydroxy-substituted forms of monatin have been found to be sweet. U.S. Published Patent Application No. 2005/0118317. Halogens and hydroxyl groups should be substitutable for hydrogen, particularly on positions 1-4 of the benzene ring in the indole of tryptophan, without interfering in subsequent conversions to D- or L-tryptophan, indole-3-pyruvate, MP, or monatin. Substituted indoles have been shown in the literature to be suitable substrates for PLP-enzymes and have yielded substituted tryptophans. Fukuda, D. S., et al., "Production of Substituted L-Tryptophans by Fermentation," *Appl. Environ. Microbiol.*, 21:841-43 (1971). The halogen does not appear to sterically hinder the tryptophan synthase beta subunits catalytic mechanism and the enantiospecificity was also intact.

The individual reactions shown in the biosynthetic pathways described herein can be facilitated (catalyzed) by a single enzyme or by a mixture of multiple enzymes acting concurrently.

The methods of the invention can be used to make a monatin composition that contains a desired percentage of R,R-monatin, or a minimum desired percentage of R,R-monatin. In addition to the reaction steps described above, a specific reaction step can be catalyzed by more than one enzyme, for example, a mixture of enzymes, so that the resulting composition or preparation contains a desired percentage of R,R-monatin, including, for example, a minimum desired percentage of R,R-monatin, or a maximum desired percentage of R,R-monatin. Alternatively, the monatin made by two separate engineered pathways according to the methods of the invention be combined to produce a composition or preparation containing such desired percentage of R,R-monatin.

When an enzyme of a designated class of enzymes is utilized as an example, it is expected that an enzyme with at least about 50%, 55%, 60%, 65%, 70%, 75%, 80%, 82%, 85%, 87%, 90%, 91%, 92%, 93%, 94%, 95%, 96%, 97%, 98%, and 99% homology could also be utilized in that reaction. For example, an R-specific aldolase with at least about 50%, 55%, 60%, 65%, 70%, 75%, 80%, 82%, 85%, 87%, 90%, 91%, 92%, 93%, 94%, 95%, 96%, 97%, 98%, and 99% homology to the aldolase of SEQ ID NO:22 could be utilized in any of the above described pathways to yield R,R monatin. Another non-limiting example of an enzyme that could be utilized in any of the above described pathways to yield R,R monatin includes a D-aminotransferase with at least about 50%, 55%, 60%, 65%, 70%, 75%, 80%, 82%, 85%, 87%, 90%, 91%, 92%, 93%, 94%, 95%, 96%, 97%, 98%, and 99% homology to the D-aminotransferase corresponding to ATCC 4978 with a T243N mutation. Yet another non-limiting example of an enzyme that could be utilized in any of the above described pathways to yield R,R monatin includes a broad specificity amino acid racemase with at least about 50%, 55%, 60%, 65%, 70%, 75%, 80%, 82%, 85%, 87%, 90%, 91%, 92%, 93%, 94%, 95%, 96%, 97%, 98%, and 99% homology to the broad specificity amino acid racemase of SEQ ID NO:120.

Additionally, when an enzyme of a designated class of enzymes is utilized as an example, it is expected that a fragment of that enzyme that has the same activity could also be utilized in that reaction. For example, a fragment of the aldolase of SEQ ID NO:22 that also functions as an aldolase could be utilized in any of the above described pathways to yield R,R monatin.

Monatin that is produced utilizing one or more of the polypeptides or biosynthetic pathways disclosed herein, is generally at least about 0.5-30% R,R-monatin, by weight of the total monatin produced. In other embodiments, the monatin produced utilizing one or more of the polypeptides or biosynthetic pathways disclosed herein, is greater than 30% R,R-monatin, by weight of the total monatin produced; for example, the R,R-monatin is 40%, 50%, 60%, 65%, 70%, 75%, 80%, 85%, 90%, 95% or 99% of the total monatin produced Alternatively, various amounts of two or more preparations of monatin can be combined so as to result in a preparation that is a desired percentage of R,R-monatin. For example, a monatin preparation that is 30% R,R-monatin can be combined with a monatin preparation that is 90% R,R-monatin; if equal amounts of 30% and 90% R,R-monatin preparations are combined, the resulting monatin preparation would be 60% R,R-monatin.

The monatin, or an intermediate (including monatin precursor), produced utilizing one or more of the polypeptides or biosynthetic pathways disclosed herein, may be purified from the components of the reaction. In one embodiment, the monatin or intermediate, such as monatin precursor, may be purified simply by removing the substance that is to be purified from the enzyme preparation in which it was synthesized.

In other embodiments, the intermediate, monatin precursor or monatin is purified from a preparation in which it was synthesized so that the resulting "purified" composition or preparation is at least about 5-60% monatin by weight of total organic compounds. In another embodiment, the monatin or intermediate, such as monatin precursor, may be purified to a degree of purity of at least about 70%, 80%, 90%, 95% or 99% by weight of total organic compounds. The monatin, or the intermediate (including monatin precursor), produced utilizing one or more of the polypeptides or biosynthetic pathways disclosed herein, may be purified from the components of the reaction by any method known to a person of ordinary skill in the art. In one embodiment, the monatin or intermediate may be purified as described in Example 13. Optimally, the purified monatin or intermediate may be repeatedly recrystallized until the desired degree of purity is achieved.

All patents and publications cited herein are fully incorporated by reference herein in their entirety.

EXAMPLES

Example 1

Detection of Monatin, Monatin Precursor, Tryptophan, Alanine, Aspartate, and Glutamate This example describes methods used to detect the presence of monatin, monatin precursor ("MP"), tryptophan, aspartate, alanine, and glutamate. It also describes a method for the separation and detection of the four stereoisomers of monatin.

LC/MS/MS Multiple Reaction Monitoring ("MRM") Analysis of Monatin and Tryptophan Analyses of mixtures for monatin and tryptophan derived from in vitro or in vivo biochemical reactions were performed using a Waters/Micromass liquid chromatography-tandem mass spectrometry (LC/MS/MS) instrument including a Waters 2795 liquid chromatograph with a Waters 996 Photo-Diode Array (PDA) absorbance monitor placed in series between the chromatograph and a Micromass Quattro Ultima triple quadrupole mass spectrometer. LC separations were made using an Xterra MS $C_8$ reversed-phase chromatography column, 2.1 mm×250 mm at 40° C. The LC mobile phase consisted of A) water containing either (i) 0.05% (v/v) trifluoroacetic acid or (ii) 0.3% formic acid and 10 mM ammonium formate and B) methanol containing either (i) 0.05% (v/v) trifluoroacetic acid or (ii) 0.3% formic acid and 10 mM ammonium formate.

If the LC mobile phase consisted of A) water containing 0.05% (v/v) trifluoroacetic acid and B) methanol containing 0.05% (v/v) trifluoroacetic acid, gradient elution was linear from 5% B to 35% B, 0-4 min, linear from 35% B to 60% B, 4-6.5 min, linear from 60% B to 90% B, 6.5-7 min, isocratic at 90% B 7-11 min, linear from 90% B to 95% B, 11-12 min, linear from 95% B to 5% B, 12-13 min, with a 2 min re-equilibration period between runs. The flow rate was 0.25 mL/min, and PDA absorbance was monitored from 200 nm to 400 nm. All parameters of the ESI-MS were optimized and selected based on generation of protonated molecular ions ([M+H]$^+$) of the analytes of interest, and production of characteristic fragment ions. The following instrumental parameters were used for LC/MS/MS Multiple Reaction Monitoring (MRM) analysis of monatin and tryptophan: Capillary: 3.5 kV; Cone: 40 V; Hex 1:20 V; Aperture: 0 V; Hex 2:0 V; Source temperature: 100° C.; Desolvation temperature: 350° C.; Desolvation gas: 500 L/h; Cone gas: 50 L/h; Low mass resolution (Q1): 12.0; High mass resolution (Q1): 12.0; Ion energy: 0.2; Entrance: −5 V; Collision Energy: 8; Exit: 1V; Low mass resolution (Q2): 15; High mass resolution (Q2): 15; Ion energy (Q2): 3.5; Multiplier: 650. Five monatin-specific parent-to daughter MRM transitions are used to specifically detect monatin in in vitro and in vivo reactions. The transitions monitored are 293.1 to 158.3, 293.1 to 168.2, 293.1 to 211.2, 293.1 to 230.2, and 293.1 to 257.2. Tryptophan is monitored with the MRM transition 204.7 to 146.4. For internal standard quantification of monatin and tryptophan, four calibration standards containing four different ratios of each analyte to d5-tryptophan and d5-monatin, are analyzed. These data are subjected to a linear least squares analysis to form a calibration curve for monatin and tryptophan. To each sample is added a fixed amount of d5-tryptophan and d5-monatin (d5-monatin was synthesized from d5-tryptophan according to the methods from WO03/091396 A2), and the response ratios (monatin/d5-monatin; tryptophan/d5-tryptophan) used in conjunction with the calibration curves described above to calculate the amount of each analyte in the mixtures.

If the LC mobile phase was A) water containing 0.3% formic acid and 10 mM ammonium formate and B) methanol containing 0.3% formic acid and 10 mM ammonium formate, the gradient elution was linear from 5% B to 45% B, 0-8.5 min, linear from 45% B to 90% B, 8.5-9 min, isocratic from 90% B to 90% B, 9-12.5 min, linear from 95% B to 5% B, 12.5-13 min, with a 4 min re-equilibration period between runs. The flow rate was 0.27 mL/min, and PDA absorbance was monitored from 210 nm to 400 nm. All parameters of the ESI-MS were optimized and selected based on generation of protonated molecular ions ([M+H]$^+$) of the analytes of interest, and production of characteristic fragment ions. The instrumental parameters used for this secondary mobile phase are the same as above. Four monatin-specific parent-to daughter MRM transitions and one tryptophan specific parent to daughter transition are used to specifically detect monatin and tryptophan in in vitro and in vivo reactions. The transitions monitored are 293.1 to 158.0, 293.1 to 168.0, 293.1 to 211.5, and 293.1 to 257.0. Tryptophan is monitored with the MRM transition 205.2 to 146.1. For internal standard quantification of monatin and tryptophan, four calibration standards containing four different ratios of each analyte to d5-tryptophan and d5-monatin, are analyzed. These data are subjected to a linear least squares analysis to form a calibration curve for monatin and tryptophan. To each sample is added a fixed amount of d5-tryptophan and d5-monatin (d5-monatin was synthesized from d5-tryptophan according to the methods from WO03/091396 A2), and the response ratios (monatin/d5-monatin; tryptophan/d5-tryptophan) in conjunction with the calibration curves described above are used to calculate the amount of each analyte in the mixtures. Parent to daughter mass transitions monitored for d5-tryptophan and d5-monatin are 210.2 to 151.1, and 298.1 to 172.0 respectively.

Accurate Mass Measurement of Monatin

High resolution MS analysis was carried out using an Applied Biosystems-Perkin Elmer Q-Star hybrid quadrupole/time-of-flight mass spectrometer. The measured mass for protonated monatin used tryptophan as an internal mass calibration standard. The calculated mass of protonated monatin, based on the elemental composition $C_{14}H_{17}N_2O_5$ is 293.1137. Monatin produced using the biocatalytic process described in Examples 2 and 3 showed a measured mass of 293.1144. This is a mass measurement error of less than 2 parts per million ("ppm"), providing conclusive evidence of the elemental composition of monatin produced enzymatically.

Chiral LC/MS/MS ("MRM") Measurement of Monatin

Determination of the stereoisomer distribution of monatin in in vitro and in vivo reactions was accomplished by derivitization with 1-fluoro-2-4-dinitrophenyl-5-L-alanine amide ("FDAA"), followed by reversed-phase LC/MS/MS MRM measurement.

Derivatization of Monatin with FDAA

To 50 μL of sample or standard and 10 μL of internal standard was added either 100 μL or 200 μL of a 1% solution of FDAA in acetone. Twenty or forty μL, respectively, of 1.0 M sodium bicarbonate was added, and the mixture incubated for 1 h at 40° C. with occasional mixing. The sample was removed and cooled, and neutralized with 20 μL of 2.0 M HCl (more HCl may be required to effect neutralization of a buffered biological mixture). After degassing was complete, samples were ready for analysis by LC/MS/MS.

LC/MS/MS Multiple Reaction Monitoring for the Determination of the Stereoisomer Distribution of Monatin in in Vitro and in Vivo Reactions Analyses were performed using the LC/MS/MS instrumentation described above. LC separations capable of separating all four stereoisomers of monatin (specifically FDAA-monatin) were performed on a Phenomenex Luna 2.0×250 mm (3 μm) C18 (2) reversed phase chromatography column at 40° C. The LC mobile phase consisted of A) water containing 0.05% (mass/volume) ammonium acetate and B) acetonitrile. The elution was isocratic at 13% B, 0-2 min, linear from 13% B to 30% B, 2-15 min, linear from 30% B to 80% B, 15-16 min, isocratic at 80% B 16-21 min, and linear from 80% B to 13% B, 21-22 min, with an 8 min re-equilibration period between runs. The flow rate was 0.23 mL/min, and PDA absorbance was monitored from 200 nm to 400 nm. All parameters of the ESI-MS were optimized and selected based on generation of deprotonated molecular ions ([M–H]⁻) of FDAA-monatin, and production of characteristic fragment ions.

The following instrumental parameters were used for LC/MS analysis of monatin in the negative ion ESI/MS mode: Capillary: 2.0 kV; Cone: 25 V; Hex 1:10 V; Aperture: 0 V; Hex 2:0 V; Source temperature: 100° C.; Desolvation temperature: 350° C.; Desolvation gas: 500 L/h; Cone gas: 50 L/h; Low mass resolution (Q1): 12.0; High mass resolution (Q1): 12.0; Ion energy: 0.2; Entrance: −5V; Collision Energy: 20; Exit: 1V; Low mass resolution (Q2): 12; High mass resolution (Q2): 12; Ion energy (Q2): 3.0; Multiplier: 650. Three FDAA-monatin-specific parent-to daughter transitions are used to specifically detect FDAA-monatin in in vitro and in vivo reactions. The transitions monitored for monatin are 543.2 to 268.1, 543.2 to 499.3, and 543.2 to 525.3. Monatin internal standard derivative mass transition monitored was 548.2 to 530.3. Identification of FDAA-monatin stereoisomers is based on chromatographic retention time as compared to purified synthetic monatin stereoisomers, and mass spectral data. An internal standard is used to monitor the progress of the reaction and for confirmation of retention time of the S,S stereoisomer.

Liquid Chromatography-Post Column Fluorescence Detection of Amino Acids Including Glutamate and Alanine Liquid chromatography with post-column fluorescence detection (LC/OPA) for the determination of glutamate and alanine in in vitro and in vivo reactions was performed on a Waters 2690 LC system or equivalent combined with a Waters 474 scanning fluorescence detector, and a Waters post-column reaction module. Semi-quantitative analyses of monatin and tryptophan were also performed using this method. LC separations were performed on an Interaction-Sodium loaded ion exchange column at 60° C. Mobile phase A was Pickering Na 328 buffer (Pickering Laboratories, Inc.; Mountain View, Calif.). Mobile phase B was Pickering Na 740 buffer. The gradient elution was from 0% B to 100% B, 0-20 min, isocratic at 100% B, 20-36 min, and linear from 100% B to 0% B, 36-37 min, with at least a 5 min re-equilibration period between runs, depending on sample matrix. The flow rate for the mobile phase was 0.5 mL/min. The flow rate for the OPA post-column derivatization solution was 0.5 mL/min. The fluorescence detector settings were EX 338-340 nm and Em 420-425 nm. Norleucine was employed as an internal standard for the analysis. Identification of amino acids was based on chromatographic retention time data for purified standards.

Detection of L- and D-Amino Acids by LC/MS/MS

Samples containing a mixture of L- and D-amino acids such as lysine, alanine, methionine, tyrosine, leucine, phenylalanine, tryptophan, glutamate, and aspartate from biochemical reaction experiments were first treated with formic acid to denature protein. The sample was then centrifuged and filtered through a 0.45 μm nylon syringe filter prior to LC/MS/MS analysis. Identification of L- and D-amino acids was based on retention time and mass selective detection. LC separation was accomplished by using Waters 2690 liquid chromatography system and an ASTEC 2.1 mm×250 mm Chirobiotic TAG chromatography column with column temperature set at 45° C. LC mobile phase A and B were 0.25% acetic acid and 0.25% acetic acid in methanol, respectively. Isocratic elution was used for all methods to separate the L and D isomers. Lysine was eluted using 80% mobile phase A, and 20% B. Glutamate, alanine, and methionine were separated with elution of 60% mobile phase A and 40% B and a flow rate of 0.25 mL/min. Aspartate, tryptophan, tyrosine, leucine, and phenylalanine were separated isomerically with 30% mobile phase A and 70% B with a flow rate of 0.3 mL/min for all but phenylalanine, which was run at a flow rate of 0.25 mL/min.

The detection system for analysis of L- and D-amino acids included a Waters 996 Photo-Diode Array (PDA) detector and a Micromass Quattro Ultima triple quadrupole mass spectrometer. The PDA, scanning from 195 to 350 nm, was placed in series between the chromatography system and the mass spectrometer. Parameters for the Micromass Quattro Ultima triple quadrupole mass spectrometer operating in positive electrospray ionization mode (+ESI) were set as the following: Capillary: 3.0 kV; Cone: 20 V; Hex 1:15 V; Aperture: 1 V; Hex 2:0 V; Source temperature: 100° C.; Desolvation temperature: 350° C.; Desolvation gas: 530 L/h; Cone gas: 30 L/h; Low mass Q1 resolution: 12.5; High mass Q1 resolution: 12.5; Ion energy 1:0.2; Entrance: −5; Collision: 8; Exit 1:10; Low mass Q2 resolution: 12.5; High mass Q2 resolution: 12.5; Ion energy 2:0.5; Multiplier: 650 V. MS/MS experiments with Multiple Reaction Monitoring (MRM) mode were set up to selectively monitor reaction transitions of 147.8 to 84.2 and 147.8 to 102.1 for glutamate, 134.00 to 74.30, and 134.00 to 88.2 for aspartate, 147.3 to 85.0 for lysine, 150.3 to 104.8 for methionine, 182.3 to 137.0 for tyrosine, 132.3 to 87.0 for leucine, and 166.3 to 121.0 for phenylalanine. In the case where two transitions are listed, the latter transitions were used for quantification. For tryptophan, MS/MS experiments with Multiple Reaction Monitoring (MRM) mode were set up to selectively monitor reaction transitions of 205.2 to 118.2, 205.2 to 146.1, and 205.2 to 188.2, and the transition from 212.1 to 151.1 for d8-DL tryptophan. Tryptophan quantification was achieved by determining the ratio of analyte response of transition 205.2 to 146.1 to that of the internal standard, d8-D,L tryptophan. Alternatively, quantification of tryptophan, glutamate, and aspartic acids were based off signal responses of m/z=146.5, m/z=102.1, and m/z=88.2, respectively.

Production of Monatin and Monatin Precursor ("MP") for Standards and for Assays

Production of Monatin

A racemic mixture of R,R and S,S monatin was synthetically produced as described in U.S. Pat. No. 5,128,482.

The R,R and S,S monatin were separated by a derivatization and hydrolysis step. Briefly, the monatin racemic mixture was esterified, the free amino group was blocked with Cbz, a lactone was formed, and the S,S lactone was selectively hydrolyzed using an immobilized protease enzyme. The monatin can also be separated as described in Bassoli, A. et al., *Eur. J. Org. Chem.*, 8:1652-1658, (2005).

MP Production

R-MP was produced by the transamination of R,R monatin using AT-103 broad range D-aminotransferase (BioCatalytics) in 0.1 M potassium phosphate buffer, using sodium pyruvate as the amino acceptor. S-MP was produced by the transamination of S,S monatin using AT-102 L-aminotransferase (BioCatalytics) in 0.1 M potassium phosphate buffer, using sodium pyruvate as the amino acceptor. Both reactions were carried out at 30° C. and at a pH of approximately 8.0-8.3, for approximately 20 hours. Both compounds were purified using preparative scale HPLC with a Rohm and Haas (Philadelphia, Pa.) hydrophobic resin (XAD™ 1600), eluting in water. Samples containing greater than 90% purity monatin precursor were collected and freeze-dried.

Example 2

Production of Monatin from Indole-3-Pyruvate

AT-103 transaminase was part of a transaminase library purchased from BioCatalytics (Pasadena, Calif.) and the enzyme was tested for production of monatin in coupled reactions using the ProA aldolase from *C. testosteroni*. The aldolase was prepared as described in WO 03/091396 A2. AT-103 is a broad specificity D-transaminase (EC 2.6.1.21) from a *Bacillus* species that requires a D-amino acid (such as D-glutamate, D-aspartate, or D-alanine) as the amino acid donor. Enzymes and additional components/substrates were added directly to the reaction buffer provided in the kit, which contained 100 mM potassium phosphate buffer pH 7.5, 100 mM amino donor, and 0.1 mM pyridoxal-5'-phosphate ("PLP"). To one mL of reaction buffer were added: 4 mg indole-3-pyruvate, 20 mg pyruvate, approximately 50 μg ProA provided in a cellular extract, 1 μL 2 M $MgCl_2$, and 2 mg of the aminotransferase enzyme (AT-103). Reactions were performed in duplicate. The reactions were incubated overnight at 30° C. with gentle shaking (100 rpm). The samples were filtered and submitted for reversed-phase LC/MS/MS analysis as described in Example 1. The results indicated that approximately 370 μg/mL monatin were produced using AT-103 enzyme. The results were further analyzed to determine ratios of S,R/R,S versus R,R/S,S monatin, on the basis of the peak areas of the two stereoisomer pools that resolve during the chromatographic separation. Of the total monatin produced by AT-103, 69% was R,R/S,S monatin in comparison to the mixed isomers. This enzyme (AT-103) is homologous to the *Bacillus subtilis* DAT enzyme described in WO 03/091396 A2, which is known to have a broad specificity for D-amino acids. Chiral analysis was performed using the FDAA methodology described in Example 1, which verified that the D-aminotransferase was making predominantly R,R monatin, and some S,R monatin as expected. Further transamination experiments with S,S monatin or R,R monatin and α-ketoglutarate as substrates verified that the BioCatalytics enzyme was highly selective for the D-configuration at carbon 4, as expected. In these experiments, no glutamate was detected in the reaction with S,S monatin and α-ketoglutarate as substrates.

To decrease the amount of S,S monatin or R,S monatin produced as byproducts in coupled reactions with AT-103 (the broad range D-transaminase) and the ProA aldolase, the aldolase was purified using His-Bind cartridges, following manufacturer's protocols (Novagen, Madison, Wis.). The purified enzyme preferably should not contain wild-type L-aminotransferase activities that can be present in cellular extracts (such as the native *E. coli* AspC or TyrB activities). The His-Bind eluent was desalted to remove imidazole using PD-10 columns (G25 Sephadex, Amersham-Pharmacia) and was eluted in 50 mM Tris-Cl, pH 7. Experiments were carried out in duplicate in a volume of 1 mL and contained 100 mM Tris-Cl buffer, pH 7.8, 50 μg ProA aldolase, 4 mg indole-3-pyruvate, 1 or 2 mg D-aminotransferase, 200 mM sodium pyruvate, 2 mM $MgCl_2$, 3 mM potassium phosphate, 0.1 mM PLP, and 14.7 mg of D-glutamate. The tubes were incubated at 30° C. with gentle shaking. Two-hour time points were taken and frozen immediately at −20° C. The pH was adjusted at two hours from 5 to between 7-8 using NaOH, and the assays were incubated overnight. Samples were filtered and analyzed for monatin as described in Example 1. The two-hour samples did not have detectable amounts of monatin, probably due to the low pH. The overnight samples contained approximately 190 ng/mL monatin when 1 mg of D-aminotransferase was used, and approximately 84% was R,R monatin and 16% was S,R monatin. When 2 mg of D-aminotransferase were used, 540 ng/mL monatin was produced, approximately 71% was R,R monatin.

Similar experiments were conducted using Biocatalytics Aminotransferase buffer, which contained 100 mM potassium phosphate pH 7.5, 0.1 mM PLP, and 100 mM D-glutamate. Solid indole-3-pyruvate and D-aminotransferase were added as above. ProA aldolase (50 μg), $MgCl_2$, and 50 mM pyruvate were added from stock solutions. The assays were treated as above, although no pH adjustment was required in this case. A negative control was done with just the BioCatalytics supplied enzyme and buffer, which did not contain monatin. The experimental results are shown in Table 1.

TABLE 1

Production of Monatin from Indole-3-Pyruvate in Phosphate Buffer

| D-Aminotransferase (mg) | Time (hours) | Total Monatin (ng/mL) | % R,R |
|---|---|---|---|
| 0 | 2 | 0 | n/a |
| 1 | 2 | 6780 | not determined |
| 2 | 2 | 13170 | 55% |
| 0 | 16 | 0 | n/a |
| 1 | 16 | 15000 | not determined |
| 2 | 16 | 28930 | 51% |

The production of monatin in phosphate buffer is clearly higher than that in Tris buffered systems.

To compare activities of the cloned *B. subtilis* DAT from WO 03/091396 A2 with the BioCatalytics enzyme (AT-103) additional assays were done. The *B. subtilis* dat gene was also subcloned into pET30a to remove the His-6 tag. Untagged and tagged enzyme were produced in BL21(DE3), as described in WO 03/091396 A2. Cellular extracts were made and total protein assays were done to estimate protein concentration as described previously. Duplicate one mL reactions were done which contained: 500 µg D-aminotransferase, 50 µg ProA aldolase, 100 mM potassium phosphate pH 7.5, 3 mM MgCl$_2$, 4 mg indole-3-pyruvate, 200 mM sodium pyruvate, 7.35 mg (50 mM) D-glutamate, and 0.1 mM PLP. Samples were incubated at 30° C. for 1 hour, 2 hours, and overnight, and were filtered for LC/MS/MS analysis. The samples contained only the S,R and R,R stereoisomers of monatin, as determined by the FDAA derivitization protocol described in Example 1. The results are summarized in Table 2 below. The % RR was determined by peak areas that were separated by reversed phase chromatography.

TABLE 2

Comparison of D-Aminotransferase Enzymes

| Enzyme | Time (Hours) | Monatin (ppb) | % RR Monatin |
|---|---|---|---|
| B. sub DAT-HIS | 1 | 512 | not determined |
| B. sub DAT untagged | 1 | 1056 | not determined |
| BioCatalytics AT-103 | 1 | 2353 | not determined |
| B. sub DAT-HIS | 2 | 894 | ~80-90% |
| B. sub DAT untagged | 2 | 1913 | ~80% |
| BioCatalytics AT-103 | 2 | 6887 | 92.5% |
| B. sub DAT-HIS | 16 | 3014 | 31 |
| B. sub DAT untagged | 16 | 5612 | 33 |
| BioCatalytics AT-103 | 16 | 16131 | 66 |

The removal of the HIS-6 tag appears to have improved the activity of the *B. subtilis* D-aminotransferase; however, the BioCatalytics D-aminotransferase homolog clearly had the highest activity. It also showed greater substrate preference for the R-monatin precursor. Increased incubation times appear to reduce the enantiomeric excess of R,R monatin that is produced.

Because the *Bacillus* D-aminotransferase enzymes have a preference for pyruvate as an amino acceptor, and D-alanine as an amino donor, it was expected that D-alanine could be utilized as the amino donor for conversion of MP to monatin with similar or better results. Duplicate one mL reactions were done which contained: 500 µg D-aminotransferase, 50 µg purified ProA aldolase, 100 mM potassium phosphate pH 7.5, 3 mM MgCl$_2$, 4 mg indole-3-pyruvate, 100 mM sodium pyruvate, 25 mM D-glutamate or D-alanine, and 0.1 mM PLP. Samples were incubated for 2 hours, and treated as above prior to analysis. When D-alanine was used as the amino donor, slightly higher levels of monatin were produced (23 versus 21 ppm) as expected. Additionally, it is expected that high concentrations of pyruvate may inhibit the transamination step, thus dosing in smaller amounts of pyruvate over time may improve the overall rate of monatin production. One can see from the above data that even though one-half of the pyruvate was used in this case compared to the above table, significantly more monatin was produced. Even though ProA aldolases in the literature were reported to produce primarily S-enantiomers of aldol condensation products, the ProA aldolase used in this study clearly makes a high percentage of R-MP and in coupled assays produces up to 92% R,R monatin. The high percentage of R,R monatin is not due to D-aminotransferase selectivity, as was shown in Example 19.

Example 3

3A: Production of R,R Monatin from D-Tryptophan

The following were added per 1 mL of reaction mixture: approximately 60 µg *C. testosteroni* ProA aldolase (supplied in cellular extracts, as described in WO 03/091396 A2), 4 mM MgCl$_2$, 50 mM D-tryptophan, 0.5 mg BioCatalytics D-aminotransferase (AT-103), 100 mM sodium pyruvate, 100 mM potassium phosphate buffer pH 7.5 or 100 mM sodium acetate buffer pH 8, 0.05 mM PLP, 3 mM potassium phosphate (only to the acetate reactions), and 10 mM α-ketoglutarate. Experiments were run in duplicate, with negative controls in which no aldolase was added. Samples were incubated overnight (20 hours) at 30° C. with gentle shaking. The actual pH of the sodium acetate samples was approximately 5, while the final pH for the phosphate buffered samples was approximately 7. None of the aldolases appeared to have significant activity at pH 5; the sample containing ProA aldolase was slightly above the negative control but probably not above experimental error. In potassium phosphate, the ProA aldolase produced 73.4 ppm monatin with a ratio of R,R:S,R of 1.7:1 (~63% R,R from D-tryptophan).

Because the *Bacillus* D-aminotransferase enzymes have a preference for pyruvate as an amino acceptor, and D-alanine as an amino donor, it was expected that the addition of alpha-ketoglutarate is unnecessary when producing R,R or S,R monatin from D-tryptophan. The above experiment was repeated (in 100 mM potassium phosphate buffer) using purified ProA aldolase (50-60 µg), and an incubation time of 2.5 hours. Duplicate experiments were run, with and without alpha-ketoglutarate. When 10 mM alpha-ketoglutarate was added, 56.1 ppm monatin was formed using D-tryptophan as the substrate (79.5% R,R, 20.5% S,R). When alpha-ketoglutarate was omitted, 102.5 ppm monatin was formed (79% R,R, 21% S,R).

Comparison of Total Monatin Production and Isomeric Distribution for HMG Aldolases from *Sinorhizobium meliloti*, *C. testosteroni*, and the Aldolase of SEQ ID NO:22.

AT-103 transaminase (a broad specificity D-aminotransferase) was purchased from BioCatalytics (Pasadena, Calif.) and either this enzyme or the *B. sphaericus* recombinant enzyme produced in Example 18 was used in coupled reactions with HMG aldolases to produce monatin from D-tryptophan and pyruvate as described in U.S. Published Application No. 2005282260.

The HMG aldolases from *C. testosteroni* (ProA) and *S. meliloti* were prepared and purified as described in U.S. Publication No. 20040063175 and WO 03091396 A2. To produce test quantities of the aldolase of SEQ ID NO:22, a 50 mL culture was grown in Luria-Bertani ("LB") medium containing ampicillin (100 µg/mL), to an OD$_{600}$ of approximately 0.5. The strain containing the SEQ ID NO:21 construct was induced with 200 µg/L anhydrotetracycline. The cells were grown 5 hours post-induction, and cellular extracts were prepared according to manufacturer's protocols (Novagen, Madison, Wis., Bugbuster reagent). Benzonuclease and protease inhibitor were also added. The soluble proteins in the cellular extracts were separated on a BioRad Laboratories Experion Automated Electrophoresis Station and analyzed for concentration and percent expression using the Experion Software version 1.1.98.0. The aldolase of SEQ ID NO:22 was used as a crude (unpurified) enzyme for the reactions below.

The following were added per 1 mL of reaction mixture: approximately 50 µg aldolase, 4 mM MgCl$_2$, 50 mM D-tryptophan, 0.5 mg purified *B. sphaericus* D-aminotransferase, 200 mM sodium pyruvate, 100 mM potassium phosphate buffer pH 7.5, and 0.05 mM PLP. Experiments were run in duplicate, with negative controls in which no aldolase was added. Samples were incubated 1 hour and overnight (18 hours) at 30° C. with gentle shaking. Small amounts of monatin (<0.5 ppm) are produced without aldolase in overnight reactions, due to non-enzymatic reactions catalyzed by magnesium and phosphate. Those values were subtracted from the numbers shown below, and averaged results are shown. The only stereoisomers detected when producing monatin using these methods are R,R and S,R. The percent R,R is listed below in Table 3, and was determined by reversed-phase LC peak area.

TABLE 3

Total Monatin Produced from D-Tryptophan and % R,R

| Enzyme (time point) | Total Monatin (ppm) | % R,R Monatin |
|---|---|---|
| C. testosteroni ProA (1 hour) | 16.63 | 86.45 |
| C. testosteroni ProA (18 hours) | 86.86 | 63.1 |
| S. meliloti HMG (1 hour) | 20.5 | 96.7 |
| S. meliloti HMG (18 hours) | 88.3 | 89.9 |
| SEQ ID NO: 22 (1 hour) | 14.70 | 100 |
| SEQ ID NO: 22 (18 hours) | 95.14 | 97.35 |

The 18 hour sample for the aldolase of SEQ ID NO:22 was also analyzed for stereoisomeric distribution by the FDAA derivatization method listed in Example 1, which yielded a result of 94.9% R,R and 5.1% S,R monatin. The aldolase of SEQ ID NO:22 has a higher enantiospecificity for production of R-MP as compared to C. testosteroni and S. meliloti HMG aldolases.

The same experiments were done, side by side, using L-tryptophan as the starting substrate and coupling the aldolases with HexAspC broad specificity L-aminotransferase produced and purified as described in U.S. Published Application No. 2005282260. These reactions should yield primarily S,S monatin and R,S monatin. The reactions were also supplemented with 10 mM alpha-ketoglutarate as the amino acceptor for L-tryptophan transamination. Again, duplicate results are averaged below for total monatin (subtracting background levels without aldolase present), and percent S,S monatin is shown based on reversed phase LC peak area. In some cases, because the aldolases are quite R-specific and produce little total monatin, the reversed phase estimates of stereoisomeric distribution are less accurate due to some tailing of the tryptophan peak that can co-elute with the S,S/R,R monatin peak. The trends are still informative in comparing R-specificity of the aldolases. Results from further analysis using the FDAA derivatization method are shown below in Table 4 in parentheses for several samples, and are more accurate. Total monatin numbers above approximately 400 ppm are higher than the linear range of the scale of the standards used to quantitate the results, so are qualitative results. The C. testosteroni ProA aldolase typically produces 95-100% S,S monatin, as shown in U.S. Published Application No. 2005282260.

TABLE 4

Total Monatin Produced from L-Tryptophan and % S,S

| Enzyme (time point) | Total Monatin (ppm) | % S,S Monatin |
|---|---|---|
| C. testosteroni ProA (1 hour) | 440.35 | 92.5 |
| C. testosteroni ProA (18 hour) | 958.3 | 92.2 |
| S. meliloti HMG (1 hour) | 45.9 | 66.3 |
| S. meliloti HMG (18 hour) | 108.1 | 61.4 |
| SEQ ID NO: 22 (1 hour) | 17.85 | 55.1 (18.9) |
| SEQ ID NO: 22 (18 hour) | 135.5 | 27.3 (19.1) |

One can see that the R-specificity of the aldolase of SEQ ID NO:22 is quite high compared to the benchmark ProA enzyme. This R-specificity is also reflected in the low % S,S monatin produced, despite the high degree of specificity of the HexAspC aminotransferase for S-MP in these reactions. Again the S. meliloti HMG aldolase falls between the C. testosteroni ProA aldolase and the aldolase of SEQ ID NO:22 in terms of R-specificity, based on the levels of S,S monatin produced. The total monatin numbers, when comparing S,S monatin production versus R,R monatin production, are not indicative of the aldolase activity. The D-aminotransferase is less active than HexAspC for MP transamination reactions, particularly at the concentrations of MP that are present in these reactions.

For further comparison of the aldolase of SEQ ID NO:22 to the ProA enzyme from C. testosteroni, varying ratios of D-aminotransferase to aldolase were utilized in reactions starting with D-tryptophan (no duplicate samples for these experiments). The reactions were carried out as described above. For the reactions in which the aldolase concentration was kept constant, approximately 50 µg aldolase was used. For reactions in which the amount of D-aminotransferase was kept constant, 0.5 mg was used. For the 2 and 10 mg/mL concentration of D-aminotransferase, lyophilized enzyme was used. For the 2 highest D-aminotransferase concentrations, duplicates were run.

TABLE 5

Effect of D-Aminotransferase Concentration on R,R Monatin Production

| Aldolase | Concentration of D-Amino-transferase | Time | Total Monatin (approximate ppm) | % R,R Monatin |
|---|---|---|---|---|
| SEQ ID NO: 22 | 0.25 mg/mL | 1 hour | 2 | 100 |
| SEQ ID NO: 22 | 0.25 mg/mL | overnight | 141 | 97.1 |
| SEQ ID NO: 22 | 0.5 mg/mL | 1 hour | 8 | 100 |
| SEQ ID NO: 22 | 0.5 mg/mL | overnight | 273 | 96.5 |
| SEQ ID NO: 22 | 1 mg/mL | 1 hour | 34 | 100 |
| SEQ ID NO: 22 | 1 mg/mL | overnight | 638 | 96.5 |
| SEQ ID NO: 22 | 2 mg/mL | 1 hour | 979 | 100 |
| SEQ ID NO: 22 | 2 mg/mL | overnight | 1910 | 97.3 |
| SEQ ID NO: 22 | 10 mg/mL | 1 hour | 2930 | 99.1 |
| SEQ ID NO: 22 | 10 mg/mL | overnight | 2950 | 96.5 |
| C. testosteroni ProA | 0.25 mg/mL | 1 hour | 4 | 78.7 |
| C. testosteroni ProA | 0.25 mg/mL | overnight | 257 | 61.1 |
| C. testosteroni ProA | 0.5 mg/mL | 1 hour | 25 | 79.0 |
| C. testosteroni ProA | 0.5 mg/mL | overnight | 480 | 62.5 |
| C. testosteroni ProA | 1 mg/mL | 1 hour | 74 | 73.8 |
| C. testosteroni ProA | 1 mg/mL | overnight | 810 | 68.1 |
| C. testosteroni ProA | 2 mg/mL | 1 hour | 325 | 73.1 |
| C. testosteroni ProA | 2 mg/mL | overnight | 2220 | 71.9 |
| C. testosteroni ProA | 10 mg/mL | 1 hour | 2910 | 59.7 |
| C. testosteroni ProA | 10 mg/mL | overnight | 2450 | 67.5 |

For monatin levels above 400 ppm, the results are not in the linear range of the standard curve and are approximate values only. The maximum amount of R,R monatin produced, when diluted appropriately, was approximately 1100 ppm. FDAA stereoisomeric analysis was done for the aldolase of SEQ ID NO:22 with 10 mg/mL D-aminotransferase samples. At two hours, the sample contained 98.5% R,R monatin. At 17 hours, the sample contained 95.9% R,R monatin. The aldolase of SEQ ID NO:22 produced high percentages of R,R monatin, even after long incubation times and using large amounts of aminotransferase. If adequate D-aminotransferase is supplied, the aldolase of SEQ ID NO:22 produces as much total monatin as C. testosteroni ProA aldolase, indicating a similar specific activity.

TABLE 6

Effect of Aldolase Concentration on R,R Monatin Production

| Aldolase | Concentration of Aldolase | Time | Total Monatin (ppm) | % R,R Monatin |
|---|---|---|---|---|
| SEQ ID NO: 22 | 25 µg/mL | 1 hour | 7.0 | 100 |
| SEQ ID NO: 22 | 25 µg/mL | overnight | 275 | 97.4 |
| SEQ ID NO: 22 | 50 µg/mL | 1 hour | 9.0 | 97.3 |
| SEQ ID NO: 22 | 50 µg/mL | overnight | 334 | 95.7 |
| SEQ ID NO: 22 | 100 µg/mL | overnight | 297 | 93.3 |
| C. testosteroni ProA | 25 µg/mL | 1 hour | 16 | 78.2 |
| C. testosteroni ProA | 25 µg/mL | overnight | 491 | 73.2 |
| C. testosteroni ProA | 50 µg/mL | 1 hour | 18 | 64.1 |
| C. testosteroni ProA | 50 µg/mL | overnight | 437 | 63.0 |
| C. testosteroni ProA | 100 µg/mL | 1 hour | 26 | 62.5 |
| C. testosteroni ProA | 100 µg/mL | overnight | 513 | 61.5 |

When the aldolase concentration is varied, there is not much of an increase in total monatin. The percent R,R decreases with time and also with aldolase concentration, particularly when the D-aminotransferase is limiting.

To further examine the R-specificity of the aldolases tested, experiments were done starting with L-tryptophan and HexAspC aminotransferase, which was produced and purified as described in U.S. Published Application No. 2005282260. The HexAspC shows a strong selectivity for transamination of S-MP versus R-MP, thus percentages above 50% R,S monatin indicate a highly stereospecific aldolase. Ten mM alpha-ketoglutarate was supplied as an amino acceptor; however, at high concentrations, pyruvate is also utilized by the L-aminotransferase. In these reactions, typically only S,S and R,S monatin are produced within the limits of detection of the FDAA derivatization protocol.

TABLE 7

Effect of L-Aminotransferase Concentration on S,S Monatin Production

| Aldolase | Concentration of L-Amino-transferase | Time | Total Monatin (approximate ppm) | % S,S Monatin |
|---|---|---|---|---|
| SEQ ID NO: 22 | 0.25 mg/mL | 1 hour | 13 | 33.8 |
| SEQ ID NO: 22 | 0.25 mg/mL | overnight | 127 | 34.2 |
| SEQ ID NO: 22 | 0.5 mg/mL | 1 hour | 31 | 30.9 |
| SEQ ID NO: 22 | 0.5 mg/mL | overnight | 272 | 26.8 |
| SEQ ID NO: 22 | 1 mg/mL | 1 hour | 34 | 20.3 |
| SEQ ID NO: 22 | 1 mg/mL | overnight | 385 | 23.5 |
| C. testosteroni ProA | 0.25 mg/mL | 1 hour | 523 | 94.2 |
| C. testosteroni ProA | 0.25 mg/mL | overnight | 1817 | 93.7 |
| C. testosteroni ProA | 0.5 mg/mL | 1 hour | 602 | 91.8 |
| C. testosteroni ProA | 0.5 mg/mL | overnight | 2122 | 89.9 |
| C. testosteroni ProA | 1 mg/mL | 1 hour | 873 | 90.2 |
| C. testosteroni ProA | 1 mg/mL | overnight | 1237 | 82.6 |

TABLE 8

Effect of Aldolase Concentration on S,S Monatin Production

| Aldolase | Concentration of Aldolase | Time | Total Monatin (ppm) | % S,S Monatin |
|---|---|---|---|---|
| SEQ ID NO: 22 | 25 µg/mL | 1 hour | 11 | 25.1 |
| SEQ ID NO: 22 | 25 µg/mL | overnight | 112 | 20.0 |
| SEQ ID NO: 22 | 50 µg/mL | 1 hour | 18 | 31.8 |
| SEQ ID NO: 22 | 50 µg/mL | overnight | 160 | 27.0 |
| SEQ ID NO: 22 | 100 µg/mL | 1 hour | 33 | 33.2 |
| SEQ ID NO: 22 | 100 µg/mL | overnight | 238 | 41.4 |
| C. testosteroni ProA | 25 µg/mL | 1 hour | 305 | 86.4 |
| C. testosteroni ProA | 25 µg/mL | overnight | 1094 | 87.5 |
| C. testosteroni ProA | 50 µg/mL | 1 hour | 575 | 90.9 |
| C. testosteroni ProA | 50 µg/mL | overnight | 1449 | 89.5 |
| C. testosteroni ProA | 100 µg/mL | 1 hour | 817 | 93.6 |
| C. testosteroni ProA | 100 µg/mL | overnight | 1360 | 89.7 |

For aldolases that are highly R-specific, such as SEQ ID NO:22, less total monatin is produced and increasing the amount of aldolase does increase total monatin (as well as % S,S). These aldolases produce less S-MP substrate, the preferred substrate for the L-aminotransferase used. For enzymes that are less R-specific, such as ProA, increasing aldolase does not significantly improve total monatin production or % S,S monatin. Increasing the amount of L-aminotransferase added decreases the percentage of S,S monatin produced.

The activity and specificity of the aldolase of SEQ ID NO:22 was further studied in two buffer systems—100 mM potassium phosphate, as above, and 100 mM 3-(N-morpholino)propanesulfonic acid ("MOPS") (with 3 mM potassium phosphate). The assays were performed as above, using 1 mg/ml AT-103 D-aminotransferase and 50 mM D-tryptophan. Experiments were run in duplicate for 4.5 hours. The aldolase of SEQ ID NO:22 produced 116 ppm monatin and 99.1% R,R monatin in potassium phosphate (FDAA derivatization method). In MOPS, the aldolase of SEQ ID NO:22 produced 75.5 ppm monatin, and 96.2% was R,R monatin. The background levels of monatin produced in MOPS, without the aldolase of SEQ ID NO:22, were significantly higher, and the percent R,R was lower with MOPS, even in the controls. It is possible that the D-aminotransferase selectivity and activity are affected by the presence of the MOPS.

Subcloning of SEQ ID NO:21

The aldolase gene of SEQ ID NO:21 was received from Diversa Corporation, San Diego, Calif. SEQ ID NO:21 was part of an environmental library which was screened by Diversa Corporation for aldolase genes. However, the aldolase gene of SEQ ID NO:21 may be reconstructed by any method known to a person of ordinary skill in the art. For example, the aldolase gene of SEQ ID NO:21 may be reconstructed utilizing assembly PCR methods, as described in Examples 10, 18 and 19.

The following primers were used to PCR amplify the aldolase gene (SEQ ID NO:21): 5'-gaggagctcgagtcagacg-tatttcagtccttttc-3' (SEQ ID NO:23) and 5'-agaagacatatgatttat-cagccggggac-3' (SEQ ID NO:24). The resulting PCR product was digested with Xho I and Nde I to cut at the sites that had been engineered into the primers. The fragment was gel purified (QIAquick® Gel extraction Kit (Qiagen, Valencia, Calif.)) and ligated (using T4 DNA ligase) with pET28b (EMD Biosciences/Novagen Madison, Wis.) that had been digested with Xho I and Nde I and gel purified. The ligation was transformed into TOP10F' chemically competent cells (Invitrogen, Carlsbad, Calif.). Colonies growing on the plates were screened for inserts and several isolates with inserts were submitted for DNA sequence analysis (Agencourt, Beverly, Mass.).

Purification of the Aldolase of SEQ ID NO:22

Confirmed aldolase clones were transformed into either BL21(DE3) or BL21 (DE3) pLysS competent cells (Novagen Madison, Wis.). Overnight cultures grown with the appropriate antibiotic were diluted into fresh media (typically 1:100) and grown to an $OD_{600}$~0.6 with aeration at 37° C. Cultures were then induced with 1 mM isopropyl thiogalacatoside ("IPTG") and shifted to 30° C. (with aeration) and incubation was continued overnight. Cells were harvested by centrifugation. The cell pellet was typically subjected to one freeze thaw cycle to assist with cell lysis. The cell pellet was lysed in BugBuster and Benzonase (Novagen, Madison, Wis.) (according to the manufacturer's protocol). Cell debris was removed by centrifugation. The crude protein extract was applied to a HisBind column (Novagen, Madison, Wis.) that had been prepared according to the manufacturer's protocol. The column was washed and protein was eluted according to the manufacturer's protocol. The purified protein was desalted with PD-10 columns (GE Healthcare, Piscataway, N.J.). The buffer used for the exchange was 50 mM potassium phosphate pH 7.5, 100 mM NaCl, 4 mM $MgCl_2$. Purified protein was concentrated with Amicon centrifugal concentrators (Millipore, Billerica, Mass.).

3B: Cloning of SEQ ID NO:103 and Assay of the Aldolase of SEQ ID NO:104

The gene encoding the aldolase of SEQ ID NO:104 (the DNA sequence of the gene is shown as SEQ ID NO:103) was subcloned into the pET28b expression vector (EMD Biosciences/Novagen, Madison, Wis.) with an N-terminal His-tag to allow for purification.

The primers used for cloning are shown below:

```
                                          (SEQ ID NO: 105)
5'-ATAAGACATATGCCTATCGTTGTTACGAAG-3'
(Nde I restriction site)
and (SEQ ID NO: 106)
5'-ATAAGAGGATCCTTATTCCTCGGGCAGCCGCTC-3'
(BamH I restriction site).
```

A clone containing SEQ ID NO:103 was received from Diversa Corporation, San Diego, Calif., and used as a template for PCR. However, SEQ ID NO:103 can be reconstructed by other methods known to a person of ordinary skill in the art. For example, SEQ ID NO:103 can be reconstructed utilizing assembly PCR methods, as described in Examples 10, 18 and 19. SEQ ID NO:103 was amplified by PCR, digested with appropriate enzymes (Nde I and BamH I), and gel purified (QIAquick® Gel extraction Kit (Qiagen, Valencia, Calif.)). The digest was ligated into pET28b (EMD Biosciences/Novagen Madison, Wis.) that had been digested with Nde I and BamH I and gel purified. The ligation was transformed into TOP10 E. coli cells (Invitrogen, Carlsbad, Calif.). Miniprep DNA from colonies was analyzed for the presence of inserts by size comparison using agarose gel electrophoresis. Isolates with an insert were submitted for DNA sequence analysis (Agencourt, Beverly, Mass.).

Purification of Aldolases

The confirmed aldolase clone was transformed into BL21 (DE3)pLysS competent cells (Novagen Madison, Wis.). The aldolase of SEQ ID NO: 22 was also prepared simultaneously for comparison of activity. Induction was overnight in Terrific Broth (Tartoff and Hobbs, Bethesda Research Laboratories Focus 9:12 (1987) at 30° C. with 50 μg/mL kanamycin. Overnight cultures grown with the appropriate antibiotic were diluted into fresh media (typically 1:100) and grown to an $OD_{600}$~0.6, with aeration, at 37° C. The cultures were then induced with 1 mM IPTG and shifted to 30° C. (with aeration) and incubation was continued overnight. The cells were harvested by centrifugation. The cell pellet was typically subjected to one freeze thaw cycle to assist with cell lysis. The cell pellet was lysed in BugBuster and Benzonase Nuclease (EMD Biosciences/Novagen, Madison, Wis.) (according to the manufacturer's protocol). Cell debris was removed by centrifugation. The crude protein extract was applied to a 10 mg capacity HIS-Bind column (EMD Biosciences/Novagen, Madison, Wis.) that had been prepared according to the manufacturer's protocol. The column was washed and protein was eluted according to the manufacturer's protocol. The purified protein was desalted with PD-10 columns (GE Healthcare, Piscataway, N.J.) and eluted in 50 mM potassium phosphate buffer, pH 7.5 containing 4 mM $MgCl_2$ and 200 mM NaCl. Purified protein was concentrated with Amicon centrifugal concentrators (5000 MW cutoff) (Millipore, Billerica, Mass.). After concentration, it was noted that some of the aldolase of SEQ ID NO:104 had precipitated. However, the precipitation did not appear to affect the level of activity of the enzyme. Protein was stored at −80° C. until assayed. The protein assays were done using the Pierce BCA kit (Rockford, Ill.) and the microtiter plate protocol using Bovine Serum Albumin ("BSA") as the protein standard. The Experion Pro260 electrophoresis system (Bio-Rad, Hercules, Calif.) was used to calculate the percentage of aldolase in the purified sample, and to evaluate expression levels in the soluble cell extract and in total protein.

Testing of Purified Aldolases

Purified aldolases were tested for their ability to produce R,R monatin from D-tryptophan. Assays were done in microcentrifuge tubes in duplicate with purified protein, using the same concentration of enzyme per assay (50 μg/mL). Two mg/mL of Biocatalytics AT-103 was used as the D-aminotransferase. The following were added per 1 mL of reaction mixture: aldolase, 4 mM $MgCl_2$, 50 mM D-tryptophan, D-aminotransferase, 200 mM sodium pyruvate, 100 mM potassium phosphate buffer pH 7.5, and 0.05 mM PLP. The samples were incubated at 30° C. with shaking. Thirty minute, 1 hour, 3 hour, and overnight (19 hour) samples were taken. Table 9 shows the averaged results of total monatin produced at each time point and the % R,R monatin produced, as determined by reversed phase peak areas. Additional FDAA-derivatization LC/MS/MS analysis as described in Example 1 was done for some of the reactions and is shown in parentheses.

TABLE 9

Total Monatin Produced from D-tryptophan and % R,R

| Aldolase (hr) | Total monatin (ppm) | % R,R monatin (Reversed Phase LC peak area) |
|---|---|---|
| SEQ ID NO: 22 (0.5) | 16 | 99.1 |
| SEQ ID NO: 22 (1) | 53.2 | 99.2 (99.0) |
| SEQ ID NO: 22 (3) | 207.8 | 98.6 (98.1) |
| SEQ ID NO: 22 (19) | 544.9 | 95.3 (93.2) |
| SEQ ID NO: 104 (0.5) | 37.8 | 98.8 |
| SEQ ID NO: 104 (1) | 71.2 | 99.3 (99.5) |
| SEQ ID NO: 104 (3) | 245.2 | 99.0 (99.0) |
| SEQ ID NO: 104 (19) | 585.4 | 96.7 (96.1) |
| no aldolase (0.5) | 0 | |
| no aldolase (1) | 0 | |
| no aldolase (3) | 0.6 | 58.3 |
| no aldolase (19) | 6.5 | 61.5 |

The aldolase of SEQ ID NO:104 had higher activity than the aldolase of SEQ ID NO:22 and higher stereospecificity for production of R,R monatin.

The DNA sequence of the gene that encodes the aldolase of SEQ ID NO:104 is shown below:

```
                                              (SEQ ID NO: 103)
atgcctatcg ttgttacgaa gatcgaccga cccagcgcgg cggacgtcga aaggatcgcc gcctatggtg tcgcgacctt gcatgaagcg caaggacgaa ccggggttgat ggcgtccaat atgcgcccaa tctatcgccc tgcgcacatt gccgggcccg cggtgacctg ccttgtggcg cctggcgaca attggatgat ccatgtcgcc gtcgaacagt gccagccggg agatgtcctg gtcgtggtac cgaccagccc ctgcgaagac ggctatttcg gcgatctgct ggcgacctcg ctgcggtcgc gcggggtcaa aggtctgatc atcgaggccg gcgtacgcga tatcgcgaca ttgaccgaga tgaaattccc ggtctggtcc aaggcggtgt tcgcgcaagg aacggtcaag gagaccatcg ccagcgtcaa tgtgcccctc gtctgcgcgg gcgcccgcat cgtgccgggc gatctgatcg ttgccgacga cgacggggtc gtcgtgattc caagacgttc cgttccggcg gtcctttcca gcgccgaggc ccgcgaagag aaggaagccc gcaaccgcgc ccgcttcgaa gctggcgagc tgggcctcga cgtctacaac atgcgccagc gcctggccga caagggcttg cgctatgtcg agcggctgcc cgaggaatag.
```

The protein sequence of the aldolase of SEQ ID NO:104 is as follows:

```
                                              (SEQ ID NO: 104)
Met Pro Ile Val Val Thr Lys Ile Asp Arg Pro Ser

Ala Ala Asp Val Glu Arg Ile Ala Ala Tyr Gly Val

Ala Thr Leu His Glu Ala Gln Gly Arg Thr Gly Leu

Met Ala Ser Asn Met Arg Pro Ile Tyr Arg Pro Ala

His Ile Ala Gly Pro Ala Val Thr Cys Leu Val Ala

Pro Gly Asp Asn Trp Met Ile His Val Ala Val Glu

Gln Cys Gln Pro Gly Asp Val Leu Val Val Val Pro

Thr Ser Pro Cys Glu Asp Gly Tyr Phe Gly Asp Leu

Leu Ala Thr Ser Leu Arg Ser Arg Gly Val Lys Gly

Leu Ile Ile Glu Ala Gly Val Arg Asp Ile Ala Thr

Leu Thr Glu Met Lys Phe Pro Val Trp Ser Lys Ala

Val Phe Ala Gln Gly Thr Val Lys Glu Thr Ile Ala

Ser Val Asn Val Pro Leu Val Cys Ala Gly Ala Arg

Ile Val Pro Gly Asp Leu Ile Val Ala Asp Asp Asp

Gly Val Val Val Ile Pro Arg Arg Ser Val Pro Ala

Val Leu Ser Ser Ala Glu Ala Arg Glu Glu Lys Glu

Ala Arg Asn Arg Ala Arg Phe Glu Ala Gly Glu Leu

Gly Leu Asp Val Tyr Asn Met Arg Gln Arg Leu Ala

Asp Lys Gly Leu Arg Tyr Val Glu Arg Leu Pro Glu

Glu.
```

Example 4

4A: (1) Tryptophan Racemase

R,R-monatin has been produced using D-aminotransferase and an aldolase when D-tryptophan was used as the starting material (Example 3). That notwithstanding, L-tryptophan may be a preferred starting material for several reasons. For example, L-tryptophan may be less expensive and more readily available than D-tryptophan. This disclosure describes several methods for obtaining an active tryptophan racemase. Yields of R,R monatin are improved by using an R-specific aldolase, i.e., an aldolase that preferentially or selectively produces R-MP. FIGS. 1 and 2 illustrate methods for producing stereoisomerically-enriched R,R monatin from L-tryptophan using a tryptophan racemase, a D-aminotransferase and an R-specific aldolase.

A selection for a tryptophan racemase was created by constructing a strain that requires an active racemase for growth. A tryptophan auxotroph needs a source of L-tryptophan when grown on minimal medium. Supplementing the medium with D-tryptophan is one way to select for a racemase that converts D-tryptophan to L-tryptophan. The tryptophan auxotrophs were tested for growth on minimal medium supplemented with D-tryptophan. The strains, CAG18455 and CAG18579 from the Coli Genetic Stock Center and NRRL B-12264 (also lipA⁻, λDE3 lysogenized, and cured of its plasmid), did not grow when supplemented with D-tryptophan but grew when supplemented with L-tryptophan. E. coli may be used as a host organism but other host organisms also may used, such as yeast, other bacteria, or other eukaryotic organisms. A tryptophan auxotroph (specifically NRRL B-12264 (also lipA⁻, λDE3 lysogenized and cured of its plasmid)) will grow on D-tryptophan when it has been transformed with a D-aminotransferase. This confirms the ability of E. coli to transport D-tryptophan into the cell.

Salcher and Lingens described the presence of a tryptophan racemase in *Pseudomonas aurereofaciens* (ATCC15926). Salcher, O., and Lingens, F., *J. Gen. Microbiol.* 121:465-471 (1980). Tryptophan racemase has also been described in several plants including tobacco, beets, tomato, and wheat and the enzyme appears to be induced by conditions of osmotic stress or drought. Tryptophan racemase may play a role in *Sclerochiton ilicifolius* in the native monatin production pathway. To isolate this racemase activity, an expression library is constructed from ATCC15926 (or another organism with tryptophan racemase activity) and the library is transformed into the tryptophan auxotroph. A strain is selected that will grow using D-tryptophan as the tryptophan source. A similar method is also used to screen many strains with known racemases to look for a racemase with activity on D-tryptophan. Examples of racemases that may have activity on D-tryptophan include alanine, serine, and glutamate racemases. Yoshimura T., and Esaki, N., "Amino Acid Racemases: Functions and Mechanisms," *Journal of Bioscience and Bioengineering* 96, 103-109, (2003).

Alanine racemase is pyridoxal 5'-phosphate (PLP) dependent and has been cloned from *Salmonella typhimurium* (dadB gene). Other sources of alanine racemases are *Escheri-* chia coli, Bacillus subtilis, Pseudomonas aeruginosa, Vibrio cholerae, Schizosaccharomyces pombe, and Bacillus cereus. A basidiomycetous mushroom, Lentinus edodes, also contains a broad activity alanine racemase.

Serine racemase is also PLP dependent and is found in Eukaryotes (e.g. silkworm, rat brain, mouse brain cDNA), as well as in bacteria (Enterococcus gallinarum).

Glutamate racemase is PLP-independent and has been cloned from Pediococcus pentosaceus, Bacillus pumilus, Lactobacillus fermenti, Lactobacillus brevis, E. coli, Aquifex pyrophilus, and Bacillus subtilis. Some glutamate racemases are very specific and, consequently, even structurally similar amino acids aspartate, asparagine, and glutamine may not be substrates for the enzyme.

Aspartate racemases also exist and are PLP independent. Aspartate racemases are found in Lactobacilli, Streptococcus strains, and some archaea such as Desulfurococcus and Thermococcus strains. The bivalve mollusk Scapharca brouhtonii also contains an aspartate racemase.

Other racemases found in the literature include amino acid racemase (EC 5.1.1.10) from Anabaena sp. and Pseudomonas striata, proline racemase, and multifunctional phenylalanine racemase. Related epimerases or racemases are also being tested. Potential racemases are tested to make sure they are not D-tryptophan aminotransferases. The screening of potential racemases is done by sequence analysis and/or an enzyme assay. This screening method for selection of a tryptophan racemase is also used for other bacteria or archaea for which tryptophan racemase has been described, as well as for eukaryotic cDNA libraries that have been constructed in such a manor as to allow expression.

Enzymes that pass the test as a tryptophan racemase are screened for activity on monatin as described in Example 8. Ideally, one obtains an enzyme that is very specific for tryptophan and has little or no racemase activity on monatin.

A tryptophan racemase also may be evolved and/or improved (via mutagenesis or recombinant engineering) from an existing racemase, transaminase, or epimerase. Additionally, because crystal structures for alanine aminotransferases (and other aminotransferases) are known, these may be used as a basis for rational, structure based mutagenesis. The process described above is used as an initial selection for tryptophan racemase activity and as a screen for improved activity.

(2) Tryptophan Racemase Libraries

Construction of Libraries:
Burkholderia pyrrocina (ATCC15958) and Pseudomonas chlororaphis (ATCC15926) were obtained from the American Type Culture Collection, P.O. Box 1549, Manassas, Va., 20108, USA. They were grown as recommended by ATCC and genomic DNA was prepared according to the method described in Mekalanos, J. J., "Duplication and amplification of toxin genes in Vibrio cholerae," Cell 35:253-263, (1983). The genomic DNA was partially digested with the Sau3A I restriction enzyme. 1-3 Kbp fragments were gel purified using a Qiagen QIAquick® Gel Extraction Kit (Qiagen, Valencia, Calif.). The purified DNA was ligated into pTrc99a (Amersham, Piscataway, N.J.) that had been digested with BamH I and purified as above. The ligation was done at room temperature with overnight incubation using a 3:1 molar ratio of insert to vector. The ligated library was transformed into TOP10F' chemically competent cells (Invitrogen, Carlsbad, Calif.) and plated on LB medium with 100 µg/mL ampicillin. After overnight incubation of the transformation plates, colonies were scraped off of the plates, washed with liquid LB medium and an appropriate size cell pellet was mini-prepped using a Qiagen QIAquick® mini-prep kit (Qiagen, Valencia, Calif.). Approximately 30,000 colonies were pooled and mini-prepped.

The pooled plasmid was transformed into CAG18455 (trpC83::Tn10, rph-1) or CAG18579 (trpC::Tn10kan, rph-1) (from the Coli Genetic Stock Center). Both strains are tryptophan auxotrophs so they will not grow on M9 minimal medium (Difco) unless the medium is supplemented with tryptophan. The transformants were plated on M9 minimal medium supplemented with D-tryptophan. This selects for a strain that can convert D-tryptophan to L-tryptophan.

Prior to transformation of the library, the strains were tested for growth on minimal medium with L- or D-tryptophan. The strains were tested for growth on minimal medium supplemented with D-tryptophan and no growth was observed. Both strains grew on identical medium supplemented with L-tryptophan instead of D-tryptophan. Additionally, a derivative of NRRL B-12264 (the strain used had been cured of the tryptophan operon plasmid, lysogenized with λDE3, and deleted for lipA, in addition to the other chromosomally encoded mutations (serB, ΔtrpED, tnaA2, aroP)) was transformed with a D-specific aminotransferase from Bacillus subtilis (WO 03/091396). The NRRL B-12264 strain could not grow on minimal medium supplemented with D-tryptophan, but grew on identical medium supplemented with L-tryptophan instead of D-tryptophan. Expression of the D-aminotransferase was driven by the T7 promoter. The transformed strain was able to grow on M9 minimal medium supplemented with D-tryptophan.

The colonies that grow on the D-tryptophan medium are screened. The plasmid is isolated and retransformed into the parent strain (CAG18455 or CAG18579) to confirm that growth on D-tryptophan medium is dependent on the plasmid and not on a host mutation. The nucleotide sequence of the plasmids that complement the tryptophan auxotrophy are analyzed. Clones that are determined to contain a tryptophan racemase gene are further analyzed.

The tryptophan racemase from other tissue sources is isolated in a similar fashion. There are literature reports of tryptophan racemase activity in both tobacco tissue culture cells (Nicotiana tabacum L. var. Wisconsin 38) (Miura, G. A., and Mills, S. E., "The conversion of D-tryptophan to L-tryptophan in cell cultures of tobacco," Plant Physiol. 47:483-487, (1974)) and in crude protein extracts of wheat (Triticum aestivum) (Rekoslavskaya, N. I., et al., "Synthesis and physiological function of D-tryptophan during wheat germination," Russian J. Plant Physiol. 44:196-203, (1997)). A cDNA expression library is made from tissue, as described in the literature, and the expression library is used to transform a tryptophan auxotroph as described above.

It would be expected that if the same strains are used and the same growth conditions are reproduced as described in the literature, the enzyme with tryptophan racemase activity could be isolated or the mRNA could be isolated and a cDNA expression library could be prepared that would contain a coding sequence for an enzyme with tryptophan racemase activity. For instance, certain growth stages or certain medium components may be required to induce cellular production of an enzyme with tryptophan racemase activity.

(3) Tryptophan Racemase Assay

Clones that are identified as potentially having a tryptophan racemase are transformed into a strain of E. coli commonly used for expression of recombinant proteins, such as BL2 1. The cells are grown in LB broth to an optical density at 600 nm of 0.4-0.6. The promoter driving expression of the racemase is induced with IPTG (isopropyl-beta-D-thiogalactopyranoside) (0.1 mM final concentration). After induction, the cells are allowed to express the protein for 1-3 hours at 37° C. (with aeration). The cells are harvested and lysed by French press, sonication, or by chemical means (such as BugBuster (Novagen, Madison, Wis.)). The lysed cells are centrifuged to remove the cell debris. The clarified extract is used directly in assays.

Varying amounts of extract is added to a solution such that the final concentration is 50 mM potassium phosphate (pH 7.0) and 2 mM L-tryptophan. Pyridoxal-5'-phosphate is added at a final concentration of 10 μM. The samples are incubated and then analyzed by LC/MS. The presence of a D-tryptophan peak when only L-tryptophan is used as a substrate indicates a positive result. D-tryptophan concentration should increase with increasing time until equilibrium is reached, and the rate should also increase with protein concentration until the concentration of enzyme is high enough that it is no longer saturated with substrate. D-tryptophan may also be converted to L-tryptophan as above.

A complementing gene may code for a D-aminotransferase. This transamination reaction requires an alpha-keto acid such as α-ketoglutarate, oxaloacetate, or pyruvate as an amino acceptor. These compounds will likely be present in a cell extract, usually in small amounts. These compounds may be removed using a PD-10 desalting column and the assay may still be performed in a crude extract. Likewise, a complementing gene may also code for a D-amino acid oxidase or D-amino acid dehydrogenase. These enzymes also require cofactors and co-substrates that can be removed by a PD-10 desalting column. The tryptophan racemase activity is purified using conventional column chromatography. Finally, the open reading frame identified as a potential tryptophan racemase is cloned into an expression vector with an affinity tag. The potential tryptophan racemase is then purified by affinity chromatography. In either case the purified protein is used in enzyme assays essentially as described above.

(4) Reverse Genetic Engineering of Tryptophan Racemase

The tryptophan racemase can be purified from either plant or microbial sources by conventional protein purification techniques, including ammonium sulfate fractionation and conventional column chromatography. Once the protein has been purified such that a spot can be isolated on a 2-D gel, peptide microsequencing techniques or conventional Edman type amino acid sequencing are utilized (on the internet, see "golgi.harvard.edu/microchem/" for descriptions of the protocols and equipment typically used for this type of work). In some cases, however, the genome sequence of the organism cannot be used as a source of the protein for the protein purification because such sequence has not been determined yet. In that situation, the first set of degenerate primers may be designed based on sequence available from the closest known relative of the protein source. Degenerate PCR and genome walking is then be performed according to established protocols to isolate the tryptophan racemase coding sequence.

(5) Cloning of Alanine Racemase from *Geobacillus stearothermophilus*

The alanine racemase (SEQ ID NO:41) from *Geobacillus stearothermophilus* was cloned. Genomic DNA from *G. stearothermophilus* (ATCC12980D) was purchased from the ATCC (Manassas, Va.). The following primers were used to amplify the alanine racemase gene from *G. stearothermophilus*: 5'-atggacgagtttcaccgcga-3' (SEQ ID NO:25) and 5'-ttatgcatcgcttcatccgc-3' (SEQ ID NO:26). The PCR product was ligated to pCR-Blunt-TOPO using the Zero Blunt TOPO PCR cloning kit (Invitrogen, Carlsbad, Calif.). Correct clones were confirmed by sequencing (Agencourt, Beverly, Mass.). A correct clone was used as template in a subsequent PCR reaction.

The following primers were used to amplify the alanine racemase: 5'-ataataggatcctcatccgcggccaacggcg-3' (SEQ ID NO:27) and 5'-gggaaaggtaccgaggaataataaatggacgagtttcaccgcg-3' (SEQ ID NO:28). The PCR product was digested with the restriction enzymes Kpn I and BamH I. These enzymes cut at sites that had been engineered into the primers. The digested PCR product was gel purified and ligated to the *E. coli* plasmid vector pTrc99a that had been digested with Kpn I and BamH I and subsequently gel purified. The ligation was transformed into TOP10F' chemically competent cells and plated on LB plated supplemented with 50 μg/mL kanamycin. Isolates were screened for inserts and several isolates with an insert were confirmed to have the correct sequence (SEQ ID NO:40) by sequence analysis (Agencourt, Beverly, Mass.).

The pTrc99a/alanine racemase construct was subjected to Site-Directed Mutagenesis ("SDM") using the Stratagene (La Jolla, Calif.) Quick-Change Multi Site-Directed Mutagenesis kit. The mutagenic primers were as follows:

```
                                    (SEQ ID NO:29)
5'-gccggacgacacgcacattnnkgcggtcgtgaaggcgaacgcc-3';

(SEQ ID NO:30)
5'-gtgaaggcgaacgcctatggannkggggatgtgcaggtggcaag g-3';

(SEQ ID NO:31)
5'-cctcccgcctggcggttgccnnkttggatgaggcgctcgcttta a-3';

(SEQ ID NO:32)
5'-caaccaggcgaaaaggtgagcnnkggtgcgacgtacactgcgca g-3';

(SEQ ID NO:33)
5'-gatcgggacgattccgatcggcnnkgcggacggctggctccgcc g-3';
and (SEQ ID NO:34)
5'-gccatttggaaacgatcaacnnkgaagtgccttgcacgatcag-3'
(n =10 any nucleotide and k = g or t).
```

Residues for mutagenesis were selected by analysis of the existing crystal structure of *G. stearothermophilus* alanine racemase. Large amino acid residues located between 5 and 10 Å from the active site were chosen.

All six primers were used in the SDM reaction as directed in the manufacturer's protocol. The SDM reaction was transformed into XL-10 Gold according to the manufacturer's protocol. The transformation reaction was plated on LB medium supplemented with 100 μg/mL ampicillin. LB broth was added to the plates and the colonies were scraped off the plates. The resuspended cells were allowed to grow at 37° C. for several hours and the plasmids were mini-prepped using the QIAquick® mini-prep kit. The resulting mutagenized library was then used to transform the tryptophan auxotroph CAG18455. The transformation was plated on M9 minimal medium that had been supplemented with glucose, trace elements, vitamins, 100 µg/mL ampicillin, 100 µM IPTG, and 3 mM D-tryptophan. After several days of incubation at 37° C., colonies grew. These colonies were streaked on LB (100 µg/mL ampicillin). The plasmids were isolated from these isolates and were retransformed into CAG18455. The retransformed cells were plated on LB containing 100 µg/mL ampicillin. After isolated colonies formed, they were streaked on M9 D-tryptophan medium as described above. The colonies all seemed to re-grow, indicating that the growth was because of the mutagenized version of the racemase. No growth of the control cells was observed.

Several of the isolates were assayed for in vitro activity. Cells were grown to an $OD_{600}$ approximately 0.6 and induced with 100 µM IPTG. Cells were incubated at 37° C. for an additional two hours and were harvested by centrifugation. Cell pellets were stored at −80° C. until use the next day. Cell pellets were thawed on ice. Cells were disrupted with BugBuster (primary amine free) cell lysis reagent and Benzonase (Novagen, Madison, Wis.). Cell debris was removed by centrifugation (~10,000×g for 30 minutes at 4° C.). The supernatant was saved as the crude cell extract.

Assay buffer contained 50 mM potassium phosphate (pH 8.0), 10 µM pyridoxal phosphate, 0.01% β-mercaptoethanol, and 50 mM D- or L-tryptophan. 200 µL extract was added per mL of assay. Samples were frozen representing a time 0 time point, as well as, 30 minute and overnight time points. The samples were spun, filtered, and submitted for chiral LC/MS/MS analysis as described in Example 1.

TABLE 10

Results of Assay Starting from L-Tryptophan

| Time (Minutes) | L-Tryptophan (ppm) | D-Tryptophan (ppm) |
| --- | --- | --- |
| 0 | 1240 | 3.6 |
| 30 | 1193 | 24.5 |
| Overnight | 1192 | 583.2 |

TABLE 11

Results of Assay Starting from D-Tryptophan

| Time (minutes) | L-Tryptophan (ppm) | D-Tryptophan (ppm) |
| --- | --- | --- |
| 0 | 0.5 | 7506 |
| 30 | 0.5 | 7519 |
| Overnight | 14.9 | 7463 |

The DNA sequence of the racemase gene in this isolate was determined (SEQ ID NO:42) and the isolate was found to have three mutations. The mutations in the corresponding protein isolate are as follows: M35C, F66E, and Y354A (SEQ ID NO:43). An additional mutation (P197L) was found in this mutant. This is a spontaneous mutation and was not part of the site-directed mutagenesis.

The mutagenized racemase was cloned into pET30 (Novagen, Madison, Wis.) for expression and purification. The following primers were used to PCR amplify the racemase gene from the pTrc99a construct: 5'-gggaaaggtaccgaggaataataaatggacgagtttcaccgcg-3' (SEQ ID NO:35) and 5'-gcggcgccatggacgagtttcaccgcg-3' (SEQ ID NO:36). The PCR product was digested with Nco I and BamH I, gel purified, and ligated to pET30 that had been digested with Nco I and BamH I and subsequently gel purified. The ligation was transformed into TOP10 chemically competent cells (Invitrogen, Carlsbad, Calif.). Isolates from the transformation were screened for inserts. Plasmids with an insert were submitted for sequencing (Agencourt, Beverly, Mass.). Isolates with the correct sequence were transformed into BL21 λDE3 or BL21 λDE3 pLysS for expression and purification. The new construct is designated pET30Trp racemase.

(6) Purification of Tryptophan Racemase

An overnight culture with the pET30Trp racemase construct was subcultured into fresh LB medium with the appropriate antibiotics (50 µg/mL kanamycin and 20 µg/mL chloramphenicol) and grown to an $OD_{600}$~0.6 (37° C. with aeration). Expression was induced with 100 µM IPTG and incubation was continued at 37° C. with aeration for 2 hours. The cells were harvested by centrifugation and stored at −80° C. until use. The cell pellet was thawed on ice and cells were lysed using BugBuster Primary Amine Free Cell Lysis Reagent and Benzonase Nuclease (Novagen, Madison, Wis.). Cell debris was removed by centrifugation and the supernatant was used as the crude protein extract. The crude protein extract was filtered using a 0.45 µm syringe filter and applied to a HisBind column (Novagen, Madison, Wis.) that had been pre-equilibrated according to the manufacturer's instructions. The column was washed and the protein was eluted as directed in the manufacturer's protocol. The purified protein was desalted with a PD-10 column (GE Healthcare, Piscataway, N.J.) using 50 mM potassium phosphate pH 8.0, 10 µM pyridoxal-5'-phosphate ("PLP") as the eluent. The desalted protein was concentrated using Amicon centrifugal concentrators (Millipore, Billerica, Mass.). Wild-type alanine racemase was purified as described above.

(7) Assay of Tryptophan Racemase

The purified racemase was tested in several assays. In one assay, the production of hydrogen peroxide by a D-amino acid oxidase was used as a detection system. D-tryptophan substrate for the oxidase was produced from L-tryptophan via the racemase enzyme isolated as described in this Example. The assay included 0, 1, 10, 25, 50, 100, 200 µg of enzyme per assay, 50 mM potassium phosphate pH 8.0, 10 µM PLP, 50 mM L-tryptophan. The assays were incubated 1 hour at 37° C. After incubation, 100 mg/mL D-amino acid oxidase (AOD-101 BioCatalytics, Pasadena, Calif.) and 0.5 mM FAD was added to the reaction mix. The generation of hydrogen peroxide was measured using the Amplex Red reagent kit (Molecular Probes, Eugene, Oreg.) and a Perkin Elmer HTS 7000 Plus BioAssay Reader Fluorometer (Wellesley, Mass.). The assay data is summarized in Tables 12 and 13 below:

TABLE 12

Standard Curve

| $H_2O_2$ Concentration (µM) | Fluorometer Reading |
| --- | --- |
| 0 | 485 |
| 1 | 8691 |
| 2 | 16958 |
| 3 | 24719 |
| 4 | 31692 |
| 5 | 38083 |

TABLE 13

Results of Assay

| Protein Concentration (μg/assay) | Wild-type Racemase (Fluorometer Reading) | Mutant (Trp) Racemase (Fluorometer Reading) |
|---|---|---|
| 0 | 5226 | 5192 |
| 1 | 4272 | 6215 |
| 10 | 4149 | 10543 |
| 25 | 4239 | 21177 |
| 50 | 3141 | 30465 |
| 100 | 3160 | 39068 |
| 200 | 2370 | 35163 |

The results of the assay indicate that the mutant racemase is required for production of hydrogen peroxide. The amount of hydrogen peroxide produced increased when the amount of the mutant racemase added was increased.

The activity of the racemase (wild-type and mutant) on alanine was analyzed. The reaction buffer contained: 100 mM potassium phosphate pH 8.0, 10 μM PLP, 50 mM L-alanine, 12 μg/mL wild-type racemase or 94 μg/ml mutant racemase. The reactions were stopped with 1 volume of 0.5 M formic acid and analyzed by LC/MS/MS using a Chirobiotic column as described in Example 1.

The assay data is summarized in Table 14 below.

TABLE 14

| Time (minutes) | Wild-type Racemase (ppm D-Alanine Produced) | Mutant Racemase (ppm D-Alanine Produced) |
|---|---|---|
| 0 | 65 | 87 |
| 5 | 334 | 2430 |
| 10 | 1161 | 3257 |
| 20 | 1670 | 4003 |
| 30 | 3075 | 4621 |
| 40 | 3177 | 4931 |
| 60 | 3986 | 5328 |

The mutated racemase appears to retain activity on the original substrate, alanine.

The activity of the mutated racemase was tested using one of L-tryptophan, D-tryptophan, L-alanine, and D-alanine as the substrate. The reaction buffer contained: 100 mM potassium phosphate pH 8.0, 10 μM PLP, 50 mM substrate, 94 μg/mL mutant racemase. The reactions were stopped with 1 volume of 0.5 M formic acid and analyzed as described in Example 1. The assays with alanine as the substrate were incubated at room temperature (~22° C.) and assays with tryptophan as the substrate were incubated at 37° C. The results are summarized in Table 15 below.

TABLE 15

| Time (minutes) | ppm D-trp Produced from L-trp | ppm L-trp Produced from D-trp | ppm D-ala Produced from L-ala | ppm L-ala Produced from D-ala |
|---|---|---|---|---|
| 0 | None detected | 0.8 | 420.5 | 565.9 |
| 5 | None detected | 1 | 1268 | 1874 |
| 10 | None detected | 1.4 | 1448 | 1968 |
| 20 | None detected | 2.2 | 1590 | 1505 |
| 30 | 0.3 | 2.8 | 1840 | 1923 |
| 40 | 3.1 | 2.8 | 1779 | 1960 |
| 60 | 9 | 3.7 | 1295 | 1070 |
| 1080 | 57.4 | 66.7 | 1611 | 2932 |

The racemase enzyme works in both directions and retains wild-type activity.

The mutant racemase was tested on several substrates. The enzyme used in the assay was purified as previously discussed. The assay conditions are as follows: 50 mM potassium phosphate pH 8.0, 10 μM PLP, 25 mM substrate, 40 μg/mL mutant racemase. The reactions were stopped with 1 volume of 2 M formic acid and analyzed as described in Example 1. The assays were incubated at 37° C. The results (in ppm D-isomer produced from the L-isomer) are summarized in Table 16 below (nd=none detected).

TABLE 16

| Time (Minutes) | Lys | Ala | Glu | Met | Tyr | Leu | Trp | Phe |
|---|---|---|---|---|---|---|---|---|
| 0 | 12 | 156 | 86 | 104 | nd | nd | nd | nd |
| 3 | 2310 | 2180 | 607 | 1200 | nd | 37 | nd | nd |
| 5 | 2450 | 1310 | 1110 | 1290 | nd | 80 | nd | 14 |
| 10 | 6630 | 2850 | 1950 | 2260 | 11 | 139 | nd | 14 |
| 20 | 9550 | 1970 | 4660 | 2090 | 30 | 280 | nd | 47 |
| 30 | 15500 | 2090 | 4860 | 1750 | 63 | 320 | nd | 22 |
| 60 | 10200 | 2540 | 4490 | 2150 | 136 | 710 | nd | 54 |
| 120 | 18000 | 2430 | 6340 | 1940 | 224 | 1050 | nd | 188 |
| 240 | 13200 | 1830 | 6560 | 1990 | 515 | 1170 | 15 | 490 |

It is likely that this racemase will racemize other amino acids in addition to the ones tested here.

Although the mutated racemase appears to have activity on a wide variety of amino acids, there does not appear to be any racemase activity on monatin. The enzyme used in the assay was purified as previously discussed. The assay conditions are as follows: 100 mM potassium phosphate pH 8.0, 10 μM PLP, 50 mM monatin, 1 mg/mL mutant racemase. The assays were incubated at 37° C. The assays were analyzed by FDAA derivitization as described in Example 1. The results of the assay are shown in Table 17 below.

TABLE 17

| Time (Hours) | S,S Monatin Starting Substrate | R,R Monatin Starting Substrate |
|---|---|---|
| 0 | 100% SS | 100% RR |
| 1 | 100% SS | 100% RR |
| 18 | 100% SS | 100% RR |

Even after 18 hours there was no apparent conversion of S,S monatin to S,R monatin or of R,R monatin to R,S monatin using the mutant racemase.

The ideal enzyme has activity on tryptophan, but little or no activity on other amino acids or amino acid like compounds, particularly monatin. If the enzyme has significant activity on monatin, the enzyme may be mutagenized to decrease the activity on monatin and/or glutamate, while keeping the tryptophan activity unchanged or at a level high enough for the enzyme to be useful in monatin production. Techniques that may be used for mutagenesis include, but are not limited to, error prone PCR, site-directed mutagenesis, modeling to identify site-directed mutagenesis targets (sites that may be involved in substrate binding), passage through mutagenic strains, and DNA shuffling.

(8) Tryptophan Racemase Monatin Production

The following were added per 1 mL of reaction mixture: approximately 50 µg aldolase of SEQ ID NO:22, 16 mg/mL purified tryptophan racemase, 4 mM $MgCl_2$, 50 mM L-tryptophan, 0.5 mg D-aminotransferase (purified from *Bacillus sphaericus* as described in Example 14), 100 mM sodium pyruvate, 100 mM potassium phosphate buffer pH 7.5, and 0.05 mM PLP. Because pyruvate is an acceptable amino acceptor for the broad specificity D-aminotransferase, α-ketoglutarate was not used. A control was included in which D-tryptophan was the starting substrate and no racemase was included. The samples were incubated 2 hours or overnight (20 hours) at 30° C. with gentle shaking. Samples were analyzed as described in Example 1. The results of the assay are shown below in Table 18 (nd=none detected).

TABLE 18

| Time (Hours) | Starting Substrate | ppm Total Monatin | RR/SS % RPLC | RS/SR % RPLC | % RR FDAA | % SR FDAA |
|---|---|---|---|---|---|---|
| 2 | L-trp | nd | 0 | 0 | | |
| 18 | L-trp | 7.4 | 100 | 0 | 96.5 | 3.5 |
| 2 | D-trp | 12 | 99.17 | 0.83 | | |
| 18 | D-trp | 170 | 98.65 | 1.35 | 97.5 | 2.5 |

Table 18 shows production of R,R monatin using a tryptophan racemase to convert the L-tryptophan substrate to D-tryptophan. The production of R,R monatin from D-tryptophan, without using the tryptophan racemase, was utilized as a control. The percent R,R monatin produced is nearly the same with either L- or D-tryptophan as the starting material. This result indicates the racemase does not have detectable activity in catalyzing the racemization of R,R monatin.

(9) Isolation of the Key Amino Acid Changes

Several revertants of the mutagenized alanine racemase were created. The revertants were made by site-directed mutagenesis using the QuikChange Multi Site-Directed Mutagenesis Kit (Stratagene, La Jolla, Calif.) as previously described using the following primers:

```
                                          (SEQ ID NO:37)
5'-gccatttggaaacgatcaactatgaagtgccttgcacgatcag-3';

(SEQ ID NO:38)
5'-ctcccgcctggcggttgccttcttggatgaggcgctcgctttaa
g-3';
and
                                          (SEQ ID NO:39)
5'-gccggacgacacgcacattatggcggtcgtgaaggcgaacgcc-3'.
```

The primers were used individually, and in combination, in an attempt to make the six possible combinations of the three mutations in positions 35, 66, and 354 (numbering based on the ATCC 12980 derived amino acid sequence). Several combinations of the mutations were created and tested for tryptophan racemase activity. The assay conditions were as follows: 50 mM potassium phosphate pH 8.0, 10 µM PLP, 30 mM L-tryptophan, 100 µg/mL enzyme. The assays were incubated at 37° C. for the specified time period. The samples were analyzed as described in Example 1.

The results of the assays are summarized in Table 19 below (nd=none detected).

TABLE 19

| Time (Minutes) | MF1 | MF2 | MY1 | Mutated Racemase |
|---|---|---|---|---|
| 0 | nd | Nd | nd | nd |
| 5 | nd | Nd | nd | nd |
| 10 | nd | Nd | nd | nd |
| 20 | nd | Nd | nd | nd |
| 30 | nd | Nd | nd | nd |
| 40 | nd | Nd | nd | nd |
| 60 | 9.8 | Nd | nd | 12.5 |
| 1080 | 54.8 | 90.8 | nd | 92.4 |

Mutation List:
MF1: N41S (spontaneous mutation), P197L, Y354A
MF2: F66E, P197L, Y354A
MY1: M35C, F66E, P197L
Mutagenized racemase: M35C, F66E, P197L, Y354A The results indicate that the Y354A mutation is required for activity on tryptophan. When this mutation was absent there was no detectable activity on tryptophan. See also W. M. Patrick, J. Weisner, and J. M. Blackburn, ChemBioChem 2002 No. 8, 789-792, which also illustrates the importance of this residue in broadening substrate specificity.

An alanine racemase may be further converted to a broader specificity racemase by random methods such as mutagenic PCR, passage through mutagenic strains, or other methods to those known in the art. A more focused evolution of the alanine racemase may be focused on active site residues, including Lys129, Met134, and the residues including and between Gly283 and Trp288 (numbering from *Geobacillus stearothermophilus*).

4B: Isolation of the Y354A Single Mutant

The wild-type *Geobacillus stearothermophilus* alanine racemase (SEQ ID NO:41) cloned into pET30 in Example 4A was used as a template for site-directed mutagenesis to make the Y354A change. The mutagenesis was performed using the QuickChange-Multi site-directed mutagenesis kit (Stratagene, La Jolla, Calif.). The following mutagenic primer was used to make the Y354A change, 5'-gccatttggaaacgatcaacgcggaagtgccttgcacgatcag-3' (SEQ ID NO:107). The site-directed mutagenesis was done as described in the manufacturer's protocol. Several isolates were sequenced (Agencourt, Beverly, Mass.) and an isolate with the correct sequence was selected and used for further analysis.

The pET30Y354A single mutant was transformed into *E. coli* BL21(DE3)pLysS competent cells. Purified protein was prepared in the following manner. The strain was grown in LB or Terrific Broth (at 37° C. with aeration) to an $OD_{600}$ of 0.4-0.6 and induced with 1 mM IPTG. Incubation was continued at 37° C. with aeration for ~3 hours. The cells were harvested by centrifugation and the cell pellet was stored at −80° C.

The cell pellet was thawed on ice and then resuspended in an appropriate volume of BugBuster (Novagen, Madison, Wis.) plus Benzonase nuclease (Novagen, Madison, Wis.). Cell debris was removed by centrifugation, and the cell-free extract was applied to a HIS-Bind column (Novagen, Madison, Wis.) that had been equilibrated with Binding buffer. The column was washed with Binding buffer and Wash buffer and the protein was eluted with Elution buffer (as directed in the manufacturer's protocol). The purified protein was desalted using a PD-10 column (GE Healthcare, Piscataway, N.J.). The protein was desalted into 50 mM potassium phosphate pH 8.0 and 10 µM pyridoxal-5'-phosphate according to the manufacturer's protocol. The protein was concentrated using an Amicon centrifugal concentrator (Millipore, Billercia, Mass.). The purified and concentrated protein was divided into a small aliquots and stored at −80° C. until use.

The purified Y354A was compared to wild-type alanine racemase (prepared in the manner described above) in both alanine and tryptophan assays. Assays were performed in 50 mM potassium phosphate buffer, pH 8, and 10 µM PLP as described in Example 4A using 400 µL of purified concentrated protein (>1 mg/mL final concentration) and 50 mM substrate. Detection of D-alanine and D-tryptophan was performed using the chiral amino acid methodology described in Example 1. The results are shown in Table 20 below.

TABLE 20

| Enzyme | Substrate | Time (min) | D isomer produced (ppm) |
|---|---|---|---|
| Wild-type | L-tryptophan | 0 | nd* |
| | | 10 | nd |
| | | 30 | nd |
| | | 60 | nd |
| | | 1080 | nd |
| Y354A | | 0 | nd |
| | | 10 | 198 |
| | | 30 | 568 |
| | | 60 | 1386 |
| | | 1080 | 10080 |
| Wild-type | L-alanine | 0 | 5140 |
| | | 10 | 5960 |
| | | 30 | 6280 |
| | | 60 | 6500 |
| | | 1080 | 5040 |
| Y354A | | 0 | 4760 |
| | | 10 | 4980 |
| | | 30 | 4980 |
| | | 60 | 4200 |
| | | 1080 | 5000 |

*nd = none detected

These data were analyzed without the use of an internal standard, and are thus semi-quantitative and should be used for comparative purposes. Nonetheless, these results show that the Y354A single mutation is sufficient to broaden the specificity of the alanine racemase so that it can catalyze amino acid racemization using alternative substrates. Note that the enzyme is so active with alanine as a substrate that at time zero the reaction has essentially reached equilibrium already.

4C: Saturation Mutagenesis of Position 354 of the *Geobacillus stearothermophilus* Alanine Racemase Several mutants were isolated in the following manner. A primer was made to conduct "NNK" random mutagenesis at position 354. The primer, 5'-gccatttggaaacgatcaacnnkgaagtgccttgcacgatcag-3' (SEQ ID NO:108), was used with the QuikChange Multi Site Directed Mutagenesis Kit (Stratagene, La Jolla, Calif.). The template used for the reaction was the wild-type *G. stearothermophilus* alanine racemase cloned into pET30. Mutagenesis was conducted according to the manufacturer's protocol. Several mutants were isolated using this method. The following mutants were isolated using this method: Y354D, Y354E, Y354L, Y354H, and Y354K. Other amino acid substitutions were made using the Quick-Change Multi Kit and these primers:

Y354N
(SEQ ID NO:109)
5'-ccatttggaaacgatcaacaacgaagtgccttgcacgatcag-3'
and

Y354G
(SEQ ID NO:110)
5'-gccatttggaaacgatcaacggcgaagtgccttgcacgatcag-3'.

Additional mutations were made with the standard Quick-Change Kit and the

Y354C (SEQ ID NO: 111)
5'-TCGCCATTTGGAAACGATCAACTGCGAAGTGCCTTGCACG-3'
and

Y354T (SEQ ID NO: 112)
5'-GGAAACGATCAACACGGAAGTGCCTTGCACG-3' and their respective reverse complements. The plasmids with the desired sequences (Agencourt, Beverly, Mass.) were transformed into the expression strain *E. coli* BL21(DE3). Gene induction was carried out as described in Example 4B. The mutants with activity are compared in the table below. The assays were done using L-tryptophan as a substrate as described above, with the Y354A mutant as a positive control. The relative activities of the mutant racemases are all compared to Y354A in the table below. The proteins were purified and assays were performed as described in Example 4B using 100 µg of purified protein. The results are shown in Table 21 below.

TABLE 21

| Mutant | Relative activity |
|---|---|
| Y354A | 1.0 |
| Y354C | 0.18 |
| Y354T | 0.22 |
| Y354G | 0.69 |
| Y354L | 0.37 |
| Y354N | 0.03 |
| Y354S | 0.02 |

Y354I, Y354M, and Y354P had trace amounts of activity that were not quantifiable given the limits of detection.

Y354D, Y354E, Y354H, and Y354K had little or no activity under the conditions in this assay.

Y354F, Y354Q, Y354R, and Y354W mutants were constructed using similar methods as above, and also appeared to have no activity under the conditions of this assay.

4D: Mutagenesis of Amino Acid Positions 35 and 265 of the *Geobacillus stearothermophilus* Alanine Racemase Several mutants were isolated in the following manner. Two primers were made to conduct "NNK" random mutagenesis at amino acid positions 35 and 265 using the Y354A mutant (described in Example 4B) as the template. The gene encoding Y254A was subcloned into pPRONco vector using Nco I and BamH I restriction sites; this construct was used in mutagenesis reactions. The pPRONco plasmid is a derivative of the pPROLar.A122 vector (BD Biosciences Clontech, Palo Alto, Calif.) in which one of the Nco I sites was removed by mutation T1538C. The following primers (5'-phosphorylated) were used with the QuikChange Multi Site Directed Mutagenesis Kit (Stratagene, La Jolla, Calif.):

Y265X:

(SEQ ID NO: 113)
5'-CAA CCA GGC GAA AAG GTG AGC NNK GGT GCG ACG TAC ACT GCG CAG-3' and

M35X:

(SEQ ID NO: 114)
5'-GCC GGA CGA CAC GCA CAT TNN KGC GGT CGT GAA GGC GAA CGC C-3' wherein N indicates G, C, T, or A and K indicates G or T.

Mutagenesis was conducted according to the manufacturer's protocol. Plasmids containing mutant genes were transformed into electrocompetent tryptophan auxotrophic strain CY15077 (obtained from the *E. coli* Genetic Stock Center, Yale). Several mutants were isolated after several days of growth on M9 minimal medium-containing Nobel agar plates that had been supplemented with 0.4% glucose, trace elements, vitamins, 50 μg/mL kanamycin, 100 μM IPTG, and 3 mM D-tryptophan. R195H spontaneous mutations occurred in some cases.

The following mutants were isolated using this method (all also contain Y354A): Y265M, Y265C, M35V/R195H, M35S/Y265S.

Clones were induced with 1 mM IPTG in LB medium containing kanamycin as described in Example 4B. Assays were conducted using cell free extracts. The level of expression of the target protein was estimated using the Experion-Pro260 electrophoresis system (Bio-Rad). One mL assays contained 30 mM L-tryptophan, 50 mM potassium phosphate pH 8, and 50 μM PLP, and approximately 200 μg of mutant enzyme. Samples were incubated at 30° C. overnight. Samples were acidified with 2% formic acid, spun, filtered, and diluted 10-fold for detection of D-tryptophan as described in Example 1. Only the M35V/R195H mutant had detectable activity, and it appears to be on the same order of magnitude as the Y354A alone.

Additionally, Y265A amino acid substitutions were made in Y354A (from Example 4B), Y354N (from Example 4C), and wild-type backgrounds in pET30 constructs using the QuickChange Multi Kit (Stratagene) and the following primer, using the manufacturer's protocols:

(SEQ ID NO: 115)
5'-AGGCGAAAAGGTGAGCGCGGGTGCGACGTACACTG-3'.

Plasmid DNA was isolated, transformed into *E. coli* BL21 (DE3), and induced and assayed as above. None of the constructs containing the Y265A mutation appeared to have activity under these conditions.

4E: Cloning of *Pseudomonas putida* KT2440 Broad-Specificity Amino Acid Racemase ("BAR")

A BAR (Broad specificity Amino acid Racemase) was identified in *P. putida* KT2440 using information from literature (Roise, D., Soda, K., Yagi, T., Walsch, C. T., *Biochemistry* 23, 5195-5201, (1984)). *P. putida* KT2440 is also known as ATCC 47054. The active site of a BAR enzyme from *P. striata* was sequenced and reported—LTAVLKADAYGXGIGL (SEQ ID NO:116), wherein X indicates any naturally occurring amino acid. This sequence was used to BLAST the *P. putida* KT2440 genome sequence available in NCBI. A protein with a nearly identical consensus sequence was identified. The primers were designed to clone the gene from genomic DNA obtained from the American Type Culture Collection (ATCC, Manassas, Va.) and are as follows:

(SEQ ID NO:117)
5'-AGAAGACATATGCCCTTTCGCCGTAGGG-3' and (SEQ ID NO:118)
5'-AGAAGAGGATCCTCAGTCGACGAGTATCTTCG-3').

PCR was conducted under standard conditions and the PCR product was purified (QIAquick® PCR purification kit, Qiagen, Valencia, Calif.). The purified PCR product was digested with Nde I and BamH I. The digested PCR product was gel purified (QIAquick® Gel Extraction Kit, Qiagen, Valencia, Calif.) and ligated to pET30 and pET28 that had been digested and gel purified in a similar manner. Clones with inserts were sequenced (Agencourt, Beverly, Mass.) and isolates with the correct sequence were identified (pET30 KT2440 BAR and pET28 KT2440BAR) and used in later studies.

The KT2440 BAR DNA sequence (SEQ ID NO:119) is as follows:

atgccctttcgccgtaccttctggctgcatccctggcacttctgatcac cggacaggcccccctgtatgcggcaccaccgttgtcgatggacaacggca ccaacaccctgaccgtgcaaaacagcaatgcctgggtcgaagtcagcgcc agcgccctgcagcacaacatccgcacgctgcaggccgagctggccggcaa gtccaagctgtgcgccgtgctcaaggccgatgcctatggccacggtatcg gcctggtaatgccatcgatcatcgcccaaggcgtgccctgcgtggcggtg gccagcaacgaggagcccgcgtggtccgcgccagtggcttcaccgggca actggtgcgggtacgcctggccagcctcagcgagctggaagatggcttgc agtacgacatggaagagctggtgggcagcgcggaatttgcccgccaggcc gatgccatcgccgcgcgccatggcaagaccttgcgcattcacatggcgct caactccagcggcatgagccgcaacggggtggagatggccacctggtccg gccgtggcgaagcgctgcagatcaccgaccagaagcacctcaagctggtc gcgctgatgacccacttcgccgtggaagacaaggacgatgtacgcaaggg cctggcggcattcaacgagcagaccgactggttgatcaagcacgccaggc tggaccgcagcaagctcaccctgcacgccgccaactcgttcgctacgctg gaagtgccggaagcgcgcctggacatggtacgaacgggtggcgcgctgtt cggcgacaccgtgccggcgcgcaccgagtacaaacgtgcgatgcagttca aatcgcacgtggcggcggtgcacagctatccggccggcaacaccgtgggc tatgaccgcaccttcaccctggcccgtgattcgcggctggccaacattac ggtcgggtactccgatggctaccgccgggtattcaccaacaagggccatg tgctgatcaacggccaccgtgtgccggtcgtgggcaaggtgtcgatgaac acgctgatggtcgatgtcaccgacttccctgatgtgaaggggggtaacga agtggtgctgttcggcaagcaggccggggcgaaatcacccaggccgaga tggaagaaatcaacgcgcgttgctcgccgatttgtacaccgtatgggc aattccaacccgaagatactcgtcgactga.

The KT2440 BAR amino acid sequence (SEQ ID NO:120) is as follows:

Mpfrrtllaaslallitgqaplyaapplsmdngtntltvqnsnawvevsa salqhnirtlqaelagksklcavlkadayghgiglvmpsiiaqgvpcvav asneearvvrasgftgqlvrvrlaslseledglqydmeelvgsaefarqa daiaarhgktlrihmalnssgmsrngvematwsgrgealqitdqkhlklv almthfavedkddvrkglaafneqtdwlikharldrskltlhaansfatl evpearldmvrtggalfgdtvparteykramqfkshvaavhsypagntvg ydrtftlardsrlanitvgysdgyrrvftnkghvlinghrvpvvgkvsmn tlmvdvtdfpdvkggnevvlfgkqaggeitqaemeeingalladlytvwg nsnpkilvd.

Purification of *P. putida* KT2440 BAR.

The pET30 KT2440 BAR plasmid described above was transformed into BL21 DE3 pLysS (Invitrogen, Carlsbad, Calif.). The resulting strain was grown in LB or Terrific Broth at 37° C with aeration to an $OD_{600}$ of 0.4-0.6 and induced with 1 mM IPTG. Incubation was continued 3-4 hours at 37° C. with aeration. The cells were harvested by centrifugation and the cell pellet was stored at −80° C. until use. The cell pellet was thawed on ice. The cells were lysed with BugBuster and Benzonase (Novagen, Madison, Wis.). Cell debris was removed by centrifugation and the cell free extract was either used immediately or stored at −80° C. The KT2440 BAR gene was also cloned into the NdeI-BamH I sites of pET28 and transformed into BL21 DE3 pLysS competent cells. This construct did not appear to express soluble protein very efficiently so the untagged version (pET30 KT2440 BAR) was used in future studies.

The extract was applied to an UnoQ column (BioRad, Hercules, Calif.) that had been equilibrated with at least 5 column volumes buffer A (25 mM potassium phosphate pH 8.0, 10 μM pyridoxal-5'-phosphate (PLP)). The column was washed with 2 column volumes of buffer A. The protein was eluted with a linear gradient of buffer B (buffer A+1 M NaCl) from 0-100% buffer B over 20 column volumes and 5 ml fractions were collected from the time the gradient started. Fractions were assayed using the Amplex Red method described in Example 4A(7). Briefly, 100 μg D-amino acid oxidase (Sigma, St. Louis, Mo.), 0.05 mM FAD, 25 mM L-trp, and a small volume of the fraction to be assayed were combined in 50 μL $H_2O$ and added to 50 μL Amplex Red reaction buffer prepared as directed in the manufacturer's protocol. Fractions with activity were desalted with a PD-10 column (GE Healthcare, Piscataway, N.J.) and concentrated with Amicon centrifugal concentrators (Millipore, Billercia, Mass.). Purified protein was stored at −80° C.

Assay of BAR Enzyme

Amplex Red assays were set up as described in this example. *P. putida* KT2440 BAR was used at 200 μg (purified as described in this example). Wild-type *G. stearothermophilus* alanine racemase and the Y354A were purified as described in Example 4B and used at either 200 μg or 1000 μg. CE is cell-free extract that was prepared as described in this example. The results for the 60 minute time point are shown in Table 22 below. The entire timecourse is shown in FIG. 11.

TABLE 22

| Enzyme | Fluorometer reading (at 60 minutes) |
| --- | --- |
| BAR (200) | 56943 |
| Y354A (200) | 7860 |
| Y354A (1000) | 13587 |
| WT alanine racemase (200) | 3646 |
| WT alanine racemase (1000) | 3639 |
| BAR CE (5 μL) | 16228 |
| BAR CE (10 μL) | 26662 |
| BAR CE (50 μL) | >58000 |
| No Enzyme | 1510 |

The purified protein was also assayed for tryptophan racemase activity in 50 mM potassium phosphate pH 8, 10 μM PLP, and 30 mM L-tryptophan as described in Example 4A. Either 200 μg or 1000 μg of purified enzyme was used in the assays (indicated in parentheses). D-tryptophan was analyzed using the chiral amino acid method in Example 1 for detection. The results are shown in Table 23 below.

TABLE 23

| Enzyme | Time | ppm of D-tryptophan |
| --- | --- | --- |
| BAR (200) | 0 | 0 |
|  | 5 | 172 |
|  | 10 | 410 |
|  | 20 | 844 |
|  | 30 | 1318 |
|  | 60 | 2362 |
|  | 120 | 2594 |
|  | 240 | 2762 |
|  | 1080 | 2294 |
| Y354A (200) | 0 | 0 |
|  | 5 | 0 |
|  | 10 | 0 |
|  | 20 | 0 |
|  | 30 | 12 |
|  | 60 | 22 |
|  | 120 | 44 |
|  | 240 | 56 |
|  | 1080 | 368 |
| Y354A (1000) | 0 | 0 |
|  | 5 | 0 |
|  | 10 | 12 |
|  | 20 | 18 |
|  | 30 | 40 |
|  | 60 | 80 |
|  | 120 | 146 |
|  | 240 | 218 |
|  | 1080 | 1164 |

The assays indicate that the *P. putida* KT2440 BAR enzyme is much more active on tryptophan than the *G. stearothermophilus* derived enzymes and mutants thereof. While the BAR enzymes of *P. putida* KT2440 and *P. putida* NBRC 12996 are described in U.S. Published Application No. 2005/0095670 A1, they were not assayed for their ability to racemize tryptophan.

The KT2440 BAR amino acid sequence was used to search for other potential BAR proteins present in organisms whose whole genome sequences are available in the public domain. The following table presents a list of organisms with enzymes that are homologous to KT2440 BAR and the BLAST P-score. The results are shown in Table 24. The Genbank accession numbers of the corresponding proteins are indicated in the left-hand column.

TABLE 24

| Accession number | P-Score | Organism |
|---|---|---|
| YP_070906.1 GI: 51596715 | $1.16^{-127}$ | Yersinia pseudotuberculosis |
| NP_669165.1 GI: 22125742 | $1.82^{-127}$ | Yersinia pestis KIM |
| NP_937085.1 GI: 37676689 | $3.53^{-127}$ | Vibrio vulnificus YJ016 |
| YP_131472.1 GI: 54310452 | $2.30^{-125}$ | Photobacterium profundum SS9 |
| YP_204118.1 GI: 59711342 | $9.84^{-126}$ | Vibrio fischeri ES114 (IG-30) |
| NP_230956.1 GI: 15641324 | $3.92^{-124}$ | Vibrio cholerae El Tor N16961 |
| NP_799227.1 GI: 28899622 | $8.23^{-124}$ | Vibrio parahaemolyticus RIMD 2210633 |
| YP_133597.1 GI: 54303604 | $1.87^{-122}$ | Photobacterium profundum SS9 |
| NP_859997.1 GI: 32265965 | $1.07^{-118}$ | Helicobacter hepaticus ATCC51449 |
| ABC20456.1 GI: 83573904 | $3.91^{-56}$ | Moorella thermoacetica |
| YP_461029.1 GI: 85858827 | $2.19^{-52}$ | Syntrophus sp. |
| YP_320911.1 GI: 75906615 | $1.50^{-50}$ | Anabaena variabilis ATCC29413 |
| YP_388039.1 GI: 78356590 | $1.38^{-45}$ | Desulfovibrio desulfuricans G20 (JGI) |
| NP_971703.1 GI: 42526605 | $2.95^{-45}$ | Tremponema denticola 35405 |

The BLAST P-score indicates that there are enzymes that are highly homologous to the KT2440 BAR and these highly homologous enzymes may have activity on substrates other than alanine even though they have been annotated as alanine racemases in public databases. One can see that there is a grouping of highly related racemases, and then a drop-off in homology occurs from Moorella thermoacetica onward. By blasting NCBI, another closely related homologous gene was found from P. taetrolens (Genbank Accession No. AB096176, nucleotide sequence) as well as in P. putida F1 (ZP_00898332.1 GI:82735470, protein sequence, coded by NZ_AALM01000002 nucleotides 53173 . . . 54402). Based on this information, further cloning work was done to isolate BAR genes in other Pseudomonas species, Vibrio, Yersinia, and Photobacterium. See examples 4I, 4J, 4K, 4L, and 4N.

Additionally a literature review gave other indications of where broad specificity amino acid racemases might exist. The following is a list of organisms which have had publications suggesting the presence of a broad specificity amino acid racemase, along with one reference for each organism:

1. P. putida IF012996, also known as NBRC 12996, P. putida 12996, and P. striata (Nagata, Shinji; Esaki, Nobuyoshi; Tanizawa, Katsuyuki; Tanaka, Hidehiko; Soda, Kenji, Agricultural and Biological Chemistry (1985), 49(4), 1137-41)
2. P. putida SCRC-744 (Asano, Yasuhisa; Endo, Kaori, Applied Microbiology and Biotechnology (1988), 29(6), 523-7)
3. P. graveolens, also known as P. taetrolens (Soda, Kenji; Yorifuji, Takamitsu; Ogata, Koichi, Journal of Biological Chemistry (1971), 246(16), 5085-92)
4. Aeromonas caviae, also known as Aeromonas punctata subspecies caviae (Inagaki, Kenji; Tanizawa, Katsuyuki; Tanaka, Hidehiko; Soda, Kenji, Agricultural and Biological Chemistry (1987), 51(1), 173-80)
5. P. striata AKU 0813 (Soda, Kenji; Osumi, Takaharu, Biochemical and Biophysical Research Communications (1969), 35(3), 363-8)
6. P. aureofaciens (Salcher, Olga; Lingens, Franz, Journal of General Microbiology (1980), 121(2), 465-71)
7. P. putida 12633 (Wolf, Larissa B.; Sonke, Theo; Tjen, Kim C. M. F.; Kaptein, Bernard; Broxterman, Quirinus B.; Schoemaker, Hans E.; Rutjes, Floris P. J. T., Advanced Synthesis & Catalysis (2001), 343(6+7), 662-674)
8. P. fluorescens strains (Ju, Jiansong; Yokoigawa, Kumio; Misono, Haruo; Ohnishi, Kouhei, Journal of Bioscience and Bioengineering (2005), 100(4), 409-417)
9. P. miyamizu (Chibata, Ichiro; Tosa, Tetsuya; Sano, Ryujiro, Applied Microbiology (1965), 13(4), 618-24)
10. P. oleovorans strains, also known as P. putida
11. Pseudomonas strain 2150 (Okazaki, Hiroshi, Agricultural and Biological Chemistry (1968), 32(2), 254-6)

Based upon this literature, further work was done to successfully isolate BAR-encoding genes from P. putida 12996 and Aeromonas species, as described in Examples 4I and 4O. One skilled in the art would be able to isolate the genes encoding the BAR enzymes from the rest of these organisms (where genomic sequence data is limited) using reverse genetics techniques or genomic/cDNA expression libraries, as described in Example 11 for instance. Because the two Pseudomonas putida racemase homologs tested in this example (4E and 4I) were both broad specificity amino acid racemases, as well as the P. taetrolens (graveolens) enzyme (as described in Example 4L), it is expected that all homologous Pseudomonas derived racemases (such as those described in the above literature) would also have broad activity.

4F: Monatin Production with P. putida KT2440 BAR

A monatin production assay was done with the purified P. putida KT2440 BAR (as purified in Example 4E) (100 μg) or purified Y354A (as purified in Example 4B) (500 μg), D-aminotransferase (BioCatalytics AT-103 (Pasadena, Calif.)) (500 μg), and the aldolase of SEQ ID NO:104 (Example 3B) (50 μg). In addition to the enzymes above, the following were added per 1 mL of reaction mixture: 4 mM $MgCl_2$, 50 mM L-tryptophan, 100 mM sodium pyruvate, 100 mM potassium phosphate buffer pH 7.5, and 0.05 mM PLP. As a control, the experiment was done without racemase and starting with D-tryptophan. A summary of the results is presented in Table 25, below.

TABLE 25

| Substrate | Racemase | Time | Total Monatin | % R,R | % S,S | % R,S | % S,R |
|---|---|---|---|---|---|---|---|
| L-trp | Y354A | 2 hours | None detected | | | | |
| | | 18 hours | None detected | | | | |
| L-trp | BAR | 2 hours | None detected | | | | |
| | | 18 hours | 38.6 ppm | 92.1 | 5 | | 2.9 |

TABLE 25-continued

| Substrate | Racemase | Time | Total Monatin | % R,R | % S,S | % R,S | % S,R |
|---|---|---|---|---|---|---|---|
| L-trp | None | 2 hours | None detected | | | | |
| | | 18 hours | None detected | | | | |
| D-trp | None | 2 hours | 19.9 ppm | Not tested | Not tested | Not tested | Not tested |
| | | 18 hours | 221.25 ppm | 97.8 | 0.2 | | 2 |

No monatin was detected using Y354A in this experiment. This racemase has been used in the past to produce monatin, but a much higher level of enzyme was used (at least 2 mg and up to 10 mg to see higher levels of monatin). The *P. putida* KT2440 BAR was used to produce monatin from L-tryptophan. The 100 µg KT2440 BAR used in this experiment was not enough to see monatin production after two hours, but was sufficient to see monatin production after 18 hours. The stereoisomer distribution indicated that most of the monatin produced is the R,R isomer. There was no R,S isomer produced. This indicates that KT2440 BAR is not able to detectably racemize the R,R isomer of monatin (racemization of the R,R isomer would produce the R,S isomer). There was a significant amount of the S,S isomer produced in this experiment. This is probably due to the fact that the AT-103 used in this experiment is not highly purified and may contain L-aminotransferases from the cellular extract, and that there is a large amount of L-tryptophan present to serve as an amino donor for transamination of S-MP.

4G: Mutagenesis of *P. putida* KT2440 BAR at Position 396

The gene encoding the BAR enzyme from *P. putida* KT2440 (described in Example 4E) was modified to produce an enzyme with a Y396C mutation. A similar mutation was described in a poster entitled "Tryptophan Racemase Derived from Broad Specificity Amino Acid Racemase by Directed Evolution" (Sato, M., et al., 10$^{th}$ International Symposium on the Genetics of Industrial Microorganisms, Prague, Jun. 24-28, 2006) and K. Kino, M. Sato, M. Yoneyama, and K. Kirimura, Appl Microbiol Biotechnol (2007) 73:1299-1305. Mutagenesis was done using the QuickChange-Multi site-directed mutagenesis kit (Stratagene, La Jolla, Calif.), using the BAR gene in pET30 which results in an untagged protein. The following mutagenic primer was used to make the Y396C change:

```
                                     (SEQ ID NO: 121)
5'-TTGCTCGCCGATTTGTGCACCGTATGGGCAATTC-3'.
```

The site-directed mutagenesis was done as described in the manufacturer's protocol. Several isolates were sequenced (Agencourt, Beverly, Mass.) and an isolate with the correct sequence was selected and used for further analysis.

The plasmid was transformed into BL21(DE3) (Novagen, Madison, Wis.). Recombinant protein was produced in Overnight Express II medium (Novagen, Madison, Wis.) containing 50 µg/mL kanamycin according to manufacturer's protocols. Cell-free extracts were prepared using BugBuster (Novagen, Madison, Wis.) according to manufacturer's protocols, and analyzed for percent expression of the target protein using the Experion method described above.

Total protein assays were done using a Pierce BCA kit (Rockford, Ill.). Tryptophan racemase assays with the mutant enzyme were performed in triplicate using the wild-type enzyme prepared in the same manner as a positive control. The assays contained per mL: 30 mM L-tryptophan, 50 mM potassium phosphate pH 8, 10 µM PLP, and approximately 200 µg of racemase protein in a cell free extract. Zero, 20 minute, 1 hour, and overnight samples were collected, treated with 2% formic acid, filtered, and diluted 1:10 for analysis using the chiral amino acid method described in Example 1. At the 20 minute time point, the Y396C mutant produced approximately 264 ppm D-tryptophan, as compared to 761 ppm for the wild-type enzyme. At 1 hour, the mutant produced an average of 444 ppm D-tryptophan, as compared to 1110 ppm for the wild-type enzyme. The overnight samples contained 2300 ppm D-tryptophan, whereas the wild-type enzyme had reached equilibrium by producing approximately 3000 ppm D-tryptophan.

The activity of the mutant enzyme is approximately 35-40% of the wild-type under the conditions tested. However, this mutant was expected to have significantly less activity on alanine compared to the wild-type, which may be advantageous in reactions to produce monatin. Less D-alanine would be expected to be converted to L-alanine as a byproduct. Sato et al. reported that the BAR enzyme derived from *P. putida* IFO 12996 containing the I384M mutation alone had a specific activity of 26000 nmol/min/mg for alanine, whereas the I384M/Y396C mutant had only 825 nmol/min/mg activity for alanine. The KT2440 enzyme already contains methionine at position 384 inherently, thus is comparable to the I384M mutant described in IFO 12996.

Further experiments were conducted to assay the alanine racemase activity of the Y396C mutant. The conditions were as described above for L-tryptophan racemase activity, although 40 minute and 2 hour time points were taken. When compared to wild-type BAR from KT2440, the Y396C mutant did in fact have less alanine racemase activity. However, when monatin production experiments were repeated as in Example 4F, this mutant did not provide an advantage in production of total monatin (produced approximately $\frac{1}{3}^{rd}$ the amount of monatin). The Y396C mutant also produced lower purity of R,R monatin (86.2-87.3% R,R versus 97.6-99.3% R,R monatin for the wild-type enzyme, using the FDAA-derivatization technique described in Example 1).

4H: Cloning of *P. putida* KT2440 BAR with Alternative Sequence Tags

Experimental Overview

The *Pseudomonas putida* KT2440 BAR described in Example 4E was expressed with a variety of sequence tags to improve solubility and aid in purification because the N-terminal His-tag from the pET28 construct appeared to produce an insoluble protein. The gene was subcloned, expressed, and tested for activity in conversion of L-tryptophan to D-tryptophan.

Polymerase Chain Reaction Protocol

The gene encoding the *P. putida* KT2440 BAR was subcloned from the pET30 construct described in Example 4E. Polymerase chain reactions were performed using approximately 100 ng of plasmid DNA using primers designed with 5' restriction sites and overhangs for cloning into the pET30a vector (without a stop codon, producing a C-terminal His-tag) (Novagen, Madison, Wis.), pET22-b(+) (periplasmic leader sequence), and pASK-IBA3 (IBA, Göttingen, Germany), producing a C-terminal Strep-tag. The same N-terminal primer was used for the pET30a cloning as in Example 4E. The primer sequences used are as follows:

```
                                        (SEQ ID NO: 122)
pET30 C term-XhoI: 5'-
AAGTCGCTCGAGGTCGACGAGTATCTTCGGG-3';

(SEQ ID NO: 123)
pASK N term: 5'-
ACGGTAGGTCTCAAATGCCCTTTCGCCGTACC-3';

(SEQ ID NO: 124)
pASK C term: 5'-
AACCGTGGTCTCAGCGCTGTCGAGGAGTATCTTCGGG-3';

(SEQ ID NO: 125)
pET 22 N term: 5'-
GCTCCACATGTCTCCCTTTCGCCGTACCCTTCTGGCTGCA
TC-3';
and (SEQ ID NO: 126)
pET22 C term: 5'-
CCGCCGGATCCTCAGTCGACGAGTATCTTCGGGTTGGAA
TTGC-3'.
```

The following PCR protocol was used for the pET30 and pASK constructs: in a 50 µL reaction 1 µL template, 1 µM of each primer, 0.2 mM each dNTP, 3.5 U Expand High Fidelity Polymerase, and 1× Expand buffer (Roche, Indianapolis, Ind.) with Mg were used. The thermocycler program used included a hot start at 94° C. for 3 minutes, followed by 8 repetitions of the following steps: 94° C. for 30 seconds, 51° C. for 30 seconds, and 72° C. for 2 minutes. Twenty-two more cycles were carried out using a 55° C. annealing temperature. After 30 cycles, the sample was maintained at 72° C. for 7 minutes and then stored at 4° C. Clean PCR products of the correct size were obtained (approximately 1200 bp). For the pET22 construct, a similar amplification protocol was utilized. However, PfuTurbo (Stratagene) was used as the polymerase in a protocol recommended by the manufacturer.

Cloning

The PCR products for the pET30 and pASK-IBA3 constructs were purified using the Qiagen PCR purification kit (Qiagen, Valencia, Calif.). The products and vectors were digested with Nde I/Xho I (pET30a) or Bsa I (pASK-IBA3) followed by purification from 0.8% TAE-agarose gels using the Qiagen gel extraction kit (Qiagen, Valencia, Calif.). The digested vectors and insert were ligated using the Rapid™ DNA Ligation Kit (Roche, Indianapolis, Ind.). Approximately 50 ng of treated insert, 100 ng of treated vector (3 to 1 molar ratio of insert to vector), 5 U of T4 DNA ligase, and 1× ligation buffer were incubated for 20 minutes at room temperature. The ligation mixtures were transformed into TOP10 chemically competent *E. coli* cells and plated on LB plates containing appropriate antibiotics. The PCR product for the pET22 construct was purified using the QIAquick® Gel Extraction Kit (Qiagen, Valencia, Calif.) and cloned into pCR-Blunt II-TOPO (Invitrogen). The insert sequence was verified and cloned as a BamH I/Pci I fragment into the Nco I and BamH I restriction sites of pET-22b(+) (Novagen, Madison, Wis.).

Plasmid DNA was purified from the resulting transformants using the Qiagen spin miniprep kit (Qiagen, Valencia, Calif.) and screened for the correct inserts by restriction digest. The sequences of plasmids appearing to have the correct insert were verified by dideoxy chain termination DNA sequencing (Agencourt, Beverly, Mass.).

Gene Expression and Assays

Plasmid DNA was transformed into *E. coli* expression host BL21(DE3) (Novagen, Madison, Wis.). Induction of the pET30 and pET22 constructs in BL21 (DE3) were performed using the Overnight Express II protocol (Novagen, Madison, Wis.). Induction of the pASK-IBA3 construct was performed according to manufacturer's protocols. Cell extracts were prepared from the overnight cultures by suspending cell pellets in Novagen BugBuster™ reagent containing benzonase nuclease according to manufacturer's protocols. The supernatants (cell extracts) were loaded onto 4-15% gradient gels for analysis of the soluble proteins and estimation of percent expression. Total protein assays were conducted using the Bio-Rad kit (Bradford assay method) using BSA as a standard. The C-terminally His-tagged BAR expressed well and was soluble, a marked improvement over the N-terminally His-tagged protein. However, the pASK-IBA3 Strep-tagged protein did not appear to express well in total protein or in the soluble fraction. The C-terminally His-tagged BAR was purified using Novagen His-Bind columns, and still appeared to be soluble after elution. However, upon storage at −80° C. in imidazole overnight, the protein precipitated upon thawing. The protein was therefore assayed in cellular extracts. It is expected that if the protein is removed from imidazole elution buffer more expediently, it would remain soluble.

Cell extracts were assayed for tryptophan racemase activity using the following protocol. One mL reactions were carried out in 50 mM potassium phosphate (pH 8.0), 10 µM PLP, and 30 mM L tryptophan. The reactions were initiated by the addition of approximately 200 µg of racemase enzyme and were incubated at 30° C. overnight for 5 minutes, 30 minutes, 120 minutes, and overnight. Three percent formic acid was added to each time point to stop the reaction and the precipitated protein was removed by centrifugation. Samples were diluted 1:10 and frozen at −80° C. until they were analyzed for D-tryptophan by the chiral amino acid method described in Example 1. In this assay, an internal standard was not employed, resulting in semi-quantitative analysis. Untagged *P. putida* KT2440 BAR was prepared in the same way and used as a positive control. Purified BAR (from Example 4E) was also used as a positive control. Results are shown in Table 26 below.

TABLE 26

| Production of D-tryptophan by KT2440 BAR constructs | | |
|---|---|---|
| Tag | Time (minutes) | ppm D tryptophan |
| untagged | 5 | 247 |
|  | 30 | 1842 |
|  | 120 | off scale |
|  | Overnight | 4671 |
| untagged-purified | 5 | 173 |
|  | 30 | 1689 |

TABLE 26-continued

Production of D-tryptophan by KT2440 BAR constructs

| Tag | Time (minutes) | ppm D tryptophan |
|---|---|---|
| | 120 | 5235 |
| | overnight | 4176 |
| C-terminal His tag | 5 | 257 |
| | 30 | 2113 |
| | 120 | 3810 |
| | overnight | 4535 |
| Periplasmic | 5 | 397 |
| | 30 | 4243 |
| | 120 | 4686 |
| | overnight | 2978 |

The pASK-IBA3 cell extracts typically had undetectable activity, or very low activity as expected because expression was so poor. The C-terminally His-tagged and periplasmic tagged BAR enzymes clearly have as much or greater activity than the untagged BAR enzyme from KT2440. Reactions have typically reached equilibrium by 2 hours, 30 minutes for the periplasmic-tagged BAR. Reactions were repeated using different amounts of enzyme. The trend was consistent, that the periplasmic KT2440 BAR has similar or greater activity than untagged BAR. It was noted that activity does not scale linearly with the amount of cellular extracts added to the assays; however, it is possible that there is something inhibitory in the BugBuster buffer or that increased concentrations cause aggregation of the enzyme. Assays were repeated after desalting the protein using a PD-10 column as described elsewhere, and eluting in 50 mM potassium phosphate buffer pH 8 containing 10 μM PLP. Removal of the detergent and Tris buffer (from Bugbuster) does appear to improve the results when larger volumes of cell extract are utilized in the assay.

Cellular extracts were prepared again for the C-terminally HIS-tagged KT2440 BAR enzyme. As expected, when the imidazole from the elution buffer was removed immediately using a PD-10 column, the protein remained in solution. Analysis by SDS-PAGE showed a highly purified band at the expected molecular weight. The purified C-terminally HIS tagged protein was re-assayed as above and compared to the wildtype (untagged) BAR enzyme, both before and after freezing. In both cases the C-tagged purified enzyme showed comparable activity to the untagged protein.

Analysis using the Signal P 3.0 Server at the Technical University of Denmark (www.cbs.dtu.dk/services/SignalP/) predicts a leader sequence of 24 amino acids in length for this racemase.

4I: Cloning of P. putida NBRC 12996 BAR

The P. putida NBRC 12996 BAR sequence is 91% identical at the DNA level and 94% identical at the protein level to the BAR protein described above from strain KT2440. The NBRC 12996 strain of P. putida was obtained from the NITE (National Institute of Technology and Evaluation) Biological Resource Center in Japan. Primers were the same as the primers used for the cloning of the P. putida KT2440 BAR gene described in Example 4E. The strain was grown on medium containing peptone 10 g, yeast extract 2 g, MgSO4.7H2O 1 g, distilled water 1 L, agar 15 g, pH 7.0. Cells were scraped off a Petri plate and resuspended in 400 μL deionized and autoclaved $H_2O$. This cell suspension was used as template for the PCR reaction. The resulting PCR product was purified with the QIAquick® PCR purification kit (Qiagen, Valencia, Calif.) and digested with BamH I and Nde I. The digested DNA was run on a 1% agarose gel and the most prominent band was cut out of the gel. The DNA was purified with the QIAquick® gel extraction kit (Qiagen, Valencia, Calif.). The resulting fragment was ligated to pET30 that had been digested with Nde I and BamH I and purified as described above. The ligation was transformed in to TOP10 chemically competent cells (Invitrogen, Carlsbad, Calif.) and plated on LB plates supplemented with 50 μg/mL kanamycin. Isolated colonies were streak purified and used to start cultures for plasmid preps. The plasmids were run on a gel to confirm the presence of an insert. Plasmids with an insert were sent to Agencourt for sequencing (Beverly, Mass.). An isolate with the correct sequence was identified and used in later studies.

The NBRC12996 BAR DNA sequence is (SEQ ID NO:127):

```
atgcccttcgccgtaccctcctggctgcatccctcgctctgctgatcactggccaggcccgct gtacgccgcaccgcccctgtcgatggacaacggcaccaccgccctgaccgcgcagaacag caacgcctgggtcgaaatcagtgccggcgcactgcaacacaacatccgtaccttgcaggccg agttgggcggcaagtccaagctgtgcgccgtgctcaaggccgacgcctatggccacggtatc ggcctggtgatgccgtcgatcatcgcccagggcgtgccctgcgtggcggtggccagcaacg aggaggcacgcgtggtccgcgccagtggcttcaccgggcaactggtgcgggtacgcctggc cagcctcggcgaagtggaagatgccttgcagtacgacatggaagagctggttggcagcgcc gagttcgcccgccagctcgatgccatcgccgaacgccacggcaagaccctgcgcattcacat ggcgctcaattccagcggcatgagccgcaacggcgtggaaatgaccacctggtccggccgg ggtgaagcgctgcagatcactgaccagaagcacctccagctggtcgcgctgatgactcacttc gccgtggaagacaaggacgatgtgcgcaaaggcctggcagcgttcaacgaacagaccgact ggctgatcaagcacgcgaagcttgatcgcagcaagctcaccctgcatgccgccaactccttcg ctacgctggaagtgccggaagcgcacctggacatggtgcgtaccggtggcgcgctgttcggc gacaccgtgccgacgcgcaccgaataccaacgtgtcatgcagttcaagtcgcacgtggcggc
```

```
ggtgcacagctacccggcaggcaacaccgtcggctacgaccgcaccttcaccctggcgcgt gattcgcgcctggccaacatcaccgtgggttactccgatggctaccgcgggtgttcaccaac aagggccatgtgctgatcaacggccaccgagtgccagtggtgggcaaggtgtcgatgaacac cttgatggtcgatgtcaccgatttccccgatgtgaaggggggcaacgaagtggtgctgttcggc aaacaggccgggagggagatcacccaggccgagatagaagaaatcaacggcgcgctgctc gccgacctctacaccgtatggggcagttccaacccgaagatactcgtcgactga.
```

The NBRC12996 BAR amino acid sequence (SEQ ID NO:128) is:

```
Mpfrrtllaaslallitgqaplyaapplsmdngttaltaqnsnawveisagalqhnirtlqaelg gksklcavlkadayghgiglvmpsiiaqgvpcvavasneearvvrasgftgqlvrvrlaslg evedalqydmeelvgsaefarqldaiaerhgktlrihmalnssgmsrngvemttwsgrge alqitdqkhlqlvalmthfavedkddvrkglaafneqtdwlikhakldrskltlhaansfatle vpeahldmvrtggalfgdtvptrteyqrvmqfkshvaavhsypagntvgydrtftlardsrl anitvgysdgyrrvftnkghvlinghrvpvvgkvsmntlmvdvtdfpdvkggnevvlfg kqagreitqaeieeingalladlytvwgssnpkilvd.
```

Analysis using the Signal P 3.0 program (www.cbs.dtu.dk/services/SignalP/) predicts a signal peptide 24 amino acids in length for this racemase.

Assay of NBRC 12996 BAR

The pET30 NBRC 12996 BAR was transformed into BL21 DE3 pLysS competent cells and the protein was expressed and a cell-free extract was prepared as described in Example 4E. The purified KT2440 BAR (described in Example 4E) (100 μg) was compared to the 12996 BAR (100 μL of cell-free extract). The results are shown in Table 27 below.

TABLE 27

| Enzyme | Time (min) | ppm L-trp produced |
|---|---|---|
| KT2440 BAR | 0 | 0 |
|  | 30 | 692 |
|  | 60 | 1296 |
|  | 120 | 2020 |
|  | 360 | 2716 |
|  | 1080 | 868 |
| NBRC12996 BAR | 0 | 0 |
|  | 30 | 114 |
|  | 60 | 254 |
|  | 120 | 504 |
|  | 360 | 1310 |
|  | 1080 | 1312 |

The NBRC 12996 BAR has activity for racemization of tryptophan. It is not possible to quantitatively compare activities of the KT2440 BAR with the NBRC 12996 BAR because the NBRC BAR was not purified or quantified for this experiment.

A poster entitled "Tryptophan Racemase Derived from Broad Specificity Amino Acid Racemase by Directed Evolution" (M. Sato, M. Yoneyama, K. Kirimura, and K. Kino, 10th International Symposium on the Genetics of Industrial Microorganisms, Prague, Jun. 24-28 2006) suggested that I384M mutants of this protein would result in higher tryptophan racemase activity. See also K. Kino, M. Sato, M. Yoneyama, and K. Kirimura, Appl Microbiol Biotechnol (2007) 73:1299-1305.

Mutagenesis was done using the QuickChange-Multi site-directed mutagenesis kit (Stratagene, La Jolla, Calif.), using the 12996 BAR gene in pET30 which results in an untagged protein. The following mutagenic primer was used to make the I384M change:

```
                                          (SEQ ID NO: 129)
5'-ACCCAGGCCGAGATGGAAGAAATCAACG-3'.
```

The site-directed mutagenesis was done as described in the manufacturer's protocol. Several isolates were sequenced (Agencourt, Beverly, Mass.) and an isolate with the correct sequence was selected and used for further analysis. The plasmid was transformed into BL21(DE3) (Novagen, Madison, Wis.) competent cells. Recombinant protein was produced in Overnight Express II medium (Novagen, Madison, Wis.) containing 50 μg/mL kanamycin according to manufacturer's protocols. Cell-free extracts were prepared using BugBuster (Novagen, Madison, Wis.) according to manufacturer's protocols, desalted, and analyzed for percent expression of the target protein using the Experion method described above.

Total protein assays were done using a Pierce BCA kit (Rockford, Ill.). Tryptophan racemase assays with the mutant enzyme were performed using the wild-type enzyme prepared in the same manner as a positive control. Assays contained per mL: 30 mM L-tryptophan, 50 mM potassium phosphate pH 8, 10 μM PLP, and approximately 100 μg of racemase protein in a cell free extract. In the case where 100 μg was not used (based on Experion % expression and Pierce total protein numbers), results were normalized. Zero, 30 minute, 2 hour, and overnight samples were collected, treated with 2% formic acid, filtered, and diluted 1:10 for analysis using the chiral amino acid method described in Example 1.

Although not completely quantitative since unpurified protein was utilized, the data suggest that the I384M mutation did not appear to significantly impact the activity of the enzyme.

4J: Cloning and Expression of *Vibrio fischeri* Alanine Racemase

Experimental Overview

The gene encoding the *Vibrio fischeri* putative alanine racemase (Genbank Protein Accession No. AAW85230.1 or YP_204118) was cloned, expressed, and tested for activity in conversion of L-tryptophan to D-tryptophan.

Polymerase Chain Reaction Protocol

*Vibrio fischeri* genomic DNA (ATCC 700601D) was used as a template for PCR amplification of the alanine racemase gene. Primers were designed based on the published gene sequence from strain ES114 (CP000020.1 GI:59478708 (also listed as NC_006840) region 800842 . . . 802053). Polymerase chain reaction was performed on genomic DNA using primers designed with 5' restriction sites and overhangs for cloning into the pET 28 and pET30 vectors (Novagen, Madison, Wis.).

Primer sequences:

```
N term:
                              (SEQ ID NO: 130)
5'-GCGGCCCATATGAAGTTTACTAAATGTGCAT-3'
and C term:
                              (SEQ ID NO: 131)
5'-GGCCGCGGATCCCTATTTGTAGATCTTAGGATTTG-3'.
```

The gene derived from *V. fischeri* was amplified using the following PCR protocol. 2 μL of genomic DNA (100 ng/μL) was used as template for PCR. In a 100 μL reaction 2 μL template (genomic DNA 100 ng/μL), 0.5 μL of each primer (100 μM stock solution), 0.3 mM each dNTP (Roche dNTP mix (Roche, Indianapolis, Ind.)), 1 μL Pfu Turbo Polymerase (Stratagene), and 1× Pfu buffer (Stratagene). The thermocycler program used included a hot start at 95° C. for 3 minutes, 10 repetitions of the following steps: 94° C. for 30 seconds, 52° C. for 45 seconds, and 72° C. for 3 minutes, followed by 20 repetitions of the following steps: 94° C. for 30 seconds, 55° C. for 45 seconds, and 72° C. for 3 minutes. After the 20 repetitions the sample was maintained at 72° C. for 7 minutes and then stored at 4° C. This PCR protocol produced a product of 1.2-Kb.

Cloning

The PCR product was gel purified from 0.8% TAE-agarose gel using the Qiagen gel extraction kit (Qiagen, Valencia, Calif.). The product was TOPO cloned and transformed into TOP10 cells according to manufacturer's protocol (Invitrogen, Carlsbad, Calif.). Plasmid DNA was purified from the resulting transformants using the Qiagen spin miniprep kit (Qiagen, Valencia, Calif.) and screened for the correct inserts by restriction digest with Nde I and BamH I. The sequences of plasmids appearing to have the correct insert were verified by dideoxy chain termination DNA sequencing with universal M13 forward and M13 Reverse primers, and the sequence was found to be identical to the accession number listed above.

The correct TOPO clone was digested with restriction enzymes Nde I and BamH I following the manufacturer's recommended protocols (New England Biolabs, Beverly, Mass.) and gel purified from 0.8% TAE-agarose gels using the Qiagen gel extraction kit (Qiagen, Valencia, Calif.). Vectors pET28 and pET 30 were prepared by digestion with restriction enzymes Nde I and BamH I followed by treatment with shrimp alkaline phosphatase (Roche, Indianapolis, Ind.) and purification from 0.8% TAE-agarose gels using the Qiagen gel extraction kit (Qiagen, Valencia, Calif.).

The digested vectors and insert were ligated using the Rapid™ DNA Ligation Kit (Roche, Indianapolis, Ind.). Approximately 50 ng of treated insert, 100 ng of treated vector (3 to 1 molar ratio of insert to vector), 5 U of T4 DNA ligase, and 1× ligation buffer were incubated for 5 minutes at room temperature. The ligation reaction was used to transform *E. coli* TOP10 chemical competent cells (Invitrogen, Carlsbad, Calif.). 3 μL of each ligation reaction was added to 40 μL of TOP10 cells, which were transformed using a 30 second heat shock pulse at 42° C., followed by incubation on ice for 5 min. The cells were allowed to recover in 250 μL of room temperature SOC medium (Sambrook, J., et al. *Molecular Cloning: A Laboratory Manual* 2nd ed., Plainview, N.Y., (1989), 1.76-1.81 & A.2)) for 1 hour at 37° C. with shaking at 225 rpm. Cells were plated on LB plates containing kanamycin (50 μg/mL). Plasmid DNA was purified from the resulting transformants using the Qiagen spin miniprep kit (Qiagen, Valencia, Calif.) and screened for the correct inserts by restriction digest with Nde I and BamH I.

Gene Expression and Assays

Plasmid DNA was subcloned into *E. coli* expression host BL21(DE3) pLysS (Novagen, Madison, Wis.). The cultures were grown and the plasmids were isolated using Qiagen miniprep kit (Qiagen, Valencia, Calif.), and analyzed by restriction digest to confirm identity.

Induction in BL21DE3 was performed in pET28 (tagged) and pET 30 (untagged) vectors. A time course study was performed with cultures grown at 37° C. in 100 mL LB containing kanamycin (50 mg/L) to an $OD_{600}$ of 0.5 and induced with 100 mM IPTG (isopropyl thiogalacatoside) and sampled at 0 and 3 hours post induction. Cells from 0 hour and 4 hour time points were resuspended in 1× sodium dodecyl sulfate buffer containing 2-mercaptoethanol, and heated at 95° C. for 10 minutes, and cooled. Aliquots of these total cellular protein samples were analyzed by SDS-PAGE using a 4-15% gradient gel.

Cell extracts were also prepared from the 4 hour cultures by suspending cell pellets from 5 mL of culture in Novagen BugBuster™ reagent containing benzonase nuclease and protease inhibitor cocktail set #3 (Calbiochem-Novabiochem Corp., San Diego, Calif.) at room temperature for 20 minutes with gentle shaking and centrifuging at 16,000×g to remove cell debris. The supernatants (cell extracts) were loaded onto 4-15% gradient gels for analysis of the cellular soluble proteins. The 4 hour sample from cloned *V. fischeri* alanine racemase showed a total protein band that corresponded to the correct size (approximately 45 kDa) in the pET 28 (tagged) and pET 30 (untagged) vector.

Cells from the induced cultures (100 mL) were centrifuged and washed once with 0.85% NaCl. Cell pellets were resuspended in 5 mL/g wet cell weight of BugBuster™ (Novagen, Madison, Wis.) reagent containing 5 μL/mL protease inhibitor cocktail set #3 (Calbiochem-Novabiochem Corp., San Diego, Calif.) and 1 μL/mL benzonase nuclease. Samples were incubated at room temperature for 20 minutes on an orbital shaker. Insoluble cell debris was removed by centrifugation at 16,000×g for 20 minutes at 4° C.

Cell extracts were assayed for tryptophan racemase activity using the following protocol. 1 mL reactions were carried out in 50 mM potassium phosphate (pH 8.0), with 0.05 mM PLP and 30 mM L tryptophan. The reactions were initiated by the addition of cell free extracts (or purified positive control racemase) and were incubated at 30° C. overnight. Sample aliquots were taken after overnight incubation (zero minute samples served as control reaction). Concentrated formic acid (5 μL) was added to each 250 μL sample aliquot to stop the reaction and the precipitated protein was removed by centrifugation. Supernatants were removed and frozen at −80° C. until they were analyzed for D-tryptophan by the chiral amino acid method in Example 1.

Assay results from cell extracts from pET28 and pET30 induction with 100 mM IPTG (3 hours) demonstrate that *V. fischeri* clones show racemase activity on L-tryptophan, resulting in D-tryptophan production, as did the positive control KT2440 BAR purified racemase produced in Example 4E. All attempts were made to add equivalent amounts of racemase protein to each tube. Under the conditions of the assay we observed higher D-tryptophan production when the *V. fischeri* racemase was cloned in pET30 (untagged) vs pET28 (His-tagged). The results are shown in Table 28. One skilled in the art could improve the enzyme activity of the *V. fischeri* racemase through ensurance of proper folding, increased soluble expression and stability, and mutagenesis methods as described elsewhere.

TABLE 28

| Enzyme Source | Time Point | substrate | Racemase Volume (200 µg) | D-trp conc (µg/mL) | Average D-Trp (µg/mL) |
|---|---|---|---|---|---|
| KT2440 purified racemase | Overnight | L-trp | 75 µL | 337.2 | ≧337.2 |
| pET28/*V. fischeri* racemase | Overnight | L-trp | 93 µL | 0.68 | |
| pET28/*V. fischeri* racemase | Overnight | L-trp | 93 µL | 1.08 | 0.88 |
| pET30/*V. fischeri* racemase | Overnight | L-trp | 167 µL | 4.04 | |
| pET30/*V. fischeri* racemase | Overnight | L-trp | 167 µL | 3.5 | 3.77 |

4K: Cloning of the *Photobacterium profundum* BAR Homologs

The amino acid sequences of two *P. profundum* BAR homologs were obtained from public databases (NCBI). The CR378673 (nucleotides 342444 . . . 343658) putative alanine racemase coding sequence was assembled from primers. The amino acid sequence (NCBI accession number CAG21670) was used to design an optimal DNA sequence using the GeneComposer software package (Version 1.0, Emerald Biosciences, Bainbridge Island, Wash.). The CR378673 optimized DNA sequence (SEQ ID NO:132) is:

```
atgaagctgaagctgagcctggtcgccctggcactgatgggtcagactactgctaatgccgca
ccactgctggtggacttcgataacaatgagcgtgaggaacgtgtgcaaagctctaatgcgtgg
ctggagattgatacccaagcattcagtggcaatattcagttactgcagaaccaactgaaagccg
acaccaagatctgtgcgattatgaaggcggatgcatacggtaatggcattgccggcttgatgcc
tagtatcattgctaaccaagtgccttgtgttggtatcaccagcaatgaggaagcgcgggtggttc
gtaaacatggctttattgggaagatcatgcgtgtccgtgcagcctcgaagaatgaaattgaggg
tggcttgcagtaccagatggaagaattgatcggtacgaaggctcaagccgatcaaatcatcga
aattgcacgcgcaaatggcacgacgattccggttcatttagccttgaatacaagcggcatgggc
cgcaacggtctggacctgacgacctacgaaggccaagttgaaggtgtagagattgctggcga
tccaaacctggagattgtcggcatgatgactcatttcccgaacgagggactggacgaaatcaa
acggaaagtcaaacgtttcaaagtagaaacgaaatggttaatggattccactgacttgaagcgc
aaagatgtgacgctccacgtcgcaaacagctatatccaccttgaatctgcctgaagcgcatctgg
atatggtacgcccaggtggcatgctgtatggcgactatccggcgacagcgccgtatcagcgta
tcgtaagcttcaagacccacgttgcctctttgcaccactttccggctggctcaaccattgggtacg
gatctaccgctgttctggaacgtgattcagttctggctaatctgccgattggctattcggatggctt
cgcgcgctcgttaggaaataaagccgaagtcctgattaacggccagcgtgcgcgcgtcatgg
gtatggtcagtatgaacacgacgatggtcgatgtaacggatattgtggatgttcagaccaatgaa
gaagtcgtgatctttggccgccagggtttcgaagagattacgggcgaggagacggaagagaa
gtctaatcgtattcttccggaacattacactgtgtggggcgccacaaacccgcgtatttatcgcta
a.
```

Primers were designed to cover the entire sequence and both the coding and non-coding strand. The sequence was assembled as in Example 10 using the following primers for the final amplification 5'-agaagacatatgaagctgaagctgagcc-3' (SEQ ID NO:133) and 5'-agaagaggatccttagcgataaatacgcggg-3' (SEQ ID NO:134). The resulting PCR product was cloned into pCR-Blunt II-TOPO using the Zero Blunt TOPO PCR cloning kit (Invitrogen, Carlsbad, Calif.). Plasmids with an insert were sent to Agencourt (Beverly, Mass.) for sequencing. A plasmid with the correct sequence was identified and used for subsequent cloning steps. The TOPO isolate with the correct sequence was digested with Nde I and BamH I, the digest was run on a 1% agarose gel and the correct fragment was cut out of the gel. The DNA was purified using the QIAquick® gel extraction kit (Qiagen, Valencia, Calif.). The resulting DNA fragment was ligated to pET30 that had been digested and purified as described above. Clones with an insert were isolated and sent to Agencourt (Beverly, Mass.) for sequencing. A clone with the correct sequence was isolated and used in further studies.

The CR378681 (nucleotides 60191 ... 61408) gene encoding a putative alanine racemase (protein sequence accession number CAG23797) from *P. profundum* was isolated in the same manner as above using the following primers for the final amplification (5'-GGCCTTGGCATATGAACTTTAA-GATGACTCTG-3' (SEQ ID NO:135) and 5'-TTCCAATTG-GATCCTTACTTCAGGTAGTAACGCGGATTC-3' (SEQ ID NO:136)).

The DNA sequence of the optimized CR378681 racemase (SEQ ID NO:137) is:

```
                                    (SEQ ID NO: 137)
ATGAACTTTAAGATGACTCTGTTAAGCCTGGCCATTACAT

TCCCGAGCTTCAGCATCTATAGCGCGCCACTGGTCATTGA

TCAGAACCTGCCAAGCGAACAGTCGATTCAGCAAAGCAA

CAGCTGGCTGGAAGTTAGCCTGGGCCAGTTTAAATCCAA

TATTGAACAATTTAAATCTCATATTAAAGCCGATACTAAG

ATTTGTGCCGTTATGAAAGCCGATGCATACGGCAATGGC

ATCTTCGGTCTGATGCCGACAATTCTGGAACAGCAAATC

CCATGCGTGGCGATTGCAAGTAACGCGGAAGCTCGCGCT

GTGCGTGAAAGCGGGTTTAAGGGCCAGCTGCTGCGTGTC

CGCAGCGCGAGCTTAGGCGAGATTAAACAGTCACTGGAC

CTGAACATTGAAGAACTGATCGGCTCACATCAGCAGGCG

AAGTTCATTGCAGAGCTGGGTGTAGAACGTAATCAGAAG

ATTAACGTTCATTTAGCTCTGAACGACGGAGGGATGGGT

CGCAATGGGATCGATATGTCTACCGAACAAGGCAAAGCC

GAGGCCCTCGACATCGCGACCCAGGCAAATCTGAACATT

GTTGGTATTATGACTCACTTCCCGAACTATAATGCGGATA

AAGTGCGTGTGAAGCTGAAAGACTTCCAGACAAACTCCA

GCTGGCTGATCAAGCAGGCGGATCTGAAGCGCGATGAAC

TCACGCTCCACGTGGCCAACAGCTATGTGTCCATTAATGT

TCCAGAAGCGCAACTGGATATGGTTCGCCCGGGCGGCGT

GCTGTATGGCGATCTTCCGACCAATCCGGAATATCCGAG
```

-continued

```
CATCGTATCGTTCAAGACGCGGATTGCGTCAATTCACCA

GCTGCCAGCATCCCAGACCGTGGGCTACGATTCGACCTA

TATTACGAAACGTGATAGCGTTCTGGCAAACCTGCCAGT

CGGCTACAGTGATGGCTATCCGCGCCGTATGGGTAATCA

GGCTGATGTGATTATCAACGGACAACGCGCCAAAGTGGT

GGGTGTGACCAGCATGAATACTAGTATCGTCGATATTAC

CGATATTAAAGGCGTTAAACAGGGTCAAGAAGTTACCCT

GTTTGGCAAGCAGAAGAATGTGCAGATTAGCGTGGCCGA

AATGGAGGATTATTCGAAGTTAATCTTCCCGGAACTGTA

CACCATGTGGGGTCAGGCGAATCCGCGTTACTACCTGAA

GTAA.
```

The plasmids were transformed into BL21 DE3 pLysS and this strain was used for expression. The stain with the plasmids was grown to an $OD_{600}$ of ~0.6 and expression was induced with 1 mM IPTG. After incubation at 30° C. (CR378681) or 26° C. (CR378673), with aeration, the cell pellet was harvested by centrifugation and the cell pellet was frozen at −80° C. The cell pellet was thawed on ice and the cells were lysed with an appropriate volume of BugBuster and Benzonase nuclease (see product insert) (Novagen, Madison, Wis.). The lysate was centrifuged to remove cell debris and the resulting cell-free extract was used in racemase assays. Under these conditions, it was not possible to detect conversion of L-trp to D-trp. The enzymes also did not appear to catalyze the conversion of L-alanine to D-alanine when assayed in similar manner as above for tryptophan, even when the detergent was removed from the cell free extracts. The levels of D-alanine produced in assays were similar as compared to cellular extracts without overexpressed racemase genes, indicating that the background production of D-tryptophan was due to endogenous *E. coli* alanine racemase. The enzymes did not appear to express well and activity may be detected if expression is enhanced or if the enzyme is improved through mutagenesis methods known to those in the art. Protein activity may also be enhanced by methods that can encourage proper folding, as many of the racemase enzymes produced did not appear to be soluble and aggregated or precipitated quite easily. The enzyme activity may be difficult to detect due to improper folding or improper insertion of the pyridoxal-5'-phosphate cofactor. Encouraging proper folding or cofactor insertion may greatly enhance enzyme activity.

4L: Cloning and Expression of *Pseudomonas taetrolens* Arginine Racemase

Experimental Overview

*Pseudomonas taetrolens* (also known as *P. graveolens*) arginine racemase (Genbank Accession No. AB096176, nucleic acid sequence) and an I384M mutant thereof, was cloned, expressed, and tested for activity in conversion of L-tryptophan to D-tryptophan. This gene is 72% identical to the *P. putida* BAR gene from KT2440 and 73% identical to the *P. putida* BAR gene from NBRC 12996 described above. The amino acid sequence is 72% identical to both *P. putida* BAR proteins.

Polymerase Chain Reaction Protocol

*Pseudomonas taetrolens* (ATCC 4683) was grown in nutrient broth at 28° C. with shaking at 225 rpm. Polymerase chain reaction was performed on whole cells using primers designed with 5' restriction sites and overhangs for cloning into the pET 28 and pET30 vectors (Novagen, Madison, Wis.).

The primer sequences were:

```
                                              (SEQ ID NO: 138)
N term:    5'-ATAATACATATGCCCTTCTCCCGTACCC-3'
and
                                              (SEQ ID NO: 139)
C term:    5'-GCGGCGGGATCCTTACTGATCTTTCAGGATT-3'.
```

The gene derived from *P. taetrolens* was amplified using the following PCR protocol. Twenty-five μL of grown cells were lysed at 96° C. for 10 minutes. Cell debris was removed by centrifugation and the supernatant was used as template for PCR. A 100 μL reaction contained 5 μL template (lysed cell supernatant), 1.6 μM of each primer, 0.3 mM each dNTP, 10 U rT$^{th}$ Polymerase XL (Applied Biosystems, Foster City, Calif.), 1×XL buffer and 1 mM Mg(OAc)$_2$. The thermocycler program used included a hot start at 94° C. for 3 minutes, 8 repetitions of the following steps: 94° C. for 30 seconds, 52° C. for 30 seconds, and 68° C. for 2 minutes, followed by 22 repetitions of the following steps: 94° C. for 30 seconds, 58° C. for 30 seconds, and 68° C. for 2 minutes. After the 22 repetitions, the sample was maintained at 68° C. for 7 minutes and then stored at 4° C. This PCR protocol produced a product of 1230 bp.

Cloning

The PCR product was gel purified from 0.8% TAE-agarose gel using the Qiagen gel extraction kit (Qiagen, Valencia, Calif.). The product was TOPO cloned and transformed into TOP 10 cells according to manufacturer's protocol (Invitrogen, Carlsbad, Calif.). Plasmid DNA was purified from the resulting transformants using the Qiagen spin miniprep kit (Qiagen, Valencia, Calif.) and screened for the correct inserts by restriction digest with Nde I and BamH I. The sequences of plasmids appearing to have the correct insert were verified by dideoxy chain termination DNA sequencing with universal M13 forward and M13 Reverse primers.

The correct TOPO clone was digested with restriction enzymes Nde I and BamH I following the manufacturer's recommended protocols (New England Biolabs, Beverly, Mass.) and gel purified from 0.8% TAE-agarose gels using the Qiagen gel extraction kit (Qiagen, Valencia, Calif.). Vectors pET 28 and pET 30 were prepared by digestion with restriction enzymes Nde I and BamH I followed by treatment with shrimp alkaline phosphatase (Roche, Indianapolis, Ind.) and purification from 0.8% TAE-agarose gels using the Qiagen gel extraction kit (Qiagen, Valencia, Calif.). The digested vectors and insert were ligated using the Rapid™ DNA Ligation Kit (Roche, Indianapolis, Ind.). Approximately 50 ng of treated insert, 100 ng of treated vector (3 to 1 molar ratio of insert to vector), 5 U of T4 DNA ligase, and 1× ligation buffer were incubated for 5 minutes at room temperature. The ligation reaction was desalted using the High Pure PCR Product Purification Kit (Roche, Indianapolis, Ind.) and used to transform *E. coil* DH10B electrocompetent cells (Invitrogen, Carlsbad, Calif.). Ten μL of each ligation reaction was added to 40 μL of DH10B cells, which were transformed by electroporation using the BioRad Gene Pulsar II under the following conditions: 2.5 kV, 25 μF, 200 ohm in a 0.2 cm cuvette. The cells were allowed to recover in 1 mL of room temperature SOC for 1 hour at 37° C. with shaking at 225 rpm. Cells were plated on LB plates containing kanamycin (50 μg/mL). Plasmid DNA was purified from the resulting transformants using the Qiagen spin miniprep kit (Qiagen, Valencia, Calif.) and screened for the correct inserts by restriction digest with Nde I and BamH I.

Gene Expression and Assays

Plasmid DNA was transformed into *E. coli* expression host BL21(DE3) pLysS (Novagen, Madison, Wis.). The cultures were grown and the plasmids were isolated using the Qiagen miniprep kit (Qiagen, Valencia, Calif.) and analyzed by restriction digest to confirm identity.

Induction in BL21DE3 pLysS was initially performed in both pET 28 (histidine-tagged) and pET 30 (untagged) vectors. A time course study was performed with cultures grown at 37° C. in 100 mL LB containing kanamycin (50 mg/L) to an OD$_{600}$ of 0.5 and induced with 100 μM IPTG (isopropyl thiogalacatoside) and sampled at 0 and 3 hours post induction. Cells from 0 hour and 3 hour time points were resuspended in 1× sodium dodecyl sulfate buffer containing 2-mercaptoethanol and heated at 95° C. for 10 minutes, and cooled. Aliquots of these total cellular protein samples were analyzed by SDS-PAGE using a 4-15% gradient gel.

Cell extracts were also prepared from the 3 hour cultures by suspending cell pellets from 5 mL of culture in Novagen BugBuster™ reagent containing benzonase nuclease and protease inhibitor cocktail set #3 (Calbiochem-Novabiochem Corp., San Diego, Calif.) at room temperature for 20 minutes with gentle shaking and centrifuging at 16,000×g to remove cell debris. The supernatants (cell extracts) were loaded onto 4-15% gradient gels for analysis of the cellular soluble proteins.

The 3 hour sample from cloned *P. taetrolens* arginine racemase showed a total protein band that corresponded to the correct size (approximately 45 kDa) in the pET 30 (untagged) vector. The *P. taetrolens* pET 30 gene product was overexpressed at a higher level than the *P. taetrolens* pET 28 (histidine-tagged) gene product, but neither of the vectors gave a visible soluble protein band.

Cells from the induced cultures (100 mL) were centrifuged and washed once with 0.85% NaCl. Cell pellets were resuspended in 5 mL/g wet cell weight of BugBuster™ (Novagen, Madison, Wis.) reagent containing 5 μL/mL protease inhibitor cocktail set #3 (Calbiochem-Novabiochem Corp., San Diego, Calif.) and 1 μL/mL benzonase nuclease. Samples were incubated at room temperature for 20 minutes on an orbital shaker. Insoluble cell debris was removed by centrifugation at 16,000×g for 20 minutes at 4° C.

Cell extracts were assayed for tryptophan racemase activity using the following protocol. One mL reactions were carried out in 50 mM potassium phosphate (pH 8.0), 0.05 mM PLP and 30 mM L tryptophan. The reactions were initiated by the addition of cell free extracts and were incubated at 30° C. overnight. Sample aliquots were taken after overnight incubation (zero minute samples served as control reaction). Concentrated formic acid (5 μL) was added to each 250 μL sample aliquot to stop the reaction and the precipitated protein was removed by centrifugation. Supernatants were removed and frozen at −80° C. until they were analyzed for D-tryptophan by the chiral amino acid method described in Example 1.

Assay results from cell extracts from pET28 and pET30 induction with 100 μM IPTG (3 hours) demonstrate that *P. taetrolens* clones show racemase activity on L-tryptophan. Again, the tagged version of the BAR appears to be less active and may precipitate or be less soluble than the untagged (pET28). Table 29, below, shows the initial results, although not quantitative as very poor soluble protein was obtained.

TABLE 29

| Treatment | Time Point | Substrate | Racemase extract (200 µg) | D-trp conc (µg/mL) |
|---|---|---|---|---|
| pET28/P. taetrolens | 0 | L-trp | 500 µL | nd |
| pET30/P. taetrolens | 0 | L-trp | 500 µL | nd |
| pET28/P. taetrolens | overnight | L-trp | 500 µL | 140 |
| pET30/P. taetrolens | overnight | L-trp | 500 µL | 226 |

Induction of the pET30 (untagged) construct was repeated using same conditions as mentioned above and a visible soluble protein band was observed in SDS-PAGE. The assay was repeated using same the conditions described above and the results, as shown in Table 30, were obtained.

TABLE 30

| Treatment | Time Point | Substrate | Racemase extract (µL) | D-trp conc (µg/mL) |
|---|---|---|---|---|
| P. taetrolens-pET30 | 0 | L-trp | 300 | Nd |
| P. taetrolens-pET30 | 0 | L-trp | 150 | Nd |
| P. taetrolens-pET30 | 2 hr | L-trp | 300 | 319 |
| P. taetrolens-pET30 | 2 hr | L-trp | 150 | 308 |
| P. taetrolens-pET30 | Overnight | L-trp | 300 | 1586 |
| P. taetrolens-pET30 | Overnight | L-trp | 150 | 1658 |

Again, it was noted that doubling of the volumes did not scale to more activity. For future work, it was determined to remove the protein from Bugbuster as quickly as possible after preparation of cell extracts and to store the protein in 50 mM phosphate buffer pH 8 containing 0.01 mM PLP. The detergent in Bugbuster may inhibit the reaction or may cause a loss of activity upon storage.

Induction of the pET30 construct was carried out again and the cell extract was processed with anion exchange chromatography (as in Example 4E) to give a more pure extract. The assay was repeated with this partially purified prep. The numbers in parenthesis in the Racemase extract column of Table 31 below indicate the approximate amount of partially purified racemase enzyme used in the assay. The results of the assay are shown in Table 31 below.

TABLE 31

| Enzyme Source | Time Point | Substrate | Racemase extract | D-trp conc (µg/mL) |
|---|---|---|---|---|
| KT2440 | 0 | L-trp | 75 µL (90 µg) | nd |
| NBRC 12996 | 0 | L-trp | 42 µL (200 µg) | nd |
| NBRC 12996 | 0 | L-trp | 21 µL (100 µg) | nd |
| P. taetrolens | 0 | L-trp | 108 µL (200 µg) | nd |
| P. taetrolens | 0 | L-trp | 54 µL (100 µg) | nd |
| KT2440 | 2 hr | L-trp | 75 µL (90 µg) | 661 |
| NBRC 12996 | 2 hr | L-trp | 42 µL (200 µg) | 408 |
| NBRC 12996 | 2 hr | L-trp | 21 µL (100 µg) | 208 |
| P. taetrolens | 2 hr | L-trp | 108 µL (200 µg) | 862 |
| P. taetrolens | 2 hr | L-trp | 54 µL (100 µg) | 547 |
| KT2440 | overnight | L-trp | 75 µL (90 µg) | 2386 |
| NBRC 12996 | overnight | L-trp | 42 µL (200 µg) | 2382 |
| NBRC 12996 | overnight | L-trp | 21 µL (100 µg) | 1706 |
| P. taetrolens | overnight | L-trp | 108 µL (200 µg) | 2029 |
| P. taetrolens | overnight | L-trp | 54 µL (100 µg) | 2099 |

The non-linearity of the overnight sample in this case is probably due to the fact that the reactions are reaching equilibrium. Clearly, the *P. taetrolens* BAR has significant activity for racemization of tryptophan, as do the 12996 BAR and KT2440 BAR. It appears that the KT2440 BAR and the *P. taetrolens* BAR have similar activity, which is slightly higher than the 12996 BAR.

The DNA Sequence of the *P. taetrolens* arginine racemase is shown below as SEQ ID NO:140. The PCR sequence gave two changes as compared with the published NCBI sequence. Specifically, the PCR sequence contained an adenosine rather than a guanine at position 902 and a cytosine rather than a guanine at position 921. These DNA changes resulted in one silent mutation as well as one change from glycine to aspartate at amino acid position 301.

```
ATGCCCTTCTCCCGTACCCTGCTCGCCCTTTCCCTTGGCAT

GGCATTGCTGCAAAACCCGGCCTTTGCTGCGCCACCCCTG

TCGATGACCGACGGCGTAGCTCAAGTGAATACCCAGGAC

AGCAATGCCTGGGTCGAAATCAATAAAGCCGCGTTCGAG

CACAACATACGGACTCTGCAAACCGCCCTCGCCGGCAAG

TCGCAGATCTGCGCCGTACTCAAGGCGGATGCCTATGGC

CACGGTATCGGCTTGTTGATGCCCTCGGTGATCGCCATGG

GTGTTCCCTGTGTCGGTGTCGCCAGCAACGAAGAAGCCC

GCGTCGTGCGCGAGAGCGGTTTCAAGGGTCAACTGATAC

GCGTGCGCACCGCTGCCCTGAGCGAACTGGAAGCTGCAC

TGCCGTACAACATGGAAGAGCTGGTGGGCAACCTGGACT

TCGCGGTCAAGGCCAGCCTGATTGCCGAGGATCACGGTC

GCCCGCTGGTGGTGCACCTGGGTCTGAATTCCAGCGGCA

TGAGCCGTAACGGAGTGGACATGACCACCGCTCAGGGCC

GTCGTGATGCGGTAGCTATCACCAAGGTGCCAAACCTGG

AAGTGCGGGCGATCATGACCCACTTCGCGGTCGAAGATG

CTGCCGACGTGCGTGCCGGGCTCAAGGCCTTCAATCAGC

AAGCCCAATGGCTGATGAACGTGGCCCAGCTTGATCGCA

GCAAGATCACCCTGCACGCGGCCAACTCGTTCGCCACAC

TGGAGGTGCCCGAATCGCATCTGGACATGGTCCGCCCCG

GCGGCGCGCTGTTCGGCGACACCGTACCGTCCCACACCG

AGTACAAGCGGGTCATGCAGTTCAAGTCCCACGTGGCGT

CGGTCAACAGCTACCCCAAGGGCAACACCGTCGGTTATG

ACCGCACGTACACCCTGGGCCGCGACTCGCGGCTGGCCA

ACATCACCGTCGGCTACTCTGACGGCTACCGCCGCGTT

TACCAATAAAGGGATTGTGCTGATCAACGGCCATCGCGT

GCCAGTGGTGGGCAAAGTCTCGATGAACACCCTGATGGT

GGACGTCACTGACGCGCCGGATGTGAAAAGCGGCGATGA

AGTGGTGCTGTTCGGGCACCAGGGCAAGGCCGAGATTAC

CCAGGCTGAGATCGAAGACATCAACGGTGCACTGCTTGC

GGATCTGTATACCGTGTGGGGCAATTCCAACCCTAAAAT

CCTGAAAGATCAGTAA.
```

The amino acid sequence of the *P. taetrolens* arginine racemase is shown below as SEQ ID NO:204.

```
                                          (SEQ ID NO: 204)
MPFSRTLLALSLGMALLQNPAFAAPPLSMTDGVAQVNTQD

SNAWVEINKAAFEHNIRTLQTALAGKSQICAVLKADAYGH

GIGLLMPSVIAMGVPCVGVASNEEARVVRESGFKGQLIRVR

TAALSELEAALPYNMEELVGNLDFAVKASLIAEDHGRPLV

VHLGLNSSGMSRNGVDMTTAQGRRDAVAITKVPNLEVRAI

MTHFAVEDAADVRAGLKAFNQQAQWLMNVAQLDRSKITL

HAANSFATLEVPESHLDMVRPGGALFGDTVPSHTEYKRVM

QFKSHVASVNSYPKGNTVGYDRTYTLGRDSRLANITVGYS

DGYRRAFTNKGIVLINGHRVPVVGKVSMNTLMVDVTDAP

DVKSGDEVVLFGHQGKAEITQAEIEDINGALLADLYTVWG

NSNPKILKDQ.
```

The protein encoded by the gene of SEQ ID NO:140 was analyzed by the signal peptide prediction program Signal P 3.0 (www.cbs.dtu.dk/services/SignalP/) and a leader sequence of 23 amino acids was predicted.

The following PCR primer pair was used to clone the *P. taetrolens* gene without amino acids 2-23 of the leader sequence:

```
                                          (SEQ ID NO: 180)
P.taetMinus leader F NdeI:
5'-GGTTAATTCATATGGCGCCACCCCTGTCGAT-3'

(SEQ ID NO: 181)
P taetCtermXho:
5'- AAGTCGCTCGAGCTGATCTTTCAGGATTTTAG-3'.
```

The C-terminal primer shown above was also used with SEQ ID NO:138 to produce the wildtype protein in a manner which allowed for purification, as described in Example 4H for the *P. putida* KT2440 BAR. The leaderless *P. taetrolens* racemase, when expressed, was found to lose a significant amount of the activity, as compared with the expression product of the full-length gene. The periplasmic and cytoplasmic protein fractions were isolated for the wildtype expression products, as well as the leaderless constructs, as described in the pET System Manual (Novagen, Madison, Wis.). The expressed wildtype BAR was present in the periplasmic fraction, while the expression of the leaderless BAR was significantly reduced. The loss in activity of the leaderless *P. taetrolens* BAR may be due to a change in processing and/or folding when expressed in the cytoplasm.

I384M Mutagenesis of *P. taetrolens* BAR

Mutagenesis was done using the QuickChange-Multi site-directed mutagenesis kit (Stratagene, La Jolla, Calif.), using the *P. taetrolens* BAR gene in pET30 which results in an untagged protein. The following mutagenic primer was used to make the I384M change:

```
                                          (SEQ ID NO: 141)
5'-TACCCAGGCTGAGATGGAAGACATCAACG-3'.
```

The site-directed mutagenesis was done as described in the manufacturer's protocol. Several isolates were sequenced (Agencourt, Beverly, Mass.) and an isolate with the correct sequence was selected and used for further analysis.

The plasmid was transformed into BL21(DE3) cells (Novagen, Madison, Wis.). Recombinant protein was produced in Overnight Express II medium (Novagen, Madison, Wis.) containing 50 µg/mL kanamycin according to manufacturer's protocols. Cell-free extracts were prepared using BugBuster (Novagen, Madison, Wis.) according to manufacturer's protocols, desalted, and analyzed for percent expression of the target protein using the Experion method described above.

Total protein assays were done using a Pierce BCA kit (Rockford, Ill.). Tryptophan racemase assays with the mutant enzyme were performed using the wild-type enzyme prepared in the same manner as a positive control. Assays contained per mL: 30 mM L-tryptophan, 50 mM potassium phosphate pH 8, 10 µM PLP, and approximately 100 µg of racemase protein in a cell free extract. In the case where 100 µg was not used (based on Experion % expression and Pierce total protein numbers), the results were normalized. Zero, 30 minute, 2 hour, and overnight samples were collected, treated with 2% formic acid, filtered, and diluted 1:10 for analysis using the chiral amino acid method described in Example 1.

Quantification was difficult due to the fact that crude lysates were utilized. The wild-type enzyme appeared to produce similar amounts of D-tryptophan in 30 minutes and in the 2 hour time point, as compared with the I384M mutant. The I384M mutant appeared to have, at most, approximately twice the activity of the wildtype under the conditions tested. When assays were done for monatin production, as in Example 4F, the I384M did not appear to provide any benefit over the wild-type *P. taetrolens* enzyme under the conditions tested.

4M: *Streptomyces coelicolor* Racemase Assays

*Streptomyces* species are known to produce calcium-dependent antibiotics that contain D-amino acids such as D-tryptophan. It is not known whether the tryptophan is racemized prior to or after incorporation in the antibiotic. Although public *Streptomyces* genomes do not contain a highly homologous alanine racemase to those that have activity from *Pseudomonas* species, cloning work was undertaken to determine if in fact the enzymes had broad specificity as well.

*Streptomyces violaceoruber* (ATCC BAA-471 deposited as *Streptomyces coelicolor*) was grown in ISP Medium 1 (BD catalog #276910, Franklin Lakes, N.J.). Cells were lysed by ultrasonication and cell debris was removed by centrifugation. Cell-free extracts were assayed for tryptophan racemase activity (starting with L-tryptophan). Under the conditions tested, it was not possible to detect conversion of L-trp to D-trp.

*Streptomyces coelicolor* was annotated in ERGO™ as containing 3 alanine racemases (NCBI Accession numbers NP_628903, NP_628089, and NP_629139). The published DNA sequences were amplified from *S. coelicolor* by PCR. Each gene was cloned into vector pET30 using restriction sites Nde I and BamH I.

The plasmids were transformed into expression host BL21 DE3. Strains with the plasmids encoding proteins NP_628089 and NP_629139 were grown to an $OD_{600}$ of ~0.6 and expression was induced with 100 µM IPTG. After incubation at 37° C. with aeration, the cell pellets were harvested by centrifugation and frozen at −80° C. Strain with the plasmid encoding protein NP_628903 was grown in Overnight Express medium II at 30° C. and induced per manufacturer's instructions (Novagen, Inc, Madison, Wis.). The cell pellet was harvested by centrifugation and frozen at −80° C.

The cell pellets were thawed on ice and the cells were lysed with an appropriate volume of BugBuster and Benzonase nuclease (Novagen, Madison, Wis.). The lysates were centrifuged to remove cell debris and the resulting cell-free extracts were used in racemase assays as described in Example 4E. Under these conditions, it was not possible to detect conversion of L-tryptophan to D-tryptophan, even when the detergent was removed from the cellular extract. The enzymes also did not appear to produce D-alanine from L-alanine when assayed similarly, as compared to cellular extracts of E. coli without a recombinant racemase present. It is possible that these enzymes are mis-annotated or have very low activity under the conditions they were assayed. However, it is also possible that the enzymes were not produced correctly in E. coli.

4N: Cloning the Yersinia pseudotuberculosis BAR Homolog

The Y. pseudotuberculosis BAR homolog was cloned from genomic DNA obtained from Virginia Miller and Matt Lawrenz at Washington University in St. Louis, Mo. (strain YPIII). The primers used are as follows: 5'-gcggcgcatatg-cacgttcgttttcgtc-3' (SEQ ID NO:142) and 5'-ggcggcgggatc-ccggtgaaataacttaatctac-3' (SEQ ID NO:143). The gene was amplified from the genomic DNA by PCR and was purified with the QIAquick® PCR purification kit (Qiagen, Valencia, Calif.). The fragment was digested with Nde I and BamH I. The digest was run on a 1% agarose gel and the racemase fragment was cut out of the gel. The DNA was purified from the gel with the QIAquick® gel extraction kit (Qiagen, Valencia, Calif.). The fragment was ligated to pET30 that had been digested and purified as described above. The ligation was transformed into TOP10 chemically competent cells (Invitrogen, Carlsbad, Calif.). Plasmid DNA was isolated and run on a 1% agarose gel to screen for inserts. Several plasmid isolates with an insert were sent to Agencourt (Beverly, Mass.) for sequencing. An isolate with the correct sequence was selected and transformed into BL21 DE3 pLysS competent cells to make the expression strain.

The expression strain was grown to an $OD_{600}$ of about 0.6 and then induced with 1 mM IPTG. The culture was grown at 37° C. for 3 hours and the cell pellet was harvested by centrifugation. The cell pellet was stored at −80° C. until use.

The cell pellet was thawed on ice and resuspended in an appropriate volume of BugBuster plus Benzonase nuclease (see product insert) (Novagen, Madison, Wis.) to lyse the cells. The cell debris was removed by centrifugation and the resulting cell-free lysate was used in racemase assays as in Example 4E. The extract did not appear to have detectable tryptophan racemase activity.

The expression strain was again grown to an $OD_{600}$ of 0.6 (3 100 ml cultures) and induced with 1 mM IPTG. One of the cultures was incubated at 37° C. for 6 hours, another was incubated at 30° C. overnight and the third was incubated at 26° C. overnight. Cells were harvested by centrifugation and the cell pellets were stored frozen. The cell pellets were thawed on ice and a cell-free extract was made using BugBuster and Benzonase (Novagen, Madison, Wis.) as described in this example. An SDS gel (4-15% gradient (Bio-Rad, Hercules, Calif.)) was run. Induction at 37° C. leads to the expression of very little soluble racemase and the level of soluble racemase was higher when 30° C. was the expression temperature and was even higher when 26° C. was the expression temperature. The cell-free extract made at 26° C. was used in racemase assays and again no tryptophan racemase was detected in this cell-free extract. However, activity assays using L-alanine as the substrate gave very low conversion to D-tryptophan, which can be accounted for by native *E. coli* alanine racemases. The *Y. pseudotuberculosis* BAR homolog may have activity under different conditions and it is possible to improve the activity to the *Y. pseudotuberculosis* BAR homolog by mutagenesis techniques known to those in the art. Protein activity is also enhanced by methods that can encourage proper folding. The enzyme activity may be difficult to detect due to improper folding or improper insertion of the pyridoxal-5'-phosphate cofactor. Encouraging proper folding or cofactor insertion may greatly enhance enzyme activity.

The *Y. pseudotuberculosis* YPIII BAR homolog DNA sequence is SEQ ID NO:144 and is shown below:

```
                                                (SEQ ID NO:144)
atgcacgttcgttttcatcatttattcttattaccattaataactttggt cgcttgtagccaacccgtatcaaaaaaccatcttagcctgacctcactat ctgccaacgcccagcaacctgtagtaaataatgcgtggcttgaaatctct caaggtgcgctggatttcaatactaaaaagatgcttacactgctggataa taaatccacactttgtgcaatattaaaaggtgatgcctatggacatgacc tgaccttagtcacaccggtgatgctaaaaaacaatgtgcaatgtattggg gttgccagcaatcaggaactaaaaacggtacgtgatctaggatttacggg gcagttgatacgggtcagaagtgcaacattaaaagaaatgcaacaagcta tggcttacgatgttgaagaacttattggcgataaaaccgtcgctgagcag ttaaataatattgcaaaactgaatggaaaagttctgcgtatccatctggc actgaactccgcagggatgtctcgtaatgggctggaggtcagtaaggccc gcggtttaaatgacgcaaagacaattgtaggtttaaaaaatctgacaatc gttggcatcatgtcgcactacccggtggaagatgctagcgaaatcaaagc agacttggctcgattccagcaacaagccaaagatgttatcgcggtcacgg ggctaaaacgtgaaaagattaagctccacgtcgccaatacattcgcgacc ttagcggtgcctgattcatggttggatatggtccgtgtgggaggggtgtt ttatggtgacaccatcgccagcacagagtataagcgggtcatgaccttca aatctaacatcgcatcgctgaacaactaccctaagggcggtactgttggc tatgaccggacctatacattgaaacgtgattccctgctggcgaatatccc cgtgggttatgccgatgggtatcgccgagtatttagtaatgcggggcatg tgattattcaaggtcagcgcctgcccgtattaggcaaaacatcaatgaat acggtcatggtagacgtcaccgatctgaaaaaagtgagtttaggtgatga agttgtcttgttcggtaagcaaggcaatgcggaaattcaggcagaagaaa ttgaagatctcagtggcgcactctttaccgaaatgtcaattctgtggggc gcaaccaataagcgtattctggtagattaa.
```

The *Y. pseudotuberculosis* YPIII BAR homolog amino acid sequence is SEQ ID NO:145 and is shown below:

```
                                                (SEQ ID NO:145)
Mhvrfhhlfllplitlvacsqpvsknhlsltslsanaqqpvvnnawleis qgaldfntkkmltlldnkstlcailkgdayghdltlvtpvmlknnvqcig vasnqelktvrdlgftgqlirvrsatlkemqqamaydveeligdktvaeq
```

-continued lnniaklngkvlrihlalnsagmsrnglevskarglndaktivglknlti vgimshypvedaseikadlarfqqqakdviavtglkrekiklhvantfat lavpdswldmvrvggvfygdtiasteykrvmtfksniaslnnypkggtvg ydrtytlkrdsllanipvgyadgyrrvfsnaghviiqgqrlpvlgktsmn tvmvdvtdlkkvslgdevvlfgkqgnaeiqaeeiedlsgalftemsilwg atnkrilvd.

4O: Identification of *Aeromonas* Species BAR Genes

As mentioned in Example 4E, there is evidence in the literature that the *Aeromonas* species contain a broad specificity amino acid racemase with properties similar to the *Pseudomonas* derived enzymes. This example describes identification and isolation of broad specificity amino acid racemases in *A. hydrophila, A. jandei, A. sobria* and *A. caviae*, as well as identification of tryptophan racemase activity in *A. caviae* cellular extracts. This example also describes the isolation of the partial nucleic acid sequences of BAR homologs in *A. schubertii* and *A. salmonicida*.

A blast analysis of the *Aeromonas hydrophila* ATCC7966$^T$ genome on the TIGR website (tigrblast.tigr.org/ufmg/index.cgi?database=a_hydrophila%7Cseq) with the BAR protein sequence from the public *Pseudomonas taetrolens* arginine racemase protein sequence (coded for by accession number AB096176) resulted in the identification of a partial protein sequence with 60% identity at the amino acid level. DNA positions 33912-32746 on contig 1047085923747 corresponded to a region of homology of 390 amino acids. The partial sequence is shown below.

Partial sequence of Putative BAR from *Aeromonas hydrophila*—Protein 1 (SEQ ID NO:146):

```
                                              (SEQ ID NO:146)
AVAAPYLPLASDHRNGEVQTASNAWLEVDLGAFEHNIQTLKDRLGDKGPK

ICAIMKADAYGHGIDLLVPSVVKAGIPCIGIASNEEARVAREKGFTGRLM

RVRAATPAEVEQALPYKMEELIGSLVSAQGIADIAQRHHTNIPVHIALNS

AGMSRNGIDLRLADSKEDALAMLKLKGITPVGIMTHFPVEEKEDVKMGLA

QFKLDSQWLLEAGKLDRSKITIHAANSFATLEVPDAYFDMVRPGGLLYGD

SIPSYTEYKRVMAFKTQVASVNHYPAGNTVGYDRTFTLKRDSWLANLPLG

YSDGYRRALSNKAYVLIQGQKVPVVGKTSMNTIMVDVTDLKGVKPGDEVV

LFGRQGEAEVKQADLEEYNGALLADMYTIWGYTNPKKIK.
```

Blasting NCBI with the partial putative BAR amino acid sequence from *Aeromonas hydrophila* identifies alanine racemases with highest sequence identity to *Pseudomonas putida* F1 (Accession number ZP_00898332.1 GI:82735470), then *Pseudomonas* KT2440, confirming that this is most likely an amino acid racemase protein. Example 4E demonstrates that the BAR protein from *Pseudomonas* KT2440 is active and converts L-tryptophan to D-tryptophan. Thus, it was thought to be likely that the *A. hydrophila* ATCC7966$^T$ racemase also has broad specificity as well.

When the *Pseudomonas taetrolens* BAR gene sequence (Accession number AB096176) or the *Pseudomonas* KT2440 BAR gene sequence (Accession number NC_002947.3:6018117 . . . 6019190) was used to blast the TIGR website, a DNA sequence with high homology (69%) over 1216 base pairs was observed on contig 1047085923747: a_hydrophila. A P score of 1.5 E-110 was observed. The nucleotide numbers corresponding to the match are 32754-33954. The sequence of the *A. hydrophila* partial gene sequence obtained from these alignments is as follows (SEQ ID NO:147):

```
                                              (SEQ ID NO:147)
tcttggggtt ggtgtagccc cagatggtgt acatgtccgc cagcagggcg ccgttgtact cttccagatc cgcctgtttc acctcagcct caccctggcg gccgaacagc accacctcgt caccgggttt gacccctttc agatcggtca cgtccaccat gatggtgttc atggaggtct tgcccaccac cggcaccttc tggccctgga tcagcacata ggccttgttg ctcagcgccc ggcgatagcc gtcggagtag cccagcggca ggttggcgag ccaggagtcg cgcttgaggg tgaaggtgcg gtcataaccg acggtgttgc cggccgggta gtggttgacg gaggcaacct gggtcttgaa cgccatcacc cgcttgtact cggtgtagga ggggatggag tcaccgtaca gcaggccgcc cgggcgcacc atgtcgaagt aggcgtccgg cacttccagg gtggcgaagg agttggcggc gtggatggtg atcttgctgc gatccagctt gcccgcttcc agcagccact gggagtccag tttgaactgg gccagcccca tcttgacgtc ctctttctcc tccaccggga agtgggtcat gatgccgacc ggggtgatcc ccttgagctt gagcatggcc agcgcgtctt ccttggagtc agccaggcgc agatcgatgc cgttgcggct catgccggcg gagttgagcg cgatgtgcac cgggatattg gtgtggtggc gctgggcgat gtcggcgatg ccctgagcac tcaccaggct gccgatgagc tcttccatct tgtagggcag ggcctgttcc acttcggccg gggtggcggc acgtacccgc atcaggcggc cggtgaagcc cttctcacgg gccacgcggg cctcttcgtt gctggcgatg ccgatgcagg ggatgccggc cttgaccacc gagggcacca gcaggtcgat gccgtggccg taggcgtcgg ccttcatgat ggcgcagatc ttcggccctt tgtcaccgag gcgatccttg agggtctgga tgttgtgctc gaaggcgccg agatcgactt ccagccaggc attgctggcg gtctgcactt cgccgttgcg atgatcgctg gccagcggca ggtaaggggc cgcgacggcc tgaccggcca gcaggcccag gatcagcgtg gccagcagtg t.
```

Pileup analysis suggested that only 5 amino acids from each end of the protein sequence were absent, so a chimeric protein was designed using the known protein sequence fragment above and consensus sequences based on other broad specificity racemases. The following primers were designed to construct this chimera for cloning into pET28 and pET30 using Nde I and BamH I sites.

```
hydrophila F NdeI (SEQ ID NO:148):
5'-TTCCAAGGCATATGCCCTTCTCCCGTACACTGCTGGCCACGCTGATC CT 3';
and hydrophila R BamH1 (SEQ ID NO:149):
5'-GGAACCTTGGATCCTCAATCTTTGATTTTCTTGGGGTTGGTGTAGCC

CCAGATG 3'.
```

The chimeric gene derived from *A. hydrophila* was amplified using the primers described above and the following PCR protocol. In a 50 μL reaction, 1 μL template (genomic DNA ATCC 7965), 1.6 μM of each primer, 0.3 mM each dNTP, 2.5 U Pfu Polymerase (Stratagene, La Jolla, Calif.), 1×Pfu buffer, and 2.5 μL dimethyl sulfoxide were used. The thermocycler program used included a hot start at 94° C. for 3 minutes, 8 repetitions of the following steps: 94° C. for 30 seconds, 53° C. for 45 seconds, and 72° C. for 2.5 minutes, followed by 22 repetitions of the following steps: 94° C. for 30 seconds, 60° C. for 45 seconds, and 72° C. for 2.5 minutes. After the 22 repetitions, the sample was maintained at 72° C. for 7 minutes and then stored at 4° C. This PCR protocol produced a product of ~1230 bp.

Cloning

The PCR product was gel purified from 0.8% TAE-agarose gel using the Qiagen gel extraction kit (Qiagen, Valencia, Calif.). The product was TOPO cloned and transformed into TOP 10 cells according to manufacturer's protocol (Invitrogen, Carlsbad, Calif.). Plasmid DNA was purified from the resulting transformants using the Qiagen spin miniprep kit (Qiagen, Valencia, Calif.) and screened for the correct inserts by restriction digest with Nde I and BamH I. The sequences of plasmids appearing to have the correct insert were verified by dideoxy chain termination DNA sequencing with universal M13 forward and M13 Reverse primers.

The consensus sequence obtained below codes for a protein that is 95% homologous at the amino acid level to the published TIGR sequence for *A. hydrophila* (protein 1 above).

The amino acid sequence for the *A. hydrophila* chimeric protein is shown below as SEQ ID NO:151.

```
(SEQ ID NO:151)
MPFSRTLLATLILGLLAGQAVAAPYLPLASDHRNGEVQTASNAWLEVDLT

AFEQNLQTKTRLGDKGPQICAIMKADAYGHGIDLLVPSVIKAEIPCIGIA

SNEEARVAREKGFSGRLMRVRAATPIEVEQALPYKLEELVGSLVSAQGIS

DIALRHHTTIPVHVALNSAGMSRNGIDLRLADAKQDALAMLKLKGITPVG

IMTHFPVEEKEDVKLGLAQFKLDSQWLLEAGKLDRSKITIHAANSFATLA

VPDAYFDMVRPGGLLYGDSIPSYTEYKRVMAFKTQVASVNHYAAGNTVGY

DRTFTLKRDSWLANLPLGYSDGYRRALSNKAYVLIQGQKVPVVGKTSMNT

IMVDVTDLKGVKPGDEVVLFGRQGEAEVKQADLEEYNGALLADMYTIWGY

TNPKKIKD.
```

The DNA sequence of the *A. hydrophila* chimeric sequence obtained from PCR is shown below as SEQ ID NO:150:

```
(SEQ ID NO:150)
ATGCCCTTCTCCCGTACACTGCTGGCCACGCTGATCCTGGGCCTGCTGGC

CGGTCAAGCCGTCGCAGCCCCCTATCTGCCTCTGGCAAGCGATCATCGCA

ACGGCGAAGTACAAACCGCCAGCAACGCCTGGCTGGAAGTAGATCTGACC

GCGTTTGAACAGAATCTGCAGACCCTCAAGACCCGCCTCGGCGACAAGGG

CCCGCAGATCTGCGCCATCATGAAGGCGGACGCCTACGGTCACGGTATCG

ATCTGCTGGTTCCCTCCGTCATCAAGGCCGAGATCCCCTGTATCGGCATC

GCCAGCAACGAAGAGGCCCGCGTCGCCCGCGAGAAGGGGTTCAGCGGCCG

CCTGATGCGGGTACGGGCCGCCACACCTATCGAAGTGGAACAGGCCCTGC

CCTACAAGCTGGAAGAGCTGGTTGGCAGCCTGGTGAGTGCTCAGGGGATC

TCCGACATCGCCCTGCGCCACCACACCACCATTCCGGTGCATGTCGCCCT

CAACTCCGCCGGTATGAGCCGCAACGGCATCGACCTGCGTCTGGCCGATG

CCAAGCAAGATGCGCTGGCCATGCTCAAGCTCAAGGGGATCACCCCGGTC

GGCATCATGACCCACTTCCCGGTGGAGGAGAAAGAGGACGTCAAGCTGGG

GCTGGCTCAGTTCAAGCTGGACTCCCAGTGGCTGCTGGAAGCAGGCAAGC

TGGATCGCAGCAAGATCACCATCCATGCCGCCAACTCCTTCGCCACCCTG

GCAGTGCCGGACGCCTACTTTGACATGGTGCGCCCGGGCGGCCTGCTCTA

CGGCGACTCCATCCCCTCCTACACCGAATACAAGCGGGTGATGGCATTCA

AGACCCAGGTCGCCTCGGTCAACCACTATGCGGCGGGCAACACAGTCGGT

TATGACCGCACCTTTACTCTCAAACGTGACTCCTGGCTCGCCAACCTGCC

GCTCGGTTACTCCGACGGCTATCGCCGTGCGCTCAGCAACAAGGCCTATG

TGCTGATCCAGGGTCAGAAGGTGCCGGTGGTCGGCAAGACCTCCATGAAC

ACCATCATGGTGGACGTGACCGATCTCAAAGGGGTAAAGCCCGGTGATGA

AGTGGTGCTGTTTGGCCGTCAGGGTGAGGCAGAAGTGAAACAGGCTGATC

TGGAGGAGTACAACGGCGCCCTGTTGGCGGACATGTACACCATCTGGGGC

TACACCAACCCCAAGAAAATCAAAGATTGA.
```

The correct TOPO clone was digested with restriction enzymes Nde I and BamH I following the manufacturer's recommended protocols (New England Biolabs, Beverly, Mass.) and gel purified from 0.8% TAE-agarose gels using the Qiagen gel extraction kit (Qiagen, Valencia, Calif.). Vector pET30a (Novagen, Madison, Wis.) was prepared by digestion with appropriate restriction enzymes followed by treatment with shrimp alkaline phosphatase (Roche, Indianapolis, Ind.) and purification from 0.8% TAE-agarose gels using the Qiagen gel extraction kit (Qiagen, Valencia, Calif.). The digested vector and insert were ligated using the Rapid™ DNA Ligation Kit (Roche, Indianapolis, Ind.). Approximately 65 ng of treated insert, 100 ng of treated vector (3 to 1 molar ratio of insert to vector), 5 U of T4 DNA ligase, and 1× ligation buffer were incubated for 5 minutes at room temperature. The ligation reaction was desalted using the High Pure PCR Product Purification Kit (Roche, Indianapolis, Ind.) and used to transform *E. coli* DH10B electrocompetent cells (Invitrogen, Carlsbad, Calif.). Ten μL of each ligation reaction was added to 40 μL of DH10B cells, which were transformed by electroporation using the BioRad Gene Pulsar II under the following conditions: 2.5 kV, 25 μF, 200 Ohm in a 0.2 cm cuvette. The cells were allowed to recover in 1 mL of room temperature SOC for 1 hour at 37° C. with shaking at 225 rpm. Cells were plated on LB plates containing kanamycin (50 µg/mL). The plasmid DNA was purified from the resulting transformants using the Qiagen spin miniprep kit (Qiagen, Valencia, Calif.).

Gene Expression and Assays

Plasmid DNA was transformed into *E. coli* expression host BL21(DE3) (Novagen, Madison, Wis.). The cultures were grown and the plasmids were isolated using Qiagen miniprep kit (Qiagen, Valencia, Calif.), and analyzed by restriction digest to confirm identity. Induction in BL21DE3 was performed in Overnight Express medium as per manufacturer's instructions (Novagen, Madison, Wis.).

Cells from the induced cultures were centrifuged and washed once with 0.85% NaCl. Cell pellets were resuspended in 5 mL/g wet cell weight of BugBuster™ (Novagen, Madison, Wis.) reagent containing 5 µL/mL protease inhibitor cocktail set #3 (Calbiochem-Novabiochem Corp., San Diego, Calif.) and 1 µL/mL benzonase nuclease. Samples were incubated at room temperature for 20 minutes on an orbital shaker. Insoluble cell debris was removed by centrifugation at 16,000×g for 20 minutes at 4° C. The extract was desalted using PD10 columns which were equilibrated in 50 mM potassium phosphate, pH 8.0 containing 10 µM PLP. The cell extract protein was quantified using the Pierce BCA protein assay (Pierce, Rockford, Ill.) and visualized by SDS-PAGE. SDS-PAGE showed a protein of the expected size of approximately 45 kDa.

The cell extracts were assayed for tryptophan racemase activity using the following protocol. One mL reactions were carried out in 50 mM potassium phosphate (pH 8.0), with 0.05 mM PLP and 30 mM L tryptophan. The reactions were initiated by the addition of cell free extracts and were incubated at 30° C. overnight. Sample aliquots were taken at 2 hours and after overnight incubation (zero minute samples served as control reaction). Concentrated formic acid (5 µL) was added to each 250 µL sample aliquot to stop the reaction and the precipitated protein was removed by centrifugation. Supernatants were removed and frozen at −80° C. until they were analyzed for D-tryptophan by the chiral amino acid method described in Example 1.

The assay results from the cell extracts from pET30 induction demonstrate that *A. hydrophila* clones show racemase activity on L-tryptophan. In light of these data it was expected that the full-length TIGR *A. hydrophila* wild-type sequence (Protein 1 above with N and C terminal regions completed) would also give a protein with racemase activity on tryptophan. The full length gene sequence of the *A. hydrophila* BAR was determined using Genome Walker Methods described in Example 15. The gene sequence of the native *A. hydrophila* gene is shown below as SEQ ID NO:176.

```
                                          (SEQ ID NO:176)
atgcacaaga  agacactgct  ggccaccttg  atcctgggcc tgctggccgg  tcaagccgtc  gcagccccct  atctgcctct ggcaagcgat  catcgcaacg  gcgaagtaca  aaccgccagc aacgcctggc  tggaagtaga  tctgaccgcg  tttgaacaga atctgcagac  cctcaagacc  cgcctcgcg   acaagggccc gcagatctgc  gccatcatga  aggcggacgc  ctacggtcac ggtatcgatc  tgctggttcc  ctccgtcatc  aaggccgaga
```
tcccctgtat cggcatcgcc agcaacgaag aggcccgcgt cgcccgcgag aaggggttca gcggccgcct gatgcgggta cgggccgcca cacctatcga agtggaacag gccctgccct acaagctgga agagctggtt ggcagcctgg tgagtgctca ggggatctcc gacatcgccc tgcgccacca caccaccatt ccggtgcatg tcgccctcaa ctccgccggt atgagccgca acggcatcga cctgcgtctg gccgatgcca agcaagatgc gctggccatg ctcaagctca aggggatcac cccggtcggc atcatgaccc acttcccggt ggaggagaaa gaggacgtca agctggggct ggctcagttc aagctggact cccagtggct gctggaagca ggcaagctgg atcgcagcaa gatcaccatc catgccgcca actccttcgc caccctggca gtgccggacg cctactttga catggtgcgc ccgggcggcc tgctctacgg cgactccatc ccctcctaca ccgaatacaa gcgggtgatg gcattcaaga cccaggtcgc ctcggtcaac cactatgcgg cgggcaacac agtcggttat gaccgcacct ttactctcaa acgtgactcc tggctcgcca acctgccgct cggttactcc gacggctatc gccgtgcgct cagcaacaag gcctatgtgc tgatccaggg tcagaaggtg ccggtggtcg gcaagacctc catgaacacc atcatggtgg acgtgaccga tctcaaaggg gtaaagcccg gtgatgaagt ggtgctgttt ggccgtcagg gtgaggcaga agtgaaacag gctgatctgg aggagtacaa cggcgccctg ttggcggaca tgtacaccat ctggggctac accaacccca agaagatcaa acgctga.

The corresponding native protein for the *A. hydrophila* BAR is shown below as SEQ ID:177.

```
                                        (SEQ ID NO:145)
  1 mhkktllatl  ilgllagqav  aapylplasd  hrngevqtas 41 nawlevdlta  feqnlqtlkt  rlgdkgpqic  aimkadaygh 81 gidllvpsvi  kaeipcigia  sneearvare  kgfsgrlmrv 121 raatpieveq  alpykleelv  gslvsaqgis  dialrhhtti 161 pvhvalnsag  msrngidlrl  adakqdalam  lklkgitpvg 201 imthfpveek  edvklglaqf  kldsqwllea  gkldrskiti 241 haansfatla  vpdayfdmvr  pggllygdsi  psyteykrvm 281 afktqvasvn  hyaagntvgy  drtftlkrds  wlanlplgys 321 dgyrralsnk  ayvliqgqkv  pvvgktsmnt  imvdvtdlkg 361 vkpgdevvlf  grqgeaevkq  adleeyngal  ladmytiwgy 401 tnpkkikr.
```

The first 21 N-terminal amino acid residues are predicted to be a signal peptide using the program Signal P 3.0 as described in Example 4L.

TABLE 32

| Enzyme preparation | Time Point | Racemase extract | D-trp conc (μg/mL) | D-trp/μg BAR |
|---|---|---|---|---|
| A. hydrophila - chimera | 0 | 100 μL | | |
| A. hydrophila - chimera | 0 | 600 μL | | |
| KT2440 BAR untagged | 0 | 100 μL | | |
| A. hydrophila - chimera | 2 hr | 100 μL | 846 | 3.9 |
| A. hydrophila - chimera | 2 hr | 600 μL | 1952 | 1.5 |
| KT2440 BAR untagged | 2 hr | 100 μL | 1756 | 10.98 |
| A. hydrophila - chimera | overnight | 100 μL | 3423 | 15.6 |
| A. hydrophila - chimera | overnight | 600 μL | 2652 | 2 |
| KT2440 BAR untagged | overnight | 100 μL | 3040 | 19 |

The native *A. hydrophila* gene was cloned and expressed in a manner similar to that described above for the chimera. The same N-terminal primer was utilized for both untagged and C-terminally His-tagged constructs in pET30. The following primers were used:

```
A. hydroph F NdeI
                            (SEQ ID NO:182)
5'-GGAACCTTCATATGCACAAGAAGACACTGCTGG-3';

A. hydroph R BamH1 (untagged)
                            (SEQ ID NO:183)
5'-GGTTCCAAGGATCCTCAGCGTTTGATCTTCTTGGG-3';
and A. hydroph R XhoI (C-term tag)
                            (SEQ ID NO:184)
5'-GGCCAATTCTCGAGGCGTTTGATCTTCTTGGGGT-3'.
```

The native *A. hydrophila* BARs (both C-tagged and untagged versions) were found to have comparable activity and had the same order of magnitude of activity as the chimeric protein. Calculation of specific activities was difficult due to the use of unpurified enzymes.

*A. caviae* Extract Assay

*Aeromonas caviae* ATCC 14486 was grown in nutrient broth at 37° C. Cells from the culture (200 mL) were centrifuged and washed once with 0.85% NaCl. Cell pellets were resuspended in 5 mL/g wet cell weight of BugBuster™ (Novagen, Madison, Wis.) reagent containing 5 μL/mL protease inhibitor cocktail set #3 (Calbiochem-Novabiochem Corp., San Diego, Calif.) and 1 μL/mL benzonase nuclease. Samples were incubated at room temperature for 20 minutes on an orbital shaker. Insoluble cell debris was removed by centrifugation at 16,000×g for 20 minutes at 4° C. Cell-free extract was desalted on a PD-10 column (GE Healthcare, Piscataway, N.J.).

Cell-free extract was assayed for tryptophan racemase activity using the following protocol. One mL reactions were carried out in 50 mM potassium phosphate (pH 8.0), 0.05 mM PLP and 30 mM L tryptophan. The reactions were initiated by the addition of cell free extract (either 100 μL or 500 μL) and were incubated at 30° C. overnight. Sample aliquots were taken at 2 hours and after overnight incubation (zero minute samples served as control reactions). Concentrated formic acid (5 μL) was added to each 250 μL sample aliquot to stop the reaction and the precipitated protein was removed by centrifugation. Supernatants were removed and frozen at −80° C. until they were analyzed for D-tryptophan by the chiral amino acid method described in Example 1.

The assay results from cell extracts of *A. caviae* demonstrated racemase activity on L-tryptophan, as shown in Table 33.

TABLE 33

| Treatment | Time Point | substrate | Racemase extract | D-trp conc (μg/mL) |
|---|---|---|---|---|
| A. caviae | 0 | L-trp | 100 μL | nd |
| A. caviae | 0 | L-trp | 500 μL | nd |
| A. caviae | 2 hr | L-trp | 100 μL | 2 |
| A. caviae | 2 hr | L-trp | 500 μL | 19 |
| A. caviae | overnight | L-trp | 100 μL | 45 |
| A. caviae | overnight | L-trp | 500 μL | 130 |

After finding activity in the *A. caviae* cell extracts, degenerate primers were designed (based on conserved regions of known BAR homologs) to obtain the BAR gene from this species. Degenerate primer sequences are shown below:

```
Aer deg F2:
5'-GCCAGCAACGARGARGCMCGCGT-3';   (SEQ ID NO:152)
and

Aer deg R1:
5'-TGGCCSTKGATCAGCACA-3'          (SEQ ID NO:153)
``` wherein K indicates G or T, R indicates A or G, S indicates C or G, and M indicates A or C.

The above primers were used to PCR amplify a 715 bp DNA fragment from *A. caviae* (ATCC 14486) genomic DNA. The following PCR protocol was used: A 50 μL reaction contained 0.5 μL template (~100 ng of *A. caviae* genomic DNA), 1.6 μM of each primer, 0.3 mM each dNTP, 10 U rT$^{th}$ Polymerase XL (Applied Biosystems, Foster City, Calif.), 1× XL buffer, 1 mM Mg(OAc)$_2$ and 2.5 μL dimethyl sulfoxide. The thermocycler program used included a hot start at 94° C. for 3 minutes and 30 repetitions of the following steps: 94° C. for 30 seconds, 53° C. for 30 seconds, and 68° C. for 2 minutes. After the 30 repetitions, the sample was maintained at 68° C. for 7 minutes and then stored at 4° C. This PCR protocol produced a product of 715 bp.

Cloning

The PCR product was gel purified from 0.8% TAE-agarose gel using the Qiagen gel extraction kit (Qiagen, Valencia, Calif.). The product was TOPO cloned and transformed into TOP 10 cells according to manufacturer's protocol (Invitrogen, Carlsbad, Calif.). The plasmid DNA was purified from the resulting transformants using the Qiagen spin miniprep kit (Qiagen, Valencia, Calif.) and screened for the correct inserts by restriction digest with EcoR 1. The sequences of plasmids appearing to have the correct insert were verified by dideoxy chain termination DNA sequencing with universal M13 forward primers.

The DNA sequence of the *A. caviae* PCR product is shown below as SEQ ID NO:154), with degenerate primer sequence regions underlined:

```
                                       (SEQ ID NO: 154)
GCCAGCAACGARGARGCMCGCGTTGCCCGCGAGAAGGGCTTCGAAGGTCGC

CTGATGCGGGTACGTGCCGCCACCCCGGATGAAGTGGAGCAGGCCCTGCCC

TACAAGCTGGAGGAGCTCATCGGCAGCCTGGAGAGCGCCAAGGGGATCGCC

GACATCGCCCAGCGCCATCACACCAACATCCCGGTGCACATCGGCCTGAAC

TCCGCCGGCATGAGCCGCAACGGCATCGATCTGCGCCAGGACGATGCCAAG

GCCGATGCCCTGGCCATGCTCAAGCTCAAGGGGATCACCCCGGTCGGCATC

ATGACCCACTTCCCGGTGGAGGAGAAAGAGGACGTCAAGCTGGGGCTGGCC
```

-continued

```
CAGTTCAAGCTGGACTACCAGTGGCTCATCGACGCCGGCAAGCTGGATCGC

AGCAAGCTCACCATCCACGCCGCCAACTCCTTCGCCACCCTGGAAGTACCG

GAAGCCTACTTTGACATGGTGCGCCCGGGCGGCATCATCTATGGCGACACC

ATTDDDTDDTACACCGAGTACAAGAAGGTGATGGCGTTCAAGACCCAGGTC

GCCTCCGTCAACCACTACCCGGCGGGCAACACCGTCGGCTATGACCGCACC

TTCACCCTCAAGCGCGACTCCCTGCTGGCCAACCTGCCGATGGGCTACTCC

GACGGCTACCGCCGCGCCATGAGCAACAAGGCCTATGTGCTGATCMASGGC

CA,
``` wherein R indicates

A or G, S indicates C or G, and M indicates A or C.

The amino acid sequence of the partial *A. caviae* BAR enzyme is shown below.

```
                                            (SEQ ID NO:155)
ASNEEARVAREKGFEGRLMRVRAATPDEVEQALPYKLEELIGSLESAKGI

ADIAQRHHTNIPVHIGLNSAGMSRNGIDLRQDDAKADALAMLKLKGITPV

GIMTHFPVEEKEDVKLGLAQFKLDYQWLIDAGKLDRSKLTIHAANSFATL

EVPEAYFDMVRPGGIIYGDTIPSYTEYKKVMAFKTQVASVNHYPAGNTVG

YDRTFTLKRDSLLANLPMGYSDGYRRAMSNKAYVLIXG.
``` wherein X is H, Q, N, or K.

The consensus protein sequence fragment of SEQ ID NO:155 above is 89% homologous at the amino acid level to the published TIGR sequence for *A. hydrophila* (protein 1 (SEQ ID NO:146) above). It was expected that because the highly related *Aeromonas hydrophila* protein exhibited broad specificity racemase activity, as well as the *A. caviae* cellular extracts, the full length coding region for *A. caviae*, once obtained, would produce a racemase that also would have a broad specificity with activity on tryptophan. Genome Walker methods were utilized, as described in Example 15, to obtain the full-length gene sequence of the *A. caviae* BAR gene shown below as SEQ ID NO:178.

```
                                            (SEQ ID NO:178)
   atgcacaaga aaacactgct cgcgaccctg atctttggcc tgctggccgg ccaggcagtc gccgcccct atctgccgct cgccgacgac caccgcaacg gtcaggaaca gaccgccgcc aacgcctggc tggaagtgga tctcggcgcg ttcgagcaca acatccagac cctgaagaat cgcctcggtg acaagggccc gcagatctgc gccatcatga aggcggacgc ctacggtcac ggcatcgacc tgctggtccc ttccgtggtc aaggcaggca tcccctgcat cggcatcgcc agcaacgaag aagcacgtgt tgcccgcgag aagggcttcg aaggtcgcct gatgcgggta cgtgccgcca ccccggatga agtggagcag gccctgccct acaagctgga ggagctcatc ggcagcctgg agagcgccaa ggggatcgcc gacatcgccc agcgccatca caccaacatc ccggtgcaca tcggcctgaa ctccgccggc atgagccgca
```

```
   acggcatcga tctgcgccag gacgatgcca aggccgatgc cctggccatg ctcaagctca aggggatcac cccggtcggc atcatgaccc acttcccggt ggaggagaaa gaggacgtca agctggggct ggcccagttc aagctggact accagtggct catcgacgcc ggcaagctga tcgcagcaa gctcaccatc cacgccgcca actccttcgc caccctggaa gtaccggaag cctactttga catggtgcgc ccgggcggca tcatctatgg cgacaccatt ccctcctaca ccgagtacaa gaaggtgatg gcgttcaaga cccaggtcgc ctccgtcaac cactacccgg cgggcaacac cgtcggctat gaccgcacct tcaccctcaa gcgcgactcc ctgctggcca acctgccgat gggctactcc gacggctacc gccgcgccat gagcaacaag gcctatgtgc tgatccatgg ccagaaggcc cccgtcgtgg gcaagacttc catgaacacc accatggtgg acgtcaccga catcaagggg atcaaacccg gtgacgaggt ggtcctgttc ggacgccagg gtgatgccga ggtgaaacaa tctgatctgg aggagtacaa cggtgccctc ttggcggaca tgtacaccgt ctggggctat accaacccca agaagatcaa gcgctaa.
```

The corresponding amino acid sequence for the *A. caviae* native BAR is shown below as SEQ ID NO:179.

```
                                            (SEQ ID NO:179)
   1 mhkktllatl ifgllagqav aapylpladd hrngqeqtaa 41 nawleydlga fehniqtlkn rlgdkgpqic aimkadaygh 81 gidllvpsvv kagipcigia sneearvare kgfegrlmrv 121 raatpdeveq alpykleeli gslesakgia diaqrhhtni 161 pyhiglnsag msrngidlrq ddakadalam lklkgitpvg 201 imthfpveek edvklglaqf kldyqwlida gkldrsklti 241 haansfatle vpeayfdmvr pggiiygdti psyteykkvm 281 afktqvasvn hypagntvgy drtftlkrds llanlpmgys 321 dgyrramsnk ayvlihgqka pvvgktsmnt tmvdvtdikg 361 ikpgdevvlf grqgdaevkq sdleeyngal ladmytvwgy 401 tnpkkikr.
```

The following PCR primers were utilized to clone the native full-length *A. caviae* BAR in a manner similar to that described above, both tagged and C-terminally his-tagged:

A. caviae F Nde1
(SEQ ID NO:185)
5'-GGAACCTTCATATGCACAAGAAAACACTGCTCGCGACC-3';

A. caviae R BamH1 (untagged)
(SEQ ID NO:186)
5'-GGTTCCAAGGATCCTTAGCGCTTGATCTTCTTGGGGTTG-3';
and A. caviae R Xho1 (C-term tag)
(SEQ ID NO:187)
5'-TTCCAAGGCTCGAGGCGCTTGATCTTCTTGGGGTTGGTA-3'.

The C-terminally tagged enzyme had comparable activity to the untagged native A. caviae BAR. When 200 µg of purified (tagged) racemase enzymes were used in a tryptophan racemase assay as described above, at 30 minutes A. hydrophila BAR had produced 249 µg/mL of D-tryptophan, whereas A. caviae BAR produced 1034 µg/mL and P. taetrolens BAR produced 799 µg/mL.

The first 21 N-terminal amino acid residues of SEQ ID NO:179 are predicted to be a signal peptide using the program Signal P 3.0, as described in Example 4L. The following N-terminal primer was used to clone the A. caviae gene without amino acids 2-21 of the leader sequence:

A.cavMinus leader F Nde1
(SEQ ID NO:188)
5'CCTTGGAACATATGGCCCCCTATCTGCCGCT3.'

The leaderless racemase, when expressed, was found to retain approximately 65% of the activity, as compared with the expression product of the full-length gene. The periplasmic and cytoplasmic protein fractions were isolated for the wildtype expression products, as well as the leaderless constructs, as described in the pET System Manual (Novagen, Madison, Wis.). The majority of expressed wildtype BAR was found in the periplasm, while the leaderless BAR appeared to remain in the cytoplasm. The reduction in activity of the leaderless A. caviae BAR may be due to a change in processing and/or folding when expressed in the cytoplasm.

Based on mutations made in the P. putida BAR sequences in Examples 4I and 4G, similar modifications were introduced, using the site-directed mutagenesis methods described above, to yield Y395H, Y395C, and L383M mutants in the A. caviae wildtype BAR. Mutagenesis at Y395 causes a loss of over 95% of the activity using L-tryptophan as a substrate, even when combined with the L383M mutation. The L383M mutant had approximately 83% of the activity on L-tryptophan at a 2-hour time point. These results suggest that the mutations made in the Kino et al. paper are not universally applicable to improvement of BAR enzymes for activity on L-tryptophan. Additional Aeromonas BAR sequences were obtained by degenerative PCR methods described above, but using the following primers:

Aer deg F1 mod: 5'-AAGGCSGAYGCCTAYGGY-CACGG-3' (SEQ ID NO:189) where S is C or G and Y is C or T; and Aer deg R3:5'-CGGCGRTAGCCRTCRGAGTA-3' (SEQ ID NO:190), where R is A or G.

This primer pair gave partial sequences for A. sobria (ATCC 35994), A. jandei (ATCC 49572), A. schubertii (ATCC 43701), and A. salmonicida (ATCC 27013 and ATCC 14174). The full-length sequences obtained are as follows:

The A. sobria DNA sequence is shown below as SEQ ID NO:191:

(SEQ ID NO:191)
ATGCACAAGAAAACGCTATTGGCCACCCTGATCTTCGGCCTGCTCGCGGG

CCAAGCCGTTGCGGCTCCCTATCTGCCCCTTGCGACGGATCATCGCAACG

GTCAGGAGCAAACCGCCAGCAACGCCTGGTTGGAAGTGGATCTGGGCGCC

TTCGAACACAATATCCAGACCCTCAAGGATCGCCTCGGTGACAAGGGTCC

GCAGATCTGCGCCATCATGAAGGCCGACGCCTATGGTCATGGCATCGACC

TGCTGGTCCCCTCCGTGGTCAAGGCCAATATCCCCTGCATCGGCATCGCC

AGCAACGAAGAGGCCCGCGTCGCCCGCGAGAAGGGCTTTACCGGCCGTCT

GATGCGGGTGCGTGCCGCCACACCGGCCGAAGTGGAGCAGGCGCTGCCCT

ACAAGATGGAAGAGCTGATCGGCAGTCTGGTGAGTGCTCAGGGGATCGCC

GACATCGCCCAGCGCCACCACACCAATATTCCGGTACACATTGGTCTCAA

CTCTGCTGGCATGAGCCGCAACGGTATCGACCTGCGTCTGGCCGATGCCA

AGCAGGATGCGCTGGCCATGCTCAAGCTCAAGGGGATCACCCCGGTCGGC

ATCATGACCCACTTCCCGGTGGAGGAGAAAGAGGACGTCAAGATGGGGCT

GGCCCAGTTCAAACTGGACTCTCAGTGGCTGCTGGAAGCGGGCAAGCTGG

ATCGCAGCAAGATCACCATCCACGCCGCCAACTCCTTCGCCACCCTGGAA

GTGCCGGATGCCTACTTCGACATGGTGCGTCCGGGTGGCCTGCTCTACGG

CGACTCCATCCCCTCCTACACCGAATACAAGCGGGTGATGGCATTCAAGA

CCCAGGTCGCCTCGGTCAACCACTACCCGGCGGGCAATACCGTTGGCTAT

GACCGTACCTTTACCCTCAAGCGTGAATCCTGGCTCGCCAACCTGCCGCT

GGGCTACTCCGATGGCTACCGCCGTGCGCTCAGCAACAAGGCCTATGTGC

TGATCCAGGGTCAGAAGGTGCCGGTGGTCGGCAAGACCTCCATGAACACC

ATCATGGTGGACGTCACTGATCTCAAAGGGGTGAAACCCGGTGATGAGGT

GGTGCTGTTTGGCCGTCAGGGCGAGGCCGAGGTGAAACAGGCTGATCTGG

AAGAGTACAACGGCGCCCTGTTAGCGGACATGTACACCATCTGGGGCTAC

ACCAACCCCAAGAAGATCAAACGCTGA.

The A. sobria protein sequence is shown below as SEQ ID NO:192:

(SEQ ID NO:192)
MHKKTLLATLIFGLLAGQAVAAPYLPLATDHRNGQEQTASNAWLEVDLGA

FEHNIQTLKDRLGDKGPQICAIMKADAYGHGIDLLVPSVVKANIPCIGIA

SNEEARVAREKGFTGRLMRVRAATPAEVEQALPYKMEELIGSLVSAQGIA

DIAQRHHTNIPVHIGLNSAGMSRNGIDLRLADAKQDALAMLKLKGITPVG

IMTHFPVEEKEDVKMGLAQFKLDSQWLLEAGKLDRSKITIHAANSFATLE

VPDAYFDMVRPGGLLYGDSIPSYTEYKRVMAFKTQVASVNHYPAGNTVGY

DRTFTLKRESWLANLPLGYSDGYRRALSNKAYVLIQGQKVPVVGKTSMNT

IMVDVTDLKGVKPGDEVVLFGRQGEAEVKQADLEEYNGALLADMYTIWGY

TNPKKIKR.

The *A. jandei* DNA sequence is shown below as SEQ ID NO:193:

```
(SEQ ID NO:193)
ATGCACAAGAAAACACTGCTGGCCACCCTGATCCTCGGCCTGCTGGCCGG
GCAAGCGGTTGCAGCCCCCTACCTGCCGCTGGCCAGCGATCACCGCAACG
GCGAAGTCCAGACCGCCAGCAATGCCTGGCTGGAAGTCGATCTCGGCGCC
TTCGAGCACAATATCCAGACCCTCAAGGATCGTCTCGGTGACAAGGGGCC
GAAGATCTGCGCCATCATGAAGGCGGATGCCTATGGCCACGGTATCGATC
TGCTGGTTCCCTCGGTGGTGAAAGCGGGTATCCCCTGCATCGGTATCGCC
AGCAATGAAGAAGCTCGTGTCGCCCGCGAGAAGGGCTTCACCGGTCGTCT
GATGCGGGTACGTGCTGCCACCCCGGACGAAGTGGAGCAGGCCCTGCCCT
ACAAGATGGAGGAGCTGATCGGCAGTCTGGTGAGTGCTCAGGGCATCGCC
GATATCGCCCAGCGCCACCACACCACCATTCCGGTGCATATCGCCCTCAA
CTCCGCCGGCATGAGCCGCAACGGCATCGATCTGCGGCTGGCCGACTCCA
AGCAGGATGCGCTGGCCATGCTCAAGCTCAAGGGGATCACCCCGGTCGGC
ATCATGACCCACTTCCCGGTGGAGGAGAAAGAGGACGTCAAGATGGGTCT
GGCCCAGTTCAAACTGGACTCCCAGTGGCTGCTGGAAGCGGGCAAGCTGG
ATCGCAGCAAGATCACCATCCACGCCGCCAACTCCTTCGCAACACTTGAA
GTGCCGGATGCCTACTTCGACATGGTGCGCCCGGGTGGCCTGCTCTACGG
TGACTCCATCCCCTCCTACACCGAGTACAAGCGGGTGATGGCGTTCAAGA
CCCAGGTTGCCTCCGTCAACCACTACCCGGCCGGCAACACCGTCGGTTAT
GACCGCACCTTCACCCTCAAGCGCGACTCCTGGCTCGCCAACCTGCCGCT
CGGTTACTCCGATGGCTATCGCCGCTCCCTGAGCAACAAGGCCTATGTGC
TGATCCAGGGCCAGAAGGTGCCGGTGGTCGGCAAGACCTCCATGAACACC
ATCATGGTGGATGTGACCGACCTGAAAGGGGTGAAACCCGGTGACGAAGT
GGTGCTGTTCGGCCGTCAGGGAAATGCCGAGGTGAAGCAGGCGGATCTGG
AGGAGTACAACGGCGCCCTGCTGGCGGACATGTACACCATCTGGGGCTAC
ACCAACCCCAAGAAGATCAAGCACTAA.
```

The *A. jandei* protein sequence is shown below as SEQ ID NO:194:

```
(SEQ ID NO:194)
MHKKTLLATLILGLLAGQAVAAPYLPLASDHRNGEVQTASNAWLEVDLGA
FEHNIQTLKDRLGDKGPKICAIMKADAYGHGIDLLVPSVVKAGIPCIGIA
SNEEARVAREKGFTGRLMRVRAATPDEVEQALPYKMEELIGSLVSAQGIA
DIAQRHHTTIPVHIALNSAGMSRNGIDLRLADSKQDALAMLKLKGITPVG
IMTHFPVEEKEDVKMGLAQFKLDSQWLLEAGKLDRSKITIHAANSFATLE
VPDAYFDMVRPGGLLYGDSIPSYTEYKRVMAFKTQVASVNHYPAGNTVGY
DRTFTLKRDSWLANLPLGYSDGYRRSLSNKAYVLIQGQKVPVVGKTSMNT
IMVDVTDLKGVKPGDEVVLFGRQGNAEVKQADLEEYNGALLADMYTIWGY
TNPKKIKH.
```

The following partial DNA sequences were also obtained:
*A. salmonicida* (ATCC 27013 and ATCC 14174) (SEQ ID NO:195):

```
AAGGCSGATGCCTAYGGTCACGGTATCGACCTGCTGGTCCCCTCCGTGGTC
AAGGCCAATATCCCCTGTATCGGCATCGCCAGCAACGAAGAGGCCCGCGTG
GCGCGCGAGAAGGGGTTCAGCGGCCGCCTGATGCGGGTACGGGCCGCCACA
CCGATCGAAGTGGAACAGGCCCTGCCCTACAAGCTGGAAGAGCTGGTTGGC
AGCCTGGTGAGTGCTCAGGGGATCTCCGACATCGCCCTGCGCCACCACACC
ACCATTCCGGTGCATGTCGCCCTCAACTCCGCCGGCATGAGCCGCAACGGC
ATCGACCTGCGTCTGGCCGATGCCAAGCAAGATGCGCTGGCCATGCTCAAG
CTCAAGGGGATCACCCCGGTCGGCATCATGACCCACTTCCCGGTGGAGGAG
AAAGAGGACGTCAAGCTGGGGCTGGCCCAGTTCAAGCTGGACTCCCAGTGG
CTGCTGGAAGCAGGCAAGCTGGATCGCAGCAAGATCACCATCCATGCCGCC
AACTCCTTCGCCACCCTGGCAGTGCCGGACGCCTACTTTGACATGGTGCGC
CCGGGCGGCCTGCTCTACGGCGACTCCATCCCCTCCTACACCGAATACAAG
CGGGTGATGGCATTCAAGACCCAGGTCGCCTCGGTCAACCACTATGCGGCG
GGCAACACAGTCGGTTATGACCGCACCTTTACTCTCAAACGTGACTCCTGG
CTCGCCAACCTGCCTCTCGGTTACTCCGAYGGCTAYCGCCG
```

(SEQ ID NO:195) where S is C or G and Y is C or T.

*A. schubertii* (ATCC 43701) (SEQ ID NO:196):

```
AAGGCGGATGCCTATGGTCACGGCATCGATCTGCTGGTCCCCTCCGTGAT
CAAGGCCGGCATTCCTTGCATCGGCATCGCCAGCAACGAAGAGGCTCGCG
TCGCCCGTGAGAAGGGCTTCGAAGGCCGTCTGATGCGGGTGCGCGCCGCC
ACCCCGCAAGAGGTGGAAGCCGCCCTCCCCTACAAGATGGAGGAGCTGGT
CGGCAGCCTGGAGAGCGCCCGTCTGATGTCGGAGATTGCCCTGCGTCACC
ACACCACCATTGCGTACCATCTGGGGCTCAACTCCGCCGGCATGAGCCGC
AACGGCCTGGATCTGCGCCTCTCCGACGCCAAGCGCGACGCACTCGACCT
GATGAAGCTCAAGGGGCTGCAGGTGGTCGGCATCATGACCCACTTCCCGG
TCGAGGAGAAAGAGGACGTGAAGATGGGCTTCGCCCAGTTTCAGCTCGAC
ACCCAGTGGCTCATCGAAGCCGCTCGTCTGGATCGCAGCAAGTTGACCCT
GCACTGTGCCAACTCCTTTACCACCCTGGAGGTGCCCGAGGCCTATCTGG
ACATGGTCCGCCCGGGCGGCATCATCTATGGCGACACCATTCCCTCCTAC
ACCGAATACAAGAAGGTGATGGCCTTCAAGACCCGGGTCGCCTCGGTCAA
TCACTACCCGAAGGGAAATAGCGTCGGCTATGACCGCACCTTCACCCTGG
CACGCGACTCCTGGCTCGCCAACCTGCCGCTGGGCTACTCCGACGGCTAC
CGCCGGGCGCTGAGCAACAAGGCCTATGCTGGTGAATGGCCAGAAGGC
CCCCGTGGTGGGCAAGACATCCATGAACACCATCATGGTGGACGTGACCG
ACATCAAGGGGGTCAAACCGGGTGACGAGGTGGTGCTGTTTGGCCGCCAG
GGCAACGCCGAGGTGAAGCAGTCCGATCTCGAGGAGTACAACGGCGCCCT
CCTGGCGGACATGTACACCATCTGGGGCTACACCAATCCACGTATCATCA
AGCGCTGA
```

It is expected that the full length gene sequences of *A. salmonicida* and *A. schubertii*, obtainable by Genome Walking methods described above, would also encode active BAR enzymes.

The following PCR primers were designed for cloning the *A. jandei* and *A. sobria* BAR genes:

*A. jandei*:

```
                                           (SEQ ID NO:197)
Forward NdeI 5'-
CCGGAACCTTCATATGCACAAGAAAACACTGCTGGCCAC-3'
and (SEQ ID NO:198)
Reverse XhoI 5'-
TTCCAAGGCTCGAGGTGCTTGATCTTCTTGGGGTTGGT-3'.
```

*A. sobria*

```
                                           (SEQ ID NO:199)
Forward NdeI 5'-
CCGGAACCTTCATATGCACAAGAAAACGCTATTGGCCAC-3'
and (SEQ ID NO:200)
Reverse XhoI 5'-
TTCCAAGGCTCGAGGCGTTTGATCTTCTTGGGGTTGGT-3'.
```

Cloning, expression, and purification methods for the BAR enzymes are described above. Purified C-terminally tagged BARs (100 μg in a 1 mL assay) from *P. taetrolens*, *A. caviae*, *A. jandei*, and *A. sobria* were assayed as described above, except that the initial concentration of L-tryptophan used was approximately 7 mg/mL. At the 60 minute time point, the following amounts of D-tryptophan were produced by each BAR enzyme: *A. caviae*, 1452 μg/mL; *A. jandei*, 407 μg/mL; *A. sobria*, 145 μg/mL; and *P. taetrolens*, 502 μg/mL. The *A. caviae* BAR consistently has a higher reaction rate and reaches equilibrium faster than the other BAR enzymes tested.

Highly active BAR homologs were analyzed for primary sequence conservation. It was noted that in the motif described in Example 4E (SEQ ID NO:116), the broad specificity racemases of this example all contain the motif KADAYGHGI (SEQ ID NO:201), whereas the alanine racemases with lower activity for tryptophan racemization typically contain the motif KANAYGHGI (SEQ ID NO:202). A D76N mutant of *A. caviae* BAR was made to determine if this position was critical for broad activity. Mutagenesis was done using the QuickChange-Multi site-directed mutagenesis kit (Stratagene, La Jolla, Calif.), using the C-tagged *A. caviae* BAR gene in pET30. The following mutagenic primer was used to make a D76N change (nucleotide position 226): 5'-CGCCATCATGAAGGCGAACGCCTACGGTCACG-3' (SEQ ID NO:203). The site-directed mutagenesis was done as described in the manufacturer's protocol. The mutant and the wildtype enzyme were produced as described above and assayed as described above using 200 micrograms of purified protein and approximately 7 mg/mL of L-tryptophan as substrate. At the 30 minute time point, the mutant produced 1929 micrograms per mL of D-tryptophan as compared to 1149 micrograms per mL for the wildtype enzyme. The D76N mutant also reached equilibrium at an earlier time point. The improvement in activity was unexpected. Based on the high homology in this region for *Aeromonas* and *Pseudomonas* BAR enzymes, it is expected that similar mutations in other broad activity racemases would also be beneficial.

4P: Processing of N-Terminal Leader Sequences of BAR Enzymes

Samples of purified C-terminally His-tagged broad amino acid racemase (BAR) from *P. taetrolens* (SEQ ID NO:204), *A. caviae* (SEQ ID NO:179) and *A. hydrophila* (SEQ ID NO:177) produced in *E. coli* were characterized by reversed-phase liquid chromatography/electrospray ionization-quadruple-time-of-flight mass spectrometry (LC/ESI-QTOF-MS) to determine at which position the leader sequence of each protein was cleaved. Mass spectra were collected over the range m/z 300 to m/z 1300. Deconvolution (mathematical conversion of the envelope of m/z values resulting from protein molecules of the same mass with different numbers of protons attached, to molecular mass) of mass spectra acquired for each protein was accomplished using the maximum entropy deconvolution software supplied with the MS instrumentation. The molecular mass observed for the *P. taetrolens* BAR was 42651 Da, indicating cleavage of this protein after amino acid A23 (theoretical molecular mass=42654 Da). The molecular mass observed for the *A. caviae* BAR was 43565 Da, indicating cleavage of this protein after amino acid 21 (theoretical molecular mass=43568 Da). The molecular mass observed for the *A. hydrophila* BAR was 43450 Da, indicating cleavage of this protein after amino acid 21 (theoretical molecular mass=43453 Da). When the codons coding for amino acids 2-23 of SEQ ID NO:204 are removed and a partial gene is expressed in *E. coli* in the same manner as described above, the molecular mass observed for the purified expression product is 42483 Da. Based on this result, the mature protein of the leaderless expression product appears to have the first 2 or 3 amino acids removed, making it 1 or 2 amino acids shorter than the mature protein of the wildtype product. When the codons coding for amino acids 2-21 of SEQ ID NO:179 are removed, the molecular mass observed for the purified expression product is 43500, corresponding to the first two amino acids (MA) being removed (theoretical molecular mass=43498). The mature protein is therefore missing one additional alanine as compared to the wildtype mature protein, and as shown in Example 4O does not appear to be secreted into the periplasm. If the mature protein from the *P. taetrolens* (SEQ ID NO:204) leaderless expression product is missing a proline in addition to the alanine that is cleaved from both *A. caviae* and *P. taetrolens* leaderless expression products, it may explain the increased reduction in activity. However, the protein may never express and fold appropriately, as evidenced by the dramatic reduction in expression as judged by SDS-PAGE. It is likely that the *P. putida* BAR enzymes described above are processed similarly by *E. coli*, because the N-terminal His-tagged proteins would not purify on a nickel affinity column and the Signal P 3.0 program predicted a leader sequence.

Example 5

Selection Method for Screening of Pyruvate Aldolases in Recombinant *E. coli*

Many of the processes described in Examples 4A(5), 9 and 10(3), and shown in FIGS. 1-8, will work optimally with an aldolase that preferentially produces R-MP from indole-3-pyruvate and pyruvate. Therefore, methods are described to isolate and test clones containing a nucleic acid encoding an aldolase that preferentially produces R-MP. Strains of *Escherichia coli* that require pyruvate supplementation when grown on M9 minimal medium with ribose as the carbon source have been described previously. Ponce, E., et al., "Cloning of the two pyruvate kinase isoenzymes structural genes from *Escherichia coli.*: The relative roles of these enzymes in pyruvate biosynthesis," *J. Bacteriol.* 177:5719-5722, (1995). The relevant genotype of the strain is: ΔpykA ΔpykF. The double knockout was generated by the method of Datsenko and Wanner, *Proceed. Natl. Acad. Sci. USA* 97:6640-6645, (2000). These strains can form a basis for a pyruvate-generating aldolase screen and to screen for aldolases that are more active on a specific stereoisomer of monatin, a particular stereoisomer of monatin precursor, or an analog of monatin or monatin precursor. An analog of monatin precursor includes compounds that have been identified as substrates for ProA aldolases or KHG aldolases, such as 4-hydroxy-4-methyl-2-oxoglutarate, 4-carboxy-4-hydroxy-2-oxoadipate, 4-hydroxy-4-methyl-2-oxoadipate, or other carboxyl rich compounds that are converted to pyruvate in an aldol reaction. An example of an analog of monatin that can be used is 4-hydroxy-4-methyl glutamic acid, which can be easily transaminated to 4-hydroxy-4-methyl-2-oxoglutarate (a substrate of ProA) by native aminotransferases in a test cell.

Cloning

The following primers were used to generate the pykA knockout:

(SEQ ID NO:3)
5'-ATGTCCAGAAGGCTTCGCAGAACAAAAATCGTTACCACGTTAGGTGT

AGGCTGGAGCTGCTTC-3'
and (SEQ ID NO:4)
5'-CTCTACCGTTAAAATACGCGTGGTATTAGTAGAACCCACGGTACCAT

ATGAATATCCTCCTTAG-3'.

The following primers were used to generate the pykF knockout:

(SEQ ID NO:5)
5'-AGGACGTGAACAGATGCGGTGTTAGTAGTGCCGCTCGGTACCAGCAT

ATGAATATCCTCCTTAG-3'
and (SEQ ID NO:6)
5'-ATGAAAAAGACCAAAATTGTTTGCACCATCGGACCGAAAACCGGTGT

AGGCTGGAGCTGCTTC-3'.

A PCR reaction was performed with either pKD3 or pKD4 as template using standard protocols. The PCR product was electroporated into a strain of *E. coil* that expresses the lambda red homologous recombination system. The PCR product had homology to pykA or pykF and recombined into the chromosome at those sites. When the double crossover occurred, the resulting progeny carried a deleted pykA or pykF gene and an antibiotic resistance marker. The deleted genes with the antibiotic resistance markers were transduced into an *E. coli* strain (MG1655) using standard P1 transduction techniques.

Strain Analyses

The double knockout was tested for growth on minimal medium (M9 salts) (Difco) supplemented with Balch's vitamin solution, Balch's modified trace element solution (Balch, W. E., et al., "Methanogens: reevaluation of a unique biological group," *Microbiol. Rev.* 43:260-296, (1979)), and 0.4% D-ribose. No growth was seen for the double mutant unless 5 mM pyruvate was also included in the media. Wild-type MG1655 grew on the above media both in the presence and absence of pyruvate. The double knockout was tested for growth on the minimal medium described above supplemented with 0.4% glucose rather than ribose. Growth on this medium was similar to that seen with the wild-type strain. With this medium, pyruvate can be generated from glucose via the ptsI gene product (the enzyme of the phosphotransferase system that makes pyruvate from phosphoenolpyruvate and transfers the phosphate to glucose). The double knockout strain was also tested for growth using the medium as described above supplemented with 0.4% L-arabinose or 0.4% D-xylose rather than ribose. Pyruvate is not generated from growth on these 5-carbon containing (non-PTS) substrates. The double knockout did not grow under these conditions unless it was supplemented with 5 mM pyruvate, while the wild-type strain grew normally both in the presence and absence of pyruvate.

The proA aldolase gene from *Comamonas testosteroni* described in Example 2 of WO 03/091396 A2 (cloned in pET30 Xa/LIC) and the aspC/proA gene operon described in Example 3 of WO 03/091396 A2 (cloned in pET30 Xa/LIC and pET32) were subcloned into pBAD-TOPO using the pBAD TOPO TA expression kit (Invitrogen).

Expression of the gene(s), in these constructs, is regulated by the inducible araBAD promoter. In the presence of arabinose (for example 0.4%) and IPTG, the gene(s) are expressed. Unless supplemented with pyruvate or a source of pyruvate, the strain will not grow on minimal medium. The medium can be supplemented with monatin, monatin precursor, or an analog of monatin or monatin precursor. Typical ranges of substrate used in the literature are 0.5-5 mM. The ProA aldolase can, for example, convert the monatin precursor into pyruvate and indole-3-pyruvate, thus, providing the strain with a source of pyruvate and allowing growth on minimal medium with 0.4% arabinose. The construct expressing both the proA and the aspC genes can convert monatin into the monatin precursor and the monatin precursor into pyruvate and indole-3-pyruvate. Additionally, the aminotransferase can convert indole-3-pyruvate to L-tryptophan and complement a tryptophan auxotrophy. This system is used to screen for aldolases and to screen for aldolases that are more active on a specific stereoisomer of monatin, a specific stereoisomer of monatin precursor, or an analog of monatin or monatin precursor. For example, if directed evolution is performed on any of the aldolases disclosed in Example 2 of WO 03/091396 A2, a plate assay utilizing media containing either R or S monatin precursor is used to compare the enantiospecificity of the resulting mutant enzyme. If growth occurs on the plates containing R-monatin precursor and little or no growth occurs on the plate containing S-monatin precursor, the aldolase has a specificity for substrates containing the R-chirality at the reaction site.

M9 minimal medium plates were made containing 1× Balch's vitamin solution and Balch's modified trace element solution. Balch, W. E., et al., "Methanogens: reevaluation of a unique biological group." *Microbiol. Rev.* 43:260-296, (1979). Glucose or arabinose was included as the carbon source (0.4% w/v) and plates were supplemented with either 5 mM monatin (R,R; S,S racemic mixture) that had been dissolved in 20 mM potassium phosphate buffer (pH 8.0) or an equal volume of potassium phosphate buffer without monatin. Growth is summarized in Table 34 below.

TABLE 34

|  | Glucose | Glucose monatin | Arabinose | Arabinose monatin |
|---|---|---|---|---|
| MG1655 | ++++ | ++++ | ++++ | ++++ |
| MG1655 ΔpykA ΔpykF | ++++ | ++++ | + | + |
| MG1655 ΔpykA ΔpykF + aspCproA/pBAD-TOPO | ++++ | ++++ | + | ++ |

It is expected that the screen could be optimized by controlling the levels of ProA and AspC, increasing uptake of monatin, using monatin precursor in the place of monatin (in this case the aminotransferase would not need to be present), or using a less hydrophobic analog of monatin such as those described above. Methods for increasing the uptake of monatin include addition of amino acid mixtures, addition of specific amino acids, the use of detergents, antibiotics, antibiotic analogs, or enzymes that help to permeabilize the cell wall, and the addition of a small amount of pyruvate to allow for growth in case the aldolase cannot provide enough pyruvate to support growth. Polymyxin B nonapeptide (Dixon and Chopra, *Antimicrobial Agents and Chemotherapy* 29:781-788 (1986)) and microcystin RR (Dixon, et al., *FEMS Microbiology Letters* 230:167-170 (2004)) have been described as agents that permeabilize the outer membrane of *E. coli*.

It is expected that other promoter systems/plasmids can be used in this screening system with equivalent results. Examples include T7 promoter systems and IPTG inducible promoters such as tac and lac.

The aspC and the proA genes were cloned into the pTrc99a expression vector (Amersham, Piscataway, N.J.). The resulting vector was transformed into the tryptophan auxotrophs CAG18455 or CAG18579 (see Example 4 for strain descriptions). The transformants were plated on M9 minimal medium with 0.1 mM IPTG and 5 mM monatin. After 3 days at 37° C., the strains with the operon plasmids formed colonies, while the parent strains did not appear to grow. Additionally, the growth was dependent on the presence of IPTG indicating that expression of the operon was required for growth. In this complementation study, the aspC/proA operon formed MP from monatin and indole-3-pyruvate from MP. The indole-3-pyruvate could then be converted to L-tryptophan allowing the tryptophan auxotrophs to grow on M9 minimal medium.

Several potential organisms may have the R-specific aldolase and can be tested as described above. The presence of R,R-monatin has been detected in culture supernatants of *Corynebacterium glutamicum*. This suggests the presence of an enzyme that is capable of making the R-monatin precursor. Additionally, the presence of multiple isomers of monatin has been detected in cell free extracts of *Sinorhizobium meloti* using reversed phase chromatography, again indicating the possible presence of an aldolase or aminotransferase capable of making an R stereoisomer of monatin precursor.

*Pseudomonas straminea* (*Pseudomonas ochraceae* NGJ1), *Sinorhizobium meloti*, *Sphingomonas* sp. LB 126, *Arthrobacter keyseri* 12B, *Yersinia pestis* strain CO92, *Bradyrhizobium japonicum* str. USDA 110, *Sphingomonas* (*Pseudomonas*) *paucimobilis*, *Yersinia pestis* KIM, *Ralstonia metallidurans* CH34, *Yersinia pseudotuberculosis* IP 32953, *Rhizobium leguminosarum* biovar *viciae* rhiz23g02-plk_1009_341 (Sanger Institute), *Novosphingobium aromaticivorans* DSM 12444, *Pseudomonas putida* KT2440, *Magnetospirillum magnetotacticum* MS-1, *Rhodopseudomonas palustris* CGA009, *Xanthomonas campestris* ATCC-33913, *Xanthomonas axonopodis* citri 306, and *Streptomyces avermitilis* MA-4680 have homologs that have been discovered by BLAST analysis using proA (*Comamonas testosteroni*) as the template. See U.S. Application No. 20050282260. These organisms can be used as a source of DNA and tested in the screen mentioned above.

Organisms capable of growth on gallic acid, syringic acid, protocatechuate, phtalate, parahydroxybenzoate, and fluorene may have an aldolase that may make monatin and have potential for the screen mentioned above. The following organisms metabolize protocatechuate via the 4,5-dioxygenase pathway and may have an aldolase that may be of utility: *Bordetella bronchiseptica* RB50, *Bordetella parapertussis* 12822, *Klebsiella pneumoniae* MGH78578, *Magnetospirillum magnetotacticum* MS-1, *Rhodopseudomonas palustris* CGA009, *Sphingomonas aromaticivorans* F199, *Xanthomonas axonopodis* citri 306, *Xanthomonas campestris* ATCC 33913.

And the following organisms degrade protocatechuate via the 3,4 dioxygenase pathway and have an aldolase that may be of utility: *Acinetobacter calcoaceticus* ADP1, *Acinetobacter species* ATCC 33305, ADP1, *Agrobacterium tumefaciens* C58, *Azotobacter vinelandii* AvOP, *Bradyrhizobium japonicum* str. USDA 110, *Bradyrhizobium japonicum* tr. USDA 438, *Brucella abortus*, *Brucella melitensis* 16M, *Brucella melitensis* suis 1330, *Burkholderia cepacia* J2315, *Burkholderia fungorum* LB400, *Burkholderia pseudomallei* K96243, *Corynebacterium efficiens* YS-314, *Corynebacterium glutamicum* ATCC-13032, *Mesorhizobium loti* MAFF303099, *Mycobacterium avium* subsp. *paratuberculosis* str. k10, *Pseudomonas aeruginosa* PAO1, *Pseudomonas fluorescens* Pf0-1, *Pseudomonas fluorescens* SBW25, *Pseudomonas putida* KT2440, *Pseudomonas syringae* pv. *tomato* str. DC3000, *Ralstonia solanacearum*, *Rhodococcus* sp. strain I24 (IG-15), *Sinorhizobium meliloti* 1021, *Streptomyces avermitilis* MA-4680, *Streptomyces coelicolor* A3 (2), and *Xanthomonas axonopodis* citri 306, *Xanthomonas campestris* ATCC-33913.

Example 6

6A: Site Directed Mutagenesis of HEXAspC

Experimental Overview

A hexamutant of *E. coli* AspC (HEXaspC) was found to have better activity as compared to AspC for the production of S,S monatin, as described in Example 6 of WO 03/091396 A2. HEX (accession number:/AHFA gi:127190) contains the following mutations from AspC (*E. coli* numbering): V35L, K37Y, T43I, N64L, T104S, and N285S. Based on structural analysis and literature reports (Rothman, S., and Kirsch, J., *J. Mol. Biol.* 327:593-608, (2003); Rothman, S., et al., *Protein Science* 13:763-772, (2004)), 5 more mutants were created that were expected to increase the kinetic activity toward substrates utilized in the monatin production pathway: L-tryptophan, S-MP, or both. Two of the mutants increased transamination rates for both tryptophan and S,S monatin. Two of the mutants showed an increased stereoselectivity for the formation of S,S monatin while one was less stereoselective. Based on this, it is expected that a broad specificity D-aminotransferase from *Bacillus* sp. with similar mutations would be useful as the D-aminotransferase in the R,R monatin pathways shown in FIG. 3, and described in Example 4A(4). One of the mutants (HEXaspCP9T/R122G) had increased activity for L-tryptophan transamination, but activity in S,S monatin production or S,S monatin transamination was decreased significantly. Thus, it is expected that this enzyme is useful in the first step of the R,R monatin production pathways shown in FIGS. 1, 2, 4, 5, 6, 7, and 8 and described in Examples 9 and 10(3) In general, an aminotransferase that has activity similar to that of AspC on L-tryptophan, and limited activity on R-MP and S-MP, would be useful for the processes depicted in FIGS. 1, 2, 4, 5, 6, 7, and 8.

Methods and Materials

The HEX gene cloned in pUC19 was provided by Professor J. F. Kirsch (Department of Molecular and Cell Biology, University of California, Berkeley, Berkeley, Calif. 94720-3206) and used as the template for the cloning of the gene into pET23a. See Onuffer, J. J., and Kirsch, J. F., "Redesign of the substrate specificity of *Escherichia coli* aspartate aminotransferase to that of *Escherichia coil* tyrosine aminotransferase by homology modeling and site-directed mutagenesis," *Protein Science* 4:1750-1757 (1995). See also NCBI accession number 1AHF_A GI:1127190 (HEX amino acid sequence). The following primers were designed for cloning the HEX gene into the pET23a vector (Novagen, Madison, Wis.):

HEXaspC Primers:

(SEQ ID NO:7)
N term:   5'-GCGGAACATATGTTTGAGAACATTACCGCC-3';

(SEQ ID NO:8)
C term:   5'-ATAACCGGATCCTTACAGCACTGCCACAATCG-3'.

The following PCR protocol was used for gene amplification: In a 100 µL reaction, 50 ng DNA template, 1.0 µM of each primer, 0.2 mM each dNTP, 1 U Pfu Turbo Polymerase (Stratagene; LaJolla, Calif.), and 1× Cloned Pfu buffer were added. The thermocycler program utilized a hot start of 94° C. for 5 minutes; followed by 25 cycles of a denaturing step at 94° C. (30 sec), an annealing step at 55° C. (1 min), an extension step at 72° C. (2 min), and finally a finishing step at 72° C. (7 min). The purified PCR product was digested with BamH I and NdeI (New England Biolabs) restriction enzymes. The PCR product was ligated into pET23a that was also digested with NdeI and BamH I, using the Roche Rapid DNA Ligation kit (Roche, Indianapolis, Ind.). The desalted ligations were electroporated into *E. coli* DH10B cells using a Bio-Rad Gene Pulser II system, according to manufacturer's protocols. Miniprep DNA was prepared using a Qiagen Spin Miniprep kit (Qiagen, Valencia, Calif.) and was used as a template for mutagenesis reactions. The plasmid was transformed into *E coli* BL21 (DE3) cells according to the manufacturer's protocols (Novagen, Madison, Wis.).

The tryptophan residue at position 130 is thought to be important for stacking interactions with the pyridoxyl ring, but also appears to be a source of steric hindrance with the S-monatin precursor ("S-MP") substrate, based on protein modeling observations. Therefore, an amino acid with a smaller hydrophobic side chain (phenylalanine) was used to replace the tryptophan. The rest of the mutations were based on kinetics data in literature, although new combinations of desirable mutations were created. All mutations to HEXaspC, with the exception of W130F, were made using the Stratagene Multi-Change kit by following the manufacturer's instructions. The W130F mutation was made using the Stratagene QuikChange kit according to the manufacturer's instructions with the only exception being that the extension temperature for the PCR reaction was decreased to 66° C. The primers for the multi-change kit were designed using the QuikChange multi-kit primer design tool on <www.stratagene.com>, except for the W130F single mutation primers.

The primer sequences are listed in Table 35 below:

TABLE 35

| Primer | Sequence (5' to 3') |
|---|---|
| aspCW130F_backward | CGCTCTTATGGTTCGGTTTGCTTGGGTTGCTC ACCC (SEQ ID NO:9) |
| aspCW130F_forward | GGGTGAGCAACCCAAGCTTTCCGAACCATAAG AGCG (SEQ ID NO:10) |
| R122G-1<sup>a</sup> | CAAAAAATACCAGCGTTAAGGGAGTGTGGGTG AGCAACC (SEQ ID NO:11) |
| P9T_4<sup>a</sup> | CATTACCGCCGCTACTGCCGACCCGATTC (SEQ ID NO:12) |
| I68V-1<sup>a</sup> | CACCAAAAATTACCTCGGCGTAGACGGCATCC CTGAATT (SEQ ID NO:13) |
| T156A<sup>a</sup> | TGATGCGGAAAATCACGCTCTTGACTTCGATG CAC (SEQ ID NO:14) |

<sup>a</sup>Denotes a primer that was modified by 5' phosphorylation

Expression of HEXaspC Mutant Genes and Analysis of Enzyme Activity

Liquid cultures (5 mL) of Novagen Overnight Express™ Autoinduction System 2 (Catalog #71366-3; solutions 1-6) were inoculated from fresh plates or frozen glycerol stocks of the following strains:

*E. coli* BL21(DE3)::HEXaspCpET23a
*E. coli* BL21(DE3)::HEXaspCW130FpET23a
*E. coli* BL21(DE3)::HEXaspCT156ApET23a
*E. coli* BL21(DE3)::HEXaspCP9T/T156ApET23a
*E. coli* BL21(DE3)::HEXaspCP9T/R122GpET23a
*E. coli* BL21(DE3)::HEXaspCR122G/T156ApET23a The cultures were incubated at 37° C. at 230 rpm for 6-8 h. The $OD_{600}$ of each culture was determined and the volume of culture necessary to obtain an $OD_{600}$ of 0.03-0.05 in 25 mL was calculated. The calculated volumes of each liquid culture were transferred to flasks containing 25 mL of the same medium. The Overnight Express™ Autoinduction System 2 is a complete, chemically defined medium for high-level expression with IPTG-inducible expression systems that uses lactose as the inducing agent and does not require monitoring of cell growth. The Overnight Express cultures were incubated at 30° C. with shaking at 230 rpm for 18 h. The cells were harvested by centrifugation and washed once with cold 50 mM MOPS, pH 7.0. The cells were then lysed using Bugbuster™ (primary amine free) Extraction Reagent (Novagen Catalog #70923-3, Madison, Wis.) containing 1 µL/mL benzonase nuclease (Novagen Catalog #70746-3, Madison, Wis.), 5 µL/mL Protease Inhibitor Cocktail Set II (Novagen Catalog #539132, Madison, Wis.) and 0.33 µL/10 mL r-Lysozyme (Novagen Catalog #71110-3, Madison, Wis.) following the Novagen recommended protocol. After incubation at 25° C. for 15 min with gentle shaking, the cell debris from each suspension was pelleted by centrifugation at 21,000 g for 15 min at 4° C. The supernatant was carefully decanted and analyzed as the cell free extract. Inclusion body fractions were isolated by suspending the cell debris fractions in 30% Bugbuster™ (primary amine free) Extraction Reagent, centrifuging at 21,000×g for 10 min; suspending the centrifuged pellets in 10% Bugbuster™ (primary amine free) Extraction Reagent, centrifuging again to isolate the washed pellets.

The cell free extracts and inclusion body fractions were analyzed for protein expression by SDS-PAGE on 4-15% gradient gels (Bio-Rad #161-1104). For the cell extract samples, twenty micrograms of soluble protein were loaded in each gel lane (premixed with 1× protein loading buffer and heated at 95° C. for 5 min). The inclusion body fractions were dissolved in 1× protein loading buffer (0.2 mL) and heated for 10 minutes at 95° C. 5 μL of each solution was loaded per gel lane. The amount of each HEX mutant in comparison to the total soluble protein loaded into each lane was calculated by band intensity analysis using Labworks BioImaging 1D-gel tool (UVP, Inc. Upland, Calif.), and is reported in Table 36 below:

TABLE 36

| Sample | HEXaspC Protein/Total Soluble Protein |
|---|---|
| E. coli BL21(DE3)::HEXaspCP9T/T156ApET23a CFE | 0.310 |
| E. coli BL21(DE3)::HEXaspCP9T/R122ApET23a CFE | 0.145 |
| E. coli BL21(DE3)::HEXaspCpET23a CFE | 0.172 |
| E. coli BL21(DE3)::HEXaspCR122A/T156ApET23a CFE | 0.174 |
| E. coli BL21(DE3)::HEXaspCW130FpET23a CFE | 0.114 |
| E. coli BL21(DE3)::HEXaspCT156ApET23a CFE | 0.120 |

Analysis of the gels showed that the HEXaspCR122A/T156A mutant was the only protein that was found in substantial quantities as inclusion bodies. The HEXaspCP9T/T156A protein gave the highest level of expression, approximately 90% better than HEXaspC protein. In contrast, the W130F, T156A and P9T/R122G proteins were expressed in lower concentrations than HEXaspC.

The activity of the HEXaspC mutant proteins for the production of S,S-monatin was measured using the following reaction conditions: Each 1 mL reaction contained 50 mM TAPS, pH 8.2, 4 mM MgCl$_2$, 3 mM sodium phosphate, pH 8.0, 200 mM sodium pyruvate (pH adjusted to 8), 5 mM α-ketoglutarate (pH adjusted to 8), 50 mM tryptophan, 0.05 mM pyridoxal 3-phosphate, 50 μg/mL ProA aldolase (added as a cell free extract) and varying concentrations (approximately 50 and 500 μg/mL) of aminotransferase (added as a cell free extract). De-aerated water was used to prepare the stock solutions and to adjust the volume of the reaction mixtures to 1.0 mL. The pyridoxal phosphate was added just prior to the addition of the enzymes. The reaction tubes were incubated at 30° C. with gentle shaking for 4 h. Samples (0.01 mL) were withdrawn at 1, 2, and 4 h after the addition of the enzymes, filtered, and analyzed by LC/MS/MS, as described in Example 1. Monatin production was normalized based on the amount of aminotransferase present in the reactions.

Under the conditions of these assays, the HEXaspC and the HEXaspCT156A produced the most total monatin per mg of aminotransferase while the P9T/R122G protein produced the least, followed by HEXaspCW130F. The HEXaspCW130F and P9T/R122G enzymes showed the greatest stereoselectivity for S-MP (greater than 98% S,S-monatin), even when high enzyme concentrations were used (greater than 300 μg/mL). The percentage of S,S-monatin product decreased to less than 90% in the enzymatic reactions containing the P9T/T156A enzyme at high concentration. The other mutants showed a product stereoselectivity very similar to the original HEXaspC mutant (approximately 95% S,S-monatin). Analysis of the product of the reaction containing the HEXaspC enzyme using the FDAA derivitization reagent described in Example 1 showed that the second stereoisomer formed is R,S-monatin.

Assaying of Tryptophan and Monatin Aminotransferase Activity

The mutants were tested for transamination activity using S,S monatin and L-tryptophan as substrates. The aminotransferase activity was measured by following the formation of the co-product of the reaction, glutamate, by HPLC with OPA-post-column derivatization as described in Example 1. The reaction mixture contained, in 1.0 mL, 100 mM HEPPS buffer, pH 8.0, 20 mM alpha-ketoglutarate, 0.08 mM pyridoxal phosphate, 25 mM tryptophan or S,S monatin, and enzyme (supplied as 2.5 mg of in cellular extracts protein). All components except the enzyme were mixed together. The enzyme was added to start the reaction and the reaction solution was incubated at 30° C. (gentle shaking) for 90 min. Reactions were done in duplicate, with negative controls in which no enzyme was added. The reaction was stopped by the addition of 10% formic acid (final concentration), the mixture was centrifuged at 21,000 rpm, and the supernatant was carefully removed and filtered. The data were corrected for background levels of glutamate and for the dilution from the addition of acid to precipitate the proteins, then normalized by amount of mutant aminotransferase added. When tryptophan was utilized as a substrate, HEXaspC produced 13.0 mM glutamate per mg of aminotransferase per hour. The relative activity, expressed as a percentage, of the mutants is as follows: HEXaspCW130F (156%), HEXaspCT156A (151%), HEXaspCP9T/T156A (63.7%), HEXaspCP9T/R122G (116%), and HEXaspCR122G/T156A (107%). When S,S monatin was utilized as a substrate, HEXaspC produced 7.43 mM glutamate per mg of aminotransferase per hour. The relative activity, expressed as a percentage, of the mutants is as follows: HEXaspCW130F (113%), HEXaspCT156A (87.7%), HEXaspCP9T/T156A (67.3%), HEXaspCP9T/R122G (11.2%), and HEXaspCR122G/T156A (114%).

The HEXaspCP9T/R122G mutant had increased activity for tryptophan to indole-3-pyruvate conversion, but decreased activity for S,S monatin transamination. The ratio of tryptophan to monatin activity was 18.2 in comparison to 1.75 for HEXaspC, making it a desirable candidate for production of R,R monatin using pathways that require an L-aminotransferase, such as those described in Examples 9 and 10(2). As such, the HEXaspCP9T/R122G is an example of an aminotransferase with limited activity on S,S monatin, as well as, MP.

Most of the mutations improved L-tryptophan activity, but only two mutants increase activity toward both L-tryptophan and S,S monatin (HEXaspCW130F and HEXaspCR122G/T156A). Because 25 mM of substrate was used in these assays, the enzymes were most likely saturated and the activity is a reflection of the $k_{cat}$ of the enzymes. However, under the conditions in which the assays for S,S monatin production were performed, described above, it is unlikely that the concentration of S-MP is sufficient to saturate the enzyme, thus there is no overall increase in S,S monatin production because the increase in $k_{cat}$ is offset by an increase in $K_m$. It has been reported, for similar substrates, that some of the mutations made increase the $k_{cat}$ but also increase the apparent $K_m$ for the amino acid substrate. If increasing concentrations of substrates were used, it is expected that these two mutants would provide a benefit in production rates of S,S monatin in comparison to HEXaspC. The HEXaspCT156A mutation appears to have increased tryptophan transamination rates without having a significant effect on MP transamination rate under the conditions above for S,S monatin production.

By comparison of the structures of HEXaspC and one of the *Bacillus* sp. D-aminotransferase enzymes (see, for example, Sugio, S., et al., *Biochemistry* 34:9661-9669, (1995)), the W130F, R122G, T156A, and HEX mutations of AspC could be mapped to corresponding residues in the D-aminotransferase structure. It is expected that similar mutations in the broad specificity D-aminotransferase would improve the overall production of R,R monatin, as described in Example 3A. For example, the functionality provided by tryptophan 130 in AspC is replaced in *Bacillus* D-aminotransferases by hydrogen bonding between the side chains of serines 179-181 and glutamate 166 (YM-1 numbering scheme). To lessen steric hindrance, the glutamate could be mutated to an aspartate residue. Some D-aminotransferases have a threonine residue at position 179, which would increase steric hindrance and should be avoided. The *B. sphaericus* enzyme has an alanine in place of serine at position 181, which may also reduce steric hindrance.

Additional information from studies of aspartate aminotransferase can be applied to the D-aminotransferase as well. While the AspC enzyme has an arginine in the active site that interacts with the side chain of dicarboxylate substrates, the D-aminotransferase has a loop from Ser240 to Ser243. The side chains of Ser240, Thr242, and Ser243 face the same direction and form a pocket with the hydroxyl group of Ser180 which provides a surface for both nonpolar and polar substrates can interact. Ser180 is involved in PLP binding; however, to improve the activity of a D-aminotransferase with R-MP, one can modify the Ser240, Thr242, or Ser243 residues to accept larger substrates or to favor negatively charged substrates. For instance, Thr242 can be mutated to Ser to reduce the side chain length. One of the residues can be mutated to lysine or arginine, such as Ser243. The residues (YM-1 numbering) Val30-Val36 are located in a beta strand across the active site of the D-aminotransferase and are also important for activity. Tyr31, Val33, Glu32, and Lys35 are thought to face the active site. Tyr31, Glu32, and Val33 are invariant in all the *Bacillus* homologs. Ro, et al., *FEBS Lett* 398:141-145, (1996)) mutagenized Val33 to Ala and found a slightly increased catalytic efficiency for alpha-ketoglutarate transamination and a significantly improved catalytic efficiency for bulkier substrates (less steric hindrance). In some homologs Lys35 is replaced with Arg, but if steric hindrance is a concern, the Lys residue may be preferable. Valines 34 and 36 are also preferable over conservative substitutions such as isoleucine, again due to less steric hindrance for large molecules such as MP. Because the novel D-aminotransferase ("4978") described in Examples 15 and 16 had higher activity than the *B. sphaericus* enzyme and the hybrid DAT described in Example 19, it is the obvious choice for further mutagenesis reactions. The ideas above, based upon crystal structure analysis of YM-1 D-aminotransferase, can be applied to the D-aminotransferase from ATCC strain 4978. The numbering above is one amino acid less than the corresponding amino acid in the 4978 protein sequence.

6B: Characterization of Mutants of D-Aminotransferase from ATCC 4978

Experimental Overview

The novel D-aminotransferase gene (described in Example 15) from *Bacillus* strain ATCC 4978 was mutagenized using site-directed methods. The mutant genes were expressed and assayed for activities of interest for monatin production pathways.

In addition to the ideas listed in Example 6A for site directed mutagenesis targets, other ideas were developed by actual docking of R-MP into the active site of the YM-1 crystal structure and using primary amino acid sequence alignments to determine if the 4978 protein was likely to have similar structural characteristics in that region. It was expected that the following additional mutations would be beneficial (using 4978 amino acid numbering). It was thought that mutagenesis of alanine 153 to arginine would stabilize the second carboxyl group of the substrate (R-MP). This change is likely to increase steric hindrance, so to compensate, the serine residues at positions 181 and 182 were changed to alanine or glycine. It was also hypothesized that one could introduce an arginine at position 180, 181, or 182 and convert one or more of the other serine residues to alanine or glycine to make room for the bulkier side chain of arginine. The phenylalanine at amino acid 200 is spatially close to where R-MP is predicted to dock into the active site and there is a large amount of variability in this residue amongst the D-aminotransferases that catalyze monatin transamination fairly well. It was thought that amino acid modifications at this position could be useful. Mutation of leucine 151 to phenylalanine was predicted to potentially improve interactions with the indole ring of the substrate.

Based upon literature, it was hypothesized that mutation of threonine 243 to asparagine may improve R-MP selectivity for transamination reactions. Likewise, it was thought that mutagenesis of asparagine 100 to alanine may improve the specific activity of the enzyme for monatin transamination reactions (Ro, et al., *FEBS Lett* 398:141-145, (1996); Sugio, S, et al., *Biochemistry* 34:9661-9669, (1995); EP1580268).

Lee et al. characterized mutants of the 141-144 region (loop) and found that D-aminotransferases with the EYcY rather than the LRcD (which is native to the 4978 protein) tend to have a lower $K_m$ for dicarboxylic acid substrates. (Lee S G, Hong S P, Song J J, Kim S J, Kwak M S, Sung M H. Functional and structural characterization of thermostable D-amino acid aminotransferases from *Geobacillus* spp. Appl Environ Microbiol. 2006 February; 72(2):1588-94). Because MP is a dicarboxylic acid substrate, similar to alpha-keto glutarate, and the concentrations of MP are fairly low in a typical monatin production reaction mixture, a decreased $K_m$ could potentially help the activity of a mutant DAT for monatin production.

The methods below describe creation of the 4978 D-aminotransferase mutants, as well as assay results using these mutants.

Mutagenesis

The primers for mutagenesis were designed following the suggestions listed in the Stratagene Multi-Change kit (La Jolla, Calif.). The primers were 5'-phosphorylated. Mutagenesis was done using the Stratagene Multi-Change kit following the manufacturer's instructions. The templates used for mutagenesis were either the pET30 (untagged) or pET28 (tagged) 4978 DAT constructs described in Example 15. The primers are listed below in Table 37:

TABLE 37

| Mutant name | Amino acid change | Primer |
|---|---|---|
| 4978-22 | T243N | 5'-GTGATTGTTTCATCAACGAATTCAGAAG TAACGCC-3' (SEQ ID NO:156) |
| 10 | T243R | 5'-GTGATTGTTTCATCAACGCGTTCA- GAAGT AACGCC-3' (SEQ ID NO:157) |

TABLE 37-continued

| Mutant name | Amino acid change | Primer |
|---|---|---|
| 7 | T243S | 5'-GTGATTGTTTCATCAACGAGTTCA-GAAGT AACGCC-3' (SEQ ID NO:158) |
| 19 | T243A | 5'-GTGATTGTTTCATCAACGGCTTCA-GAAGT AACGCC-3' (SEQ ID NO:159) |
| 15 | N100A | 5'-GTGCAGGCCCTCGTGCTCATATTTTC-CCT GG-3' (SEQ ID NO:160) |
| B | T243Q | 5'-GAAGTGATTGTTTCATCAACGCAGT-CAGA AGTAACGCCAATTATC-3' (SEQ ID NO:161) |
| 2 | T243N/N100A | above primers used together |

E. coli XL10-Gold cells (Stratagene) were transformed and the resultant purified plasmid preparations were sequenced to verify that the correct mutations were incorporated.

Expression and Assay

Plasmid DNA containing the correct mutations was transformed into E. coil BL21(DE3) competent cells and induced as described in Example 16. Cellular extracts were prepared with BugBuster Reagent and Benzonase Nuclease (EMD Biosciences/Novagen, Madison, Wis.). One mL assays were performed at 30° C. with gentle shaking and contained 10.2 mg D-tryptophan, 0.05 mM PLP, 4 mM $MgCl_2$, 100 mM potassium phosphate buffer pH 7.5, approximately 50 µg of aldolase, 200 mM pyruvate, and 0.150-0.5 mg/mL D-aminotransferase supplied as cellular extracts. Total protein assays were done using the Bio-Rad (Hercules, Calif.) total protein kit (Coomassie) or the Pierce (Rockford, Ill.) BCA kit, and percent expression of the D-aminotransferase was estimated by SDS-PAGE or the Bio-Rad Experion Automated Electrophoresis System. Samples were taken at 3 hours and overnight.

Using approximately 0.150 mg/mL of D-aminotransferase with the R-specific aldolase of SEQ ID NO:22, the first assays showed that the following mutants (untagged) had transamination activity (in order of highest to lowest): T243N, T243S, T243N/N100A, N100A. It was also noted that the T243N appeared to raise the stereo-purity of the R,R monatin produced. Assays were repeated using purified Comamonas testosteroni ProA aldolase (100 µg/mL) and 0.50 mg/mL of D-aminotransferase mutants (untagged, supplied as cellular extract). Samples were taken at 2 hours and overnight. The results for the active proteins are shown below, duplicate results were averaged. The % R,R monatin was determined by peak area on reversed phase HPLC and then measured using the FDAA derivatization method described in Example 1 (results shown in parentheses). The results are shown in Table 38. Only R,R and S,R monatin are produced from D-tryptophan. The T243R mutant did not appear to produce monatin under the conditions tested, and the T243A mutant produced very low levels of monatin.

TABLE 38

| Enzyme - Untagged (time) | Total monatin (ppm) | % R,R |
|---|---|---|
| 4978 wild-type (2 hours) | 4.7 | 41.6 |
| 4978 wild-type (overnight) | 43.2 | 35.1 (30.9) |
| T243S (2 hours) | 55.0 | 37.4 (21.7) |
| T243S (overnight) | 97.7 | 35.5 (29.8) |
| T243N (2 hours) | 73.2 | 86.7 (88.3) |
| T243N (overnight) | 120.9 | 86.3 (86.1) |
| N100A (2 hours) | 12.0 | 40.8 |
| N100A (overnight) | 22.3 | 41 |
| T243A (2 hours) | 0.8 | ~100 |
| T243A (overnight) | 1.3 | ~100 |

Although the assays were performed estimating percent D-aminotransferase using Bio-Rad Experion® software, it is clear that the T243S and T243N mutants had increased activity compared to the wild-type enzyme. The T243N mutant also provided an additional benefit of increasing dramatically the % R,R monatin formed. This enzyme has an increased preference for R-MP as compared to S-MP in transamination reactions. The N100A mutant did not increase activity alone or in combination with T243N as suggested in the literature. A V34A site directed mutant of the untagged 4978 DAT was also created using similar methods, as described above. The V34A sited directed mutant was found to have significantly less activity than the wild-type enzyme under the conditions tested.

Another point of interest in the initial assays was that the wild-type enzyme appeared to have more activity when it was produced with an N-terminal His-tag. Subsequent mutagenesis was done on the tagged version of the gene. Additionally, the most promising mutants above were subcloned into pET28b that has an N-terminal His-tag. These were purified using Novagen HIS-bind columns and the manufacturer's protocol with the recommended buffers (EMD Biosciences/Novagen, Madison, Wis.). The buffer of the eluent fractions was exchanged, using GE Healthcare PD10 columns (Piscataway, N.J.), to the buffer used in the assays.

One mL assays with purified D-aminotransferase (0.5 mg/mL) and purified R-specific aldolase of SEQ ID NO:104 (50 µg/mL) were conducted at 30° C. with gentle shaking and contained 10.2 mg D-tryptophan, 0.05 mM PLP, 200 mM pyruvate, 4 mM $MgCl_2$, and 100 mM potassium phosphate buffer pH 7.5. Duplicate samples were incubated for 2 hours and overnight. As a positive control, the Bacillus sphaericus DAT (cloned in Example 18) was used in the same assays. The results are shown in Table 39, below (the % R,R as shown by the FDAA assay are indicated in parentheses):

TABLE 39

| Enzyme - Tagged (time) | Total monatin (ppm) | % R,R |
|---|---|---|
| 4978 wild-type (2 hours) | 43 | 98.4 |
| 4978 wild-type (overnight) | 96.7 | 98.3 (95.9) |
| T243N (2 hours) | 197.5 | 100 |
| T243N overnight | 301.2 | 99.9 (99.6) |
| B. sphaericus DAT (2 hours) | 58.2 | 99.7 |
| B. sphaericus DAT (overnight) | 221.7 | 98.7 (96.6) |
| T243Q (2 hours) | 7.1 | 100 |
| T243Q (overnight) | 12.4 | 98.8 |

One can see from the data above that the T243N mutant clearly produces the highest amount of monatin at 2 hours. As time increases, the ratio of T243N mutant to B. sphaericus DAT positive control is reduced. This result suggests that the T243N mutant is not as stable during the monatin reaction as the *B. sphaericus* DAT. When assayed under similar conditions, the T243S (purified tagged) enzyme had similar levels of activity to the T243N mutant; however, the percent R,R monatin produced was lower (97.2% at both 2 h and overnight). The T243N/N100A mutant had less activity than the T243N mutant. However, both T243S and T243N/N100A had higher activity than the wild-type 4978 DAT.

Transamination assays were performed to determine which reaction rates were improved when using the T243N mutant in place of the *B. sphaericus* DAT. One-half mL assays were performed at 30° C. taking time points at 1 hour, 2 hours, and 5 hours. The assays contained 25 mM monatin or D-tryptophan, 25 mM pyruvate, 100 mM potassium phosphate pH 7.5, 50 μM PLP, and 0.1 mg D-aminotransferase (tagged, purified). In the case where less than 100 μg DAT was used, the amount of alanine was normalized to 100 μg of D-aminotransferase. Samples were treated with formic acid and analyzed by LC with post column fluorescence detection (as described in Example 1) for the presence of the co-product, alanine. The results are shown in Tables 40 and 41.

TABLE 40

Transamination activity with R,R monatin as substrate

| Enzyme (assay time) | D-alanine (mM) |
|---|---|
| wild-type 4978 DAT (2 hr) | 0.54 |
| wild-type 4978 DAT (5 hr) | 1.11 |
| T243N/N100A (2 hr) | 1.32 |
| T243N/N100A (5 hr) | 2.78 |
| T243S (2 hr) | 1.5 |
| T243S (5 hr) | 2.61 |
| T243N (2 hr) | 1.26 |
| T243N (5 hr) | 2.65 |
| *B. sphaericus* DAT (2 hr) | 0.97 |
| *B. sphaericus* DAT (5 hr) | 2.2 |

TABLE 41

Transamination activity with D-tryptophan as substrate

| Enzyme (assay time) | D-alanine (mM) |
|---|---|
| wild-type 4978 DAT (1 hr) | 4.55 |
| wild-type 4978 DAT (2 hr) | 8.47 |
| T243N/N100A (1 hr) | 8.52 |
| T243N/N100A (2 hr) | 12.67 |
| T243S (1 hr) | 4.89 |
| T243S (2 hr) | 8.1 |
| T243N (1 hr) | 7.19 |
| T243N (2 hr) | 10.83 |
| *B. sphaericus* DAT (1 hr) | 8.7 |
| *B. sphaericus* DAT (2 hr) | 12.54 |

For the D-tryptophan reactions, the results show that some of the enzymes had reached equilibrium at 2 hours. The R,R monatin reactions are clearly rate-limiting and improvements to this activity have more of an impact on monatin production rates from D-tryptophan.

Further assays were done to examine the stability of the T243N 4978 DAT mutant. The wild-type enzyme also loses activity over time. Example 6C describes methods to improve the stability of the T243N D-aminotransferase mutant. When freshly prepared untagged and tagged versions of the T243N mutant are prepared and compared for activity, it was found that the untagged version had a better temporal stability, making it overall a better version of the enzyme to use in monatin production reactions.

Additional mutants of 4978 DAT were made by methods commonly known to those skilled in the art. However, these mutations all resulted in protein that was insoluble under the conditions that they were prepared, and thus could not be assayed for activity. The mutations that resulted in insoluble protein were:

S180A/S181A/S182R;
L151F;
V34G
S181R
A153R/S181A/S182A;
A153R/S182A;
A153R/S182G;
S180R/S181A/S182G;
S180R/S181A/S182A;
S180R/S181G/S182G;
S180G/S181R/S182G; and
S180A/S181R/S182A.

Additional Mutagenesis

To create the F200M 4978 DAT mutant, the wild-type 4978 DAT open reading frame from Example 15 (tagged) was amplified with primers 73 and 80 and PfuTurbo® DNA Polymerase (Stratagene), cloned into pCRII-Blunt (Invitrogen, Carlsbad, Calif.) and its sequence was verified (Agencourt, Beverly, Mass.). The 5' and 3' regions were amplified using primers 80 and 96 and 99 and 103, respectively (Table 42). The amplified DNA was then gel purified using Qiagen QIAquick® Gel Extraction Kit (Qiagen, Valencia, Calif.). They were combined and subjected again to PCR using primers 80 and 99 (Table 42). The amplified DNA was gel purified as described above and cloned into pCRII Blunt and its sequence verified. The DAT open reading frame was subcloned as an Nde I/Xho I restriction digest fragment into pET28b.

TABLE 42

| Primer Number | Sequence |
|---|---|
| 73 | 5'-CATATGAGTTATAGCTTATGGAATGACCAAATTGTGAATG-3' (SEQ ID NO:162) |
| 80 | 5'-CTCGAGTGCGGCCGCAAGCTTGTCGACGGAGCTC-3' (SEQ ID NO:163) |
| 96 | 5'-AATATTTATGGAATTAAAGATGGCGTATTATACACACATCCAGCGAATAACATGATCTTAAATGGTATTACACGTCAAGTAATCATTAAATGTGC-3' (SEQ ID NO:164) |
| 99 | 5'-GGCCAGTGAATTGTAATACGACTCACTATAGGGC-3' (SEQ ID NO:165) |
| 103 | 5'-CGCCATCTTTAATTCCATAAATATTTGAAGAAGAGCCTTCTG-3' (SEQ ID NO:166) |

The following primers (Table 43) were designed for additional site-directed mutagenesis using the QuikChange® Multi Site-Directed Mutagenesis Kit (Stratagene). Mutagenesis was done using the Stratagene Multi-Change kit following the manufacturer's instructions. The template used for mutagenesis was the pET28 (tagged) 4978 DAT construct described in Example 15. A double mutant was also created using the F200Y mutant as the template and doing an additional round of mutagenesis with the T243N (listed above) primer.

TABLE 43

| Mutant | Oligo |
|---|---|
| 141-LRcD-144 -> EYcY | GCAACATTTGTAGAAGACATTCGTTGGGA<br>ATACTGTTACATTAAATCATTAAATTTAC<br>TTGGTGCG<br>(SEQ ID NO:167) |
| F200Y | GTATTATACACACATCCAGCGAATAACTA<br>CATCTTAAATGGTATTACACGTCAAG<br>(SEQ ID NO:168) |
| S244K | GCAATGGATGAAGTGATTGTTTCATCAAC<br>GACTAAAGAAGTAACGCCAATTATCGACA<br>TAGATG<br>(SEQ ID NO:169) |
| 243-TS-244 -> NK | GCAATGGATGAAGTGATTGTTTCATCAAC<br>GAATAAAGAAGTAACGCCAATTATCGACA<br>TAGATG<br>(SEQ ID NO:170) |
| 243-TS-244 -> NR | GCAATGGATGAAGTGATTGTTTCATCAAC<br>GAATCGTGAAGTAACGCCAATTATCGACA<br>TAGATG<br>(SEQ ID NO:171) |

The mutant coding regions were verified by DNA sequencing (Agencourt). The sequence verified plasmids were transformed into BL21(DE3) cells (Novagen, Madison, Wis).

Expression and Assay

Cultures containing 100 mL LB with 50 µg/mL kanamycin in a 500 mL baffled flask were inoculated with one mL of an overnight culture and grown at 37° C. to an optical density (at 600 nm) of approximately 0.6. Production of the protein was induced by IPTG at a final concentration of 1 mM. Cells were incubated at 30° C. for 4.5 hours after the addition of the IPTG. Cells were centrifuged and frozen at −80° C. Cells were disrupted (prepared using Novagen BugBuster reagent containing 1 µL/mL benzonase nuclease, 5 µL/mL protease inhibitor cocktail II, and 0.033 µL/mL rLysozyme following Novagen's recommended protocol) and analyzed by SDS-PAGE. Mutants (141-LRcD-144→EYcY) and (243-TS-244→NR) resulted in insoluble proteins under the conditions in which they were prepared. Mutant 243-TS-244→NK did not have quantifiable activity under the conditions tested and is probably a weak activity enzyme in comparison to wild-type, as is the S244K mutant.

His-tagged proteins were purified as follows. HIS-bind columns (Novagen, Madison, Wis.) were equilibrated with 10 mL of 100 mM potassium phosphate, pH 7.8, containing 200 mM NaCl and 50 µM PLP. Cell-free extracts were loaded on the column. The columns were washed with 10 mL of equilibration buffer, 10 mL equilibration buffer containing 25 mM imidazole, and 10 mL equilibration buffer containing 50 mM imidazole. Proteins were eluted with 5 ml equilibration buffer containing 500 mM imidazole. Proteins were desalted using PD10 columns which were equilibrated in 100 mM potassium phosphate, pH 7.8 containing 50 µM PLP. The purified proteins were concentrated and quantified using the Bradford Assay (Bio-Rad).

The D-aminotransferase mutants were assayed using 500 µg/mL of the D-aminotransferase, 50 µg/mL of the aldolase of SEQ ID NO:104, 4 mM MgCl₂, 50 mM potassium phosphate pH 8, 200 mM sodium pyruvate, 0.05 mM PLP and 20.4 mg/mL D-tryptophan for assay conditions. The final volume was 1.25 mL. Samples (200 µL) were taken after 0.5, 1, 2 and 14 hours and frozen until the experiment was complete. Samples were filtered, diluted 1 to 10, and analyzed by LC/MS/MS as described in Example 1.

The wild-type 4978 D-aminotransferase from Example 16 was used as a reference for percent relative activity. Table 44 shows relative activity of each mutant at each time point.

TABLE 44

| D-aminotransferase | Time (hr) | % Activity |
|---|---|---|
| 4978 wild-type | 0.5 | 100 |
| T243N | 0.5 | 270 |
| F200M | 0.5 | 50 |
| F200Y | 0.5 | 70 |
| F200M/T243N | 0.5 | 183 |
| S244K | 0.5 | 4 |
| 4978 wild-type | 1 | 100 |
| T243N | 1 | 289 |
| F200M | 1 | 55 |
| F200Y | 1 | 81 |
| F200M/T243N | 1 | 203 |
| S244K | 1 | 6 |
| 4978 wild-type | 2 | 100 |
| T243N | 2 | 266 |
| F200M | 2 | 51 |
| F200Y | 2 | 79 |
| F200M/T243N | 2 | 185 |
| S244K | 2 | 6 |
| 4978 wild-type | 14 | 100 |
| T243N | 14 | 254 |
| F200M | 14 | 56 |
| F200Y | 14 | 80 |
| F200M/T243N | 14 | 168 |
| S244K | 14 | 8 |

The T243N was the best mutant of all tested for activity in the production of R,R monatin.

6C: Stabilization of the T243N Mutant of the D-Aminotransferase from Strain ATCC 4978

As shown in Example 6B, the initial activity of the T243N mutant DAT is significantly higher than the *B. sphaericus* DAT, but activity decreases more rapidly. Additional experiments, using the anaerobic protocol described below, indicated that the initial activity of the T243N mutant DAT was up to 8-fold higher than the *B. sphaericus* DAT, however the activity decreased rapidly even under the anaerobic conditions. The following studies were done to try to maintain the higher activity for an extended period of time.

The T243N mutant of the D-aminotransferase from strain 4978 (described in Example 6B) was purified as the HIS₆-tagged protein as described in Example 26. The aldolase of SEQ ID NO:104 (described in Example 3B) and the *S. meliloti* HMG aldolase were purified as the HIS₆-tagged proteins as described in Examples 22 and 27.

Conical polypropylene tubes (14 mL) containing 143 mg of D-tryptophan were de-oxygenated in an anaerobic glove box overnight. Stock solutions of 1 M EPPS buffer (pH 8.2), 2 M MgCl₂, 2 M sodium pyruvate and 10 mM PLP were prepared in degassed water and equilibrated in an anaerobic glove box overnight. Stock solutions of 10% (v/v) Tween® 80, 1% (v/v) Tween® 20, 1% (v/v) Triton X-100, 100% acetone, 100% ethanol and 50% (w/v) glycerol were equilibrated in the anaerobic glove box along with 0.7 g each of trehalose, inositol, sorbitol and erythritol in 2 mL microcentrifuge tubes. Preparations of the purified enzymes were thawed on ice and used immediately in the anaerobic glove box. The stock solutions were added to the 14 mL conical tubes to give a final concentration of 100 mM EPPS, 200 mM pyruvate, 100 mM tryptophan, 1 mM MgCl₂, 0.05 mM PLP, 0.5 mg/mL D-aminotransferase, and 0.01 mg/mL of the aldolase of SEQ ID NO:104 or 0.05 mg/mL of *S. meliloti* HMG aldolase. The proposed enzyme stabilizing components were added at various final concentrations (Tables 45 and 46) to bring the final reaction volume to 7 mL per tube. The reactions were incubated at room temperature in the anaerobic glove box with gentle agitation for up to 24 hours. Samples were removed periodically and analyzed for monatin as described in Example 1 using the LC/MS/MS multiple reaction monitoring method. The initial rates were calculated from the samples withdrawn between 0 and 3 h after the addition of the enzyme.

TABLE 45

(S. meliloti HMG Aldolase)

| Additive | Fold Improvement in Initial Rate of Monatin Formation | Fold Improvement in Final Monatin Titer (20 h) |
|---|---|---|
| None | 1.0 | 1.0 |
| 0.01% (v/v) Tween ® 80 | 1.3 | 1.4 |
| 0.1% (v/v) Tween ® 80 | 1.3 | 1.5 |
| 0.01% (v/v) Tween ® 20 | 1.1 | 1.5 |
| 0.01% (v/v) Triton X-100 | 1.1 | 1.2 |
| 5% (v/v) Acetone | 0.4 | 0.3 |
| 5% (v/v) Ethanol | 0.7 | 0.5 |
| 1% (w/v) Glycerol | 1.9 | 1.1 |
| 5% (w/v) Glycerol | 1.4 | 1.4 |
| 10% (w/v) Glycerol | 1.1 | 1.7 |
| 10% (w/v) Trehalose | 1.0 | 1.3 |
| 10% (w/v) Inositol | 1.3 | 1.5 |
| 10% (w/v) Sorbitol | 1.1 | 1.3 |
| 10% (w/v) Erythritol | 0.8 | 1.0 |

TABLE 46

(Aldolase of SEQ ID NO: 104)

| Additive | Fold Improvement in Initial Rate of Monatin Formation | Fold Improvement in Final Monatin Titer at 22 h |
|---|---|---|
| 0.01% (v/v) Tween ® 80 | 1.0 | 1.0 |
| 1% (w/v) Glycerol | 1.2 | 0.9 |
| 5% (w/v) Glycerol | 1.5 | 1.5 |
| 10% (w/v) Glycerol | 1.7 | 2.1 |

The addition of 0.01%-0.1% (v/v) detergent, such as Triton X-100, Tween® 20 or Tween® 80, or 1%-10% (w/v) polyol, such as glycerol, trehalose, inositol or sorbitol, improved the stability of the T243N D-aminotransferase over the lifetime of the experiment.

Example 7

Use of Branched Chain Aminotransferases ("BCAT") in the Production of Monatin

AT-102 and AT-104 are branched chain L-transaminases (EC 2.6.1.42) that were purchased from BioCatalytics (Pasadena, Calif.). The enzymes were tested for transamination activity using S,S and R,R monatin substrates that were produced chemically. Reactions were performed in a total volume of 0.5 mL, and run in duplicate. The assays contained 50 mM Tris pH 7.8, 0.08 mM PLP, 10 mM α-ketoglutarate ("α-KG"), 5 mM monatin, and 1 mg/mL aminotransferase enzyme. Negative controls did not contain exogenous aminotransferase enzyme. The samples were incubated for 2 hours at 30° C. at 100 rpm shaking. The samples were filtered and LC/MS/MS analysis, as described in Example 1, was run to ascertain glutamate levels. Glutamate levels should correlate stoichiometrically with MP production. When R,R was used as the reaction substrate, very low levels of glutamate were present in the negative controls. AT-104 produced slightly more glutamate than the negative controls, indicating a low level of activity with the R,R monatin substrate (a D-amino acid). Both of the branched chain L-aminotransferases showed activity on S,S monatin. AT-102 produced 102 μg/mL glutamate and AT-104 produced 64 μg/mL glutamate. For comparison, a broad specificity aminotransferase (AT-101, also from BioCatalytics) produced 75 μg/mL under these conditions. The high activity with a branched chain aminotransferase is somewhat unexpected because monatin has more structural similarities to dicarboxylic amino acids and aromatic amino acids that normally serve as substrates for the broad specificity or aspartate aminotransferases. However, due to the glutamic acid backbone of monatin, many of the aminotransferases that can utilize glutamate as an amino donor may also have activity on monatin.

Monatin Production from Indole-3-Pyruvate Using BCAT

AT-102 and AT-104 were tested for production of monatin in coupled reactions using the ProA aldolase from C. testosteroni (produced as described in WO 03091396 A2). Enzymes and additional components/substrates were added directly to the reaction buffer provided in the kit, which contained 100 mM potassium phosphate buffer pH 7.5, 100 mM L-glutamate, and 0.1 mM PLP. To one mL of reaction buffer were added 4 mg indole-3-pyruvate, 20 mg pyruvate, approximately 50 μg ProA provided in a cellular extract, 1 μL 2 M $MgCl_2$, and 2 mg of the aminotransferase enzyme to be tested. All reactions were performed in duplicate, and a negative control reaction was done with no additional aminotransferase added. A positive control (AT-101) was utilized for comparison; this enzyme is a broad specificity L-aminotransferase. Background production of monatin is due to native E. coli aminotransferases present in the cellular extract of the recombinant ProA enzyme. The reactions were incubated overnight at 30° C. with gentle shaking (100 rpm). The samples were filtered and submitted for reverse phase LC/MS/MS analysis as described in Example 1. The results are presented in Table 47 below.

TABLE 47

| Enzyme | μg/mL Monatin Produced |
|---|---|
| AT-101 | 173.05 |
| AT-102 | 122.05 |
| AT-104 | 133.05 |
| negative | 73.25 |

AT-102 and AT-104 aminotransferases clearly produced more monatin than the negative control and were about 50-60% as active as the positive control.

The branched chain aminotransferase enzyme from E. coli has been well studied and crystal structures have been analyzed in detail. Okada, K., et al., (1997) J. Biochem (Tokyo) 121:637-641, (1997). The enzyme has a similar overall fold and significant sequence homology to Bacillus D-aminotransferase enzymes such as those mentioned in Examples 2, 3A, and 6A. In addition, the BCAT enzymes and the D-aminotransferases from Bacillus are the only two types of PLP-dependent aminotransferases to show stereospecificity for re face addition of hydrogen to PLP. Yoshimura, T., et al., J. Am. Chem. Soc. 115:3897-3900, (1993). BCAT is thought to be the only enzyme in which the alpha-amino acid substrate is bound with its carboxyl group on the same side as the phosphate group, allowing the enzyme to have a similar fold and mechanism to the D-aminotransferases while still retaining specificity for L-amino acids. Peisach, D., et al., *Biochemistry* 37:4958-4967, (1998). It is thought that the L-specificity of BCAT comes from the fact that the polar amino acid side chains of the D-aminotransferase that position the alpha-carboxyl group of the substrate are replaced by nonpolar residues in BCAT. It is expected that if all, or some, of these residues are mutated to the corresponding amino acids of the *Bacillus* D-aminotransferase, one could convert the BCAT into a D-specific aminotransferase. The following mutations can be made to the *E. coli* BCAT (numbering based on accession number gi:14719463): Phe37 to Tyr, Val110 to His, Met108 to Arg. Other polar amino acid substitutions could be made at these sites as well, to tailor the enzyme active site to accept large dicarboxylic acid substrates as described in Example 6A. Tyr165 may need to be converted to Leu as well, to mirror the PLP interaction of the D-aminotransferase; Tyr96 (to Phe), Arg41, and Arg98 may also need to be mutated to prevent binding of the alpha carboxyl group in the incorrect orientation in the BCAT enzyme. Trp127 can also be mutated to Tyr to decrease the likelihood of the hydrophobic side chains binding in a pro-S configuration; Tyr32 and Tyr130 may interact with L-glutamate in the active site of BCAT and can be mutated to negatively charged amino acids to minimize this interaction. Goto, M., et al., *Biochemistry* 42:3725-3733, (2003); Okada, K., *Biochemistry* 40:7453-7463, (2001).

Because both the D-aminotransferase enzymes and the branched-chain aminotransferase have activity in production of monatin, it is expected that the BCAT can be converted to a D-aminotransferase with activity in R,R monatin production, while providing another possible D-aminotransferase enzyme to be utilized in the reaction schemes described in many of the Examples. Based on the above results, it is possible that the AT-104 enzyme already shows some activity toward D-amino configurations of monatin.

*Bacillus* Branched-Chain Aminotransferase Cloning and Mutagenesis

*Bacillus licheniformis* contains a putative branched-chain aminotransferase that is more closely related to D-aminotransferases than the *E. coli* branched chain aminotransferase is. It was assayed for D-transamination activity and mutagenized based on predicted active site residues mentioned above for the *E. coli* BCAT.

Strain

*B. licheniformis* (ATCC number 14580) was grown on Nutrient Agar at 30° C. overnight. Groups of colonies were placed in 100 µL of sterile water and heated for 10 minutes at 95° C. to disrupt the cells. Three µL were used in subsequent Polymerase Chain Reaction (PCR) amplifications.

Polymerase Chain Reaction Protocol

Primers were designed for the *B. licheniformis* gene (915 bp) for cloning into pET 28b and pET 30a vectors (Novagen, Madison, Wis.) and pTRC99a (GE Healthcare Life Sciences), using the Nco I and Sal I sites. The pET30 construct contains an N-terminal His-tag and S-tag, whereas the pET 28 construct is untagged.

The *B. licheniformis* bcat primers were:

```
                                        (SEQ ID NO: 44)
N term    5'-GGTTAAGGCCATGGGGGACCAGAAAGACCA-3';
and
                                        (SEQ ID NO: 45)
C term:   5'-GGCCTTCCGTCGACTCAGCTGACACTTAAGCT-3'.
```

The coding region was amplified using the following PCR protocol. In a 50 µL reaction, 3 µL template, 1 µM of each primer, 0.4 mM each dNTP, 3.5 U Expand High Fidelity Polymerase, and 1× Expand™ buffer (Roche, Indianapolis, Ind.) with Mg were used. The thermocycler program used included a hot start at 96° C. for 5 minutes, followed by 30 repetitions of the following steps: 94° C. for 30 seconds, 50° C. for 1 minute 45 seconds, and 72° C. for 2 minutes 15 seconds. After 30 cycles, the sample was maintained at 72° C. for 7 minutes and then stored at 4° C. Clean PCR products of the correct size were obtained (approximately 900 bp).

Cloning

The PCR product was purified and digested with Sal I and Nco I in Sal I buffer (New England Biolabs, Ipswich, Mass.). The digested vectors (pET28, pET30, and pTRC99a) and the insert were purified using the Qiagen QIAquick® Gel Extraction Kit (Qiagen, Valencia, Calif.). The ligations were done using the Roche Rapid DNA Ligation Kit (Roche, Indianapolis, Ind.) and purified. The ligations were transformed into *Escherichia coli* DH10B using a 0.2 cm cuvette and a Bio-Rad Gene Pulser® II system, as described in the Bio-Rad electroporation manual. The cells were allowed to recover in 900 µL SOC medium for 30 minutes at 37° C. with shaking at 225 rpm. The cells were plated on LB-agar plates containing kanamycin (25 µg/mL). The plasmid DNA was purified using the Qiagen spin miniprep kit (Qiagen, Valencia, Calif.) and screened for the correct inserts by restriction digest with Sal I and Nco I. The sequences of plasmids that appeared to have the correct insert were verified by dideoxy chain termination DNA sequencing at Agencourt BioScience Corporation (Beverly, Mass.). Sequencing verified the coding sequence found in NCBI accession number CP000002 GI 56160984 2851268 ... 2850354, which produces a protein with amino acid sequence as listed in accession number AAU24468 GI:52004526.

Gene Expression and Assays

Plasmid DNA (pET vectors) was transformed into *E. coli* expression host BL21(DE3) cells (Novagen, Madison, Wis.) for constructs in pET vectors. The cultures were grown and the plasmids were isolated using Qiagen miniprep kit (Qiagen, Valencia, Calif.) and analyzed by restriction digest to confirm identity. Induction was typically performed in LB medium containing kanamycin (50 µg/mL). The cells were grown to an $OD_{600}$ of 0.4-0.8 at 37° C., induced with 0.1 mM IPTG (isopropyl thiogalacatoside) and sampled at 3-4 hours post induction. Cell extracts were prepared according to the protocol accompanying the Novagen BugBuster™ reagent (with benzonase nuclease and Roche complete protease inhibitor cocktail added). High levels of soluble protein were obtained at the predicted molecular weight, as judged by SDS-PAGE. The soluble proteins in the cellular extracts were separated by SDS-PAGE.

Cell extracts were analyzed for D-aminotransferase activity by following production of alanine from pyruvate (or glutamate from alpha-ketoglutarate) and D-tryptophan using the following protocol. Duplicate one mL reactions were typically carried out in 100 mM potassium phosphate buffer (pH 7.5), 50 µM pyridoxal phosphate, 25 mM sodium pyruvate, and 50 mM D-tryptophan. The reactions were initiated by the addition of cell free extracts or purified enzyme and were incubated 15 minutes overnight at 30° C., with mild shaking. Approximately the same level of D-aminotransferase was added (typically around 0.5 mg) in each assay for comparative purposes and AT-103 (BioCatalytics) was often used as a benchmark enzyme. Formic acid was added to a final concentration of two percent to stop the reaction and the precipitated protein was removed by centrifugation. Control reactions without added protein were also performed. Zero time points were also used as negative controls. Alanine and glutamate were detected using OPA post-column derivatization as described in Example 1. The branched-chain aminotransferase had low levels of D-aminotransferase activity in comparison to the AT-103 and *B. sphaericus* enzymes.

The branched chain aminotransferase was also tested for the ability to produce monatin from D-tryptophan (as in Example 3A), but did not appear to have activity under the conditions tested.

The pTRC99a construct was transformed into electrocompetent *E. coli* CAG18455 cells, which are auxotrophic for tryptophan production. Cells were grown in M9 minimal medium with Balch's vitamins with 100 mg/L L-tryptophan, 0.4% glucose, and calcium chloride. Cells were not able to grow without L-tryptophan. Induction was tested at 10, 100 and 1000 µM IPTG, at an OD600 of 0.4 for 4.5 hours. Bands at the correct MW were visible on SDS-PAGE. The plasmid was mutagenized using the QuikChange® Multi Site-Directed Mutagenesis Kit (Stratagene). The primers in Table 48 below were designed as described by the manufacturer.

TABLE 48

| Amino Acid Mutation (*E. coli* Numbering) | Nucleotide Mutation (*B. lich* Numbering) | Primer Sequence |
|---|---|---|
| Y32F | tac 96 --> ttc | ATCACGGATTTTTATTCGGGGACGGCGTG (SEQ ID NO: 46) |
| Y32D | tac 96 --> gac | ATCACGGATTTTTAGACGGGGACGGCGTG (SEQ ID NO: 47) |
| F37Y | ttt 111 --> tat | GGACGGCGTGTATGAAGGGATCAGGG (SEQ ID NO: 48) |
| R41K | agg 123 --> aag | TGTTTGAAGGGATCAAGGTATACGACGGCAAC (SEQ ID NO: 49) |
| F37Y + R41K | | GACGGCGTGTATGAAGGGATCAAGGTATACGACG (SEQ ID NO: 50) |
| Y96F | tac276 --> ttc | GCTGAAAGACGCTTTCATCCGCTTGGTCG (SEQ ID NO: 51) |
| Y96H | tac276 --> cac | GCTGAAAGACGCTCACATCCGCTTGGTC (SEQ ID NO: 52) |
| R98Y | cgc282 --> tac | CTGAAAGACGCTTACATCTACTTGGTCGTTTCAAGAGG (SEQ ID NO: 53) |
| Y96F + R98Y | | GGCTGAAAGACGCTTTCATCTACTTGGTCGTTTCAAGAGG (SEQ ID NO: 54) |
| Y96H + R98Y | | GCTGAAAGACGCTCACATCTACTTGGTCGTTTCAAGAGG (SEQ ID NO: 55) |
| L108R | ctc 312 --> cgc | GCAGGTGACCGCGGACTCGATCCAAAC (SEQ ID NO: 56) |
| L110H | ctc318 --> cac | GCAGGTGACCTCGGACACGATCCAAAC (SEQ ID NO: 57) |
| L108R + L110H | | GCAGGTGACCGCGGACACGATCCAAACAATTG (SEQ ID NO: 58) |
| L127Y | ttg369 --> tac | GTCATCATAATTGTCGAACCATACGCAATATTCCCGAAAC (SEQ ID NO: 59) |
| L127K | ttg369 --> aag | GTCATCATAATTGTCGAACCAAGGCAATATTCCCGAAAC (SEQ ID NO: 60) |
| I130E | ata375 --> gaa | GTCATCATAATTGTCGAACCATTGGCAGAATTCCCGAAAC (SEQ ID NO: 61) |
| L127Y + I130E | | CGAGTGTCATCATAATTGTCGAACCATACGCAGAATTCCCGAAAC (SEQ ID NO: 62) |
| L127K + I130E | | CCGAGTGTCATCATAATTGTCGAACCAAAGGCAGAATTCCCGAAAC (SEQ ID NO: 63) |
| Y165L | tac477 --> ttg | AATCGCTGAACTTGTTAAACAATATTCTTGTCCGGATCGAGG (SEQ ID NO: 64) |

Amino acid mutations were based on the *E. coli* BCAT crystal structure and the numbering in the above table is for the *E. coli* protein. The numbering for the DNA mutations is based on the *B. licheniformis* bcat gene.

The primers were diluted to 0.1 mg/mL and approximately 100 ng of each oligonucleotide primer was typically used in a 50 µL mutagenesis reaction, proportionately higher concentrations were used for larger primers. For oligonucleotide primers that were essentially competing for annealing to the same template region, sometimes a sum of 100 ng was used for the whole pool of primers in that region. Two hundred nanograms of template (*B. lich* bcat in pTRC99a) were used in the reaction, with 5 µL of 10× QuikChange® buffer, 2 µL dNTPs, and 2 µL of the enzyme blend. The amplification products were treated with Dpn I restriction endonuclease (Stratagene) (2 µL) for 2 hours at 37° C. and transferred to a thick wall 1.5 mL tube for ethanol precipitation. The resuspended (concentrated) reaction mix was transformed (2.5 µL) into XL10-Gold Ultracomp cells included in the QuikChange® kit. Several colonies were mini-prepped and sequenced to ensure that mutations were random and to estimate the level of mutagenesis achieved. Colonies were resuspended from the plate and bulk minipreps were done. The miniprep DNA was then transformed into the tryptophan auxotroph strain and plated on minimal medium (with IPTG) described above or using minimal medium containing D-tryptophan as the sole nitrogen source. A second and third round of mutagenesis was done on the bulk minipreps using primers that did not appear to incorporate well in the previous rounds. At each stage, colonies that grew quickly on the minimal medium (larger colonies) were retained for further analysis. The mutants shown in Table 49 below were isolated from the selection plates. In some cases these same mutants appeared on the selection medium more than one time.

TABLE 49

| Clone | Mutations |
|---|---|
| 4 | F37Y, Y96F |
| 6 | Y96F |
| 28 | F37Y, Y165L |
| 32 | Y96F, L127K |
| 5-1 | F37Y, Y96F, R98Y, L108R, L110H, L127Y |
| 5-2 | F37Y, R41K, Y96F, R98Y, L108R, L110H, L127Y |

The mutant constructs were induced to make recombinant protein in LB media; cell extracts were prepared as above. The soluble proteins in the cellular extracts were separated on a BioRad Laboratories Experion® Automated Electrophoresis Station and analyzed for concentration and percent expression using the Experion® Software version 1.1.98.0. Very low levels of soluble recombinant protein were observed; thus quantitation of the band of interest was not possible. Assays were done to test D-tryptophan transamination as above using 50-250 µL of cellular extracts. Clones 4, 6, 28, and 32 were assayed using both alpha-ketoglutarate and pyruvate as the amino acceptor and incubated for 2 hours and overnight at 30° C. The background levels of alanine/glutamate present from the cellular extracts was subtracted. For the assays with 5-1 and 5-2, the protein concentrations estimated by the Experion® software for the BCATs were 275.1 ng/µL for the wild-type enzyme, 409.3 ng/µL for BCAT 5-1, and 148.2 ng/µL for BCAT 5-2. The results of the assays are shown in Tables 50-52 below.

TABLE 50

| BCAT | Glutamate (mM) 2 Hours | Glutamate (mM) Overnight |
|---|---|---|
| wild-type (100 µL) | 0.0912 | 0.2304 |
| wild-type (250 µL) | 0.251 | 0.521 |
| 4 (100 µL) | 0.0642 | 0.1202 |
| 4 (250 µL) | 0.154 | 0.295 |
| 6 (100 µL) | 0.053 | 0.112 |
| 6 (250 µL) | 0.141 | 0.289 |
| 28 (100 µL) | 0.0586 | 0.1402 |
| 28 (250 µL) | 0.155 | 0.367 |
| 32 (100 µL) | 0.0616 | 0.1236 |
| 32 (250 µL) | 0.167 | 0.339 |

TABLE 51

| BCAT | Alanine (mM) 2 Hours | Alanine (mM) Overnight |
|---|---|---|
| wild-type (250 µL) | 0.199 | 0.438 |
| 4 (250 µL) | 0.093 | 0.249 |
| 6 (250 µL) | 0.097 | 0.249 |
| 28 (250 µL) | 0.117 | 0.325 |
| 32 (250 µL) | 0.102 | 0.285 |

TABLE 52

| BCAT | Glutamate (mM) 1 Hour | Glutamate (mM) Overnight |
|---|---|---|
| wild-type (50 µL) | 0.018 | 0.075 |
| wild-type (100 µL) | 0.037 | 0.152 |
| 5-1 (50 µL) | 0.005 | 0.017 |
| 5-1 (100 µL) | 0.01 | 0.045 |

TABLE 52-continued

| BCAT | Glutamate (mM) 1 Hour | Glutamate (mM) Overnight |
|---|---|---|
| 5-2 (50 µL) | 0.001 | 0.011 |
| 5-2 (100 µL) | 0.003 | 0.031 |

It is evident that like most L-aminotransferases, the enzymes have a preference for alpha-ketoglutarate compared to pyruvate for the amino acceptor. All the mutants did have D-aminotransferase activity, as did the wild-type parent. It is not clear whether the wild-type enzyme had more or less D-aminotransferase activity, because exact quantitation of the BCAT protein from cellular extracts was not possible. However, it is expected that the mutant enzymes have less L-aminotransferase activity than the wild-type; thus the ratio of D- to L-transamination rate is being improved. Continued mutagenesis could provide an alternative enzyme in pathways to monatin.

Example 8

Cloning, Expression, and Testing of Glutamate and Aspartate Racemases

This example describes methods used to clone and test amino acid racemase enzymes, which can be used to interconvert between L-glutamate and D-glutamate (or L- and D-aspartate or L- and D-alanine). Glutamate, aspartate, or alanine racemases are useful in a biosynthetic pathway to produce R,R monatin when a step in that pathway produces an L-amino acid (e.g., L-glutamate, L-aspartate, or L-alanine) and another step in the pathway consumes a D-amino acid (e.g., D-glutamate, D-aspartate, or D-alanine). FIG. 4 illustrates a biosynthetic pathway for producing R,R monatin from L-tryptophan using an L-tryptophan-specific aminotransferase, an R-specific aldolase, a D-aminotransferase and a glutamate (or aspartate or alanine) racemase.

Genes were cloned into the pET28 and pET30 vectors to generate both non-tagged proteins and fusion proteins with cleavable N-terminal $HIS_6$-Tag/T7-Tags. The resulting proteins were purified using immobilized metal affinity chromatography.

Experimental Overview

Genes encoding glutamate racemases (EC 5.1.1.3) from *Lactobacillus brevis* (Genbank Accession No. D29627, nucleic acid sequence), and *Pediococcus pentosaceus* (murI gene) (Genbank Accession No. L22789) were cloned and expressed in *E. coli*. The extracts were tested for activity in conversion of L-glutamate to D-glutamate and D-glutamate to L-glutamate. BioCatalytics aspartate racemase enzyme (EC 5.1.1.13) was also tested for interconversion between L- and D-aspartate.

Isolation of Genomic DNA for Cloning

*L. brevis* genomic DNA (ATCC 8287D) was obtained from the American Type Culture Collection. *P. pentosaceus* (ATCC 25745) was grown at 37° C. in *lactobacilli* MRS broth and 2 mL was used for genomic DNA isolation using the method of Mekalanos, J. J., "Duplication and amplification of toxin genes in *Vibrio cholerae*," *Cell* 35:253-263, (1983).

Polymerase Chain Reaction Protocol

Primers were designed with 5' restriction sites and overhangs for cloning into the pET 28 and pET30 vectors (Novagen, Madison, Wis.).

*L. brevis* glutamate racemase primers:

(SEQ ID NO: 15)
N term:
5'-GCGGCGCCATGGAAAATGATCCGATTGGTCTAATG-3',
and (SEQ ID NO: 16)
C term:
5'-GCGGCGGTCGACGCAATTACAATTGTGTTTGTC-3'.

*P. pentosaceus* glutamate racemase primers:
(SEQ ID NO: 17)
N term:
5'-GCGGCGCCATGGATGTATGTATAATTTTATTTAG-3',
and (SEQ ID NO: 18)
C term:
5'-GCGGCGGTCGACAAATTTCATTATTCATTCTAATTT-3'.

The gene derived from *L. brevis* was amplified using the following PCR protocol. In a 50 µL reaction, 0.150 µg template, 1.6 µM of each primer, 0.4 mM each dNTP, 2.8 U Expand High Fidelity™ Polymerase (Roche, Indianapolis, Ind.), 0.5 U Pfu polymerase (Stratagene, La Jolla, Calif.) and 1× Expand™ buffer with Mg were used. The thermocycler program used included a hot start at 96° C. for 3 minutes, 8 repetitions of the following steps: 94° C. for 30 seconds, 52° C. for 45 seconds, and 72° C. for 2 minutes, followed by 22 repetitions of the following steps: 94° C. for 30 seconds, 60° C. for 45 seconds, and 72° C. for 2 minutes. After the 22 repetitions, the sample was maintained at 72° C. for 7 minutes and then stored at 4° C. This PCR protocol produced a product of ~830 bp, as judged by comparison to DNA size markers.

The gene derived from *P. pentosaceus* was amplified using the following PCR protocol. In a 50 µL reaction, 0.15 µg template, 1.6 µM of each primer, 0.4 mM each dNTP, 2.8 U Expand High Fidelity™ Polymerase, 0.5 U Pfu polymerase and 1× Expand™ buffer with Mg were used. The thermocycler program used included a hot start at 96° C. for 3 minutes, followed by 8 repetitions of the following steps: 94° C. for 30 seconds, 37° C. for 45 seconds, and 72° C. for 2 minutes, followed by 8 repetitions of the following steps: 94° C. for 30 seconds, 45° C. for 45 seconds, and 72° C. for 2 minutes, followed by 14 repetitions of the following steps: 94° C. for 30 seconds, 55° C. for 45 seconds, and 72° C. for 2 minutes. After the 14 repetitions, the sample was maintained at 72° C. for 7 minutes and then stored at 4° C. This PCR protocol produced a product of ~840 bp, as judged by comparison to DNA size markers.

Cloning

The PCR products were gel purified from 0.8% TAE-agarose gels using the Qiagen gel extraction kit (Qiagen, Valencia, Calif.). The PCR products were quantified using a SmartSpec 3000™ spectrophotometer. The products were digested with restriction enzymes Nco I and Sal I following the manufacturer's recommended protocols (New England Biolabs, Beverly, Mass.) and gel purified from 0.8% TAE-agarose gels using the Qiagen gel extraction kit (Qiagen, Valencia, Calif.). Vectors pET28 and pET30 were prepared by digestion with restriction enzymes Nco I and Sal I, followed by treatment with shrimp alkaline phosphatase and purification from 0.8% TAE-agarose gels using the Qiagen gel extraction kit (Qiagen, Valencia, Calif.).

The digested vectors and inserts were ligated using the Rapid™ DNA Ligation Kit (Roche, Indianapolis, Ind.). Approximately 50 ng of treated insert, 100 ng of treated vector (3 to 1 molar ratio of insert to vector), 5 U of T4 DNA ligase (included with the Rapid™ DNA Ligation Kit, and 1× ligation buffer were incubated for 5 minutes at room temperature. The ligation reactions were purified using the High Pure PCR Product Purification Kit (Roche, Indianapolis, Ind.) and were used to transform *E. coli* DH10B electrocompetent cells (Invitrogen, Carlsbad, Calif.). Ten µL of each ligation reaction was added to 40 µL of DH10B cells and were transformed by electroporation using the BioRad Gene Pulser® II under the following conditions: 2.5 kV, 25 µF, 200 ohm in a 0.2 cm cuvette. The cells were allowed to recover in 1 mL of room temperature SOC for 1 hour at 37° C. with shaking at 225 rpm. The cells were plated on LB plates containing kanamycin (50 µg/mL).

Plasmid DNA was purified from the resulting transformants using the Qiagen spin miniprep kit (Qiagen, Valencia, Calif.) and screened for the correct inserts by restriction digest with Nco I and Sal I. The sequences of plasmids appearing to have the correct insert were verified by dideoxy chain termination DNA sequencing.

Gene Expression and Assays

Plasmid DNA, verified by sequence analysis, was subcloned into *E. coli* expression host BL21(DE3) (Novagen, Madison, Wis.). The cultures were grown and the plasmids were isolated using Qiagen miniprep kit (Qiagen, Valencia, Calif.), and analyzed by restriction digest to confirm identity.

Induction in BL21(DE3) was initially performed with *L. brevis* and *P. pentosaceus* glutamate racemases in both pET28 (untagged) and pET 30 (histidine-tagged) vectors. A time course study was performed with cultures grown in 250 mL LB containing kanamycin (50 mg/L) to an $OD_{600}$ of 0.5-0.6 and induced with 100 mM IPTG (isopropyl thiogalacatoside) and sampled at 0 and 3 hours post induction. Cells from 600 µL (0 hour) and 275 µL (3 hour) were resuspended in 40 µL sodium dodecyl sulfate buffer containing 2-mercaptoethanol, heated at 95° C. for 10 minutes, and cooled. Aliquots of these total cellular protein samples were analyzed by SDS-PAGE using a 4-15% gradient gel.

Cell extracts were also prepared from the 3 hour cultures by suspending cell pellets from 5 mL of culture in 0.625 mL Novagen BugBuster™ reagent containing 0.625 µL benzonase nuclease and 3 µL protease inhibitor cocktail set #3 (Calbiochem-Novabiochem Corp., San Diego, Calif.) at room temperature for 20 minutes with gentle shaking and centrifuging at 16,000×g to remove cell debris. The supernatants (cell extracts) were loaded onto 4-15% gradient gels for analysis of the cellular soluble proteins.

The 3 hour samples from cloned *L. brevis* glutamate racemase and *P. pentosaceus* glutamate racemase showed both total and soluble protein that corresponded to the correct size (approximately 31 kDa). The *L. brevis* pET30 (histidine-tagged) gene product was over-expressed at a higher level than, and was also more soluble (>20% of soluble protein) than, the *L. brevis* pET 28 (untagged) gene product, as well as the *P. pentosaceus* gene products in both vectors. The *P. pentosaceus* gene product showed equal overexpression and solubility in the pET28 and pET30 vectors, which was significantly less than that observed for the *L. brevis* pET30 gene product.

Cells from the induced cultures (250 mL) were centrifuged and washed once with 0.85% NaCl. Cell pellets were resuspended in 5 mL/g wet cell weight of BugBuster™ (Novagen, Madison, Wis.) reagent containing 5 µL/mL protease inhibitor cocktail set #3 (Calbiochem-Novabiochem Corp., San Diego, Calif.) and 1 µL/mL benzonase nuclease. Samples were incubated at room temperature for 20 minutes on an orbital shaker. Insoluble cell debris was removed by centrifugation at 16,000×g for 20 minutes at 4° C.

Cell extracts were assayed for glutamate racemase activity using the following protocol. 400 μL reactions were carried out in 10 mM potassium phosphate (pH 8.0), 0.2 mM dithiothreitol ("DTT"), and 10 mM L-glutamate or D-glutamate. The reactions were initiated by the addition of 20-100 μL of cell free extracts and were incubated at room temperature. Sample aliquots were taken over a time course of 1 minute, 5 minutes, 10 minutes, 20 minutes and 1 hour (zero minute samples served as control reactions). 2 M formic acid (25 μL) was added to each 40 μL sample aliquot to stop the reaction and the precipitated protein was removed by centrifugation. Supernatants were removed and frozen at −80° C. until they were analyzed by LC/MS/MS as described in Example 1.

Assay results from cell extracts from pET30 induction with 100 mM IPTG (3 hours) demonstrate that *L. brevis* (Genbank Accession No. BAA06106.1 GI:468450) and *P. pentosaceus* (Genbank Accession No. AAA16761.1 GI:349029) enzymes have significant levels of racemase activity on both glutamate isomers. The *P. pentosaceus* racemase (20 μL of cellular extracts) reached equilibrium between L-and D-glutamate in 10-20 minutes starting with either substrate. The *L. brevis* enzyme (20 μL of cellular extracts) also reached equilibrium in approximately 20 minutes.

A partially purified aspartate racemase enzyme (catalog #ASPR-101) purchased from BioCatalytics, Inc. (Pasadena, Calif.) was assayed for activity on L-aspartate and D-aspartate using a protocol similar to the one above. The commercial enzyme showed racemase activity on both isomers. Using 0.5-1 mg of enzyme, equilibrium was achieved in 20-60 minutes.

All three racemases (*L. brevis* glutamate racemase, *P. pentosaceus* glutamate racemase and BioCatalytics aspartate racemase were also assayed for activity on S,S monatin using the following protocol. 400 μL reactions were carried out in 10 mM potassium phosphate (pH 8.0), 0.2 mM DTT, and 10 mM S,S monatin. The reactions were initiated by the addition of cell free extracts (*L. brevis* and *P. pentosaceus*) or purified enzyme (BioCatalytics aspartate racemase) and were incubated at room temperature. Sample aliquots were taken over a time course of 1 minute, 5 minutes, 10 minutes, 20 minutes and 1 hour (zero minute samples served as control reactions as well as samples without enzyme). 2 M formic acid (25 μL) was added to each 40 μL sample aliquot to stop the reaction and the precipitated protein was removed by centrifugation. Supernatants were removed and frozen at −80° C. until they were analyzed by LC/MS/MS (Example 1). No decrease in S,S monatin concentration was noted over time, nor was there any increase in S,R monatin (present initially as <5% contaminating byproduct, even in the no enzyme control). Therefore, none of the racemases assayed showed activity towards monatin.

Example 9

Production of R,R Monatin from L-Tryptophan Using Alanine, Glutamate, or Aspartate Racemases This example describes methods of producing stereoisomerically-enriched R,R monatin from L-tryptophan using an L-tryptophan (L-tyrosine, or aromatic) aminotransferase, ProA aldolase, alanine, glutamate or aspartate racemase, and a broad specificity D-amino acid aminotransferase. FIG. 5 is a diagram that illustrates the pathway. This approach to production of stereoisomerically enriched R,R monatin requires an enzyme for step 1 that has low activity in the production of monatin from monatin precursor (MP). Based upon earlier results, we used the *Sinorhizobium meliloti* and *Rhodobacter sphaeroides* tatA gene products described in Example 1 from WO 03/091396 A2.

Materials and Methods

Glutamate racemases from *L. brevis* and *P. pentosaceus* were produced in *E. coli* as described in Example 8. In some cases, the $His_6$-tagged version of these enzymes were purified using His-Bind 900 cartridges according to manufacturer's protocols (Novagen, Madison, Wis.) and were desalted to remove imidazole using PD-10 columns (G25 Sephadex, Amersham-Pharmacia). The enzymes were eluted in 25 mM potassium phosphate pH 8.0. Aspartate racemase (ASPR-101) and D-aminotransferase (AT-103) were purchased from BioCatalytics, Inc., alanine racemase was purchased from Sigma (St. Louis, Mo.) (catalog number A8936). *S. meliloti* and *R. sphaeroides* tyrosine (aromatic) aminotransferases were prepared as described in Example 1 from WO 03/091396 A2. *Comamonas testosteroni* ProA aldolase was prepared as described in Example 4 from WO 03/091396 A2. Total protein assays were done utilizing the Bio-Rad Protein Assay according to manufacturer's protocols (Hercules, Calif.).

Reduction in Amount of S,S Monatin Produced Using Racemases

Reaction mixtures (1 mL volume, run in duplicate) contained 100 mM potassium phosphate buffer (pH 8), 2 mM $MgCl_2$, 0.05 mM pyridoxal 5'-phosphate ("PLP"), 200 mM sodium pyruvate, 5 mM sodium α-ketoglutarate or oxaloacetate, approximately 280 μg/mL *S. meliloti* TatA supplied in a cellular extract, 1 mg/mL BioCatalytics D-aminotransferase (AT-103), 100 μL/mL of glutamate racemase cellular extract or 1 mg/mL aspartate racemase, and approximately 100 μg/mL of ProA aldolase provided as a cellular extract. Solid tryptophan was added at a concentration of 10.2 mg/mL. Negative controls did not contain racemase. Samples were incubated at 30° C. (shaking at 250 rpm) for 1 hour, 2 hours, or overnight. Samples were centrifuged to remove precipitate, syringe filtered, and stored at −80° C. prior to analysis for monatin using the LC/MS/MS method described in Example 1.

Most of the samples contained >95% S,S monatin, due to the amounts of native L-aminotransferase present in the cellular extracts. However, the samples that contained racemase had a reduced amount of total monatin as a result of the racemase enzymes making L-glutamate less available for transamination of MP. Without racemase, 1545-2355 ppm monatin (predominantly S,S) was produced during the time-course. With the racemases present, only 340-879 ppm (*L. brevis* enzyme), 444-531 ppm (*P. pentosaceus* enzyme), and 506-1460 ppm monatin (aspartate racemase) were produced. These data indicate that the racemases are active in the reaction conditions required to produce monatin. To minimize formation of S,S monatin from cellular extract enzymes, such as aspartate aminotransferases, further experiments were done with purified enzymes and a higher ratio of D-aminotransferase to L-aminotransferase enzymes.

Conversion of L-tryptophan to 4-R Containing Isomers of Monatin

The above experiments were repeated using approximately 54 μg of purified L-aminotransferase (either *S. meliloti* or *R. sphaeroides* TatA), 1 mg aspartate aminotransferase (Bio-Catalytics), 1 mg D-aminotransferase, 5 mM oxaloacetate as the amino acceptor, and 75 μg purified aldolase. The reactions were run in duplicate with a 2 hour sampling time and an overnight incubation time. Negative controls were done with *S. meliloti* L-aminotransferase, but with no racemase. In addition to quantification of R,R/S,S and S,R/R,S monatin peak quantification based on reversed phase chromatography, the percentage of each stereoisomer was determined using the FDAA derivitization technique described in Example 1. The results are shown in Table 53 below.

With about 10% of the total monatin being 4S at the two-hour time point, the *S. meliloti* TatA could be considered as having limited activity on MP.

The experiments were repeated with the purified *S. meliloti* TatA (54 μg) and the *L. brevis* glutamate racemase. When purified glutamate racemase was used, approximately 64 μg was used per 1 mL reaction. Cellular extracts containing the glutamate racemase were also tested and 1.4 mg of soluble protein was used. A no racemase negative control was utilized again and all samples were run in duplicate. The results are shown in Table 54 below.

TABLE 53

| L-Aminotransferase | Incubation Time | Total Monatin (ppm) | % S,S | % R,R | % R,S | % S,R |
|---|---|---|---|---|---|---|
| *S. meliloti* TatA | 2 h | 17.1 | 10.2 | 58.1 | 0.8 | 31.0 |
| *S. meliloti* TatA | 2 h | 15.8 | 13.3 | 55.3 | 1.0 | 30.4 |
| *S. meliloti* TatA | overnight | 77.7 | 25.8 | 40.0 | 1.3 | 32.9 |
| *S. meliloti* TatA | overnight | 67.9 | 29.4 | 37.3 | 1.5 | 31.8 |
| *R. sphaeroides* TatA | 2 h | 241.2 | 96.3 | 2.3 | 0.8 | 0.6 |
| *R. sphaeroides* TatA | 2 h | 223.2 | 95.7 | 2.7 | 1.0 | 0.6 |
| *R. sphaeroides* TatA | overnight | 600.4 | 96.6 | 1.8 | 0.5 | 1.1 |
| *R. sphaeroides* TatA | overnight | 618.5 | 96.1 | 2.1 | 0.5 | 1.3 |
| no racemase control | 2 h | 7.1 | 92.0 | 1.4 | 6.6 | 0.0 |
| no racemase control | 2 h | 5.7 | 94.0 | 1.2 | 4.8 | 0.0 |
| no racemase control | overnight | 44.6 | 93.5 | 1.3 | 4.7 | 0.5 |
| no racemase control | overnight | 37.5 | 95.4 | 0.9 | 3.7 | 0.0 |

Clearly, the presence of the racemase increased the total amount of monatin produced when *S. meliloti* TatA was used as the enzyme for L-tryptophan transamination. Monatin levels increased from an average of 6.4 to 16.5 ppm in the two hour assay and from 41-73 ppm in the overnight assay. Additionally, the percent of R,R formed increased from about 1% up to as much as 58% by utilizing the racemase enzyme. The S,R stereoisomer of monatin, another potent sweetener, was the other major component, increasing from nearly 0 in the negative controls to 31%. The *R. sphaeroides* TatA clearly had more activity on S-MP than the *S. meliloti* L-transaminase, demonstrating the importance of having an enzyme that has a high substrate specificity for L-tryptophan as compared to MP when 4-R isomers of monatin are the desired products.

TABLE 54

| Glutamate racemase | Incubation Time | Total Monatin (ppm) | % S,S | % R,R | % R,S | % S,R |
|---|---|---|---|---|---|---|
| *L. brevis* (purified) | 2 h | 3.3 | 49.1 | 34.2 | 3.7 | 13.0 |
| *L. brevis* (purified) | 2 h | 3.6 | 47.9 | 35.2 | 3.5 | 13.4 |
| *L. brevis* (purified) | overnight | 29.3 | 58.9 | 24.7 | 3.2 | 13.2 |
| *L. brevis* (purified) | overnight | 40.2 | 55.1 | 25.0 | 4.7 | 15.3 |
| *L. brevis* (cell extract) | 2 h | 10.5 | 45.8 | 35.9 | 1.1 | 17.2 |
| *L. brevis* (cell extract) | 2 h | 10.5 | 47.4 | 33.9 | 1.1 | 17.6 |
| *L. brevis* (cell extract) | overnight | 79.4 | 70.3 | 17.9 | 1.3 | 10.5 |
| *L. brevis* (cell extract) | overnight | 80.1 | 69.1 | 19.1 | 1.1 | 10.7 |
| none | 2 h | 2.7 | 84.1 | 7.1 | 6.3 | 2.4 |
| none | 2 h | 3.2 | 84.9 | 6.0 | 6.8 | 2.2 |
| none | overnight | 36.5 | 92.3 | 2.3 | 4.2 | 1.2 |
| none | overnight | 30.5 | 92.7 | 2.0 | 4.1 | 1.3 |

Again, it is clear that the addition of the racemase increases the total monatin produced from L-tryptophan, as well as increases the relative amounts of 4R-containing isomers of monatin as compared to S,S monatin. The use of purified aldolase, racemase, and L-aminotransferase greatly improves the ability to control the desired stereoisomer formation. The ratio of L to D aminotransferase is also a way to manipulate stereochemistry of the final product.

When comparing results shown in Tables 1 and 2 in Example 2, to results with reaction conditions similar to the conditions above, one can see that approximately 7-29 ppm of monatin were formed from indole-3-pyruvate and the percentages of R,R monatin formed were approximately 51-90%. Using the aspartate racemase increased the total amount of monatin produced to 16-78 ppm monatin, with % R,R of approximately 40-58%. Additionally, a more stable and less expensive raw material (L-tryptophan) was utilized. In Example 3A, approximately 73 ppm monatin was produced from D-tryptophan at a ratio of R,R:S,R of approximately 1.7:1. The total amount of 4R isomers was >80% of the total monatin. Because both R,R-monatin and R,S-monatin are potent sweeteners (>1000 times sweeter than sucrose), the ability to enrich for these isomers, without the need for expensive D-amino acid substrates, is critical.

It is expected that the availability of a non-specific or R-specific aldolase would increase the reaction rate as well as increasing the percentage of R,R monatin formed. See Example 5. Although the ProA aldolase from *C. testosteroni* used in these assays is reported to predominantly favor substrates in the S-configuration for fission reactions, this Pro A aldolase clearly does produce R-MP. Thus, aldolases that more preferentially produce MP in the R-configuration can help generate even greater percentages of R,R monatin. Additionally, it is expected that finding an L-tryptophan aminotransferase with even lower activity for monatin production would also decrease the amount of S,S and R,S monatin formed. Lastly, improvements can be made to the D-aminotransferase enzyme, or alternative D-aminotransferase enzymes can be used, that would have increased substrate specificity for R-MP versus S-MP. This would also increase formation of the R,R product, if so desired.

The aspartate racemase experiments were repeated to compare the activity of R-selective aldolase of SEQ ID NO:22 with the activity of the ProA aldolase from *C. testosteroni*. Approximately 50 µg of purified L-aminotransferase (*S. meliloti* TatA), 1 mg aspartate racemase (BioCatalytics), 1 mg D-aminotransferase (AT-103, BioCatalytics), 5 mM oxaloacetate as the amino acceptor, and 50 µg of the appropriate purified aldolase. The reactions were run in duplicate and incubated overnight at 30° C. The percentage of each stereoisomer was determined using the FDAA derivitization technique described in Example 1. The results are shown below in Table 55.

TABLE 55

| Aldolase | Total Monatin (ppm) | % S,S | % R,R | % R,S | % S,R |
|---|---|---|---|---|---|
| SEQ ID NO: 22 | 211 | | 72.7 | | 27.3 |
| C. testosteroni | 422 | 30.2 | 38.5 | | 31.3 |

The *C. testosteroni* ProA distribution of isomers is consistent with the earlier experiments above, whereas when the R-selective aldolase of SEQ ID NO:22 is used, the percent R,R is much higher, undetectable amounts of S,S are formed, and the amount of S,R monatin is lower.

As described in Examples 2 and 3A, D-alanine can serve as the amino donor for transamination of MP to monatin. Many L-aminotransferases have the ability to utilize pyruvate as an amino acceptor to some extent and produce L-alanine. Because the above-mentioned reactions use high concentrations of pyruvate, it is likely that some of the pyruvate is converted to L-alanine. For example, during transamination of L-tryptophan, the HexAspC enzyme described in Example 6A has been found to convert 10-18% of pyruvate (50-200 mM initial concentrations) to L-alanine in 2 hours if alpha-ketoglutarate is absent. The enzyme showed a 10-fold preference for alpha-ketoglutarate when both amino acceptors were present at high (>50 mM) concentrations. AspC (described in WO 03/091396 A2) also produced some L-alanine from pyruvate. Therefore, it was expected that one can omit the addition of alpha-ketoglutarate or oxaloacetate in the above reactions and utilize an alanine racemase (EC 5.1.1.1) in place of glutamate or aspartate racemase.

Alanine racemase enzymes were first identified in *Brucella abortus* and *Streptococcus faecalis*. Marr, A G., and Wilson, P. W., Arch. Biochem. Biophys., 49:424-433, (1954); Wood, W. A., and Gunsalus, I. C., J. Biol. Chem. 190:403-416, (1951). The dadB gene in *Salmonella typhimurium* was identified as the source of alanine racemase activity and several hundred homologs can be found in genomics databases. Other known sources of alanine racemase activity are *Escherichia coli*, *Bacillus subtilis*, *Pseudomonas aeruginosa*, *Vibrio cholerae*, *Schizosaccharomyces pombe*, and *Bacillus cereus*. A basidiomycetous mushroom, *Lentinus edodes*, also contains a broad activity alanine racemase. A thermostable homolog from *Bacillus stearothermophilus* is available for purchase from Sigma-Aldrich (catalog #A8936) and has been immobilized for commercial applications. Inagaki, K., Biochemistry 25:3268 (1986).

Monatin Production with Alanine Racemase

Monatin production was tested using ProA aldolase from *C. testosteroni*. Approximately 50 µg of purified L-aminotransferase (*S. meliloti* TatA), 1 mg D-aminotransferase (AT-103, BioCatalytics), pyruvate as the amino acceptor, 50 µg purified aldolase, and 70 µg alanine racemase purchased from Sigma (St. Louis, Mo.) (catalog number A8936). The reactions were run in duplicate and incubated overnight. The percentage of each stereoisomer was determined using the FDAA derivitization technique described in Example 1. Controls with no racemase were included. The results are shown in Table 56 below.

TABLE 56

| Conditions | Total Monatin | % SS | % RS | % RR | % SR |
|---|---|---|---|---|---|
| Ala racemase (1 hour) | 4 | 66 | 21 | 12 | 1 |
| No ala racemase (1 hour) | 2.7 | 69 | 26 | 5 | 0 |
| Ala racemase (24 hours) | 82.9 | 90 | 5 | 4 | 2 |
| No ala racemase (24 hours) | 170.3 | 89 | 5 | 4 | 2 |

There was three-fold more R,R monatin in the one hour time point when alanine racemase was present compared to the sample with no alanine racemase. This result shows that it is possible to produce R,R monatin using alanine racemase. The percentage of R,R monatin produced could be improved using an aldolase that selectively produces R-monatin precursor, an L-aminotransferase that does not work or has limited activity on R-monatin precursor and a D-aminotransferase that does not work or has limited activity on indole-3-pyruvate.

Example 10

D-phenylglycine Aminotransferase
(D-4-Hydroxyphenylglycine Aminotransferase)

As shown in FIG. 3, a stereoinverting aminotransferase is useful in a biosynthetic pathway for the production of monatin. For example, a D-phenylglycine aminotransferase or mutant thereof could produce R,R monatin from R-MP with L-glutamate as the amino donor.

(1) PCR Synthesis of *P. stutzeri* 4 D-Hydroxyphenylglycine Aminotransferase from Oligonucleotide Primers This example describes methods that were used to synthesize 4 D-hydroxyphenylglycine aminotransferase, a stereoinverting enzyme that can be used to convert R monatin precursor to R,R monatin using L-glutamate as the amino donor.

Primer Design

The published sequence (Genbank Accession No. AY319935, nucleic acid sequence; Genbank Accession No. AAQ8290, protein sequence) for *Pseudomonas stutzeri* 4 D-hydroxyphenylglycine aminotransferase (4 D-HPG AT) was used as a template for PCR primer design. Alternatively, the 4-D-hydroxyphenylglycine aminotransferase from *Pseudomonas putida*, (CAD42450 (protein), AX467211 (nucleotide)) is used as a sequence template. A total of 34 forward primers and 35 reverse primers were designed; forward and reverse primers were 40-mers sharing 20 overlapping base pairs. In addition, 2 outer primers were designed with 5' restriction sites and overhangs for cloning into the pET 28 and pET30 vectors (Novagen, Madison, Wis.).

*P. stutzeri* 4 D-HPG AT outer primers: N term (with NdeI Site):

(SEQ ID NO: 19)
5'-GGCCGGCATATGTCGATCCTTAACGACTACAAACGT-3',
and

C term (with XhoI site):
(SEQ ID NO: 20)
5'-GGAAGGCTCGAGTCATGATTGGTTTCCAGACAAATT-3'.

Polymerase Chain Reaction Protocol

The gene sequence from *P. stutzeri* was amplified using the following protocols. The primary 100 μL PCR reaction included 0.05 μM of each of the internal 69 primers, 0.4 mM each dNTP, 10 U rTth Polymerase XL (Roche, Indianapolis, Ind.), 0.625 U Pfu polymerase (Stratagene, La Jolla, Calif.), 1× XL buffer and 1 mM Mg(OAc)$_2$. The thermocycler program used included a hot start at 94° C. for 3 minutes, 15 repetitions of the following steps: 94° C. for 30 seconds, 42° C. for 30 seconds, and 68° C. for 15 seconds, followed by 10 repetitions of the following steps: 94° C. for 30 seconds, 52° C. for 30 seconds, and 68° C. for 30 seconds, followed by 10 repetitions of the following steps: 94° C. for 30 seconds, 60° C. for 30 seconds, and 68° C. for 1 minute and 15 seconds. After the final 10 cycles, the sample was maintained at 68° C. for 7 minutes and then stored at 4° C. This PCR protocol produced a smear of product at ~0.5 kb on a 0.8% TAE-agarose gel.

The secondary PCR reaction was set up using the primary PCR reaction as template. The secondary 100 μL PCR reaction included 2.5 μL of the primary PCR reaction, 0.5 μM of each of the 2 outer primers (with Nde I and Xho I restriction sites), 0.4 mM each dNTP, 10 U rTth Polymerase XL, 0.625 U Pfu polymerase, 1× XL buffer and 1 mM Mg(OAc)$_2$. The thermocycler program used included a hot start at 94° C. for 3 minutes, 10 repetitions of the following steps: 94° C. for 30 seconds, 52° C. for 30 seconds, and 68° C. for 1 minute 30 seconds, followed by 15 repetitions of the following steps: 94° C. for 30 seconds, 60° C. for 30 seconds, and 68° C. for 1 minute 30 sec After the 15 repetitions, the sample was maintained at 68° C. for 7 minutes and then stored at 4° C. This PCR protocol produced a distinctive product band at ~1.4 kb on a 0.8% TAE-agarose gel.

The PCR product was gel purified from 0.8% TAE-agarose gel using the Qiagen gel extraction kit (Qiagen, Valencia, Calif.). The product was TOPO cloned and transformed into TOP 10 cells according to manufacturer's protocol (Invitrogen, Carlsbad, Calif.). Plasmid DNA was purified from the resulting transformants using the Qiagen spin miniprep kit (Qiagen, Valencia, Calif.) and screened for the correct inserts by restriction digest with Nde I and Xho I. The sequences of plasmids appearing to have the correct insert were verified by dideoxy chain termination DNA sequencing with universal M13 forward and M13 Reverse primers. Of the 10 clones sequenced, all had at least one mutation from the desired sequence. The best clone had a single base-pair mutation that resulted in an amino acid change. The sequence of this clone was corrected using the QuickChange Mutagenesis protocol according to manufacturer recommendations (Stratagene, La Jolla, Calif.).

The corrected TOPO clone was digested with restriction enzymes Nde I and Xho I following the manufacturer's recommended protocols (New England Biolabs, Beverly, Mass.) and gel purified from 0.8% TAE-agarose gels using the Qiagen gel extraction kit (Qiagen, Valencia, Calif.). Vectors pET 28 and pET 30 were prepared by digestion with restriction enzymes Nde I and Xho I, followed by treatment with shrimp alkaline phosphatase and purification from 0.8% TAE-agarose gels using the Qiagen gel extraction kit (Qiagen, Valencia, Calif.).

The digested vectors and insert were ligated using the NEB Quick Ligation Kit (Beverly, Mass.). Approximately 50 ng of treated insert, 100 ng of treated vector (3 to 1 molar ratio of insert to vector), 5 U of T4 DNA ligase, and 1× ligation buffer were incubated for 5 minutes at room temperature. The ligation mixture was transformed into TOP10F' chemically competent cells (Invitrogen). The cells were allowed to recover in 0.25 mL of room temperature SOC for 1 hour at 37° C. with shaking at 225 rpm. The cells were plated on LB plates containing kanamycin (50 μg/mL). The plasmid DNA was purified from the resulting transformants using the Qiagen spin miniprep kit (Qiagen, Valencia, Calif.) and screened for the correct inserts by restriction digest with NdeI and XhoI.

Gene Expression and Assays

Plasmid DNA was transformed into *E. coli* expression host BL21(DE3) (Novagen, Madison, Wis.). The cultures were grown and the plasmids were isolated using Qiagen miniprep kit (Qiagen, Valencia, Calif.) and analyzed by restriction digest to confirm identity.

Induction in BL21(DE3) was performed with *P. stutzeri* D-4-hydroxyphenylglycine aminotransferase in both pET 28 (histidine-tagged) and pET 30 (untagged) vectors. A time course study was performed with cultures grown in 250 mL LB containing kanamycin (50 mg/L) to an OD$_{600}$ of 0.5-0.6, induced with 100 mM isopropyl thiogalacatoside ("IPTG") and sampled at 0 and 3 hours post induction. An appropriate volume of cells from 0 hours and 3 hours was resuspended in 40 μL sodium dodecyl sulfate buffer containing 2-mercaptoethanol, heated at 95° C. for 10 minutes, and cooled. Aliquots of these total cellular protein samples were analyzed by SDS-PAGE using a 4-15% gradient gel.

The cell extracts were also prepared from the 3 hour cultures by suspending cell pellets from 5 mL of culture in 0.625 mL Novagen BugBuster™ reagent containing 0.625 μL benzonase nuclease and 3 μL protease inhibitor cocktail set #3 (Calbiochem-Novabiochem Corp., San Diego, Calif.) at room temperature for 20 minutes with gentle shaking and centrifuging at 16,000×g to remove cell debris. The supernatants (cell extracts) were loaded onto 4-15% gradient gels for analysis of the cellular soluble proteins. When noted, the protein was purified using His-Bind 900 cartridges according to manufacturer's protocols (Novagen, Madison, Wis.) and were desalted to remove imidazole using PD-10 columns (G25 Sephadex, Amersham-Pharmacia).

(2) Isolation of Organisms with D-Phenylglycine Aminotransferase ("DPGAT")

Organisms of the genus *Pseudomonas* and like genera, with a stereoinverting D-phenylglycine aminotransferase (also called D-4-hydroxyphenylglycine aminotransferase) are isolated in the following manner. Soil samples are incubated on petri plates with the following medium: (per liter) 15 g agar, 3.4 g $KH_2PO_4$, 3.55 g $Na_2HPO_4$, 0.2 g $MgSO_4.7H_2O$, 8 mg $CaCl_2.2H_2O$, 10 mg yeast extract, 1 ml 1000× trace elements solution (Balch, W. E., et al., "Methanogens: reevaluation of a unique biological group," *Microbiol. Rev.* 43:260-296, (1979)), and 1 g D-phenylglycine (D-4-hydroxyphenylglycine).

Isolates are tested by PCR for the presence of a stereoinverting aminotransferase (primers are designed from known D-phenylglycine aminotransferases) or are further enriched for the presence of a stereoinverting aminotransferase as follows: isolates from the plates could be grown in liquid medium as above, without the agar, at 30° C. with shaking to an $OD_{600}$ of about 1.0. The cells are harvested by centrifugation and washed twice with 0.85% NaCl. A 10 mg (wet weight) sample is suspended in 1 ml potassium phosphate buffer (pH 7.0) and 5 mM D-phenylglycine or D-4-hydroxyphenylglycine. Neutralized 15 mM (aminooxy)acetic acid is added to duplicate samples prepared as described above. Consumption of D-phenylglycine (or D-4-hydroxyglycine) is measured by HPLC.

Isolates capable of degrading D-phenlyglycine (or D-4-hydroxyphenylglycine), but do so at a slower rate in the presence of (aminooxy)acetic acid, are selected for further analysis. Isolates are tested, by PCR, for the presence of a stereoinverting aminotransferase (primers are designed from known D-phenylglycine aminotransferases).

The presence of the stereoinverting aminotransferase is confirmed by growing a culture in a liquid medium as described above, harvesting the cells and making a cell-free crude extract ("CFE") and testing for D-phenylglycine aminotransferase or D-4-hydroxyphenylglycine aminotransferase enzyme activity. CFE is added to a reaction mixture with the following final concentrations: 0.1 M 3-(cyclohexylamino)-1-propanesulfonic acid ("CAPS") (pH 9.5), 60 mM L-glutamate (sodium salt), 5 mM benzoylformate or 4-hydroxybenzoate and 50 µM PLP.

The reverse reaction is measured by adding CFE to a reaction mixture with the following concentrations: 50 mM potassium phosphate (pH 7.0), 60 mM D-phenylglycine or D-4-hydroxyphenylglycine, 5 mM α-ketoglutarate, and 50 µM PLP. The assays are incubated at 35° C. and aliquots are taken at time points and stopped by boiling for 2 minutes. The product will be quantitated by the HLPC method of Gil-Av, E., et al., "Resolution of underivatized amino acids by reversed phase chromatography," *J. Am. Chem. Soc.*, 102: 5115-5117, (1980), or by the methods described in Example 1 directed to the measurement of glutamate formation.

As an alternative to PCR based methods, the stereoinverting D-phenylglycine aminotransferase is purified from the isolated bacteria by conventional protein purification techniques, including ammonium sulfate fractionation, and conventional column chromatography. Once the protein has been purified to a reasonable degree, peptide microsequencing techniques or conventional Edman type amino acid sequencing are utilized (see http://golgi.harvard.edu/microchem/ for descriptions of the protocols and equipment used for this type of work). Degenerate primers are designed based on the sequence available from the closest known relative of the protein source. Degenerate PCR and genome walking is then performed according to established protocols to isolate the stereoinverting D-phenylglycine aminotransferase coding sequence.

(3) DPGAT Monatin Production

D-hydroxyphenylglycine aminotransferases, as described in (1) and (2) above, are used in crude cell free protein extracts, or purified as described in (1) above. *S. meliloti* and *R. sphaeroides* tyrosine (aromatic) aminotransferases are prepared as described in Example 1 from WO 03/091396 A2. *Comamonas testosteroni* ProA aldolase is prepared as described in Example 4 from WO 03/091396 A2. Total protein assays are done utilizing the Bio-Rad Protein Assay according to manufacturer's protocols (Hercules, Calif.).

Reaction mixtures (1 mL volume, run in duplicate) contain 100 mM potassium phosphate buffer (pH 8), 2 mM $MgCl_2$, 0.05 mM pyridoxal 5'-phosphate ("PLP"), 200 mM sodium pyruvate, 5 mM sodium α-ketoglutarate, approximately 280 µg/mL *S. meliloti* TatA supplied in a cellular extract, 100 µL/mL of D-hydroxyphenylglycine aminotransferase cellular extract or 1 mg/mL purified D-hydroxyphenylglycine aminotransferase, and approximately 100 µg/mL of ProA aldolase provided as a cellular extract. Solid tryptophan is added at a concentration of 10.2 mg/mL. Negative controls are set up without D-hydroxyphenylglycine aminotransferase. The samples are incubated at 30° C. with gentle shaking for ~1 hour or overnight. The samples are centrifuged to remove precipitate, syringe filtered, and stored at −80° C. prior to analysis for monatin using the LC/MS/MS method described in Example 1.

D-hydroxyphenylglycine aminotransferases with improved activity for monatin production are made using mutagenesis techniques known to those in the art, including: mutagenic PCR, passage through mutagenic strains, site-directed mutagenesis, error-prone PCR, or by methods such as DNA shuffling or other directed evolution technologies. The improved D-hydroxyphenylglycine aminotransferases are selected by growth on minimal medium with R,R-monatin as the source of nitrogen. Initially, the selection is based on growth, but as improved aminotransferases are selected, the screen is growth rate based. That is, cells with mutated versions of the gene are grown and the gene is expressed in minimal medium with R,R-monatin as the nitrogen source. The growth rates of the cells with the mutated versions of the gene are compared to the unmutated version. Those cells with a faster growth rate are selected and the aminotransferase is analyzed further. The D-hydroxyphenylglycine aminotransferase may be further mutagenized until the desired activity is obtained.

(4) DPGAT Assay

The un-His-tagged version of the DPGAT was expressed as described in (1) above and extracts were used in assays. Assays were set up and included 100 mM potassium phosphate pH 7.0, 60 mM D-phenylglycine, 5 mM α-ketoglutarate, and 50 µM pyridoxal-5'-phosphate. The assays were started by adding 100 µL of extract, prepared as described above in this example, per mL of assay volume. Samples were taken at several time points (0, 1, 2, 5, 10, 30, 60, and 120 minutes) and were stopped with an equal volume of 2 M formic acid. A sample was also taken after overnight incubation (~1200 minutes). The samples were analyzed for glutamate production by the LC/post-column flourescence detection (OPA) method described in Example 1. The results are summarized in Table 57 below.

TABLE 57

| Condition | Time (Minutes) | μmole/mL L-Glutamate |
|---|---|---|
| No substrate | 0 | 0.033 |
| | 1 | 0.033 |
| | 2 | 0.033 |
| | 5 | 0.035 |
| | 10 | 0.034 |
| | 30 | 0.036 |
| | 60 | 0.044 |
| | 120 | 0.038 |
| | ~1200 | 0.058 |
| D-phenylglycine | 0 | 0.055 |
| | 1 | 0.112 |
| | 2 | 0.169 |
| | 5 | 0.315 |
| | 10 | 0.387 |
| | 30 | 0.892 |
| | 60 | 1.304 |
| | 120 | 1.514 |
| | ~1200 | 1.056 |

The enzyme clearly has some activity on the D-phenylglycine. The enzyme activity was also tested on R,R monatin. The assay was set up as described above and R,R monatin was included at a concentration of 60 mM. The results are indicated below in Table 58.

TABLE 58

| Condition | Time (Minutes) | μmole/mL L-Glutamate |
|---|---|---|
| R,R monatin | 0 | 0.041 |
| | 1 | 0.040 |
| | 2 | 0.041 |
| | 5 | 0.041 |
| | 10 | 0.041 |
| | 30 | 0.042 |
| | 60 | 0.041 |
| | 120 | 0.040 |
| | ~1200 | 0.045 |

There did not appear to be any detectable activity on R,R monatin. However, it is expected that the random or SDM methods described in this part (3) of this Example could be utilized to improve the transmission activity on R,R monatin or R-MP. For instance, the crystallization and preliminary analysis of the *P. stutzeri* enzyme has been done. Kongsaeree, P., et al., *Acta Cryst.* D59:953-954, (2003). Once the structure is published, docking experiments can be done using software such as Accelrys, to determine where steric hindrances or ionic repulsion may be prohibiting the R,R monatin from binding to the D-hydroxyphenylglycine substrate binding site. D-hydroxyphenylglycine is a somewhat large amino acid, as is R,R monatin. Both compounds have hydrophobic regions and hydroxyl groups. Modifications can be done to the binding pocket, as described in Example 6A, to make the enzyme more amenable to dicarboxylic acid substrates. For instance, a residue near the second carboxyl group may be modified to a base such as arginine. Additionally, The *P. putida* gene described in part (1) and the additional genes that may be isolated as described in (2) can be used as templates for gene shuffling. Additionally, the *P. stutzeri* gene assembled in this Example can be mutagenized using oligonucleotide shuffling or other random mutagenesis methods, and screened as described in (3) above.

Example 11

Discovery of a D-Methionine Aminotransferase Gene

Background

D-methionine-pyruvate aminotransferase (EC 2.6.1.41) is thought to be another example, although rare, of a stereoinverting transaminase. This enzyme catalyzes the reversible conversion of D-methionine and pyruvate to L-alanine and 4-methylthio-2-oxobutanoate. Oxaloacetate, phenylpyruvate, 2-oxobutyrate, 2-oxovalerate, 2-oxoheptanoate, glyoxylate, and oxoglutarate can also serve as amino acceptors. Transamination of D or L methionine is thought to be part of a pathway to ethylene production in higher plants (cauliflower, tomato, apple, pea stem, banana, peanut), as well as in soil microorganisms (*Escherichia coli, Pseudomonas pisi, Pseudomonas aeruginosa, Bacillus mycoides, Acinetobacter calcoaceticus, Aeromonas hydrophila* B12E, *Rhizobium trifolii* N2P7, *Penicillium digitatum, Saccharomyces cerevisiae, Corynebacterium* D7F). Billington, D. C., et al., *Biochem J.* 182:827-836, (1978). In bacteria, L-methionine is typically used as the substrate in the ethylene production studies and broad specificity enzymes such as TyrB or AspC from *E. coli* are thought to be responsible for the transamination. However, Primrose, S. B., *J. Gen. Microbiol.* 95:159-65, (1976) and Primrose, S. B., *J. Gen. Microbiol.* 98:519-528, (1977) showed that *E. coli* strain SPA O (University of Warwick culture collection) produced nearly as much ethylene from D-methionine as from L-methionine in batch cultures. Because no broad specificity D-aminotransferase has been identified in *E. coli*, one possible explanation could be that the *E. coli* D-amino acid dehydrogenase (encoded by the dadA gene) converts the D-methionine to 4-methylthio-2-oxobutanoate. It is also possible that there is a methionine racemase in *E. coli*; however, no such enzyme has been described in the literature.

In contrast to *E. coli*, in cauliflower florets (mitochondrial extract preparations) and germinating peanut seeds production of ethylene was higher when D-methionine and pyruvate were supplied to the enzyme extract as compared to L-methionine and pyruvate. Mapson, L. W., et al., *Biochem J.* 115:653-661, (1969); Durham, J. I., et al., *Phytochemistry* 12:2123-2126, (1973). Therefore, the possibility of a combination of methionine racemase and an L-aminotransferase is not supported by the data. Dehydrogenase activity was ruled out by dialysis of cellular extracts of cauliflower; no NAD was present in the assay mixtures. Oxidase activity was ruled out as no consumption of oxygen was noted and there was no requirement for FAD. The D-methionine aminotransferase from peanut tissues was purified, shown to be dependent on PLP, and shown to be independent of L-methionine aminotransferase activity. There is a possibility that these D-methionine-pyruvate aminotransferases actually produce D-alanine as a byproduct (similar to the *Bacillus* enzymes described in Examples 2 and 3A) and that the cells contain alanine racemase to recycle the D-alanine back to L-alanine (or an analogous amino donor). In either case, discovery of the broad specificity D-aminotransferase from higher plants is advantageous for development of processes that produce R,R monatin or S,R monatin.

Experimental Overview

D-methionine aminotransferase is partially purified from cauliflower florets and germinating peanut embryos using standard chromatography protocols and a Pharmacia AKTA Explorer system. The protein sequences of homologous proteins are determined by LC/MS/MS fingerprinting techniques and database searching performed by Harvard Microchemistry facility. The coding regions of the plant genes are cloned from a cDNA library using standard PCR protocols or by synthesis of the gene as described in Example 10(1).

Alternatively, cDNA expression libraries are constructed (Stratagene, La Jolla, Calif.) from cauliflower tissue or peanut seeds grown in the presence of D-methionine (and producing ethylene). The libraries are transformed into *E. coli* methionine auxotrophs from the *E. coli* Genetic Stock Center (Yale) such as strains RC519 or AB 1931. Plasmids of strains capable of growth on minimal media containing D-methionine contain the coding region of interest (see Example 4A(1), an analogous screening technique).

Once the coding regions of interest are obtained and are expressed in a standard *E. coli* laboratory strain, the resulting gene products can be used in assays to produce R,R monatin, as described in Example 10(3), in place of the D-hydroxyphenylglycine aminotransferase, with the exception of the pH being 7.5 (the optimal pH for the aminotransferase). If the D-methionine aminotransferase has a strict requirement for D-amino acid donor substrates, the enzyme can be used to make R,R monatin as described in Example 2 and 3. The gene can be mutagenized and screened for increased activity as described in Example 10(3).

Methods

Isolation from Cauliflower

Four hundred grams of freshly picked cauliflower florets are extracted with 400 mL of a 4° C. sucrose/buffer solution (0.4 M sucrose and 0.1 M sodium phosphate buffer pH 7.4) by alternating soaking and mixing using a blender. Cell debris is removed by filtration with cheesecloth and the resulting solution is centrifuged at 40,000×g for 30 minutes at 4° C. The solid material (containing mitochondrial organelles) is resuspended in 20 mL 10 mM sodium phosphate buffer pH 7.4 and enzymes are extracted with 200 mL cold (−30° C.) acetone. The suspension is re-centrifuged and the precipitate is dried using a Savant Speed Vac. The solid material is dissolved in 10 mM sodium phosphate buffer pH 7.4 and residual acetone is removed using a PD-10 column.

Aminotransferase activity is assayed by incubation of the enzyme preparation with 5 mM D-methionine, 1 mM pyruvate, 0.05 mM PLP and 2 mM EDTA in 0.1 M sodium phosphate buffer pH 7.4. Assays are performed at 25° C. for 16 hours. The 4-methylthio-2-oxobutanoate is measured by formation of the 2,4-dinitrophenylhydrazone derivative, using LC/MS (m/z of 328) and similar methodology described in Example 1. A 0.4% (w/v) solution of 2,4-dinitrophenylhydrazine in 2 M sulfuric acid is prepared and a half volume is added to the assay mixture after incubation. The mixture is mixed with gentle shaking at 30° C. for 30 minutes and the precipitate is collected by centrifugation and analyzed by LC/MS. Protein fractions separated by standard chromatographic techniques are assayed for activity in a similar manner, but the co-product alanine is measured by the OPA post-column derivatization technique described in Example 1.

Isolation from Peanut (*Arachia hypogea* L. cv. *Starr*)

The D-methionine aminotransferase enzyme from germinating peanut embryo homogenate (minus the cotyledons) is purified according to the method of Durham, J. I., et al., *Phytochemistry* 12:2123-2126, (1973). Reducing agents are used during the preparation of crude extracts to stabilize the enzymes and the cell debris is removed by centrifugation at 33,000×g. A 35-50% ammonium sulfate fraction is further purified by incubation at low temperature and by removal of the proteins in the precipitate. The supernatant is further fractionated using acetone. The active pools are then further purified by gel filtration chromatography (Sephadex 200 G.E. Healthcare, Piscataway, N.J.).

As protein fractions become enriched with the transaminase protein, 2D-gel electrophoresis is utilized to separate the enzyme of interest for microsequencing. After elucidation of homologous coding regions in plant sequences deposited at NCBI, the D-aminotransferase protein is produced recombinantly in *Escherichia coil* using standard molecular biology techniques. It is expected that the cellular extracts from cauliflower florets or peanut seeds or recombinantly produced homologous enzymes can be used in production of R,R monatin as described in Example 10(3) (if a stereoinverting transaminase) or Examples 2 and 3A (if a broad specificity D-aminotransferase).

Example 12

L-Alanine Aminotransferase/Alanine Racemase/D-Alanine Aminotransferase

FIG. 8 illustrates the biosynthetic pathway for producing stereoisomerically-enriched R,R monatin from L-tryptophan using L-amino acid aminotransferases (such as L-aromatic aminotransferases, L-alanine-aminotransferases and/or L-tryptophan-aminotransferases), an R-specific aldolase, an alanine racemase and a D-alanine aminotransferase.

A tryptophan-specific aminotransferase is described in Example 6A. Alternatively, *S. meliloti* and *R. sphaeroides* tyrosine (aromatic) aminotransferases are prepared as described in Example 1 from WO 03/091396 A2. *Comamonas testosteroni* ProA aldolase is prepared as described in Example 4 from WO 03/091396 A2. Total protein assays are done utilizing the Bio-Rad Protein Assay according to manufacturer's protocols (Hercules, Calif.). Alanine racemase is purchased from Sigma (St. Louis, Mo.) (catalog number A8936). D-alanine aminotransferase is purchased from Bio-Catalytics (Pasadena, Calif.) (catalog number AT-103).

L-alanine aminotransferases are widely distributed in eukaryotes, bacteria, and archaea. The following organisms have been identified (based on sequence homology) as containing an L-alanine aminotransferase (EC 2.6.1.2): *Arabidopsis thaliana, Ashbya gossypii, Azotobacter vinelandii, Bifidobacterium longum, Caenorhabditis elegans, Candida albicans, Candida glabrata, Chlamydomonas reinhardtii, Cryptococcus neoformans, Debaryomyces hansenii, Homo sapiens, Hordeum vulgare, Kluyveromyces lactis, Magnaporthe grisea, Medicago truncatula, Mus musculus, Neurospora crassa, Oryza sativa, Phanerochaete chrysosporium, Pinus taeda, Pseudomonas putida, Pyrococcus abyssi, Pyrococcus furiosus, Pyrococcus horikoshii, Rattus norvegicus, Saccharomyces cerevisiae, Schizosaccharomyces pombe, Takifugu rubripes, Trypanosoma cruzi, Vibrio cholerae, Vibrio parahaemolyticus, Vibrio vulnificus, Yarrowia lipolytica,* and *Zea mays*. Additionally, many aminotransferases have low-level alanine aminotransferase activity and given high levels of L-glutamate and pyruvate can convert it to L-alanine and α-ketoglutarate. An enzyme with low activity is improved with standard mutagenesis techniques, such as error-prone PCR and passage through mutagenic strains, or by directed evolution techniques. The gene for an L-alanine aminotransferase is cloned using publicly available sequences to design primers and using standard techniques to amplify, clone, express and purify the gene/enzyme.

The reaction mixtures (1 mL volume, run in duplicate) contain 100 mM potassium phosphate buffer (pH 8), 2 mM $MgCl_2$, 0.05 mM pyridoxal 5'-phosphate ("PLP"), 200 mM sodium pyruvate, 5 mM sodium α-ketoglutarate, approximately 280 μg/mL *S. meliloti* TatA supplied in a cellular extract (or other L-tryptophan specific aminotransferase) (as in Example 4A(5), 100 μg of an L-alanine aminotransferase, 100 μL/mL of alanine racemase cellular extract or 1 mg/mL purified alanine racemase (Sigma), approximately 280 μg/mL of a broad specificity D-alanine aminotransferase supplied in a cellular extract (Examples 15 and 18 have examples of D-aminotransferases that could work for this reaction) and approximately 100 μg/mL of ProA aldolase provided as a cellular extract. Solid tryptophan is added at a concentration of 10.2 mg/mL. Negative controls are set up without alanine racemase. The samples are incubated at 30° C. with gentle shaking for ~1 hour or overnight. The samples are centrifuged to remove precipitate, syringe filtered, and stored at −80° C. prior to analysis for monatin using the LC/MS/MS method described in Example 1.

Example 13

Purification of R,R-Monatin from an Enzymatic Reaction Mixture

The product, R,R-monatin, was purified from the following reaction mixture. In 0.33 liter, 50 mM ammonium bicarbonate, pH 8.2, 4 mM $MgCl_2$, 0.05 mM pyridoxal phosphate ("PLP"), 200 mM sodium pyruvate, and 50 mM D-tryptophan were mixed at room temperature in a 500 mL glass bottle until the tryptophan dissolved. The liquid was flushed with nitrogen for several minutes and then 3.0 mg/mL Biocatalytics, Inc. (Pasadena, Calif.) Broad range D-transaminase (catalog #AT-103) and 0.1 mg/mL purified aldolase of SEQ ID NO:22 were added. The reaction mixture was stirred gently at room temperature. The aldolase was purified as described in Example 3A. Additional aliquots of 50 mM D-tryptophan were added as a solid 15 hours and 22 hours after the mixture was initially prepared. The head space was flushed with nitrogen after each addition. All of the added tryptophan did not dissolve, but the concentration was maintained at about 50 mM. After 40 hours, the remaining solid tryptophan was filtered off. Analysis of the reaction mixture by post column fluorescence detection liquid chromatography (see Example 1) showed that the concentration of tryptophan in the solution was 49 mM and the concentration of monatin was 3.9 mM.

The product monatin was purified utilizing two ion exchange chromatography steps. The filtered reaction solution was first applied to a column of BioRad AG50W-X8 resin (140 mL; binding capacity of 1.7 meq/mL). The column was washed with 2×150 mL $H_2O$ and then eluted with 1 M $NH_4OH$ (1×450 mL, followed by 3×150 mL). The $NH_4OH$ fractions were combined, neutralized with HCl and filtered successively through Whatman (Maidstone, England) glass microfibre filters and Gelman Sciences (Ann Arbor, Mich.) 0.45 μm filters. The clarified solution was then ultrafiltered using an Amicon ultrafiltration stirred cell (Model 8200) with a YM100 (MWCO 100 kDa) (Millipore; Billerica, Mass.). The filtrate from the ultrafiltration was evaporated to approximately 160 mL using a roto-evaporator with a tepid water bath. The liquid was again clarified by filtering through glass microfibre filters.

The resulting solution was applied to a 1 L Fast Flow DEAE Sepharose (Amersham Biosciences) column previously converted to the bicarbonate form by washing with 0.5 L 1 M NaOH, $H_2O$, and 1.0 M ammonium bicarbonate, pH 8.3, followed by an additional washing using $H_2O$. The solution was loaded at <2 mL/min and the column was washed with water at 3-4 mL/min until the absorbance at 280 nm was <1. The R,R-monatin was eluted with 50 mM ammonium bicarbonate, pH 8.3 (2.5 L). This fraction was evaporated using a roto-evaporator with a tepid water bath. The resulting syrup was incubated at 4° C. for several days until crystals formed. The crystals were collected, washed with cold 100% ethanol and dried in a vacuum dessicator (0.38 g).

Analysis of the solid product for isomeric purity using FDAA derivitization, followed by LC/MS/MS multiple reaction monitoring, (see Example 1) showed that the sample was 96.3% R,R monatin and 3.7% S,R-monatin.

The sample was also analyzed for purity with respect to other organic compounds using the total monatin method (see Example 1). The UV absorbance was scanned from 200-500 nm using a Photodiode Array detector. Based upon the integrated peak areas, monatin accounted for 96.1% of the area (including both R,R and S,R peaks).

Analysis of the sample by post column fluorescence detection liquid chromatography showed that the amino acid composition of the sample was 98.8% monatin with trace amounts of tryptophan (1.2%) and alanine (0.02%).

Elemental analysis was performed at Midwest Microlab, LLC (Indianapolis, Ind.). This analysis indicated that the sample contained 1% non-combustible (inorganic) material by weight, and ammonium and bicarbonate residuals.

Example 14

Improvement of D-Aminotransferase Activity Retention During Purification

Standard Procedure for the Purification of *B. sphaericus* $HIS_6$-D-Alanine Aminotransferase Starting from a fresh culture plate (LB agar with 50 μg/mL kanamycin) of BL21(DE3)::*B. sphaericus* dat pET30a (Example 18), the cells were grown in 5 mL of Luria-Bertani broth ("LB") with 50 μg/mL kanamycin, at 37° C. with shaking at 225 rpm for 3-5 hours. Subsequently, the culture was transferred at 0.25% (v/v) into flasks containing Novagen Overnight Express System II solutions 1-6 (EMD Bioscience, Madison, Wis.) plus 50 μg/mL kanamycin. The cells were grown at 37° C. and 225 rpm overnight (16-18 hours). When the $OD_{600}$ was approximately 8.0, the cells were harvested by centrifugation in a Beckman (Fullerton, Calif.) J25II centrifuge with a JS-16.25 rotor at 10,000 rpm for 10 minutes. The cell pellet was washed once with cold 50 mM EPPS buffer (pH 8.2), and the cells were centrifuged again. The washed cell pellet was harvested and used immediately or frozen at −80° C. until needed for purification.

To prepare cell-free extract containing the *B. sphaericus* $HIS_6$-D-alanine aminotransferase ($HIS_6$-BsphDAT) protein, the cells were suspended in 3-4 volumes of 50 mM EPPS, pH 8.2 and then disrupted using a Microfluidics homogenizer (Newton, Mass.) (3 passes at 20,000 psi), maintaining the temperature of the suspension below 15° C. All subsequent purification steps were carried out at 4° C. The cell extract was centrifuged for 15 minutes at 15,000×g to remove the cell debris. The supernatant was decanted and used immediately or frozen at −80° C. An aliquot of the cell free extract was applied either to Novagen HIS-Bind columns (catalog #70971-4) or to a column of GE Healthcare Chelating Sepharose™ Fast Flow resin (nickel(II) form) (Piscataway, N.J.) (at a ratio of 1.2-1.5 v/v) that had been previously equilibrated with 50 mM EPPS, pH 8.2, containing 200 mM sodium chloride. After loading the sample, the column was washed/eluted successively with 3-5 volumes of the equilibration buffer, 3-5 volumes of the equilibration buffer containing 25 mM imidazole, 3-5 volumes of the equilibration buffer containing 50 or 100 mM imidazole and 3-5 volumes of the equilibration buffer containing 500 mM imidazole. The HIS$_6$-BsphDAT protein eluted in the last wash. The 500 mM imidazole wash was concentrated 2-10× with Amicon Centricon-70 or Ultra-15 centrifugal filter devices (MWCO 5-10 kDa) (Billerica, Mass.). The imidazole and sodium chloride were removed by passage through disposable GE Healthcare PD10 desalting columns previously equilibrated with 50 mM EPPS, pH 8.2, containing 50 µM PLP.

The protein concentration of the desalted solution was determined using the Pierce BCA assay kit (Rockford, Ill.). The purity of each fraction and the level of expression in the cell free extract fraction were determined using a Bio-Rad Experion Pro260 microcapillary chip system (Hercules, Calif.) or by SDS-PAGE with 4-15% gradient gels. Typically, this procedure produces more than 300 mg of enzyme (from 600 mL of Overnight Express II culture) that is ~90% pure as judged by the Experion software. Aliquots (1-5 mL) of the purified enzyme were stored at –80° C. until use.

Improved Procedure

Cell-free extract was prepared as described above. His$_6$-BsphDAT protein was similarly purified with the following changes: all buffers used for cell disruption and protein purification contained 100 mM potassium phosphate, pH 7.8, with 50 µM PLP. The protein was purified exclusively with GE Healthcare Chelating Sepharose™ Fast Flow resin (nickel(II) form).

Activity Assay

The formation of indole-3-pyruvate and alanine from tryptophan and pyruvate was assayed using the enzyme prepared by both purification procedures. The reaction mixtures contained 100 mM potassium phosphate, pH 7.8, 0.05 mM pyridoxal phosphate (PLP), 100 mM sodium pyruvate, 40 mM D-tryptophan, and 0.03-0.1 mg/mL of purified enzyme. The tryptophan was added as a solid. All components except the enzyme were mixed together and incubated at 30° C. until the tryptophan dissolved. The enzyme was then added and the reaction solution was incubated at room temperature. At predetermined time points, the reactions were sampled and the samples immediately stored on ice and diluted for alanine analysis by the post-column fluorescence detection liquid chromatography method described in Example 1. Table 59 below lists the specific activity of the enzyme preparations as the concentration of alanine formed per mg of enzyme per minute.

TABLE 59

Effect of Improved Purification Procedure on Enzyme Activity

| Enzyme Preparation | Specific Activity (µmole Alanine(mg)$^{-1}$(min)$^{-1}$) |
|---|---|
| HIS$_6$-BsphDAT purified without 50 µM PLP | 2.9 |
| HIS$_6$-BsphDAT purified with 50 µM PLP | 14.2 |

The results shown in Table 59 indicate that the use of pyridoxal phosphate (PLP) during the purification process resulted in an enhanced activity.

Example 15

Cloning of Two Novel *Bacillus* D-Amino Acid Aminotransferases

Several *Bacillus* D-amino acid aminotransferases (EC 2.6.1.21, also known as D-alanine aminotransferase or D-aspartate aminotransferase) were produced recombinantly for use in coupled assays for production of R,R monatin, as described in Example 18. These enzymes are homologous to D-aminotransferases described previously for production of monatin (U.S. Publication No. 20040063175 and U.S. Publication No. 2005282260). An approach used for the selection of strains that could be candidates containing novel D-amino acid aminotransferases ("DAATs") was to review the list of *B. sphaericus* strains deposited in ATCC and analyze some that were previously deposited under different species names. The following organisms were ordered from the ATCC: ATCC 4978—*Bacillus sphaericus* originally deposited as *Bacillus rotans* and ATCC 7063—*Bacillus sphaericus* originally deposited as *Bacillus serositidis* and ATCC 21538—*Bacillus sphaericus* originally deposited as *Bacillus circulars*. Known DAAT protein sequences from *Bacillus sphaericus*, *Bacillus halodurans*, *Geobacillus stearothermophilus*, *Bacillus cereus*, *Bacillus subtilis*, and *Bacillus licheniformis* were aligned to obtain sequence regions that were conserved in the various DAAT proteins. Primers were designed in the regions of protein sequence conservation and used for polymerase chain reactions ("PCR") amplification of DAAT gene sequences from the ATCC strains mentioned above.

Five PCR primers were designed based on conserved regions in alignment of published *Bacillus* DAAT sequences (see alignment in FIG. 9).

Polymerase Chain Reaction Protocol

Primers were designed as mentioned above based on conserved regions in an alignment of DAATs. Oligonucleotide Primer Sequences are indicated below:

```
5'-GAAGACCGTGGTTATCAAATTT-3'   (SEQ ID NO: 65)
(forward primer),

5'-GATGGTATTTACGAAGTAATC-3'    (SEQ ID NO: 55)
(forward primer),

5'-AGATTTAATATCACAACGTAAC-3'   (SEQ ID NO: 67)
(reverse primer),

5'-GCCAAGTAAAATTTAAGATTTA-3'   (SEQ ID NO: 68)
(reverse primer),

5-ATTTGCTGGGTGCGTATAAAG-3'     (SEQ ID NO: 69)
(reverse primer).
```

Expected sizes of PCR fragments based on primer combinations alignment with known DAATs: SEQ ID NO:65 and SEQ ID NO:67—approximately 380 bp; SEQ ID NO:65 and SEQ ID NO:68—approximately 395 bp; SEQ ID NO:65 and SEQ ID NO:69—approximately 534 bp; SEQ ID NO:66 and SEQ ID NO:67—approximately 336 bp; SEQ ID NO:66 and SEQ ID NO:68—approximately 346 bp; SEQ ID NO:66 and SEQ ID NO:69—approximately 510 bp.

Combinations of the above primers were used for colony PCR from the following ATCC strains: ATCC 4978—*Bacillus sphaericus*, originally deposited as *Bacillus rotans*; ATCC 7063—*Bacillus sphaericus*, originally deposited as *Bacillus serositidis*; and ATCC 21538—*Bacillus sphaericus*, originally deposited as *Bacillus circulans*.

The three above mentioned strains were grown on nutrient agar at 30° C. A single colony was scraped from plates and resuspended in 25 µL sterile distilled water. The cells were lysed at 96° C. for 10 minutes. PCR was carried out as follows: per 50 µL reaction, 5 µL lysed cells, 0.8 µL of each primer, 2 µL dNTPs, 0.8 µL Expand High Fidelity Polymerase (Roche, Indianapolis, Ind.) and 1× Expand™ buffer were added. A 3 minute hot start was done at 94° C., followed by 15 cycles of 94° C. for 30 seconds, 40° C. for 45 seconds, and 72° C. for 2 minutes. Fifteen more cycles were done with an increased annealing temperature of 45° C. Lastly, a chain extension step was done for seven minutes at 72° C. Several primer combinations gave expected PCR product sizes for the above strains. PCR products were cloned using the Zero Blunt TOPO® cloning kit as per manufacturers' protocols (Invitrogen) and sequenced by dideoxy chain termination DNA sequencing at Agencourt BioScience Corporation (Beverly, Mass.). Sequences at both the DNA and amino acid level were aligned with the B. sphaericus DAAT sequence. Valid DAAT/DAT sequences were obtained from all three strains, ATCC 4978, ATCC 7063 and ATCC 21538. Two specific strains, ATCC 4978 and ATCC 7063 gave PCR products which when translated yielded protein sequences with distinct amino acid residue changes when compared to the *B. sphaericus* D-aminotransferase sequence.

Genome walking was carried out to obtain the complete gene sequences for the ATCC 4978 and ATCC 7063 strains. Strain ATCC 4978 was grown up in nutrient broth at 30° C. Strain ATCC 7063 was grown up on nutrient agar. Genomic DNA was prepared from each strain using the Gentra Kit (Gentra Systems, Minneapolis, Minn.) as per manufacturer's protocols. Four libraries were constructed for each strain as per manufacturer's protocols (BD GenomeWalker™ Universal Kit, Clontech, www.Clontech.com). Gene-specific primers were designed as per GenomeWalker™ manufacturer's protocols based on sequences obtained using conserved primer combinations (see above), allowing for a few hundred homologous base pair overlap with original product. These gene-specific primers were subsequently used with GenomeWalker™ adaptor primers for PCR of upstream and downstream sequences to complete DAT ORFS.

The gene-specific oligonucleotide primer sequences are indicated below:

```
                                          (SEQ ID NO: 70)
4978 DAT GSP1 5'-GACATGCTCCTCCGCTGTAAATAATTCACC-3';
Upstrm (SEQ ID NO: 71)
4978 DAT GSP1 5'-CCCTGGTGATGAAGTGAAGCCAGTATTAAC-3';
Dwnstr (SEQ ID NO: 72)
4978 DAT GSP2 5'-ATCGCCAAATTGATAACCACGGTCTTC-3';
Upstrm (SEQ ID NO: 73)
4978 DAT GSP2 5'-ACGTCCCGTAGCAAACTTTGAAAAAGGTGT-3';
Dwnstr (SEQ ID NO: 74)
7063 DAT GSP1 5'-TGCATAGAATCGGTCGATATGTTCAGTAGC-3';
Upstrm (SEQ ID NO: 75)
7063 DAT GSP1 5'-GCGGAGAAACGATTACAGAAGGTTCTTCAA-3';
Dwnstr (SEQ ID NO: 76)
7063 DAT GSP2 5'-GTCACCAAATTGATAACCACGGTCTTC-3';
Upstrm
and (SEQ ID NO: 77)
7063 DAT GSP2 5'-GGTGTACTTTATACGCACCCAGCAAAT-3'.
Dwnstr
```

Adaptor oligonucleotide primer sequences:

```
AP1  5'-GTAATACGACTCACTATAGGGC-3'  (SEQ ID NO: 78)
and

AP2  5'-ACTATAGGGCACGCGTGGT-3'.    (SEQ ID NO: 79)
```

Primary GenomeWalker™ PCRs were carried out as follows: per 50 μL reaction, 2.5 μL of DNA library, 2 μL of each primer (AP1 (SEQ ID NO:78) and the appropriate GSP1), 1.5 μL dNTPs, 1× XL PCR buffer, 1 mM magnesium acetate, and 1 μL $RT^{TH}$ polymerase (Roche, Indianapolis, Ind.) were added. A 3 minute hot start was done at 94° C., followed by 10 cycles of 94° C. for 30 seconds, 55° C. for 30 seconds, and 68° C. for 1 minute. Twenty more cycles were done with a decreased annealing temperature of 48° C. Lastly, a chain extension step was done for seven minutes at 68° C. Secondary Genome Walker™ PCRs were carried out as follows: per 50 μL reaction, 1.0 μL (of a 1:50 dilution) of the primary PCR reaction, 2 μL of each primer (AP2 (SEQ ID NO:79) and the appropriate GSP2), 1.5 μL dNTPs, 1× XL PCR buffer, 1 mM magnesium acetate, and 1 μL $RT^{TH}$ polymerase were added. A 3 minute hot start was done at 94° C., followed by 10 cycles of 94° C. for 30 seconds, 55° C. for 30 seconds, and 68° C. for 1 minute. Fifteen more cycles were done with a decreased annealing temperature of 48° C. Lastly, a chain extension step was done for seven minutes at 68° C.

Several libraries gave PCR products ranging in size from ~200 bp to ~1.5 Kb. PCR products were TOPO cloned (as above) and sequenced by dideoxy chain termination DNA sequencing at Agencourt BioScience Corporation (Beverly, Mass.); these new sequences were aligned with initial sequences obtained using conserved primer combinations and start and stop codons were identified. In this way the DAAT complete ORFs were obtained. New primer pairs were designed (with restriction sites for cloning) based on the specific complete DAAT sequences to PCR the entire DAAT gene from ATCC strains 4978 and 7063 individually.

Oligonucleotide Primer Sequences are indicated below:

```
ATCC4978DAATNde1F
                                         (SEQ ID NO: 80)
5'-GGCCTTGGCATATGAGTTATAGCTTATGGAATGACC-3';

ATCC4978DAATBamH1R
                                         (SEQ ID NO: 81)
5'-GGCCTTAAGGATCCTTATGCGCGAATACCTTTTGGG-3';

ATCC7063DAATNde1F
                                         (SEQ ID NO: 82)
5'-GGCCTTGGCATATGAGCTACACTTTATGGAATGA-3';
and ATCC7063DAATBamH1R2a
                                         (SEQ ID NO: 83)
5'-GGCCAAGGATCCGCTACCCACTAATCATTAGA-3'.
```

The coding regions of the ATCC 4978 and ATCC 7063 DAAT genes were amplified using the following PCR protocol. In a 50 μL reaction, 3 μL genomic DNA, 0.8 μL of each primer, 2 μL dNTPs, 0.8 μL Expand High Fidelity Polymerase (Roche, Indianapolis, Ind.), 1× Expand™ buffer with Mg, and 0.2 μL Pfu polymerase (Stratagene, La Jolla, Calif.) were added. The thermocycler program used included a hot start at 94° C. for 3 minutes, followed by 8 repetitions of the following steps: 94° C. for 30 seconds, 50° C. for 30 seconds, and 72° C. for 90 seconds. Twenty-two subsequent cycles were done with an annealing temperature of 58° C. Lastly, a chain extension step was done for seven minutes at 72° C.

Clean PCR products of the correct size (approximately 850 bp) were obtained for both strains.

The PCR products for ATCC 4978 and ATCC 7063 DAAT genes were purified using the Qiagen QIAquick® PCR purification kit (Qiagen, Valencia, Calif.), and digested with Nde I and BamH I in BamH I buffer (New England Biolabs, Ipswich, Mass.). Nde I and BamH I digested vectors (pET28 and pET30) and insert were purified using the Qiagen QIAquick® Gel Extraction Kit (Qiagen, Valencia, Calif.). The ligations were done using the Roche Rapid DNA Ligation Kit (Roche, Indianapolis, Ind.) and purified using the QIAquick® PCR purification kit. The ligations were transformed into *Escherichia coli* DH10B using a 0.2 cm cuvette and a Bio-Rad Gene Pulser® II system as described in the Bio-Rad electroporation manual. The cells were allowed to recover in 900 µL SOC medium for 30 minutes at 37° C. with shaking at 225 rpm. The cells were plated on LB-agar plates containing kanamycin (50 µg/mL). The plasmid DNA was purified using the Qiagen spin miniprep kit (Qiagen, Valencia, Calif.) and screened for the correct inserts by PCR and restriction digestion with Nde I and BamH I. The sequences of plasmids that appeared to have the correct insert were verified by dideoxy chain termination DNA sequencing at Agencourt BioScience Corporation (Beverly, Mass.). Sequence analyses verified the coding sequence for DAAT genes from ATCC 4978 and ATCC 7063, which produced the DNA sequences of SEQ ID NO:84 (ATCC 4978 DAAT DNA sequence) and SEQ ID NO:85 (ATCC 7063 DAAT DNA sequence) and the amino acid sequence of SEQ ID NO:86 (ATCC 4978 DAAT amino acid sequence) and SEQ ID NO:87 (ATCC 7063 DAAT amino acid sequence).

The alignments of the two novel DAATs from ATCC 4978 and ATCC 7063 with the *B. sphaericus* DAAT (cloned in Example 18) shown in FIG. 10.

We obtained novel D-aminotransferases from strains ATCC 4978 and ATCC 7063 with protein sequences that have distinct amino acid residue changes when compared to the *B. sphaericus* D-aminotransferase. The DAATs from ATCC 4978 and ATCC 7063 have only 72% and 67% identity with the DAAT from *B. sphaericus* (ATCC 10208). While both of these strains are currently listed as *B. sphaericus* in the ATCC, they were deposited as *B. rotans* and *B. serositidis*. Based on the sequence alignments and the highlighted differences between these two novel DAATs and the DAAT from *B. sphaericus*, a number of candidate residues are identified that can be evaluated for their role (individually or in combination) in increasing DAAT activity for R,R monatin biosynthesis, in these, as well as other DAAT sequences.

Example 16

Gene Expression and Assays for ATCC 4978 and ATCC 7063 DAAT Proteins

The novel DAATs from ATCC 4987 and ATCC 7063, as described in Example 15, (in pET vectors) were transformed into the *E. coli* expression host BL21(DE3) (Novagen, Madison, Wis.). The cultures were grown using the protocols described above and the plasmids were isolated using Qiagen miniprep kit (Qiagen, Valencia, Calif.) and analyzed by restriction digestion, as described above, to confirm plasmid identity.

Induction of the DAAT gene was typically performed in LB medium containing kanamycin (50 μg/mL). The cells were grown to an $OD_{600}$ of 0.4-0.8 at 37° C., induced with 0.1 mM IPTG (isopropyl thiogalacatoside) and sampled at 3-4 hours post induction. Cell extracts were prepared according to the protocol accompanying the Novagen BugBuster™ reagent (with benzonase nuclease and Roche complete protease inhibitor cocktail added). Soluble proteins were obtained at the predicted molecular weight, as judged by SDS-PAGE, for both ATCC 4978 and ATCC 7063 gene products in pET vectors. Higher levels of soluble protein were observed using constructs without His tags (pET 30). Soluble proteins in the cellular extracts were separated on a BioRad Laboratories Experion Automated Electrophoresis Station (Hercules, Calif.) and analyzed for concentration and percent expression using the Experion Software version 1.1.98.0.

Protein extracts from cells with untagged (pET30) constructs were analyzed for D-aminotransferase activity by following production of alanine from pyruvate and D-tryptophan (or R,R monatin) using the following protocol. Duplicate 500 μL reactions were, unless specified below, carried out in 100 mM potassium phosphate buffer (pH 7.5), 80 μM pyridoxal phosphate, 25 mM sodium pyruvate, and 50 mM D-tryptophan or R,R monatin. The reactions were initiated by the addition of cell free extracts (4978 or 7063) or purified enzyme (*B. sphaericus*) and were incubated 15 minutes-2 hours at 30° C., with mild shaking. Approximately the same level of total protein was added (1.0 mg), unless specified below, in each assay for comparative purposes. Purified *B. sphaericus* (ATCC number 10208) aminotransferase was used as a benchmark enzyme. Formic acid was added to a final concentration of two percent to stop the reaction and the precipitated protein was removed by centrifugation. Control reactions without added protein were also performed. Alanine was detected using LC/OPA post-column derivatization as described in Example 1. The averaged results of the duplicate reactions are shown in Tables 60 and 61 below.

TABLE 60

Transamination Activity of ATCC 4978 and ATCC 7063 D-Aminotransferases (15 min)

| D-aminotransferase | Alanine (mM) D-Tryptophan as Substrate | Alanine (mM) R,R Monatin as Substrate |
|---|---|---|
| ATCC 4978 | 7.78 | 0.32 |
| ATCC 7063 | 0.28 | 0.025 |
| *B. sphaericus* (untagged) | 11.93 | 3.57 |

TABLE 61

Transamination Activity of ATCC 4978 and ATCC 7063 D-Aminotransferases (2 Hours)

| D-aminotransferase | Alanine (mM) D-Tryptophan as Substrate | Alanine (mM) R,R Monatin as Substrate |
|---|---|---|
| ATCC 4978 | 16.46 | 2.33 |
| ATCC 7063 | 2.51 | 0.21 |
| *B. sphaericus* (untagged) | 13.73 | 12.23 |

Thus, we demonstrated that the D-amino acid aminotransferases from ATCC 4978 and ATCC 7063 indeed possessed D-aminotransferase activity and have the capability to make R,R monatin. The activity of the ATCC 4978 DAAT was higher than that observed for the ATCC 7063 DAAT. Quantitative comparison between 4978 and *B. sphaericus* could not be made since 4978 was unpurified.

Example 17

Production of R,R Monatin using the DAAT from ATCC 4978

The aminotransferase from ATCC 4978 was also tested for the ability to produce monatin from D-tryptophan (as in Example 3A). The following were added per 1 mL of reaction mixture: approximately 50 μg aldolase (*C. testosteroni* ProA aldolase or the aldolase of SEQ ID NO:22, purified), 4 mM $MgCl_2$, 50 mM D-tryptophan (supplied as solid), 1.0 mg D-aminotransferase, 100 mM sodium pyruvate, 100 mM potassium phosphate buffer pH 7.5, and 0.05 mM PLP. Experiments were run in duplicate, with negative controls in which no aminotransferase was added. Samples were incubated for various lengths of time at 30° C. with gentle shaking. The only stereoisomers detected when producing monatin using these methods are R,R and S,R. The total monatin and percent R,R monatin were detected as described in Example 1 are listed in Tables 62-64 below. The results shown in each of Tables 62-64 is the average value from duplicate reactions.

TABLE 62

Comparison of *B. sphaericus* and ATCC 4978 D-Aminotransferases for Production of Monatin using Approximately 50 μg *C. testosteroni* ProA

| D-Aminotransferase | Total Monatin (mg per g DAT protein) 15 Minutes | Total Monatin (mg per g DAT protein) 30 Minutes | Total Monatin (mg per g DAT protein) 1 Hour | Total Monatin (mg per g DAT protein) 2 Hours |
|---|---|---|---|---|
| ATCC 4978 | 419.3 | 598 | 1017 | 1348 |
| *B. sphaericus* (tagged) | 46.5 | 128 | 232 | 241 |

TABLE 63

Comparison of *B. sphaericus* and ATCC 4978 D-Aminotransferases for Production of Monatin using Approximately 50 μg *C. testosteroni* ProA

| D-Aminotransferase | % R,R Monatin 15 Minutes | % R,R Monatin 30 Minutes | % R,R Monatin 1 Hour | % R,R Monatin 2 Hours |
|---|---|---|---|---|
| ATCC 4978 | 48.9 | 38.4 | 34.4 | 33.25 |
| *B. sphaericus* (tagged) | 72.3 | 63.4 | 56.1 | 53.5 |

TABLE 64

Comparison of *B. sphaericus* and ATCC 4978 D-Aminotransferases for Production of Monatin using Approximately 50 μg of the Aldolase of SEQ ID NO: 22

| D-Aminotransferase | Total Monatin (mg per g DAT Protein) 2 Hours | % R,R Monatin 2 Hours |
|---|---|---|
| ATCC 4978 | 501 | 92.1 |
| *B. sphaericus* (tagged) | 201 | 95.6 |

Thus, we demonstrated that the D-amino acid aminotransferase from ATCC 4978 has the capability to make R,R monatin. The activity of the ATCC 4978 DAAT, when comparing total monatin production in terms of mg monatin per gram protein, was higher than that observed for the *B. sphaericus* DAAT. The use of an R-specific aldolase of SEQ ID NO:22 clearly made an improvement in percentage of R,R monatin formed in comparison to the amount of total monatin produced.

Example 18

Cloning of Published *Bacillus* D-Amino Acid Aminotransferases

Several *Bacillus* D-amino acid aminotransferases (EC 2.6.1.21, also known as D-alanine aminotransferase or D-aspartate aminotransferase) were produced recombinantly for use in coupled assays for production of R,R monatin. These enzymes are homologous to D-aminotransferases described previously for production of monatin (U.S. Publication No. 20040063175 and U.S. Publication No. 2005282260).

Strains

*B. sphaericus* (ATCC number 10208) and *B. licheniformis* (ATCC 10716) were grown on Nutrient Agar at 30° C. overnight. Groups of colonies were placed in 100 μL of sterile water and heated for 5 minutes at 95° C. to disrupt the cells. Three μL was used in subsequent Polymerase Chain Reaction ("PCR") amplifications. Genomic DNA was ordered for *B. halodurans* (ATCC number BAA-125D) and resuspended in water to a concentration of 100 ng/μL. *Bacillus cereus* genomic DNA (ATCC numbers 1-987D and 14579D) was ordered for cloning as well.

Polymerase Chain Reaction Protocol

Primers were designed for the *B. sphaericus* dat gene for cloning into pET 28b and pET 30a vectors (Novagen, Madison, Wis.), using the Nco I and BamH I sites. The pET30 construct contains an N-terminal His-tag and S-tag, whereas the pET 28 construct is untagged.

*Bacillus sphaericus* dat primers:

```
                                      (SEQ ID NO: 88)
N term   5'-GATATACCATGGCATACTCATTATGGAATG-3'
and (SEQ ID NO: 89)
C term   5'-GTTATCGGATCCTTAGGCATTAATTGAAATTG-3'.
```

The *B. licheniformis* primers and *B. halodurans* primers were designed for cloning into pET 28b and pET 30a vectors using Nde I and BamH I sites. The pET30 constructs were untagged in this case, whereas the pET 28 constructs contain a small N-terminal his-tag.

*B. licheniformis* Dat Primers:

```
                                      (SEQ ID NO: 90)
N term   5'-GGCCGGTTCATATGAAAGTTCTTTTTAACGGC-3'
and (SEQ ID NO: 91)
C term   5'-CCTTCCGGATCCTTAAACCGTTTTGGCTGTCT-3'.
```

*B. halodurans* Primers:

```
                                      (SEQ ID NO: 92)
N term   5'-GATATACATATGGATTATTGCCTTTACCAA-3'
and
```

```
                                              (SEQ ID NO: 93)
C term  5'-GAATCCGGATCCTCACTGCTTCATCGCTGTTTG-3'.
```

Primers were designed for the *B. cereus* coding sequences. One set of primers yielded the sequence listed in NCBI as accession AE016877 gi:29899096 5138634 . . . 5139506 (873 bp). One set of primers yielded a product with an additional 12 bp upstream, similar to the *B. thuringiensis* predicted dat NCBI accession number AE017355 gi:49328240 4965653 . . . 4966537 (885 bp). Both sets of primers were designed with Nde I for the N-terminal region and BamH I restriction site for the C-terminal region. The primers were designed for cloning into pBAD-TOPO TA cloning.

*B. cereus* Primers:

```
                                         (SEQ ID NO: 94)
N term     5'-TAAGAGGAATAACATATGGCATACGAAAGATTT-3'
and (SEQ ID NO: 95)
C-term     5'-GAATTCGGATCCTTAAGAAGATGACATATTGG-3'
           (shorter PCR product).

(SEQ ID NO: 96)
N term     5'-TAAGAGGAATAACATATGGGATCGAAATTGGCA-3'
           (longer PCR product).
```

The coding regions of the *B. sphaericus, B. halodurans*, and *B. licheniformis* dat genes were amplified using the following PCR protocol. In a 50 μL reaction, 3 μL template (2 μL for genomic DNA), 1.6 μM of each primer, 0.25 mM each dNTP, 3.5 U Expand High Fidelity Polymerase (Roche, Indianapolis, Ind.), and 1× Expand™ buffer with Mg were used. The thermocycler program used included a hot start at 94° C. for 3 minutes, followed by 8 repetitions of the following steps: 94° C. for 30 seconds, 52° C. for 30 seconds, and 72° C. for 2 minutes. Twenty-two subsequent cycles were done with an annealing temperature of 58° C. After 30 cycles the sample was maintained at 72° C. for 7 minutes and then stored at 4° C. Clean PCR products of the correct size were obtained (approximately 850 bp for the dat gene).

*Geobacillus stearothermophilus* dat (accession number J04460 gi:142541), which codes for protein accession number AAA22252 (gi:142542) was constructed using assembly PCR techniques. The source of this gene/protein is often described as *Bacillus* sp., thermostable *Bacillus* species, or *Bacillus* YM-1. The assembly process is as follows: 43 oligonucleotides (40 mers) were ordered from IDT based on the gene sequence above and its complementary DNA sequence with 20 basepair overlaps between the sense and antisense strands. The primers were diluted to 250 μM in water and 5 μL of each primer was mixed together in a microfuge tube. PCR was carried out as follows: per 100 μL reaction, 1.5 μL of the primer pool, 4 μL dNTPs, 1× XL PCR buffer, 1 mM magnesium acetate, 2 μL rTth polymerase (Roche, Indianapolis, Ind.), and 0.25 μL Pfu polymerase (Stratagene, La Jolla, Calif.) were added. A 3 minute hot start was done at 94° C., followed by 15 cycles of 94° C. for 30 seconds, 40° C. for 30 seconds, and 68° C. for 15 seconds. Ten more cycles were done with an increased annealing temperature of 44° C. and an extension time of 30 seconds (at 68° C.). Ten more cycles were performed at an annealing temperature of 48° C. and an extension time of 75 seconds. Lastly, a chain extension step was done for seven minutes at 68° C. A secondary PCR was done using the following primers, designed for cloning with Nde I (N-term) and BamH I (C-term):

```
                                         (SEQ ID NO: 97)
N-term   5'-GGCCTTGGCATATGGGATACACTTTATGGAATGACC-3'
and (SEQ ID NO: 98)
C-term   5'-TTGGAACCGGATCCTTATATATGAAGCGGTTTTGG-3'.
```

The second PCR reaction contained per 100 μL, 2.5 μL of the primary reaction, 0.4 μL of each primer, 3 μL dNTPs, 1× XL PCR buffer, 1 mM magnesium acetate, 2 μL rTth polymerase, and 0.25 μL Pfu polymerase. A 3 minute hot start was done at 94° C., followed by 10 cycles of 94° C. for 30 seconds, 42° C. for 30 seconds, and 68° C. for 90 seconds. Fifteen more cycles were done with an increased annealing temperature of 48° C. Lastly, a chain extension step was done for seven minutes at 68° C. A third PCR reaction was done using template from the second PCR using the same conditions as the second PCR reaction. A product of approximately 900 bp was visible on an agarose gel.

Cloning

The PCR product for *B. sphaericus* DAT was purified using the Qiagen QIAquick® PCR purification kit (Qiagen, Valencia, Calif.) and digested with BamH I and Nco I in BamH I buffer (New England Biolabs, Ipswich, Mass.). The digested vectors (pET28 and pET30) and insert were purified using the Qiagen QIAquick® Gel Extraction Kit (Qiagen, Valencia, Calif.). The ligations were done using the Roche Rapid DNA Ligation Kit (Roche, Indianapolis, Ind.) and purified using the QIAquick® PCR purification kit. The ligations were transformed into *Escherichia coli* DH10B using a 0.2 cm cuvette and a Bio-Rad Gene Pulser® II system as described in the Bio-Rad electroporation manual. The cells were allowed to recover in 900 μL SOC medium for 30 minutes at 37° C. with shaking at 225 rpm. The cells were plated on LB-agar plates containing kanamycin (25 μg/mL). The plasmid DNA was purified using the Qiagen spin miniprep kit (Qiagen, Valencia, Calif.) and screened for the correct inserts by restriction digest with BamH I and Nco I. The sequences of plasmids that appeared to have the correct insert were verified by dideoxy chain termination DNA sequencing at Agencourt BioScience Corporation (Beverly, Mass.). Sequencing verified the coding sequence found in NCBI accession number AF081278 Region: 134 . . . 985 (gi: 3513754), which produces a protein with amino acid sequence as listed in accession number AAC33964 (gi: 3513755).

The PCR products for *B. licheniformis* DAT (~850 bp) and *G. stearothermophilus* were gel purified and cloned using the Zero Blunt TOPO® cloning kit as per manufacturers' protocols (Invitrogen). The plasmids were transformed into TOP10 chemically competent cells for initial screening. The plasmid DNA was screened by restriction digest and the sequences were verified to match the coding sequence found in NCBI. For *B. licheniformis*, the sequence matched accession number U26947 region 247 . . . 1098 (gi:857560), which produces a protein with an amino acid sequence as listed in accession number P54692 (gi:1706292), with the exception of one silent mutation at position 429 from A to G. For *G. stearothermophilus*, the sequence matched the accession number listed above. The coding regions were subcloned by restriction digest (Nde I/BamH I), ligated into the pET vectors, and transformed into electrocompetent DH10B cells for amplification.

The PCR product for *B. halodurans* DAT was gel purified, digested with Nde I and BamH I and ligated into pET 28 and pET 30 vectors as above. Amplification of the vector was done in DH10B cells. The miniprep DNA was screened by PCR and the sequence was verified. The gene sequence can be found in accession number NC_002570 (gi:57596592) 2934903 . . . 2935754 coding for a protein with amino acid sequence listed in accession number NP_243677 (gi: 15615374).

The *B. cereus* coding sequences were amplified using a typical PCR protocol and cloned according to manufacturer's protocols (Invitrogen).

Gene Expression and Assays

Plasmid DNA was subcloned into *E. coli* expression host BL21(DE3) (Novagen, Madison, Wis.) for constructs in pET vectors. The cultures were grown and the plasmids were isolated using Qiagen miniprep kit (Qiagen, Valencia, Calif.), and analyzed by restriction digest to confirm identity. Induction was typically performed in LB medium containing kanamycin (50 μg/mL). The cells were grown to an $OD_{600}$ of 0.4-0.8 at 37° C., induced with 0.1 mM IPTG (isopropyl thiogalactatoside) and sampled at 3-4 hours post induction. The cell extracts were prepared according to the protocol accompanying the Novagen BugBuster™ reagent (with benzonase nuclease and Roche complete protease inhibitor cocktail added). High levels of soluble protein were obtained at the predicted molecular weight, as judged by SDS-PAGE, for both *B. halodurans* gene products, both *B. sphaericus* gene products, both *G. stearothermophilus* gene products, and the untagged *B. licheniformis* gene product. For reactions in which purified protein was used, the His-tagged gene products were purified using His-Bind cartridges following manufacturer's protocols (Novagen, Madison, Wis.). The eluent fractions were desalted on PD-10 (Amersham Biosciences, Piscataway, N.J.) columns and eluted in 25-100 mM potassium phosphate buffer, pH 7.5. Total protein assays were done using the Pierce BCA kit (Rockford, Ill.) and percent expression was estimated from SDS-PAGE. Alternatively, the soluble proteins in the cellular extracts were separated on a BioRad Laboratories Experion Automated Electrophoresis Station and analyzed for concentration and percent expression using the Experion Software version 1.1.98.0. The pBAD-TOPO constructs containing the *B. cereus* genes were expressed as recommended by Invitrogen, but the levels of expression of the DAATs was such that the recombinant protein could not be distinguished from the other proteins during SDS-PAGE analysis.

The cell extracts were analyzed for D-aminotransferase activity by following production of alanine from pyruvate and D-tryptophan (or R,R monatin) using the following protocol. Duplicate one mL reactions were typically carried out in 100 mM potassium phosphate buffer (pH 7.5), 50 μM pyridoxal phosphate, 25 mM sodium pyruvate, and 50 mM D-tryptophan or R,R monatin. The reactions were initiated by the addition of cell free extracts or purified enzyme and were incubated 15 minutes-overnight at 30° C., with mild shaking. Approximately the same level of D-aminotransferase was added (typically around 0.5 mg) in each assay for comparative purposes. AT-103 (BioCatalytics) was used as a positive control (or benchmark). Formic acid was added to a final concentration of two percent to stop the reaction and the precipitated protein was removed by centrifugation. Control reactions, without added protein, were also performed. Zero time points were also used as negative controls. Alanine was detected using LC/post-column OPA derivatization as described in Example 1.

The aminotransferases were also tested for their ability to produce monatin from D-tryptophan (as in Example 3A). The following were added per 1 mL of reaction mixture: approximately 50-100 μg aldolase (typically *C. testosteroni* ProA aldolase, purified), 4 mM $MgCl_2$, 50 mM D-tryptophan (supplied as solid), 0.5-2 mg D-aminotransferase, 200 mM sodium pyruvate, 100 mM potassium phosphate buffer pH 7.5, and 0.05 mM PLP. Experiments were run in duplicate, with negative controls in which no aminotransferase was added. The samples were incubated 1 hour, 2 hours, and overnight (17-20 hours) at 30° C. with gentle shaking. The only stereoisomers detected when producing monatin using these methods are R,R and S,R. The percent R,R is listed below and was determined by reversed-phase LC peak area. The results of the transamination activity of *B. sphaericus, B. licheniformis*, and *B. halodurans* D-aminotransferases after 1 hour is shown in Table 65 below. The data was normalized to 0.5 mg of the D-aminotransferase per mL.

TABLE 65

Transamination Activity of *B. sphaericus, B. licheniformis*, and *B. halodurans* D-Aminotransferases

| D-Aminotransferase | Alanine (mM) D-Tryptophan as Substrate | Alanine (mM) R,R Monatin as Substrate |
|---|---|---|
| *B. halodurans* (tagged) | 15.5 | 1.3 |
| *B. halodurans* (untagged) | 17.5 | 1.4 |
| *B. licheniformis* (untagged) | 28.4 | 0.21 |
| *B. sphaericus* (untagged) | 29.0 | 22.5 |
| *B. sphaericus* (tagged) | 17.1 | 12.0 |

The production of monatin using *B. sphaericus, B. licheniformis*, and *B. halodurans* D-aminotransferases is shown in Table 66 below. Each reaction contained approximately 90 μg *C. testosteroni* Pro A. The data for the total monatin produced was normalized to the use of 0.5 mg of the D-aminotransferase.

TABLE 66

Comparison of *B. sphaericus, B. licheniformis*, and *B. halodurans* D-Aminotransferases for Production of Monatin

| D-Aminotransferase | Total Monatin (ppm) 3 Hours | Total Monatin (ppm) Overnight | % R,R 3 Hours | % R,R Overnight |
|---|---|---|---|---|
| *B. halodurans* (tagged) | 3.2 | 13.7 | 100 | 99.3 |
| *B. halodurans* (untagged) | 4 | 15.5 | 100 | 99.3 |
| *B. licheniformis* (untagged) | 0.6 | 8.1 | 100 | 29.3 |
| *B. sphaericus* (untagged) | 279.6 | 577.6 | 61.55 | 65.7 |
| *B. sphaericus* (tagged) | 111.2 | 246 | 61.0 | 63.1 |

The *B. sphaericus* D-aminotransferase (untagged) had the highest activity for production of monatin from D-tryptophan, but the *B. halodurans* enzyme had much higher selectivity for R-MP versus S-MP than the other enzymes, resulting in higher stereopurity of R,R monatin. The *B. cereus* cell extracts did not have detectable amounts of activity under the conditions tested, although the genes may not have been expressed in the hosts chosen.

The *G. stearothermophilus* DAT (untagged, which expressed better) was assayed as above and compared to the purified *B. sphaericus* DAT and AT-103 (BioCatalytics). The results are shown in Tables 67 and 68 below. The transamination activity of *G. stearothermophilus*, AT-103, and *B.* sphaericus D-aminotransferase was tested using 0.5 mg of D-aminotransferase per mL (Table 67).

TABLE 67

Transamination Activity of G. stearothermophilus, AT-103, and B. sphaericus (Purified) D-Aminotransferases

| D-Aminotransferase | Alanine (mM)-15 Minutes D-Tryptophan as Substrate | Alanine (mM)-15 Minutes R,R Monatin as Substrate | Alanine (mM)-2 Hours D-Tryptophan as Substrate | Alanine (mM)-2 Hours R,R Monatin as Substrate |
|---|---|---|---|---|
| AT-103 | 8.91 | 1.21 | 9.47 | 6.13 |
| B. sphaericus (tagged) | 8.91 | 1.65 | 9.53 | 7.17 |
| G. stearothermophilus (untagged) | 2.05 | 0.053 | 8.10 | 0.78 |

TABLE 68

Comparison of G. stearothermophilus, AT-103, and B. sphaericus (purified) for Total Monatin Production

| D-Aminotransferase | Total Monatin (ppm) 2 Hours | Total Monatin (ppm) Overnight | % R,R 2 Hours | % R,R Overnight |
|---|---|---|---|---|
| AT-103 | 450 | 645 | 65.5 | 60.6 |
| B. sphaericus (tagged) | 110 | 175 | 64 | 54 |
| G. stearothermophilus (untagged) | nd | 10 | n/a | 27 |

The native G. stearothermophilus enzyme is clearly less active for monatin transamination than the AT-103 and B. sphaericus enzymes.

Example 19

Creation of a Hybrid D-Aminotransferase

Several Bacillus D-amino acid aminotransferases were described in Examples 18 and 15. Although the G. stearothermophilus enzyme had low transamination activity on monatin, causing less total monatin to be produced from D-tryptophan, it still had structural elements of interest and it is a thermostable enzyme. Therefore, a hybrid protein was created between the higher activity enzyme (B. sphaericus) and the Geobacillus enzyme.

Assembly of Hybrid DAT Coding Sequence

The target protein sequence that was designed is SEQ ID NO:99. SEQ ID NO:100, the coding sequence corresponding to SEQ ID NO:99, was designed based on E. coli codon usage.

The hybrid DAT was constructed using assembly PCR techniques. The assembly process is as follows: 43 oligonucleotides (40 mers) were ordered from IDT based on the gene sequence above and its complementary DNA sequence, with 20 basepair overlaps between the sense and antisense strands. The primers were diluted to 250 µM in water and 5 µL of each primer was mixed together in a microfuge tube. PCR was carried out as follows: per 100 µL reaction, 1.5 µL of the primer pool, 4 µL dNTPs, 1× XL PCR buffer, 1 mM magnesium acetate, 2 µL rTth polymerase (Roche, Indianapolis, Ind.), and 0.25 µL Pfu polymerase (Stratagene, La Jolla, Calif.) were added. A 3 minute hot start was done at 94° C., followed by 15 cycles of 94° C. for 30 seconds, 40° C. for 15 seconds, and 68° C. for 30 seconds. Ten more cycles were done with an increased annealing temperature of 44° C. and an increased annealing time of 30 seconds. Ten more cycles were performed at an annealing temperature of 48° C. and an extension time of 75 seconds. Lastly, a chain extension step was done for seven minutes at 68° C. A secondary PCR was done using the following primers, designed for cloning with Nde I (N-term) and BamH I (C-term):

N-term
(SEQ ID NO: 101)
5'-GGCCTTGGCATATGGGATACACTTTATGGAATGACCA-3'
and

C-term
(SEQ ID NO: 102)
5'-TTGGAACCGGATCCTTAGCTGTTAAGGCTCAGTGGAA-3'

The PCR contained per 100 µL, 2.5 µL of the primary reaction, 3 µL dNTPs, 1× XL PCR buffer, 1 mM magnesium acetate, 2 µL rTth, and 0.25 µL Pfu polymerase. A 3 minute hot start was done at 94° C., followed by 10 cycles of 94° C. for 30 seconds, 42° C. for 30 seconds, and 68° C. for 75 seconds. Fifteen more cycles were done with an increased annealing temperature of 48° C. Lastly, a chain extension step was done for seven minutes at 68° C. A product of approximately 850 bp was visible on an agarose gel.

Cloning

The PCR product was gel purified using the Qiagen QIAquick® Gel Extraction Kit (Qiagen, Valencia, Calif.), and cloned using the Zero Blunt TOPO® cloning kit as per manufacturers' protocols (Invitrogen). The plasmids were transformed into TOP10 chemically competent cells for initial screening by PCR. The plasmid DNA was screened by restriction digest and the DNA sequence was verified.

The plasmid minipreps were digested with BamH I and Nde I (New England Biolabs, Ipswich, Mass.). The digested vectors (pET28 and pET30) and insert were ligated using the Roche Rapid DNA Ligation Kit (Roche, Indianapolis, Ind.) and purified using the Roche High-Pure PCR Product Purification Kit (Roche, Indianapolis, Ind.). The ligations were transformed into Escherichia coli DH10B cells using a 0.2 cm cuvette and a Bio-Rad Gene Pulser® II system as described in the Bio-Rad electroporation manual. The cells were allowed to recover in 900 µL SOC medium for 30 minutes at 37° C. with shaking at 225 rpm. The cells were plated on LB-agar plates containing kanamycin (25 µg/mL). The plasmid DNA was purified using the Qiagen spin miniprep kit (Qiagen, Valencia, Calif.) and screened for the correct inserts by restriction digest with BamH I and Nde I.

Gene Expression and Assays

Plasmid DNA was transformed into E. coil expression host BL21(DE3) according to manufacturers' protocols (Novagen, Madison, Wis.). The cultures were grown and the plasmids were isolated using Qiagen miniprep kit (Qiagen, Valencia, Calif.) and analyzed by PCR to confirm identity. The induction was performed in LB medium containing kanamycin (50 µg/mL). The cells were grown to an $OD_{600}$ of 0.5 at 37° C., induced with 0.1 mM IPTG (isopropyl thiogalacatoside) and sampled at 3 hours post induction. The cell extracts were prepared according to the protocol accompanying the Novagen BugBuster™ reagent (with benzonase nuclease and Roche complete protease inhibitor cocktail added). High levels of total protein were obtained at the predicted molecular weight, as judged by SDS-PAGE, for both gene products. However, the soluble levels of protein were lower. The untagged version of the gene product expressed better and was assayed as a cellular extract. The soluble proteins in the cellular extracts were separated on a BioRad Laboratories Experion Automated Electrophoresis Station and analyzed for concentration and percent expression using the Experion Software version 1.1.98.0, to normalize the amount of D-aminotransferase used in comparative assays.

The cell extracts were analyzed for D-aminotransferase activity by following production of alanine from pyruvate and D-tryptophan (or R,R monatin) using the following protocol. Duplicate one mL reactions were carried out in 100 mM potassium phosphate buffer (pH 7.5), 50 µM pyridoxal phosphate, 25 mM sodium pyruvate, and 50 mM D-tryptophan or R,R monatin (unless otherwise noted). The reactions were initiated by the addition of cell free extracts or purified enzyme and were incubated 15 minutes-overnight at 30° C., with mild shaking. Approximately the same level of D-aminotransferase was added (0.5 mg) in each assay for comparative purposes (unless otherwise noted). AT-103 (BioCatalytics) or *B. sphaericus* D-aminotransferase (Example 18) was used as a benchmark enzyme. Formic acid was added to a final concentration of two percent to stop the reaction and the precipitated protein was removed by centrifugation. Control reactions without added protein were also performed. Zero time points were also used as negative controls. Alanine was detected using LC/OPA post-column derivatization as described in Example 1. The results of the reactions using 0.5 mg D-aminotransferase per 1 mL reaction volume are shown in Table 69 below.

TABLE 69

Transamination Activity of *B. sphaericus* (purified), *G. stearothermophilus*, and Hybrid D-Aminotransferases

| D-Aminotransferase | Alanine (mM)-15 Minutes D-Tryptophan as Substrate | Alanine (mM)-15 Minutes R,R Monatin as Substrate | Alanine (mM)- 2 Hours D-Tryptophan as Substrate | Alanine (mM)-2 Hours R,R Monatin as Substrate |
|---|---|---|---|---|
| Hybrid DAT (untagged) | 13.5 | 0.084 | 14.2 | 0.54 |
| *B. sphaericus* (tagged) | 13.6 | 4.60 | 13.9 | 10.6 |
| *G. stearothermophilus* (untagged) | 6.6 | 0.18 | 13.5 | 2.2 |

The aminotransferases were also tested for their ability to produce monatin from D-tryptophan (as in Example 3A). The following were added per 1 mL of reaction mixture: approximately 50-100 µg purified *C. testosteroni* ProA aldolase, 4 mM MgCl$_2$, 50 mM D-tryptophan (supplied as a solid), 0.5-2 mg D-aminotransferase, 200 mM sodium pyruvate, 100 mM potassium phosphate buffer pH 7.5, and 0.05 mM PLP. Experiments were run in duplicate, with negative controls in which no aminotransferase was added. The samples were incubated 1 hour, 2 hours, and overnight (17-20 hours) at 30° C. with gentle shaking. The only stereoisomers detected when producing monatin using these methods were R,R and S,R. The percent R,R is listed in Table 70 below and was determined by reversed-phase LC peak area. At low monatin concentrations, the percent R,R is not as accurate as judged by RPLC peak area. Therefore, some of the samples were further analyzed by the FDAA derivatization method described in Example 1. The numbers from those results are shown in Table 70 in parentheses.

TABLE 70

Comparison of *G. stearothermophilus*, Hybrid DAT, and *B. sphaericus* (purified) for Total Monatin Production

| D-Aminotransferase | Total Monatin (ppm) 2 Hours | Total Monatin (ppm) Overnight | % R,R 2 Hours | % R,R Overnight |
|---|---|---|---|---|
| Hybrid DAT (untagged) | 9.5 | 42.5 | 84.1 (79.8) | 81.1 (69.6) |
| *B. sphaericus* (tagged) | 68.5 | 182.5 | 62.7 (53.8) | 55.1 (53.5) |
| *G. stearothermophilus* (untagged) | 4.5 | 15.0 | 34.1 (20.7) | 32.1 (21.7) |

The Hybrid DAT makes more monatin than the *G. stearothermophilus* enzyme, although the monatin transamination rate of the Hybrid DAT is lower. It is possible that under the conditions for monatin production (where there are low MP concentrations), the Hybrid DAT performs better possibly due to a lower K$_m$. Also, the Hybrid DAT makes a higher percentage of R,R than either of the parent enzymes. This enzyme appears to have a higher enantioselectivity for R-MP than the parent enzymes. The same assays were done (4 hour incubation time) using the *Sinorhizobium* aldolase described in Example 3A with the Hybrid DAT. The Hybrid DAT produced similar amounts of monatin as above, but using the alternative aldolase, produced 95% R,R (according to FDAA derivatization), as opposed to 80% with the *C. testosteroni* ProA aldolase.

The Hybrid DAT was also tested for transamination activity of R-MP versus S-MP (produced as described in Example 1). Two hour and overnight assays were conducted at 30° C. using 10 mM R-MP or S-MP, 50 mM D-alanine, 100 mM potassium phosphate pH 7.5, 0.5 mg/mL D-aminotransferase, and 50 µM PLP. Experiments were run in duplicate and the background levels of monatin from the MP samples was subtracted. The ratios of monatin produced from each substrate are reported for both D-aminotransferases in Table 71 below. Similar trends were observed when pyruvate (produced) ratios were plotted. It is clear that the Hybrid DAT is more selective for R-MP than the AT-103 D-aminotransferase, which does not appear to be selective.

TABLE 71

Comparison of Hybrid DAT and AT-103 for S-MP and R-MP Transamination

| D-Aminotransferase | R-Activity/S-Activity 2 Hours | R-Activity/S-Activity Overnight |
|---|---|---|
| Hybrid DAT (untagged) | 8.6 | 2.2 |
| AT-103 | 0.68 | 1.68 |

In an effort to further improve the Hybrid DAT activity, site directed mutagenesis was done. Primers were designed as suggested in the QuikChange Multi Site-Directed Mutagenesis Kit (Stratagene). Two different mutants were created: Hybrid DAT 2 and Hybrid DAT 3. The Hybrid DAT 2 includes a mutation at amino acid position 153 from alanine to arginine and a deletion of serine 181. The alanine to arginine mutation was designed to help coordinate the second carboxyl group in the monatin precursor substrate, as has been shown to be present in the AspC L-aminotransferase. The serine deletion was an attempt to remove some steric hindrance such that the larger monatin precursor molecule can get to the active site more easily. The Hybrid DAT 3 contains a deletion of serines 180-182, replaced by one arginine. Two additional mutants were created, having only the 153 ala to arg mutation or the serine deletion, respectively. All three of the mutants that contained deletions did not make soluble protein, although they overexpressed at very high concentrations. Clearly it is important structurally not to remove amino acids in this region. The ala153arg mutant did not produce monatin under the conditions tested (as above). There is a fair amount of steric hindrance near the 153 position which would make it more difficult to fit the monatin precursor substrate in without the deletions in the 180-182 region. It is expected that mutating the serines to smaller amino acids, such as glycine or alanine, would improve activity toward monatin precursor, particularly when combined with the ala153arg mutation.

Example 20

Use of Commercially Available D-Amino acid Dehydrogenase Enzymes

D-amino acid dehydrogenases were part of a library purchased from BioCatalytics (Pasadena, Calif.).

Interconversion between MP and Monatin

The amination of MP to form monatin can be catalyzed by aminotransferases or by dehydrogenases that require a reducing cofactor such as NADH or NADPH. These reactions are reversible and can be measured in either direction. The directionality when using a dehydrogenase enzyme can be largely controlled by the concentration of ammonium salts.

Conversion of Monatin to MP (Monatin Precursor) Using Commercially Available Dehydrogenases The oxidative deamination of monatin was monitored by following the increase in absorbance at 340 nm as $NAD^+$ was converted to the more chromophoric NADH.

The assay mixture contained 100 mM sodium bicarbonate, pH 9, 10 mM $NAD^+$, 20 mg/mL of D-amino acid dehydrogenase (D-AADH-101 through 108, BioCatalytics), and 50 mM R,R monatin (monopotassium salt) in 0.2 mL. The assay was performed, in duplicate, in a UV-transparent microtiter plate, with incubation at 30° C. Endpoint absorbances were measured using a Molecular Devices SpectraMax Plus plate_reader. Negative controls were carried out without the addition of enzyme. The change in absorbance for overnight reactions was as follows: no enzyme control, 0.05; D-AADH-101, 0.865; D-AADH-102, 1.075; D-AADH-103, 0.94; D-AADH-104, 0.335; D-AADH-105, 0.78; D-AADH-106, 0.745; D-AADH-107, 0.925; and D-AADH-108, 1.06.

Production of Monatin from MP Using Dehydrogenases

R-MP used as a substrate for this assay was produced by the transamination of R,R monatin using AT-103 broad range D-aminotransferase (BioCatalytics) in potassium phosphate buffer, using pyruvate as the amino acceptor. S-MP was produced by the transamination of S,S monatin using AT-102 L-aminotransferase (BioCatalytics) in potassium phosphate buffer, using 2-oxoglutarate as the amino acceptor. Both compounds were purified using preparative scale HPLC.

The assay mixture contained 200 mM ammonium formate, 50 mM potassium phosphate pH 7.5, 5 mM NADH, 20 mg/mL D-amino acid dehydrogenase (D-AADH-101 through 108, BioCatalytics), and 10 mM MP (potassium salt) in 0.25 mL. To half of the assays, 2 mg/mL formate dehydrogenase ("FDH") was added (FDH-101, BioCatalytics, 4.8 U/mg). The samples were incubated for 16 hours at 30° C. The samples were analyzed for monatin using LC/MS/MS and the isomeric distribution was determined using the FDAA method described in Example 1. The background levels of the no D-amino acid dehydrogenase control were subtracted to account for the monatin contamination present in the MP.

For production of R,R monatin from R-MP, the enzyme activity was as follows: D-AADH-103>D-AADH-101>D-AADH-107>D-AADH 106>D-AADH-108>D-AADH-105. The amount of monatin generated from D-AADH 102 was quite low and D-AADH-104 did not appear to produce monatin from R-MP. Approximately 43 ppm of R,R monatin was produced by D-AADH-103 during the reaction in the absence of formate dehydrogenase. The addition of FDH improved the production of monatin for all the enzymes that had activity. The improvements ranged from 2.4 fold higher monatin to 10.1 fold higher monatin (D-AADH-103). D-AADH-103 produced approximately 434 ppm R,R monatin.

When S-MP was used as the reaction substrate and production of S,R monatin was followed, the enzyme activity was as follows: D-AADH-106>D-AADH-107>D-AADH-105>D-AADH-101>D-AADH-102>D-AADH-103>D-AADH-108. D-AADH-104 did not appear to produce S,R monatin in the assays. Approximately 15 ppm S,R monatin was generated by D-AADH-106, 26 ppm when FDH enzyme was also used.

Production of Monatin from Indole-3-Pyruvate

Production of monatin from indole-3-pyruvate and pyruvate, using BioCatalytics amino acid dehydrogenase enzymes coupled with the aldolase of SEQ ID NO:22, was assayed under the following conditions: 1 mg/mL dehydrogenase enzyme, 10 mM NADH, 500 µg/mL aldolase (purified), 50 mM potassium phosphate buffer pH 7.5, 4 mM $MgCl_2$, 20 mg/mL indole-3-pyruvate, 200 mM ammonium formate, and 200 mM pyruvate were incubated at 30° C. at 100 rpm for 20 hours. Negative controls contained no amino acid dehydrogenase enzyme. The experiments were performed in duplicate. None of the dehydrogenases appeared to produce quantifiable amounts of monatin from indole pyruvate and pyruvate (as measured by LC/MS/MS as described in Example 1) in comparison to the negative controls. However, large amounts of alanine and tryptophan were produced.

It is expected that increasing the ratio of aldolase to dehydrogenase would improve monatin production. It is also expected that directed evolution approaches can be used to improve the ratio of reductive amination activity on MP versus pyruvate and indole-3-pyruvate.

Example 21

Immobilization of B. sphaericus D-Alanine Aminotransferase

The Bacillus sphaericus D-alanine aminotransferase was purified as the $HIS_6$-tagged protein as described in Example 14.

The enzyme was immobilized onto Eupergit® C resin beads according to the procedure of Mateo, C, et al., Biotechnology Progress 18:629-634, (2002). The purified enzyme (4 mL at 6.0 mg/mL) was dialyzed in 0.4 L of 0.5 M potassium phosphate, pH 7.8 using a Pierce Slide-A-Lyzer Dialysis Cassette (7K MWCO; catalog #66370; Rockford, Ill.) for 1 hour at ambient temperature. The buffer was changed and the dialysis was continued for 1 hour. Pyridoxal phosphate ("PLP") was added to a final concentration of 0.05 mM and the resulting solution was mixed with 0.2 g of Eupergit® C resin purchased from Sigma-Aldrich (Fluka catalog #46115; St. Louis, Mo.). The enzyme-resin suspension was incubated at ambient temperature with gentle mixing overnight. The resin beads were separated from the enzyme solution by centrifugation at 4000×g for 5 minutes. The supernatant was removed and the resin was washed with 3×3 mL of 100 mM potassium phosphate, pH 7.8 containing 0.05 mM PLP. The mixture was centrifuged at 3000×g for 5 minutes between washes. The amount of protein bound to the resin was determined by measuring the amount of protein in each supernatant and subtracting the sum from the original amount of protein to be immobilized. The protein concentrations were measured using a Pierce BCA™ Protein Assay Kit with bovine serum albumin as the standard (catalog #23225; Rockford, Ill.). The washed immobilized-enzyme beads were finally suspended in 4 mL of 100 mM potassium phosphate, pH 7.8 containing 0.05 mM PLP. The unreacted epoxy groups of the immobilized-enzyme beads were blocked by incubation with 1.9 M alanine at ambient temperature with gentle mixing. After 24 hours, the beads were washed, as described above, to remove the excess alanine and finally resuspended in 100 mM potassium phosphate, pH 7.8 containing 0.05 mM PLP. The final concentration of immobilized enzyme was 118 mg protein per g resin bead.

Example 22

Immobilization of S. meliloti ProA Aldolase

The Sinorhizobium meliloti HMG aldolase ("proA") was purified as the $HIS_6$-tagged protein using a procedure similar to the one described in Example 14 for the $HIS_6$-tagged B. sphaericus D-alanine aminotransferase.

Starting from a fresh culture plate (LB agar with 50 μg/mL kanamycin) of BL21(DE3)::S. meliloti proA pET30(Xa/LIC), cells were grown in 5 mL of Luria-Bertani broth ("LB") with 50 μg/mL kanamycin at 37° C. with shaking at 225 rpm overnight. Subsequently, the culture was transferred at 0.5-0.6% (v/v) into flasks containing 800 mL of LB broth with 50 μg/mL kanamycin. The cells were grown at 37° C. with shaking at 225 rpm until the $OD_{600}$ reached 0.6-0.7. The gene expression was induced by the addition of 0.2 mM IPTG. The cultures were further incubated at 30° C. for 4 hours with shaking at 225 rpm and then harvested by centrifugation in a Beckman J25II centrifuge (Fullerton, Calif.) with a JS-16.25 rotor at 10,000 rpm for 10 minutes. The cell pellet was washed once with cold 50 mM EPPS buffer, pH 8.2, and the cells were centrifuged again. The washed cell pellet was harvested and used immediately. To prepare cell-free extract containing the S. meliloti $HIS_6$-proA aldolase ($HIS_6$-SmelproA) protein, the cells were suspended in 3-4 volumes of 50 mM EPPS, pH 8.2, containing 100 mM NaCl, and then disrupted using a Microfluidics homogenizer (Newton, Mass.) (3 passes at 20,000 psi) while maintaining the temperature of the suspension below 15° C. All subsequent purification steps were carried out at 4° C. The cell extract was centrifuged for 15 minutes at 15,000×g to remove the cell debris. Aliquots of the cell free extract, each containing between 15 and 20 mg of soluble protein, were applied to Novagen HIS-Bind columns (Novagen catalog #70971-4, Madison, Wis.) that had been previously equilibrated with the Novagen Bind buffer. The columns were washed with 2×10 mL of the Novagen Bind buffer and 1×10 mL of the Novagen Wash buffer diluted 1:1 with the Bind buffer. The $HIS_6$-SmelproA was eluted with 5 mL of the Novagen Elute buffer from each column. The elution fractions from each column were combined and concentrated 2× with Amicon Ultra-15 centrifugal filter devices (MWCO 10 kDa) (Billerica, Mass.). The buffer was exchanged by passage through disposable GE Healthcare PD10 desalting columns (catalog #17-0851-01) previously equilibrated with 50 mM EPPS, pH 8.2, containing 100 mM NaCl.

The protein concentration of the desalted solution was determined using the Pierce BCA™ Protein Assay Kit (catalog #23225; Rockford, Ill.). The purity of each fraction and the level of expression in the cell free extract fraction were determined by SDS-PAGE with a Bio-Rad Protean II minigel system (Hercules, Calif.) and 4-15% gradient gels. Typically, this procedure produced about 60-70 mg of enzyme from 3200 mL of LB culture with a purity of ~90%. Aliquots (1-5 mL) of the purified enzyme were stored at −80 C. until use.

The enzyme was immobilized onto Eupergit® C resin beads according to the procedure of Mateo, C., et al., (2002) Biotechnology Progress 18:629-634, (2002) and as described in Example 21 for the B. sphaericus D-alanine aminotransferase, except that 4 mM magnesium chloride was present in the buffer during immobilization instead of 0.05 mM PLP. After blocking with glycine, the washed immobilized enzyme was suspended in 100 mM potassium phosphate, pH 7.8 containing 4 mM magnesium chloride. The final concentration of S. meliloti proA aldolase was 52 mg protein per gram resin bead.

Example 23

Production of R,R-Monatin Using Immobilized Enzymes

The B. sphaericus $HIS_6$-tagged D-alanine aminotransferase and the R. meliloti $HIS_6$-tagged proA aldolase were purified and immobilized as described in Examples 21 and 22.

Solutions of 50 mM sodium pyruvate, 40 mM D-tryptophan, 4 mM $MgCl_2$, and 50 μM PLP in 100 mM potassium phosphate, pH 7.8 were prepared in 15-mL polypropylene tubes with screw caps. To each of these solutions was added both of the immobilized enzymes to a final volume of 4 mL. The resulting suspensions were incubated at room temperature with gentle mixing for up to 24 hours. The progress of each reactions was followed by HPLC and/or LC-MS analyses, measuring D-tryptophan, D-alanine, R,R-monatin, and pyruvic acid. The isomeric purity of the product monatin was determined using chiral LC/MS/MS. All analytical methods are described in Example 1. Typical results from experiments using immobilized enzymes are shown in Table 72 below. Analysis of the isomeric purity of the monatin formed during the reaction showed that the product of the enzymatic reactions was between 74 and 80% R,R.

TABLE 72

Production of R,R-Monatin Using Immobilized Enzymes

| proA Aldolase Concentration (μg/mL) | D-Alanine Aminotransferase Concentration (μg/mL) | Monatin Concentration (mM) (4 Hour Time point) | Tryptophan Concentration (mM) (4 Hour Time point) | Alanine Concentration (mM) (4 Hour Time point) |
|---|---|---|---|---|
| 50 | 500 | 0.06 | 17.75 | 20.51 |
| 50 | 1000 | 0.29 | 15.03 | 24.71 |
| 100 | 1000 | 0.33 | 15.17 | 24.73 |
| 100 | 2000 | 0.54 | 14.40 | 29.45 |

Example 24

In Vivo R,R Monatin Production and Transport by *E. coli*

Operons were constructed to demonstrate in vivo production of R,R monatin in *E. coli* using a D-aminotransferase ("DAT") and an R-specific aldolase. The R,R monatin was made from D-tryptophan using the pathway described in U.S. patent application Publication No. US 2005/0282260 A1 (FIGS. 1 and 2 and Example 11). Briefly, D-tryptophan is converted, in vivo, to indole-3-pyruvate by a transamination reaction in which an alpha-keto acid is also converted into a D-amino acid. Pyruvate is reacted with indole-3-pyruvate in vivo in an aldol condensation using an R-specific aldolase to produce predominantly R-MP. Lastly, the R-MP and the D-amino acid from the first reaction (or any D-amino acid in the cell) are converted in vivo to R,R monatin and the corresponding alpha-keto acid.

Construction of Plasmid pCEC-Nde

Plasmid pCEC-Nde was constructed by replacing the p15A origin of replication of the pPRONde plasmid (pProLAR from Clontech, modified as described in U.S. Published Application No. 20040235123) with the Col E1 origin of replication from pPROTet.E133 (Clontech Laboratories, Inc., Mountain View, Calif.). Both plasmids were treated with restriction enzymes Avr II and Aat II (New England Biolabs, Beverly, Mass.) and the appropriate fragments (1731-bp fragment from pPROTet.E133 carrying the Col E1 origin and chloramphenicol-resistance gene and 760-bp from pPRONde carrying the $P_{lac/ara}$ promoter region and multiple cloning site) were purified by agarose gel electrophoresis followed by extraction and recovery using the QIAquick® Gel Extraction Kit (Qiagen, Valencia, Calif.). The purified DNA fragments were ligated together using the Quick Ligation Kit (New England Biolabs, Beverly, Mass.) and the ligation mixture transformed into chemically-competent *E. coli* TOP10 cells (Invitrogen, Carlsbad, Calif.). Clones were isolated on LB agar containing 50 μg/mL chloramphenicol and confirmed by restriction digests of the plasmid.

Vector pCEC-Nde was digested with Nde I and BamH I in BamH I buffer (New England Biolabs, Ipswich, Mass.) and treated with shrimp alkaline-phosphatase as per manufacturer's protocols (Roche, Indianapolis, Ind.). ATCC 4978 DAT (SEQ ID NO. 84) was digested from vector pET28 (Novagen, Madison, Wis.) (cloned in Example 15) with Nde I and BamH I in BamH I buffer. The Nde I and BamH I digested vector and insert were purified using the Qiagen QIAquick® Gel Extraction Kit (Qiagen, Valencia, Calif.). Ligations were done using the Roche Rapid DNA Ligation Kit (Roche, Indianapolis, Ind.) and purified using the Roche High-Pure PCR purification kit (Roche, Indianapolis, Ind.). The ligations were transformed into *Escherichia coli* DH10B cells (Invitrogen, Carlsbad, Calif.) using a 0.2 cm cuvette and a Bio-Rad Gene Pulser® II system as described in the Bio-Rad electroporation manual. The cells were allowed to recover in 1.0 mL SOC medium (Sambrook, J., et al. *Molecular Cloning: A Laboratory Manual* 2nd ed., Plainview, N.Y., (1989), 1.76-1.81 & A.2)) for 1 hour at 37° C. at 250 rpm. Cells were plated on LB-agar plates containing chloramphenicol (25 μg/mL). Plasmid DNA was purified using the Qiagen spin miniprep kit (Qiagen, Valencia, Calif.) and screened for the correct inserts by PCR and restriction digestion with Nde I and BamH I. The amino acid sequence of ATCC 4978 DAT is shown as SEQ ID NO. 86.

PCR of the Aldolase Gene of SEQ ID NO:172 from Diversa

Primers were designed based on the DNA sequence of SEQ ID NO:172, which encodes an enzyme having R-selective aldolase activity. The aldolase of SEQ ID NO:173 and the plasmid containing the nucleic acid sequence encoding that aldolase (the gene sequence of the specific aldolase is shown as SEQ ID NO:172, were obtained from Diversa Corporation, San Diego, Calif. SEQ ID NO:172 was part of a library which was screened by Diversa Corp. for aldolase genes. However, the aldolase gene of SEQ ID NO:172 may be reconstructed by any method known to a person of ordinary skill in the art. For example, the aldolase gene of SEQ ID NO:172 may be reconstructed utilizing assembly PCR methods known to one skilled in the art. The primers were designed to contain restriction sites and a ribosomal binding site in front of the aldolase gene for cloning and expression. The oligonucleotide primer sequences that were used were:

AldolaseFpstIrbs:
(SEQ ID NO: 174)
5'-GGCCGGAACTGCAGAAGAAGGAGATATATAATGAAGCCGGTGGTGGT
G-3'
and AldolaseRxbaI
(SEQ ID NO: 175)
5'-GGCCAAGGTCTAGATTAGACATAGGTGAGCCC-3'.

PCR was done using the above primers, with template pET28/SEQ ID NO:172. PCR was carried out as follows: per 50 μL reaction, 0.5 μL template, 0.8 μL of each primer, 2 μL dNTPs, 0.8 μL Expand High Fidelity Polymerase (Roche, Indianapolis, Ind.), 1× Expand™ buffer, and 0.2 μL Pfu polymerase (Stratagene, La Jolla, Calif.) were added. A 3 minute hot start was done at 94° C., followed by 8 cycles of 94° C. for 30 seconds, 50° C. for 30 seconds, and 72° C. for 90 seconds. Twenty-two more cycles were done with an increased annealing temperature of 55° C. Lastly, a chain extension step was done for seven minutes at 72° C. The PCR product was purified using the Qiagen QIAquick® PCR purification kit (Qiagen, Valencia, Calif.), and digested with Pst I and Xba I in Buffer 3 (New England Biolabs, Ipswich, Mass.). Pst I and Xba I digested vector pCECNde/4978 DAT and insert were ligated using the Roche Rapid DNA Ligation Kit (Roche, Indianapolis, Ind.) and purified using the QIAquick® PCR purification kit. The ligation was transformed into *Escherichia coli* DH10B cells using a 0.2 cm cuvette and a Bio-Rad Gene Pulser® II system as described in the Bio-Rad electroporation manual. The cells were allowed to recover in 1.0 mL SOC medium for 1 hour at 37° C. with shaking at 250 rpm. Cells were plated on LB-agar plates containing chloramphenicol (25 µg/mL).

Transformants were grown in LB broth containing chloramphenicol (25 µg/mL) at 37° C. with shaking at 250 rpm. Plasmid DNA was purified using the Qiagen spin miniprep kit (Qiagen, Valencia, Calif.) and inserts were verified by restriction digestion with Pst I and Xba I. The sequences of plasmids appearing to have the correct insert were verified by dideoxy chain termination DNA sequencing (Agencourt; Beverly, Mass.). The resulting plasmid, pCECNde/4978DAT/SEQ ID NO:172, designated RR2 (vector RR2), was used to transform strain *Escherichia coli* MG1655 as described below.

*E. coli* MG1655 strain was grown in LB broth at 37° C. with shaking at 250 rpm. Electrocompetent *E. coli* MG1655 were prepared by subculturing a 1% inoculum of cells to an OD 600 of ~0.6. The bacteria were pelleted by centrifugation (10 minutes at 10,000×g) and washed in an equal volume of 10% glycerol. The wash was repeated twice in half volume of 10% glycerol. Finally, the cells were washed in one-fourth volume of 10% glycerol. Following centrifugation, the cells were resuspended in 500 µL of 10% glycerol. Thirty µL aliquots were frozen and kept at −80° C. until use.

Vector RR2 (i.e., plasmid pCECNde/4978DAT/SEQ ID NO:172, prepared above), was transformed into electrocompetent *E. coli* MG1655 cells using a 0.2 cm cuvette and a Bio-Rad Gene Pulser® II system as described in the Bio-Rad electroporation manual. The cells were allowed to recover in 1 mL SOC medium for 1 hour at 37° C. with shaking at 250 rpm. Cells were plated on LB-agar plates containing chloramphenicol (25 µg/mL).

For inoculum preparation, the *E. coli* MG1655::pCECNde/4978 DAT/SEQ ID NO:172 were grown overnight at 37° C. with shaking at 250 rpm in Luria-Bertani ("LB") medium with 25 µg/mL chloramphenicol. For the experimental treatments, Trp-1+glucose medium, a minimal medium that has been used for increased production of tryptophan in *E. coli* cells (Zeman et al. *Folia Microbiol.* 35:200-4, 1990), was prepared as follows. To 800 mL nanopure water the following reagents were added: 2 g $(NH_4)_2SO_4$, 13.6 g $KH_2PO_4$. The pH was adjusted to 7.0, the volume was increased to 948 mL, and the medium was autoclaved. Following sterilization, 0.2 g $MgSO_4.7H_2O$, 0.01 g $CaCl_2.2H_2O$, and 0.5 mg $FeSO_4.7H_2O$ were added to the medium in a 1.8 mL volume followed by addition of 0.2 mL of Neidhardt's micronutrient solution (Neidhardt F. C., Bloch P. L., and Smith D. F., 1974. Culture medium for *Enterobacteria*. J. Bacteriol. 119:736-746).

Neidhardt's medium includes (per liter): 0.18 g $(NH_4)_6(MO_7)_{24}.4H_2O$, 1.24 g $H_3BO_3$, 0.36 g $CoCl_2.6H_2O$, 0.12 g $CuCO_4$ (anhydrous), 0.8 g $MnCl_2.4H_2O$, and 0.14 g $ZnSO_4.7H_2O$. A 50% glucose solution was prepared separately and sterile-filtered. Forty mL of glucose solution and 10 mL of 1 M 3-morpholinopropanesulfonic acid ("MOPS") buffer were added to the base medium (950 mL) for a 1 L final volume.

For treatments, 3.1 v/v % of inoculum was added to 100 mL medium volume in 500 mL baffled shake flasks with 25 µg/mL chloramphenicol. Conditions for the treatments included 250 rpm agitation throughout and 37° C. up to induction, then 30° C. following induction. At 0.50-0.526 $OD_{600}$, induction of the plasmid genes was initiated. At induction, 1.0 mM IPTG, 0.5% L-arabinose, 0.5 mM pyridoxine hydrochloride, and 0.2 mL of Balch's vitamins (Balch, W. E., et al., 1979, Microbiol. Rev. 43:260-296) were added. Additions of 10 g/L D-tryptophan, 10 g/L sodium pyruvate, 0.04 mM pyridoxal-5'-phosphate ("PLP") were made at 3 hours following induction, while 0.2% Tween® 20 (polyoxyethylene 20-sorbitan monolaurate) and 10 µg/mL ampicillin were added 6 hours following induction. Either 5 mM D-glutamate or D-alanine was also added at 3 hours following induction. A second addition of 10 g/L sodium pyruvate was made at 24 hours following inoculation. Samples for monatin and dry cell weight determination were taken at 48 hours.

The monatin from the 48 hour samples was concentrated via a solid phase extraction ("SPE") column using the methodology described below. The R,R and S,S stereoisomers were analyzed by the FDAA derivatization method of Example 1. Results are shown in Table 73 below.

Method For Concentration Of Monatin Utilizing Solid Phase Extraction

An Oasis® HLB 3 cc (60 mg) Extraction Cartridge (Waters Corp., Milford, Mass.) was used to concentrate the samples. The fermentation samples were first centrifuged to remove cell material. Formic acid was added to the fermentation sample for a final concentration of about 1%. The extraction cartridge was conditioned with at least 2 mL methanol, followed by 2 mL 1% formic acid prior to the addition of the fermentation sample. Each solution was drawn through the extraction cartridge separately. Then, up to 5 mL of the undiluted, centrifuged fermentation sample containing 1% formic acid was added to the extraction cartridge. The fermentation solution was allowed to draw through the cartridge slowly. The cartridge was rinsed with at least 2 mL of 1% formic acid. 1 mL of either acetonitrile or methanol was added to the cartridge and was allowed to draw through the cartridge slowly. This eluent was placed under a gentle stream of nitrogen until it was dry. The dry sample was reconstituted into 150-200 µL water or mobile phase. 150 µL was placed into a 300 µL HPLC plastic vial and was injected into the liquid chromatograph. Table 73 shows the total monatin per dry cell weight and the portion of the total that was the R,R or S,S stereoisomer.

TABLE 73

R,R Monatin excreted by E. coli

| Strain | D-amino acid treatment | 48 hour Monatin/dry cell wt. (mg/g) Total Monatin | Portion as: R,R Monatin | Portion as: S,S Monatin |
|---|---|---|---|---|
| E. coli MG1655::pCECNde/4978 DAT/SEQ ID NO: 172 | D-glutamate | 0.47 | ~50% | ~50% |
| E. coli MG1655::pCECNde/4978 DAT/SEQ ID NO: 172 | D-alanine | 0.33 | nd | nd |

R,R Monatin production and transport was conclusively demonstrated using the strain E. coli MG165::pCECNde/4978 DAT/SEQ ID NO:172 and D-glutamate. Some S,S monatin was produced, probably as a result of using the E. coli MG1655 strain that normally expresses endogenous L-aminotransferases that are capable of making S,S monatin from S-MP. The total monatin produced with D-alanine was not enough to conduct an analysis to determine the stereoisomeric ratio of monatin produced. However, it is expected that the same ratio of R,R monatin would be formed, even though the amount produced was below the threshold of analysis. It is also expected that the same transporters capable of transporting S,S monatin should be capable of transporting R,R monatin as well.

The DNA sequence of SEQ ID NO:172 is shown below.

```
                                      (SEQ ID NO: 172)
gaagccgg tggtggtgca gactatcgag cgggccgacc gagcgatcat cgagggtctg gccgcgtgtg gcgttgccac cgtccatgag gcgcaggggc gccggggct gcttgcgtcc tacatgcgcc cgatctattc gggcgctgcg gttgcggcct cggccgtcac catcctctct ccaccctgcg acaactggat gctgcacgtc gccatcgagc agatccagcc gggcgacatt ctcgttctcg gcacgacctc tccgtccgat gccggctatt tcggtgatct gctggcgact tcggccaagg cgcgcggttg cgtcgggttg gtcatcgatg ccggcgtacg cgatatccgc gacctgacag cgatgcagtt tccggtctgg tccaaggccg tttcggccca gggcacgatc aaggagacgc tgggttcggt caacgtcccc gtcgtctgcg ccggtgctct ggtcaatccc ggcgacgtcg tcgtggccga tgacgacggt gtctgcgtgg tgcgccgcga ggaagccgcg gaaacgctgg aaaaggcccg ggcgcggatc gccaatgagg aggaaaagcg ccagcgcttt gccgctggcg aactcgggct cgacatctac aagatgcgcg aacgcctcgc tgccctgggg ctcacctatg tctga.
```

The amino acid sequence of the aldolase of SEQ ID NO:173 is shown below.

```
                                      (SEQ ID NO: 173)
Met Lys Pro Val Val Val Gln Thr Ile Glu Arg Ala

Asp Arg Ala Ile Ile Glu Gly Leu Ala Ala Cys Gly

Val Ala Thr Val His Glu Ala Gln Gly Arg Arg Gly

Leu Leu Ala Ser Tyr Met Arg Pro Ile Tyr Ser Gly

Ala Ala Val Ala Ala Ser Ala Val Thr Ile Leu Ser

Pro Pro Cys Asp Asn Trp Met Leu His Val Ala Ile

Glu Gln Ile Gln Pro Gly Asp Ile Leu Val Leu Gly

Thr Thr Ser Pro Ser Asp Ala Gly Tyr Phe Gly Asp

Leu Leu Ala Thr Ser Ala Lys Ala Arg Gly Cys Val

Gly Leu Val Ile Asp Ala Gly Val Arg Asp Ile Arg

Asp Leu Thr Ala Met Gln Phe Pro Val Trp Ser Lys

Ala Val Ser Ala Gln Gly Thr Ile Lys Glu Thr Leu

Gly Ser Val Asn Val Pro Val Val Cys Ala Gly Ala

Leu Val Asn Pro Gly Asp Val Val Val Ala Asp Asp

Asp Gly Val Cys Val Val Arg Arg Glu Glu Ala Ala

Glu Thr Leu Glu Lys Ala Arg Ala Arg Ile Ala Asn

Glu Glu Glu Lys Arg Gln Arg Phe Ala Ala Gly Glu

Leu Gly Leu Asp Ile Tyr Lys Met Arg Glu Arg Leu

Ala Ala Leu Gly Leu Thr Tyr Val.
```

Example 25

Production of R,R-Monatin Using the Aldolase of SEQ ID NO:104: Optimization of Reaction Conditions The Bacillus sphaericus (ATCC strain 10208) D-alanine aminotransferase cloned in Example 18 was purified as the HIS$_6$-tagged protein as described in Example 14 using the improved method, with potassium phosphate buffers containing PLP). The aldolase of SEQ ID NO:104 (cloned in Example 3B) was purified as the HIS$_6$-tagged protein as described in Example 27.

The preferred metal cofactor for the aldolase of SEQ ID NO:104 was determined by screening a variety of divalent metals. The reactions were set up anaerobically in 10 mL serum bottles with 7 mL final volumes. A bulk solution consisting of 100 mM potassium phosphate (pH 7.8), 200 mM sodium pyruvate, 0.05 mM PLP and 0.01% (v/v) Tween 80 was prepared to a final volume of 48.8 mL and sparged with nitrogen for 30 minutes. D-Tryptophan (143 mg; final concentration of 100 mM) was dispensed into seven 10 mL serum vials. To each of the vials was added 0.014 mL of a 2 M stock solution of a divalent metal cation, prepared from the chloride salt (final concentration of 4 mM). For the negative control, 0.014 mL of dH$_2$O was added. The serum vials were capped with rubber septa and sparged with nitrogen via 16-18 gauge needles. Under anaerobic conditions, 5.625 mL of the anaerobic bulk solution was added to each anaerobic serum bottle. Subsequently, the *B. sphaericus* D-alanine aminotransferase and the aldolase of SEQ ID NO:104 were added anaerobically to each serum bottle to a final concentration of 2 mg/mL and 0.05 mg/mL, respectively. The solutions were incubated at room temperature with gentle mixing for 18 hours. Final monatin was analyzed according to the methods described in Example 1 using the Liquid Chromatography-Post Column Fluorescence Detection of Amino Acids method. (Table 74).

TABLE 74

| Metal Cofactor | Final Monatin (mM) at 18 h |
| --- | --- |
| None (negative control) | 1.7 |
| Magnesium | 10.6 |
| Manganese | 10.0 |
| Cobalt | 6.7 |
| Zinc | 4.9 |
| Nickel | 1.5 |
| Calcium | 0.7 |

The reaction conditions for the aldolase of SEQ ID NO:104 were further investigated with a two-level fractional factorial experiment designed using the statistical software Design Expert 7.0.0 (Stat-Ease, Inc.; Minneapolis, Minn.). The screening design consisted of a single block of five factors at two levels with four centerpoints (20 runs total). The five factors to be optimized were the metal cofactor concentration, reaction pH, Tween® 80 concentration, pyruvate to tryptophan ratio, and the aldolase concentration (Table 75).

Conical polypropylene tubes (14 mL) containing 143 mg of D-tryptophan were de-oxygenated in an anaerobic glove box (Coy Laboratory Products, Inc; Grass Lake, Mich.) overnight. Stock solutions of 2 M MgCl$_2$; 1 M potassium phosphate at pH 7.0, 7.75, and 8.5; 10% (v/v) Tween 80; 2 M sodium pyruvate, and 10 mM PLP were prepared in degassed water and equilibrated in the anaerobic glove box overnight. Stock solutions of purified *B. sphaericus* D-alanine aminotransferase and the aldolase of SEQ ID NO:104 were thawed on ice and used in the anaerobic glove box immediately. Stock solutions were added to the 14 mL conical tubes containing the D-tryptophan to obtain the concentrations determined by the statistical design (Table 75). Degassed water was added to each tube to bring the final volume, along with the enzyme additions, to 7.0 mL. The tubes were incubated at room temperature in the anaerobic glove box with gentle mixing for up to 24 hours. Monatin concentration and isomeric purity were analyzed according to the methods described in Example 1 using the Liquid Chromatography-Post Column Fluorescence Detection of Amino Acids method and the LC/MS/MS Multiple Reaction Monitoring for the Determination of the Stereoisomer Distribution of Monatin in in vitro and in vivo Reactions method (FDAA derivatization method).

TABLE 75

| Run # | std # | Block | Mg (mM) | pH | Tween® (%) | Pyr:Trp | Aldolase of SEQ ID NO: 104 (mg/mL) |
| --- | --- | --- | --- | --- | --- | --- | --- |
| 20 | 1 | Block 1 | 5.00 | 7.75 | 0.01 | 2.00 | 0.05 |
| 8 | 2 | Block 1 | 9.00 | 8.50 | 0.02 | 1.00 | 0.01 |
| 3 | 3 | Block 1 | 1.00 | 8.50 | 0.00 | 1.00 | 0.01 |
| 16 | 4 | Block 1 | 9.00 | 8.50 | 0.02 | 3.00 | 0.09 |
| 7 | 5 | Block 1 | 1.00 | 8.50 | 0.02 | 1.00 | 0.09 |
| 12 | 6 | Block 1 | 9.00 | 8.50 | 0.00 | 3.00 | 0.01 |
| 6 | 7 | Block 1 | 9.00 | 7.00 | 0.02 | 1.00 | 0.09 |
| 2 | 8 | Block 1 | 9.00 | 7.00 | 0.00 | 1.00 | 0.01 |
| 15 | 9 | Block 1 | 1.00 | 8.50 | 0.02 | 3.00 | 0.01 |
| 4 | 10 | Block 1 | 9.00 | 8.50 | 0.00 | 1.00 | 0.09 |
| 5 | 11 | Block 1 | 1.00 | 7.00 | 0.02 | 1.00 | 0.01 |
| 1 | 12 | Block 1 | 1.00 | 7.00 | 0.00 | 1.00 | 0.09 |
| 13 | 13 | Block 1 | 1.00 | 7.00 | 0.02 | 3.00 | 0.09 |
| 14 | 14 | Block 1 | 9.00 | 7.00 | 0.02 | 3.00 | 0.01 |
| 17 | 15 | Block 1 | 5.00 | 7.75 | 0.01 | 2.00 | 0.05 |
| 11 | 16 | Block 1 | 1.00 | 8.50 | 0.00 | 3.00 | 0.09 |
| 18 | 17 | Block 1 | 5.00 | 7.75 | 0.01 | 2.00 | 0.05 |
| 9 | 18 | Block 1 | 1.00 | 7.00 | 0.00 | 3.00 | 0.01 |
| 19 | 19 | Block 1 | 5.00 | 7.75 | 0.01 | 2.00 | 0.05 |
| 10 | 20 | Block 1 | 9.00 | 7.00 | 0.00 | 3.00 | 0.09 |

Statistical analysis of the data indicated that reaction pH, pyruvate:tryptophan ratio and aldolase concentration were the significant factors affecting monatin titer, isomeric purity and carbon yield. A desirability graph was generated using the Design Expert software in which the factors were varied in order to maximize the goals of highest monatin titer and highest isomeric purity under conditions of excess pyruvate. The reactions conditions indicated as optimum were 1 mM MgCl$_2$, pH >8.0, 0.01% (v/v) Tween® 80, and 0.01 mg/mL aldolase of SEQ ID NO:104. This is a 5-fold reduction in the typical amount of aldolase utilized, as well as a 4-fold reduction in the amount of divalent metal typically used.

Additional experiments were performed to determine the optimum pH range for the reaction process. Stock solutions of 1 M EPPS buffer were prepared at increments of 0.2 pH units between pH 7.0 and 9.0. These solutions were degassed and equilibrated in the anaerobic glove box overnight. Polypropylene tubes (14 mL) containing 143 mg of D-tryptophan were de-oxygenated in an anaerobic glove box overnight. Stock solutions of 2 M MgCl$_2$, 10% (v/v) Tween® 80, 2 M sodium pyruvate and 10 mM PLP were prepared in degassed water and equilibrated in the anaerobic glove box. Preparations of purified *B. sphaericus* D-alanine aminotransferase and the aldolase of SEQ ID NO:104 were thawed on ice and used immediately in the anaerobic glove box. The stock solutions were added to the 14 mL conical tubes to give a final concentration of 100 mM EPPS, 200 mM pyruvate, 100 mM tryptophan, 1 mM $MgCl_2$, 0.01% (v/v) Tween® 80, 0.05 mM PLP, 2 mg/mL B. sphaericus D-alanine aminotransferase, and 0.01 mg/mL aldolase of SEQ ID NO:104 in a total volume of 7 mL per tube. The reactions were incubated at room temperature in the anaerobic glove box with gentle agitation for 22 hours. Samples were removed and analyzed for monatin as described in Example 1 using the LC/MS/MS multiple reaction monitoring method (Table 76).

TABLE 76

| Reaction pH | Monatin (mM) at 22 h |
| --- | --- |
| 7.0 | 5.8 |
| 7.2 | 9.9 |
| 7.4 | 7.8 |
| 7.6 | 10.6 |
| 7.8 | 14.0 |
| 8.0 | 14.2 |
| 8.2 | 14.3 |
| 8.4 | 12.6 |
| 8.6 | 12.3 |
| 8.8 | 10.8 |
| 9.0 | 11.1 |

The results indicated that monatin formation increased with increasing pH between 7.0-8.0. Monatin formation reached a maximum in the range of pH 8.0-8.2 and decreased above pH 8.4. Additionally, the isomeric purity of monatin decreased above pH 8.4.

Example 26

Purification of the T243N Mutant of the D-Aminotransferase from ATCC Strain 4978

The T243N mutant of the D-aminotransferase from ATCC strain 4978 with an amino-terminal $HIS_6$-purification tag (described in Example 6B) was produced using the EMD Biosciences Overnight Express System II (solutions 1-6) (La Jolla, Calif.) containing 50 µg/mL kanamycin in shake flasks. This expression system induces the expression of IPTG-inducible systems without the need to monitor cell growth. After inoculation of 200 mL aliquots of the medium (in 1 L flasks) from either liquid cultures or plates of the E. coli BL21(DE3) host cells carrying the gene for the T243N mutant D-aminotransferase from ATCC strain 4978 on the plasmid pET28b, the cultures were incubated at 30° C. overnight with shaking at 225 rpm. When the $OD_{600}$ had reached a minimum of 6, the cells were harvested by centrifugation and washed once with buffer.

Cell free extract was prepared using EMD Biosciences BugBuster® (primary amine-free) Extraction Reagent (La Jolla, Calif.) containing 1 µL/mL Benzonase® Nuclease, 5 µL/mL Protease Inhibitor Cocktail Set II, and 0.033 µL/mL rLysozyme™ according to the manufacturer's protocol. All subsequent purification steps were carried out at 4° C. The cell extract was centrifuged for 20-30 minutes at 15,000×g to remove the cell debris. A 20-25 mL aliquot of the cell free extract was applied to a 45 mL column of GE Healthcare Chelating Sepharose™ Fast Flow resin (nickel (II) form) (Piscataway, N.J.) that had been previously equilibrated with 100 mM potassium phosphate containing 200 mM sodium chloride and 50 µM PLP. To generate the nickel form of the resin, the resin was washed with 150 mL of 200 mM nickel (II) sulfate hexahydrate and then with 150 mL of distilled water. After loading the sample, the column was washed/eluted with 150 mL of the equilibration buffer containing 25 mM imidazole, 150 mL of the equilibration buffer containing 50 mM imidazole and 150 mL of the equilibration buffer containing 500 mM imidazole. The $HIS_6$-tagged protein eluted in the last wash. The 500 mM imidazole wash was concentrated with Millipore/Amicon Centricon Plus-70 centrifugal filter devices (MWCO 10 kDa) (Billerica, Mass.) to 15-20 mL according to the manufacturer's instructions. The imidazole and sodium chloride were removed by passage through disposable GE Healthcare PD10 columns (2.5 mL sample per column) previously equilibrated with 100 mM potassium phosphate, pH 7.8 containing 50 µM PLP. The purified aminotransferase was eluted with 3.5 mL per column of the same buffer. The protein concentration of each fraction was determined using the Pierce BCA assay kit (Rockford, Ill.) with BSA as the protein standard. The purity of each fraction and the level of expression in the cell free extract fraction were determined using a Bio-Rad Experion microcapillary chip system (Hercules, Calif.) or using Bio-Rad 4-15% SDS-polyacrylamide gradient gels run in a Mini PROTEAN® 3 cell apparatus. The protein was visualized in the polyacrylamide gels using BioRad Bio-Safe G-250 Coomassie stain and destained with water. Typically this procedure produces ~20 mg of enzyme from 200 mL of overnight culture that is 85-90% pure as judged by the Experion software or from analysis of the SDS-PAGE gels. Aliquots (1-5 mL) of the purified enzyme were stored at −80° C. until use.

Example 27

Expression and Purification of the Aldolase of SEQ ID NO:104

The cloning of the E. coli BL21(DE3)pLysS host cells carrying the gene for the aldolase of SEQ ID NO:104 (the gene is shown as SEQ ID NO:103) on the pET28b plasmid is described in Example 3B.

The aldolase of SEQ ID NO:104 with an amino-terminal $HIS_6$-purification tag was produced using the EMD Biosciences Overnight Express System II (solutions 1-6) (La Jolla, Calif.) containing 50 µg/mL kanamycin in shake flasks. This expression system induces the expression of IPTG-inducible systems without the need to monitor cell growth. After inoculation of 200 mL aliquots of the medium (in 1 L flasks) from either liquid cultures or plates of the aldolase construct, the cultures were incubated at 30° C. overnight with shaking at 225 rpm. When the $OD_{600}$ had reached a minimum of 6, the cells were harvested by centrifugation and washed once with buffer.

To prepare cell free extract containing the aldolase, the cells were suspended in 3-4 volumes of 100 mM potassium phosphate, pH 7.8 and then disrupted using a Microfluidics homogenizer (Newton, Mass.) (3 passes at 18,000 psi), maintaining the temperature of the suspension at less than 15° C. Alternatively, cell free extract was prepared using EMD Biosciences BugBuster® (primary amine-free) Extraction Reagent (La Jolla, Calif.) containing 1 µL/mL Benzonase® Nuclease, 5 µL/mL Protease Inhibitor Cocktail Set II, and 0.033 µL/mL rLysozyme™ according to the manufacturer's protocol. All subsequent purification steps were carried out at 4° C. The cell suspension was centrifuged for 20-30 minutes at 15,000-20,000×g to remove the cell debris. A 20-25 mL aliquot of the cell free extract was applied to a 45 mL column of GE Healthcare Chelating Sepharose™ Fast Flow resin (nickel (II) form) (Piscataway, N.J.) that had been previously equilibrated with 100 mM potassium phosphate containing 200 mM sodium chloride. To generate the nickel form of the resin, the resin was washed with 150 mL of 200 mM nickel (II) sulfate hexahydrate and then with 150 mL of distilled water. After loading the sample, the column was washed/eluted with 150 mL of the equilibration buffer containing 25 mM imidazole, 150 mL of the equilibration buffer containing 50 mM imidazole and 150 mL of the equilibration buffer containing 500 mM imidazole. The $HIS_6$-tagged protein eluted in the last wash. The 500 mM imidazole wash was concentrated with Millipore/Amicon Centricon Plus-70 centrifugal filter devices (MWCO 10 kDa) (Billerica, Mass.) to 15-20 mL according to the manufacturer's instructions. The imidazole and sodium chloride were removed by passage through disposable GE Healthcare PD10 columns (2.5 mL sample per column) previously equilibrated with 100 mM potassium phosphate, pH 7.8. The purified aldolase was eluted with 3.5 mL per column of the same buffer. The protein concentration of each fraction was determined using the Pierce BCA assay kit (Rockford, Ill.) using BSA as the protein standard. The purity of each fraction and the level of expression in the cell free extract fraction were determined using a Bio-Rad Experion microcapillary chip system (Hercules, Calif.) or using Bio-Rad 4-15% SDS-polyacrylamide gradient gels run in a Mini PROTEAN® 3 cell apparatus. The protein was visualized in the polyacrylamide gels using Bio-Rad Bio-Safe G-250 Coomassie stain and destained with water. Typically this procedure produces ~50 mg of enzyme from 400 mL of overnight culture that is 85-95% pure, as judged by the Experion software. Aliquots (1-5 mL) of the purified enzyme were stored at −80° C. until use. Preparation of the enzyme in this manner reduced the level of precipitation of the enzyme previously noted. The presence of magnesium in the storage buffer had no effect on the level of precipitation.

SEQUENCE LISTING

<160> NUMBER OF SEQ ID NOS: 213

<210> SEQ ID NO 1
<211> LENGTH: 684
<212> TYPE: DNA
<213> ORGANISM: Comamonas testosteroni

<400> SEQUENCE: 1

```
atgtacgaac tgggagttgt ctaccgcaat atccagcgcg ccgaccgcgc tgctgctgac      60
ggcctggccg ccctgggctc cgccaccgtg cacgaggcca tgggccgcgt cggtctgctc     120
aagccctata tgcgccccat ctatgccggc aagcaggtct cgggcaccgc cgtcacggtg     180
ctgctgcagc ccggcgacaa ctggatgatg catgtggctg ccgagcagat tcagcccggc     240
gacatcgtgg tcgcagccgt caccgcagag tgcaccgacg gctacttcgg cgatctgctg     300
gccaccagct tccaggcgcg cggcgcacgt gcgctgatca tcgatgccgg cgtgcgcgac     360
gtgaagacgc tgcaggagat ggactttccg gtctggagca aggccatctc ttccaagggc     420
acgatcaagg ccaccctggg ctcggtcaac atccccatcg tctgcgccgg catgctggtc     480
acgcccggtg acgtgatcgt ggccgacgac gacggcgtgg tctgcgtgcc cgccgcgcgt     540
gccgtggaag tgctggccgc cgcccagaag cgtgaaagct tcgaaggcga aaagcgcgcc     600
aagctggcct cgggcatcct cggcctggat atgtacaaga tgcgcgagcc cctggaaaag     660
gccggcctga aatatattga ctaa                                            684
```

<210> SEQ ID NO 2
<211> LENGTH: 227
<212> TYPE: PRT
<213> ORGANISM: Comamonas testosteroni

<400> SEQUENCE: 2

```
Met Tyr Glu Leu Gly Val Val Tyr Arg Asn Ile Gln Arg Ala Asp Arg
1               5                   10                  15

Ala Ala Ala Asp Gly Leu Ala Ala Leu Gly Ser Ala Thr Val His Glu
            20                  25                  30

Ala Met Gly Arg Val Gly Leu Leu Lys Pro Tyr Met Arg Pro Ile Tyr
        35                  40                  45

Ala Gly Lys Gln Val Ser Gly Thr Ala Val Thr Val Leu Leu Gln Pro
    50                  55                  60

Gly Asp Asn Trp Met Met His Val Ala Ala Glu Gln Ile Gln Pro Gly
```

```
                65                  70                  75                  80
Asp Ile Val Val Ala Ala Val Thr Ala Glu Cys Thr Asp Gly Tyr Phe
                    85                  90                  95

Gly Asp Leu Leu Ala Thr Ser Phe Gln Ala Arg Gly Ala Arg Ala Leu
                100                 105                 110

Ile Ile Asp Ala Gly Val Arg Asp Val Lys Thr Leu Gln Glu Met Asp
                115                 120                 125

Phe Pro Val Trp Ser Lys Ala Ile Ser Ser Lys Gly Thr Ile Lys Ala
            130                 135                 140

Thr Leu Gly Ser Val Asn Ile Pro Ile Val Cys Ala Gly Met Leu Val
145                 150                 155                 160

Thr Pro Gly Asp Val Ile Val Ala Asp Asp Gly Val Val Cys Val
                165                 170                 175

Pro Ala Ala Arg Ala Val Glu Val Leu Ala Ala Gln Lys Arg Glu
                180                 185                 190

Ser Phe Glu Gly Glu Lys Arg Ala Lys Leu Ala Ser Gly Ile Leu Gly
            195                 200                 205

Leu Asp Met Tyr Lys Met Arg Glu Pro Leu Glu Lys Ala Gly Leu Lys
    210                 215                 220

Tyr Ile Asp
225

<210> SEQ ID NO 3
<211> LENGTH: 63
<212> TYPE: DNA
<213> ORGANISM: Artificial sequence
<220> FEATURE:
<223> OTHER INFORMATION: pykA Knockout Primer 1

<400> SEQUENCE: 3
atgtccagaa ggcttcgcag aacaaaaatc gttaccacgt taggtgtagg ctggagctgc      60
ttc                                                                   63

<210> SEQ ID NO 4
<211> LENGTH: 64
<212> TYPE: DNA
<213> ORGANISM: Artificial sequence
<220> FEATURE:
<223> OTHER INFORMATION: pykA Knockout Primer 2

<400> SEQUENCE: 4
ctctaccgtt aaaatacgcg tggtattagt agaacccacg gtaccatatg aatatcctcc      60
ttag                                                                  64

<210> SEQ ID NO 5
<211> LENGTH: 64
<212> TYPE: DNA
<213> ORGANISM: Artificial sequence
<220> FEATURE:
<223> OTHER INFORMATION: pykF Knockout Primer 1

<400> SEQUENCE: 5
aggacgtgaa cagatgcggt gttagtagtg ccgctcggta ccagcatatg aatatcctcc      60
ttag                                                                  64

<210> SEQ ID NO 6
<211> LENGTH: 63
<212> TYPE: DNA
<213> ORGANISM: Artificial sequence
<220> FEATURE:
```

<223> OTHER INFORMATION: pykF Knockout Primer 2

<400> SEQUENCE: 6
atgaaaaaga ccaaaattgt tgcaccatc ggaccgaaaa ccggtgtagg ctggagctgc    60
ttc    63

<210> SEQ ID NO 7
<211> LENGTH: 30
<212> TYPE: DNA
<213> ORGANISM: Artificial sequence
<220> FEATURE:
<223> OTHER INFORMATION: HEXaspC Primer 1

<400> SEQUENCE: 7
gcggaacata tgtttgagaa cattaccgcc    30

<210> SEQ ID NO 8
<211> LENGTH: 32
<212> TYPE: DNA
<213> ORGANISM: Artificial sequence
<220> FEATURE:
<223> OTHER INFORMATION: HEXaspC Primer 2

<400> SEQUENCE: 8
ataaccggat ccttacagca ctgccacaat cg    32

<210> SEQ ID NO 9
<211> LENGTH: 36
<212> TYPE: DNA
<213> ORGANISM: Artificial sequence
<220> FEATURE:
<223> OTHER INFORMATION: aspCW130F Backward Primer

<400> SEQUENCE: 9
cgctcttatg gttcggtttg cttgggttgc tcaccc    36

<210> SEQ ID NO 10
<211> LENGTH: 36
<212> TYPE: DNA
<213> ORGANISM: Artificial sequence
<220> FEATURE:
<223> OTHER INFORMATION: aspCW130F Forward Primer

<400> SEQUENCE: 10
gggtgagcaa cccaagcttt ccgaaccata agagcg    36

<210> SEQ ID NO 11
<211> LENGTH: 39
<212> TYPE: DNA
<213> ORGANISM: Artificial sequence
<220> FEATURE:
<223> OTHER INFORMATION: R122G-1 Primer

<400> SEQUENCE: 11
caaaaaatac cagcgttaag ggagtgtggg tgagcaacc    39

<210> SEQ ID NO 12
<211> LENGTH: 29
<212> TYPE: DNA
<213> ORGANISM: Artificial sequence
<220> FEATURE:
<223> OTHER INFORMATION: P9T_4 Primer

<400> SEQUENCE: 12
cattaccgcc gctactgccg acccgattc    29

```
<210> SEQ ID NO 13
<211> LENGTH: 39
<212> TYPE: DNA
<213> ORGANISM: Artificial sequence
<220> FEATURE:
<223> OTHER INFORMATION: I68V-1 Primer

<400> SEQUENCE: 13
caccaaaaat tacctcggcg tagacggcat ccctgaatt                   39

<210> SEQ ID NO 14
<211> LENGTH: 35
<212> TYPE: DNA
<213> ORGANISM: Artificial sequence
<220> FEATURE:
<223> OTHER INFORMATION: T156A Primer

<400> SEQUENCE: 14
tgatgcggaa aatcacgctc ttgacttcga tgcac                       35

<210> SEQ ID NO 15
<211> LENGTH: 35
<212> TYPE: DNA
<213> ORGANISM: Artificial sequence
<220> FEATURE:
<223> OTHER INFORMATION: L. brevis Glutamate Racemase Primer 1

<400> SEQUENCE: 15
gcggcgccat ggaaaatgat ccgattggtc taatg                       35

<210> SEQ ID NO 16
<211> LENGTH: 33
<212> TYPE: DNA
<213> ORGANISM: Artificial sequence
<220> FEATURE:
<223> OTHER INFORMATION: L. brevis Glutamate Racemase Primer 2

<400> SEQUENCE: 16
gcggcggtcg acgcaattac aattgtgttt gtc                         33

<210> SEQ ID NO 17
<211> LENGTH: 34
<212> TYPE: DNA
<213> ORGANISM: Artificial sequence
<220> FEATURE:
<223> OTHER INFORMATION: P. pentosaceus Glutamate Racemase Primer 1

<400> SEQUENCE: 17
gcggcgccat ggatgtatgt ataattttat ttag                        34

<210> SEQ ID NO 18
<211> LENGTH: 36
<212> TYPE: DNA
<213> ORGANISM: Artificial sequence
<220> FEATURE:
<223> OTHER INFORMATION: P. pentosaceus Glutamate Racemase Primer 2

<400> SEQUENCE: 18
gcggcggtcg acaaatttca ttattcattc taattt                      36

<210> SEQ ID NO 19
<211> LENGTH: 36
<212> TYPE: DNA
<213> ORGANISM: Artificial sequence
<220> FEATURE:
<223> OTHER INFORMATION: P. stutzeri 4 D-HPG AT Outer Primer 1
```

-continued

<400> SEQUENCE: 19
ggccggcata tgtcgatcct taacgactac aaacgt                                    36

<210> SEQ ID NO 20
<211> LENGTH: 36
<212> TYPE: DNA
<213> ORGANISM: Artificial sequence
<220> FEATURE:
<223> OTHER INFORMATION: P. stutzeri 4 D-HPG AT Outer Primer 2

<400> SEQUENCE: 20
ggaaggctcg agtcatgatt ggtttccaga caaatt                                    36

<210> SEQ ID NO 21
<211> LENGTH: 693
<212> TYPE: DNA
<213> ORGANISM: Aldolase (Bacillus subtilis)

<400> SEQUENCE: 21
atgatttatc agccggggac aacaggcatc gtcgtgcagg atattgcacg cgctgatcaa          60
gccattatcg atggcctagc agaatgtggt gtggcgacgg tgcatgaggc acagggcgc          120 aagggcctgt tggcggatta tatgacgccg atttactcgg gcgcgcgcat cgctggatct        180
gcggtgacca ttctggcacc gccgtgtgac aattggatga tccatgtggc ggtagaacag        240
ttgcaaaagg gcgatgtgtt gctgctgggc acgatcacac cgtccaatgc tggctatttc        300
ggtgacttgc tggccacgtc agccatggcg cacggttgtc gcggattgat cattgatggc        360
ggtgtgcgcg atgtgcaaga gctgacggat atgggctttc cggtttggtc caaggccgta        420
catgcccaag gcacaatcaa agaaacgctg ggatcggtca acgtgccagt tgtctgcggc        480
caagagttgg taaaccccgg tgatattgtg gtggccgacg atgacggggt gtgcgttgtg        540
cgccgcgaag aagctgctga tgtgctggct aaggcgcggg cgcgcgagag caatgaagcg        600
gccaagcgcg cgcgttttga ggccggtgag ctggggctgg atatctatga catgcgcgcg        660
cggctggccg aaaaaggact gaaatacgtc tga                                     693

<210> SEQ ID NO 22
<211> LENGTH: 230
<212> TYPE: PRT
<213> ORGANISM: Aldolase (Bacillus subtilis)

<400> SEQUENCE: 22

Met Ile Tyr Gln Pro Gly Thr Thr Gly Ile Val Val Gln Asp Ile Ala
1               5                   10                  15

Arg Ala Asp Gln Ala Ile Ile Asp Gly Leu Ala Glu Cys Gly Val Ala
                20                  25                  30

Thr Val His Glu Ala Gln Gly Arg Lys Gly Leu Leu Ala Asp Tyr Met
            35                  40                  45

Thr Pro Ile Tyr Ser Gly Ala Arg Ile Ala Gly Ser Ala Val Thr Ile
        50                  55                  60

Leu Ala Pro Pro Cys Asp Asn Trp Met Ile His Val Ala Val Glu Gln
65                  70                  75                  80

Leu Gln Lys Gly Asp Val Leu Leu Leu Gly Thr Ile Thr Pro Ser Asn
                85                  90                  95

Ala Gly Tyr Phe Gly Asp Leu Leu Ala Thr Ser Ala Met Ala His Gly
            100                 105                 110

Cys Arg Gly Leu Ile Ile Asp Gly Gly Val Arg Asp Val Gln Glu Leu
        115                 120                 125

```
Thr Asp Met Gly Phe Pro Val Trp Ser Lys Ala Val His Ala Gln Gly
130                 135                 140

Thr Ile Lys Glu Thr Leu Gly Ser Val Asn Val Pro Val Cys Gly
145                 150                 155                 160

Gln Glu Leu Val Asn Pro Gly Asp Ile Val Ala Asp Asp Gly
                165                 170                 175

Val Cys Val Val Arg Arg Glu Glu Ala Ala Asp Val Leu Ala Lys Ala
                180                 185                 190

Arg Ala Arg Glu Ser Asn Glu Ala Ala Lys Arg Ala Arg Phe Glu Ala
            195                 200                 205

Gly Glu Leu Gly Leu Asp Ile Tyr Asp Met Arg Ala Arg Leu Ala Glu
210                 215                 220

Lys Gly Leu Lys Tyr Val
225                 230

<210> SEQ ID NO 23
<211> LENGTH: 36
<212> TYPE: DNA
<213> ORGANISM: Artificial sequence
<220> FEATURE:
<223> OTHER INFORMATION: Aldolase Primer

<400> SEQUENCE: 23
gaggagctcg agtcagacgt atttcagtcc tttttc                          36

<210> SEQ ID NO 24
<211> LENGTH: 29
<212> TYPE: DNA
<213> ORGANISM: Artificial sequence
<220> FEATURE:
<223> OTHER INFORMATION: Aldolase Primer

<400> SEQUENCE: 24
agaagacata tgatttatca gccggggac                                  29

<210> SEQ ID NO 25
<211> LENGTH: 20
<212> TYPE: DNA
<213> ORGANISM: Artificial sequence
<220> FEATURE:
<223> OTHER INFORMATION: Alanine Racemase Primer

<400> SEQUENCE: 25
atggacgagt ttcaccgcga                                            20

<210> SEQ ID NO 26
<211> LENGTH: 20
<212> TYPE: DNA
<213> ORGANISM: Artificial sequence
<220> FEATURE:
<223> OTHER INFORMATION: Alanine Racemase Primer

<400> SEQUENCE: 26
ttatgcatcg cttcatccgc                                            20

<210> SEQ ID NO 27
<211> LENGTH: 31
<212> TYPE: DNA
<213> ORGANISM: Artificial sequence
<220> FEATURE:
<223> OTHER INFORMATION: Alanine Racemase Primer

<400> SEQUENCE: 27
ataataggat cctcatccgc ggccaacggc g                               31
```

```
<210> SEQ ID NO 28
<211> LENGTH: 43
<212> TYPE: DNA
<213> ORGANISM: Artificial sequence
<220> FEATURE:
<223> OTHER INFORMATION: Alanine Racemase Primer

<400> SEQUENCE: 28
gggaaaggta ccgaggaata taaatggac gagtttcacc gcg                          43

<210> SEQ ID NO 29
<211> LENGTH: 43
<212> TYPE: DNA
<213> ORGANISM: Artificial sequence
<220> FEATURE:
<223> OTHER INFORMATION: Mutagenic Primer
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (22)..(22)
<223> OTHER INFORMATION: k is g or t

<400> SEQUENCE: 29
gccggacgac acgcacattn nkgcggtcgt gaaggcgaac gcc                         43

<210> SEQ ID NO 30
<211> LENGTH: 45
<212> TYPE: DNA
<213> ORGANISM: Artificial sequence
<220> FEATURE:
<223> OTHER INFORMATION: Mutagenic Primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 30
gtgaaggcga acgcctatgg annkggggat gtgcaggtgg caagg                       45

<210> SEQ ID NO 31
<211> LENGTH: 45
<212> TYPE: DNA
<213> ORGANISM: Artificial sequence
<220> FEATURE:
<223> OTHER INFORMATION: Mutagenic Primer
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (23)..(23)
<223> OTHER INFORMATION: k is g or t

<400> SEQUENCE: 31
cctcccgcct ggcggttgcc nnkttggatg aggcgctcgc tttaa                       45

<210> SEQ ID NO 32
<211> LENGTH: 45
```

```
<212> TYPE: DNA
<213> ORGANISM: Artificial sequence
<220> FEATURE:
<223> OTHER INFORMATION: Mutagenic Primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 32
caaccaggcg aaaaggtgag cnnkggtgcg acgtacactg cgcag            45

<210> SEQ ID NO 33
<211> LENGTH: 45
<212> TYPE: DNA
<213> ORGANISM: Artificial sequence
<220> FEATURE:
<223> OTHER INFORMATION: Mutagenic Primer
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (25)..(25)
<223> OTHER INFORMATION: k is g or t

<400> SEQUENCE: 33
gatcgggacg attccgatcg gcnnkgcgga cggctggctc cgccg            45

<210> SEQ ID NO 34
<211> LENGTH: 43
<212> TYPE: DNA
<213> ORGANISM: Artificial sequence
<220> FEATURE:
<223> OTHER INFORMATION: Mutagenic Primer
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (23)..(23)
<223> OTHER INFORMATION: k is g or t

<400> SEQUENCE: 34
gccatttgga aacgatcaac nnkgaagtgc cttgcacgat cag              43

<210> SEQ ID NO 35
<211> LENGTH: 43
<212> TYPE: DNA
<213> ORGANISM: Artificial sequence
<220> FEATURE:
<223> OTHER INFORMATION: Racemase Primer

<400> SEQUENCE: 35
gggaaaggta ccgaggaata taaatggac gagtttcacc gcg               43

<210> SEQ ID NO 36
<211> LENGTH: 27
<212> TYPE: DNA
<213> ORGANISM: Artificial sequence
<220> FEATURE:
<223> OTHER INFORMATION: Racemase Primer

<400> SEQUENCE: 36
gcggcgccat ggacgagttt caccgcg                                27
```

```
<210> SEQ ID NO 37
<211> LENGTH: 43
<212> TYPE: DNA
<213> ORGANISM: Artificial sequence
<220> FEATURE:
<223> OTHER INFORMATION: Alanine Racemase Primer

<400> SEQUENCE: 37
gccatttgga aacgatcaac tatgaagtgc cttgcacgat cag          43

<210> SEQ ID NO 38
<211> LENGTH: 45
<212> TYPE: DNA
<213> ORGANISM: Artificial sequence
<220> FEATURE:
<223> OTHER INFORMATION: Alanine Racemase Primer

<400> SEQUENCE: 38
ctcccgcctg gcggttgcct tcttggatga ggcgctcgct ttaag        45

<210> SEQ ID NO 39
<211> LENGTH: 43
<212> TYPE: DNA
<213> ORGANISM: Artificial sequence
<220> FEATURE:
<223> OTHER INFORMATION: Alanine Racemase Primer

<400> SEQUENCE: 39
gccggacgac acgcacatta tggcggtcgt gaaggcgaac gcc          43

<210> SEQ ID NO 40
<211> LENGTH: 1152
<212> TYPE: DNA
<213> ORGANISM: Alanine Racemase (Geobacillus stearothermophilus)

<400> SEQUENCE: 40
atggacgagt tcaccgcga tacgtgggcg aagtggatt tggacgccat ttacgacaat    60
gtggagaatt tgcgccgttt gctgccggac gacacgcaca ttatggcggt cgtgaaggcg   120
aacgcctatg gacatgggga tgtgcaggtg gcaaggacag cgctcgaagc gggggcctcc   180
cgcctggcgg ttgccttttt ggatgaggcg ctcgctttaa gggaaaaagg aatcgaagcg   240
ccgattctag ttctcggggc ttcccgtcca gctgatgcgg cgctggccgc ccagcagcgc   300
attgccctga ccgtgttccg ctccgactgg ttggaagaag cgtccgccct ttacagcggc   360
cctttttccta ttcatttcca tttgaaaatg gacaccggca tgggacggct tggagtgaaa   420
gacgaggaag agacgaaacg aatcgtagcg ctgattgagc gccatccgca ttttgtgctt   480
gaagggtgt acacgcattt tgcgactgcg gatgaggtga acaccgatta ttttttcctat   540
cagtataccc gtttttttgca catgctcgaa tggctgccgt cgcgcccgcc gctcgtccat   600
tgcgccaaca gcgcagcgtc gctccgtttc cctgaccgga cgttcaatat ggtccgcttc   660
ggcattgcca tgtatgggct tgcccccgtcg cccggcatca agccgctgct gccgtatcca   720
ttaaaagaag cattttcgct ccatagccgc ctcgtacacg tcaaaaaact gcaaccaggc   780
gaaaaggtga gctatggtgc gacgtacact gcgcagacgg aggagtggat cgggacgatt   840
ccgatcggct atgcggacgg ctggctccgc cgcctgcagc actttcatgt ccttgttgac   900
ggacaaaagg cgccgattgt cggccgcatt tgcatggacc agtgcatgat ccgcctgcct   960
ggtccgctgc cggtcggcac gaaggtgaca ctgattggtc gccaaggga cgaggtaatt  1020
tccattgatg atgtcgctcg ccatttggaa acgatcaact acgaagtgcc ttgcacgatc  1080
```

```
agttatcgag tgccccgtat ttttttccgc cataagcgta taatggaagt gagaaacgcc    1140
gttggccgcg ga                                                        1152
```

<210> SEQ ID NO 41
<211> LENGTH: 384
<212> TYPE: PRT
<213> ORGANISM: Alanine Racemase (Geobacillus stearothermophilus)

<400> SEQUENCE: 41

Met Asp Glu Phe His Arg Asp Thr Trp Ala Glu Val Asp Leu Asp Ala
1               5                   10                  15

Ile Tyr Asp Asn Val Glu Asn Leu Arg Arg Leu Leu Pro Asp Asp Thr
            20                  25                  30

His Ile Met Ala Val Val Lys Ala Asn Ala Tyr Gly His Gly Asp Val
        35                  40                  45

Gln Val Ala Arg Thr Ala Leu Glu Ala Gly Ala Ser Arg Leu Ala Val
    50                  55                  60

Ala Phe Leu Asp Glu Ala Leu Ala Leu Arg Glu Lys Gly Ile Glu Ala
65                  70                  75                  80

Pro Ile Leu Val Leu Gly Ala Ser Arg Pro Ala Asp Ala Ala Leu Ala
                85                  90                  95

Ala Gln Gln Arg Ile Ala Leu Thr Val Phe Arg Ser Asp Trp Leu Glu
            100                 105                 110

Glu Ala Ser Ala Leu Tyr Ser Gly Pro Phe Pro Ile His Phe His Leu
        115                 120                 125

Lys Met Asp Thr Gly Met Gly Arg Leu Gly Val Lys Asp Glu Glu Glu
    130                 135                 140

Thr Lys Arg Ile Val Ala Leu Ile Glu Arg His Pro His Phe Val Leu
145                 150                 155                 160

Glu Gly Val Tyr Thr His Phe Ala Thr Ala Asp Glu Val Asn Thr Asp
                165                 170                 175

Tyr Phe Ser Tyr Gln Tyr Thr Arg Phe Leu His Met Leu Glu Trp Leu
            180                 185                 190

Pro Ser Arg Pro Pro Leu Val His Cys Ala Asn Ser Ala Ala Ser Leu
        195                 200                 205

Arg Phe Pro Asp Arg Thr Phe Asn Met Val Arg Phe Gly Ile Ala Met
    210                 215                 220

Tyr Gly Leu Ala Pro Ser Pro Gly Ile Lys Pro Leu Leu Pro Tyr Pro
225                 230                 235                 240

Leu Lys Glu Ala Phe Ser Leu His Ser Arg Leu Val His Val Lys Lys
                245                 250                 255

Leu Gln Pro Gly Glu Lys Val Ser Tyr Gly Ala Thr Tyr Thr Ala Gln
            260                 265                 270

Thr Glu Glu Trp Ile Gly Thr Ile Pro Ile Gly Tyr Ala Asp Gly Trp
        275                 280                 285

Leu Arg Arg Leu Gln His Phe His Val Leu Val Asp Gly Gln Lys Ala
    290                 295                 300

Pro Ile Val Gly Arg Ile Cys Met Asp Gln Cys Met Ile Arg Leu Pro
305                 310                 315                 320

Gly Pro Leu Pro Val Gly Thr Lys Val Thr Leu Ile Gly Arg Gln Gly
                325                 330                 335

Asp Glu Val Ile Ser Ile Asp Asp Val Ala Arg His Leu Glu Thr Ile
            340                 345                 350

Asn Tyr Glu Val Pro Cys Thr Ile Ser Tyr Arg Val Pro Arg Ile Phe

```
                      355                 360                 365
Phe Arg His Lys Arg Ile Met Glu Val Arg Asn Ala Val Gly Arg Gly
        370                 375                 380

<210> SEQ ID NO 42
<211> LENGTH: 1152
<212> TYPE: DNA
<213> ORGANISM: Artificial sequence
<220> FEATURE:
<223> OTHER INFORMATION: Mutagenized Ala Racemase

<400> SEQUENCE: 42
atggacgagt tcaccgcga tacgtgggcg gaagtggatt tggacgccat ttacgacaat      60
gtggagaatt tgcgccgttt gctgccggac gacacgcaca tttgtgcggt cgtgaaggcg     120
aacgcctatg gacatgggga tgtgcaggtg gcaaggacag cgctcgaagc gggggcctcc     180
cgcctggcgg ttgccgagtt ggatgaggcg ctcgctttaa gggaaaaagg aatcgaagcg     240
ccgattctag ttctcggggc ttcccgtcca gctgatgcgg cgctgccgc ccagcagcgc      300 attgccctga ccgtgttccg ctccgactgg ttgaagaag cgtccgccct tacagcggc      360 cctttttccta ttcatttcca tttgaaaatg gacaccggca tgggacgct tggagtgaaa     420 gacgaggaag agacgaaacg aatcgtagcg ctgattgagc gccatccgca ttttgtgctt     480 gaagggtgt acacgcattt tgcgactgcg gatgaggtga acaccgatta ttttttcctat    540 cagtataccc gttttttgca catgctcgaa tggctgccgt cgcgcccgct gctcgtccat     600
tgcgccaaca gcgcagcgtc gctccgtttc cctgaccgga cgttcaatat ggtccgcttc     660
ggcattgcca tgtatgggct tgccccgtcg cccggcatca agccgctgct gccgtatcca     720
ttaaaagaag catttttcgct ccatagccgc tcgtacacg tcaaaaaact gcaaccaggc     780
gaaaaggtga gctatggtgc gacgtacact gcgcagacgg aggagtggat cgggacgatt     840
ccgatcggct atgcggacgg ctggctccgc gcctgcagc actttcatgt ccttgttgac      900
ggacaaaagg cgccgattgt cggccgcatt tgcatggacc agtgcatgat ccgcctgcct     960
ggtccgctgc cggtcggcac gaaggtgaca ctgattggtc gccaagggga cgaggtaatt    1020
tccattgatg atgtcgctcg ccatttggaa acgatcaacg cggaagtgcc ttgcacgatc    1080
agttatcgag tgccccgtat ttttttccgc cataagcgta atggaagt gagaaacgcc     1140 gttggccgcg ga                                                        1152

<210> SEQ ID NO 43
<211> LENGTH: 384
<212> TYPE: PRT
<213> ORGANISM: Artificial sequence
<220> FEATURE:
<223> OTHER INFORMATION: Mutagenized Ala Racemase

<400> SEQUENCE: 43

Met Asp Glu Phe His Arg Asp Thr Trp Ala Glu Val Asp Leu Asp Ala
1               5                   10                  15

Ile Tyr Asp Asn Val Glu Asn Leu Arg Arg Leu Leu Pro Asp Asp Thr
            20                  25                  30

His Ile Cys Ala Val Val Lys Ala Asn Ala Tyr Gly His Gly Asp Val
        35                  40                  45

Gln Val Ala Arg Thr Ala Leu Glu Ala Gly Ala Ser Arg Leu Ala Val
    50                  55                  60

Ala Glu Leu Asp Glu Ala Leu Ala Leu Arg Glu Lys Gly Ile Glu Ala
65                  70                  75                  80
```

```
Pro Ile Leu Val Leu Gly Ala Ser Arg Pro Asp Ala Ala Leu Ala
                85                  90                  95
Ala Gln Gln Arg Ile Ala Leu Thr Val Phe Arg Ser Asp Trp Leu Glu
            100                 105                 110
Glu Ala Ser Ala Leu Tyr Ser Gly Pro Phe Pro Ile His Phe His Leu
            115                 120                 125
Lys Met Asp Thr Gly Met Gly Arg Leu Gly Val Lys Asp Glu Glu Glu
130                 135                 140
Thr Lys Arg Ile Val Ala Leu Ile Glu Arg His Pro His Phe Val Leu
145                 150                 155                 160
Glu Gly Val Tyr Thr His Phe Ala Thr Ala Asp Glu Val Asn Thr Asp
                165                 170                 175
Tyr Phe Ser Tyr Gln Tyr Thr Arg Phe Leu His Met Leu Glu Trp Leu
            180                 185                 190
Pro Ser Arg Pro Leu Leu Val His Cys Ala Asn Ser Ala Ala Ser Leu
            195                 200                 205
Arg Phe Pro Asp Arg Thr Phe Asn Met Val Arg Phe Gly Ile Ala Met
210                 215                 220
Tyr Gly Leu Ala Pro Ser Pro Gly Ile Lys Pro Leu Leu Pro Tyr Pro
225                 230                 235                 240
Leu Lys Glu Ala Phe Ser Leu His Ser Arg Leu Val His Val Lys Lys
                245                 250                 255
Leu Gln Pro Gly Glu Lys Val Ser Tyr Gly Ala Thr Tyr Thr Ala Gln
            260                 265                 270
Thr Glu Glu Trp Ile Gly Thr Ile Pro Ile Gly Tyr Ala Asp Gly Trp
            275                 280                 285
Leu Arg Arg Leu Gln His Phe His Val Leu Val Asp Gly Gln Lys Ala
290                 295                 300
Pro Ile Val Gly Arg Ile Cys Met Asp Gln Cys Met Ile Arg Leu Pro
305                 310                 315                 320
Gly Pro Leu Pro Val Gly Thr Lys Val Thr Leu Ile Gly Arg Gln Gly
                325                 330                 335
Asp Glu Val Ile Ser Ile Asp Asp Val Ala Arg His Leu Glu Thr Ile
            340                 345                 350
Asn Ala Glu Val Pro Cys Thr Ile Ser Tyr Arg Val Pro Arg Ile Phe
            355                 360                 365
Phe Arg His Lys Arg Ile Met Glu Val Arg Asn Ala Val Gly Arg Gly
370                 375                 380

<210> SEQ ID NO 44
<211> LENGTH: 30
<212> TYPE: DNA
<213> ORGANISM: Artificial sequence
<220> FEATURE:
<223> OTHER INFORMATION: B. licheniformis BCAT Primer

<400> SEQUENCE: 44
ggttaaggcc atgggggacc agaaagacca                                    30

<210> SEQ ID NO 45
<211> LENGTH: 32
<212> TYPE: DNA
<213> ORGANISM: Artificial sequence
<220> FEATURE:
<223> OTHER INFORMATION: B. licheniformis BCAT Primer

<400> SEQUENCE: 45
ggccttccgt cgactcagct gacacttaag ct                                 32
```

<210> SEQ ID NO 46
<211> LENGTH: 29
<212> TYPE: DNA
<213> ORGANISM: Artificial sequence
<220> FEATURE:
<223> OTHER INFORMATION: Mutagenic Primer

<400> SEQUENCE: 46
atcacggatt tttattcggg gacggcgtg                              29

<210> SEQ ID NO 47
<211> LENGTH: 29
<212> TYPE: DNA
<213> ORGANISM: Artificial sequence
<220> FEATURE:
<223> OTHER INFORMATION: Mutagenic Primer

<400> SEQUENCE: 47
atcacggatt tttagacggg gacggcgtg                              29

<210> SEQ ID NO 48
<211> LENGTH: 26
<212> TYPE: DNA
<213> ORGANISM: Artificial sequence
<220> FEATURE:
<223> OTHER INFORMATION: Mutagenic Primer

<400> SEQUENCE: 48
ggacggcgtg tatgaaggga tcaggg                                 26

<210> SEQ ID NO 49
<211> LENGTH: 32
<212> TYPE: DNA
<213> ORGANISM: Artificial sequence
<220> FEATURE:
<223> OTHER INFORMATION: Mutagenic Primer

<400> SEQUENCE: 49
tgtttgaagg gatcaaggta tacgacggca ac                          32

<210> SEQ ID NO 50
<211> LENGTH: 34
<212> TYPE: DNA
<213> ORGANISM: Artificial sequence
<220> FEATURE:
<223> OTHER INFORMATION: Mutagenic Primer

<400> SEQUENCE: 50
gacggcgtgt atgaagggat caaggtatac gacg                        34

<210> SEQ ID NO 51
<211> LENGTH: 29
<212> TYPE: DNA
<213> ORGANISM: Artificial sequence
<220> FEATURE:
<223> OTHER INFORMATION: Mutagenic Primer

<400> SEQUENCE: 51
gctgaaagac gctttcatcc gcttggtcg                              29

<210> SEQ ID NO 52
<211> LENGTH: 28
<212> TYPE: DNA
<213> ORGANISM: Artificial sequence
<220> FEATURE:
<223> OTHER INFORMATION: Mutagenic Primer

<400> SEQUENCE: 52
gctgaaagac gctcacatcc gcttggtc                                          28

<210> SEQ ID NO 53
<211> LENGTH: 38
<212> TYPE: DNA
<213> ORGANISM: Artificial sequence
<220> FEATURE:
<223> OTHER INFORMATION: Mutagenic Primer

<400> SEQUENCE: 53
ctgaaagacg cttacatcta cttggtcgtt tcaagagg                               38

<210> SEQ ID NO 54
<211> LENGTH: 40
<212> TYPE: DNA
<213> ORGANISM: Artificial sequence
<220> FEATURE:
<223> OTHER INFORMATION: Mutagenic Primer

<400> SEQUENCE: 54
ggctgaaaga cgctttcatc tacttggtcg tttcaagagg                             40

<210> SEQ ID NO 55
<211> LENGTH: 39
<212> TYPE: DNA
<213> ORGANISM: Artificial sequence
<220> FEATURE:
<223> OTHER INFORMATION: Mutagenic Primer

<400> SEQUENCE: 55
gctgaaagac gctcacatct acttggtcgt ttcaagagg                              39

<210> SEQ ID NO 56
<211> LENGTH: 27
<212> TYPE: DNA
<213> ORGANISM: Artificial sequence
<220> FEATURE:
<223> OTHER INFORMATION: Mutagenic Primer

<400> SEQUENCE: 56
gcaggtgacc gcggactcga tccaaac                                           27

<210> SEQ ID NO 57
<211> LENGTH: 27
<212> TYPE: DNA
<213> ORGANISM: Artificial sequence
<220> FEATURE:
<223> OTHER INFORMATION: Mutagenic Primer

<400> SEQUENCE: 57
gcaggtgacc tcggacacga tccaaac                                           27

<210> SEQ ID NO 58
<211> LENGTH: 32
<212> TYPE: DNA
<213> ORGANISM: Artificial sequence
<220> FEATURE:
<223> OTHER INFORMATION: Mutagenic Primer

<400> SEQUENCE: 58
gcaggtgacc gcggacacga tccaaacaat tg                                     32

<210> SEQ ID NO 59
<211> LENGTH: 40

```
<212> TYPE: DNA
<213> ORGANISM: Artificial sequence
<220> FEATURE:
<223> OTHER INFORMATION: Mutagenic Primer

<400> SEQUENCE: 59
gtcatcataa ttgtcgaacc atacgcaata ttcccgaaac                                40

<210> SEQ ID NO 60
<211> LENGTH: 40
<212> TYPE: DNA
<213> ORGANISM: Artificial sequence
<220> FEATURE:
<223> OTHER INFORMATION: Mutagenic Primer

<400> SEQUENCE: 60
gtcatcataa ttgtcgaacc aaaggcaata ttcccgaaac                                40

<210> SEQ ID NO 61
<211> LENGTH: 40
<212> TYPE: DNA
<213> ORGANISM: Artificial sequence
<220> FEATURE:
<223> OTHER INFORMATION: Mutagenic Primer

<400> SEQUENCE: 61
gtcatcataa ttgtcgaacc attggcagaa ttcccgaaac                                40

<210> SEQ ID NO 62
<211> LENGTH: 45
<212> TYPE: DNA
<213> ORGANISM: Artificial sequence
<220> FEATURE:
<223> OTHER INFORMATION: Mutagenic Primer

<400> SEQUENCE: 62
cgagtgtcat cataattgtc gaaccatacg cagaattccc gaaac                          45

<210> SEQ ID NO 63
<211> LENGTH: 46
<212> TYPE: DNA
<213> ORGANISM: Artificial sequence
<220> FEATURE:
<223> OTHER INFORMATION: Mutagenic Primer

<400> SEQUENCE: 63
ccgagtgtca tcataattgt cgaaccaaag gcagaattcc cgaaac                         46

<210> SEQ ID NO 64
<211> LENGTH: 42
<212> TYPE: DNA
<213> ORGANISM: Artificial sequence
<220> FEATURE:
<223> OTHER INFORMATION: Mutagenic Primer

<400> SEQUENCE: 64
aatcgctgaa cttgttaaac aatattcttg tccggatcga gg                             42

<210> SEQ ID NO 65
<211> LENGTH: 21
<212> TYPE: DNA
<213> ORGANISM: Artificial sequence
<220> FEATURE:
<223> OTHER INFORMATION: Oligo Primer

<400> SEQUENCE: 65
gaagaccgtg gttatcaatt t                                                    21
```

<210> SEQ ID NO 66
<211> LENGTH: 21
<212> TYPE: DNA
<213> ORGANISM: Artificial sequence
<220> FEATURE:
<223> OTHER INFORMATION: Oligo Primer

<400> SEQUENCE: 66
gatggtattt acgaagtaat c                                          21

<210> SEQ ID NO 67
<211> LENGTH: 22
<212> TYPE: DNA
<213> ORGANISM: Artificial sequence
<220> FEATURE:
<223> OTHER INFORMATION: Oligo Primer

<400> SEQUENCE: 67
agatttaata tcacaacgta ac                                         22

<210> SEQ ID NO 68
<211> LENGTH: 22
<212> TYPE: DNA
<213> ORGANISM: Artificial sequence
<220> FEATURE:
<223> OTHER INFORMATION: Oligo Primer

<400> SEQUENCE: 68
gccaagtaaa atttaagatt ta                                         22

<210> SEQ ID NO 69
<211> LENGTH: 21
<212> TYPE: DNA
<213> ORGANISM: Artificial sequence
<220> FEATURE:
<223> OTHER INFORMATION: Oligo Primer

<400> SEQUENCE: 69
atttgctggg tgcgtataaa g                                          21

<210> SEQ ID NO 70
<211> LENGTH: 30
<212> TYPE: DNA
<213> ORGANISM: Artificial sequence
<220> FEATURE:
<223> OTHER INFORMATION: 4978 DAT GSP1 Upstrm Primer

<400> SEQUENCE: 70
gacatgctcc tccgctgtaa ataattcacc                                 30

<210> SEQ ID NO 71
<211> LENGTH: 30
<212> TYPE: DNA
<213> ORGANISM: Artificial sequence
<220> FEATURE:
<223> OTHER INFORMATION: 4978 DAT GSP1 Dwnstr Primer

<400> SEQUENCE: 71
ccctggtgat gaagtgaagc cagtattaac                                 30

<210> SEQ ID NO 72
<211> LENGTH: 27
<212> TYPE: DNA
<213> ORGANISM: Artificial sequence
<220> FEATURE:
<223> OTHER INFORMATION: 4978 DAT GSP2 Upstrm Primer

```
<400> SEQUENCE: 72
atcgccaaat tgataaccac ggtcttc                                          27

<210> SEQ ID NO 73
<211> LENGTH: 30
<212> TYPE: DNA
<213> ORGANISM: Artificial sequence
<220> FEATURE:
<223> OTHER INFORMATION: 4978 DAT GSP2 Dwnstr Primer

<400> SEQUENCE: 73
acgtcccgta gcaaactttg aaaaaggtgt                                       30

<210> SEQ ID NO 74
<211> LENGTH: 30
<212> TYPE: DNA
<213> ORGANISM: Artificial sequence
<220> FEATURE:
<223> OTHER INFORMATION: 7063 DAT GSP1 Upstrm Primer

<400> SEQUENCE: 74
tgcatagaat cggtcgatat gttcagtagc                                       30

<210> SEQ ID NO 75
<211> LENGTH: 30
<212> TYPE: DNA
<213> ORGANISM: Artificial sequence
<220> FEATURE:
<223> OTHER INFORMATION: 7063 DAT GSP1 Dwnstr Primer

<400> SEQUENCE: 75
gcggagaaac gattacagaa ggttcttcaa                                       30

<210> SEQ ID NO 76
<211> LENGTH: 27
<212> TYPE: DNA
<213> ORGANISM: Artificial sequence
<220> FEATURE:
<223> OTHER INFORMATION: 7063 DAT GSP2 Upstrm Primer

<400> SEQUENCE: 76
gtcaccaaat tgataaccac ggtcttc                                          27

<210> SEQ ID NO 77
<211> LENGTH: 27
<212> TYPE: DNA
<213> ORGANISM: Artificial sequence
<220> FEATURE:
<223> OTHER INFORMATION: 7063 DAT GSP2 Dwnstr Primer

<400> SEQUENCE: 77
ggtgtacttt atacgcaccc agcaaat                                          27

<210> SEQ ID NO 78
<211> LENGTH: 22
<212> TYPE: DNA
<213> ORGANISM: Artificial sequence
<220> FEATURE:
<223> OTHER INFORMATION: Adaptor Oligo Primer 1

<400> SEQUENCE: 78
gtaatacgac tcactatagg gc                                               22

<210> SEQ ID NO 79
<211> LENGTH: 19
```

```
<212> TYPE: DNA
<213> ORGANISM: Artificial sequence
<220> FEATURE:
<223> OTHER INFORMATION: Adaptor Oligo Primer 2

<400> SEQUENCE: 79
actatagggc acgcgtggt                                                  19

<210> SEQ ID NO 80
<211> LENGTH: 36
<212> TYPE: DNA
<213> ORGANISM: Artificial sequence
<220> FEATURE:
<223> OTHER INFORMATION: ATCC4978DAATNdelF Oligo Primer

<400> SEQUENCE: 80
ggccttggca tatgagttat agcttatgga atgacc                               36

<210> SEQ ID NO 81
<211> LENGTH: 36
<212> TYPE: DNA
<213> ORGANISM: Artificial sequence
<220> FEATURE:
<223> OTHER INFORMATION: ATCC4978DAATBamH1R Oligo Primer

<400> SEQUENCE: 81
ggccttaagg atccttatgc gcgaatacct tttggg                               36

<210> SEQ ID NO 82
<211> LENGTH: 34
<212> TYPE: DNA
<213> ORGANISM: Artificial sequence
<220> FEATURE:
<223> OTHER INFORMATION: ATCC7063DAATNdelF Oligo Primer

<400> SEQUENCE: 82
ggccttggca tatgagctac actttatgga atga                                 34

<210> SEQ ID NO 83
<211> LENGTH: 32
<212> TYPE: DNA
<213> ORGANISM: Artificial sequence
<220> FEATURE:
<223> OTHER INFORMATION: ATCC7063DAATBamH1R2a Oligo Primer

<400> SEQUENCE: 83
ggccaaggat ccgctaccca ctaatcatta ga                                   32

<210> SEQ ID NO 84
<211> LENGTH: 852
<212> TYPE: DNA
<213> ORGANISM: Bacillus rotans

<400> SEQUENCE: 84
atgagttata gcttatggaa tgaccaaatt gtgaatgatg aagaagtagt agttgataag     60
gaggaccgtg gctatcaatt tggcgatggt gtttatgaag ttgtaaaagt atataacggt    120
gaattattta cagcggagga gcatgtcgat cgttttttacg cgagtgctga aaaaattcgc    180
gttacgatcc cttatacaaa agacaaattg catcaattat tgcatcagtt agttgaaatg    240
aataaagttc aaacaggaca tatttatttc caaattcgc gtggtgcagg ccctcgtaat    300 catatttttcc ctggtgatga agtgaagcca gtattaacag gtaataccaa ggaaaatcca    360
cgtcccgtag caaactttga aaaggtgtg aaagcaacat tgtagaaga cattcgttgg    420 ttacgctgtg acattaaatc attaaattta cttggtgcgg tacttgctaa caagaagca    480
```

```
catgaaaaag gatgctatga agcggtttta catcgtgatg aaatcgtaac agaaggctct    540
tcttcaaata tttatggaat taaagatggc gtattataca cacatccagc gaataacttc    600
atcttaaatg gtattacacg tcaagtaatc attaaatgtg ctgctgaaat tggcttacca    660
gtgaaggaag aagcaatgac aaaaactcag cttcttgcaa tggatgaagt gattgtttca    720
tcaacgactt cagaagtaac gccaattatc gacatagatg gaacagtaat tggtgcgggt    780
aaaccgggtg actggacacg taaattacaa gcacaatttg atacgaaaat cccaaaaggt    840
attcgcgcat aa                                                        852
```

<210> SEQ ID NO 85
<211> LENGTH: 870
<212> TYPE: DNA
<213> ORGANISM: Bacillus serositidis

<400> SEQUENCE: 85

```
atgagctaca ctttatggaa tgacaaaatt gtggatgata accaagtatt cattaataaa     60
gaagacagag gctatcaatt tggtgacggc gtttatgaag ttataaaagt atatgatggg    120
gaaatgttta ctgctactga acatatcgac cgattctatg caagtgcaga gaagattaaa    180
ttgactgtac cctatacaaa gcataaactg catcaattac tgcatgaatt agtggaagca    240
aacgagctga aaactggaaa cttatacttt cagataacac gcggtgcgtc tccgcgtaat    300
catctatttc caggagacga tgtacttccg gtattaacgg gaaatgtaaa agaagcacca    360
cgctccatcg aaaatgcgca aaaaggtgta aaagccacat ttgcagaaga tattcgctgg    420
ctgcgctgcg atattaaatc gctaaatctt ttaggggctg ttttagcgaa acaagaggca    480
catgaaaagg gctgctacga agcaatttta catcgcggag aaacgattac agaaggttct    540
tcaacaaacg ttttcggtat aaaaaatggt gtactctata cacatccagc tgataatttc    600
atcttaagcg gcattacacg cggtgttgtt ttggcatgtg cgaacgaaat tggacttcct    660
gtaaaacaag aagcatttac aaaagacaaa gcactgcaaa tggacgaaat gttcgtatcc    720
tctactactt ctgaaataac accagttatc gatcttgatg gagtggccat taatggtgga    780
gaaattggcg aatggacgcg caagctgcaa aagcaatttg caacgaagct tccgggaagc    840
ccagcatata atttaacaga atataaatag                                     870
```

<210> SEQ ID NO 86
<211> LENGTH: 283
<212> TYPE: PRT
<213> ORGANISM: Bacillus rotans

<400> SEQUENCE: 86

```
Met Ser Tyr Ser Leu Trp Asn Asp Gln Ile Val Asn Asp Glu Glu Val
1               5                   10                  15

Val Val Asp Lys Glu Asp Arg Gly Tyr Gln Phe Gly Asp Gly Val Tyr
            20                  25                  30

Glu Val Val Lys Val Tyr Asn Gly Glu Leu Phe Thr Ala Glu Glu His
        35                  40                  45

Val Asp Arg Phe Tyr Ala Ser Ala Glu Lys Ile Arg Val Thr Ile Pro
    50                  55                  60

Tyr Thr Lys Asp Lys Leu His Gln Leu Leu His Gln Leu Val Glu Met
65                  70                  75                  80

Asn Lys Val Gln Thr Gly His Ile Tyr Phe Gln Ile Thr Arg Gly Ala
                85                  90                  95

Gly Pro Arg Asn His Ile Phe Pro Gly Asp Glu Val Lys Pro Val Leu
```

```
            100                 105                 110
Thr Gly Asn Thr Lys Glu Asn Pro Arg Pro Val Ala Asn Phe Glu Lys
            115                 120                 125
Gly Val Lys Ala Thr Phe Val Glu Asp Ile Arg Trp Leu Arg Cys Asp
            130                 135                 140
Ile Lys Ser Leu Asn Leu Leu Gly Ala Val Leu Ala Lys Gln Glu Ala
145                 150                 155                 160
His Glu Lys Gly Cys Tyr Glu Ala Val Leu His Arg Asp Glu Ile Val
            165                 170                 175
Thr Glu Gly Ser Ser Ser Asn Ile Tyr Gly Ile Lys Asp Gly Val Leu
            180                 185                 190
Tyr Thr His Pro Ala Asn Asn Phe Ile Leu Asn Gly Ile Thr Arg Gln
            195                 200                 205
Val Ile Ile Lys Cys Ala Ala Glu Ile Gly Leu Pro Val Lys Glu Glu
            210                 215                 220
Ala Met Thr Lys Thr Gln Leu Leu Ala Met Asp Glu Val Ile Val Ser
225                 230                 235                 240
Ser Thr Thr Ser Glu Val Thr Pro Ile Ile Asp Ile Asp Gly Thr Val
            245                 250                 255
Ile Gly Ala Gly Lys Pro Gly Asp Trp Thr Arg Lys Leu Gln Ala Gln
            260                 265                 270
Phe Asp Thr Lys Ile Pro Lys Gly Ile Arg Ala
            275                 280

<210> SEQ ID NO 87
<211> LENGTH: 289
<212> TYPE: PRT
<213> ORGANISM: Bacillus serositidis

<400> SEQUENCE: 87

Met Ser Tyr Thr Leu Trp Asn Asp Lys Ile Val Asp Asp Asn Gln Val
1               5                   10                  15
Phe Ile Asn Lys Glu Asp Arg Gly Tyr Gln Phe Gly Asp Gly Val Tyr
            20                  25                  30
Glu Val Ile Lys Val Tyr Asp Gly Glu Met Phe Thr Ala Thr Glu His
            35                  40                  45
Ile Asp Arg Phe Tyr Ala Ser Ala Glu Lys Ile Lys Leu Thr Val Pro
50                  55                  60
Tyr Thr Lys His Lys Leu His Gln Leu Leu His Glu Leu Val Glu Ala
65                  70                  75                  80
Asn Glu Leu Lys Thr Gly Asn Leu Tyr Phe Gln Ile Thr Arg Gly Ala
            85                  90                  95
Ser Pro Arg Asn His Leu Phe Pro Gly Asp Val Leu Pro Val Leu
            100                 105                 110
Thr Gly Asn Val Lys Glu Ala Pro Arg Ser Ile Glu Asn Ala Gln Lys
            115                 120                 125
Gly Val Lys Ala Thr Phe Ala Glu Asp Ile Arg Trp Leu Arg Cys Asp
            130                 135                 140
Ile Lys Ser Leu Asn Leu Leu Gly Ala Val Leu Ala Lys Gln Glu Ala
145                 150                 155                 160
His Glu Lys Gly Cys Tyr Glu Ala Ile Leu His Arg Gly Glu Thr Ile
            165                 170                 175
Thr Glu Gly Ser Ser Thr Asn Val Phe Gly Ile Lys Asn Gly Val Leu
            180                 185                 190
Tyr Thr His Pro Ala Asp Asn Phe Ile Leu Ser Gly Ile Thr Arg Gly
```

```
                195                 200                 205
Val Val Leu Ala Cys Ala Asn Glu Ile Gly Leu Pro Val Lys Gln Glu
        210                 215                 220

Ala Phe Thr Lys Asp Lys Ala Leu Gln Met Asp Glu Met Phe Val Ser
225                 230                 235                 240

Ser Thr Thr Ser Glu Ile Thr Pro Val Ile Asp Leu Asp Gly Val Ala
                245                 250                 255

Ile Asn Gly Gly Glu Ile Gly Glu Trp Thr Arg Lys Leu Gln Lys Gln
        260                 265                 270

Phe Ala Thr Lys Leu Pro Gly Ser Pro Ala Tyr Asn Leu Thr Glu Tyr
        275                 280                 285

Lys

<210> SEQ ID NO 88
<211> LENGTH: 30
<212> TYPE: DNA
<213> ORGANISM: Artificial sequence
<220> FEATURE:
<223> OTHER INFORMATION: B. sphaericus DAT Primer 1

<400> SEQUENCE: 88
gatataccat ggcatactca ttatggaatg                                    30

<210> SEQ ID NO 89
<211> LENGTH: 32
<212> TYPE: DNA
<213> ORGANISM: Artificial sequence
<220> FEATURE:
<223> OTHER INFORMATION: B. sphaericus DAT Primer 2

<400> SEQUENCE: 89
gttatcggat ccttaggcat taattgaaat tg                                 32

<210> SEQ ID NO 90
<211> LENGTH: 32
<212> TYPE: DNA
<213> ORGANISM: Artificial sequence
<220> FEATURE:
<223> OTHER INFORMATION: B. licheniformis DAT Primer 1

<400> SEQUENCE: 90
ggccggttca tatgaaagtt cttttttaacg gc                                32

<210> SEQ ID NO 91
<211> LENGTH: 32
<212> TYPE: DNA
<213> ORGANISM: Artificial sequence
<220> FEATURE:
<223> OTHER INFORMATION: B. licheniformis DAT Primer 2

<400> SEQUENCE: 91
ccttccggat ccttaaaccg ttttggctgt ct                                 32

<210> SEQ ID NO 92
<211> LENGTH: 30
<212> TYPE: DNA
<213> ORGANISM: Artificial sequence
<220> FEATURE:
<223> OTHER INFORMATION: B. halodurans Primer 1

<400> SEQUENCE: 92
gatatacata tggattattg cctttaccaa                                    30
```

```
<210> SEQ ID NO 93
<211> LENGTH: 33
<212> TYPE: DNA
<213> ORGANISM: Artificial sequence
<220> FEATURE:
<223> OTHER INFORMATION: B. halodurans Primer 2

<400> SEQUENCE: 93
gaatccggat cctcactgct tcatcgctgt ttg                       33

<210> SEQ ID NO 94
<211> LENGTH: 33
<212> TYPE: DNA
<213> ORGANISM: Artificial sequence
<220> FEATURE:
<223> OTHER INFORMATION: B. cereus Primer 1

<400> SEQUENCE: 94
taagaggaat aacatatggc atacgaaaga ttt                       33

<210> SEQ ID NO 95
<211> LENGTH: 32
<212> TYPE: DNA
<213> ORGANISM: Artificial sequence
<220> FEATURE:
<223> OTHER INFORMATION: B. cereus Primer 2

<400> SEQUENCE: 95
gaattcggat ccttaagaag atgacatatt gg                        32

<210> SEQ ID NO 96
<211> LENGTH: 33
<212> TYPE: DNA
<213> ORGANISM: Artificial sequence
<220> FEATURE:
<223> OTHER INFORMATION: B. cereus Primer 3

<400> SEQUENCE: 96
taagaggaat aacatatggg atcgaaattg gca                       33

<210> SEQ ID NO 97
<211> LENGTH: 36
<212> TYPE: DNA
<213> ORGANISM: Artificial sequence
<220> FEATURE:
<223> OTHER INFORMATION: Primer

<400> SEQUENCE: 97
ggccttggca tatgggatac actttatgga atgacc                    36

<210> SEQ ID NO 98
<211> LENGTH: 35
<212> TYPE: DNA
<213> ORGANISM: Artificial sequence
<220> FEATURE:
<223> OTHER INFORMATION: Primer

<400> SEQUENCE: 98
ttggaaccgg atccttatat atgaagcggt tttgg                     35

<210> SEQ ID NO 99
<211> LENGTH: 283
<212> TYPE: PRT
<213> ORGANISM: Artificial sequence
<220> FEATURE:
<223> OTHER INFORMATION: Hybrid DAT

<400> SEQUENCE: 99
```

```
Met Gly Tyr Thr Leu Trp Asn Asp Gln Ile Val Glu Asp Gly Ser Val
1               5                   10                  15

Ser Ile Ser Pro Glu Asp Arg Gly Tyr Gln Phe Gly Asp Gly Val Tyr
            20                  25                  30

Glu Val Val Lys Val Tyr Asn Gly Asn Met Phe Thr Val Asn Glu His
        35                  40                  45

Ile Asp Arg Leu Tyr Ala Ser Ala Glu Lys Ile Arg Ile Val Ile Pro
50                  55                  60

Tyr Thr Lys Asp Val Phe His Lys Leu Leu His Glu Leu Val Glu Lys
65                  70                  75                  80

Asn Asn Leu Asn Thr Gly His Ile Tyr Phe Gln Val Thr Arg Gly Thr
                85                  90                  95

Ser Ser Arg Ala His Val Phe Pro Glu Ala Thr Val Pro Ala Val Ile
            100                 105                 110

Thr Gly Asn Val Lys Ser Gly Glu Arg Ala Leu Glu Asn Leu Glu Lys
        115                 120                 125

Gly Val Lys Ala Thr Phe Val Glu Asp Ile Arg Trp Leu Arg Cys Asp
130                 135                 140

Ile Lys Ser Leu Asn Leu Leu Gly Ala Val Leu Ala Lys Gln Glu Ala
145                 150                 155                 160

Ser Glu Lys Gly Cys Tyr Glu Ala Ile Leu His Arg Gly Asp Ile Val
            165                 170                 175

Thr Glu Cys Ser Ser Ser Asn Val Phe Gly Ile Lys Asp Gly Lys Leu
        180                 185                 190

Tyr Thr His Pro Ala Asn Asn Leu Ile Leu Asn Gly Ile Thr Arg Gln
    195                 200                 205

Val Val Ile Lys Cys Ala Glu Glu Ile Asn Ile Pro Val Val Glu Glu
        210                 215                 220

Pro Phe Thr Lys Gly Glu Ile Leu Thr Met Asp Glu Leu Phe Val Thr
225                 230                 235                 240

Ser Val Thr Ser Glu Ile Thr Pro Val Ile Glu Ile Asp Gly Asn Gln
            245                 250                 255

Ile Gly Ala Gly Val Pro Gly Glu Trp Thr Arg Lys Leu Gln Lys Ala
        260                 265                 270

Phe Glu Ala Lys Ile Pro Leu Ser Leu Asn Ser
    275                 280
```

<210> SEQ ID NO 100
<211> LENGTH: 852
<212> TYPE: DNA
<213> ORGANISM: Artificial sequence
<220> FEATURE:
<223> OTHER INFORMATION: Hybrid DAT

<400> SEQUENCE: 100

```
atgggataca ctttatggaa tgaccaaatc gtggaagatg gtagcgtcag tattagcccg      60
gaagatcgcg gttatcaatt cggtgatggc gtatatgaag ttgtgaaagt atataacggt     120
aacatgttta ctgtaaatga acatattgac cgcttatatg catcagctga aaaaatccgt     180
attgttattc catatacaaa ggatgtgttt cataagttgc tgcatgaatt agtggaaaaa     240
aataacttaa acactgggca tatttatttt caagttactc gcggaacttc gagtcgtgcg     300
catgttttcc ctgaggccac tgtaccagcg gtaatcaccg gtaacgtgaa agcggcgag     360 cgtgcgttag aaaatcttga aaaaggtgta aagctaccct tgtggaaga tatccgttgg     420 ttacgctgtg atattaaatc tttgaacttg cttggtgcag tattagcaaa acaagaagct     480
```

| | |
|---|---|
| agcgaaaaag gctgctatga agcgattctg catcgaggcg acatcgtaac agaatgctct | 540 |
| tcttcaaatg tatttggaat caaagatggt aagttgtata cccatcctgc aaacaatctg | 600 |
| attttaaatg gaatcactcg ccaggttgtc attaaatgtg cagaggaaat taatatccct | 660 |
| gtagtggaag agccatttac aaaaggcgaa atcttgacga tggatgaatt atttgtaaca | 720 |
| agtgttactt ctgaaattac gccggttatt gaaatcgatg gtaatcagat tggtgcagga | 780 |
| gtgccaggag aatggactcg taaattacaa aaagcttttg aagccaaaat tccactgagc | 840 |
| cttaacagct aa | 852 |

```
<210> SEQ ID NO 101
<211> LENGTH: 37
<212> TYPE: DNA
<213> ORGANISM: Artificial sequence
<220> FEATURE:
<223> OTHER INFORMATION: Primer

<400> SEQUENCE: 101
```

| | |
|---|---|
| ggccttggca tatgggatac actttatgga atgacca | 37 |

```
<210> SEQ ID NO 102
<211> LENGTH: 37
<212> TYPE: DNA
<213> ORGANISM: Artificial sequence
<220> FEATURE:
<223> OTHER INFORMATION: Primer

<400> SEQUENCE: 102
```

| | |
|---|---|
| ttggaaccgg atccttagct gttaaggctc agtggaa | 37 |

```
<210> SEQ ID NO 103
<211> LENGTH: 690
<212> TYPE: DNA
<213> ORGANISM: Artificial Sequence
<220> FEATURE:
<223> OTHER INFORMATION: R-specific aldolase

<400> SEQUENCE: 103
```

| | |
|---|---|
| atgcctatcg ttgttacgaa gatcgaccga cccagcgcgg cggacgtcga aaggatcgcc | 60 |
| gcctatggtg tcgcgaccct tgcatgaagcg caaggacgaa ccgggttgat ggcgtccaat | 120 |
| atgcgcccaa tctatcgccc tgcgcacatt gccgggcccg cggtgacctg ccttgtggcg | 180 |
| cctggcgaca attggatgat ccatgtcgcc gtcgaacagt gccagccggg agatgtcctg | 240 |
| gtcgtggtac cgaccagccc ctgcgaagac ggctatttcg gcgatctgct ggcgacctcg | 300 |
| ctgcggtcgc gcggggtcaa aggtctgatc atcgaggccg gcgtacgcga tatcgcgaca | 360 |
| ttgaccgaga tgaaattccc ggtctggtcc aaggcggtgt cgcgcaagg aacggtcaag | 420 |
| gagaccatcg ccagcgtcaa tgtgccccct gtctgcgcgg gcgcccgcat cgtgccgggc | 480 |
| gatctgatcg ttgccgacga cgacgggtc gtcgtgattc caagacgttc cgttccggcg | 540 |
| gtcctttcca gcgccgaggc ccgcgaagag aaggaagccc gcaaccgcgc ccgcttcgaa | 600 |
| gctgcgagc tgggcctcga cgtctacaac atgcgccagc gcctggccga caagggcttg | 660 |
| cgctatgtcg agcggctgcc cgaggaatag | 690 |

```
<210> SEQ ID NO 104
<211> LENGTH: 229
<212> TYPE: PRT
<213> ORGANISM: Artificial sequence
<220> FEATURE:
<223> OTHER INFORMATION: R-specific Aldolase
```

```
<400> SEQUENCE: 104

Met Pro Ile Val Val Thr Lys Ile Asp Arg Pro Ser Ala Ala Asp Val
1               5                   10                  15
Glu Arg Ile Ala Ala Tyr Gly Val Ala Thr Leu His Glu Ala Gln Gly
            20                  25                  30
Arg Thr Gly Leu Met Ala Ser Asn Met Arg Pro Ile Tyr Arg Pro Ala
        35                  40                  45
His Ile Ala Gly Pro Ala Val Thr Cys Leu Val Ala Pro Gly Asp Asn
    50                  55                  60
Trp Met Ile His Val Ala Val Glu Gln Cys Gln Pro Gly Asp Val Leu
65                  70                  75                  80
Val Val Val Pro Thr Ser Pro Cys Glu Asp Gly Tyr Phe Gly Asp Leu
                85                  90                  95
Leu Ala Thr Ser Leu Arg Ser Arg Gly Val Lys Gly Leu Ile Ile Glu
            100                 105                 110
Ala Gly Val Arg Asp Ile Ala Thr Leu Thr Glu Met Lys Phe Pro Val
        115                 120                 125
Trp Ser Lys Ala Val Phe Ala Gln Gly Thr Val Lys Glu Thr Ile Ala
    130                 135                 140
Ser Val Asn Val Pro Leu Val Cys Ala Gly Ala Arg Ile Val Pro Gly
145                 150                 155                 160
Asp Leu Ile Val Ala Asp Asp Gly Val Val Ile Pro Arg Arg
                165                 170                 175
Ser Val Pro Ala Val Leu Ser Ser Ala Glu Ala Arg Glu Glu Lys Glu
            180                 185                 190
Ala Arg Asn Arg Ala Arg Phe Glu Ala Gly Leu Gly Leu Asp Val
        195                 200                 205
Tyr Asn Met Arg Gln Arg Leu Ala Asp Lys Gly Leu Arg Tyr Val Glu
    210                 215                 220
Arg Leu Pro Glu Glu
225

<210> SEQ ID NO 105
<211> LENGTH: 30
<212> TYPE: DNA
<213> ORGANISM: Artificial sequence
<220> FEATURE:
<223> OTHER INFORMATION: Primer

<400> SEQUENCE: 105
ataagacata tgcctatcgt tgttacgaag                                    30

<210> SEQ ID NO 106
<211> LENGTH: 33
<212> TYPE: DNA
<213> ORGANISM: Artificial sequence
<220> FEATURE:
<223> OTHER INFORMATION: Primer

<400> SEQUENCE: 106
ataagaggat ccttattcct cgggcagccg ctc                                33

<210> SEQ ID NO 107
<211> LENGTH: 43
<212> TYPE: DNA
<213> ORGANISM: Artificial sequence
<220> FEATURE:
<223> OTHER INFORMATION: Mutagenic Primer
```

-continued

<400> SEQUENCE: 107
gccatttgga aacgatcaac gcggaagtgc cttgcacgat cag　　　　　　　　　43

<210> SEQ ID NO 108
<211> LENGTH: 43
<212> TYPE: DNA
<213> ORGANISM: Artificial sequence
<220> FEATURE:
<223> OTHER INFORMATION: Mutagenic Primer
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (23)..(23)
<223> OTHER INFORMATION: k is g or t

<400> SEQUENCE: 108
gccatttgga aacgatcaac nnkgaagtgc cttgcacgat cag　　　　　　　　　43

<210> SEQ ID NO 109
<211> LENGTH: 42
<212> TYPE: DNA
<213> ORGANISM: Artificial sequence
<220> FEATURE:
<223> OTHER INFORMATION: Primer

<400> SEQUENCE: 109
ccatttggaa acgatcaaca acgaagtgcc ttgcacgatc ag　　　　　　　　　　42

<210> SEQ ID NO 110
<211> LENGTH: 43
<212> TYPE: DNA
<213> ORGANISM: Artificial sequence
<220> FEATURE:
<223> OTHER INFORMATION: Primer

<400> SEQUENCE: 110
gccatttgga aacgatcaac ggcgaagtgc cttgcacgat cag　　　　　　　　　43

<210> SEQ ID NO 111
<211> LENGTH: 40
<212> TYPE: DNA
<213> ORGANISM: Artificial sequence
<220> FEATURE:
<223> OTHER INFORMATION: Primer

<400> SEQUENCE: 111
tcgccatttg gaaacgatca actgcgaagt gccttgcacg　　　　　　　　　　　40

<210> SEQ ID NO 112
<211> LENGTH: 31
<212> TYPE: DNA
<213> ORGANISM: Artificial sequence
<220> FEATURE:
<223> OTHER INFORMATION: Primer

<400> SEQUENCE: 112
ggaaacgatc aacacggaag tgccttgcac g　　　　　　　　　　　　　　31

<210> SEQ ID NO 113
<211> LENGTH: 45
<212> TYPE: DNA
<213> ORGANISM: Artificial sequence
<220> FEATURE:
<223> OTHER INFORMATION: Primer
<220> FEATURE:

```
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 113
caaccaggcg aaaaggtgag cnnkggtgcg acgtacactg cgcag          45

<210> SEQ ID NO 114
<211> LENGTH: 43
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (22)..(22)
<223> OTHER INFORMATION: k is g or t

<400> SEQUENCE: 114
gccggacgac acgcacattn nkgcggtcgt gaaggcgaac gcc            43

<210> SEQ ID NO 115
<211> LENGTH: 35
<212> TYPE: DNA
<213> ORGANISM: Artificial sequence
<220> FEATURE:
<223> OTHER INFORMATION: Primer

<400> SEQUENCE: 115
aggcgaaaag gtgagcgcgg gtgcgacgta cactg                     35

<210> SEQ ID NO 116
<211> LENGTH: 16
<212> TYPE: PRT
<213> ORGANISM: Artificial sequence
<220> FEATURE:
<223> OTHER INFORMATION: P. striata
<220> FEATURE:
<221> NAME/KEY: misc_feature
<222> LOCATION: (12)..(12)
<223> OTHER INFORMATION: Xaa can be any naturally occurring amino acid

<400> SEQUENCE: 116

Leu Thr Ala Val Leu Lys Ala Asp Ala Tyr Gly Xaa Gly Ile Gly Leu
1               5                   10                  15

<210> SEQ ID NO 117
<211> LENGTH: 28
<212> TYPE: DNA
<213> ORGANISM: Artificial sequence
<220> FEATURE:
<223> OTHER INFORMATION: Primer

<400> SEQUENCE: 117
agaagacata tgcccttcg ccgtaggg                              28

<210> SEQ ID NO 118
<211> LENGTH: 32
<212> TYPE: DNA
<213> ORGANISM: Artificial sequence
<220> FEATURE:
<223> OTHER INFORMATION: Primer
```

```
<400> SEQUENCE: 118
agaagaggat cctcagtcga cgagtatctt cg                                    32

<210> SEQ ID NO 119
<211> LENGTH: 1230
<212> TYPE: DNA
<213> ORGANISM: Artificial sequence
<220> FEATURE:
<223> OTHER INFORMATION: KT2440 BAR

<400> SEQUENCE: 119
atgccctttc gccgtaccct tctggctgca tccctggcac ttctgatcac cggacaggcc     60
cccctgtatg cggcaccacc gttgtcgatg acaacggca ccaacaccct gaccgtgcaa     120
aacagcaatg cctgggtcga agtcagcgcc agcgccctgc agcacaacat ccgcacgctg    180
caggccgagc tggccggcaa gtccaagctg tgcgccgtgc tcaaggccga tgcctatggc    240
cacggtatcg gcctggtaat gccatcgatc atcgcccaag gcgtgccctg cgtggcggtg    300
gccagcaacg aggaggcccg cgtggtccgc gccagtggct tcaccgggca actggtgcgg    360
gtacgcctgg ccagcctcag cgagctggaa atggccttgc agtacgacat ggaagagctg    420
gtgggcagcg cggaatttgc ccgccaggcc gatgccatcg ccgcgcgcca tggcaagacc    480
ttgcgcattc acatggcgct caactccagc ggcatgagcc gcaacggggt ggagatggcc    540
acctggtccg gccgtggcga agcgctgcag atcaccgacc agaagcacct caagctggtc    600
gcgctgatga cccacttcgc cgtggaagac aaggacgatg tacgcaaggg cctggcggca    660
ttcaacgagc agaccgactg gttgatcaag cacgccaggc tggaccgcag caagctcacc    720
ctgcacgccg ccaactcgtt cgctacgctg gaagtgccgg aagcgcgcct ggacatggta    780
cgaacgggtg gcgcgctgtt cggcgacacc gtgccggcgc gcaccgagta caaacgtgcg    840
atgcagttca atcgcacgt ggcggcggtg cacagctatc cggccggcaa caccgtgggc    900
tatgaccgca ccttcacccct ggcccgtgat cgcggctgg ccaacattac ggtcgggtac    960
tccgatggct accgccgggt attcaccaac aagggccatg tgctgatcaa cggccaccgt   1020
gtgccggtcg tgggcaaggt gtcgatgaac acgctgatgg tcgatgtcac cgacttccct   1080
gatgtgaagg ggggtaacga agtggtgctg ttcggcaagc aggccggggg cgaaatcacc   1140
caggccgaga tggaagaaat caacggcgcg ttgctcgccg atttgtacac cgtatgggc    1200 aattccaacc cgaagatact cgtcgactga                                    1230

<210> SEQ ID NO 120
<211> LENGTH: 409
<212> TYPE: PRT
<213> ORGANISM: Artificial sequence
<220> FEATURE:
<223> OTHER INFORMATION: KT2440 BAR

<400> SEQUENCE: 120

Met Pro Phe Arg Arg Thr Leu Leu Ala Ala Ser Leu Ala Leu Leu Ile
1               5                   10                  15

Thr Gly Gln Ala Pro Leu Tyr Ala Ala Pro Pro Leu Ser Met Asp Asn
            20                  25                  30

Gly Thr Asn Thr Leu Thr Val Gln Asn Ser Asn Ala Trp Val Glu Val
        35                  40                  45

Ser Ala Ser Ala Leu Gln His Asn Ile Arg Thr Leu Gln Ala Glu Leu
    50                  55                  60

Ala Gly Lys Ser Lys Leu Cys Ala Val Leu Lys Ala Asp Ala Tyr Gly
```

```
            65                  70                  75                  80
His Gly Ile Gly Leu Val Met Pro Ser Ile Ala Gln Gly Val Pro
                    85                  90                  95
Cys Val Ala Val Ala Ser Asn Glu Glu Ala Arg Val Val Arg Ala Ser
                100                 105                 110
Gly Phe Thr Gly Gln Leu Val Arg Val Arg Leu Ala Ser Leu Ser Glu
            115                 120                 125
Leu Glu Asp Gly Leu Gln Tyr Asp Met Glu Leu Val Gly Ser Ala
        130                 135                 140
Glu Phe Ala Arg Gln Ala Asp Ala Ile Ala Arg His Gly Lys Thr
145                 150                 155                 160
Leu Arg Ile His Met Ala Leu Asn Ser Ser Gly Met Ser Arg Asn Gly
                165                 170                 175
Val Glu Met Ala Thr Trp Ser Gly Arg Gly Glu Ala Leu Gln Ile Thr
                180                 185                 190
Asp Gln Lys His Leu Lys Leu Val Ala Leu Met Thr His Phe Ala Val
                195                 200                 205
Glu Asp Lys Asp Asp Val Arg Lys Gly Leu Ala Ala Phe Asn Glu Gln
        210                 215                 220
Thr Asp Trp Leu Ile Lys His Ala Arg Leu Asp Arg Ser Lys Leu Thr
225                 230                 235                 240
Leu His Ala Ala Asn Ser Phe Ala Thr Leu Glu Val Pro Glu Ala Arg
                245                 250                 255
Leu Asp Met Val Arg Thr Gly Gly Ala Leu Phe Gly Asp Thr Val Pro
                260                 265                 270
Ala Arg Thr Glu Tyr Lys Arg Ala Met Gln Phe Lys Ser His Val Ala
                275                 280                 285
Ala Val His Ser Tyr Pro Ala Gly Asn Thr Val Gly Tyr Asp Arg Thr
        290                 295                 300
Phe Thr Leu Ala Arg Asp Ser Arg Leu Ala Asn Ile Thr Val Gly Tyr
305                 310                 315                 320
Ser Asp Gly Tyr Arg Arg Val Phe Thr Asn Lys Gly His Val Leu Ile
                325                 330                 335
Asn Gly His Arg Val Pro Val Val Gly Lys Val Ser Met Asn Thr Leu
                340                 345                 350
Met Val Asp Val Thr Asp Phe Pro Asp Val Lys Gly Asn Glu Val
        355                 360                 365
Val Leu Phe Gly Lys Gln Ala Gly Gly Glu Ile Thr Gln Ala Glu Met
        370                 375                 380
Glu Glu Ile Asn Gly Ala Leu Leu Ala Asp Leu Tyr Thr Val Trp Gly
385                 390                 395                 400
Asn Ser Asn Pro Lys Ile Leu Val Asp
                405

<210> SEQ ID NO 121
<211> LENGTH: 35
<212> TYPE: DNA
<213> ORGANISM: Artificial sequence
<220> FEATURE:
<223> OTHER INFORMATION: Primer

<400> SEQUENCE: 121
ttgctcgccg atttgtgcac cgtatggggc aattc                              35

<210> SEQ ID NO 122
<211> LENGTH: 31
```

```
<212> TYPE: DNA
<213> ORGANISM: Artificial sequence
<220> FEATURE:
<223> OTHER INFORMATION: pET30 C term-XhoI Primer

<400> SEQUENCE: 122
aagtcgctcg aggtcgacga gtatcttcgg g                               31

<210> SEQ ID NO 123
<211> LENGTH: 32
<212> TYPE: DNA
<213> ORGANISM: Artificial sequence
<220> FEATURE:
<223> OTHER INFORMATION: pASK N term Primer

<400> SEQUENCE: 123
acggtaggtc tcaaatgccc tttcgccgta cc                              32

<210> SEQ ID NO 124
<211> LENGTH: 37
<212> TYPE: DNA
<213> ORGANISM: Artificial sequence
<220> FEATURE:
<223> OTHER INFORMATION: pASK C term Primer

<400> SEQUENCE: 124
aaccgtggtc tcagcgctgt cgaggagtat cttcggg                         37

<210> SEQ ID NO 125
<211> LENGTH: 42
<212> TYPE: DNA
<213> ORGANISM: Artificial sequence
<220> FEATURE:
<223> OTHER INFORMATION: pET 22 N term Primer

<400> SEQUENCE: 125
gctccacatg tctcccttcc gccgtaccct tctggctgca tc                   42

<210> SEQ ID NO 126
<211> LENGTH: 43
<212> TYPE: DNA
<213> ORGANISM: Artificial sequence
<220> FEATURE:
<223> OTHER INFORMATION: pET22 C term Primer

<400> SEQUENCE: 126
ccgccggatc ctcagtcgac gagtatcttc gggttggaat tgc                  43

<210> SEQ ID NO 127
<211> LENGTH: 1230
<212> TYPE: DNA
<213> ORGANISM: Artificial sequence
<220> FEATURE:
<223> OTHER INFORMATION: NBRC12996 BAR

<400> SEQUENCE: 127 atgcccttc gccgtaccct cctggctgca tccctcgctc tgctgatcac tggccaggcc    60
ccgctgtacg ccgcaccgcc cctgtcgatg acaacggca ccaccgccct gaccgcgcag   120
aacagcaacg cctgggtcga atcagtgcc ggcgcactgc aacacaacat ccgtaccttg    180
caggccgagt tgggcggcaa gtccaagctg tgcgccgtgc tcaaggccga cgcctatggc   240
cacggtatcg gctggtgat gccgtcgatc atcgcccagg gcgtgccctg cgtggcggtg   300
gccagcaacg aggaggcacg cgtggtccgc gccagtggct tcaccgggca actggtgcgc   360
gtacgcctgg ccagcctcgg cgaagtggaa gatgcctttgc agtacgacat ggaagagctg   420
```

```
gttggcagcg ccgagttcgc ccgccagctc gatgccatcg ccgaacgcca cggcaagacc    480
ctgcgcattc acatggcgct caattccagc ggcatgagcc gcaacggcgt ggaaatgacc    540
acctggtccg gccggggtga agcgctgcag atcactgacc agaagcacct ccagctggtc    600
gcgctgatga ctcacttcgc cgtggaagac aaggacgatg tgcgcaaagg cctggcagcg    660
ttcaacgaac agaccgactg gctgatcaag cacgcgaagc ttgatcgcag caagctcacc    720
ctgcatgccg ccaactcctt cgctacgctg gaagtgccgg aagcgcacct ggacatggtg    780
cgtaccggtg gcgcgctgtt cggcgacacc gtgccgacgc gcaccgaata ccaacgtgtc    840
atgcagttca gtcgcacgt ggcggcgtg cacagctacc cggcaggcaa caccgtcggc    900
tacgaccgca ccttcaccct ggcgcgtgat tcgcgcctgg ccaacatcac cgtgggttac    960
tccgatggct accgccgggt gttcaccaac aaggcgcatg tgctgatcaa cggccaccga   1020
gtgccagtgg tgggcaaggt gtcgatgaac accttgatgg tcgatgtcac cgatttcccc   1080
gatgtgaagg ggggcaacga agtggtgctg ttcggcaaac aggccgggag ggagatcacc   1140
caggccgaga tagaagaaat caacggcgcg ctgctcgccg acctctacac cgtatggggc   1200
agttccaacc cgaagatact cgtcgactga                                    1230
```

<210> SEQ ID NO 128
<211> LENGTH: 409
<212> TYPE: PRT
<213> ORGANISM: Artificial sequence
<220> FEATURE:
<223> OTHER INFORMATION: NBRC12996 BAR

<400> SEQUENCE: 128

```
Met Pro Phe Arg Arg Thr Leu Leu Ala Ala Ser Leu Ala Leu Leu Ile
1               5                   10                  15

Thr Gly Gln Ala Pro Leu Tyr Ala Ala Pro Leu Ser Met Asp Asn
            20                  25                  30

Gly Thr Thr Ala Leu Thr Ala Gln Asn Ser Asn Ala Trp Val Glu Ile
        35                  40                  45

Ser Ala Gly Ala Leu Gln His Asn Ile Arg Thr Leu Gln Ala Glu Leu
    50                  55                  60

Gly Gly Lys Ser Lys Leu Cys Ala Val Leu Lys Ala Asp Ala Tyr Gly
65                  70                  75                  80

His Gly Ile Gly Leu Val Met Pro Ser Ile Ile Ala Gln Gly Val Pro
                85                  90                  95

Cys Val Ala Val Ala Ser Asn Glu Glu Ala Arg Val Val Arg Ala Ser
            100                 105                 110

Gly Phe Thr Gly Gln Leu Val Arg Val Arg Leu Ala Ser Leu Gly Glu
        115                 120                 125

Val Glu Asp Ala Leu Gln Tyr Asp Met Glu Glu Leu Val Gly Ser Ala
    130                 135                 140

Glu Phe Ala Arg Gln Leu Asp Ala Ile Ala Glu Arg His Gly Lys Thr
145                 150                 155                 160

Leu Arg Ile His Met Ala Leu Asn Ser Ser Gly Met Ser Arg Asn Gly
                165                 170                 175

Val Glu Met Thr Thr Trp Ser Gly Arg Gly Glu Ala Leu Gln Ile Thr
            180                 185                 190

Asp Gln Lys His Leu Gln Leu Val Ala Leu Met Thr His Phe Ala Val
        195                 200                 205

Glu Asp Lys Asp Asp Val Arg Lys Gly Leu Ala Ala Phe Asn Glu Gln
    210                 215                 220
```

```
Thr Asp Trp Leu Ile Lys His Ala Lys Leu Asp Arg Ser Lys Leu Thr
225                 230                 235                 240

Leu His Ala Ala Asn Ser Phe Ala Thr Leu Glu Val Pro Glu Ala His
            245                 250                 255

Leu Asp Met Val Arg Thr Gly Gly Ala Leu Phe Gly Asp Thr Val Pro
        260                 265                 270

Thr Arg Thr Glu Tyr Gln Arg Val Met Gln Phe Lys Ser His Val Ala
    275                 280                 285

Ala Val His Ser Tyr Pro Ala Gly Asn Thr Val Gly Tyr Asp Arg Thr
290                 295                 300

Phe Thr Leu Ala Arg Asp Ser Arg Leu Ala Asn Ile Thr Val Gly Tyr
305                 310                 315                 320

Ser Asp Gly Tyr Arg Arg Val Phe Thr Asn Lys Gly His Val Leu Ile
            325                 330                 335

Asn Gly His Arg Val Pro Val Val Gly Lys Val Ser Met Asn Thr Leu
        340                 345                 350

Met Val Asp Val Thr Asp Phe Pro Asp Val Lys Gly Gly Asn Glu Val
    355                 360                 365

Val Leu Phe Gly Lys Gln Ala Gly Arg Glu Ile Thr Gln Ala Glu Ile
370                 375                 380

Glu Glu Ile Asn Gly Ala Leu Leu Ala Asp Leu Tyr Thr Val Trp Gly
385                 390                 395                 400

Ser Ser Asn Pro Lys Ile Leu Val Asp
                405

<210> SEQ ID NO 129
<211> LENGTH: 28
<212> TYPE: DNA
<213> ORGANISM: Artificial sequence
<220> FEATURE:
<223> OTHER INFORMATION: Mutagenic Primer

<400> SEQUENCE: 129
acccaggccg agatggaaga aatcaacg                                    28

<210> SEQ ID NO 130
<211> LENGTH: 31
<212> TYPE: DNA
<213> ORGANISM: Artificial sequence
<220> FEATURE:
<223> OTHER INFORMATION: Primer

<400> SEQUENCE: 130
gcggcccata tgaagtttac taaatgtgca t                                31

<210> SEQ ID NO 131
<211> LENGTH: 35
<212> TYPE: DNA
<213> ORGANISM: Artificial sequence
<220> FEATURE:
<223> OTHER INFORMATION: Primer

<400> SEQUENCE: 131
ggccgcggat ccctatttgt agatcttagg atttg                            35

<210> SEQ ID NO 132
<211> LENGTH: 1215
<212> TYPE: DNA
<213> ORGANISM: Artificial sequence
<220> FEATURE:
<223> OTHER INFORMATION: CR378673 Racemase
```

```
<400> SEQUENCE: 132
atgaagctga agctgagcct ggtcgccctg gcactgatgg gtcagactac tgctaatgcc      60
gcaccactgc tggtggactt cgataacaat gagcgtgagg aacgtgtgca aagctctaat     120
gcgtggctgg agattgatac ccaagcattc agtggcaata ttcagttact gcagaaccaa     180
ctgaaagccg acaccaagat ctgtgcgatt atgaaggcgg atgcatacgg taatggcatt     240
gccggcttga tgcctagtat cattgctaac caagtgcctt gtgttggtat caccagcaat     300
gaggaagcgc gggtggttcg taaacatggc tttattggga agatcatgcg tgtccgtgca     360
gcctcgaaga atgaaattga gggtggcttg cagtaccaga tggaagaatt gatcggtacg     420
aaggctcaag ccgatcaaat catcgaaatt gcacgcgcaa atggcacgac gattccggtt     480
catttagcct tgaatacaag cggcatgggc cgcaacggtc tggacctgac gacctacgaa     540
ggccaagttg aaggtgtaga gattgctggc gatccaaacc tggagattgt cggcatgatg     600
actcatttcc cgaacgaggg actggacgaa atcaaacgga agtcaaacg tttcaaagta      660 gaaacgaaat ggttaatgga ttccactgac ttgaagcgca agatgtgac gctccacgtc      720 gcaaacagct atatcacctt gaatctgcct gaagcgcatc tggatatggt acgcccaggt     780
ggcatgctgt atggcgacta ccggcgaca gcgccgtatc agcgtatcgt aagcttcaag      840
acccacgttg cctctttgca ccactttccg gctggctcaa ccattgggta cggatctacc     900
gctgttctgg aacgtgattc agttctggct aatctgccga ttggctattc ggatggcttc     960
gcgcgctcgt taggaaataa agccgaagtc ctgattaacg ccagcgtgc gcgcgtcatg     1020 ggtatggtca gtatgaacac gacgatggtc gatgtaacgg atattgtgga tgttcagacc    1080
aatgaagaag tcgtgatctt tggccgccag ggtttcgaag agattacggg cgaggagacg    1140
gaagagaagt ctaatcgtat tcttccggaa cattacactg tgtggggcgc cacaaacccg    1200
cgtatttatc gctaa                                                    1215

<210> SEQ ID NO 133
<211> LENGTH: 28
<212> TYPE: DNA
<213> ORGANISM: Artificial sequence
<220> FEATURE:
<223> OTHER INFORMATION: Primer

<400> SEQUENCE: 133
agaagacata tgaagctgaa gctgagcc                                         28

<210> SEQ ID NO 134
<211> LENGTH: 31
<212> TYPE: DNA
<213> ORGANISM: Artificial sequence
<220> FEATURE:
<223> OTHER INFORMATION: Primer

<400> SEQUENCE: 134
agaagaggat ccttagcgat aaatacgcgg g                                     31

<210> SEQ ID NO 135
<211> LENGTH: 32
<212> TYPE: DNA
<213> ORGANISM: Artificial sequence
<220> FEATURE:
<223> OTHER INFORMATION: Primer

<400> SEQUENCE: 135
ggccttggca tatgaacttt aagatgactc tg                                    32
```

<210> SEQ ID NO 136
<211> LENGTH: 39
<212> TYPE: DNA
<213> ORGANISM: Artificial sequence
<220> FEATURE:
<223> OTHER INFORMATION: Primer

<400> SEQUENCE: 136
ttccaattgg atccttactt caggtagtaa cgcggattc                          39

<210> SEQ ID NO 137
<211> LENGTH: 1218
<212> TYPE: DNA
<213> ORGANISM: Artificial sequence
<220> FEATURE:
<223> OTHER INFORMATION: CR378681 Racemase

<400> SEQUENCE: 137
atgaacttta agatgactct gttaagcctg gccattacat tcccgagctt cagcatctat     60
agcgcgccac tggtcattga tcagaacctg ccaagcgaac agtcgattca gcaaagcaac    120
agctggctgg aagttagcct gggccagttt aaatccaata ttgaacaatt taaatctcat    180
attaaagccg atactaagat ttgtgccgtt atgaaagccg atgcatacgg caatggcatc    240
ttcggtctga tgccgacaat tctggaacag caaatcccat gcgtggcgat tgcaagtaac    300
gcggaagctc gcgctgtgcg tgaaagcggg tttaagggcc agctgctgcg tgtccgcagc    360
gcgagcttag gcgagattaa acagtcactg gacctgaaca ttgaagaact gatcggctca    420
catcagcagg cgaagttcat tgcagagctg ggtgtagaac gtaatcagaa gattaacgtt    480
catttagctc tgaacgacgg agggatgggt cgcaatggga tcgatatgtc taccgaacaa    540
ggcaaagccg aggccctcga catcgcgacc caggcaaatc tgaacattgt tggtattatg    600
actcacttcc cgaactataa tgcggataaa gtgcgtgtga agctgaaaga cttccagaca    660
aactccagct ggctgatcaa gcaggcggat ctgaagcgcg atgaactcac gctccacgtg    720
gccaacagct atgtgtccat taatgttcca gaagcgcaac tggatatggt tcgcccgggc    780
ggcgtgctgt atggcgatct tccgaccaat ccggaatatc cgagcatcgt atcgttcaag    840
acgcggattg cgtcaattca ccagctgcca gcatcccaga ccgtgggcta cgattcgacc    900
tatattacga acgtgatag cgttctggca aacctgccag tcggctacag tgatggctat    960
ccgcgccgta tgggtaatca ggctgatgtg attatcaacg acaacgcgc caaagtggtg   1020 ggtgtgacca gcatgaatac tagtatcgtc gatattaccg atattaaagg cgttaaacag   1080
ggtcaagaag ttaccctgtt tggcaagcag aagaatgtgc agattagcgt ggccgaaatg   1140
gaggattatt cgaagttaat cttcccggaa ctgtacacca tgtggggtca ggcgaatccg   1200
cgttactacc tgaagtaa                                                 1218

<210> SEQ ID NO 138
<211> LENGTH: 28
<212> TYPE: DNA
<213> ORGANISM: Artificial sequence
<220> FEATURE:
<223> OTHER INFORMATION: Primer

<400> SEQUENCE: 138
ataatacata tgcccttctc ccgtaccc                                      28

<210> SEQ ID NO 139
<211> LENGTH: 31

```
<212> TYPE: DNA
<213> ORGANISM: Artificial sequence
<220> FEATURE:
<223> OTHER INFORMATION: Primer

<400> SEQUENCE: 139
gcggcgggat ccttactgat ctttcaggat t                              31

<210> SEQ ID NO 140
<211> LENGTH: 1230
<212> TYPE: DNA
<213> ORGANISM: Artificial sequence
<220> FEATURE:
<223> OTHER INFORMATION: P. taetrolens arginine racemase

<400> SEQUENCE: 140
atgcccttct cccgtaccct gctcgccctt tccttggca tggcattgct gcaaaacccg    60
gcctttgctg cgccacccct gtcgatgacc gacggcgtag ctcaagtgaa tacccaggac   120
agcaatgcct gggtcgaaat caataaagcc gcgttcgagc acaacatacg gactctgcaa   180
accgccctcg ccggcaagtc gcagatctgc gccgtactca aggcggatgc ctatggccac   240
ggtatcggct tgttgatgcc ctcggtgatc gccatggggt ttccctgtgt cggtgtcgcc   300
agcaacgaag aagcccgcgt cgtgcgcgag agcggtttca agggtcaact gatacgcgtg   360
cgcaccgctg ccctgagcga actggaagct gcactgccgt acaacatgga agagctggtg   420
ggcaacctgg acttcgcggt caaggccagc ctgattgccg aggatcacgg tcgcccgctg   480
gtggtgcacc tgggtctgaa ttccagcggc atgagccgta acgagtgga catgaccacc   540 gctcagggcc gtcgtgatgc ggtagctatc accaaggtgc aaacctgga agtgcgggcg   600 atcatgaccc acttcgcggt cgaagatgct gccgacgtgc gtgccgggct caaggccttc   660
aatcagcaag cccaatggct gatgaacgtg gcccagcttg atcgcagcaa gatcaccctg   720
cacgcggcca actcgttcgc cacactggag gtgcccgaat cgcatctgga catggtccgc   780
cccggcggcg cgctgttcgg cgacaccgta ccgtcccaca ccgagtacaa gcgggtcatg   840
cagttcaagt cccacgtggc gtcggtcaac agctacccca agggcaacac cgtcggttat   900
gaccgcacgt acaccctggg ccgcgactcg cggctggcca acatcaccgt cggctactct   960
gacggctacc gccgcgcgtt taccaataaa gggattgtgc tgatcaacgg ccatcgcgtg  1020
ccagtggtgg gcaaagtctc gatgaacacc ctgatggtgg acgtcactga cgcgccggat  1080
gtgaaaagcg gcgatgaagt ggtgctgttc gggcaccagg gcaaggccga gattaccag   1140 gctgagatcg aagacatcaa cggtgcactg cttgcggatc tgtataccgt gtggggcaat  1200
tccaacccta aaatcctgaa agatcagtaa                                   1230

<210> SEQ ID NO 141
<211> LENGTH: 29
<212> TYPE: DNA
<213> ORGANISM: Artificial sequence
<220> FEATURE:
<223> OTHER INFORMATION: Mutagenic Primer

<400> SEQUENCE: 141
tacccaggct gagatggaag acatcaacg                                    29

<210> SEQ ID NO 142
<211> LENGTH: 28
<212> TYPE: DNA
<213> ORGANISM: Artificial sequence
<220> FEATURE:
<223> OTHER INFORMATION: Primer
```

<400> SEQUENCE: 142
gcggcgcata tgcacgttcg ttttcgtc                                              28

<210> SEQ ID NO 143
<211> LENGTH: 34
<212> TYPE: DNA
<213> ORGANISM: Artificial sequence
<220> FEATURE:
<223> OTHER INFORMATION: Primer

<400> SEQUENCE: 143
ggcggcggga tcccggtgaa ataacttaat ctac                                       34

<210> SEQ ID NO 144
<211> LENGTH: 1230
<212> TYPE: DNA
<213> ORGANISM: Artificial sequence
<220> FEATURE:
<223> OTHER INFORMATION: Y. pseudotuberculosis YPIII BAR homolog

<400> SEQUENCE: 144

| | |
|---|---|
| atgcacgttc gttttcatca tttattctta ttaccattaa taactttggt cgcttgtagc | 60 |
| caacccgtat caaaaaacca tcttagcctg acctcactat ctgccaacgc ccagcaacct | 120 |
| gtagtaaata atgcgtggct tgaaatctct caaggtgcgc tggatttcaa tactaaaaag | 180 |
| atgcttacac tgctggataa taaatccaca ctttgtgcaa tattaaaagg tgatgcctat | 240 |
| ggacatgacc tgaccttagt cacaccggtg atgctaaaaa acaatgtgca atgtattggg | 300 |
| gttgccagca atcaggaact aaaaacggta cgtgatctag gatttacggg gcagttgata | 360 |
| cgggtcagaa gtgcaacatt aaaagaaatg caacaagcta tggcttacga tgttgaagaa | 420 |
| cttattggcg ataaaaccgt cgctgagcag ttaaataata ttgcaaaact gaatggaaaa | 480 |
| gttctgcgta tccatctggc actgaactcc gcagggatgt ctcgtaatgg gctggaggtc | 540 |
| agtaaggccc gcggttttaa tgacgcaaag acaattgtag gtttaaaaaa tctgacaatc | 600 |
| gttggcatca tgtcgcacta cccggtggaa gatgctagcg aaatcaaagc agacttggct | 660 |
| cgattccagc aacaagccaa agatgttatc gcggtcacgg ggctaaaacg tgaaaagatt | 720 |
| aagctccacg tcgccaatac attcgcgacc ttagcggtgc ctgattcatg gttggatatg | 780 |
| gtccgtgtgg aggggtgtt tatggtgac accatcgcca gcacagagta taagcgggtc | 840 |
| atgaccttca aatctaacat cgcatcgctg acaactacc ctaagggcgg tactgttggc | 900 |
| tatgaccgga cctatacatt gaacgtgat tccctgctgg cgaatatccc cgtgggttat | 960 |
| gccgatgggt atcgccgagt atttagtaat gcggggcatg tgattattca aggtcagcgc | 1020 |
| ctgcccgtat taggcaaaac atcaatgaat acggtcatgg tagacgtcac cgatctgaaa | 1080 |
| aaagtgagtt taggtgatga agttgtcttg ttcggtaagc aaggcaatgc ggaaattcag | 1140 |
| gcagaagaaa ttgaagatct cagtggcgca ctctttaccg aaatgtcaat tctgtggggc | 1200 |
| gcaaccaata agcgtattct ggtagattaa | 1230 |

<210> SEQ ID NO 145
<211> LENGTH: 409
<212> TYPE: PRT
<213> ORGANISM: Artificial sequence
<220> FEATURE:
<223> OTHER INFORMATION: Y. pseudotuberculosis YPIII BAR homolog

<400> SEQUENCE: 145

Met His Val Arg Phe His His Leu Phe Leu Leu Pro Leu Ile Thr Leu

```
            1               5                  10                 15
Val Ala Cys Ser Gln Pro Val Ser Lys Asn His Leu Ser Leu Thr Ser
                20                 25                 30
Leu Ser Ala Asn Ala Gln Gln Pro Val Val Asn Asn Ala Trp Leu Glu
                35                 40                 45
Ile Ser Gln Gly Ala Leu Asp Phe Asn Thr Lys Lys Met Leu Thr Leu
 50                 55                 60
Leu Asp Asn Lys Ser Thr Leu Cys Ala Ile Leu Lys Gly Asp Ala Tyr
 65                 70                 75                 80
Gly His Asp Leu Thr Leu Val Thr Pro Val Met Leu Lys Asn Asn Val
                85                 90                 95
Gln Cys Ile Gly Val Ala Ser Asn Gln Glu Leu Lys Thr Val Arg Asp
                100                105                110
Leu Gly Phe Thr Gly Gln Leu Ile Arg Val Arg Ser Ala Thr Leu Lys
                115                120                125
Glu Met Gln Gln Ala Met Ala Tyr Asp Val Glu Glu Leu Ile Gly Asp
                130                135                140
Lys Thr Val Ala Glu Gln Leu Asn Asn Ile Ala Lys Leu Asn Gly Lys
145                 150                155                160
Val Leu Arg Ile His Leu Ala Leu Asn Ser Ala Gly Met Ser Arg Asn
                165                170                175
Gly Leu Glu Val Ser Lys Ala Arg Gly Leu Asn Asp Ala Lys Thr Ile
                180                185                190
Val Gly Leu Lys Asn Leu Thr Ile Val Gly Ile Met Ser His Tyr Pro
                195                200                205
Val Glu Asp Ala Ser Glu Ile Lys Ala Asp Leu Ala Arg Phe Gln Gln
                210                215                220
Gln Ala Lys Asp Val Ile Ala Val Thr Gly Leu Lys Arg Glu Lys Ile
225                 230                235                240
Lys Leu His Val Ala Asn Thr Phe Ala Thr Leu Ala Val Pro Asp Ser
                245                250                255
Trp Leu Asp Met Val Arg Val Gly Gly Val Phe Tyr Gly Asp Thr Ile
                260                265                270
Ala Ser Thr Glu Tyr Lys Arg Val Met Thr Phe Lys Ser Asn Ile Ala
                275                280                285
Ser Leu Asn Asn Tyr Pro Lys Gly Gly Thr Val Gly Tyr Asp Arg Thr
                290                295                300
Tyr Thr Leu Lys Arg Asp Ser Leu Leu Ala Asn Ile Pro Val Gly Tyr
305                 310                315                320
Ala Asp Gly Tyr Arg Arg Val Phe Ser Asn Ala Gly His Val Ile Ile
                325                330                335
Gln Gly Gln Arg Leu Pro Val Leu Gly Lys Thr Ser Met Asn Thr Val
                340                345                350
Met Val Asp Val Thr Asp Leu Lys Lys Val Ser Leu Gly Asp Glu Val
                355                360                365
Val Leu Phe Gly Lys Gln Gly Asn Ala Glu Ile Gln Ala Glu Glu Ile
                370                375                380
Glu Asp Leu Ser Gly Ala Leu Phe Thr Glu Met Ser Ile Leu Trp Gly
385                 390                395                400
Ala Thr Asn Lys Arg Ile Leu Val Asp
                405

<210> SEQ ID NO 146
<211> LENGTH: 389
```

```
<212> TYPE: PRT
<213> ORGANISM: Artificial sequence
<220> FEATURE:
<223> OTHER INFORMATION: Protein I

<400> SEQUENCE: 146
```

| | | | | | | | | | | | | | | | |
|---|---|---|---|---|---|---|---|---|---|---|---|---|---|---|---|
| Ala | Val | Ala | Ala | Pro | Tyr | Leu | Pro | Leu | Ala | Ser | Asp | His | Arg | Asn | Gly |
| 1 | | | | 5 | | | | | 10 | | | | | 15 | |
| Glu | Val | Gln | Thr | Ala | Ser | Asn | Ala | Trp | Leu | Glu | Val | Asp | Leu | Gly | Ala |
| | | | 20 | | | | | 25 | | | | | 30 | | |
| Phe | Glu | His | Asn | Ile | Gln | Thr | Leu | Lys | Asp | Arg | Leu | Gly | Asp | Lys | Gly |
| | | | 35 | | | | | 40 | | | | | 45 | | |
| Pro | Lys | Ile | Cys | Ala | Ile | Met | Lys | Ala | Asp | Ala | Tyr | Gly | His | Gly | Ile |
| | | | 50 | | | | | 55 | | | | | 60 | | |
| Asp | Leu | Leu | Val | Pro | Ser | Val | Val | Lys | Ala | Gly | Ile | Pro | Cys | Ile | Gly |
| 65 | | | | | 70 | | | | | 75 | | | | | 80 |
| Ile | Ala | Ser | Asn | Glu | Glu | Ala | Arg | Val | Ala | Arg | Glu | Lys | Gly | Phe | Thr |
| | | | | 85 | | | | | 90 | | | | | 95 | |
| Gly | Arg | Leu | Met | Arg | Val | Arg | Ala | Ala | Thr | Pro | Ala | Glu | Val | Glu | Gln |
| | | | | 100 | | | | | 105 | | | | | 110 | |
| Ala | Leu | Pro | Tyr | Lys | Met | Glu | Glu | Leu | Ile | Gly | Ser | Leu | Val | Ser | Ala |
| | | | | 115 | | | | | 120 | | | | | 125 | |
| Gln | Gly | Ile | Ala | Asp | Ile | Ala | Gln | Arg | His | His | Thr | Asn | Ile | Pro | Val |
| | 130 | | | | | 135 | | | | | 140 | | | | |
| His | Ile | Ala | Leu | Asn | Ser | Ala | Gly | Met | Ser | Arg | Asn | Gly | Ile | Asp | Leu |
| 145 | | | | | 150 | | | | | 155 | | | | | 160 |
| Arg | Leu | Ala | Asp | Ser | Lys | Glu | Asp | Ala | Leu | Ala | Met | Leu | Lys | Leu | Lys |
| | | | | 165 | | | | | 170 | | | | | 175 | |
| Gly | Ile | Thr | Pro | Val | Gly | Ile | Met | Thr | His | Phe | Pro | Val | Glu | Glu | Lys |
| | | | 180 | | | | | 185 | | | | | 190 | | |
| Glu | Asp | Val | Lys | Met | Gly | Leu | Ala | Gln | Phe | Lys | Leu | Asp | Ser | Gln | Trp |
| | | | 195 | | | | | 200 | | | | | 205 | | |
| Leu | Leu | Glu | Ala | Gly | Lys | Leu | Asp | Arg | Ser | Lys | Ile | Thr | Ile | His | Ala |
| | 210 | | | | | 215 | | | | | 220 | | | | |
| Ala | Asn | Ser | Phe | Ala | Thr | Leu | Glu | Val | Pro | Asp | Ala | Tyr | Phe | Asp | Met |
| 225 | | | | | 230 | | | | | 235 | | | | | 240 |
| Val | Arg | Pro | Gly | Gly | Leu | Leu | Tyr | Gly | Asp | Ser | Ile | Pro | Ser | Tyr | Thr |
| | | | | 245 | | | | | 250 | | | | | 255 | |
| Glu | Tyr | Lys | Arg | Val | Met | Ala | Phe | Lys | Thr | Gln | Val | Ala | Ser | Val | Asn |
| | | | 260 | | | | | 265 | | | | | 270 | | |
| His | Tyr | Pro | Ala | Gly | Asn | Thr | Val | Gly | Tyr | Asp | Arg | Thr | Phe | Thr | Leu |
| | | | 275 | | | | | 280 | | | | | 285 | | |
| Lys | Arg | Asp | Ser | Trp | Leu | Ala | Asn | Leu | Pro | Leu | Gly | Tyr | Ser | Asp | Gly |
| | 290 | | | | | 295 | | | | | 300 | | | | |
| Tyr | Arg | Arg | Ala | Leu | Ser | Asn | Lys | Ala | Tyr | Val | Leu | Ile | Gln | Gly | Gln |
| 305 | | | | | 310 | | | | | 315 | | | | | 320 |
| Lys | Val | Pro | Val | Val | Gly | Lys | Thr | Ser | Met | Asn | Thr | Ile | Met | Val | Asp |
| | | | | 325 | | | | | 330 | | | | | 335 | |
| Val | Thr | Asp | Leu | Lys | Gly | Val | Lys | Pro | Gly | Asp | Glu | Val | Val | Leu | Phe |
| | | | 340 | | | | | 345 | | | | | 350 | | |
| Gly | Arg | Gln | Gly | Glu | Ala | Glu | Val | Lys | Gln | Ala | Asp | Leu | Glu | Glu | Tyr |
| | | | 355 | | | | | 360 | | | | | 365 | | |
| Asn | Gly | Ala | Leu | Leu | Ala | Asp | Met | Tyr | Thr | Ile | Trp | Gly | Tyr | Thr | Asn |
| | 370 | | | | | 375 | | | | | 380 | | | | |
| Pro | Lys | Lys | Ile | Lys | | | | | | | | | | | |

<210> SEQ ID NO 147
<211> LENGTH: 1201
<212> TYPE: DNA
<213> ORGANISM: Artificial sequence
<220> FEATURE:
<223> OTHER INFORMATION: A. hydrophila

<400> SEQUENCE: 147

```
tcttggggtt ggtgtagccc cagatggtgt acatgtccgc cagcagggcg ccgttgtact      60
cttccagatc cgcctgtttc acctcagcct caccctggcg gccgaacagc accacctcgt     120
caccgggttt gacccctttc agatcggtca cgtccaccat gatggtgttc atggaggtct     180
tgcccaccac cggcaccttc tggccctgga tcagcacata ggccttgttg ctcagcgccc     240
ggcgatagcc gtcggagtag cccagcggca ggttggcgag ccaggagtcg cgcttgaggg     300
tgaaggtgcg gtcataaccg acggtgttgc cggccgggta gtggttgacg gaggcaacct     360
gggtcttgaa cgccatcacc cgcttgtact cggtgtagga ggggatggag tcaccgtaca     420
gcaggccgcc cggcgcacc atgtcgaagt aggcgtccgg cacttccagg gtggcgaagg      480
agttggcggc gtggatggtg atcttgctgc gatccagctt gcccgcttcc agcagccact     540
gggagtccag tttgaactgg gccagcccca tcttgacgtc ctctttctcc tccaccggga     600
agtgggtcat gatgccgacc ggggtgatcc ccttgagctt gagcatggcc agcgcgtctt     660
ccttggagtc agccaggcgc agatcgatgc cgttgcggct catgccggcg gagttgagcg     720
cgatgtgcac cgggatattg gtgtggtggc gctgggcgat gtcggcgatg ccctgagcac     780
tcaccaggct gccgatgagc tcttccatct tgtagggcag ggcctgttcc acttcggccg     840
gggtggcggc acgtacccgc atcaggcggc cggtgaagcc cttctcacgg ccacgcggg      900
cctcttcgtt gctggcgatg ccgatgcagg ggatgccggc cttgaccacc gagggcacca     960
gcaggtcgat gccgtggccg taggcgtcgg ccttcatgat ggcgcagatc ttcggccctt    1020
tgtcaccgag gcgatccttg agggtctgga tgttgtgctc gaaggcgccg agatcgactt    1080
ccagccaggc attgctggcg gtctgcactt cgccgttgcg atgatcgctg ccagcggca    1140
ggtaaggggc cgcgacggcc tgaccggcca gcaggcccag gatcagcgtg ccagcagtg     1200
t                                                                   1201
```

<210> SEQ ID NO 148
<211> LENGTH: 49
<212> TYPE: DNA
<213> ORGANISM: Artificial sequence
<220> FEATURE:
<223> OTHER INFORMATION: Primer

<400> SEQUENCE: 148

```
ttccaaggca tatgcccttc tcccgtacac tgctggccac gctgatcct                  49
```

<210> SEQ ID NO 149
<211> LENGTH: 54
<212> TYPE: DNA
<213> ORGANISM: Artificial sequence
<220> FEATURE:
<223> OTHER INFORMATION: Primer

<400> SEQUENCE: 149

```
ggaaccttgg atcctcaatc tttgattttc ttggggttgg tgtagcccca gatg            54
```

<210> SEQ ID NO 150

<211> LENGTH: 1230
<212> TYPE: DNA
<213> ORGANISM: A. hydrophila Chimeric Protein

<400> SEQUENCE: 150
atgcccttct cccgtacact gctggccacg ctgatcctgg gcctgctggc cggtcaagcc 60
gtcgcagccc cctatctgcc tctggcaagc gatcatcgca acggcgaagt acaaaccgcc 120
agcaacgcct ggctggaagt agatctgacc gcgtttgaac agaatctgca gaccctcaag 180
acccgcctcg gcgacaaggg cccgcagatc tgcgccatca tgaaggcgga cgcctacggt 240
cacggtatcg atctgctggt tccctccgtc atcaaggccg agatcccctg tatcggcatc 300
gccagcaacg aagaggcccg cgtcgcccgc gagaaggggt tcagcggccg cctgatgcgg 360
gtacgggccg ccacacctat cgaagtggaa caggccctgc cctacaagct ggaagagctg 420
gttggcagcc tggtgagtgc tcaggggatc tccgacatcg ccctgcgcca ccacaccacc 480
attccggtgc atgtcgccct caactccgcc ggtatgagcc gcaacggcat cgacctgcgt 540
ctggccgatg ccaagcaaga tgcgctggcc atgctcaagc tcaaggggat caccccggtc 600
ggcatcatga cccacttccc ggtggaggag aaagaggacg tcaagctggg gctggctcag 660
ttcaagctgg actcccagtg gctgctggaa gcaggcaagc tggatcgcag caagatcacc 720
atccatgccg ccaactcctt cgccaccctg gcagtgccgg acgcctactt tgacatggtg 780
cgcccgggcg gcctgctcta cggcgactcc atcccctcct acaccgaata caagcgggtg 840
atggcattca agacccaggt cgcctcggtc aaccactatg cggcgggcaa cacagtcggt 900
tatgaccgca cctttactct caaacgtgac tcctggctcg ccaacctgcc gctcggttac 960
tccgacggct atcgccgtgc gctcagcaac aaggcctatg tgctgatcca gggtcagaag 1020
gtgccggtgg tcggcaagac ctccatgaac accatcatgg tggacgtgac cgatctcaaa 1080
ggggtaaagc ccggtgatga agtggtgctg tttggccgtc agggtgaggc agaagtgaaa 1140
caggctgatc tggaggagta caacggcgcc ctgttggcgg acatgtacac catctggggc 1200
tacaccaacc ccaagaaaat caaagattga 1230

<210> SEQ ID NO 151
<211> LENGTH: 408
<212> TYPE: PRT
<213> ORGANISM: A. hydrophila Chimeric Protein

<400> SEQUENCE: 151

Met Pro Phe Ser Arg Thr Leu Leu Ala Thr Leu Ile Leu Gly Leu Leu
1 5 10 15

Ala Gly Gln Ala Val Ala Ala Pro Tyr Leu Pro Leu Ala Ser Asp His
20 25 30

Arg Asn Gly Glu Val Gln Thr Ala Ser Asn Ala Trp Leu Glu Val Asp
35 40 45

Leu Thr Ala Phe Glu Gln Asn Leu Gln Thr Lys Thr Arg Leu Gly Asp
50 55 60

Lys Gly Pro Gln Ile Cys Ala Ile Met Lys Ala Asp Ala Tyr Gly His
65 70 75 80

Gly Ile Asp Leu Leu Val Pro Ser Val Ile Lys Ala Glu Ile Pro Cys
85 90 95

Ile Gly Ile Ala Ser Asn Glu Glu Ala Arg Val Ala Arg Glu Lys Gly
100 105 110

Phe Ser Gly Arg Leu Met Arg Val Arg Ala Ala Thr Pro Ile Glu Val
115 120 125

Glu Gln Ala Leu Pro Tyr Lys Leu Glu Glu Leu Val Gly Ser Leu Val
130                 135                 140

Ser Ala Gln Gly Ile Ser Asp Ile Ala Leu Arg His His Thr Thr Ile
145                 150                 155                 160

Pro Val His Val Ala Leu Asn Ser Ala Gly Met Ser Arg Asn Gly Ile
                165                 170                 175

Asp Leu Arg Leu Ala Asp Ala Lys Gln Asp Ala Leu Ala Met Leu Lys
            180                 185                 190

Leu Lys Gly Ile Thr Pro Val Gly Ile Met Thr His Phe Pro Val Glu
        195                 200                 205

Glu Lys Glu Asp Val Lys Leu Gly Leu Ala Gln Phe Lys Leu Asp Ser
210                 215                 220

Gln Trp Leu Leu Glu Ala Gly Lys Leu Asp Arg Ser Lys Ile Thr Ile
225                 230                 235                 240

His Ala Ala Asn Ser Phe Ala Thr Leu Ala Val Pro Asp Ala Tyr Phe
                245                 250                 255

Asp Met Val Arg Pro Gly Gly Leu Leu Tyr Gly Asp Ser Ile Pro Ser
            260                 265                 270

Tyr Thr Glu Tyr Lys Arg Val Met Ala Phe Lys Thr Gln Val Ala Ser
        275                 280                 285

Val Asn His Tyr Ala Ala Gly Asn Thr Val Gly Tyr Asp Arg Thr Phe
290                 295                 300

Thr Leu Lys Arg Asp Ser Trp Leu Ala Asn Leu Pro Leu Gly Tyr Ser
305                 310                 315                 320

Asp Gly Tyr Arg Arg Ala Leu Ser Asn Lys Ala Tyr Val Leu Ile Gln
                325                 330                 335

Gly Gln Lys Val Pro Val Val Gly Lys Thr Ser Met Asn Thr Ile Met
            340                 345                 350

Val Asp Val Thr Asp Leu Lys Gly Val Lys Pro Gly Asp Glu Val Val
        355                 360                 365

Leu Phe Gly Arg Gln Gly Glu Ala Glu Val Lys Gln Ala Asp Leu Glu
370                 375                 380

Glu Tyr Asn Gly Ala Leu Leu Ala Asp Met Tyr Thr Ile Trp Gly Tyr
385                 390                 395                 400

Thr Asn Pro Lys Lys Ile Lys Asp
                405

<210> SEQ ID NO 152
<211> LENGTH: 23
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (12)..(15)
<223> OTHER INFORMATION: r is a or g
<220> FEATURE:
<221> NAME/KEY: misc_feature
<222> LOCATION: (18)..(18)
<223> OTHER INFORMATION: m is a or c

<400> SEQUENCE: 152
gccagcaacg argargcmcg cgt                                          23

<210> SEQ ID NO 153
<211> LENGTH: 18
<212> TYPE: DNA
<213> ORGANISM: Artificial sequence
<220> FEATURE:

-continued

<223> OTHER INFORMATION: Primer
<220> FEATURE:
<221> NAME/KEY: misc_feature
<222> LOCATION: (6)..(6)
<223> OTHER INFORMATION: s is c or g
<220> FEATURE:
<221> NAME/KEY: misc_feature
<222> LOCATION: (8)..(8)
<223> OTHER INFORMATION: k is g or t

<400> SEQUENCE: 153
tggccstkga tcagcaca                                                 18

<210> SEQ ID NO 154
<211> LENGTH: 716
<212> TYPE: DNA
<213> ORGANISM: A. caviae
<220> FEATURE:
<221> NAME/KEY: misc_feature
<222> LOCATION: (18)..(709)
<223> OTHER INFORMATION: m is a or c
<220> FEATURE:
<221> NAME/KEY: misc_feature
<222> LOCATION: (12)..(15)
<223> OTHER INFORMATION: r is a or g
<220> FEATURE:
<221> NAME/KEY: misc_feature
<222> LOCATION: (711)..(711)
<223> OTHER INFORMATION: s is c or g

<400> SEQUENCE: 154
gccagcaacg argargcmcg cgttgcccgc gagaagggct tcgaaggtcg cctgatgcgg      60
gtacgtgccg ccaccccgga tgaagtggag caggccctgc cctacaagct ggaggagctc     120
atcggcagcc tggagagcgc caaggggatc gccgacatcg cccagcgcca tcacaccaac     180
atcccggtgc acatcggcct gaactccgcc ggcatgagcc gcaacggcat cgatctgcgc     240
caggacgatg ccaaggccga tgccctggcc atgctcaagc tcaaggggat cacccccggtc    300 ggcatcatga cccacttccc ggtggaggag aaagaggacg tcaagctggg gctggcccag     360
ttcaagctgg actaccagtg gctcatcgac gccggcaagc tggatcgcag caagctcacc     420
atccacgccg ccaactcctt cgccaccctg gaagtaccgg aagcctactt tgacatggtg     480
cgcccgggcg gcatcatcta tggcgacacc attccctcct acaccgagta caagaaggtg     540
atggcgttca gacccaggt cgcctccgtc aaccactacc cggcgggcaa caccgtcggc      600
tatgaccgca ccttcaccct caagcgcgac tccctgctgg ccaacctgcc gatgggctac     660
tccgacggct accgccgcgc catgagcaac aaggcctatg tgctgatcma sggcca         716

<210> SEQ ID NO 155
<211> LENGTH: 238
<212> TYPE: PRT
<213> ORGANISM: A. caviae
<220> FEATURE:
<221> NAME/KEY: misc_feature
<222> LOCATION: (237)..(237)
<223> OTHER INFORMATION: Xaa is His, Gln, Asn, or Lys

<400> SEQUENCE: 155

Ala Ser Asn Glu Glu Ala Arg Val Ala Arg Glu Lys Gly Phe Glu Gly
1               5                   10                  15

Arg Leu Met Arg Val Arg Ala Ala Thr Pro Asp Glu Val Glu Gln Ala
                20                  25                  30

Leu Pro Tyr Lys Leu Glu Glu Leu Ile Gly Ser Leu Glu Ser Ala Lys
        35                  40                  45

Gly Ile Ala Asp Ile Ala Gln Arg His His Thr Asn Ile Pro Val His

```
                50                  55                  60
Ile Gly Leu Asn Ser Ala Gly Met Ser Arg Asn Gly Ile Asp Leu Arg
 65                  70                  75                  80

Gln Asp Asp Ala Lys Ala Asp Ala Leu Ala Met Leu Lys Leu Lys Gly
                 85                  90                  95

Ile Thr Pro Val Gly Ile Met Thr His Phe Pro Val Glu Glu Lys Glu
                100                 105                 110

Asp Val Lys Leu Gly Leu Ala Gln Phe Lys Leu Asp Tyr Gln Trp Leu
                115                 120                 125

Ile Asp Ala Gly Lys Leu Asp Arg Ser Lys Leu Thr Ile His Ala Ala
130                 135                 140

Asn Ser Phe Ala Thr Leu Glu Val Pro Glu Ala Tyr Phe Asp Met Val
145                 150                 155                 160

Arg Pro Gly Gly Ile Ile Tyr Gly Asp Thr Ile Pro Ser Tyr Thr Glu
                165                 170                 175

Tyr Lys Lys Val Met Ala Phe Lys Thr Gln Val Ala Ser Val Asn His
                180                 185                 190

Tyr Pro Ala Gly Asn Thr Val Gly Tyr Asp Arg Thr Phe Thr Leu Lys
                195                 200                 205

Arg Asp Ser Leu Leu Ala Asn Leu Pro Met Gly Tyr Ser Asp Gly Tyr
210                 215                 220

Arg Arg Ala Met Ser Asn Lys Ala Tyr Val Leu Ile Xaa Gly
225                 230                 235

<210> SEQ ID NO 156
<211> LENGTH: 35
<212> TYPE: DNA
<213> ORGANISM: Artificial sequence
<220> FEATURE:
<223> OTHER INFORMATION: Mutagenic Primer

<400> SEQUENCE: 156
gtgattgttt catcaacgaa ttcagaagta acgcc                           35

<210> SEQ ID NO 157
<211> LENGTH: 35
<212> TYPE: DNA
<213> ORGANISM: Artificial sequence
<220> FEATURE:
<223> OTHER INFORMATION: Mutagenic Primer

<400> SEQUENCE: 157
gtgattgttt catcaacgcg ttcagaagta acgcc                           35

<210> SEQ ID NO 158
<211> LENGTH: 35
<212> TYPE: DNA
<213> ORGANISM: Artificial sequence
<220> FEATURE:
<223> OTHER INFORMATION: Mutagenic Primer

<400> SEQUENCE: 158
gtgattgttt catcaacgag ttcagaagta acgcc                           35

<210> SEQ ID NO 159
<211> LENGTH: 35
<212> TYPE: DNA
<213> ORGANISM: Artificial sequence
<220> FEATURE:
<223> OTHER INFORMATION: Mutagenic Primer

<400> SEQUENCE: 159
```
gtgattgttt catcaacggc ttcagaagta acgcc                          35

<210> SEQ ID NO 160
<211> LENGTH: 31
<212> TYPE: DNA
<213> ORGANISM: Artificial sequence
<220> FEATURE:
<223> OTHER INFORMATION: Mutagenic Primer

<400> SEQUENCE: 160
gtgcaggccc tcgtgctcat attttccctg g                              31

<210> SEQ ID NO 161
<211> LENGTH: 45
<212> TYPE: DNA
<213> ORGANISM: Artificial sequence
<220> FEATURE:
<223> OTHER INFORMATION: Mutagenic Primer

<400> SEQUENCE: 161
gaagtgattg tttcatcaac gcagtcagaa gtaacgccaa ttatc               45

<210> SEQ ID NO 162
<211> LENGTH: 40
<212> TYPE: DNA
<213> ORGANISM: Artificial sequence
<220> FEATURE:
<223> OTHER INFORMATION: Primer

<400> SEQUENCE: 162
catatgagtt atagcttatg gaatgaccaa attgtgaatg                     40

<210> SEQ ID NO 163
<211> LENGTH: 34
<212> TYPE: DNA
<213> ORGANISM: Artificial sequence
<220> FEATURE:
<223> OTHER INFORMATION: Primer

<400> SEQUENCE: 163
ctcgagtgcg gccgcaagct tgtcgacgga gctc                           34

<210> SEQ ID NO 164
<211> LENGTH: 95
<212> TYPE: DNA
<213> ORGANISM: Artificial sequence
<220> FEATURE:
<223> OTHER INFORMATION: Primer

<400> SEQUENCE: 164
aatatttatg gaattaaaga tggcgtatta tacacacatc cagcgaataa catgatctta   60
aatggtatta cacgtcaagt aatcattaaa tgtgc                          95

<210> SEQ ID NO 165
<211> LENGTH: 34
<212> TYPE: DNA
<213> ORGANISM: Artificial sequence
<220> FEATURE:
<223> OTHER INFORMATION: Primer

<400> SEQUENCE: 165
ggccagtgaa ttgtaatacg actcactata gggc                           34

<210> SEQ ID NO 166
<211> LENGTH: 42

```
<212> TYPE: DNA
<213> ORGANISM: Artificial sequence
<220> FEATURE:
<223> OTHER INFORMATION: Primer

<400> SEQUENCE: 166
cgccatcttt aattccataa atatttgaag aagagccttc tg                          42

<210> SEQ ID NO 167
<211> LENGTH: 66
<212> TYPE: DNA
<213> ORGANISM: Artificial sequence
<220> FEATURE:
<223> OTHER INFORMATION: Mutagenic Primer

<400> SEQUENCE: 167
gcaacatttg tagaagacat tcgttgggaa tactgttaca ttaaatcatt aaatttactt       60
ggtgcg                                                                  66

<210> SEQ ID NO 168
<211> LENGTH: 55
<212> TYPE: DNA
<213> ORGANISM: Artificial sequence
<220> FEATURE:
<223> OTHER INFORMATION: Mutagenic Primer

<400> SEQUENCE: 168
gtattataca cacatccagc gaataactac atcttaaatg gtattacacg tcaag            55

<210> SEQ ID NO 169
<211> LENGTH: 64
<212> TYPE: DNA
<213> ORGANISM: Artificial sequence
<220> FEATURE:
<223> OTHER INFORMATION: Mutagenic Primer

<400> SEQUENCE: 169
gcaatggatg aagtgattgt ttcatcaacg actaagaag taacgccaat tatcgacata        60
gatg                                                                    64

<210> SEQ ID NO 170
<211> LENGTH: 64
<212> TYPE: DNA
<213> ORGANISM: Artificial sequence
<220> FEATURE:
<223> OTHER INFORMATION: Mutagenic Primer

<400> SEQUENCE: 170
gcaatggatg aagtgattgt ttcatcaacg aataagaag taacgccaat tatcgacata        60
gatg                                                                    64

<210> SEQ ID NO 171
<211> LENGTH: 64
<212> TYPE: DNA
<213> ORGANISM: Artificial sequence
<220> FEATURE:
<223> OTHER INFORMATION: Mutagenic Primer

<400> SEQUENCE: 171
gcaatggatg aagtgattgt ttcatcaacg aatcgtgaag taacgccaat tatcgacata       60
gatg                                                                    64

<210> SEQ ID NO 172
<211> LENGTH: 675
```

```
<212> TYPE: DNA
<213> ORGANISM: Unknown
<220> FEATURE:
<223> OTHER INFORMATION: R-specific aldolase

<400> SEQUENCE: 172
atgaagccgg tggtggtgca gactatcgag cgggccgacc gagcgatcat cgagggtctg      60
gccgcgtgtg gcgttgccac cgtccatgag gcgcaggggc gccggggggct gcttgcgtcc    120
tacatgcgcc cgatctattc gggcgctgcg gttgcggcct cggccgtcac catcctctct    180
ccacccctgcg acaactggat gctgcacgtc gccatcgagc agatccagcc gggcgacatt    240
ctcgttctcg gcacgacctc tccgtccgat gccggctatt tcggtgatct gctggcgact    300
tcggccaagg cgcgcggttg cgtcgggttg gtcatcgatg ccggcgtacg cgatatccgc    360
gacctgacag cgatgcagtt tccggtctgg tccaaggccg tttcggccca gggcacgatc    420
aaggagacgc tgggttcggt caacgtcccc gtcgtctgcg ccggtgctct ggtcaatccc    480
ggcgacgtcg tcgtggccga tgacgacggt gtctgcgtgg tgcgccgcga ggaagccgcg    540
gaaacgctgg aaaaggcccg ggcgcggatc gccaatgagg aggaaaagcg ccagcgcttt    600
gccgctggcg aactcgggct cgacatctac aagatgcgcg aacgcctcgc tgccctgggg    660
ctcacctatg tctga                                                    675

<210> SEQ ID NO 173
<211> LENGTH: 224
<212> TYPE: PRT
<213> ORGANISM: Unknown
<220> FEATURE:
<223> OTHER INFORMATION: R-specific aldolase

<400> SEQUENCE: 173

Met Lys Pro Val Val Val Gln Thr Ile Glu Arg Ala Asp Arg Ala Ile
 1               5                  10                  15

Ile Glu Gly Leu Ala Ala Cys Gly Val Ala Thr Val His Glu Ala Gln
            20                  25                  30

Gly Arg Arg Gly Leu Leu Ala Ser Tyr Met Arg Pro Ile Tyr Ser Gly
        35                  40                  45

Ala Ala Val Ala Ala Ser Ala Val Thr Ile Leu Ser Pro Pro Cys Asp
    50                  55                  60

Asn Trp Met Leu His Val Ala Ile Glu Gln Ile Gln Pro Gly Asp Ile
65                  70                  75                  80

Leu Val Leu Gly Thr Thr Ser Pro Ser Asp Ala Gly Tyr Phe Gly Asp
                85                  90                  95

Leu Leu Ala Thr Ser Ala Lys Ala Arg Gly Cys Val Gly Leu Val Ile
            100                 105                 110

Asp Ala Gly Val Arg Asp Ile Arg Asp Leu Thr Ala Met Gln Phe Pro
        115                 120                 125

Val Trp Ser Lys Ala Val Ser Ala Gln Gly Thr Ile Lys Glu Thr Leu
    130                 135                 140

Gly Ser Val Asn Val Pro Val Val Cys Ala Gly Ala Leu Val Asn Pro
145                 150                 155                 160

Gly Asp Val Val Val Ala Asp Asp Asp Gly Val Cys Val Val Arg Arg
                165                 170                 175

Glu Glu Ala Ala Glu Thr Leu Glu Lys Ala Arg Ala Arg Ile Ala Asn
            180                 185                 190

Glu Glu Glu Lys Arg Gln Arg Phe Ala Ala Gly Glu Leu Gly Leu Asp
        195                 200                 205
```

```
Ile Tyr Lys Met Arg Glu Arg Leu Ala Ala Leu Gly Leu Thr Tyr Val
            210                 215                 220
```

<210> SEQ ID NO 174
<211> LENGTH: 48
<212> TYPE: DNA
<213> ORGANISM: Artificial sequence
<220> FEATURE:
<223> OTHER INFORMATION: AldolaseFpstIrbs Primer

<400> SEQUENCE: 174

```
ggccggaact gcagaagaag gagatatata atgaagccgg tggtggtg            48
```

<210> SEQ ID NO 175
<211> LENGTH: 32
<212> TYPE: DNA
<213> ORGANISM: Artificial sequence
<220> FEATURE:
<223> OTHER INFORMATION: AldolaseRxbaI Primer

<400> SEQUENCE: 175

```
ggccaaggtc tagattagac ataggtgagc cc                              32
```

<210> SEQ ID NO 176
<211> LENGTH: 1227
<212> TYPE: DNA
<213> ORGANISM: Aeromonas hydrophila

<400> SEQUENCE: 176

```
atgcacaaga agacactgct ggccaccttg atcctgggcc tgctggccgg tcaagccgtc      60
gcagccccct atctgcctct ggcaagcgat catcgcaacg gcgaagtaca aaccgccagc     120
aacgcctggc tggaagtaga tctgaccgcg tttgaacaga tcctgcagac cctcaagacc     180
cgcctcggcg acaagggccc gcagatctgc gccatcatga aggcggacgc ctacggtcac     240
ggtatcgatc tgctggttcc ctccgtcatc aaggccgaga tccctgtat cggcatcgcc      300
agcaacgaag aggcccgcgt cgcccgcgag aaggggttca gcggccgcct gatgcgggta     360
cgggccgcca cactatcga agtggaacag gccctgccct acaagctgga agagctggtt     420
ggcagcctgg tgagtgctca ggggatctcc gacatcgccc tgcgccacca ccaccatt      480
ccggtgcatg tcgccctcaa ctccgccggt atgagccgca acggcatcga cctgcgtctg     540
gccgatgcca agcaagatgc gctggccatg ctcaagctca ggggatcac cccggtcggc     600
atcatgaccc acttcccggt ggaggagaaa gaggacgtca gctgggggct ggctcagttc     660
aagctggact cccagtggct gctggaagca ggcaagctgg atcgcagcaa gatcaccatc     720
catgccgcca actccttcgc caccctggca gtgccggacg cctactttga catggtgcgc     780
ccgggcggcc tgctctacgg cgactccatc ccctcctaca ccgaatacaa gcgggtgatg     840
gcattcaaga cccaggtcgc ctcggtcaac cactatgcgg cggcaacac agtcggttat     900
gaccgcacct ttactctcaa acgtgactcc tggctcgcca acctgccgct cggttactcc     960
gacggctatc gccgtgcgct cagcaacaag gcctatgtgc tgatccaggg tcagaaggtg    1020
ccggtggtcg gcaagacctc catgaacacc atcatggtgg acgtgaccga tctcaaaggg    1080
gtaaagcccg gtgatgaagt ggtgctgttt ggccgtcagg gtgaggcaga agtgaaacag    1140
gctgatctgg aggagtacaa cggcgccctg ttggcggaca tgtacaccat ctggggctac    1200
accaacccca agaagatcaa acgctga                                         1227
```

<210> SEQ ID NO 177
<211> LENGTH: 408

```
<212> TYPE: PRT
<213> ORGANISM: Aeromonas hydrophila

<400> SEQUENCE: 177

Met His Lys Lys Thr Leu Leu Ala Thr Leu Ile Leu Gly Leu Leu Ala
1               5                   10                  15

Gly Gln Ala Val Ala Ala Pro Tyr Leu Pro Leu Ala Ser Asp His Arg
            20                  25                  30

Asn Gly Glu Val Gln Thr Ala Ser Asn Ala Trp Leu Glu Val Asp Leu
        35                  40                  45

Thr Ala Phe Glu Gln Asn Leu Gln Thr Leu Lys Thr Arg Leu Gly Asp
    50                  55                  60

Lys Gly Pro Gln Ile Cys Ala Ile Met Lys Ala Asp Ala Tyr Gly His
65                  70                  75                  80

Gly Ile Asp Leu Leu Val Pro Ser Val Ile Lys Ala Glu Ile Pro Cys
                85                  90                  95

Ile Gly Ile Ala Ser Asn Glu Glu Ala Arg Val Ala Arg Glu Lys Gly
            100                 105                 110

Phe Ser Gly Arg Leu Met Arg Val Arg Ala Ala Thr Pro Ile Glu Val
        115                 120                 125

Glu Gln Ala Leu Pro Tyr Lys Leu Glu Glu Leu Val Gly Ser Leu Val
    130                 135                 140

Ser Ala Gln Gly Ile Ser Asp Ile Ala Leu Arg His His Thr Thr Ile
145                 150                 155                 160

Pro Val His Val Ala Leu Asn Ser Ala Gly Met Ser Arg Asn Gly Ile
                165                 170                 175

Asp Leu Arg Leu Ala Asp Ala Lys Gln Asp Ala Leu Ala Met Leu Lys
            180                 185                 190

Leu Lys Gly Ile Thr Pro Val Gly Ile Met Thr His Phe Pro Val Glu
        195                 200                 205

Glu Lys Glu Asp Val Lys Leu Gly Leu Ala Gln Phe Lys Leu Asp Ser
    210                 215                 220

Gln Trp Leu Leu Glu Ala Gly Lys Leu Asp Arg Ser Lys Ile Thr Ile
225                 230                 235                 240

His Ala Ala Asn Ser Phe Ala Thr Leu Ala Val Pro Asp Ala Tyr Phe
                245                 250                 255

Asp Met Val Arg Pro Gly Gly Leu Leu Tyr Gly Asp Ser Ile Pro Ser
            260                 265                 270

Tyr Thr Glu Tyr Lys Arg Val Met Ala Phe Lys Thr Gln Val Ala Ser
        275                 280                 285

Val Asn His Tyr Ala Ala Gly Asn Thr Val Gly Tyr Asp Arg Thr Phe
    290                 295                 300

Thr Leu Lys Arg Asp Ser Trp Leu Ala Asn Leu Pro Leu Gly Tyr Ser
305                 310                 315                 320

Asp Gly Tyr Arg Arg Ala Leu Ser Asn Lys Ala Tyr Val Leu Ile Gln
                325                 330                 335

Gly Gln Lys Val Pro Val Val Gly Lys Thr Ser Met Asn Thr Ile Met
            340                 345                 350

Val Asp Val Thr Asp Leu Lys Gly Val Lys Pro Gly Asp Glu Val Val
        355                 360                 365

Leu Phe Gly Arg Gln Gly Glu Ala Val Lys Gln Ala Asp Leu Glu
    370                 375                 380

Glu Tyr Asn Gly Ala Leu Leu Ala Asp Met Tyr Thr Ile Trp Gly Tyr
385                 390                 395                 400
```

```
Thr Asn Pro Lys Lys Ile Lys Arg
            405
```

<210> SEQ ID NO 178
<211> LENGTH: 1227
<212> TYPE: DNA
<213> ORGANISM: Aeromonas caviae

<400> SEQUENCE: 178

```
atgcacaaga aaacactgct cgcgaccctg atctttggcc tgctggccgg ccaggcagtc      60
gccgccccct atctgccgct cgccgacgac caccgcaacg gtcaggaaca gaccgccgcc     120
aacgcctggc tggaagtgga tctcggcgcc ttcgagcaca catccagac cctgaagaat      180
cgcctcggtg acaagggccc gcagatctgc gccatcatga aggcggacgc ctacggtcac     240
ggcatcgacc tgctggtccc ttccgtggtc aaggcaggca tccctgcat cggcatcgcc      300
agcaacgaag aagcacgtgt tgcccgcgag aagggcttcg aaggtcgcct gatgcgggta     360
cgtgccgcca ccccggatga agtggagcag gccctgccct acaagctgga ggagctcatc    420
ggcagcctgg agagcgccaa ggggatcgcc gacatcgccc agcgccatca caccaacatc    480
ccggtgcaca tcgccctgaa ctccgccggc atgagccgca acggcatcga tctgcgccag   540
gacgatgcca aggccgatgc cctggccatg ctcaagctca gggggatcac cccggtcggc  600
atcatgaccc acttcccggt ggaggagaaa gaggacgtca gctggggct ggcccagttc    660
aagctggact accagtggct catcgacgcc ggcaagctgg atcgcagcaa gctcaccatc   720
cacgccgcca actccttcgc caccctggaa gtaccggaag cctactttga catggtgcgc  780
ccgggcggca tcatctatgg cgacaccatt ccctcctaca ccgagtacaa gaaggtgatg  840
gcgttcaaga cccaggtcgc ctccgtcaac cactacccgg cggcaacac cgtcggctat   900
gaccgcacct tcaccctcaa gcgcgactcc ctgctggcca acctgccgat gggctactcc  960
gacggctacc gccgcgccat gagcaacaag gcctatgtgc tgatccatgg ccagaaggcc 1020
cccgtcgtgg gcaagacttc catgaacacc accatggtgg acgtcaccga catcaagggg 1080
atcaaacccg gtgacgaggt ggtcctgttc ggacgccagg gtgatgccga ggtgaaacaa 1140
tctgatctgg aggagtacaa cggtgccctc ttggcggaca tgtacaccgt ctggggctat 1200
accaaccccca agaagatcaa gcgctaa                                     1227
```

<210> SEQ ID NO 179
<211> LENGTH: 408
<212> TYPE: PRT
<213> ORGANISM: Aeromonas caviae

<400> SEQUENCE: 179

```
Met His Lys Lys Thr Leu Leu Ala Thr Leu Ile Phe Gly Leu Leu Ala
1               5                   10                  15

Gly Gln Ala Val Ala Ala Pro Tyr Leu Pro Leu Ala Asp Asp His Arg
            20                  25                  30

Asn Gly Gln Glu Gln Thr Ala Ala Asn Ala Trp Leu Glu Val Asp Leu
        35                  40                  45

Gly Ala Phe Glu His Asn Ile Gln Thr Leu Lys Asn Arg Leu Gly Asp
    50                  55                  60

Lys Gly Pro Gln Ile Cys Ala Ile Met Lys Ala Asp Ala Tyr Gly His
65                  70                  75                  80

Gly Ile Asp Leu Leu Val Pro Ser Val Val Lys Ala Gly Ile Pro Cys
                85                  90                  95

Ile Gly Ile Ala Ser Asn Glu Glu Ala Arg Val Ala Arg Glu Lys Gly
```

100                 105                 110
Phe Glu Gly Arg Leu Met Arg Val Arg Ala Ala Thr Pro Asp Glu Val
            115                 120                 125

Glu Gln Ala Leu Pro Tyr Lys Leu Glu Glu Leu Ile Gly Ser Leu Glu
        130                 135                 140

Ser Ala Lys Gly Ile Ala Asp Ile Ala Gln Arg His His Thr Asn Ile
145                 150                 155                 160

Pro Val His Ile Gly Leu Asn Ser Ala Gly Met Ser Arg Asn Gly Ile
                165                 170                 175

Asp Leu Arg Gln Asp Asp Ala Lys Ala Asp Leu Ala Met Leu Lys
            180                 185                 190

Leu Lys Gly Ile Thr Pro Val Gly Ile Met Thr His Phe Pro Val Glu
            195                 200                 205

Glu Lys Glu Asp Val Lys Leu Gly Leu Ala Gln Phe Lys Leu Asp Tyr
        210                 215                 220

Gln Trp Leu Ile Asp Ala Gly Lys Leu Asp Arg Ser Lys Leu Thr Ile
225                 230                 235                 240

His Ala Ala Asn Ser Phe Ala Thr Leu Glu Val Pro Glu Ala Tyr Phe
                245                 250                 255

Asp Met Val Arg Pro Gly Gly Ile Ile Tyr Gly Asp Thr Ile Pro Ser
            260                 265                 270

Tyr Thr Glu Tyr Lys Lys Val Met Ala Phe Lys Thr Gln Val Ala Ser
            275                 280                 285

Val Asn His Tyr Pro Ala Gly Asn Thr Val Gly Tyr Asp Arg Thr Phe
        290                 295                 300

Thr Leu Lys Arg Asp Ser Leu Leu Ala Asn Leu Pro Met Gly Tyr Ser
305                 310                 315                 320

Asp Gly Tyr Arg Arg Ala Met Ser Asn Lys Ala Tyr Val Leu Ile His
                325                 330                 335

Gly Gln Lys Ala Pro Val Val Gly Lys Thr Ser Met Asn Thr Thr Met
            340                 345                 350

Val Asp Val Thr Asp Ile Lys Gly Ile Lys Pro Gly Asp Glu Val Val
            355                 360                 365

Leu Phe Gly Arg Gln Gly Asp Ala Glu Val Lys Gln Ser Asp Leu Glu
        370                 375                 380

Glu Tyr Asn Gly Ala Leu Leu Ala Asp Met Tyr Thr Val Trp Gly Tyr
385                 390                 395                 400

Thr Asn Pro Lys Lys Ile Lys Arg
                405

<210> SEQ ID NO 180
<211> LENGTH: 31
<212> TYPE: DNA
<213> ORGANISM: Artificial Sequence
<220> FEATURE:
<223> OTHER INFORMATION: Synthetic primer

<400> SEQUENCE: 180
ggttaattca tatggcgcca cccctgtcga t                                  31

<210> SEQ ID NO 181
<211> LENGTH: 32
<212> TYPE: DNA
<213> ORGANISM: Artificial Sequence
<220> FEATURE:
<223> OTHER INFORMATION: Synthetic primer

<400> SEQUENCE: 181

-continued aagtcgctcg agctgatctt tcaggatttt ag                              32

<210> SEQ ID NO 182
<211> LENGTH: 33
<212> TYPE: DNA
<213> ORGANISM: Artificial Sequence
<220> FEATURE:
<223> OTHER INFORMATION: Synthetic primer

<400> SEQUENCE: 182
ggaaccttca tatgcacaag aagacactgc tgg                             33

<210> SEQ ID NO 183
<211> LENGTH: 35
<212> TYPE: DNA
<213> ORGANISM: Artificial Sequence
<220> FEATURE:
<223> OTHER INFORMATION: Synthetic primer

<400> SEQUENCE: 183
ggttccaagg atcctcagcg tttgatcttc ttggg                           35

<210> SEQ ID NO 184
<211> LENGTH: 34
<212> TYPE: DNA
<213> ORGANISM: Artificial Sequence
<220> FEATURE:
<223> OTHER INFORMATION: Synthetic primer

<400> SEQUENCE: 184
ggccaattct cgaggcgttt gatcttcttg gggt                            34

<210> SEQ ID NO 185
<211> LENGTH: 38
<212> TYPE: DNA
<213> ORGANISM: Artificial Sequence
<220> FEATURE:
<223> OTHER INFORMATION: Synthetic primer

<400> SEQUENCE: 185
ggaaccttca tatgcacaag aaaacactgc tcgcgacc                        38

<210> SEQ ID NO 186
<211> LENGTH: 39
<212> TYPE: DNA
<213> ORGANISM: Artificial Sequence
<220> FEATURE:
<223> OTHER INFORMATION: Synthetic primer

<400> SEQUENCE: 186
ggttccaagg atccttagcg cttgatcttc ttggggttg                       39

<210> SEQ ID NO 187
<211> LENGTH: 39
<212> TYPE: DNA
<213> ORGANISM: Artificial Sequence
<220> FEATURE:
<223> OTHER INFORMATION: Synthetic primer

<400> SEQUENCE: 187
ttccaaggct cgaggcgctt gatcttcttg gggttggta                       39

<210> SEQ ID NO 188
<211> LENGTH: 31
<212> TYPE: DNA
<213> ORGANISM: Artificial Sequence

```
<220> FEATURE:
<223> OTHER INFORMATION: Synthetic primer

<400> SEQUENCE: 188
ccttggaaca tatggccccc tatctgccgc t                                    31

<210> SEQ ID NO 189
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: S is C or G
<220> FEATURE:
<221> NAME/KEY: misc_feature
<222> LOCATION: (9)..(9)
<223> OTHER INFORMATION: Y is C or T
<220> FEATURE:
<221> NAME/KEY: misc_feature
<222> LOCATION: (15)..(15)
<223> OTHER INFORMATION: Y is C or T
<220> FEATURE:
<221> NAME/KEY: misc_feature
<222> LOCATION: (18)..(18)
<223> OTHER INFORMATION: Y is C or T

<400> SEQUENCE: 189
aaggcsgayg cctayggyca cgg                                             23

<210> SEQ ID NO 190
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: R is A or G
<220> FEATURE:
<221> NAME/KEY: misc_feature
<222> LOCATION: (12)..(12)
<223> OTHER INFORMATION: R is A or G
<220> FEATURE:
<221> NAME/KEY: misc_feature
<222> LOCATION: (15)..(15)
<223> OTHER INFORMATION: R is A or G

<400> SEQUENCE: 190
cggcgrtagc crtcrgagta                                                 20

<210> SEQ ID NO 191
<211> LENGTH: 1227
<212> TYPE: DNA
<213> ORGANISM: Aeromonas sobria

<400> SEQUENCE: 191
atgcacaaga aaacgctatt ggccaccctg atcttcggcc tgctcgcggg ccaagccgtt     60
gcggctccct atctgcccct tgcgacggat catcgcaacg gtcaggagca aaccgccagc    120
aacgcctggt tggaagtgga tctgggcgcc ttcgaacaca atatccagac cctcaaggat    180
cgcctcggtg acaagggtcc gcagatctgc gccatcatga aggccgacgc ctatggtcat    240
ggcatcgacc tgctggtccc ctccgtggtc aaggccaata tccnctgcat cggcatcgcc    300
agcaacgaag aggcccgcgt cgcccgcgag aagggctttta ccggccgtct gatgcgggtg    360
cgtgccgcca caccggccga agtggagcag gcgctgccct acaagatgga agagctgatc    420
```

```
ggcagtctgg tgagtgctca ggggatcgcc gacatcgccc agcgccacca ccaatatt      480 ccggtacaca ttggtctcaa ctctgctggc atgagccgca acggtatcga cctgcgtctg    540
gccgatgcca agcaggatgc gctggccatg ctcaagctca aggggatcac cccggtcggc    600
atcatgaccc acttcccggt ggaggagaaa gaggacgtca agatggggct ggcccagttc    660
aaactggact ctcagtggct gctggaagcg ggcaagctgg atcgcagcaa gatcaccatc    720
cacgccgcca actccttcgc caccctggaa gtgccggatg cctacttcga catggtgcgt    780
ccgggtggcc tgctctacgg cgactccatc ccctcctaca ccgaatacaa gcgggtgatg    840
gcattcaaga cccaggtcgc ctcggtcaac cactacccgg cgggcaatac cgttggctat    900
gaccgtacct ttaccctcaa gcgtgaatcc tggctcgcca acctgccgct gggctactcc    960
gatggctacc gccgtgcgct cagcaacaag gcctatgtgc tgatccaggg tcagaaggtg   1020
ccggtggtcg gcaagacctc catgaacacc atcatggtgg acgtcactga tctcaaaggg   1080
gtgaaacccg gtgatgaggt ggtgctgttt ggccgtcagg gcgaggccga ggtgaaacag   1140
gctgatctgg aagagtacaa cggcgccctg ttagcggaca tgtacaccat ctggggctac   1200
accaacccca gaagatcaa acgctga                                        1227
```

<210> SEQ ID NO 192
<211> LENGTH: 408
<212> TYPE: PRT
<213> ORGANISM: Aeromonas sobria

<400> SEQUENCE: 192

```
Met His Lys Lys Thr Leu Leu Ala Thr Leu Ile Phe Gly Leu Leu Ala
1               5                   10                  15

Gly Gln Ala Val Ala Ala Pro Tyr Leu Pro Leu Ala Thr Asp His Arg
            20                  25                  30

Asn Gly Gln Glu Gln Thr Ala Ser Asn Ala Trp Leu Glu Val Asp Leu
        35                  40                  45

Gly Ala Phe Glu His Asn Ile Gln Thr Leu Lys Asp Arg Leu Gly Asp
    50                  55                  60

Lys Gly Pro Gln Ile Cys Ala Ile Met Lys Ala Asp Ala Tyr Gly His
65                  70                  75                  80

Gly Ile Asp Leu Leu Val Pro Ser Val Val Lys Ala Asn Ile Pro Cys
                85                  90                  95

Ile Gly Ile Ala Ser Asn Glu Glu Ala Arg Val Ala Arg Glu Lys Gly
            100                 105                 110

Phe Thr Gly Arg Leu Met Arg Val Arg Ala Ala Thr Pro Ala Glu Val
        115                 120                 125

Glu Gln Ala Leu Pro Tyr Lys Met Glu Glu Leu Ile Gly Ser Leu Val
    130                 135                 140

Ser Ala Gln Gly Ile Ala Asp Ile Ala Gln Arg His His Thr Asn Ile
145                 150                 155                 160

Pro Val His Ile Gly Leu Asn Ser Ala Gly Met Ser Arg Asn Gly Ile
                165                 170                 175

Asp Leu Arg Leu Ala Asp Ala Lys Gln Asp Ala Leu Ala Met Leu Lys
            180                 185                 190

Leu Lys Gly Ile Thr Pro Val Gly Ile Met Thr His Phe Pro Val Glu
        195                 200                 205

Glu Lys Glu Asp Val Lys Met Gly Leu Ala Gln Phe Lys Leu Asp Ser
    210                 215                 220

Gln Trp Leu Leu Glu Ala Gly Lys Leu Asp Arg Ser Lys Ile Thr Ile
```

```
                225                 230                 235                 240
            His Ala Ala Asn Ser Phe Ala Thr Leu Glu Val Pro Asp Ala Tyr Phe
                            245                 250                 255

Asp Met Val Arg Pro Gly Gly Leu Leu Tyr Gly Asp Ser Ile Pro Ser
                        260                 265                 270

Tyr Thr Glu Tyr Lys Arg Val Met Ala Phe Lys Thr Gln Val Ala Ser
                    275                 280                 285

Val Asn His Tyr Pro Ala Gly Asn Thr Val Gly Tyr Asp Arg Thr Phe
                290                 295                 300

Thr Leu Lys Arg Glu Ser Trp Leu Ala Asn Leu Pro Leu Gly Tyr Ser
            305                 310                 315                 320

Asp Gly Tyr Arg Arg Ala Leu Ser Asn Lys Ala Tyr Val Leu Ile Gln
                            325                 330                 335

Gly Gln Lys Val Pro Val Val Gly Lys Thr Ser Met Asn Thr Ile Met
                        340                 345                 350

Val Asp Val Thr Asp Leu Lys Gly Val Lys Pro Gly Asp Glu Val Val
                    355                 360                 365

Leu Phe Gly Arg Gln Gly Glu Ala Glu Val Lys Gln Ala Asp Leu Glu
                370                 375                 380

Glu Tyr Asn Gly Ala Leu Leu Ala Asp Met Tyr Thr Ile Trp Gly Tyr
            385                 390                 395                 400

Thr Asn Pro Lys Lys Ile Lys Arg
                            405

<210> SEQ ID NO 193
<211> LENGTH: 1227
<212> TYPE: DNA
<213> ORGANISM: Aeromonas jandei

<400> SEQUENCE: 193
atgcacaaga aaacactgct ggccaccctg atcctcggcc tgctggccgg gcaagcggtt      60
gcagccccct acctgccgct ggccagcgat caccgcaacg gcgaagtcca gaccgccagc     120
aatgcctggc tggaagtcga tctcggcgcc ttcgagcaca atatccagac cctcaaggat     180
cgtctcggtg acaaggggcc gaagatctgc gccatcatga aggcggatgc ctatggccac     240
ggtatcgatc tgctggttcc ctcggtggtg aaagcgggta tcccctgcat cggtatcgcc     300
agcaatgaag aagctcgtgt cgcccgcgag aagggcttca ccggtcgtct gatgcgggta     360
cgtgctgcca ccccggacga agtggagcag gccctgccct acaagatgga ggagctgatc     420
ggcagtctgg tgagtgctca gggcatcgcc gatatcgccc agcgccacca caccaccatt     480
ccggtgcata tcgccctcaa ctccgccggc atgagccgca acggcatcga tctgcggctg     540
gccgactcca agcaggatgc gctggccatg ctcaagctca aggggatcac cccggtcggc     600
atcatgaccc acttcccggt ggaggagaaa gaggacgtca agatgggtct ggcccagttc     660
aaactggact cccagtggct gctggaagcg ggcaagctgg atcgcagcaa gatcaccatc     720
cacgccgcca actccttcgc aacacttgaa gtgccggatg cctacttcga catggtgcgc     780
ccgggtggcc tgctctacgg tgactccatc ccctcctaca ccgagtacaa gcgggtgatg     840
gcgttcaaga cccaggttgc ctccgtcaac cactacccgg ccggcaacac cgtcggttat     900
gaccgcacct tcaccctcaa gcgcgactcc tggctcgcca actgccgct cggttactcc     960 gatggctatc gccgctccct gagcaacaag gcctatgtgc tgatccaggg ccagaaggtg    1020
ccggtggtcg gcaagacctc catgaacacc atcatggtgg atgtgaccga cctgaaaggg    1080
gtgaaacccg gtgacgaagt ggtgctgttc ggccgtcagg gaaatgccga ggtgaagcag    1140
```

```
gcggatctgg aggagtacaa cggcgccctg ctggcggaca tgtacaccat ctggggctac    1200
accaacccca agaagatcaa gcactaa                                        1227
```

<210> SEQ ID NO 194
<211> LENGTH: 408
<212> TYPE: PRT
<213> ORGANISM: Aeromonas jandei

<400> SEQUENCE: 194

```
Met His Lys Lys Thr Leu Leu Ala Thr Leu Ile Leu Gly Leu Leu Ala
1               5                   10                  15

Gly Gln Ala Val Ala Ala Pro Tyr Leu Pro Leu Ala Ser Asp His Arg
            20                  25                  30

Asn Gly Glu Val Gln Thr Ala Ser Asn Ala Trp Leu Glu Val Asp Leu
        35                  40                  45

Gly Ala Phe Glu His Asn Ile Gln Thr Leu Lys Asp Arg Leu Gly Asp
    50                  55                  60

Lys Gly Pro Lys Ile Cys Ala Ile Met Lys Ala Asp Ala Tyr Gly His
65                  70                  75                  80

Gly Ile Asp Leu Leu Val Pro Ser Val Val Lys Ala Gly Ile Pro Cys
                85                  90                  95

Ile Gly Ile Ala Ser Asn Glu Glu Ala Arg Val Ala Arg Glu Lys Gly
            100                 105                 110

Phe Thr Gly Arg Leu Met Arg Val Arg Ala Ala Thr Pro Asp Glu Val
        115                 120                 125

Glu Gln Ala Leu Pro Tyr Lys Met Glu Glu Leu Ile Gly Ser Leu Val
    130                 135                 140

Ser Ala Gln Gly Ile Ala Asp Ile Ala Gln Arg His His Thr Thr Ile
145                 150                 155                 160

Pro Val His Ile Ala Leu Asn Ser Ala Gly Met Ser Arg Asn Gly Ile
                165                 170                 175

Asp Leu Arg Leu Ala Asp Ser Lys Gln Asp Ala Leu Ala Met Leu Lys
            180                 185                 190

Leu Lys Gly Ile Thr Pro Val Gly Ile Met Thr His Phe Pro Val Glu
        195                 200                 205

Glu Lys Glu Asp Val Lys Met Gly Leu Ala Gln Phe Lys Leu Asp Ser
    210                 215                 220

Gln Trp Leu Leu Glu Ala Gly Lys Leu Asp Arg Ser Lys Ile Thr Ile
225                 230                 235                 240

His Ala Ala Asn Ser Phe Ala Thr Leu Glu Val Pro Asp Ala Tyr Phe
                245                 250                 255

Asp Met Val Arg Pro Gly Gly Leu Leu Tyr Gly Asp Ser Ile Pro Ser
            260                 265                 270

Tyr Thr Glu Tyr Lys Arg Val Met Ala Phe Lys Thr Gln Val Ala Ser
        275                 280                 285

Val Asn His Tyr Pro Ala Gly Asn Thr Val Gly Tyr Asp Arg Thr Phe
    290                 295                 300

Thr Leu Lys Arg Asp Ser Trp Leu Ala Asn Leu Pro Leu Gly Tyr Ser
305                 310                 315                 320

Asp Gly Tyr Arg Arg Ser Leu Ser Asn Lys Ala Tyr Val Leu Ile Gln
                325                 330                 335

Gly Gln Lys Val Pro Val Val Gly Lys Thr Ser Met Asn Thr Ile Met
            340                 345                 350

Val Asp Val Thr Asp Leu Lys Gly Val Lys Pro Gly Asp Glu Val Val
```

```
                355                 360                 365
Leu Phe Gly Arg Gln Gly Asn Ala Glu Val Lys Gln Ala Asp Leu Glu
    370                 375                 380

Glu Tyr Asn Gly Ala Leu Leu Ala Asp Met Tyr Thr Ile Trp Gly Tyr
385                 390                 395                 400

Thr Asn Pro Lys Lys Ile Lys His
                405

<210> SEQ ID NO 195
<211> LENGTH: 755
<212> TYPE: DNA
<213> ORGANISM: Aeromonas salmonicida
<220> FEATURE:
<221> NAME/KEY: misc_feature
<222> LOCATION: (6)..(6)
<223> OTHER INFORMATION: S is C or G
<220> FEATURE:
<221> NAME/KEY: misc_feature
<222> LOCATION: (15)..(15)
<223> OTHER INFORMATION: Y is C or T
<220> FEATURE:
<221> NAME/KEY: misc_feature
<222> LOCATION: (744)..(744)
<223> OTHER INFORMATION: Y is C or T
<220> FEATURE:
<221> NAME/KEY: misc_feature
<222> LOCATION: (750)..(750)
<223> OTHER INFORMATION: Y is C or T

<400> SEQUENCE: 195
aaggcsgatg cctayggtca cggtatcgac ctgctggtcc cctccgtggt caaggccaat      60 atccctgta tcggcatcgc cagcaacgaa gaggcccgcg tggcgcgcga aaggggttc      120 agcggccgcc tgatgcgggt acgggccgcc acaccgatcg aagtggaaca ggccctgccc     180
tacaagctgg aagagctggt tggcagcctg gtgagtgctc aggggatctc cgacatcgcc     240
ctgcgccacc acaccaccat tccggtgcat gtcgccctca actccgccgg catgagccgc     300
aacggcatcg acctgcgtct ggccgatgcc aagcaagatg cgctggccat gctcaagctc     360
aaggggatca ccccggtcgg catcatgacc cacttcccgg tggaggagaa agaggacgtc     420
aagctggggc tggcccagtt caagctggac tcccagtggc tgctggaagc aggcaagctg     480
gatcgcagca agatcaccat ccatgccgcc aactccttcg ccaccctggc agtgccggac     540
gcctactttg acatggtgcg cccgggcggc ctgctctacg gcgactccat ccctcctac      600 accgaataca gcgggtgat ggcattcaag acccaggtcg cctcggtcaa ccactatgcg      660
gcgggcaaca cagtcggtta tgaccgcacc tttactctca acgtgactc ctggctcgcc      720 aacctgcctc tcggttactc cgayggctay cgccg                                755

<210> SEQ ID NO 196
<211> LENGTH: 1008
<212> TYPE: DNA
<213> ORGANISM: Aeromonas schubertii

<400> SEQUENCE: 196
aaggcggatg cctatggtca cggcatcgat ctgctggtcc cctccgtgat caaggccggc      60
attccttgca tcggcatcgc cagcaacgaa gaggctcgcg tcgcccgtga aagggcttc      120 gaaggccgtc tgatgcgggt gcgcgccgcc accccgcaag aggtggaagc cgccctcccc     180
tacaagatgg aggagctggt cggcagcctg gagagcgccc gtctgatgtc ggagattgcc     240
ctgcgtcacc acaccaccat tgcgtaccat ctggggctca actccgccgg catgagccgc     300
aacggcctgg atctgcgcct ctccgacgcc aagcgcgacg cactcgacct gatgaagctc     360
```

-continued

```
aaggggctgc aggtggtcgg catcatgacc cacttcccgg tcgaggagaa agaggacgtg      420
aagatgggct tcgcccagtt tcagctcgac acccagtggc tcatcgaagc cgctcgtctg      480
gatcgcagca agttgaccct gcactgtgcc aactcctta ccaccctgga ggtgcccgag       540
gcctatctgg acatggtccg cccgggcggc atcatctatg cgacaccat tccctcctac      600 accgaataca agaaggtgat ggccttcaag acccgggtcg cctcggtcaa tcactacccg     660
aagggaaata gcgtcggcta tgaccgcacc ttcaccctgg cacgcgactc ctggctcgcc     720
aacctgccgc tgggctactc cgacggctac cgccgggcgc tgagcaacaa ggcctatgtg     780
ctggtgaatg gccagaaggc ccccgtggtg ggcaagacat ccatgaacac catcatggtg     840
gacgtgaccg acatcaaggg ggtcaaaccg ggtgacgagg tggtgctgtt tggccgccag     900
ggcaacgccg aggtgaagca gtccgatctc gaggagtaca acggcgccct cctggcggac     960
atgtacacca tctggggcta caccaatcca cgtatcatca gcgctga                  1008
```

<210> SEQ ID NO 197
<211> LENGTH: 39
<212> TYPE: DNA
<213> ORGANISM: Artificial Sequence
<220> FEATURE:
<223> OTHER INFORMATION: Synthetic primer

<400> SEQUENCE: 197
ccggaacctt catatgcaca agaaaacact gctggccac                             39

<210> SEQ ID NO 198
<211> LENGTH: 38
<212> TYPE: DNA
<213> ORGANISM: Artificial Sequence
<220> FEATURE:
<223> OTHER INFORMATION: Synthetic primer

<400> SEQUENCE: 198
ttccaaggct cgaggtgctt gatcttcttg gggttggt                              38

<210> SEQ ID NO 199
<211> LENGTH: 39
<212> TYPE: DNA
<213> ORGANISM: Artificial Sequence
<220> FEATURE:
<223> OTHER INFORMATION: Synthetic primer

<400> SEQUENCE: 199
ccggaacctt catatgcaca agaaaacgct attggccac                             39

<210> SEQ ID NO 200
<211> LENGTH: 38
<212> TYPE: DNA
<213> ORGANISM: Artificial Sequence
<220> FEATURE:
<223> OTHER INFORMATION: Synthetic primer

<400> SEQUENCE: 200
ttccaaggct cgaggcgttt gatcttcttg gggttggt                              38

<210> SEQ ID NO 201
<211> LENGTH: 9
<212> TYPE: PRT
<213> ORGANISM: Artificial Sequence
<220> FEATURE:
<223> OTHER INFORMATION: Synthetic motif

<400> SEQUENCE: 201

```
Lys Ala Asp Ala Tyr Gly His Gly Ile
1               5
```

<210> SEQ ID NO 202
<211> LENGTH: 9
<212> TYPE: PRT
<213> ORGANISM: Artificial Sequence
<220> FEATURE:
<223> OTHER INFORMATION: Synthetic motif

<400> SEQUENCE: 202

```
Lys Ala Asn Ala Tyr Gly His Gly Ile
1               5
```

<210> SEQ ID NO 203
<211> LENGTH: 32
<212> TYPE: DNA
<213> ORGANISM: Artificial Sequence
<220> FEATURE:
<223> OTHER INFORMATION: Synthetic primer

<400> SEQUENCE: 203
cgccatcatg aaggcgaacg cctacggtca cg                                   32

<210> SEQ ID NO 204
<211> LENGTH: 409
<212> TYPE: PRT
<213> ORGANISM: Pseudomonas taetrolens

<400> SEQUENCE: 204

```
Met Pro Phe Ser Arg Thr Leu Leu Ala Leu Ser Leu Gly Met Ala Leu
1               5                   10                  15

Leu Gln Asn Pro Ala Phe Ala Ala Pro Pro Leu Ser Met Thr Asp Gly
            20                  25                  30

Val Ala Gln Val Asn Thr Gln Asp Ser Asn Ala Trp Val Glu Ile Asn
        35                  40                  45

Lys Ala Ala Phe Glu His Asn Ile Arg Thr Leu Gln Thr Ala Leu Ala
    50                  55                  60

Gly Lys Ser Gln Ile Cys Ala Val Leu Lys Ala Asp Ala Tyr Gly His
65                  70                  75                  80

Gly Ile Gly Leu Leu Met Pro Ser Val Ile Ala Met Gly Val Pro Cys
                85                  90                  95

Val Gly Val Ala Ser Asn Glu Glu Ala Arg Val Val Arg Glu Ser Gly
            100                 105                 110

Phe Lys Gly Gln Leu Ile Arg Val Arg Thr Ala Ala Leu Ser Glu Leu
        115                 120                 125

Glu Ala Ala Leu Pro Tyr Asn Met Glu Glu Leu Val Gly Asn Leu Asp
    130                 135                 140

Phe Ala Val Lys Ala Ser Leu Ile Ala Glu Asp His Gly Arg Pro Leu
145                 150                 155                 160

Val Val His Leu Gly Leu Asn Ser Ser Gly Met Ser Arg Asn Gly Val
                165                 170                 175

Asp Met Thr Thr Ala Gln Gly Arg Arg Asp Ala Val Ala Ile Thr Lys
            180                 185                 190

Val Pro Asn Leu Glu Val Arg Ala Ile Met Thr His Phe Ala Val Glu
        195                 200                 205

Asp Ala Ala Asp Val Arg Ala Gly Leu Lys Ala Phe Asn Gln Gln Ala
    210                 215                 220

Gln Trp Leu Met Asn Val Ala Gln Leu Asp Arg Ser Lys Ile Thr Leu
```

```
                225                 230                 235                 240
His Ala Ala Asn Ser Phe Ala Thr Leu Glu Val Pro Glu Ser His Leu
                245                 250                 255

Asp Met Val Arg Pro Gly Gly Ala Leu Phe Gly Asp Thr Val Pro Ser
            260                 265                 270

His Thr Glu Tyr Lys Arg Val Met Gln Phe Lys Ser His Val Ala Ser
        275                 280                 285

Val Asn Ser Tyr Pro Lys Gly Asn Thr Val Gly Tyr Asp Arg Thr Tyr
    290                 295                 300

Thr Leu Gly Arg Asp Ser Arg Leu Ala Asn Ile Thr Val Gly Tyr Ser
305                 310                 315                 320

Asp Gly Tyr Arg Arg Ala Phe Thr Asn Lys Gly Ile Val Leu Ile Asn
                325                 330                 335

Gly His Arg Val Pro Val Val Gly Lys Val Ser Met Asn Thr Leu Met
            340                 345                 350

Val Asp Val Thr Asp Ala Pro Asp Val Lys Ser Gly Asp Glu Val Val
        355                 360                 365

Leu Phe Gly His Gln Gly Lys Ala Glu Ile Thr Gln Ala Glu Ile Glu
    370                 375                 380

Asp Ile Asn Gly Ala Leu Leu Ala Asp Leu Tyr Thr Val Trp Gly Asn
385                 390                 395                 400

Ser Asn Pro Lys Ile Leu Lys Asp Gln
                405

<210> SEQ ID NO 205
<211> LENGTH: 283
<212> TYPE: PRT
<213> ORGANISM: Artificial Sequence
<220> FEATURE:
<223> OTHER INFORMATION: BsphDATgene DAAT

<400> SEQUENCE: 205

Met Ala Tyr Ser Leu Trp Asn Asp Gln Ile Val Glu Glu Gly Ser Ile
1               5                   10                  15

Thr Ile Ser Pro Glu Asp Arg Gly Tyr Gln Phe Gly Asp Gly Ile Tyr
            20                  25                  30

Glu Val Ile Lys Val Tyr Asn Gly His Met Phe Thr Ala Gln Glu His
        35                  40                  45

Ile Asp Arg Phe Tyr Ala Ser Ala Glu Lys Ile Arg Leu Val Ile Pro
    50                  55                  60

Tyr Thr Lys Asp Val Leu His Lys Leu Leu His Asp Leu Ile Glu Lys
65                  70                  75                  80

Asn Asn Leu Asn Thr Gly His Val Tyr Phe Gln Ile Thr Arg Gly Thr
                85                  90                  95

Thr Ser Arg Asn His Ile Phe Pro Asp Ala Ser Val Pro Ala Val Leu
            100                 105                 110

Thr Gly Asn Val Lys Thr Gly Glu Arg Ser Ile Glu Asn Phe Glu Lys
        115                 120                 125

Gly Val Lys Ala Thr Leu Val Glu Asp Val Arg Trp Leu Arg Cys Asp
    130                 135                 140

Ile Lys Ser Leu Asn Leu Leu Gly Ala Val Leu Ala Lys Gln Glu Ala
145                 150                 155                 160

Ser Glu Lys Gly Cys Tyr Glu Ala Ile Leu His Arg Gly Asp Ile Ile
                165                 170                 175

Thr Glu Cys Ser Ser Ala Asn Val Tyr Gly Ile Lys Asp Gly Lys Leu
            180                 185                 190
```

Tyr Thr His Pro Ala Asn Asn Tyr Ile Leu Asn Gly Ile Thr Arg Gln
            195                 200                 205

Val Ile Leu Lys Cys Ala Ala Glu Ile Asn Leu Pro Val Ile Glu Glu
            210                 215                 220

Pro Met Thr Lys Gly Asp Leu Leu Thr Met Asp Glu Ile Ile Val Ser
225                 230                 235                 240

Ser Val Ser Ser Glu Val Thr Pro Val Ile Asp Val Asp Gly Gln Gln
            245                 250                 255

Ile Gly Ala Gly Val Pro Gly Glu Trp Thr Arg Lys Leu Gln Lys Ala
            260                 265                 270

Phe Glu Ala Lys Leu Pro Ile Ser Ile Asn Ala
            275                 280

<210> SEQ ID NO 206
<211> LENGTH: 283
<212> TYPE: PRT
<213> ORGANISM: Artificial Sequence
<220> FEATURE:
<223> OTHER INFORMATION: B. halodurans DAAT

<400> SEQUENCE: 206

Met Asp Tyr Cys Leu Tyr Gln Asp Gln Leu Val Pro Arg Glu Gln Leu
1               5                   10                  15

Lys Ile Asp Pro Glu Asp Arg Gly Tyr His Phe Gly Asp Gly Ile Tyr
            20                  25                  30

Glu Val Val His Val Tyr His Gly Lys Ala Phe Ala Leu Ser Asp His
            35                  40                  45

Leu Thr Arg Phe Lys Glu Ser Ala Glu Lys Leu Asp Leu Pro Met Leu
50                  55                  60

Tyr Ser Thr Asp Lys Leu Gly Glu Leu Val Gln Gln Leu Ile Glu Lys
65                  70                  75                  80

Asn Lys Leu Glu His Gly Met Val Tyr Phe Gln Met Thr Arg Gly Ile
            85                  90                  95

Ser Pro Arg Asn His Leu Tyr Thr Arg Asn Glu Thr Pro Val Leu Thr
            100                 105                 110

Gly Phe Ser Lys Pro Leu Pro Asp Glu Lys Arg Glu Ser Val Arg Leu
            115                 120                 125

Tyr Leu Thr Asp Asp Ile Arg Trp Leu Arg Cys Asp Ile Lys Thr Ile
            130                 135                 140

Asn Leu Leu Gly Asn Val Leu Ala Lys Arg Glu Ala Thr Asp His Gln
145                 150                 155                 160

Cys Asp Glu Ala Leu Leu His Arg Asp Gly Thr Val Thr Glu Gly Ser
            165                 170                 175

Ser Ser Asn Val Phe Leu Ile Lys Asn Glu Thr Leu Tyr Thr His Pro
            180                 185                 190

Ala Thr Asn Leu Ile Leu Asn Gly Ile Thr Arg Gln Ile Thr Ile Arg
            195                 200                 205

Leu Ala Lys Ala Lys Gly Tyr Thr Val Val Glu Glu Pro Phe Pro Lys
            210                 215                 220

Glu Val Ile Lys Asp Ala Asp Glu Ala Phe Ile Thr Ser Thr Ile His
225                 230                 235                 240

Glu Ile Thr Pro Val Thr Glu Val Ile Gly Asp Glu Thr Ala His Phe
            245                 250                 255

Pro Val Gly Pro Val Thr Lys Met Leu Gln Gln Ala Phe Ala Glu Glu
            260                 265                 270

Ile Ala Lys His Ser Gln Thr Ala Met Lys Gln
            275                 280

<210> SEQ ID NO 207
<211> LENGTH: 283
<212> TYPE: PRT
<213> ORGANISM: Artificial Sequence
<220> FEATURE:
<223> OTHER INFORMATION: GsteDATgene DAAT

<400> SEQUENCE: 207

Met Gly Tyr Thr Leu Trp Asn Asp Gln Ile Val Lys Asp Glu Glu Val
1               5                   10                  15

Lys Ile Asp Lys Glu Asp Arg Gly Tyr Gln Phe Gly Asp Gly Val Tyr
            20                  25                  30

Glu Val Val Lys Val Tyr Asn Gly Glu Met Phe Thr Val Asn Glu His
        35                  40                  45

Ile Asp Arg Leu Tyr Ala Ser Ala Glu Lys Ile Arg Ile Thr Ile Pro
    50                  55                  60

Tyr Thr Lys Asp Lys Phe His Gln Leu Leu His Glu Leu Val Glu Lys
65                  70                  75                  80

Asn Glu Leu Asn Thr Gly His Ile Tyr Phe Gln Val Thr Arg Gly Thr
                85                  90                  95

Ser Pro Arg Ala His Gln Phe Pro Glu Asn Thr Val Lys Pro Val Ile
            100                 105                 110

Ile Gly Tyr Thr Lys Glu Asn Pro Arg Pro Leu Glu Asn Leu Glu Lys
        115                 120                 125

Gly Val Lys Ala Thr Phe Val Glu Asp Ile Arg Trp Leu Arg Cys Asp
    130                 135                 140

Ile Lys Ser Leu Asn Leu Leu Gly Ala Val Leu Ala Lys Gln Glu Ala
145                 150                 155                 160

His Glu Lys Gly Cys Tyr Glu Ala Ile Leu His Arg Asn Asn Thr Val
                165                 170                 175

Thr Glu Gly Ser Ser Ser Asn Val Phe Gly Ile Lys Asp Gly Ile Leu
            180                 185                 190

Tyr Thr His Pro Ala Asn Asn Met Ile Leu Lys Gly Ile Thr Arg Asp
        195                 200                 205

Val Val Ile Ala Cys Ala Asn Glu Ile Asn Met Pro Val Lys Glu Ile
    210                 215                 220

Pro Phe Thr Thr His Glu Ala Leu Lys Met Asp Glu Leu Phe Val Thr
225                 230                 235                 240

Ser Thr Thr Ser Glu Ile Thr Pro Val Ile Glu Ile Asp Gly Lys Leu
                245                 250                 255

Ile Arg Asp Gly Lys Val Gly Glu Trp Thr Arg Lys Leu Gln Lys Gln
            260                 265                 270

Phe Glu Thr Lys Ile Pro Lys Pro Leu His Ile
        275                 280

<210> SEQ ID NO 208
<211> LENGTH: 290
<212> TYPE: PRT
<213> ORGANISM: Artificial Sequence
<220> FEATURE:
<223> OTHER INFORMATION: B.cereus 145 DAAT

<400> SEQUENCE: 208

Leu Ala Tyr Glu Lys Phe Val Leu Trp Asn Asp Glu Val Ile Asp Thr
1               5                   10                  15

```
Thr Lys Gln Gln Thr Tyr Ile Glu Leu Glu Arg Gly Ser Gln Phe
             20                  25                  30

Gly Asp Gly Val Tyr Glu Val Ile Arg Leu Tyr Lys Gly Asn Phe His
             35                  40                  45

Leu Leu Asp Pro His Ile Thr Arg Leu Tyr Arg Ser Met Glu Glu Val
 50                  55                  60

Glu Leu Ser Leu Pro Phe Ser Lys Ala Glu Leu Ile Thr Leu Leu Tyr
 65                  70                  75                  80

Lys Leu Ile Glu Arg Asn His Phe His Glu Asp Gly Thr Ile Tyr Leu
                 85                  90                  95

Gln Val Ser Arg Gly Val Gln Ala Arg Thr His Val Phe Ser Tyr Asp
            100                 105                 110

Thr Pro Pro Thr Ile Tyr Ala Tyr Ile Thr Lys Lys Glu Arg Pro Ala
            115                 120                 125

Leu Trp Ile Glu Tyr Gly Ile Arg Ala Ile Ser Glu Pro Asp Thr Arg
            130                 135                 140

Trp Leu Arg Cys Asp Ile Lys Ser Leu Asn Leu Leu Pro Asn Val Leu
145                 150                 155                 160

Ala Ala Thr Lys Ala Glu Arg Lys Gly Cys Lys Glu Ala Leu Leu Val
                165                 170                 175

Arg Asn Gly Ile Val Thr Glu Gly Ser His Ser Asn Phe Phe Leu Ile
                180                 185                 190

Lys Asn Gly Thr Leu Tyr Thr His Pro Ala Asn His Leu Ile Leu Asn
            195                 200                 205

Gly Ile Ile Arg Gln Tyr Val Leu Ser Leu Ala Asn Thr Leu His Ile
            210                 215                 220

Pro Val Gln Glu Glu Leu Phe Ser Val Arg Asp Val Tyr Gln Ala Asp
225                 230                 235                 240

Glu Cys Phe Phe Thr Gly Thr Thr Ile Glu Ile Leu Pro Met Thr His
                245                 250                 255

Leu Asp Gly Thr Ala Ile Gln Asp Gly Gln Val Gly Ala Ile Thr Lys
            260                 265                 270

Lys Leu Gln Lys Ser Phe Asn Lys Ile Leu Leu Gln Ser Asn Met Ser
            275                 280                 285

Ser Ser
    290

<210> SEQ ID NO 209
<211> LENGTH: 282
<212> TYPE: PRT
<213> ORGANISM: Artificial Sequence
<220> FEATURE:
<223> OTHER INFORMATION: BsubDAT DAAT

<400> SEQUENCE: 209

Met Lys Val Leu Val Asn Gly Arg Leu Ile Gly Arg Ser Glu Ala Ser
1               5                   10                  15

Ile Asp Leu Glu Asp Arg Gly Tyr Gln Phe Gly Asp Gly Ile Tyr Glu
             20                  25                  30

Val Ile Arg Val Tyr Lys Gly Val Leu Phe Gly Leu Arg Glu His Ala
             35                  40                  45

Glu Arg Phe Phe Arg Ser Ala Glu Ile Gly Ile Ser Leu Pro Phe
             50                  55                  60

Ser Ile Glu Asp Leu Glu Trp Asp Leu Gln Lys Leu Val Gln Glu Asn
 65                  70                  75                  80

Ala Val Ser Glu Gly Ala Val Tyr Ile Gln Thr Thr Arg Gly Val Ala
```

```
                85                  90                  95
Pro Arg Lys His Gln Tyr Glu Ala Gly Leu Glu Pro Gln Thr Thr Ala
            100                 105                 110

Tyr Thr Phe Thr Val Lys Lys Pro Glu Gln Glu Gln Ala Tyr Gly Val
            115                 120                 125

Ala Ala Ile Thr Asp Glu Asp Leu Arg Trp Leu Arg Cys Asp Ile Lys
            130                 135                 140

Ser Leu Asn Leu Leu Tyr Asn Val Met Thr Lys Gln Arg Ala Tyr Glu
145                 150                 155                 160

Ala Gly Ala Phe Glu Ala Ile Leu Leu Arg Asp Gly Val Val Thr Glu
                165                 170                 175

Gly Thr Ser Ser Asn Val Tyr Ala Val Ile Asn Gly Thr Val Arg Thr
            180                 185                 190

His Pro Ala Asn Arg Leu Ile Leu Asn Gly Ile Thr Arg Met Asn Ile
            195                 200                 205

Leu Gly Leu Ile Glu Lys Asn Gly Ile Lys Leu Asp Glu Thr Pro Val
            210                 215                 220

Ser Glu Glu Leu Lys Gln Ala Glu Ile Phe Ile Ser Ser Thr
225                 230                 235                 240

Thr Ala Glu Ile Ile Pro Val Val Thr Leu Asp Gly Gln Ser Ile Gly
                245                 250                 255

Ser Gly Lys Pro Gly Pro Val Thr Lys Gln Leu Gln Ala Ala Phe Gln
            260                 265                 270

Glu Ser Ile Gln Gln Ala Ala Ser Ile Ser
            275                 280

<210> SEQ ID NO 210
<211> LENGTH: 283
<212> TYPE: PRT
<213> ORGANISM: Artificial Sequence
<220> FEATURE:
<223> OTHER INFORMATION: Bacillus lichenifomis DAAT

<400> SEQUENCE: 210

Met Lys Val Leu Phe Asn Gly Arg Leu Met Glu Arg Ser Glu Cys Ala
1               5                   10                  15

Val Asp Ile Glu Asp Arg Gly Tyr Gln Phe Gly Asp Gly Val Tyr Glu
            20                  25                  30

Val Ile Arg Ile Tyr Asn Gly Ile Leu Phe Thr Leu Asp Glu His Ile
            35                  40                  45

Ala Arg Leu Tyr Lys Ser Ala Ala Glu Ile Gly Ile Asp Leu Ser Phe
        50                  55                  60

Ser Glu Ala Glu Leu Lys Ser Gln Leu Lys Glu Leu Val Asp Ile Asn
65                  70                  75                  80

Gln Arg Arg Asp Gly Gly Leu Tyr Leu Gln Val Thr Arg Gly Lys Ala
                85                  90                  95

Pro Arg Lys His Gln Tyr Gly Ala Gly Leu Thr Pro Gln Val Thr Ala
            100                 105                 110

Tyr Thr Phe Pro Ile Gln Lys Pro Glu Lys Gln Gln Asn Gly Val
            115                 120                 125

Ser Ala Ile Thr Ala Asp Asp Met Arg Trp Leu Arg Cys Asp Ile Lys
            130                 135                 140

Ser Leu Asn Leu Leu Tyr Asn Val Met Ile Lys Gln Lys Ala Gln Glu
145                 150                 155                 160

Ala Ser Ala Phe Glu Ala Ile Leu Ile Arg Asp Gly Leu Val Thr Glu
                165                 170                 175
```

```
Gly Thr Ser Ser Asn Val Tyr Val Ala Lys Gln Asn Val Ile Tyr Thr
            180                 185                 190

His Pro Val Thr Thr Leu Ile Leu Asn Gly Ile Thr Arg Met Lys Val
            195                 200                 205

Leu Gln Leu Cys Glu Glu Asn Gly Leu Asn Tyr Glu Glu Lys Ala Val
            210                 215                 220

Thr Lys Asp Glu Leu Leu Asn Ala Asp Glu Val Phe Ile Thr Ser Thr
225                 230                 235                 240

Thr Ala Glu Val Ile Pro Val Thr Ser Ile Asp Gly Gln Thr Ile Gly
                245                 250                 255

Ser Gly Ala Pro Gly Pro Leu Thr Lys Asn Val Gln Thr Ala Leu Gln
            260                 265                 270

Asn Ser Ile Leu Ser Glu Thr Ala Lys Thr Val
            275                 280

<210> SEQ ID NO 211
<211> LENGTH: 283
<212> TYPE: PRT
<213> ORGANISM: Artificial Sequence
<220> FEATURE:
<223> OTHER INFORMATION: Bacillus rotans DAAT

<400> SEQUENCE: 211

Met Ser Tyr Ser Leu Trp Asn Asp Gln Ile Val Asn Asp Glu Glu Val
1               5                   10                  15

Val Val Asp Lys Glu Asp Arg Gly Tyr Gln Phe Gly Asp Gly Val Tyr
                20                  25                  30

Glu Val Val Lys Val Tyr Asn Gly Glu Leu Phe Thr Ala Glu Glu His
                35                  40                  45

Val Asp Arg Phe Tyr Ala Ser Ala Glu Lys Ile Arg Val Thr Ile Pro
        50                  55                  60

Tyr Thr Lys Asp Lys Leu His Gln Leu Leu His Gln Leu Val Glu Met
65                  70                  75                  80

Asn Lys Val Gln Thr Gly His Ile Tyr Phe Gln Ile Thr Arg Gly Ala
                85                  90                  95

Gly Pro Arg Asn His Ile Phe Pro Gly Asp Glu Val Lys Pro Val Leu
            100                 105                 110

Thr Gly Asn Thr Lys Glu Asn Pro Arg Pro Val Ala Asn Phe Glu Lys
            115                 120                 125

Gly Val Lys Ala Thr Phe Val Glu Asp Ile Arg Trp Leu Arg Cys Asp
130                 135                 140

Ile Lys Ser Leu Asn Leu Leu Gly Ala Val Leu Ala Lys Gln Glu Ala
145                 150                 155                 160

His Glu Lys Gly Cys Tyr Glu Ala Val Leu His Arg Asp Glu Ile Val
                165                 170                 175

Thr Glu Gly Ser Ser Ser Asn Ile Tyr Gly Ile Lys Asp Gly Val Leu
            180                 185                 190

Tyr Thr His Pro Ala Asn Asn Phe Ile Leu Asn Gly Ile Thr Arg Gln
            195                 200                 205

Val Ile Ile Lys Cys Ala Ala Glu Ile Gly Leu Pro Val Lys Glu Glu
            210                 215                 220

Ala Met Thr Lys Thr Gln Leu Leu Ala Met Asp Glu Val Ile Val Ser
225                 230                 235                 240

Ser Thr Thr Ser Glu Val Thr Pro Ile Ile Asp Ile Asp Gly Thr Val
                245                 250                 255
```

```
Ile Gly Ala Gly Lys Pro Gly Asp Trp Thr Arg Lys Leu Gln Ala Gln
            260                 265                 270

Phe Asp Thr Lys Ile Pro Lys Gly Ile Arg Ala
            275                 280
```

<210> SEQ ID NO 212
<211> LENGTH: 289
<212> TYPE: PRT
<213> ORGANISM: Artificial Sequence
<220> FEATURE:
<223> OTHER INFORMATION: Bacillus serositidis DAAT

<400> SEQUENCE: 212

```
Met Ser Tyr Thr Leu Trp Asn Asp Lys Ile Val Asp Asp Asn Gln Val
1               5                   10                  15

Phe Ile Asn Lys Glu Asp Arg Gly Tyr Gln Phe Gly Asp Gly Val Tyr
            20                  25                  30

Glu Val Ile Lys Val Tyr Asp Gly Glu Met Phe Thr Ala Thr Glu His
            35                  40                  45

Ile Asp Arg Phe Tyr Ala Ser Ala Glu Lys Ile Lys Leu Thr Val Pro
        50                  55                  60

Tyr Thr Lys His Lys Leu His Gln Leu Leu His Glu Leu Val Glu Ala
65                  70                  75                  80

Asn Glu Leu Lys Thr Gly Asn Leu Tyr Phe Gln Ile Thr Arg Gly Ala
            85                  90                  95

Ser Pro Arg Asn His Leu Phe Pro Gly Asp Asp Val Leu Pro Val Leu
            100                 105                 110

Thr Gly Asn Val Lys Glu Ala Pro Arg Ser Ile Glu Asn Ala Gln Lys
            115                 120                 125

Gly Val Lys Ala Thr Phe Ala Glu Asp Ile Arg Trp Leu Arg Cys Asp
        130                 135                 140

Ile Lys Ser Leu Asn Leu Leu Gly Ala Val Leu Ala Lys Gln Glu Ala
145                 150                 155                 160

His Glu Lys Gly Cys Tyr Glu Ala Ile Leu His Arg Gly Glu Thr Ile
            165                 170                 175

Thr Glu Gly Ser Ser Thr Asn Val Phe Gly Ile Lys Asn Gly Val Leu
            180                 185                 190

Tyr Thr His Pro Ala Asp Asn Phe Ile Leu Ser Gly Ile Thr Arg Gly
            195                 200                 205

Val Val Leu Ala Cys Ala Asn Glu Ile Gly Leu Pro Val Lys Gln Glu
        210                 215                 220

Ala Phe Thr Lys Asp Lys Ala Leu Gln Met Asp Glu Met Phe Val Ser
225                 230                 235                 240

Ser Thr Thr Ser Glu Ile Thr Pro Val Ile Asp Leu Asp Gly Val Ala
            245                 250                 255

Ile Asn Gly Gly Glu Ile Gly Glu Trp Thr Arg Lys Leu Gln Lys Gln
            260                 265                 270

Phe Ala Thr Lys Leu Pro Gly Ser Pro Ala Tyr Asn Leu Thr Glu Tyr
            275                 280                 285

Lys
```

<210> SEQ ID NO 213
<211> LENGTH: 283
<212> TYPE: PRT
<213> ORGANISM: Artificial Sequence
<220> FEATURE:
<223> OTHER INFORMATION: Bacillus sphaericus DAAT

```
<400> SEQUENCE: 213

Met Ala Tyr Ser Leu Trp Asn Asp Gln Ile Val Glu Glu Gly Ser Ile
1               5                   10                  15

Thr Ile Ser Pro Glu Asp Arg Gly Tyr Gln Phe Gly Asp Gly Ile Tyr
            20                  25                  30

Glu Val Ile Lys Val Tyr Asn Gly His Met Phe Thr Ala Gln Glu His
            35                  40                  45

Ile Asp Arg Phe Tyr Ala Ser Ala Glu Lys Ile Arg Leu Val Ile Pro
    50                  55                  60

Tyr Thr Lys Asp Val Leu His Lys Leu Leu His Asp Leu Ile Glu Lys
65                  70                  75                  80

Asn Asn Leu Asn Thr Gly His Val Tyr Phe Gln Ile Thr Arg Gly Thr
                85                  90                  95

Thr Ser Arg Asn His Ile Phe Pro Asp Ala Ser Val Pro Ala Val Leu
            100                 105                 110

Thr Gly Asn Val Lys Thr Gly Glu Arg Ser Ile Glu Asn Phe Glu Lys
            115                 120                 125

Gly Val Lys Ala Thr Leu Val Glu Asp Val Arg Trp Leu Arg Cys Asp
130                 135                 140

Ile Lys Ser Leu Asn Leu Leu Gly Ala Val Leu Ala Lys Gln Glu Ala
145                 150                 155                 160

Ser Glu Lys Gly Cys Tyr Glu Ala Ile Leu His Arg Gly Asp Ile Ile
                165                 170                 175

Thr Glu Cys Ser Ser Ala Asn Val Tyr Gly Ile Lys Asp Gly Lys Leu
            180                 185                 190

Tyr Thr His Pro Ala Asn Asn Tyr Ile Leu Asn Gly Ile Thr Arg Gln
            195                 200                 205

Val Ile Leu Lys Cys Ala Ala Glu Ile Asn Leu Pro Val Ile Glu Glu
    210                 215                 220

Pro Met Thr Lys Gly Asp Leu Leu Thr Met Asp Glu Ile Ile Val Ser
225                 230                 235                 240

Ser Val Ser Ser Glu Val Thr Pro Val Ile Asp Val Asp Gly Gln Gln
                245                 250                 255

Ile Gly Ala Gly Val Pro Gly Glu Trp Thr Arg Lys Leu Gln Lys Ala
            260                 265                 270

Phe Glu Ala Lys Leu Pro Ile Ser Ile Asn Ala
            275                 280
```

What is claimed is:

1. A method of producing monatin or salt thereof, the method comprising:

producing indole-3-pyruvate ("I3P") from L-tryptophan;

producing monatin precursor ("MP") including at least R monatin precursor ("R-MP") from the I3P; and producing the monatin from the MP, wherein:

at least about 60% by weight of total monatin produced is R,R monatin;

the production of the I3P from the L-tryptophan is facilitated by one or more first enzymes having greater activity, greater specificity, or both, for L-tryptophan than for the monatin precursor, the monatin, or both, said one or more first enzymes are chosen from an L-tryptophan aminotransferase, an L-aromatic aminotransferase, an L-aspartate aminotransferase, and an L-amino acid oxidase, and combinations thereof;

the production of the monatin precursor from the I3P is facilitated by one or more second enzymes having R-specific aldolase activity; and wherein said R,R monatin production from said R-MP is facilitated by one or more third enzymes chosen from a D-aminotransferase and a D-amino acid dehydrogenase or combinations thereof.

2. The method of claim 1, wherein said one or more first enzymes are chosen from *Sinorhizobium meliloti* TatA, HEXAspCP9T/R122G, and combinations thereof.

3. The method of claim 1,
wherein: said D-amino acid dehydrogenase is chosen from D-AADH-101, D-AADH-102, D-AADH-103, D-AADH-105, D-AADH-106, D-AADH-107, D-AADH-108, and combinations thereof; and,
wherein said D-aminotransferase is:
a) an enzyme having the activity of a D-aminotransferase chosen from one or more of: a D-aminotransferase corresponding to SEQ ID NO:86 having a T243S mutation, a T243N mutation, a N100A mutation, a T243Q mutation, T243N and N100A mutations, a F200M mutation, a F200Y mutation, and F200M and T243N mutations;

b) enzymes comprising a sequence having a percent sequence identity of at least 90% to any of the enzymes in a);

c) a *Bacillus halodurans* D-aminotransferase, a hybrid D-aminotransferase that is a hybrid between *Geobacillus stearothermophilus* D-aminotransferase and *Bacillus sphaericus* D-aminotransferase, a *Bacillus sphaericus* D-aminotransferase, a *Geobacillus stearothermophilus* D-aminotransferase, a *Bacillus licheniformis* D-aminotransferase, a D-aminotransferase from ATCC 7063, a *Bacillus licheniformis* branched chain aminotransferase having D-aminotransferase activity; or, d) combinations of a-c.

4. The method of claim 1, wherein said R,R monatin produced is at least about 90%, by weight, of total monatin produced.

5. The method of claim 1, wherein the R-MP is produced from I3P in a chemical aldol condensation reaction.

6. The method of claim 1, wherein said one or more second enzymes having R-specific aldolase activity are chosen from: a) an aldolase from *Sinorhizobium meliloti* HMG aldolase; b) enzymes comprising a sequence having a percent sequence identity of at least 90% to a); c) an aldolase having the sequence shown in SEQ ID NO:22 or SEQ ID NO:104; and d) combinations thereof.

7. The method of claim 1, wherein said one or more third enzymes have greater activity, greater specificity, or both for the R-monatin precursor than for S-alpha-keto acid monatin or indole-3-pyruvate, and optionally said one or more second enzymes have limited activity, limited specificity, or both for S-alpha-keto acid of monatin or indole-3-pyruvate.

8. The method of claim 1, wherein the enzymes are immobilized onto a solid support.

\* \* \* \* \*

UNITED STATES PATENT AND TRADEMARK OFFICE
CERTIFICATE OF CORRECTION

| | | |
|---|---|---|
| PATENT NO. | : 8,076,108 B2 | Page 1 of 1 |
| APPLICATION NO. | : 11/714279 | |
| DATED | : December 13, 2011 | |
| INVENTOR(S) | : Brian J. Brazeau et al. | |

It is certified that error appears in the above-identified patent and that said Letters Patent is hereby corrected as shown below:

On page 3, column 2, item (56), under "Other Publications", line 7, after "Chem.," insert -- 1975, --.

In column 6, lines 52-53, delete "P-alanine" and insert -- β-alanine --, therefor.

In column 60, line 10, after "the", insert -- following primers: --, therefor.

In column 105, line 51, delete "E. coil" and insert -- E. coli --, therefor.

In column 109, line 14, delete "coil" and insert -- coli --, therefor.

In column 148, line 35, after "SEQ ID NO:", delete "55" and insert -- 66 --, therefor.

In column 160, line 57, delete "E. coil" and insert -- E. coli --, therefor.

Signed and Sealed this
Twenty-ninth Day of May, 2012

David J. Kappos
*Director of the United States Patent and Trademark Office*